US008048653B2

(12) United States Patent
Damude et al.

(10) Patent No.: US 8,048,653 B2
(45) Date of Patent: Nov. 1, 2011

(54) MICROBIAL OILS PRODUCED IN TRANSFORMED HOST CELLS COMPRISING DELTA-9 ELONGASES

(75) Inventors: Howard Glenn Damude, Hockessin, DE (US); Brian McGonigle, Wilmington, DE (US); Zhixiong Xue, Chadds Ford, PA (US); Quinn Qun Zhu, West Chester, PA (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 12/619,706

(22) Filed: Nov. 17, 2009

(65) Prior Publication Data

US 2010/0075387 A1 Mar. 25, 2010

Related U.S. Application Data

(62) Division of application No. 11/601,564, filed on Nov. 16, 2006, now Pat. No. 7,645,604.

(60) Provisional application No. 60/739,989, filed on Nov. 23, 2005.

(51) Int. Cl.

| | |
|---|---|
| ***C12P 7/64*** | (2006.01) |
| ***C12N 9/00*** | (2006.01) |
| ***C12N 9/10*** | (2006.01) |
| ***C12N 1/20*** | (2006.01) |
| ***C12N 15/00*** | (2006.01) |

(52) U.S. Cl. ..... 435/134; 435/183; 435/193; 435/252.3; 435/320.1; 536/23.2

(58) Field of Classification Search ........................ None
See application file for complete search history.

(56) References Cited

U.S. PATENT DOCUMENTS 6,825,017 B1 11/2004 Browse et al.

FOREIGN PATENT DOCUMENTS

| | | | |
|---|---|---|---|
| WO | 0034439 | A1 | 6/2000 |
| WO | WO 00/34439 | A1 | 6/2000 |
| WO | 02/077213 | A2 | 10/2002 |
| WO | 02077213 | A2 | 10/2002 |
| WO | WO 02/077213 | * | 10/2002 |
| WO | WO 02/077213 | A2 | 10/2002 |
| WO | 2004/057001 | A1 | 7/2004 |
| WO | 2004057001 | A2 | 7/2004 |
| WO | WO 2004/057001 | A2 | 7/2004 |
| WO | 2004071178 | A2 | 8/2004 |
| WO | 2004071467 | A2 | 8/2004 |
| WO | WO 2004/071178 | A2 | 8/2004 |
| WO | WO 2004/071467 | A2 | 8/2004 |
| WO | 2004101753 | A2 | 11/2004 |
| WO | 2004101757 | A2 | 11/2004 |
| WO | WO 2004/101753 | A2 | 11/2004 |
| WO | WO 2004/101757 | A2 | 11/2004 |
| WO | 2005012316 | A2 | 2/2005 |
| WO | WO 2005/012316 | A2 | 2/2005 |
| WO | 2005083093 | A2 | 9/2005 |
| WO | WO 2005/083093 | A2 | 9/2005 |
| WO | 2005103253 | A1 | 11/2005 |
| WO | WO 2005/103253 | A1 | 11/2005 |
| WO | 2006012325 | A1 | 2/2006 |
| WO | 2006012326 | A1 | 2/2006 |
| WO | WO 2006/012325 | A1 | 2/2006 |
| WO | WO 2006/012326 | A1 | 2/2006 |
| WO | 2006052870 | A2 | 5/2006 |
| WO | 2006052871 | A2 | 5/2006 |
| WO | 2006055322 | A2 | 5/2006 |
| WO | WO 2006/052870 | A2 | 5/2006 |
| WO | WO 2006/052871 | A2 | 5/2006 |
| WO | WO 2006/055322 | A2 | 5/2006 |

OTHER PUBLICATIONS

U.S. Appl. No. 10/840,478, filed Dec. 16, 2004, Picataggio et al.
U.S. Appl. No. 10/840,579, filed Jun. 23, 2005, Picataggio et al.
U.S. Appl. No. 10/840,325, filed Feb. 24, 2005, Yadav et al.
U.S. Appl. No. 10/869,630, filed Jan. 20, 2005, Picataggio et al.
U.S. Appl. No. 10/882,760, filed Jul. 20, 2006, Yadav et al.
U.S. Appl. No. 10/985,109, filed Jun. 16, 2005, Damude et al.
U.S. Appl. No. 10/985,691, filed Sep. 29, 2005, Yadav et al.
U.S. Appl. No. 10/987,548, filed Jun. 16, 2005, Walters Pollak.
U.S. Appl. No. 11/024,545, filed May 4, 2006, Xue et al.
U.S. Appl. No. 11/024,544, filed May 4, 2006, Yadav et al.
U.S. Appl. No. 11/166,993, filed Dec. 29, 2005, Damude et al.
U.S. Appl. No. 11/183,664, filed Jan. 26, 2006, Picataggio et al.
U.S. Appl. No. 11/185,301, filed May 4, 2006, Xue et al.
U.S. Appl. No. 11/190,750, filed May 4, 2006, Picataggio et al.
U.S. Appl. No. 11/198,975, filed Aug. 8, 2005, Zhu et al.
U.S. Appl. No. 11/225,354, filed Mar. 16, 2006, Xue et al.
U.S. Appl. No. 11/251,466, filed May 4, 2006, Damude et al.
U.S. Appl. No. 11/254,173, filed May 4, 2006, Macool et al.
U.S. Appl. No. 11/253,882, filed Apr. 19, 2007, Macool et al.
U.S. Appl. No. 11/264,784, filed May 4, 2006, Damude et al.
U.S. Appl. No. 11/264,737, filed May 25, 2006, Damude et al.
U.S. Appl. No. 11/265,761, filed Jun. 1, 2006, Damude et al.
U.S. Appl. No. 60/739,989, filed Nov. 23, 2005, Damude et al.
U.S. Appl. No. 60/795,810, filed Apr. 28, 2006, Damude et al.
U.S. Appl. No. 60/793,575, filed Apr. 20, 2006, Xue et al.
U.S. Appl. No. 60/796,637, filed May 1, 2006, Yadav et al.
U.S. Appl. No. 60/801,172, filed May 17, 2006, Damude et al.
U.S. Appl. No. 60/801,119, filed May 17, 2006, Damude et al.
U.S. Appl. No. 60/853,563, filed Oct. 23, 2006, Damude et al.
U.S. Appl. No. 60/855,177, filed Oct. 30, 2006, Xue et al.
U.S. Appl. No. 10/776,311, filed Sep. 2, 2004, Cahoon et al.
U.S. Appl. No. 10/776,889, filed Feb. 11, 2004, Kinnay et al.
U.S. Appl. No. 11/166,003, filed Aug. 31, 2006, Damude et al.
J. Dyerberg et. al., Fatty Acid Composition of the Plasma Lipids in Greenland Eskimos, Amer. J. Clin. Nutr., 1975, vol. 28:958-966.
J. Dyerberg et. al., Eicosapentaenoic Acid and Prevention of Thrombosis and Atherosclerosis, Lancet, 1978, vol. 2:117-119.
H. Shimokawa, Beneficial Effects of Eicosapentaenoic Acid on Endothelial Vasodilator Functions in Animals and Humans, World Rev. Nutr. Diet, 2001, vol. 88:100-108.
C. Schacky et. al., 3 Fatty Acids—From Eskimos to Clinical Cardiology—What Took Us So Long? World Rev. Nutr. Dirt, 2001, vol. 88:90-99.

(Continued)

*Primary Examiner* — Christian Fronda

(57) ABSTRACT

The present invention relates to Δ9 elongases, which have the ability to convert linoleic acid [18:2, LA] to eicosadienoic acid [20:2, EDA]. Isolated nucleic acid fragments and recombinant constructs comprising such fragments encoding Δ9 elongase along with methods of making long-chain polyunsaturated fatty acids (PUFAs) using these Δ9 elongases in plants and oleaginous yeast are disclosed.

4 Claims, 16 Drawing Sheets

OTHER PUBLICATIONS

National Center for Biotechnology Information General Identifier No. AAL37626, Mar. 9, 2006, B. Qi Et. Al., Identification of a CDNA Encoding a Novel C18-Delta (9) Polyunsaturated Fatty Acid-Specific Elongating Activity From the Docosahexaenoic Acid (DHA)-Producing Microalga, Isochrysis Galbana.
Browse et. al., Polyunsaturated Fatty Acids Synthesis: What Will They Think of Next?, Trends in Biochemical Sciences, 2002, vol. 27:467-473.
Napier, Plumbing the Depths of PUFA Biosynthesis: A Novel Polyketide Synthase-Like Pathway From Marine Organisms, Trends in Plant Sciences, 2002, vol. 7:51-54.
Wallis et. al., The Desaturase of *Euglena Gracilis*: An Alternate Pathway for Synthesis of 20-Carbon Polyunsaturated Fatty Acids, Arch. Biochem. and Biopys., 1999, vol. 365:307-316.
Sayanova et. al., The Alternative Pathway C20, 8 Desaturase From the Non-Photosynthetic Organism Acanthamoeba Castellanii is an Atypical Cytochrome B5-Fusion Desaturase, FEBS Lett., 2006, vol. 580:1946-1952.
Qi, Baoxiu et al., Identification of a cDNA encoding a novel C18-Delta9 polyunsaturated fatty acid-specific elongating activity from the docosahexaenoic acid (DHA)-producing microalga, *Isochrysis galbanal*1, FEBS Letters, 2002, p. 159-165, vol. 510.
Qi, Baoxiu et al, Production of very long chain polyunsaturated omega-3 and omega-6 fatty acids in plants, Nature Biotechnology, Jun. 2004, p. 739-745, vol. 22, No. 6.
Beaudoin, Frederic et al., Heterologous reconstitution in yeast of the polyunsaturated fatty acid biosynthetic pathway, PNAS, Jun. 6, 2000, p. 6421-6426, vol. 97, No. 12.
Barsanti, Laura et al., Fatty acid content in wild type and WZSL mutant of *Euglena gracilis*, Journal of Applied Phycology, 2000, p. 515-520, vol. 12, Kluwer Academic Publishers.
Drexler, Hjordis et al., Metabolic engineering of fatty acids for breeding of new oilseed crops: strategies, problems and first results, Journal of Plant Physiology, 2003, p. 779-802, Urban & Fischer Verlag.
U.S. Appl. No. 10/840,478, filed Dec. 16, 2004, Stephen K. Picataggio et al.
U.S. Appl. No. 10/840,579, filed Jun. 23, 2005, Stephen K. Picataggio et al.
U.S. Appl. No. 10/840,325, filed Feb. 24, 2005, Narendra S. Yadav et al.
U.S. Appl. No. 10/869,630, filed Jan. 20, 2005, Stephen K. Picataggio et al.
U.S. Appl. No. 10/882,760, filed Jul. 20, 2006, Narendra S. Yadav et al.
U.S. Appl. No. 10/985,109, filed Jun. 16, 2005, Howard Glenn Damude et al.
U.S. Appl. No. 10/985,691, filed Sep. 29, 2005, Narendra S. Yadav et al.
U.S. Appl. No. 10/987,548, filed Jun. 16, 2005, Dana M. Walters Pollak.
U.S. Appl. No. 11/024,545, filed May 4, 2006, Zhixiong Xue et al.
U.S. Appl. No. 11/024,544, filed May 4, 2006, Narendra S. Yadav et al.
U.S. Appl. No. 11/166,993, filed Dec. 29, 2005, Howard Glenn Damude et al.
U.S. Appl. No. 11/183,664, filed Jan. 26, 2006, Stephen K. Picataggio et al.
U.S. Appl. No. 11/185,301, filed May 4, 2006, Zhixiong Xue et al.
U.S. Appl. No. 11/190,750, filed May 4, 2006, Stephen K. Picataggio et al.
U.S. Appl. No. 11/198,975, filed Aug. 8, 2005, Quinn Qun et al.
U.S. Appl. No. 11/225,354, filed Mar. 16, 2006, Zhixiong Xue et al.
U.S. Appl. No. 11/251,466, filed May 4, 2006, Howard Glenn Damude et al.
U.S. Appl. No. 11/254,173, filed May 4, 2006, Daniel Joseph Macool et al.
U.S. Appl. No. 11/253,882, filed Apr. 19, 2007, Daniel Joseph Macool et al.
U.S. Appl. No. 11/264,784, filed May 4, 2006, Howard Glenn Damude et al.
U.S. Appl. No. 11/264,737, filed May 25, 2006, Howard Glenn Damude et al.
U.S. Appl. No. 11/265,761, filed Jun. 1, 2006, Howard Glenn Damude et al.
U.S. Appl. No. 60/739,989, filed Nov. 23, 2005, Howard Glenn Damude et al.
U.S. Appl. No. 60/795,810, filed Apr. 28, 2006, Howard Glenn Damude et al.
U.S. Appl. No. 60/793,575, filed Apr. 20, 2006, Zhixiong Xue et al.
U.S. Appl. No. 60/796,637, filed May 1, 2006, Narendra S. Yadav et al.
U.S. Appl. No. 60/801,172, filed May 17, 2006, Howard Glenn Damude et al.
U.S. Appl. No. 60/801,119, filed May 17, 2006, Howard Glenn Damude et al.
U.S. Appl. No. 60/853,563, filed Oct. 23, 2006, Howard Glenn Damude et al.
U.S. Appl. No. 60/855,177, filed Oct. 30, 2006, Zhixiong Xue et al.
U.S. Appl. No. 10/776,311, filed Sep. 2, 2004, Edgar Benjamin Cahoon et al.
U.S. Appl. No. 10/776,889, filed Feb. 11, 2004, Anthony J. Kinnay et al.
U.S. Appl. No. 11/166,003, filed Aug. 31, 2006, Howard Glenn Damude et al.
J. Dyerberg et. al., Fatty Acid Composition of the Plasma Lipids in Greenland Eskimos, Amer. J. Clin. Nutr., 1975, vol. 28:958-966.
J. Dyerberg et. al., Eicosapentaenoic Acid and Prevention of Thrombosis and Atherosclerosis, Lancet, 1978, vol. 2:117-119.
H. Shimokawa, Beneficial Effects of Eicosapentaenoic Acid on Endothelial Vasodilator Functions in Animals and Humans, World Rev. Nutr. Diet, 2001, vol. 88:100-108.
C. Schacky et. al., 3 Fatty Acids—From Eskimos to Clinical Cardiology—What Took Us So Long? World Rev. Nutr. Dirt, 2001, vol. 88:90-99.
National Center for Biotechnology Information General Identifier No. AAL37626, Mar. 9, 2006, B. Qi et. al., Identification of a CDNA Encoding A Novel C18-DELTA(9) Polyunsaturated Fatty Acid-Specific Elongating Activity From The Docosahexaenoic Acid (DHA)-Producing Microalga, *Isochrysis Galbana*.
Browse et. al., Polyunsaturated Fatty Acids Synthesis: What Will They Think of Next?, Trends in Biochemical Sciences, 2002, vol. 27:467-473.
Napier, Plumbing the Depths of PUFA Biosynthesis: A Novel Polyketide Synthase-Like Pathway From Marine Organisms, Trends in Plant Sciences, 2002, vol. 7:51-54.
Wallis et. al., The Desaturase of *Euglena Gracilis*: An Alternate Pathway for Synthesis of 20-Carbon Polyunsaturated Fatty Acids, Arch. Biochem. and Biophys., 1999, vol. 365:307-316.
Sayanova et. al., The Alternative Pathway C20, 8 Desaturase From the Non-Photosynthetic Organism Acanthamoeba Castellanii is an Atypical Cytochrome B5-Fusion Desaturase, FEBS Lett., 2006, vol. 580:1946-1952.
Qi, Baoxiu et al., Identification of a cDNA encoding a novel C18-Delta9 polyunsaturated fatty acid-specific elongating activity from the docosahexaenoic acid (DHA)-producing microalga, *Isochrysis galbana*1, FEBS Letters, 2002, p. 159-165, vol. 510.
Qi, Baoxiu et al, Production of very long chain polyunsaturated omega-3 and omega-6 fatty acids in plants, Nature Biotechnology, Jun. 2004, p. 739-745, vol. 22, No. 6.
Beaudoin, Frederic et al., Heterologous reconstitution in yeast of the polyunsaturated fatty acid biosynthetic pathway, PNAS, Jun. 6, 2000, p. 6421-6426, vol. 97, No. 12.
Barsanti, Laura et al., Fatty acid content in wild type and WZSL mutant of *Euglena gracilis*, Journal of Applied Phycology, 2000, p. 515-520, vol. 12, Kluwer Academic Publishers.
Drexler, Hjordis et al., Metabolic engineering of fatty acids for breeding of new oilseed crops: strategies, problems and first results, Journal of Plant Physiology, 2003, p. 779-802, Urban & Fischer Verlag.

* cited by examiner

FIG. 2

```
     M.................L........W......E.L........LK..L....L.....  Consensus #1
              10        20        30        40        50        60
1    M----EVVNEIVSIGQEVLPKVDYAQLWSDASHCEVLYLSIAFVILKFTL--GPLGPKGQ  SEQ ID NO:2 (EgD9e)
1    MAAVIEVANEFVAITAETLPKVDYQRLWRDIYSCELLYFSIAFVILKFTL--GELSDSGK  SEQ ID NO:5 (E389D9e)
1    MA----------------LANDAGERIWAAVTDPEILIGTFSYLLLKPLLRNSGLVDEKK  SEQ ID NO:8 (IgD9e)

     .........YN......S..SF.....A....Y..G................C.....D.  Consensus #1
              70        80        90       100       110       120
55   SRMKFVFTNYNLLMSIYSLGSFLSMAYAM---YTIGVMSD-----------NCEKA-FDN  SEQ ID NO:2 (EgD9e)
59   KILRVLFKWYNLFMSVFSLVSFLCMGYAI---YTVGLYSN-----------ECDRA-FDN  SEQ ID NO:5 (E389D9e)
45   GAYRTSMIWYNVLLALFSALSFYVTATALGWDYGTGAWLRRQTGDTPQPLFQCPSPVWDS  SEQ ID NO:8 (IgD9e)

     ..F......FY.SK..EY.D...L.L..K....LQ.FHH.GAP.D..L......E..WIF  Consensus #1
             130       140       150       160       170       180
100  NVFRITTQLFYLSKFLEYIDSFYLPLMGKPLTWLQFFHHLGAPMDMWLFYNYRNEAVWIF  SEQ ID NO:2 (EgD9e)
104  SLFRFATKVFYYSKFLEYIDSFYLPLMAKPLSFLQFFHHLGAPMDMWLFVQYSGESIWIF  SEQ ID NO:5 (E389D9e)
105  KLFTWTAKAFYYSKYVEYLDTAWLVLKGKRVSFLQAFHHFGAPWDVYLGIRLHNEGVWIF  SEQ ID NO:8 (IgD9e)

     ...N.FIH..MY.YY........F...K.LIT.MQI.QF..GF..VW.Y...PC...D..  Consensus #1
             190       200       210       220       230       240
160  VLLNGFIHWIMYGYYWTRLIKLKFPMPKSLITSMQIIQFNVGFYIVWKYRNIPCYRQDGM  SEQ ID NO:2 (EgD9e)
164  VFLNGFIHFVMYGYYWTRLMKFNFPMPKQLITAMQITQFNVGFYLVWWYKDIPCYRKDPM  SEQ ID NO:5 (E389D9e)
165  MFFNSFIHTIMYTYYGLTAAGYKF-KAKPLITAMQICQFVGGFLLVWDYINVPCFNSDKG  SEQ ID NO:8 (IgD9e)

     ....W.FNY.YVG.V..LF..F........K......K..                      Consensus #1
             250       260       270       280
220  RMFGWFFNYFYVGTVLCLFLNFYVQTYIVRKHKGA-KKIQ                      SEQ ID NO:2 (EgD9e)
224  RMLAWIFNYWYVGTVLLLFINFFVKSYVFPKPKTADKKVQ                      SEQ ID NO:5 (E389D9e)
224  KLFSWAFNYAYVGSVFLLFCHFFYQDNLATKKSAKAGKQL                      SEQ ID NO:8 (IgD9e)
```

FIG. 4

```
      M...N..................W......E.L........LK..L...G  Consensus #1
               10        20        30        40        50
1     MEVVNEIVSIGQEVLPKVDYAQLWSDASHCEVLYLSIAFVILKFTLGPLG  SEQ ID NO:2 (EgD9e)
1     MALANDAGE------------RIWAAVTDPEILIGTFSYLLLKPLLRNSG  SEQ ID NO:8 (IgD9e)

      ...............YN.L....S..SF...A.A....Y..G........  Consensus #1
               60        70        80        90       100
51    PKGQSRMKF--VFTNYNLLMSIYSLGSFLSMAYAM---YTIGV-----MS  SEQ ID NO:2 (EgD9e)
39    LVDEKKGAYRTSMIWYNVLLALFSALSFYVTATALGWDYGTGAWLRRQTG  SEQ ID NO:8 (IgD9e)

      D.....F.......D...F..T...FY.SK..EY.D...L.L.GK....L  Consensus #1
              110       120       130       140       150
91    DNCEKAF-------DNNVFRITTQLFYLSKFLEYIDSFYLPLMGKPLTWL  SEQ ID NO:2 (EgD9e)
89    DTPQPLFQCPSPVWDSKLFTWTAKAFYYSKYVEYLDTAWLVLKGKRVSFL  SEQ ID NO:8 (IgD9e)

      Q.FHH.GAP.D..L.....NE.VWIF...N.FIH.IMY.YY.......KF  Consensus #1
              160       170       180       190       200
134   QFFHHLGAPMDMWLFYNYRNEAVWIFVLLNGFIHWIMYGYYWTRLIKLKF  SEQ ID NO:2 (EgD9e)
139   QAFHHFGAPWDVYLGIRLHNEGVWIFMFFNSFIHTIMYTYYGLTAAGYKF  SEQ ID NO:8 (IgD9e)

      ...K.LIT.MQI.QF..GF..VW.Y.N.PC...D....F.W.FNY.YVG.  Consensus #1
              210       220       230       240       250
184   PMPKSLITSMQIIQFNVGFYIVWKYRNIPCYRQDGMRMFGWFFNYFYVGT  SEQ ID NO:2 (EgD9e)
189   -KAKPLITAMQICQFVGGFLLVWDYINVPCFNSDKGKLFSWAFNYAYVGS  SEQ ID NO:8 (IgD9e)

      V..LF..F..Q.....K....A.K..                          Consensus #1
              260       270
234   VLCLFLNFYVQTYIVRKHKG-AKKIQ                          SEQ ID NO:2 (EgD9e)
238   VFLLFCHFFYQDNLATKKSAKAGKQL                          SEQ ID NO:8 (IgD9e)
```

FIG. 6

| Sample Name | Fatty Acid | 16:0 | 16:1 (9) | 18:0 | 18:1 (9) | LA | GLA | ALA | STA | EDA | DGLA | ARA | EtrA | ETA | EPA | 22:2 (13, 16) | 22:4 (7, 10,13, 16) | DPA | 24:1 | % Elo |
|---|---|---|---|---|---|---|---|---|---|---|---|---|---|---|---|---|---|---|---|---|
| pY75 | None | 12.8 | 54.4 | 3.4 | 28.5 | 0.0 | 0.0 | 0.0 | 0.0 | 0.5 | 0.0 | 0.0 | 0.0 | 0.0 | 0.1 | 0.0 | 0.0 | 0.0 | 0.3 | |
| pY119-5 | | 12.5 | 55.2 | 3.5 | 27.3 | 0.0 | 0.0 | 0.0 | 0.0 | 0.6 | 0.0 | 0.0 | 0.0 | 0.0 | 0.0 | 0.0 | 0.0 | 0.0 | 0.7 | |
| pY119-6 | | 13.0 | 53.8 | 3.6 | 28.3 | 0.0 | 0.0 | 0.0 | 0.0 | 0.5 | 0.0 | 0.0 | 0.0 | 0.0 | 0.0 | 0.0 | 0.0 | 0.0 | 0.6 | |
| pY119-8 | | 12.5 | 52.8 | 3.5 | 30.2 | 0.0 | 0.0 | 0.0 | 0.0 | 0.5 | 0.0 | 0.0 | 0.0 | 0.0 | 0.1 | 0.0 | 0.0 | 0.0 | 0.5 | |
| pY75 | LA | 17.4 | 20.5 | 4.6 | 11.1 | 45.3 | 0.0 | 0.0 | 0.0 | 0.6 | 0.0 | 0.0 | 0.0 | 0.0 | 0.0 | 0.0 | 0.0 | 0.0 | 0.5 | 1.2 |
| pY119-5 | | 13.6 | 30.9 | 3.1 | 12.2 | 32.0 | 0.0 | 0.0 | 0.0 | 7.7 | 0.0 | 0.0 | 0.0 | 0.0 | 0.0 | 0.0 | 0.0 | 0.0 | 0.5 | 19.3 |
| pY119-6 | | 15.2 | 26.7 | 4.0 | 13.4 | 30.7 | 0.0 | 0.0 | 0.0 | 8.7 | 0.0 | 0.0 | 0.5 | 0.0 | 0.0 | 0.2 | 0.0 | 0.0 | 0.6 | 22.1 |
| pY119-8 | | 14.0 | 29.1 | 3.9 | 15.2 | 27.1 | 0.0 | 0.0 | 0.0 | 10.1 | 0.0 | 0.0 | 0.0 | 0.0 | 0.0 | 0.2 | 0.0 | 0.0 | 0.4 | 27.2 |
| pY75 | ALA | 11.1 | 6.2 | 4.4 | 4.4 | 0.2 | 0.0 | 72.7 | 0.0 | 0.4 | 0.0 | 0.0 | 0.3 | 0.0 | 0.0 | 0.0 | 0.0 | 0.0 | 0.3 | 0.4 |
| pY119-5 | | 11.7 | 17.0 | 4.9 | 13.3 | 0.1 | 0.0 | 41.0 | 0.0 | 0.3 | 0.0 | 0.0 | 11.2 | 0.0 | 0.0 | 0.0 | 0.0 | 0.0 | 0.4 | 21.4 |
| pY119-6 | | 11.7 | 16.1 | 5.0 | 12.6 | 0.1 | 0.0 | 42.1 | 0.0 | 0.3 | 0.0 | 0.0 | 11.7 | 0.0 | 0.0 | 0.1 | 0.0 | 0.0 | 0.4 | 21.7 |
| pY119-8 | | 11.1 | 17.0 | 4.7 | 13.1 | 0.1 | 0.0 | 41.1 | 0.0 | 0.2 | 0.0 | 0.0 | 12.2 | 0.0 | 0.0 | 0.0 | 0.0 | 0.0 | 0.4 | 22.9 |
| pY75 | GLA | 16.4 | 7.8 | 5.4 | 6.0 | 0.0 | 62.3 | 0.0 | 0.2 | 0.4 | 0.4 | 0.0 | 0.0 | 0.0 | 0.0 | 0.4 | 0.0 | 0.0 | 0.6 | 0.6 |
| pY119-5 | | 16.4 | 10.1 | 5.8 | 8.4 | 0.0 | 57.1 | 0.0 | 0.2 | 0.4 | 0.5 | 0.0 | 0.0 | 0.0 | 0.0 | 0.5 | 0.0 | 0.0 | 0.7 | 0.8 |
| pY119-6 | | 14.6 | 9.8 | 4.7 | 7.0 | 0.0 | 61.9 | 0.0 | 0.2 | 0.3 | 0.4 | 0.0 | 0.0 | 0.0 | 0.0 | 0.6 | 0.0 | 0.0 | 0.5 | 0.7 |
| pY119-8 | | 16.4 | 8.0 | 4.9 | 6.1 | 0.0 | 62.5 | 0.0 | 0.2 | 0.2 | 0.6 | 0.0 | 0.0 | 0.0 | 0.0 | 0.5 | 0.0 | 0.0 | 0.5 | 0.9 |
| pY75 | STA | 11.5 | 5.9 | 4.9 | 5.9 | 0.0 | 0.0 | 0.0 | 70.7 | 0.2 | 0.0 | 0.0 | 0.0 | 0.4 | 0.0 | 0.0 | 0.0 | 0.0 | 0.5 | 0.5 |
| pY119-5 | | 12.5 | 5.4 | 5.0 | 5.0 | 0.0 | 0.0 | 0.0 | 70.5 | 0.3 | 0.0 | 0.0 | 0.2 | 0.5 | 0.0 | 0.0 | 0.0 | 0.0 | 0.7 | 0.7 |
| pY119-6 | | 11.4 | 6.6 | 5.2 | 7.0 | 0.0 | 0.1 | 0.0 | 68.5 | 0.3 | 0.0 | 0.0 | 0.0 | 0.4 | 0.0 | 0.0 | 0.0 | 0.0 | 0.5 | 0.6 |
| pY119-8 | | 11.3 | 5.0 | 3.9 | 4.5 | 0.0 | 0.1 | 0.0 | 74.1 | 0.2 | 0.0 | 0.0 | 0.0 | 0.5 | 0.0 | 0.0 | 0.0 | 0.0 | 0.5 | 0.6 |
| pY75 | ARA | 19.2 | 33.2 | 4.9 | 17.3 | 0.0 | 0.0 | 0.0 | 0.0 | 0.6 | 0.1 | 24.0 | 0.0 | 0.0 | 0.0 | 0.0 | 0.0 | 0.0 | 0.7 | 0.0 |
| pY119-5 | | 18.6 | 34.4 | 4.8 | 19.0 | 0.0 | 0.0 | 0.0 | 0.0 | 0.5 | 0.1 | 21.7 | 0.0 | 0.0 | 0.0 | 0.0 | 0.1 | 0.0 | 0.8 | 0.5 |
| pY119-6 | | 16.9 | 34.4 | 5.5 | 24.4 | 0.0 | 0.0 | 0.0 | 0.0 | 0.3 | 0.1 | 17.6 | 0.0 | 0.0 | 0.0 | 0.0 | 0.1 | 0.0 | 0.6 | 0.6 |
| pY119-8 | | 17.7 | 36.5 | 4.4 | 18.7 | 0.0 | 0.0 | 0.0 | 0.0 | 0.5 | 0.1 | 21.5 | 0.0 | 0.0 | 0.0 | 0.0 | 0.1 | 0.0 | 0.4 | 0.5 |
| pY75 | EPA | 16.7 | 27.7 | 4.7 | 16.4 | 0.0 | 0.0 | 0.0 | 0.0 | 0.4 | 0.0 | 0.1 | 0.0 | 0.0 | 33.7 | 0.0 | 0.0 | 0.0 | 0.4 | 0.0 |
| pY119-5 | | 16.0 | 29.9 | 5.0 | 18.7 | 0.0 | 0.0 | 0.0 | 0.0 | 0.0 | 0.0 | 0.1 | 0.0 | 0.0 | 29.6 | 0.0 | 0.0 | 0.1 | 0.5 | 0.4 |
| pY119-6 | | 17.4 | 27.3 | 6.0 | 20.8 | 0.0 | 0.0 | 0.0 | 0.0 | 0.0 | 0.0 | 0.1 | 0.0 | 0.0 | 27.7 | 0.1 | 0.0 | 0.1 | 0.5 | 0.4 |
| pY119-8 | | 16.5 | 28.8 | 5.9 | 22.1 | 0.0 | 0.0 | 0.0 | 0.0 | 0.0 | 0.0 | 0.1 | 0.0 | 0.0 | 25.9 | 0.0 | 0.0 | 0.1 | 0.6 | 0.4 |

FIG. 14
B
pKR873
12403 bp
SbfI (1)
BsWI (13)
BsWI (12384)
soy albu5'
Fm.D15
alb3'
BsWI (2524)
T7 term
HPT
T7 promoter
pSP72 (no amp r)
soybean ALS 3'UTR
soybean ALS
soy SAMS 1.3 kb
BsWI (9055)
S BD30 3'
BsWI (9584)
BsWI (9620)
BsWI (9770)
S. diclina delta 17
Soy Annex. Pro
A
pKR669
13677 bp
BsWI (13)
Kti3 promoter
Fm.D15
Kti3 3' terminator
GM-ALB TERM
BsWI (3798)
T7 term
HPT
T7 promoter
pSP72 (no amp r)
soybean ALS 3'UTR
soybean ALS
soy SAMS 1.3 kb
SbfI (10310)
BsWI (10322)
Soy Annex. Pro
S. diclina delta 17
BsWI (12936)
BsWI (13086)
BsWI (13122)
S BD30 3'
BsWI (13651)

MICROBIAL OILS PRODUCED IN TRANSFORMED HOST CELLS COMPRISING DELTA-9 ELONGASES

This application claims the benefit of U.S. Provisional Application No. 60/739,989, filed Nov. 23, 2005, the entire content of which is herein incorporated by reference.

FIELD OF THE INVENTION

This invention is in the field of biotechnology. More specifically, this invention pertains to the identification of nucleic acid fragments encoding Δ9 fatty acid elongase enzymes and the use of these elongases in making long-chain polyunsaturated fatty acids (PUFAs).

BACKGROUND OF THE INVENTION

The importance of PUFAs is undisputed. For example, certain PUFAs are important biological components of healthy cells and are recognized as: "essential" fatty acids that cannot be synthesized de novo in mammals and instead must be obtained either in the diet or derived by further desaturation and elongation of linoleic acid (LA; 18:2 ω-6) or α-linolenic acid (ALA; 18:3 ω-3); constituents of plasma membranes of cells, where they may be found in such forms as phospholipids or triacylglycerols; necessary for proper development (particularly in the developing infant brain) and for tissue formation and repair; and, precursors to several biologically active eicosanoids of importance in mammals (e.g., prostacyclins, eicosanoids, leukotrienes, prostaglandins). Additionally, a high intake of long-chain ω-3 PUFAs has cardiovascular protective effects (Dyerberg, J. et al., *Amer. J. Clin. Nutr.,* 28:958-966 (1975); Dyerberg, J. et al., *Lancet,* 2(8081):117-119 (Jul. 15, 1978); Shimokawa, H., *World Rev. Nutr. Diet,* 88:100-108 (2001); von Schacky, C. and Dyerberg, J., *World Rev. Nutr. Diet,* 88:90-99 (2001)). Numerous other studies document wide-ranging health benefits conferred by administration of ω-3 and/or ω-6 PUFAs against a variety of symptoms and diseases (e.g., asthma, psoriasis, eczema, diabetes, cancer).

Today, a variety of different hosts including plants, algae, fungi and yeast are being investigated as means for commercial PUFA production. Although the natural PUFA-producing abilities of the host organisms are sometimes specific to a given methodology, genetic engineering has also proven that the natural abilities of some hosts (even those natively limited to LA and ALA fatty acid production) can be substantially enhanced to produce high-levels of various long-chain ω-3/ω-6 PUFAs. Whether this effect is the result of natural abilities or recombinant technology, production of arachidonic acid (ARA; 20:4 ω-6), eicosapentaenoic acid (EPA; 20:5 ω-3) and docosahexaenoic acid (DHA; 22:6 ω-3) all require expression of either the Δ9 elongase/E8 desaturase pathway (which operates in some organisms, such as euglenoid species and which is characterized by the production of eicosadienoic acid [EDA; 20:2 ω-6] and/or eicosatrienoic acid [ETrA; 20:3 ω-3]) or the Δ6 desaturase/Δ6 elongase pathway (which is predominantly found in algae, mosses, fungi, nematodes and humans and which is characterized by the production of gamma-linoleic acid [GLA; 18:3 ω-6] and/or stearidonic acid [STA; 18:4 ω-3]) (FIG. 1).

For the purposes herein, the present application focuses on use of the Δ9 elongase/Δ8 desaturase pathway, and more specifically, on the use of Δ9 elongase enzymes. Most Δ9 elongase enzymes identified so far have the ability to convert both LA to EDA and ALA to ETrA (wherein DGLA and ETA are subsequently synthesized from EDA and ETrA, respectively, following reaction with a Δ8 desaturase; ARA and EPA are subsequently synthesized from DGLA and ETA, respectively, following reaction with a Δ5 desaturase; and, DHA synthesis requires subsequent expression of an additional $C_{20/22}$ elongase and a Δ4 desaturase).

In spite of the need for new methods for the production of ARA, EPA and DHA, few Δ9 elongase enzymes have been identified. For example, only a single Δ9 elongase is presently known prior to the Applicants' invention herein. Specifically, PCT Publications No. WO 2002/077213, No. WO 2005/083093, No. WO 2005/012316 and No. WO 2004/057001 describe a Δ9 elongase from *Isochrysis galbana* and its use (see also GenBank Accession No. AAL37626). Thus, there is need for the identification and isolation of additional genes encoding Δ9 elongases that will be suitable for heterologous expression in a variety of host organisms for use in the production of ω-3/ω-6 fatty acids.

Elongases which have been identified in the past differ in terms of the substrates upon which they act. They are present in both animals and plants. Those found in mammals can act upon saturated, monounsaturated and polyunsaturated fatty acids. However, those found in plants are specific for saturated and monounsaturated fatty acids. Thus, there is a need for a PUFA-specific elongase to produce PUFAs in plants.

The elongation process in plants involves a four-step process initiated by the crucial step of condensation of malonate and a fatty acid with release of a carbon dioxide molecule. The substrates in fatty acid elongation are CoA-thioesters. The condensation step is mediated by a 3-ketoacyl synthase, which is generally rate-limiting to the overall cycle of four reactions and provides some substrate specificity. The product of one elongation cycle regenerates a fatty acid that has been extended by two carbon atoms (Browse et al., *Trends in Biochemical Sciences,* 27(9):467-473 (September 2002); Napier, *Trends in Plant Sciences,* 7(2):51-54 (February 2002)).

Based on the utility of expressing Δ9 elongases in conjunction with Δ8 desaturases, there has also been considerable effort to identify and characterize Δ8 desaturases from various sources. Most efforts thus far have focused on the isolation and characterization of Δ8 desaturases from *Euglena gracilis*; and, several sequence variations of *E. gracilis* Δ8 desaturases have been reported (see, e.g., Wallis et al., *Arch. Biochem. and Biophys.,* 365(2):307-316 (May 1999); PCT Publication No. WO 2000/34439; U.S. Pat. No. 6,825,017; PCT Publication No. WO 2004/057001; U.S. application Ser. No. 11/166,003 filed Jun. 24, 2005 (PCT Publications No. WO 2006/012325 and No. WO 2006/012326; published Feb. 2, 2006)). More recently, PCT Publication No. WO 2005/103253 (published Apr. 22, 2005) discloses amino acid and nucleic acid sequences for a Δ8 desaturase enzyme from *Pavlova salina*. Sayanova et al. (*FEBS Lett.,* 580:1946-1952 (2006)) describes the isolation and characterization of a cDNA from the free living soil amoeba *Acanthamoeba castellanii* that, when expressed in *Arabidopsis*, encodes a $C_{20}$ Δ8 desaturase. Also, commonly owned, co-pending application having Provisional Application No. 60/795,810 (filed Apr. 28, 2006) discloses amino acid and nucleic acid sequences for a Δ8 desaturase enzyme from *Pavlova lutheri* (CCMP459), while commonly owned, co-pending application having U.S. Provisional Application No. 60/853,563 filed Oct. 23, 2006, discloses Δ8 desaturases from the euglenoids *Tetruetreptia pomquetensis* CCMP1491, *Eutreptiella* sp. CCMP389 and *Eutreptiella cf_gymnastica* CCMP1594.

The following commonly owned patent applications relate to the production of PUFAs in oleaginous yeasts (i.e., *Yar-*

*rowia lipolytica*), including: PCT Publication No. WO 2004/101757 and PCT Publication No. WO 2004/101753 (both published Nov. 25, 2004); U.S. application Ser. No. 11/265,761 (filed Nov. 2, 2005; corresponding to PCT Publication No. WO 2006/052870); U.S. application Ser. No. 11/264,784 (filed Nov. 1, 2005; corresponding to PCT Publication No. WO 2006/055322); and U.S. application Ser. No. 11/264,737 (filed Nov. 1, 2005; corresponding to PCT Publication No. WO 2006/052871).

Additionally, PCT Publication No. WO 2004/071467 (published Aug. 26, 2004) concerns the production of PUFAs in plants, while PCT Publication No. WO 2004/071178 (published Aug. 26, 2004) concerns annexin promoters and their use in expression of transgenes in plants; both are commonly owned and copending applications.

Applicants have solved the stated problem by isolating the genes encoding Δ9 elongase from *Euglena gracilis* and *Eutreptiella* sp. CCMP389.

SUMMARY OF THE INVENTION

The present invention relates to new genetic constructs encoding polypeptides having Δ9 elongase activity, and their use in plants, algae, bacteria, yeast and fungi for the production of PUFAs.

Accordingly the invention provides an isolated polynucleotide selected from the group consisting of:

(a) an isolated nucleic acid sequence comprising a nucleotide sequence encoding a polypeptide having Δ9 elongase activity, wherein the polypeptide has at least 70% amino acid identity, based on the Clustal V method of alignment, when compared to an amino acid sequence as set forth in SEQ ID NO:2 or SEQ ID NO:5;

(b) an isolated nucleic acid sequence comprising a nucleotide sequence encoding a polypeptide having Δ9 elongase activity, wherein the nucleotide sequence has at least 70% sequence identity, based on the BLASTN method of alignment, when compared to a nucleotide sequence as set forth in SEQ ID NO:1, SEQ ID NO:3, SEQ ID NO:4 or SEQ ID NO:6;

(c) an isolated nucleic acid sequence comprising a nucleotide sequence encoding a polypeptide having Δ9 elongase activity, wherein the nucleotide sequence hybridizes with a nucleotide sequence as set forth in SEQ ID NO:1, SEQ ID NO:3, SEQ ID NO:4 or SEQ ID NO:6 under the following stringent hybridization conditions: 0.1×SSC, 0.1% SDS, 65° C. and washed with 2×SSC, 0.1% SDS followed by 0.1×SSC, 0.1% SDS; or (d) a complement of the nucleotide sequence of (a), (b) or (c), wherein the complement and the nucleotide sequence consist of the same number of nucleotides and are 100% complementary.

Additionally invention provides polypeptides encoded by the isolated nucleic acid sequences of the invention. Specifically the invention provides a Δ9 elongase polypeptide wherein the amino acid sequence of the polypeptide is selected from the group consisting of:

(a) an amino acid sequence as set forth in SEQ ID NO:2 or SEQ ID NO:5; and (b) an amino acid sequence that differs from the amino acid sequences in (a) by at least one conservative amino acid substitution.

In another embodiment the invention provides host cells transformed with the isolated nucleic acid sequences of the invention, where preferred host cells are microbial species as for example algae, bacterial, yeast, oomycetes and fungi.

In another embodiment the invention provides a method for the production of eicosadienoic acid comprising:

a) providing an isolated transformed yeast host cell comprising:
  - i) an isolated polynucleotide sequence encoding a polypeptide having Δ9 elongase activity, selected from the group consisting of:
    - (1) an isolated nucleic acid sequence comprising a nucleotide sequence encoding a polypeptide having Δ9 elongase activity, wherein the polypeptide has at least 70% amino acid identity, based on the Clustal V method of alignment, when compared to an amino acid sequence as set forth in SEQ ID NO:2 or SEQ ID NO:5;
    - (2) an isolated nucleic acid sequence comprising a nucleotide sequence encoding a polypeptide having Δ9 elongase activity, wherein the nucleotide sequence hybridizes with a nucleotide sequence as set forth in SEQ ID NO:1, SEQ ID NO:3, SEQ ID NO:4 or SEQ ID NO:6 under the following stringent hybridization conditions: 0.1×SSC, 0.1% SDS, 65° C. and washed with 2×SSC, 0.1% SDS followed by 0.1×SSC, 0.1% SDS; and
  - (ii) a source of linoleic acid;

b) growing the yeast host cell of step (a) under conditions wherein the nucleic acid sequence encoding the Δ9 elongase polypeptide is expressed and the linoleic acid is converted to eicosadienoic acid; and, c) optionally recovering the eicosadienoic acid of step (b).

In an alternate embodiment the invention provides a method for the production of eicosatrienoic acid comprising:

a) providing an isolated transformed yeast host cell comprising:
  - i) an isolated polynucleotide sequence encoding a polypeptide having Δ9 elongase activity, selected from the group consisting of:
    - (1) an isolated nucleic acid sequence comprising a nucleotide sequence encoding a polypeptide having Δ9 elongase activity, wherein the polypeptide has at least 70% amino acid identity, based on the Clustal V method of alignment, when compared to an amino acid sequence as set forth in SEQ ID NO:2 or SEQ ID NO:5;
    - (2) an isolated nucleic acid sequence comprising a nucleotide sequence encoding a polypeptide having Δ9 elongase activity, wherein the nucleotide sequence hybridizes with a nucleotide sequence as set forth in SEQ ID NO:1, SEQ ID NO:3, SEQ ID NO:4 or SEQ ID NO:6 under the following stringent hybridization conditions: 0.1×SSC, 0.1% SDS, 65° C. and washed with 2×SSC, 0.1% SDS followed by 0.1×SSC, 0.1% SDS; and
  - (ii) a source of α-linolenic acid;

b) growing the host cell of step (a) under conditions wherein the nucleic acid sequence encoding the Δ9 elongase polypeptide is expressed and the α-linolenic acid is converted to eicosatrienoic acid; and, c) optionally recovering the eicosatrienoic acid of step (b).

In another embodiment the invention provides microbial oils produced by the transformed hosts of the invention.

In a separate embodiment the invention provides a food product comprising the microbial oils of the invention.

In another embodiment the invention provides an animal feed comprising the oils of the invention.

BIOLOGICAL DEPOSITS

The following plasmids have been deposited with the American Type Culture Collection (ATCC), 10801 University Boulevard, Manassas, Va. 20110-2209, and bear the following designations, Accession Numbers and dates of deposit (Table 1).

TABLE 1

ATCC Deposits

| Plasmid | Accession Number | Date of Deposit |
|---|---|---|
| pKR72 | PTA-6019 | May 28, 2004 |
| pKR275 | PTA-4989 | Jan. 30, 2003 |
| pKR585 | PTA-6279 | Nov. 4, 2004 |
| pKR578 | PTA-6280 | Nov. 4, 2004 |

BRIEF DESCRIPTION OF THE DRAWINGS AND SEQUENCE LISTINGS

FIG. 1 illustrates the ω-3/ω-6 fatty acid biosynthetic pathway providing for the conversion of myristic acid through various intermediates to DHA.

FIG. 2 shows a Clustal V alignment (with default parameters) of the amino acid sequence of the *Euglena gracilis* Δ9 elongase of the instant invention (SEQ ID NO:2), the amino acid sequence of the *Eutreptiella* sp. CCMP389 Δ9 elongase of the instant invention (SEQ ID NO:5) and the amino acid sequence of the long-chain PUFA elongation enzyme from *Isochrysis galbana* (NCBI Accession No. AAL37626 (GI 17226123)) (SEQ ID NO:8).

FIG. 4 shows a Clustal V alignment (with default parameters) of the amino acid sequence of the *Euglena gracilis* Δ9 elongase of the instant invention (SEQ ID NO:2) and the amino acid sequence of the long-chain PUFA elongation enzyme from *Isochrysis galbana* (NCBI Accession No. AAL37626 (GI 17226123)) (SEQ ID NO:8).

FIG. 6 are the results of functional analysis of the *Euglena gracilis* Δ9 elongase (EgD9e) in *Saccharomyces cerevisiae*.

Figure 10:
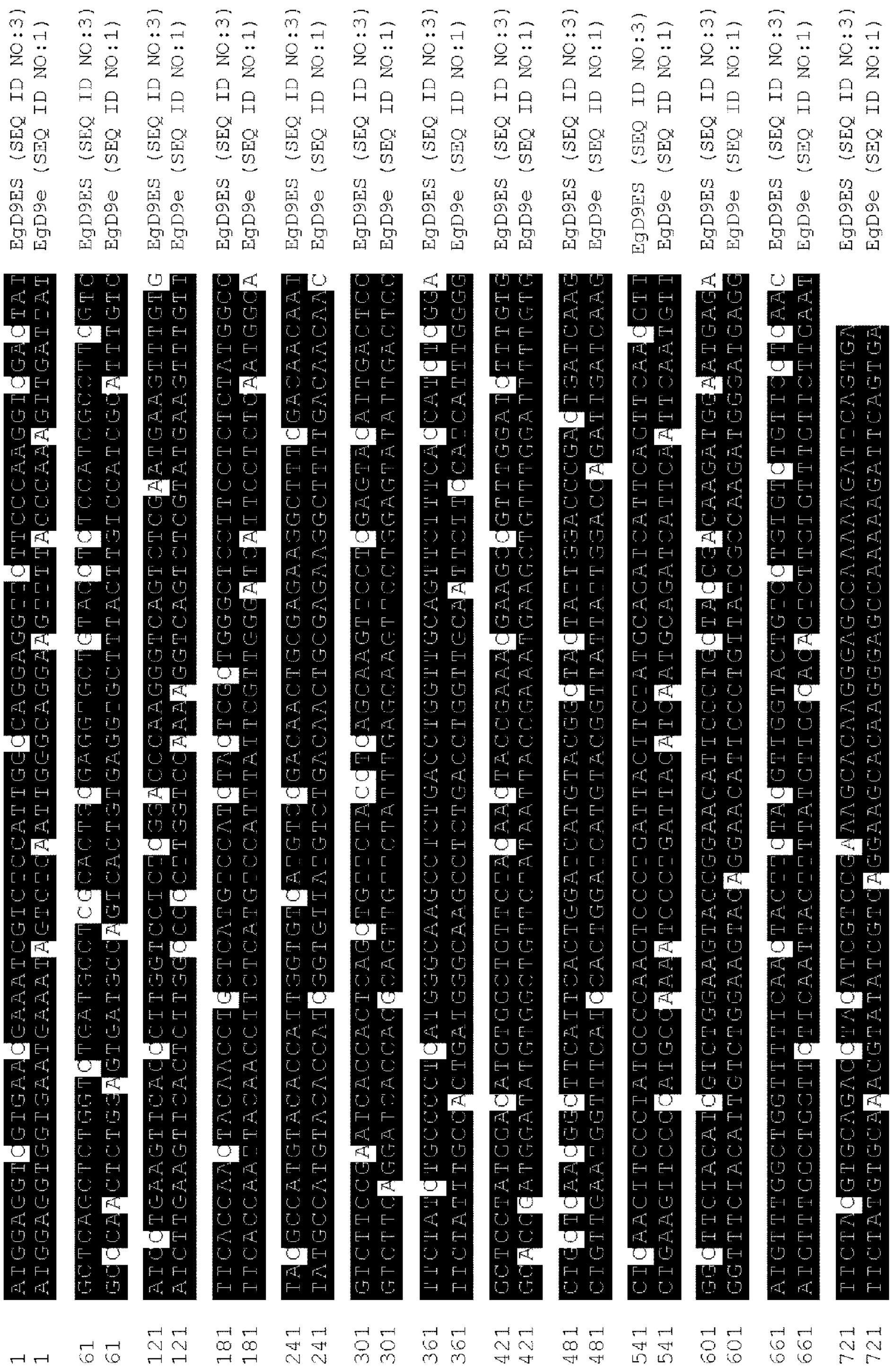

FIG. 10 shows a comparison of the DNA sequences of the *Euglena gracilis* Δ9 elongase gene (EgD9e; SEQ ID NO:1) and the synthetic gene (EgD9eS; SEQ ID NO:3) codon-optimized for expression in *Yarrowia lipolytica*.

Figure 11:
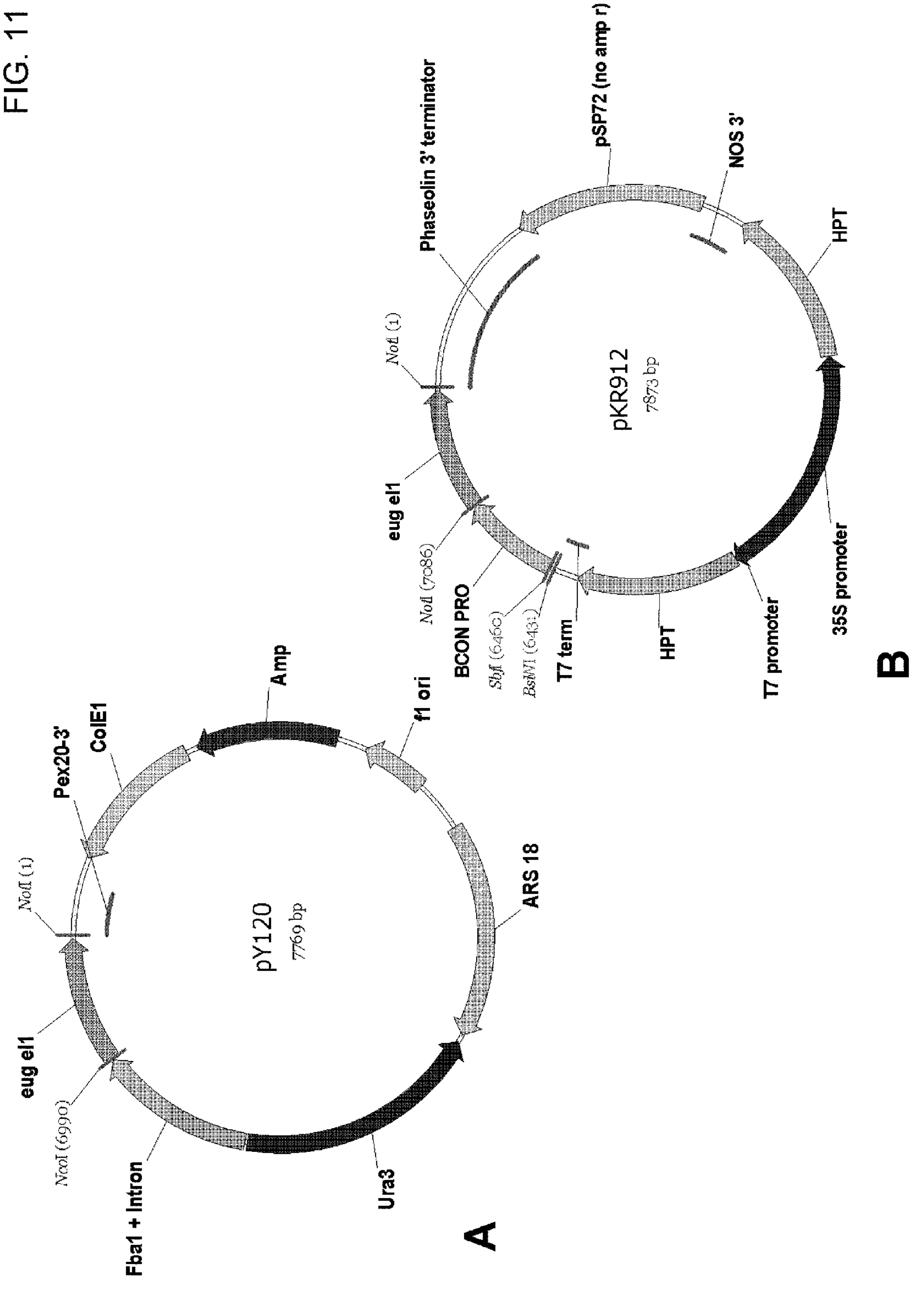

FIG. 11A is a map of plasmid pY120, while FIG. 11B is a map of plasmid pKR912.

Figure 12:
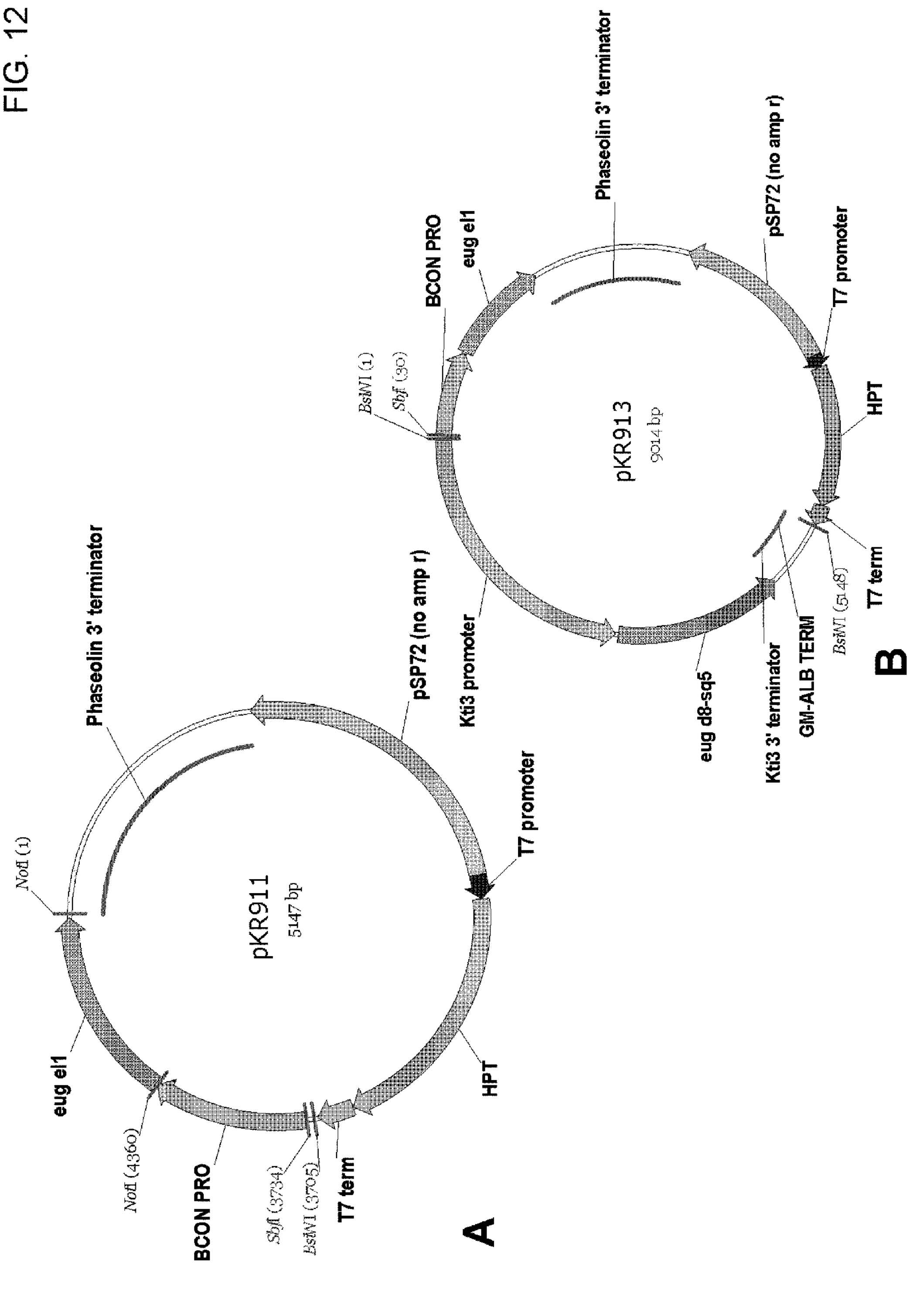

FIG. 12A is a map of plasmid pKR911, while FIG. 12B is a map of plasmid pKR913.

Figure 13:
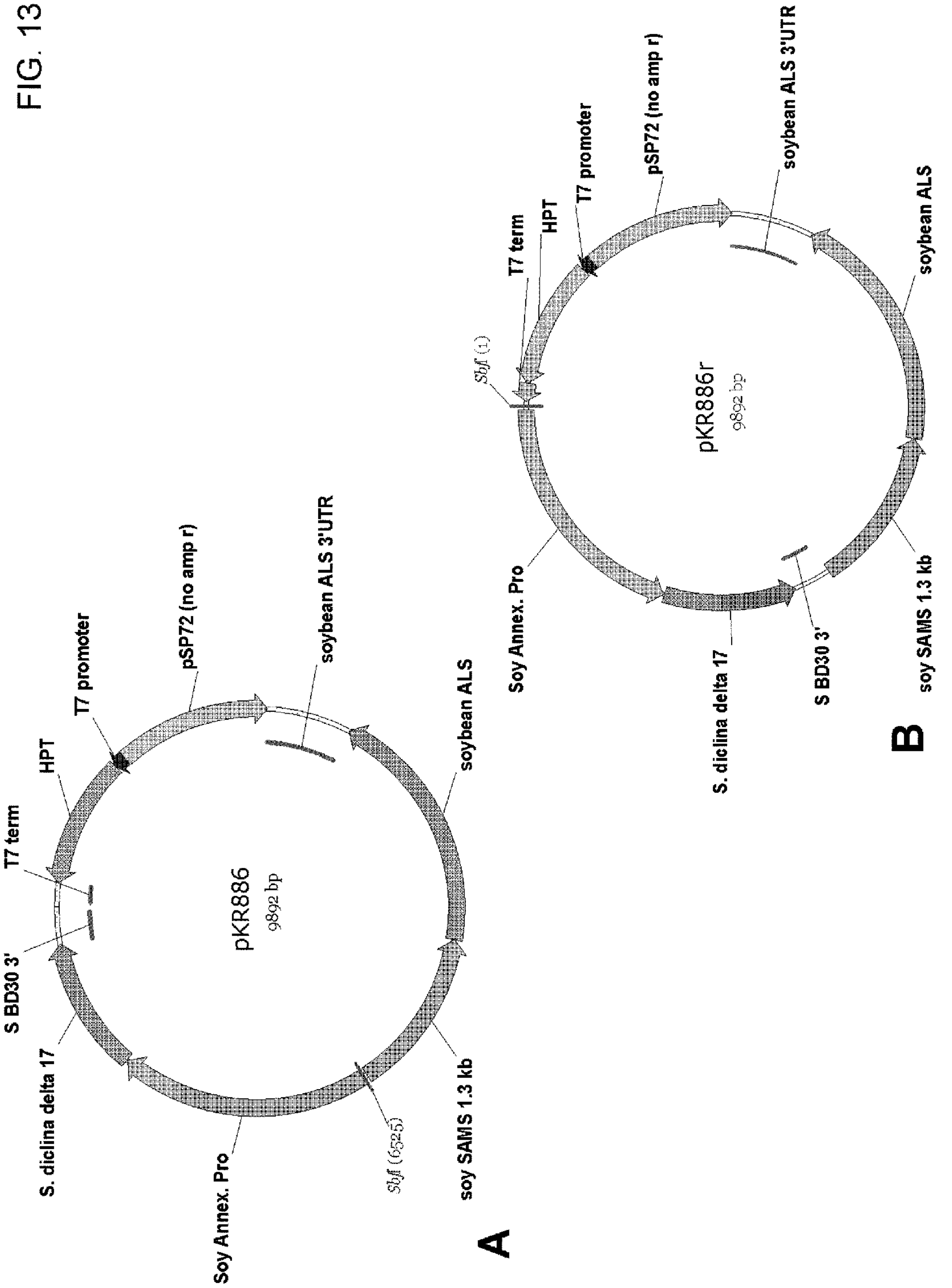

FIG. 13A is a map of plasmid pKR886, while FIG. 13B is a map of plasmid pKR886r.

Figure 14:

FIG. 14A is a map of plasmid pKR669, while FIG. 14B is a map of plasmid pKR873.

Figure 15:
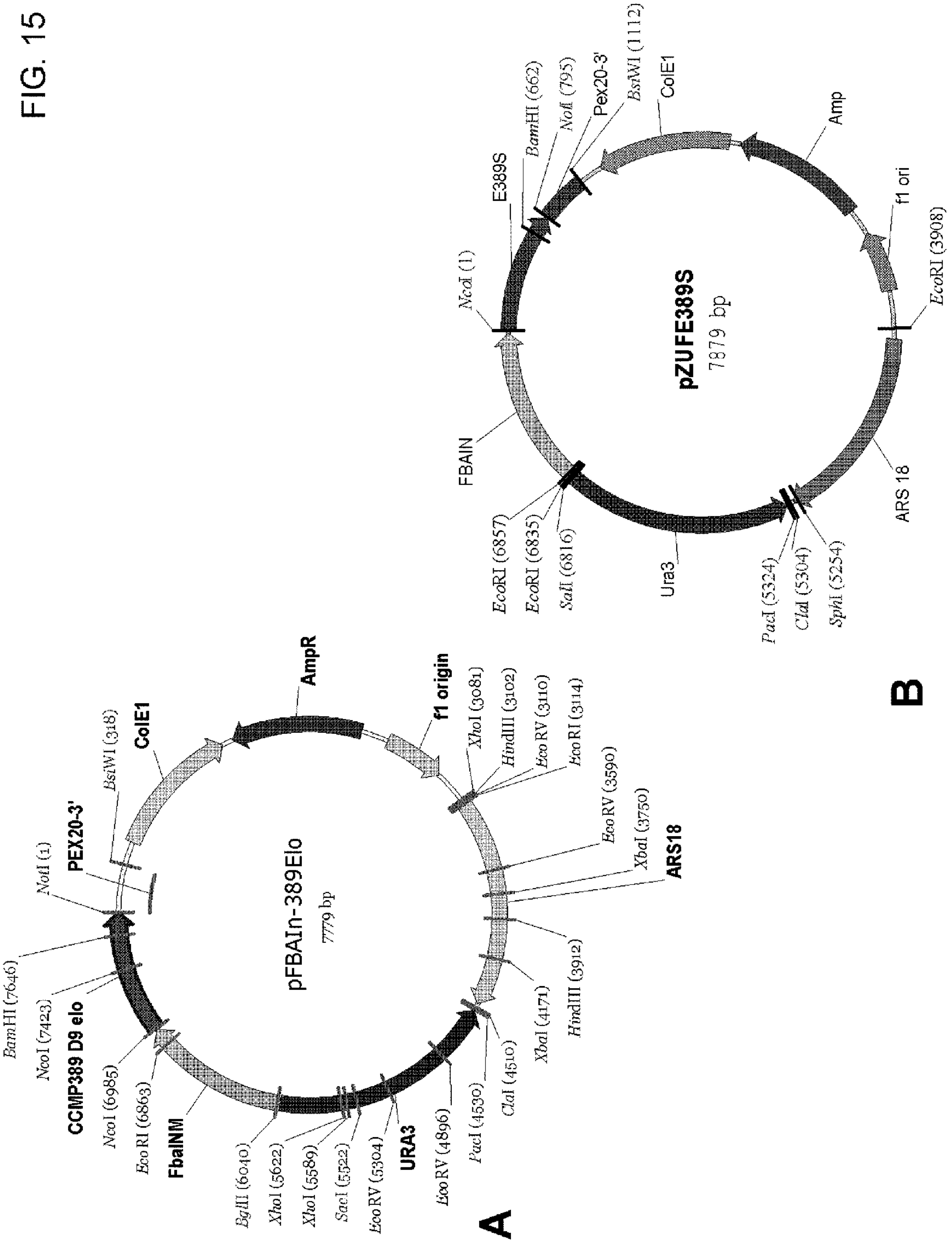

FIG. 15A is a plasmid map of pFBAIN-389Elo, while FIG. 15B is a plasmid map of pZUFE389S.

Figure 16:
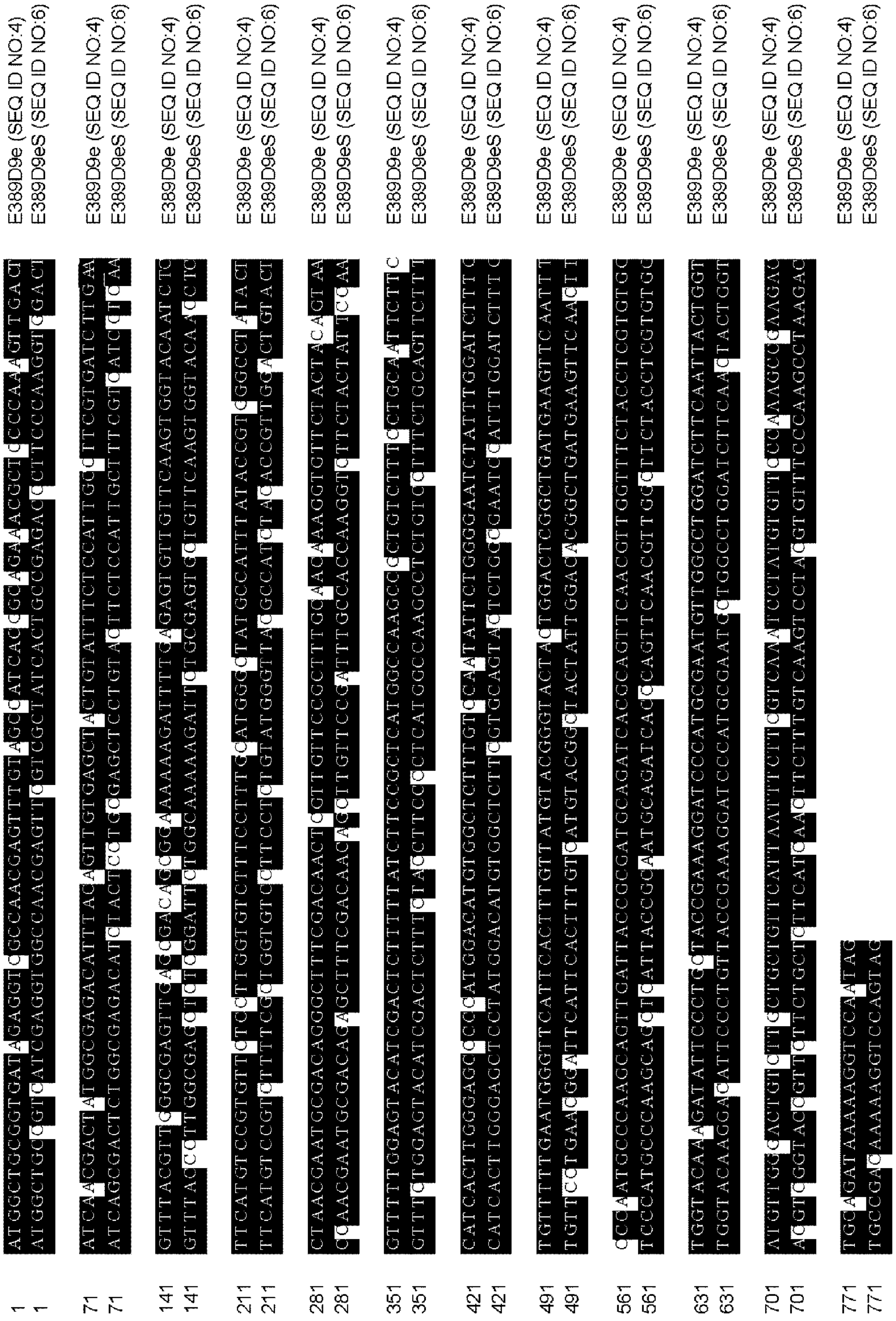

FIG. 16 shows a comparison of the DNA sequences of the *Eutreptiella* sp. CCMP389 Δ9 elongase gene (E389D9e; SEQ ID NO:4) and the synthetic gene (E389D9eS; SEQ ID NO:6) codon-optimized for expression in *Y. lipolytica*.

The invention can be more fully understood from the following detailed description and the accompanying drawings and Sequence Listing, which form a part of this application.

The following sequences comply with 37 C.F.R. §1.821-1.825 ("Requirements for patent applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

A Sequence Listing is provided herewith on Compact Disk. The contents of the Compact Disk containing the Sequence Listing are hereby incorporated by reference in compliance with 37 CFR 1.52(e). The Compact Disks are submitted in triplicate and are identical to one another. The disks are labeled "Copy 1—Sequence Listing", "Copy 2—Sequence Listing", and CRF. The disks contain the following file: CL3600_10.26.2006.5T25 having the following size: 483,000 bytes and which was created Nov. 15, 2006.

SEQ ID NOs:1-17, 21, 22, 45-48, 51-61, 68-71, 76-79, 81-93, 96-102 and 118-129 are ORFs encoding genes or proteins (or portions thereof), or plasmids, as identified in Table 2.

TABLE 2

Summary Of Nucleic Acid And Protein SEQ ID Numbers

| Description and Abbreviation | Nucleic acid SEQ ID NO. | Protein SEQ ID NO. |
|---|---|---|
| *Euglena gracilis* Δ9 elongase (EgD9e; clone eeg1c.pk001.n5.f)) | 1 (777 bp) | 2 (258 AA) |
| Synthetic Δ9 elongase, derived from *Euglena gracilis*, codon-optimized for expression in *Yarrowia lipolytica* (EgD9eS) | 3 (777 bp) | 2 (258 AA) |
| *Eutreptiella* sp. CCMP389 Δ9 elongase (E389D9e) | 4 (792 bp) | 5 (263 AA) |
| Synthetic Δ9 elongase, derived from *Eutreptiella* sp. CCMP389, codon-optimized for expression in *Yarrowia lipolytica* (E389D9eS) | 6 (792 bp) | 5 (263 AA) |
| *Isochrysis galbana* Δ9 elongase (IgD9e; NCBI Accession No. AAL37626 [GI 17226123], locus AAL37626, CDS AF390174; GenBank Accession No. AF390174) (CDS = nucleotides 2-793) | 7 (1064 bp) | 8 (263 AA) |
| Synthetic Δ9 elongase, derived from *Isochrysis galbana*, codon-optimized for expression in *Yarrowia lipolytica* (IgD9eS) (equivalent to coding sequence of SEQ ID NOs: 51 and 50 in PCT Publication No. WO 2006/052870) | 9 (792 bp) | 8 (263 AA) |
| *Euglena gracilis* EgD9e-- 5' sequence of the cDNA insert from clone eeg1c.pk001.n5.f. | 10 (757 bp) | — |
| *Euglena gracilis* EgD9e-- 3' sequence of the cDNA insert from clone eeg1c.pk001.n5.f. | 11 (774 bp) | — |
| *Euglena gracilis* EgD9e--sequence aligned from SEQ ID NO: 10 and SEQ ID NO: 11 (full cDNA sequence excluding polyA tail) | 12 (1201 bp) | — |
| *Eutreptiella* sp. CCMP389 E389D9e-internal cDNA fragment | 13 (200 bp) | — |
| *Eutreptiella* sp. CCMP389 E389D9e -5' cDNA fragment #1 | 14 (406 bp) | — |
| *Eutreptiella* sp. CCMP389 E389D9e -5' cDNA fragment #2 | 15 (197 bp) | — |
| *Eutreptiella* sp. CCMP389 E389D9e -3' cDNA fragment | 16 (920 bp) | — |

TABLE 2-continued

Summary Of Nucleic Acid And Protein SEQ ID Numbers

| Description and Abbreviation | Nucleic acid SEQ ID NO. | Protein SEQ ID NO. |
|---|---|---|
| *Eutreptiella* sp. CCMP389 E389D9e-complete assembled contig | 17 (1504 bp) | — |
| Plasmid pY119 | 21 (8306 bp) | — |
| Plasmid pDMW263 | 22 (9472 bp) | — |
| Plasmid pY115 | 45 (7783 bp) | — |
| Plasmid pDMW237 | 46 (7879 bp) | — |
| Plasmid pBY1 | 47 (8704 bp) | — |
| Plasmid pBY2 | 48 (8145 bp) | — |
| Plasmid pBY1-FAE | 51 (7877 bp) | — |
| Plasmid pZuFmEgD9E | 52 (7771 bp) | — |
| Plasmid pZuFmEgD9ES | 53 (7769 bp) | — |
| Plasmid pY120 | 54 (7769 bp) | — |
| Plasmid pKR72 | 55 (7085 bp) | — |
| Plasmid pKR912 | 56 (7873 bp) | — |
| Plasmid pKS102 | 57 (2540 bp) | — |
| Plasmid pKR197 | 58 (4359 bp) | — |
| Plasmid pKR911 | 59 (5147 bp) | — |
| *Euglena gracilis* Δ8 desaturase (EgD8) (equivalent to coding sequence of SEQ ID NOs: 1 and 2 in PCT Publications No. WO 2006/012325 and No. WO 2006/012326 [US2005-0287652-A1]) | 60 (1266 bp) | 61 (421 AA) |
| Synthetic Δ8 desaturase, derived from *Euglena gracilis*, codon-optimized for expression in *Yarrowia lipolytica* (EgD8S) (equivalent to SEQ ID NOs: 112 and 113 in PCT Publication No. WO 2006/012326) | 68 (1272 bp) | 69 (422 AA) |
| Plasmid pKS121 | 70 (4826 bp) | — |
| Plasmid pKR457 | 71 (5252 bp) | — |
| Plasmid pKR680 | 76 (6559 bp) | — |
| Plasmid pKR913 | 77 (9014 bp) | — |
| *Mortierella alpina* Δ5 desaturase | 78 (1482 bp) | 79 (446 AA) |
| Plasmid pKR767 | 81 (5561 bp) | — |
| Plasmid pKR328 | 82 (8671 bp) | — |
| Plasmid pKR886 | 83 (9892 bp) | — |
| Plasmid pKR886r | 84 (9892 bp) | — |
| Plasmid pKR271 | 85 (6021 bp) | — |
| Plasmid pKR226 | 86 (6524 bp) | — |
| Plasmid pKR275 | 87 (13,514 bp) | — |
| Plasmid pKR329 | 88 (12,323 bp) | — |
| Plasmid pKR585 | 89 (12,456 bp) | — |
| Plasmid pKR578 | 90 (9088 bp) | — |
| Plasmid pKR667 | 91 (10,309 bp) | — |
| Plasmid pKR873 | 92 (12,403 bp) | — |
| Plasmid pKR132 | 93 (3983 bp) | — |
| Plasmid pKR160 | 96 (4268 bp) | — |
| Plasmid pKR124 | 97 (4990 bp) | — |
| Plasmid pKR163 | 98 (3982 bp) | — |
| Plasmid pY34 | 99 (8878 bp) | — |
| Plasmid pKR863 | 100 (5207 bp) | — |
| Plasmid pKR869 | 101 (9035 bp) | — |
| Plasmid pKR270 | 102 (5108 bp) | — |
| Plasmid pFBAIN-MOD-1 | 118 (7222 bp) | — |
| Plasmid pFBAIN-389Elo | 119 (7779 bp) | — |
| Plasmid pE389S | 120 (3511 bp) | — |
| Plasmid pZUF17 | 121 (8165 bp) | — |
| Plasmid pZUFE389S | 122 (7879 bp) | — |
| Δ9 Elongase Motif #1 | — | 123 |
| Δ9 Elongase Motif #2 | — | 124 |
| Δ9 Elongase Motif #3 | — | 125 |
| Δ9 Elongase Motif #4 | — | 126 |
| Δ9 Elongase Motif #5 | — | 127 |
| Δ9 Elongase Motif #6 | — | 128 |
| Δ9 Elongase Motif #7 | — | 129 |

SEQ ID NO:18 is the M13F universal primer used for sequencing the *Euglena gracilis* cDNA library eeg1c.

SEQ ID NOs:19 and 20 correspond to primers oEugEL1-1 and oEugEL1-2, respectively, used for amplifying EgD9e from clone eeg1c.pk001.n5.f.

SEQ ID NOs:23-38 correspond to primers IL3-1A, IL3-1B, IL3-2A, IL3-2B, IL3-3A, IL3-3B, IL3-4A, IL3-4B, IL3-5A, IL3-5B, IL3-6A, IL3-6B, IL3-7A, IL3-7B, IL3-8A and IL3-8B, respectively, used for amplification of IgD9eS.

SEQ ID NOs:39-42 correspond to primers IL3-1F, IL3-4R, IL3-5F and IL3-8R, respectively, used for amplification of IgD9eS.

SEQ ID NO:43 is the 417 bp NcoI/PstI fragment from pT9(1-4).

SEQ ID NO:44 is the 377 bp PstI/Not1 fragment from pT9(5-8).

SEQ ID NOs:49 and 50 correspond to primers ig-s and ig-as, respectively, used for amplifying IgD9eS from vector pY115.

SEQ ID NOs:62 and 63 correspond to primers Eg5-1 and Eg3-3, respectively, used for amplifying EgD8 from cDNA.

SEQ ID NOs:64-67 correspond to primers T7, M13-28Rev, Eg3-2 and Eg5-2, respectively, used for sequencing EgD8.

SEQ ID NO:72 is the sequence of the KTi cassette 5' end multiple cloning site (MCS) for pKR457.

SEQ ID NO:73 is the sequence of the KTi cassette 3' end multiple cloning site (MCS) for pKR457 including the soy albumin transcription 3' terminator.

SEQ ID NOs:74 and 75 correspond to primers oSalb-12 and oSalb-13, respectively, used for amplifying the soy albumin transcription terminator from soy genomic DNA.

SEQ ID NO:80 corresponds to restriction sites added to pKR287 to produce pKR767.

SEQ ID NOs:94 and 95 correspond to primers oSAlb-9 and oSAlb-2, respectively, used for creation of restriction sites during production of pKR160.

SEQ ID NOs:103-105 correspond to SMART™ IV oligonucleotide primer, CDSIII/3' PCR primer and 5'-PCR primer, respectively, used for *Eutreptiella* sp. CCMP389 cDNA synthesis.

SEQ ID NO:106 is the nucleotide sequence of degenerate primer EuEF3, which encodes the peptide set forth in SEQ ID NO:107. Similarly, SEQ ID NO:108 is the nucleotide sequence of degenerate primer EuER3, which encodes the peptide set forth in SEQ ID NO:109.

SEQ ID NOs:110-113 correspond to primers 389Elo-5-1, 389Elo-5-2, DNR CDS 5'-2 and 389Elo-5-4, respectively, used for PCR amplification of the 5'-end of cDNA encoding E389D9e.

SEQ ID NOs:114 and 115 correspond to primers 389Elo-3-1 and 389Elo-3-2, respectively, used for PCR amplification of the 3'-end of cDNA encoding E389D9e.

SEQ ID NOs:116 and 117 correspond to primers 389ELO-F and 389ELO-R1, respectively, used for amplification of the full length cDNA encoding E389D9e.

DETAILED DESCRIPTION OF THE INVENTION

All patents, patent applications, and publications cited herein are incorporated by reference in their entirety. This specifically includes the following commonly owned and copending applications: U.S. patent application Ser. No. 10/840,478, Ser. No. 10/840,579 and Ser. No. 10/840,325 (filed May 6, 2004), U.S. patent application Ser. No. 10/869,630 (filed Jun. 16, 2004), U.S. patent application Ser. No. 10/882,760 (filed Jul. 1, 2004), U.S. patent application Ser. No. 10/985,109 and Ser. No. 10/985,691 (filed Nov. 10, 2004), U.S. patent application Ser. No. 10/987,548 (filed Nov. 12, 2004), U.S. patent application Ser. No. 11/024,545 and Ser. No. 11/024,544 (filed Dec. 29, 2004), U.S. patent application Ser. No. 11/166,993 (filed Jun. 24, 2005), U.S. patent application Ser. No. 11/183,664 (filed Jul. 18, 2005), U.S. patent application Ser. No. 11/185,301 (filed Jul. 20, 2005), U.S. patent application Ser. No. 11/190,750 (filed Jul. 27, 2005), U.S. patent application Ser. No. 11/198,975 (filed Aug. 8, 2005), U.S. patent application Ser. No. 11/225,354 (filed Sep. 13, 2005), U.S. patent application Ser. No. 11/251,466 (filed Oct. 14, 2005), U.S. patent application Ser. No. 11/254,173 and Ser. No. 11/253,882 (filed Oct. 19, 2005), U.S. patent application Ser. No. 11/264,784 and Ser. No. 11/264,737 (filed Nov. 1, 2005), U.S. patent application Ser. No. 11/265,761 (filed Nov. 2, 2005), U.S. Patent Application No. 60/739,989 (filed Nov. 23, 2005), U.S. Patent Application No. 60/795,810 (filed Apr. 28, 2006), U.S. Patent Application No. 60/793,575 (filed Apr. 20, 2006), U.S. Patent Application No. 60/796,637 (filed May 2, 2006), U.S. Patent Application No. 60/801,172 (filed May 17, 2006), U.S. Patent Application No. 60/801,119 (filed May 17, 2006), U.S. Patent Application No. 60/853,563 (filed Oct. 23, 2006), U.S. Patent Application No. 60/855,177 (filed Oct. 30, 2006). This additionally includes the following commonly owned and copending applications: U.S. patent application Ser. No. 10/776,311, concerning the production of PUFAs in plants; and, U.S. patent application Ser. No. 10/776,889, concerning annexin promoters and their use in expression of transgenes in plants.

The invention provides novel *Euglena gracilis* and *Eutreptiella* sp. CCMP389 Δ9 elongase enzymes and genes encoding the same that may be used for the manipulation of biochemical pathways for the production of healthful PUFAs.

PUFAs, or derivatives thereof, made by the methodology disclosed herein can be used as dietary substitutes, or supplements and infant formulas, and for patients undergoing intravenous feeding or for preventing or treating malnutrition. Alternatively, the purified PUFAs (or derivatives thereof) may be incorporated into cooking oils, fats or margarines formulated so that in normal use the recipient would receive the desired amount for dietary supplementation. The PUFAs may also be incorporated into infant formulas, nutritional supplements or other food products and may find use as anti-inflammatory or cholesterol lowering agents. Optionally, the compositions may be used for pharmaceutical use (human or veterinary).

DEFINITIONS

In the context of this disclosure, a number of terms and abbreviations are used. The following definitions are provided.

"Open reading frame" is abbreviated ORF.

"Polymerase chain reaction" is abbreviated PCR.

"American Type Culture Collection" is abbreviated ATCC.

"Polyunsaturated fatty acid(s)" is abbreviated PUFA(s).

"Triacylglycerols" are abbreviated TAGs.

The term "invention" or "present invention" as used herein is not meant to be limiting to any one specific embodiment of the invention but applies generally to any and all embodiments of the invention as described in the claims and specification.

The term "fatty acids" refers to long-chain aliphatic acids (alkanoic acids) of varying chain lengths, from about $C_{12}$ to $C_{22}$ (although both longer and shorter chain-length acids are known). The predominant chain lengths are between $C_{16}$ and $C_{22}$. Additional details concerning the differentiation between "saturated fatty acids" versus "unsaturated fatty acids", "monounsaturated fatty acids" versus "polyunsaturated fatty acids" (or "PUFAs"), and "omega-6 fatty acids" (ω-6 or n-6) versus "omega-3 fatty acids" (ω-3 or n-3) are provided in PCT Publication No. WO 2004/101757.

Fatty acids are described herein by a simple notation system of "X:Y", wherein X is the number of carbon (C) atoms in the particular fatty acid and Y is the number of double bonds. The number following the fatty acid designation indicates the position of the double bond from the carboxyl end of the fatty acid with the "c" affix for the cis-configuration of the double bond [e.g., palmitic acid (16:0), stearic acid (18:0), oleic acid (18:1, 9c), petroselinic acid (18:1, 6c), LA (18:2, 9c, 12c), GLA (18:3, 6c, 9c, 12c) and ALA (18:3, 9c, 12c, 15c)]. Unless otherwise specified 18:1, 18:2 and 18:3 refer to oleic, LA and ALA fatty acids. If not specifically written as otherwise, double bonds are assumed to be of the cis configuration. For instance, the double bonds in 18:2 (9,12) would be assumed to be in the cis configuration.

Nomenclature used to describe PUFAs in the present disclosure is shown below in Table 3. In the column titled "Shorthand Notation", the omega-reference system is used to indicate the number of carbons, the number of double bonds and the position of the double bond closest to the omega carbon, counting from the omega carbon (which is numbered 1 for this purpose). The remainder of the Table summarizes the common names of ω-3 and ω-6 fatty acids and their precursors, the abbreviations that will be used throughout the remainder of the specification, and each compounds' chemical name.

TABLE 3

Nomenclature of Polyunsaturated Fatty Acids And Precursors

| Common Name | Abbreviation | Chemical Name | Shorthand Notation |
|---|---|---|---|
| Myristic | — | tetradecanoic | 14:0 |
| Palmitic | Palmitate | hexadecanoic | 16:0 |
| Palmitoleic | — | 9-hexadecenoic | 16:1 |
| Stearic | — | octadecanoic | 18:0 |
| Oleic | — | cis-9-octadecenoic | 18:1 |
| Linoleic | LA | cis-9,12-octadecadienoic | 18:2 ω-6 |
| Gamma-linolenic | GLA | cis-6,9,12-octadecatrienoic | 18:3 ω-6 |
| Eicosadienoic | EDA | cis-11,14-eicosadienoic | 20:2 ω-6 |
| Dihomo-gamma-linolenic | DGLA | cis-8,11,14-eicosatrienoic | 20:3 ω-6 |
| Sciadonic | SCI | cis-5,11,14-eicosatrienoic | 20:3b ω-6 |
| Arachidonic | ARA | cis-5,8,11,14-eicosatetraenoic | 20:4 ω-6 |
| Alpha-linolenic | ALA | cis-9,12,15-octadecatrienoic | 18:3 ω-3 |
| Stearidonic | STA | cis-6,9,12,15-octadecatetraenoic | 18:4 ω-3 |
| Eicosatrienoic | ETrA | cis-11,14,17-eicosatrienoic | 20:3 ω-3 |
| Eicosatetraenoic | ETA | cis-8,11,14,17-eicosatetraenoic | 20:4 ω-3 |
| Juniperonic | JUP | cis-5,11,14,17-eicosatrienoic | 20:4b ω-3 |
| Eicosapentaenoic | EPA | cis-5,8,11,14,17-eicosapentaenoic | 20:5 ω-3 |
| Docosapentaenoic | DPA | cis-7,10,13,16,19-docosapentaenoic | 22:5 ω-3 |
| Docosahexaenoic | DHA | cis-4,7,10,13,6,19-docosahexaenoic | 22:6 ω-3 |

The term "essential fatty acid" refers to a particular PUFA that an organism must ingest in order to survive, being unable to synthesize the particular essential fatty acid de novo. For example, mammals can not synthesize the essential fatty acid LA. Other essential fatty acids include, but are not limited to, GLA, DGLA, ARA, EPA and DHA.

The term "fat" refers to a lipid substance that is solid at 25° C. and usually saturated.

The term "oil" refers to a lipid substance that is liquid at 25° C. and usually polyunsaturated. PUFAs are found in the oils of some algae, oleaginous yeasts and filamentous fungi. "Microbial oils" or "single cell oils" are those oils naturally produced by microorganisms during their lifespan.

The terms "triacylglycerol", "oil" and "TAGs" refer to neutral lipids composed of three fatty acyl residues esterified to a glycerol molecule (and such terms will be used interchangeably throughout the present disclosure herein). Such oils can contain long-chain PUFAs, as well as shorter saturated and unsaturated fatty acids and longer chain saturated fatty acids. Thus, "oil biosynthesis" generically refers to the synthesis of TAGs in the cell.

"Percent (%) PUFAs in the total lipid and oil fractions" refers to the percent of PUFAs relative to the total fatty acids in those fractions. The term "total lipid fraction" or "lipid fraction" both refer to the sum of all lipids (i.e., neutral and polar) within an oleaginous organism, thus including those lipids that are located in the phosphatidylcholine (PC) fraction, phosphatidyletanolamine (PE) fraction and triacylglycerol (TAG or oil) fraction. However, the terms "lipid" and "oil" will be used interchangeably throughout the specification.

The terms "conversion efficiency" and "percent substrate conversion" refer to the efficiency by which a particular enzyme (e.g., a desaturase) can convert substrate to product. The conversion efficiency is measured according to the following formula: ([product]/[substrate+product])*100, where 'product' includes the immediate product and all products in the pathway derived from it.

A metabolic pathway, or biosynthetic pathway, in a biochemical sense, can be regarded as a series of chemical reactions occurring within a cell, catalyzed by enzymes, to achieve either the formation of a metabolic product to be used or stored by the cell, or the initiation of another metabolic pathway (then called a flux generating step). Many of these pathways are elaborate, and involve a step by step modification of the initial substance to shape it into a product having the exact chemical structure desired.

The term "PUFA biosynthetic pathway" refers to a metabolic process that converts oleic acid to LA, EDA, GLA, DGLA, ARA, ALA, STA, ETrA, ETA, EPA, DPA and DHA. This process is well described in the literature (e.g., see PCT Publications No. WO 2005/003322 and No. WO 2006/052870). Simplistically, this process involves elongation of the carbon chain through the addition of carbon atoms and desaturation of the molecule through the addition of double bonds, via a series of special desaturation and elongation enzymes (i.e., "PUFA biosynthetic pathway enzymes") present in the endoplasmic reticulum membrane. More specifically, "PUFA biosynthetic pathway enzyme" refers to any of the following enzymes (and genes which encode said enzymes) associated with the biosynthesis of a PUFA, including: a Δ4 desaturase, a Δ5 desaturase, a Δ6 desaturase, a Δ12 desaturase, a Δ15 desaturase, a Δ17 desaturase, a Δ9 desaturase, a Δ8 desaturase, a Δ9 elongase, a $C_{14/16}$ elongase, a $C_{16/18}$ elongase, a $C_{18/20}$ elongase and/or a $C_{20/22}$ elongase.

Figure 1:
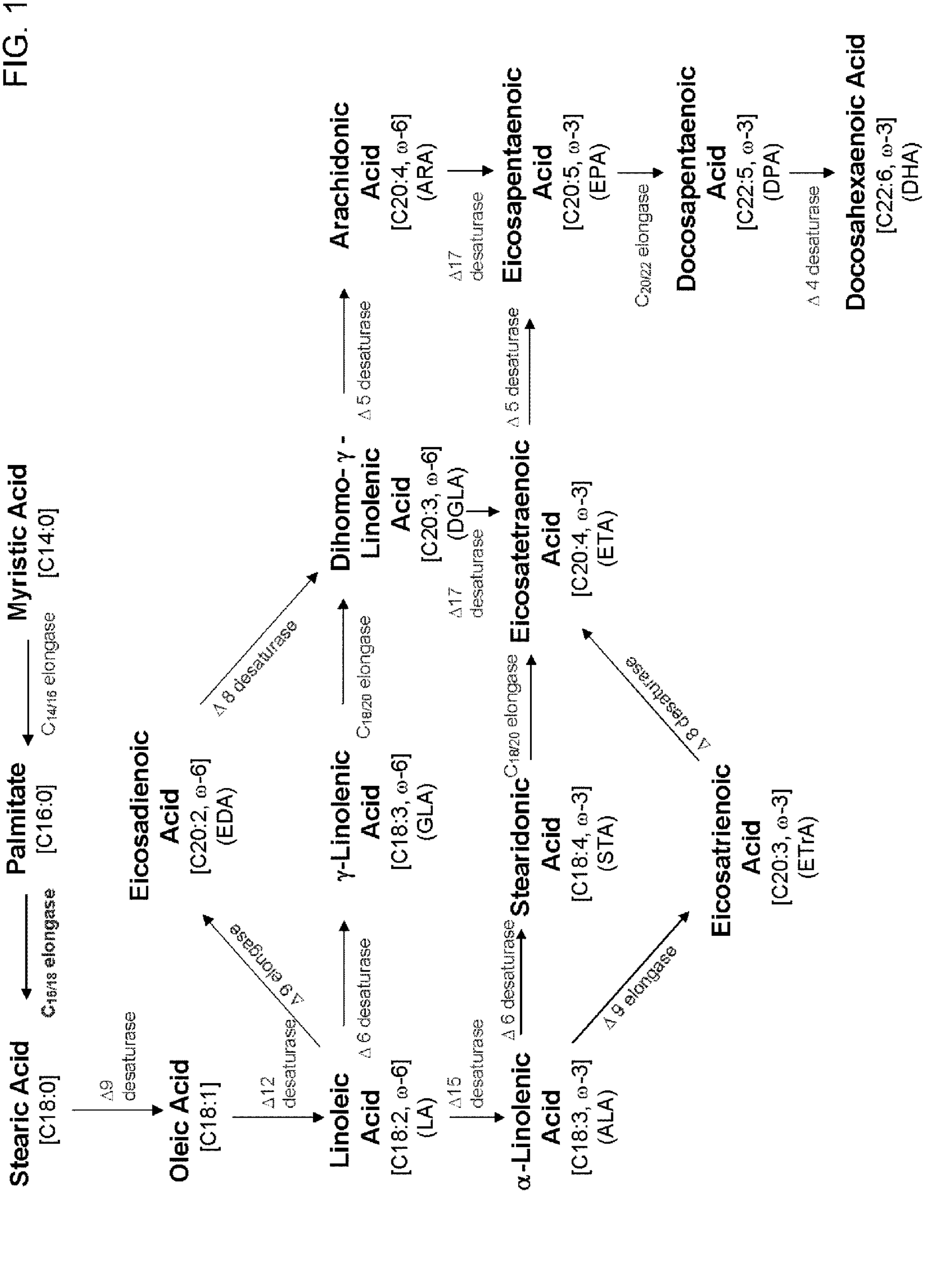

The term "omega-3/omega-6 fatty acid biosynthetic pathway" refers to a set of genes which, when expressed under the appropriate conditions encode enzymes that catalyze the production of either or both ω-3 and ω-6 fatty acids. Typically the genes involved in the ω-3/ω-6 fatty acid biosynthetic pathway encode PUFA biosynthetic pathway enzymes. A representative pathway is illustrated in FIG. 1, providing for the conversion of myristic acid through various intermediates to DHA, which demonstrates how both ω-3 and ω-6 fatty acids may be produced from a common source. The pathway is naturally divided into two portions where one portion will generate ω-3 fatty acids and the other portion, only ω-6 fatty acids.

The term "functional" as used herein in context with the ω-3/ω-6 fatty acid biosynthetic pathway means that some (or all of) the genes in the pathway express active enzymes, resulting in in vivo catalysis or substrate conversion. It should be understood that "ω-3/ω-6 fatty acid biosynthetic pathway" or "functional ω-3/ω-6 fatty acid biosynthetic pathway" does not imply that all of the PUFA biosynthetic pathway enzyme genes are required, as a number of fatty acid products will only require the expression of a subset of the genes of this pathway.

The term "Δ9 elongase/Δ8 desaturase pathway" refers to a biosynthetic pathway for production of long-chain PUFAs. This pathway, at a minimum, comprises a Δ9 elongase and a Δ8 desaturase, thereby enabling biosynthesis of DGLA and/or ETA from LA and ALA, respectively. With expression of other desaturases and elongases, ARA, EPA, DPA and DHA may also be synthesized. This pathway may be advantageous in some embodiments, as the biosynthesis of GLA and/or STA is excluded.

The term "intermediate fatty acid" refers to any fatty acid produced in a fatty acid metabolic pathway that can be further converted to an intended product fatty acid in this pathway by the action of other metabolic pathway enzymes. For instance, when EPA is produced using the Δ9 elongase/Δ8 desaturase pathway, EDA, ETrA, DGLA, ETA and ARA can be produced and are considered "intermediate fatty acids" since these fatty acids can be further converted to EPA via action of other metabolic pathway enzymes.

The term "by-product fatty acid" refers to any fatty acid produced in a fatty acid metabolic pathway that is not the intended fatty acid product of the pathway nor an "intermediate fatty acid" of the pathway. For instance, when EPA is produced using the Δ9 elongase/Δ8 desaturase pathway, sciadonic acid (SCI) and juniperonic acid (JUP) also can be produced by the action of a Δ5 desaturase on either EDA or ETrA, respectively. They are considered to be "by-product fatty acids" since neither can be further converted to EPA by the action of other metabolic pathway enzymes.

"Desaturase" is a polypeptide that can desaturate, i.e., introduce a double bond, in one or more fatty acids to produce a fatty acid or precursor of interest. Despite use of the omega-reference system throughout the specification to refer to specific fatty acids, it is more convenient to indicate the activity of a desaturase by counting from the carboxyl end of the substrate using the delta-system. Desaturases of interest include, for example: (1) Δ8 desaturases that will desaturate a fatty acid between the eighth and ninth carbon atom numbered from the carboxyl-terminal end of the molecule and that can, for example, catalyze the conversion of EDA to DGLA and/or ETrA to ETA; (2) Δ5 desaturases that catalyze the conversion of DGLA to ARA and/or ETA to EPA; (3) Δ6 desaturases that catalyze the conversion of LA to GLA and/or ALA to STA; (4) Δ4 desaturases that catalyze the conversion of DPA to DHA; (5) Δ12 desaturases that catalyze the conversion of oleic acid to LA; (6) Δ15 desaturases that catalyze the conversion of LA to ALA and/or GLA to STA; (7) Δ17 desaturases that catalyze the conversion of ARA to EPA and/or DGLA to ETA; and (8) Δ9 desaturases that catalyze the conversion of palmitate to palmitoleic acid (16:1) and/or stearate to oleic acid (18:1). In the art, Δ15 and Δ17 desaturases are also occasionally referred to as "omega-3 desaturases", "ω-3 desaturases", and/or "ω-3 desaturases", based on their ability to convert ω-6 fatty acids into their ω-3 counterparts (e.g., conversion of LA into ALA and ARA into EPA, respectively). In some embodiments, it is most desirable to empirically determine the specificity of a particular fatty acid desaturase by transforming a suitable host with the gene for the fatty acid desaturase and determining its effect on the fatty acid profile of the host.

For the purposes herein, the term "EgD8" refers to a Δ8 desaturase enzyme (SEQ ID NO:61) isolated from *Euglena gracilis*, encoded by SEQ ID NO:60 herein. EgD8 is 100% identical and functionally equivalent to "Eg5", as described in PCT Publications No. WO 2006/012325 and No. WO 2006/012326 [SEQ ID NO:2 of U.S. Publication No. 2005-0287652-A1].

Similarly, the term "EgD8S" refers to a synthetic Δ8 desaturase derived from *Euglena gracilis* that is codon-optimized for expression in *Yarrowia lipolytica* herein (i.e., SEQ ID NOs:68 and 69). EgD8S is 100% identical and functionally equivalent to "D8SF", as described in PCT Publications No. WO 2006/012325 and No. WO 2006/012326.

The term "elongase system" refers to a suite of four enzymes that are responsible for elongation of a fatty acid carbon chain to produce a fatty acid that is two carbons longer than the fatty acid substrate that the elongase system acts upon. More specifically, the process of elongation occurs in association with fatty acid synthase, whereby CoA is the acyl carrier (Lassner et al., *Plant Cell,* 8:281-292 (1996)). In the first step, which has been found to be both substrate-specific and also rate-limiting, malonyl-CoA is condensed with a long-chain acyl-CoA to yield carbon dioxide ($CO_2$) and a β-ketoacyl-CoA (where the acyl moiety has been elongated by two carbon atoms). Subsequent reactions include reduction to β-hydroxyacyl-CoA, dehydration to an enoyl-CoA and a second reduction to yield the elongated acyl-CoA. Examples of reactions catalyzed by elongase systems are the conversion of GLA to DGLA, STA to ETA and EPA to DPA.

For the purposes herein, an enzyme catalyzing the first condensation reaction (i.e., conversion of malonyl-CoA to β-ketoacyl-CoA) will be referred to generically as an "elongase". In general, the substrate selectivity of elongases is somewhat broad but segregated by both chain length and the degree of unsaturation. Accordingly, elongases can have different specificities. For example: a $C_{14/16}$ elongase will utilize a $C_{14}$ substrate (e.g., myristic acid); a $C_{16/18}$ elongase will utilize a $C_{16}$ substrate (e.g., palmitate); a $C_{18/20}$ elongase (also known as a Δ6 elongase as the terms can be used interchangeably) will utilize a $C_{18}$ substrate (e.g., GLA, STA); and a $C_{20/22}$ elongase will utilize a $C_{20}$ substrate (e.g., EPA). In like manner, and of particular interest herein, a "Δ9 elongase" is able to catalyze the conversion of LA and ALA to EDA and ETrA, respectively. It is important to note that some elongases have broad specificity and thus a single enzyme may be capable of catalyzing several elongase reactions. Thus, for example, a Δ9 elongase may also act as a $C_{16/18}$ elongase, $C_{18/20}$ elongase and/or $C_{20/22}$ elongase and may have alternate, but not preferred, specificities for Δ5 and Δ6 fatty acids such as EPA and/or GLA, respectively. In preferred embodiments, it is desirable to empirically determine the specificity of a fatty acid elongase by transforming a suitable host with the gene for the fatty acid elongase and determining its effect on the fatty acid profile of the host.

For the purposes herein, the term "EgD9e" refers to a Δ9 elongase enzyme (SEQ ID NO:2) isolated from *Euglena gracilis*, encoded by SEQ ID NO:1. In contrast, the term "EgD9eS" refers to a synthetic Δ9 elongase derived from *Euglena gracilis* that is codon-optimized for expression in *Yarrowia lipolytica* (i.e., SEQ ID NOs:3 and 2).

The term "E389D9e" refers to a Δ9 elongase enzyme (SEQ ID NO:5) isolated from *Eutreptiella* sp. CCMP389, encoded by SEQ ID NO:4. In contrast, the term "E389D9eS" refers to a synthetic Δ9 elongase derived from *Eutreptiella* sp. CCMP389 that is codon-optimized for expression in *Yarrowia lipolytica* (i.e., SEQ ID NOs:6 and 5).

The term "IgD9e" refers to a Δ9 elongase enzyme (SEQ ID NO:8; NCBI Accession No. AAL37626 [GI 17226123], locus AAL37626, CDS AF390174; GenBank Accession No. AF390174) isolated from *Isochrysis galbana*, encoded by SEQ ID NO:7. In contrast, the term "IgD9eS" refers to a synthetic Δ9 elongase derived from *Isochrysis galbana* that is codon-optimized for expression in *Yarrowia lipolytica* (i.e., SEQ ID NOs:9 and 8). Synthesis and functional analysis of IgD9eS is described in PCT Publication No. WO 2006/052870 (wherein IgD9eS is equivalent to SEQ ID NOs:51 and 50 therein).

The term "amino acid" will refer to the basic chemical structural unit of a protein or polypeptide. Amino acids are identified by either the one-letter code or the three-letter codes for amino acids, in conformity with the IUPAC-IYUB standards described in *Nucleic Acids Research,* 13:3021-3030 (1985) and in the *Biochemical Journal,* 219 (2):345-373 (1984), which are herein incorporated by reference.

The term "conservative amino acid substitution" refers to a substitution of an amino acid residue in a given protein with another amino acid, without altering the chemical or functional nature of that protein. For example, it is well known in the art that alterations in a gene that result in the production of a chemically equivalent amino acid at a given site (but that do not affect the structural and functional properties of the encoded, folded protein) are common. For the purposes of the present invention, "conservative amino acid substitutions" are defined as exchanges within one of the following five groups:

1. Small aliphatic, nonpolar or slightly polar residues: Ala [A], Ser [S], Thr [T] (Pro [P], Gly [G]);
2. Polar, negatively charged residues and their amides: Asp [D], Asn [N], Glu [E], Gln [Q];
3. Polar, positively charged residues: His [H], Arg [R], Lys [K];
4. Large aliphatic, nonpolar residues: Met [M], Leu [L], Ile [I], Val [V] (Cys [C]); and,
5. Large aromatic residues: Phe [F], Tyr [Y], Trp [W].

Conservative amino acid substitutions generally maintain: 1) the structure of the polypeptide backbone in the area of the substitution; 2) the charge or hydrophobicity of the molecule at the target site; or 3) the bulk of the side chain. Additionally, in many cases, alterations of the N-terminal and C-terminal portions of the protein molecule would also not be expected to alter the activity of the protein.

The term "non-conservative amino acid substitution" refers to an amino acid substitution that is generally expected to produce the greatest change in protein properties. Thus, for example, a non-conservative amino acid substitution would be one whereby: 1) a hydrophilic residue is substituted for/by a hydrophobic residue (e.g., Ser or Thr for/by Leu, Ile, Val); 2) a Cys or Pro is substituted for/by any other residue; 3) a residue having an electropositive side chain is substituted for/by an electronegative residue (e.g., Lys, Arg or His for/by Asp or Glu); or, 4) a residue having a bulky side chain is substituted for/by one not having a side chain (e.g., Phe for/by Gly). Sometimes, non-conservative amino acid substitutions between two of the five groups will not affect the activity of the encoded protein.

more segments of cDNA, genomic DNA, synthetic DNA, or mixtures thereof. Nucleotides (usually found in their 5'-monophosphate form) are referred to by a single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

The terms "subfragment that is functionally equivalent" and "functionally equivalent subfragment" are used interchangeably herein. These terms refer to a portion or subsequence of an isolated nucleic acid fragment in which the ability to alter gene expression or produce a certain phenotype is retained whether or not the fragment or subfragment encodes an active enzyme. For example, the fragment or subfragment can be used in the design of chimeric genes to produce the desired phenotype in a transformed plant. Chimeric genes can be designed for use in suppression by linking a nucleic acid fragment or subfragment thereof, whether or not it encodes an active enzyme, in the sense or antisense orientation relative to a plant promoter sequence.

The term "conserved domain" or "motif" means a set of amino acids conserved at specific positions along an aligned sequence of evolutionarily related proteins. While amino acids at other positions can vary between homologous proteins, amino acids that are highly conserved at specific positions indicate amino acids that are essential in the structure, the stability, or the activity of a protein. Because they are identified by their high degree of conservation in aligned sequences of a family of protein homologues, they can be used as identifiers, or "signatures", to determine if a protein with a newly determined sequence belongs to a previously identified protein family. For the purposes herein, the following Table describes motifs of the present invention which are indicative of a protein having Δ9 elongase activity.

TABLE 4

Summary Of Δ9 Elongase Motifs

| Description | Sequence | Protein SEQ ID NO. |
|---|---|---|
| Δ9 Elongase Motif #1 | Y N X (L or F) X X X X S X X S F | 123 |
| Δ9 Elongase Motif #2 | F Y X S K X X (E or D) Y X D (T or S) X X L | 124 |
| Δ9 Elongase Motif #3 | L(Q or H) X F H H X G A | 125 |
| Δ9 Elongase Motif #4 | M Y X Y Y X X X X X X X (K or R or N) F | 126 |
| Δ9 Elongase Motif #5 | K X L (I or L or M) T X X Q | 127 |
| Δ9 Elongase Motif #6 | W X F N Y X Y | 128 |
| Δ9 Elongase Motif #7 | Y X G X V X X L F | 129 |

The terms "polynucleotide", "polynucleotide sequence", "nucleic acid sequence", "nucleic acid fragment" and "isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or The terms "homology", "homologous", "substantially similar" and "corresponding substantially" are used interchangeably herein. They refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

Moreover, the skilled artisan recognizes that substantially similar nucleic acid sequences encompassed by this invention are also defined by their ability to hybridize (under moderately stringent conditions, e.g., 0.5×SSC, 0.1% SDS, 60° C.) with the sequences exemplified herein, or to any portion of the nucleotide sequences disclosed herein and which are functionally equivalent to any of the nucleic acid sequences disclosed herein. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, or 90% sequence identity, up to and including 100% sequence identity (i.e., fully complementary) with each other.

The term "stringent conditions" or "stringent hybridization conditions" includes reference to conditions under which a probe will selectively hybridize to its target sequence. Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length. Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Other exemplary stringent hybridization conditions include 0.1×SSC, 0.1% SDS, 65° C. and washed with 2×SSC, 0.1% SDS followed by 0.1×SSC, 0.1% SDS.

Specificity is typically the function of post-hybridization washes, the important factors being the ionic strength and temperature of the final wash solution. For DNA-DNA hybrids, the $T_m$ can be approximated from the equation of Meinkoth et al., *Anal. Biochem.,* 138:267-284 (1984): $T_m$=81.5° C.+16.6(log M)+0.41(% GC)−0.61(% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3 or 4° C. lower than the thermal melting point ($T_m$); moderately stringent conditions can utilize a hybridization and/or wash at 6, 7, 8, 9 or 10° C. lower than the thermal melting point ($T_m$); low stringency conditions can utilize a hybridization and/or wash at 11, 12, 13, 14, 15 or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, N.Y. (1993); and *Current Protocols in Molecular Biology*, Chapter 2, Ausubel et al., Eds., Greene Publishing and Wiley-Interscience, New York (1995). Hybridization and/or wash conditions can be applied for at least 10, 30, 60, 90, 120 or 240 minutes.

"Sequence identity" or "identity" in the context of nucleic acid or polypeptide sequences refers to the nucleic acid bases or amino acid residues in two sequences that are the same when aligned for maximum correspondence over a specified comparison window.

Thus, "percentage of sequence identity" refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. Useful examples of percent sequence identities include, but are not limited to, 50%, 55%, 60%, 65%, 70%, 75%, 80%, 85%, 90%, or 95%, or any integer percentage from 50% to 100%. These identities can be determined using any of the programs described herein.

Sequence alignments and percent identity or similarity calculations may be determined using a variety of comparison methods designed to detect homologous sequences including, but not limited to, the MegAlign™ program of the LASERGENE bioinformatics computing suite (DNASTAR Inc., Madison, Wis.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

The "Clustal V method of alignment" corresponds to the alignment method labeled Clustal V (described by Higgins and Sharp, *CABIOS,* 5:151-153 (1989); Higgins, D. G. et al., *Comput. Appl. Biosci.,* 8:189-191 (1992)) and found in the MegAlign™ program of the LASERGENE bioinformatics computing suite (supra). For multiple alignments, the default values correspond to GAP PENALTY=10 and GAP LENGTH PENALTY=10. Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program.

"BLASTN method of alignment" is an algorithm provided by the National Center for Biotechnology Information (NCBI) to compare nucleotide sequences using default parameters.

It is well understood by one skilled in the art that many levels of sequence identity are useful in identifying polypeptides, from other species, wherein such polypeptides have the same or similar function or activity. Useful examples of percent identities include, but are not limited to, 50%, 55%, 60%, 65%, 70%, 75%, 80%, 85%, 90%, or 95%, or any integer percentage from 50% to 100%. Indeed, any integer amino acid identity from 50% to 100% may be useful in describing the present invention, such as 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%. Also, of interest is any full-length or partial complement of this isolated nucleotide fragment.

The term "genome" as it applies to a plant cells encompasses not only chromosomal DNA found within the nucleus, but organelle DNA found within subcellular components (e.g., mitochondrial, plastid) of the cell.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

A "codon-optimized gene" is a gene having its frequency of codon usage designed to mimic the frequency of preferred codon usage of the host cell.

An "allele" is one of several alternative forms of a gene occupying a given locus on a chromosome. When all the alleles present at a given locus on a chromosome are the same, that plant is homozygous at that locus. If the alleles present at a given locus on a chromosome differ, that plant is heterozygous at that locus.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to: promoters, translation leader sequences, introns, polyadenylation recognition sequences, RNA processing sites, effector binding sites and stem-loop structures.

"Promoter" refers to a DNA sequence capable of controlling the expression of a coding sequence or functional RNA. The promoter sequence consists of proximal and more distal upstream elements, the latter elements often referred to as enhancers. Accordingly, an "enhancer" is a DNA sequence that can stimulate promoter activity, and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity. Promoters that cause a gene to be expressed in most cell types at most times are commonly referred to as "constitutive promoters". New promoters of various types useful in plant cells are constantly being discovered; numerous examples may be found in the compilation by Okamuro, J. K., and Goldberg, R. B. *Biochemistry of Plants,* 15:1-82 (1989).

"Translation leader sequence" refers to a polynucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D., *Mol. Biotechnol.,* 3:225-236 (1995)).

"3' non-coding sequences", "transcription terminator" or "termination sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht, I. L., et al. *Plant Cell,* 1:671-680 (1989).

"RNA transcript" refers to the product resulting from RNA polymerase-catalyzed transcription of a DNA sequence. When the RNA transcript is a perfect complementary copy of the DNA sequence, it is referred to as the primary transcript. A RNA transcript is referred to as the mature RNA when it is a RNA sequence derived from post-transcriptional processing of the primary transcript. "Messenger RNA" or "mRNA" refers to the RNA that is without introns and that can be translated into protein by the cell. "cDNA" refers to a DNA that is complementary to, and synthesized from, a mRNA template using the enzyme reverse transcriptase. The cDNA can be single-stranded or converted into double-stranded form using the Klenow fragment of DNA polymerase I. "Sense" RNA refers to RNA transcript that includes the mRNA and can be translated into protein within a cell or in vitro. "Antisense RNA" refers to an RNA transcript that is complementary to all or part of a target primary transcript or mRNA, and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that may not be translated but yet has an effect on cellular processes. The terms "complement" and "reverse complement" are used interchangeably herein with respect to mRNA transcripts, and are meant to define the antisense RNA of the message.

The term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., the coding sequence is under the transcriptional control of the promoter). Coding sequences can be operably linked to regulatory sequences in a sense or antisense orientation. In another example, the complementary RNA regions of the invention can be operably linked, either directly or indirectly, 5' to the target mRNA, or 3' to the target mRNA, or within the target mRNA, or a first complementary region is 5' and its complement is 3' to the target mRNA.

Standard recombinant DNA and molecular cloning techniques used herein are well known in the art and are described more fully in Sambrook, J., Fritsch, E. F. and Maniatis, T. Molecular Cloning: A Laboratory Manual; Cold Spring Harbor Laboratory: Cold Spring Harbor, N.Y. (1989). Transformation methods are well known to those skilled in the art and are described below.

"PCR" or "polymerase chain reaction" is a technique for the synthesis of large quantities of specific DNA segments and consists of a series of repetitive cycles (Perkin Elmer Cetus Instruments, Norwalk, Conn.). Typically, the double-stranded DNA is heat denatured, the two primers complementary to the 3' boundaries of the target segment are annealed at low temperature and then extended at an intermediate temperature. One set of these three consecutive steps is referred to as a "cycle".

The term "recombinant" refers to an artificial combination of two otherwise separated segments of sequence, e.g., by chemical synthesis or by the manipulation of isolated segments of nucleic acids by genetic engineering techniques.

The terms "plasmid", "vector" and "cassette" refer to an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitates transformation of a particular host cell. "Expression cassette" refers to a specific vector containing a foreign gene and having elements in addition to the foreign gene that allow for enhanced expression of that gene in a foreign host (i.e., to a discrete nucleic acid fragment into which a nucleic acid sequence or fragment can be moved).

The terms "recombinant construct", "expression construct", "chimeric construct", "construct", and "recombinant DNA construct" are used interchangeably herein. A recombinant construct comprises an artificial combination of nucleic acid fragments, e.g., regulatory and coding sequences that are not found together in nature. For example, a chimeric construct may comprise regulatory sequences and coding sequences that are derived from different sources, or regulatory sequences and coding sequences derived from the same source, but arranged in a manner different than that found in nature. Such a construct may be used by itself or may be used in conjunction with a vector. If a vector is used, then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the invention. The skilled artisan will also recognize that different independent transformation events will result in different levels and patterns of expression (Jones et al., *EMBO J.,* 4:2411-2418 (1985); De Almeida et al., *Mol. Gen. Genetics,* 218:78-86 (1989)), and thus it is preferable if multiple events are screened in order to obtain lines displaying the desired expression level and pattern. Such screening may be accomplished by Southern analysis of DNA, Northern analysis of mRNA expression, immunoblotting analysis of protein expression, or phenotypic analysis, among others.

The term "expression", as used herein, refers to the production of a functional end-product (e.g., a mRNA or a protein [either precursor or mature]).

The term "introduced" means providing a nucleic acid (e.g., expression construct) or protein into a cell. Introduced includes reference to the incorporation of a nucleic acid into a eukaryotic or prokaryotic cell where the nucleic acid may be incorporated into the genome of the cell, and includes reference to the transient provision of a nucleic acid or protein to the cell. Introduced includes reference to stable or transient transformation methods, as well as sexually crossing. Thus, "introduced" in the context of inserting a nucleic acid fragment (e.g., a recombinant DNA construct/expression construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

"Mature" protein refers to a post-translationally processed polypeptide (i.e., one from which any pre- or propeptides present in the primary translation product have been removed). "Precursor" protein refers to the primary product of translation of mRNA (i.e., with pre- and propeptides still present). Pre- and propeptides may be but are not limited to intracellular localization signals.

"Stable transformation" refers to the transfer of a nucleic acid fragment into a genome of a host organism, including both nuclear and organellar genomes, resulting in genetically stable inheritance. In contrast, "transient transformation"

refers to the transfer of a nucleic acid fragment into the nucleus, or DNA-containing organelle, of a host organism resulting in gene expression without integration or stable inheritance. Host organisms containing the transformed nucleic acid fragments are referred to as "transgenic" organisms.

As used herein, "transgenic" refers to a plant or a cell which comprises within its genome a heterologous polynucleotide. Preferably, the heterologous polynucleotide is stably integrated within the genome such that the polynucleotide is passed on to successive generations. The heterologous polynucleotide may be integrated into the genome alone or as part of an expression construct. Transgenic is used herein to include any cell, cell line, callus, tissue, plant part or plant, the genotype of which has been altered by the presence of heterologous nucleic acids, including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

"Antisense inhibition" refers to the production of antisense RNA transcripts capable of suppressing the expression of the target protein. "Co-suppression" refers to the production of sense RNA transcripts capable of suppressing the expression of identical or substantially similar foreign or endogenous genes (U.S. Pat. No. 5,231,020). Co-suppression constructs in plants previously have been designed by focusing on overexpression of a nucleic acid sequence having homology to an endogenous mRNA, in the sense orientation, which results in the reduction of all RNA having homology to the overexpressed sequence (Vaucheret et al., *Plant J.,* 16:651-659 (1998); Gura, *Nature,* 404:804-808 (2000)). The overall efficiency of this phenomenon is low, and the extent of the RNA reduction is widely variable. More recent work has described the use of "hairpin" structures that incorporate all, or part, of an mRNA encoding sequence in a complementary orientation that results in a potential "stem-loop" structure for the expressed RNA (PCT Publication No. WO 99/53050; PCT Publication No. WO 02/00904). This increases the frequency of co-suppression in the recovered transgenic plants. Another variation describes the use of plant viral sequences to direct the suppression, or "silencing", of proximal mRNA encoding sequences (PCT Publication No. WO 98/36083). Both of these co-suppressing phenomena have not been elucidated mechanistically, although genetic evidence has begun to unravel this complex situation (Elmayan et al., *Plant Cell,* 10:1747-1757 (1998)).

The term "oleaginous" refers to those organisms that tend to store their energy source in the form of lipid (Weete, In: Fungal Lipid Biochemistry, $2^{nd}$ Ed., Plenum, 1980). A class of plants identified as oleaginous are commonly referred to as "oilseed" plants. Examples of oilseed plants include, but are not limited to: soybean (Glycine and *Soja* sp.), flax (*Linum* sp.), rapeseed (*Brassica* sp.), maize, cotton, safflower (*Carthamus* sp.) and sunflower (*Helianthus* sp.).

Within oleaginous microorganisms the cellular oil or TAG content generally follows a sigmoid curve, wherein the concentration of lipid increases until it reaches a maximum at the late logarithmic or early stationary growth phase and then gradually decreases during the late stationary and death phases (Yongmanitchai and Ward, *Appl. Environ. Microbiol.,* 57:419-25 (1991)).

The term "oleaginous yeast" refers to those microorganisms classified as yeasts that make oil. It is not uncommon for oleaginous microorganisms to accumulate in excess of about 25% of their dry cell weight as oil. Examples of oleaginous yeast include, but are no means limited to, the following genera: *Yarrowia, Candida, Rhodotorula, Rhodosporidium, Cryptococcus, Trichosporon* and *Lipomyces.*

The term "Euglenophyceae" refers to a group of unicellular colorless or photosynthetic flagellates ("euglenoids") found living in freshwater, marine, soil and parasitic environments. The class is characterized by solitary unicells, wherein most are free-swimming and have two flagella (one of which may be nonemergent) arising from an anterior invagination known as a reservoir. Photosynthetic euglenoids contain one to many chloroplasts, which vary from minute disks to expanded plates or ribbons. Colorless euglenoids depend on osmotrophy or phagotrophy for nutrient assimilation. About 1000 species have been described and classified into about 40 genera and 6 orders. Examples of Euglenophyceae include, but are no means limited to, the following genera: *Eutreptiella, Euglena* and *Tetruetreptia.*

The term "plant" refers to whole plants, plant organs, plant tissues, seeds, plant cells, seeds and progeny of the same. Plant cells include, without limitation, cells from seeds, suspension cultures, embryos, meristematic regions, callus tissue, leaves, roots, shoots, gametophytes, sporophytes, pollen and microspores.

"Progeny" comprises any subsequent generation of a plant.

An Overview Microbial Biosynthesis of Fatty Acids and Triacylglycerols

In general, lipid accumulation in oleaginous microorganisms is triggered in response to the overall carbon to nitrogen ratio present in the growth medium. This process, leading to the de novo synthesis of free palmitate (16:0) in oleaginous microorganisms, is described in detail in PCT Publication No. WO 2004/101757. Palmitate is the precursor of longer-chain saturated and unsaturated fatty acid derivates, which are formed through the action of elongases and desaturases (FIG. 1).

TAGs (the primary storage unit for fatty acids) are formed by a series of reactions that involve: 1) the esterification of one molecule of acyl-CoA to glycerol-3-phosphate via an acyltransferase to produce lysophosphatidic acid; 2) the esterification of a second molecule of acyl-CoA via an acyltransferase to yield 1,2-diacylglycerol phosphate (commonly identified as phosphatidic acid); 3) removal of a phosphate by phosphatidic acid phosphatase to yield 1,2-diacylglycerol (DAG); and 4) the addition of a third fatty acid by the action of an acyltransferase to form TAG. A wide spectrum of fatty acids can be incorporated into TAGs, including saturated and unsaturated fatty acids and short-chain and long-chain fatty acids.

Biosynthesis of Omega Fatty Acids

The metabolic process wherein oleic acid is converted to long-chain ω-3/ω-6 fatty acids involves elongation of the carbon chain through the addition of carbon atoms and desaturation of the molecule through the addition of double bonds. This requires a series of special desaturation and elongation enzymes present in the endoplasmic reticulum membrane. However, as seen in FIG. 1 and as described below, there are often multiple alternate pathways for production of a specific ω-3/ω-6 fatty acid.

Specifically, all pathways require the initial conversion of oleic acid to LA, the first of the ω-6 fatty acids, by a Δ12 desaturase. Then, using the "Δ9 elongase/Δ8 desaturase pathway", long-chain ω-6 fatty acids are formed as follows: (1) LA is converted to EDA by a Δ9 elongase; (2) EDA is converted to DGLA by a Δ8 desaturase; and (3) DGLA is converted to ARA by a Δ5 desaturase. Alternatively, the "Δ9 elongase/Δ8 desaturase pathway" can be utilized for formation of long-chain ω-3 fatty acids as follows: (1) LA is converted to ALA, the first of the ω-3 fatty acids, by a Δ15 desaturase; (2) ALA is converted to ETrA by a Δ9 elongase; (3) ETrA is converted to ETA by a Δ8 desaturase; (4) ETA is converted to EPA by a Δ5 desaturase; (5) EPA is converted to DPA by a $C_{20/22}$ elongase; and (6) DPA is converted to DHA by a Δ4 desaturase. Optionally, ω-6 fatty acids may be converted to ω-3 fatty acids; for example, ETA and EPA are produced from DGLA and ARA, respectively, by Δ17 desaturase activity.

Alternate pathways for the biosynthesis of ω-3/ω-6 fatty acids utilize a Δ6 desaturase and $C_{18/20}$ elongase (i.e., the "Δ6 desaturase/Δ6 elongase pathway"). More specifically, LA and ALA may be converted to GLA and STA, respectively, by a Δ6 desaturase; then, a $C_{18/20}$ elongase converts GLA to DGLA and/or STA to ETA.

It is contemplated that the particular functionalities required to be introduced into a specific host organism for production of a ω-3/ω-6 fatty acids will depend on the host cell (and its native PUFA profile and/or desaturase/elongase profile), the availability of substrate, and the desired end product(s). For example, expression of the Δ9 elongase/Δ8 desaturase pathway may be preferred in some embodiments, as opposed to expression of the Δ6 desaturase/Δ6 elongase pathway, since PUFAs produced via the former pathway are devoid of GLA.

One skilled in the art will be able to identify various candidate genes encoding each of the enzymes desired for ω-3/ω-6 fatty acid biosynthesis. Useful desaturase and elongase sequences may be derived from any source, e.g., isolated from a natural source (from bacteria, algae, fungi, plants, animals, etc.), produced via a semi-synthetic route or synthesized de novo. Although the particular source of the desaturase and elongase genes introduced into the host is not critical, considerations for choosing a specific polypeptide having desaturase or elongase activity include: 1) the substrate specificity of the polypeptide; 2) whether the polypeptide or a component thereof is a rate-limiting enzyme; 3) whether the desaturase or elongase is essential for synthesis of a desired PUFA; and/or 4) co-factors required by the polypeptide. The expressed polypeptide preferably has parameters compatible with the biochemical environment of its location in the host cell (see PCT Publication No. WO 2004/101757 for additional details).

In additional embodiments, it will also be useful to consider the conversion efficiency of each particular desaturase and/or elongase. More specifically, since each enzyme rarely functions with 100% efficiency to convert substrate to product, the final lipid profile of un-purified oils produced in a host cell will typically be a mixture of various PUFAs consisting of the desired ω-3/ω-6 fatty acid, as well as various upstream intermediary PUFAs. Thus, consideration of each enzyme's conversion efficiency is also a variable when optimizing biosynthesis of a desired fatty acid that must be considered in light of the final desired lipid profile of the product.

With each of the considerations above in mind, candidate genes having the appropriate desaturase and elongase activities (e.g., Δ6 desaturases, $C_{18/20}$ elongases, Δ5 desaturases, Δ17 desaturases, Δ15 desaturases, Δ9 desaturases, Δ12 desaturases, $C_{14/16}$ elongases, $C_{16/18}$ elongases, Δ9 elongases, Δ8 desaturases, Δ4 desaturases and $C_{20/22}$ elongases) can be identified according to publicly available literature (e.g., GenBank), the patent literature, and experimental analysis of organisms having the ability to produce PUFAs. These genes will be suitable for introduction into a specific host organism, to enable or enhance the organism's synthesis of PUFAs.

Sequence Identification of Novel Δ9 Elongases

In the present invention, nucleotide sequences encoding Δ9 elongases have been isolated from *Euglena gracilis* (designated herein as "EgD9e") and *Eutreptiella* sp. CCMP389 (designated herein as "E389D9e").

Comparison of the EgD9e nucleotide base and deduced amino acid sequences to public databases reveals that the most similar known sequences (i.e., IgD9e) are about 31.8% identical to the amino acid sequence of EgD9e reported herein over a length of 258 amino acids using a Clustal V analysis.

Comparison of the E389D9e nucleotide base and deduced amino acid sequences to public databases reveals that the most similar known sequences (i.e., IgD9e) are about 33.1% identical to the amino acid sequence of E389D9e reported herein over a length of 263 amino acids using a Clustal V analysis.

For reference, comparison of the novel EgD9e and E389D9e protein sequences described herein as SEQ ID NO:2 and SEQ ID NO:5 share 65.1% identity using a Clustal V analysis.

Within the context of the present invention preferred amino acid fragments are at least about 70%-85% identical to the EgD9e and E389D9e sequences herein, where those sequences that are at least about 85%-90% identical are particularly suitable and those sequences that are at least about 90%-95% identical are most preferred. Preferred EgD9e and E389D9e encoding nucleic acid sequences corresponding to the instant ORFs are those encoding active proteins and which are at least about 70%-85% identical to the nucleic acid sequences of EgD9e and E389D9e reported herein, respectively, where those sequences that are at least 85%-90% identical are particularly suitable and those sequences that are at least about 90%-95% identical are most preferred.

In alternate embodiments, the instant EgD9e and E389D9e sequences can be codon-optimized for expression in a particular host organism. As is well known in the art, this can be a useful means to further optimize the expression of the enzyme in the alternate host, since use of host-preferred codons can substantially enhance the expression of the foreign gene encoding the polypeptide. In general, host-preferred codons can be determined within a particular host species of interest by examining codon usage in proteins (preferably those expressed in the largest amount) and determining which codons are used with highest frequency. Then, the coding sequence for a polypeptide of interest having e.g., elongase activity can be synthesized in whole or in part using the codons preferred in the host species. All (or portions) of the DNA also can be synthesized to remove any destabilizing sequences or regions of secondary structure that would be present in the transcribed mRNA. All (or portions) of the DNA also can be synthesized to alter the base composition to one more preferable in the desired host cell.

In one preferred embodiment of the invention, EgD9e and E389D9e were codon-optimized for expression in *Yarrowia lipolytica*. This was possible by first determining the *Y. lipolytica* codon usage profile (see PCT Publication No. WO 04/101757) and identifying those codons that were preferred. Further optimization of gene expression in *Y. lipolytica* was achieved by determining the consensus sequence around the 'ATG' initiation codon.

Optimization of EgD9e resulted in modification of 117 bp of the 777 bp coding region (15.1%) and optimization of 106 codons. None of the modifications in the codon-optimized gene ("EgD9eS"; SEQ ID NO:3) changed the amino acid sequence of the encoded protein (SEQ ID NO:2). As described in Example 8, the codon-optimized gene was about 16.2% more efficient elongating LA to EDA than the wild-type EgD9e gene, when expressed in *Y. lipolytica.*

Similarly, optimization of E389D9e resulted in modification of 128 bp of the 792 bp coding region (16.2%) and optimization of 113 codons. None of the modifications in the codon-optimized gene ("E389D9eS"; SEQ ID NO:6) changed the amino acid sequence of the encoded protein (SEQ ID NO:5). As described in Example 24, the codon-optimized gene elongated LA to EDA with similar efficiency as the wildtype gene, when expressed in *Y. lipolytica.*

Thus, the present invention concerns an isolated polynucleotide sequence encoding a polypeptide having Δ9 elongase activity, selected from the group consisting of:

(a) an isolated nucleic acid sequence comprising a nucleotide sequence encoding a polypeptide having Δ9 elongase activity, wherein the polypeptide has at least 70% amino acid identity, based on the Clustal V method of alignment, when compared to an amino acid sequence as set forth in SEQ ID NO:2 (EgD9e) or SEQ ID NO:5 (E389D9e);

(b) an isolated nucleic acid sequence comprising a nucleotide sequence encoding a polypeptide having Δ9 elongase activity, wherein the nucleotide sequence has at least 70% sequence identity, based on the BLASTN method of alignment, when compared to a nucleotide sequence as set forth in SEQ ID NO:1 (EgD9e), SEQ ID NO:3 (EgD9eS), SEQ ID NO:4 (E389D9e) or SEQ ID NO:6 (E389D9eS); and (c) an isolated nucleic acid sequence comprising a nucleotide sequence encoding a polypeptide having Δ9 elongase activity, wherein the nucleotide sequence hybridizes with a nucleotide sequence as set forth in SEQ ID NO:1 (EgD9e), SEQ ID NO:3 (EgD9eS), SEQ ID NO:4 (E389D9e) or SEQ ID NO:6 (E389D9eS) under the following stringent hybridization conditions: 0.1×SSC, 0.1% SDS, 65° C. and washed with 2×SSC, 0.1% SDS followed by 0.1×SSC, 0.1% SDS; and, (d) a complement of the nucleotide sequence of (a), (b) or (c), wherein the complement and the nucleotide sequence consist of the same number of nucleotides and are 100% complementary.

One skilled in the art would be able to use the teachings herein to create various other codon-optimized Δ9 elongase proteins suitable for optimal expression in alternate hosts (i.e., other than *Yarrowia lipolytica*), based on the wildtype EgD9e and/or E389D9e sequence. This alternate host organism may include, but is not limited to, a plant or plant part. Accordingly, the instant invention relates to any codon-optimized Δ9 elongase protein that is derived from either the wildtype EgD9e (i.e., encoded by SEQ ID NO:2) or the wildtype E389D9e (i.e., encoded by SEQ ID NO:5). This includes, but is not limited to: the nucleotide sequence set forth in SEQ ID NO:3 (which encodes a synthetic Δ9 elongase protein (i.e., EgD9eS)) and the nucleotide sequence set forth in SEQ ID NO:6 (which encodes a synthetic Δ9 elongase protein (i.e., E389D9eS)), both of which were codon-optimized for expression in *Yarrowia lipolytica.*

In another aspect this invention concerns an isolated nucleic acid fragment comprising a nucleic acid sequence encoding a Δ9 elongase, excluding SEQ ID NO:8 (i.e., "IgD9e", the Δ9 elongase from *Isochrysis galbana* (NCBI Accession No. AAL37626 (GI 17226123)), wherein the amino acid sequence comprising said Δ9 elongase contains at least one of the following amino acid sequence motifs selected from the group consisting of:

a) Y N X (L or F) X X X X S X X S F; (SEQ ID NO: 123)

b) F Y X S K X X (E or D) Y X D (T or S) X X L; (SEQ ID NO: 124)

c) L (Q or H) X F H H X G A; (SEQ ID NO: 125)

d) M Y X Y Y X X X X X X X (K or R or N) F; (SEQ ID NO: 126)

e) K X L (I or L or M) T X X Q; (SEQ ID NO: 127)

f) W X F N Y X Y; (SEQ ID NO: 128)
and g) Y X G X V X X L F; (SEQ ID NO: 129)

wherein X can be any amino acid.

The underlined amino acids may be unique to Δ9 elongases. FIG. 2 sets forth a comparison of the Δ9 elongases of the present invention with a Δ9 elongase from *Isochrysis galbana* using a Clustal V alignment (with default parameters). Specifically, SEQ ID NO:2 (EgD9e), SEQ ID NO:5 (E389D9e) and SEQ ID NO:8 (IgD9e) were compared. Regions comprising the motifs of the invention are shown in boxes.

Identification and Isolation of Homologs

Any of the instant elongase sequences (i.e., EgD9e, EgD9eS, E389D9e, E389D9eS) or portions thereof may be used to search for Δ9 elongase homologs in the same or other bacterial, algal, fungal, euglenoid or plant species using sequence analysis software. In general, such computer software matches similar sequences by assigning degrees of homology to various substitutions, deletions and other modifications.

Alternatively, any of the instant elongase sequences or portions thereof may also be employed as hybridization reagents for the identification of Δ9 elongase homologs. The basic components of a nucleic acid hybridization test include a probe, a sample suspected of containing the gene or gene fragment of interest and a specific hybridization method. Probes of the present invention are typically single-stranded nucleic acid sequences that are complementary to the nucleic acid sequences to be detected. Probes are "hybridizable" to the nucleic acid sequence to be detected. Although the probe length can vary from 5 bases to tens of thousands of bases, typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions that will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration, the shorter the hybridization incubation time needed. Optionally, a chaotropic agent may be added (e.g., guanidinium chloride, guanidinium thiocyanate, sodium thiocyanate, lithium tetrachloroacetate, sodium perchlorate, rubidium tetrachloroacetate, potassium iodide, cesium trifluoroacetate). If desired, one can add formamide to the hybridization mixture, typically 30-50% (v/v).

Various hybridization solutions can be employed. Typically, these comprise from about 20 to 60% volume, preferably 30%, of a polar organic solvent. A common hybridization solution employs about 30-50% v/v formamide, about 0.15 to 1 M sodium chloride, about 0.05 to 0.1 M buffers (e.g., sodium citrate, Tris-HCl, PIPES or HEPES (pH range about 6-9)), about 0.05 to 0.2% detergent (e.g., sodium dodecylsulfate), or between 0.5-20 mM EDTA, FICOLL (Pharmacia Inc.) (about 300-500 kdal), polyvinylpyrrolidone (about 250-500 kdal), and serum albumin. Also included in the typical hybridization solution will be unlabeled carrier nucleic acids from about 0.1 to 5 mg/mL, fragmented nucleic DNA (e.g., calf thymus or salmon sperm DNA, or yeast RNA), and optionally from about 0.5 to 2% wt/vol glycine. Other additives may also be included, such as volume exclusion agents that include a variety of polar water-soluble or swellable agents (e.g., polyethylene glycol), anionic polymers (e.g., polyacrylate or polymethylacrylate) and anionic saccharidic polymers (e.g., dextran sulfate).

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

In additional embodiments, any of the Δ9 elongase nucleic acid fragments described herein (or any homologs identified thereof) may be used to isolate genes encoding homologous proteins from the same or other bacterial, algal, fungal, euglenoid or plant species. Isolation of homologous genes using sequence-dependent protocols is well known in the art. Examples of sequence-dependent protocols include, but are not limited to: 1) methods of nucleic acid hybridization; 2) methods of DNA and RNA amplification, as exemplified by various uses of nucleic acid amplification technologies [e.g., polymerase chain reaction (PCR), Mullis et al., U.S. Pat. No. 4,683,202; ligase chain reaction (LCR), Tabor, S. et al., *Proc. Acad. Sci. USA,* 82:1074 (1985); or strand displacement amplification (SDA), Walker, et al., *Proc. Natl. Acad. Sci. USA,* 89:392 (1992)]; and 3) methods of library construction and screening by complementation.

For example, genes encoding similar proteins or polypeptides to the Δ9 elongases described herein could be isolated directly by using all or a portion of the instant nucleic acid fragments as DNA hybridization probes to screen libraries from e.g., any desired yeast or fungus using methodology well known to those skilled in the art (wherein those organisms producing EDA and/or ETrA would be preferred). Specific oligonucleotide probes based upon the instant nucleic acid sequences can be designed and synthesized by methods known in the art (Maniatis, supra). Moreover, the entire sequences can be used directly to synthesize DNA probes by methods known to the skilled artisan (e.g., random primers DNA labeling, nick translation or end-labeling techniques), or RNA probes using available in vitro transcription systems. In addition, specific primers can be designed and used to amplify a part of (or full-length of) the instant sequences. The resulting amplification products can be labeled directly during amplification reactions or labeled after amplification reactions, and used as probes to isolate full-length DNA fragments under conditions of appropriate stringency.

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art (Thein and Wallace, "The use of oligonucleotide as specific hybridization probes in the Diagnosis of Genetic Disorders", in *Human Genetic Diseases: A Practical Approach*, K. E. Davis Ed., (1986) pp 33-50, IRL: Herndon, Va.; and Rychlik, W., In *Methods in Molecular Biology*, White, B. A. Ed., (1993) Vol. 15, pp 31-39, PCR Protocols: Current Methods and Applications. Humania: Totowa, N.J.).

Generally two short segments of the instant sequences may be used in PCR protocols to amplify longer nucleic acid fragments encoding homologous genes from DNA or RNA. PCR may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding eukaryotic genes.

Alternatively, the second primer sequence may be based upon sequences derived from the cloning vector. For example, the skilled artisan can follow the RACE protocol (Frohman et al., *PNAS USA,* 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (Gibco/BRL, Gaithersburg, Md.), specific 3' or 5' cDNA fragments can be isolated (Ohara et al., *PNAS USA,* 86:5673 (1989); Loh et al., *Science,* 243:217 (1989)).

In other embodiments, any of the Δ9 elongase nucleic acid fragments described herein (or any homologs identified thereof) may be used for creation of new and improved fatty acid elongases. As is well known in the art, in vitro mutagenesis and selection, chemical mutagenesis, "gene shuffling" methods or other means can be employed to obtain mutations of naturally occurring elongase genes (wherein such mutations may include deletions, insertions and point mutations, or combinations thereof). This would permit production of a polypeptide having elongase activity, respectively, in vivo with more desirable physical and kinetic parameters for function in the host cell such as a longer half-life or a higher rate of production of a desired PUFA. Or, if desired, the regions of a polypeptide of interest (i.e., a Δ9 elongase) important for enzymatic activity can be determined through routine mutagenesis, expression of the resulting mutant polypeptides and determination of their activities. An overview of these techniques is described in PCT Publication No. WO 2004/101757. All such mutant proteins and nucleotide sequences encoding them that are derived from EgD9e, EgD9eS, E389D9e and E389D9eS are within the scope of the present invention.

Alternatively, improved fatty acids may be synthesized by domain swapping, wherein a functional domain from any of the Δ9 elongase nucleic acid fragments described herein are exchanged with a functional domain in an alternate elongase gene to thereby result in a novel protein.

Methods for Production of Various ω-3 and/or ω-6 Fatty Acids

It is expected that introduction of chimeric genes encoding the Δ9 elongases described herein (i.e., EgD9e, EgD9eS, E389D9e, E389D9eS or other mutant enzymes, codon-optimized enzymes or homologs thereof), under the control of the appropriate promoters will result in increased production of EDA and/or ETrA in the transformed host organism, respectively. As such, the present invention encompasses a method for the direct production of PUFAs comprising exposing a fatty acid substrate (i.e., LA and/or ALA) to the elongase enzymes described herein (e.g., EgD9e, EgD9eS, E389D9e, E389D9eS), such that the substrate is converted to the desired fatty acid product (i.e., EDA and/or ETrA).

More specifically, it is an object of the present invention to provide a method for the production of EDA in a host cell (e.g., oleaginous yeast, soybean), wherein the host cell comprises:

a) an isolated polynucleotide sequence encoding a polypeptide having Δ9 elongase activity, selected from the group consisting of:
   (1) an isolated nucleic acid sequence comprising a nucleotide sequence encoding a polypeptide having Δ9 elongase activity, wherein the polypeptide has at least 70% amino acid identity, based on the Clustal V method of alignment, when compared to an amino acid sequence as set forth in SEQ ID NO:2 (EgD9e) or SEQ ID NO:5 (E389D9e);
   (2) an isolated nucleic acid sequence comprising a nucleotide sequence encoding a polypeptide having Δ9 elongase activity, wherein the nucleotide sequence hybridizes with a nucleotide sequence as set forth in SEQ ID NO:1 (EgD9e), SEQ ID NO:3 (EgD9eS), SEQ ID NO:4 (E389D9e) or SEQ ID NO:6 (E389D9eS) under the following stringent hybridization conditions: 0.1×SSC, 0.1% SDS, 65° C. and washed with 2×SSC, 0.1% SDS followed by 0.1×SSC, 0.1% SDS; and b) a source of LA;

wherein the host cell is grown under conditions such that the Δ9 elongase is expressed and the LA is converted to EDA, and wherein the EDA is optionally recovered.

In alternate embodiments of the present invention, the Δ9 elongase may be used for the conversion of ALA to ETrA. Accordingly the invention provides a method for the production of ETrA, wherein the host cell comprises:

a) an isolated polynucleotide sequence encoding a polypeptide having Δ9 elongase activity, selected from the group consisting of:
   (1) an isolated nucleic acid sequence comprising a nucleotide sequence encoding a polypeptide having Δ9 elongase activity, wherein the polypeptide has at least 70% amino acid identity, based on the Clustal V method of alignment, when compared to an amino acid sequence as set forth in SEQ ID NO:2 (EgD9e) or SEQ ID NO:5 (E389D9e);
   (2) an isolated nucleic acid sequence comprising a nucleotide sequence encoding a polypeptide having Δ9 elongase activity, wherein the nucleotide sequence hybridizes with a nucleotide sequence as set forth in SEQ ID NO:1 (EgD9e), SEQ ID NO:3 (EgD9eS), SEQ ID NO:4 (E389D9e) or SEQ ID NO:6 (E389D9eS) under the following stringent hybridization conditions: 0.1×SSC, 0.1% SDS, 65° C. and washed with 2×SSC, 0.1% SDS followed by 0.1×SSC, 0.1% SDS; and b) a source of ALA;

wherein the host cell is grown under conditions such that the Δ9 elongase is expressed and the ALA is converted to ETrA, and wherein the ETrA is optionally recovered.

Alternatively, each Δ9 elongase gene and its corresponding enzyme product described herein can be used indirectly for the production of various ω-6 and ω-3 PUFAs, including e.g., DGLA, ETA, ARA, EPA, DPA and/or DHA (FIG. 1; see PCT Publication No. WO 2004/101757). Indirect production of ω-3/ω-6 PUFAs occurs wherein the fatty acid substrate is converted indirectly into the desired fatty acid product, via means of an intermediate step(s) or pathway intermediate(s). Thus, it is contemplated that the Δ9 elongases described herein (e.g., EgD9e, EgD9eS, E389D9e, E389D9eS or other mutant enzymes, codon-optimized enzymes or homologs thereof) may be expressed in conjunction with additional genes encoding enzymes of the PUFA biosynthetic pathway (e.g., Δ6 desaturases, $C_{18/20}$ elongases, Δ17 desaturases, Δ15 desaturases, Δ9 desaturases, Δ12 desaturases, $C_{14/16}$ elongases, $C_{16/18}$ elongases, Δ5 desaturases, Δ8 desaturases, Δ4 desaturases, $C_{20/22}$ elongases) to result in higher levels of production of longer-chain ω-3/ω-6 fatty acids (e.g., ARA, EPA, DPA and DHA).

In preferred embodiments, the Δ9 elongases of the present invention will minimally be expressed in conjunction with a Δ8 desaturase (e.g., a Δ8 desaturase as set forth in SEQ ID NO:61 [EgD8] or a codon-optimized Δ8 desaturase as set forth in SEQ ID NO:69 [EgD8S]). However, the particular genes included within a particular expression cassette will depend on the host cell (and its PUFA profile and/or desaturase/elongase profile), the availability of substrate and the desired end product(s).

In alternative embodiments, it may be useful to disrupt a host organism's native Δ9 elongase, based on the complete sequences described herein, the complement of those complete sequences, substantial portions of those sequences, codon-optimized elongases derived therefrom and those sequences that are substantially homologous thereto.

Plant Expression Systems, Cassettes & Vectors, and Transformation

In one embodiment, this invention concerns a recombinant construct comprising any one of the Δ9 elongase polynucleotides of the invention operably linked to at least one regulatory sequence suitable for expression in a plant.

A promoter is a DNA sequence that directs the cellular machinery of a plant to produce RNA from the contiguous coding sequence downstream (3') of the promoter. The promoter region influences the rate, developmental stage, and cell type in which the RNA transcript of the gene is made. The RNA transcript is processed to produce mRNA which serves as a template for translation of the RNA sequence into the amino acid sequence of the encoded polypeptide. The 5' non-translated leader sequence is a region of the mRNA upstream of the protein coding region that may play a role in initiation and translation of the mRNA. The 3' transcription termination/polyadenylation signal is a non-translated region downstream of the protein coding region that functions in the plant cell to cause termination of the RNA transcript and the addition of polyadenylate nucleotides to the 3' end of the RNA.

The origin of the promoter chosen to drive expression of the Δ9 elongase coding sequence is not important as long as it has sufficient transcriptional activity to accomplish the invention by expressing translatable mRNA for the desired nucleic acid fragments in the desired host tissue at the right time. Either heterologous or non-heterologous (i.e., endogenous) promoters can be used to practice the invention. For example, suitable promoters include, but are not limited to: the α-prime subunit of β-conglycinin promoter, the Kunitz trypsin inhibitor 3 promoter, the annexin promoter, the Gly1 promoter, the beta subunit of beta-conglycinin promoter, the P34/Gly Bd m 30K promoter, the albumin promoter, the Leg A1 promoter and the Leg A2 promoter.

The annexin, or P34, promoter is described in PCT Publication No. WO 2004/071178 (published Aug. 26, 2004). The level of activity of the annexin promoter is comparable to that of many known strong promoters, such as: (1) the CaMV $^{35}$S promoter (Atanassova et al., *Plant Mol. Biol.,* 37:275-285 (1998); Battraw and Hall, *Plant Mol. Biol.,* 15:527-538 (1990); Holtorf et al., *Plant Mol. Biol.,* 29:637-646 (1995); Jefferson et al., *EMBO J.,* 6:3901-3907 (1987); Wilmink et al., *Plant Mol. Biol.,* 28:949-955 (1995)); (2) the *Arabidopsis* oleosin promoters (Plant et al., *Plant Mol. Biol.,* 25:193-205 (1994); Li, Texas A&M University Ph.D. dissertation, pp. 107-128 (1997)); (3) the *Arabidopsis* ubiquitin extension protein promoters (Callis et al., *J. Biol. Chem.,* 265(21):12486-93 (1990)); (4) a tomato ubiquitin gene promoter (Rollfinke et al., *Gene,* 211(2):267-76 (1998)); (5) a soybean heat shock protein promoter (Schoffl et al., *Mol. Gen. Genet.,* 217(2-3):246-53 (1989)); and, (6) a maize H3 histone gene promoter (Atanassova et al., *Plant Mol. Biol.,* 37(2):275-85 (1989)).

Another useful feature of the annexin promoter is its expression profile in developing seeds. The annexin promoter is most active in developing seeds at early stages (before 10 days after pollination) and is largely quiescent in later stages. The expression profile of the annexin promoter is different from that of many seed-specific promoters, e.g., seed storage protein promoters, which often provide highest activity in later stages of development (Chen et al., *Dev. Genet.,* 10:112-122 (1989); Ellerstrom et al., *Plant Mol. Biol.,* 32:1019-1027 (1996); Keddie et al., *Plant Mol. Biol.,* 24:327-340 (1994); Plant et al., (supra); Li, (supra)). The annexin promoter has a more conventional expression profile but remains distinct from other known seed specific promoters. Thus, the annexin promoter will be a very attractive candidate when overexpression, or suppression, of a gene in embryos is desired at an early developing stage. For example, it may be desirable to overexpress a gene regulating early embryo development or a gene involved in the metabolism prior to seed maturation.

Following identification of an appropriate promoter suitable for expression of a specific Δ9 elongase coding sequence, the promoter is then operably linked in a sense orientation using conventional means well known to those skilled in the art.

Standard recombinant DNA and molecular cloning techniques used herein are well known in the art and are described more fully in Sambrook, J. et al., In *Molecular Cloning: A Laboratory Manual;* 2$^{nd}$ ed.; Cold Spring Harbor Laboratory Press: Cold Spring Harbor, N.Y., 1989 (hereinafter "Sambrook et al., 1989") or Ausubel, F. M., Brent, R., Kingston, R. E., Moore, D. D., Seidman, J. G., Smith, J. A. and Struhl, K., Eds.; In *Current Protocols in Molecular Biology*; John Wiley and Sons: New York, 1990 (hereinafter "Ausubel et al., 1990").

Once the recombinant construct has been made, it may then be introduced into a plant cell of choice by methods well known to those of ordinary skill in the art (e.g., transfection, transformation and electroporation). Oilseed plant cells are the preferred plant cells. The transformed plant cell is then cultured and regenerated under suitable conditions permitting expression of the long-chain PUFA which is then optionally recovered and purified.

The recombinant constructs of the invention may be introduced into one plant cell; or, alternatively, each construct may be introduced into separate plant cells.

Expression in a plant cell may be accomplished in a transient or stable fashion as is described above.

The desired long-chain PUFAs can be expressed in seed. Also within the scope of this invention are seeds or plant parts obtained from such transformed plants.

Plant parts include differentiated and undifferentiated tissues including, but not limited to the following: roots, stems, shoots, leaves, pollen, seeds, tumor tissue and various forms of cells and culture (e.g., single cells, protoplasts, embryos and callus tissue). The plant tissue may be in plant or in a plant organ, tissue or cell culture.

The term "plant organ" refers to plant tissue or a group of tissues that constitute a morphologically and functionally distinct part of a plant. The term "genome" refers to the following: 1) the entire complement of genetic material (genes and non-coding sequences) that is present in each cell of an organism, or virus or organelle; and/or 2) a complete set of chromosomes inherited as a (haploid) unit from one parent.

Thus, this invention also concerns a method for transforming a cell, comprising transforming a cell with a recombinant construct of the invention and selecting those cells transformed with said recombinant construct.

Also of interest is a method for producing a transformed plant comprising transforming a plant cell with the Δ9 elongase polynucleotides of the instant invention and regenerating a plant from the transformed plant cell.

Methods for transforming dicots (primarily by use of *Agrobacterium tumefaciens*) and obtaining transgenic plants have been published, among others, for: cotton (U.S. Pat. No. 5,004,863; U.S. Pat. No. 5,159,135); soybean (U.S. Pat. No. 5,569,834; U.S. Pat. No. 5,416,011); *Brassica* (U.S. Pat. No. 5,463,174); peanut (Cheng et al., *Plant Cell Rep.,* 15:653-657 (1996); McKently et al., *Plant Cell Rep.,* 14:699-703 (1995)); papaya (Ling, K. et al., *Bio/technology,* 9:752-758 (1991)); and pea (Grant et al., *Plant Cell Rep.,* 15:254-258 (1995)). For a review of other commonly used methods of plant transformation see Newell, C. A. (*Mol. Biotechnol.,* 16:53-65 (2000)). One of these methods of transformation uses *Agrobacterium rhizogenes* (Tepfler, M. and Casse-Delbart, F., *Microbiol. Sci.,* 4:24-28 (1987)). Transformation of soybeans using direct delivery of DNA has been published using PEG fusion (PCT Publication No. WO 92/17598), electroporation (Chowrira, G. M. et al., *Mol. Biotechnol.,* 3:17-23 (1995); Christou, P. et al., *Proc. Natl. Acad. Sci. Sci. USA,* 84:3962-3966 (1987)), microinjection, or particle bombardment (McCabe, D. E. et al., *Bio/Technology,* 6:923 (1988); Christou et al., *Plant Physiol.,* 87:671-674 (1988)).

There are a variety of methods for the regeneration of plants from plant tissue. The particular method of regeneration will depend on the starting plant tissue and the particular plant species to be regenerated. The regeneration, development and cultivation of plants from single plant protoplast transformants or from various transformed explants is well known in the art (Weissbach and Weissbach, In: Methods for Plant Molecular Biology, (Eds.), Academic: San Diego, Calif. (1988)). This regeneration and growth process typically includes the steps of selection of transformed cells and culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide is cultivated using methods well known to one skilled in the art.

In addition to the above discussed procedures, practitioners are familiar with the standard resource materials which describe specific conditions and procedures for: the construction, manipulation and isolation of macromolecules (e.g., DNA molecules, plasmids, etc.); the generation of recombinant DNA fragments and recombinant expression constructs; and, the screening and isolating of clones. See, for example: Sambrook et al., Molecular Cloning: A Laboratory Manual, Cold Spring Harbor: NY (1989); Maliga et al., Methods in Plant Molecular Biology, Cold Spring Harbor: NY (1995); Birren et al., Genome Analysis: Detecting Genes, Vol. 1, Cold Spring Harbor: NY (1998); Birren et al., Genome Analysis: Analyzing DNA, Vol. 2, Cold Spring Harbor: NY (1998); Plant Molecular Biology: A Laboratory Manual, eds. Clark, Springer: NY (1997).

Examples of oilseed plants include, but are not limited to: soybean, *Brassica* species, sunflower, maize, cotton, flax and safflower.

Examples of PUFAs having at least twenty carbon atoms and five or more carbon-carbon double bonds include, but are not limited to, ω-3 fatty acids such as EPA, DPA and DHA. Seeds obtained from such plants are also within the scope of this invention, as well as oil obtained from such seeds.

Thus, in one embodiment this invention concerns an oilseed plant comprising:

a) a first recombinant DNA construct comprising an isolated polynucleotide encoding a Δ9 elongase polypeptide, operably linked to at least one regulatory sequence; and, b) at least one additional recombinant DNA construct comprising an isolated polynucleotide, operably linked to at least one regulatory sequence, encoding a polypeptide selected from the group consisting of: a Δ4 desaturase, a Δ5 desaturase, a Δ6 desaturase, a Δ8 desaturase, a Δ9 desaturase, a Δ12 desaturase, a Δ15 desaturase, a Δ17 desaturase, a $C_{14/16}$ elongase, a $C_{16/18}$ elongase, a $C_{18/20}$ elongase and a $C_{20/22}$ elongase.

Such additional desaturases are discussed, for example, in U.S. Pat. No. 6,075,183, No. 5,968,809, No. 6,136,574, No. 5,972,664, No. 6,051,754, No. 6,410,288 and PCT Publications No. WO 98/46763, No. WO 98/46764, No. WO 00/12720 and No. WO 00/40705.

The choice of combination of cassettes used depends in part on the PUFA profile and/or desaturase/elongase profile of the oilseed plant cells to be transformed and the long-chain PUFA(s) which is to be expressed.

In another aspect, this invention concerns a method for making long-chain PUFAs in a plant cell comprising:

(a) transforming a cell with a recombinant construct of the invention; and, (b) selecting those transformed cells that make long-chain PUFAs.

In still another aspect, this invention concerns a method for producing at least one PUFA in a soybean cell comprising:

(a) transforming a soybean cell with a first recombinant DNA construct comprising:

(i) an isolated polynucleotide encoding a Δ9 elongase polypeptide, operably linked to at least one regulatory sequence; and, (ii) at least one additional recombinant DNA construct comprising an isolated polynucleotide, operably linked to at least one regulatory sequence, encoding a polypeptide selected from the group consisting of: a Δ4 desaturase, a Δ5 desaturase, a Δ6 desaturase, a Δ8 desaturase, a Δ9 desaturase, a Δ12 desaturase, a Δ15 desaturase, a Δ17 desaturase, a $C_{14/16}$ elongase, a $C_{16/18}$ elongase, a $C_{18/20}$ elongase and a $C_{20/22}$ elongase;

(b) regenerating a soybean plant from the transformed cell of step (a); and, (c) selecting those seeds obtained from the plants of step (b) having an altered level of PUFAs when compared to the level in seeds obtained from a nontransformed soybean plant.

In particularly preferred embodiments, the at least one additional recombinant DNA construct encodes a polypeptide having Δ8 desaturase activity, e.g., the Δ8 desaturase isolated and/or derived from *Euglena gracilis* and set forth in SEQ ID NOs:61 and 69.

Microbial Expression Systems, Cassettes & Vectors, and Transformation

The Δ9 elongase genes and gene products described herein (i.e., EgD9e, EgD9eS, E389D9e, E389D9eS, or other mutant enzymes, codon-optimized enzymes or homologs thereof) may also be produced in heterologous microbial host cells, particularly in the cells of oleaginous yeasts (e.g., *Yarrowia lipolytica*). Expression in recombinant microbial hosts may be useful for the production of various PUFA pathway intermediates, or for the modulation of PUFA pathways already existing in the host for the synthesis of new products heretofore not possible using the host.

Microbial expression systems and expression vectors containing regulatory sequences that direct high level expression of foreign proteins are well known to those skilled in the art. Any of these could be used to construct chimeric genes for production of any of the gene products of the instant sequences. These chimeric genes could then be introduced into appropriate microorganisms via transformation to provide high-level expression of the encoded enzymes.

Vectors or DNA cassettes useful for the transformation of suitable microbial host cells are well known in the art. The specific choice of sequences present in the construct is dependent upon the desired expression products (supra), the nature of the host cell and the proposed means of separating transformed cells versus non-transformed cells. Typically, however, the vector or cassette contains sequences directing transcription and translation of the relevant gene(s), a selectable marker and sequences allowing autonomous replication or chromosomal integration. Suitable vectors comprise a region 5' of the gene that controls transcriptional initiation (e.g., a promoter) and a region 3' of the DNA fragment that controls transcriptional termination (i.e., a terminator). It is most preferred when both control regions are derived from genes from the transformed microbial host cell, although it is to be understood that such control regions need not be derived from the genes native to the specific species chosen as a production host.

Initiation control regions or promoters which are useful to drive expression of the instant Δ9 elongase ORFs in the desired microbial host cell are numerous and familiar to those skilled in the art. Virtually any promoter capable of directing expression of these genes in the selected host cell is suitable for the present invention. Expression in a microbial host cell can be accomplished in a transient or stable fashion. Transient expression can be accomplished by inducing the activity of a regulatable promoter operably linked to the gene of interest. Stable expression can be achieved by the use of a constitutive promoter operably linked to the gene of interest. As an example, when the host cell is yeast, transcriptional and translational regions functional in yeast cells are provided, particularly from the host species (e.g., see PCT Publication No. WO 2004/101757 [U.S. Publication 2005-0136519-A1] and PCT Publication No. WO 2006/052870 [U.S. Publication 2006-0115881-A1] for preferred transcriptional initiation regulatory regions for use in *Yarrowia lipolytica*). Any one of a number of regulatory sequences can be used, depending upon whether constitutive or induced transcription is desired, the efficiency of the promoter in expressing the ORF of interest, the ease of construction and the like.

Nucleotide sequences surrounding the translational initiation codon 'ATG' have been found to affect expression in yeast cells. If the desired polypeptide is poorly expressed in yeast, the nucleotide sequences of exogenous genes can be modified to include an efficient yeast translation initiation sequence to obtain optimal gene expression. For expression in yeast, this can be done by site-directed mutagenesis of an inefficiently expressed gene by fusing it in-frame to an endogenous yeast gene, preferably a highly expressed gene. Alternatively, one can determine the consensus translation initiation sequence in the host and engineer this sequence into heterologous genes for their optimal expression in the host of interest.

The termination region can be derived from the 3' region of the gene from which the initiation region was obtained or from a different gene. A large number of termination regions are known and function satisfactorily in a variety of hosts (when utilized both in the same and different genera and species from where they were derived). The termination region usually is selected more as a matter of convenience rather than because of any particular property. Preferably, when the microbial host is a yeast cell, the termination region is derived from a yeast gene (particularly *Saccharomyces, Schizosaccharomyces, Candida, Yarrowia* or *Kluyveromyces*). The 3'-regions of mammalian genes encoding γ-interferon and α-2 interferon are also known to function in yeast. Termination control regions may also be derived from various genes native to the preferred hosts. Optionally, a termination site may be unnecessary; however, it is most preferred if included. Although not intended to be limiting, termination regions useful in the disclosure herein include: ~100 bp of the 3' region of the *Yarrowia lipolytica* extracellular protease (XPR; GenBank Accession No. M17741); the acyl-coA oxidase (Aco3: GenBank Accession No. AJ001301 and No. CAA04661; Pox3: GenBank Accession No. XP_503244) terminators; the Pex20 (GenBank Accession No. AF054613) terminator; the Pex16 (GenBank Accession No. U75433) terminator; the Lip1 (GenBank Accession No. Z50020) terminator; the Lip2 (GenBank Accession No. AJ012632) terminator; and the 3-oxoacyl-coA thiolase (OCT; GenBank Accession No. X69988) terminator.

As one of skill in the art is aware, merely inserting a gene into a cloning vector does not ensure that it will be successfully expressed at the level needed. In response to the need for a high expression rate, many specialized expression vectors have been created by manipulating a number of different genetic elements that control aspects of transcription, translation, protein stability, oxygen limitation and secretion from the microbial host cell. More specifically, some of the molecular features that have been manipulated to control gene expression include: 1) the nature of the relevant transcriptional promoter and terminator sequences; 2) the number of copies of the cloned gene and whether the gene is plasmid-borne or integrated into the genome of the host cell; 3) the final cellular location of the synthesized foreign protein; 4) the efficiency of translation and correct folding of the protein in the host organism; 5) the intrinsic stability of the mRNA and protein of the cloned gene within the host cell; and 6) the codon usage within the cloned gene, such that its frequency approaches the frequency of preferred codon usage of the host cell. Each of these types of modifications are encompassed in the present invention, as means to further optimize expression of the Δ9 elongases described herein.

Once the DNA encoding a polypeptide suitable for expression in an appropriate microbial host cell (e.g., oleaginous yeast) has been obtained (e.g., a chimeric gene comprising a promoter, ORF and terminator), it is placed in a plasmid vector capable of autonomous replication in a host cell, or it is directly integrated into the genome of the host cell. Integration of expression cassettes can occur randomly within the host genome or can be targeted through the use of constructs containing regions of homology with the host genome sufficient to target recombination within the host locus. Where constructs are targeted to an endogenous locus, all or some of the transcriptional and translational regulatory regions can be provided by the endogenous locus.

In the present invention, the preferred method of expressing genes in *Yarrowia lipolytica* is by integration of linear DNA into the genome of the host; and, integration into multiple locations within the genome can be particularly useful when high level expression of genes are desired. Toward this end, it is desirable to identify a sequence within the genome that is present in multiple copies.

Schmid-Berger et al. (*J. Bact.,* 176(9):2477-2482 (1994)) discovered the first retrotransposon-like element Ylt1 in *Yarrowia lipolytica*. This retrotransposon is characterized by the presence of long terminal repeats (LTRs; each approximately 700 bp in length) called zeta regions. Ylt1 and solo zeta elements were present in a dispersed manner within the genome in at least 35 copies/genome and 50-60 copies/genome, respectively; both elements were determined to function as sites of homologous recombination. Further, work by Juretzek et al. (*Yeast,* 18:97-113 (2001)) demonstrated that gene expression could be dramatically increased by targeting plasmids into the repetitive regions of the yeast genome (using linear DNA with LTR zeta regions at both ends), as compared to the expression obtained using low-copy plasmid transformants. Thus, zeta-directed integration can be ideal as a means to ensure multiple integration of plasmid DNA into *Yarrowia lipolytica*, thereby permitting high-level gene expression. Unfortunately, however, not all strains of *Yarrowia lipolytica* possess zeta regions (e.g., the strain identified as ATCC Accession No. #20362). When the strain lacks such regions, it is also possible to integrate plasmid DNA comprising expression cassettes into alternate loci to reach the desired copy number for the expression cassette. For example, preferred alternate loci include: the Ura3 locus (GenBank Accession No. AJ306421), the Leu2 gene locus (GenBank Accession No. AF260230), the Lys5 gene (GenBank Accession No. M34929), the Aco2 gene locus (Gen Bank Accession No. AJ001300), the Pox3 gene locus (Pox3: GenBank Accession No. XP_503244; or, Aco3: GenBank Accession No. AJ001301), the Δ12 desaturase gene locus (PCT Publication No. WO 2004/104167), the Lip1 gene locus (Gen Bank Accession No. Z50020) and/or the Lip2 gene locus (GenBank Accession No. AJ012632).

Advantageously, the Ura3 gene can be used repeatedly in combination with 5-fluoroorotic acid (5-fluorouracil-6-carboxylic acid monohydrate; "5-FOA") selection (infra), to readily permit genetic modifications to be integrated into the *Yarrowia* genome in a facile manner.

Where two or more genes are expressed from separate replicating vectors, it is desirable that each vector has a different means of selection and should lack homology to the other construct(s) to maintain stable expression and prevent reassortment of elements among constructs. Judicious choice of regulatory regions, selection means and method of propagation of the introduced construct(s) can be experimentally determined so that all introduced genes are expressed at the necessary levels to provide for synthesis of the desired products.

Constructs comprising the gene of interest may be introduced into a microbial host cell by any standard technique. These techniques include transformation (e.g., lithium acetate transformation [*Methods in Enzymology,* 194:186-187 (1991)]), protoplast fusion, bolistic impact, electroporation, microinjection, or any other method that introduces the gene of interest into the host cell. More specific teachings applicable for oleaginous yeasts (i.e., *Yarrowia lipolytica*) include U.S. Pat. No. 4,880,741 and U.S. Pat. No. 5,071,764 and Chen, D. C. et al. (*Appl. Microbiol. Biotechnol.,* 48(2): 232-235 (1997)).

For convenience, a host cell that has been manipulated by any method to take up a DNA sequence (e.g., an expression cassette) will be referred to as "transformed" or "recombinant" herein. The transformed host will have at least one copy of the expression construct and may have two or more, depending upon whether the gene is integrated into the genome, amplified or is present on an extrachromosomal element having multiple copy numbers.

The transformed host cell can be identified by various selection techniques, as described in PCT Publication No. WO 2004/101757 [U.S. Publication 2005-0136519-A1] and PCT Publication No. WO 2006/052870 [U.S. Publication 2006-0115881-A1]. Preferred selection methods for use herein are resistance to kanamycin, hygromycin and the amino glycoside G418, as well as ability to grow on media lacking uracil, leucine, lysine, tryptophan or histidine. In alternate embodiments, 5-FOA is used for selection of yeast Ura− mutants. The compound is toxic to yeast cells that possess a functioning URA3 gene encoding orotidine 5'-monophosphate decarboxylase (OMP decarboxylase); thus, based on this toxicity, 5-FOA is especially useful for the selection and identification of $Ura^-$ mutant yeast strains (Bartel, P. L. and Fields, S., Yeast 2-Hybrid System, Oxford University: New York, v. 7, pp 109-147, 1997). More specifically, one can first knockout the native Ura3 gene to produce a strain having a Ura− phenotype, wherein selection occurs based on 5-FOA resistance. Then, a cluster of multiple chimeric genes and a new Ura3 gene can be integrated into a different locus of the *Yarrowia* genome to thereby produce a new strain having a Ura+ phenotype. Subsequent integration produces a new Ura3− strain (again identified using 5-FOA selection), when the introduced Ura3 gene is knocked out. Thus, the Ura3 gene (in combination with 5-FOA selection) can be used as a selection marker in multiple rounds of transformation.

Following transformation, substrates suitable for the instant Δ9 elongases (and, optionally other PUFA enzymes that are co-expressed within the host cell) may be produced by the host either naturally or transgenically, or they may be provided exogenously.

Microbial host cells for expression of the instant genes and nucleic acid fragments may include hosts that grow on a variety of feedstocks, including simple or complex carbohydrates, fatty acids, organic acids, oils and alcohols, and/or hydrocarbons over a wide range of temperature and pH values. The genes described in the instant invention have been isolated for expression in an oleaginous yeast (and in particular *Yarrowia lipolytica*); however, it is contemplated that because transcription, translation and the protein biosynthetic apparatus are highly conserved, any bacteria, yeast, algae and/or fungus will be a suitable microbial host for expression of the present nucleic acid fragments.

Preferred microbial hosts, however, are oleaginous yeasts. These organisms are naturally capable of oil synthesis and accumulation, wherein the oil can comprise greater than about 25% of the cellular dry weight, more preferably greater than about 30% of the cellular dry weight, and most preferably greater than about 40% of the cellular dry weight. Genera typically identified as oleaginous yeast include, but are not limited to: *Yarrowia, Candida, Rhodotorula, Rhodosporidium, Cryptococcus, Trichosporon* and *Lipomyces*. More specifically, illustrative oil-synthesizing yeasts include: *Rhodosporidium toruloides, Lipomyces starkeyii, L. lipoferus, Candida revkaufi, C. pulcherrima, C. tropicalis, C. utilis, Trichosporon pullans, T. cutaneum, Rhodotorula glutinus, R. graminis*, and *Yarrowia lipolytica* (formerly classified as *Candida lipolytica*).

Most preferred is the oleaginous yeast *Yarrowia lipolytica*; and, in a further embodiment, most preferred are the *Y. lipolytica* strains designated as ATCC #20362, ATCC #8862, ATCC #18944, ATCC #76982 and/or LGAM S(7)1 (Papanikolaou S., and Aggelis G., *Bioresour. Technol.,* 82(1):43-9 (2002)).

Historically, various strains of *Y. lipolytica* have been used for the manufacture and production of: isocitrate lyase; lipases; polyhydroxyalkanoates; citric acid; erythritol; 2-oxoglutaric acid; γ-decalactone; γ-dodecalatone; and pyruvic acid. Specific teachings applicable for engineering ARA, EPA and DHA production in *Y. lipolytica* are provided in U.S. patent application Ser. No. 11/264,784 (PCT Publication Ser. No. WO 2006/055322), Ser. No. 11/265,761 (PCT Publication No. WO 2006/052870) and Ser. No. 11/264,737 (PCT Publication No. WO 2006/052871), respectively.

Other preferred microbial hosts include oleaginous bacteria, algae and other fungi; and, within this broad group of microbial hosts, of particular interest are microorganisms that synthesize ω-3/ω-6 fatty acids (or those that can be genetically engineered for this purpose [e.g., other yeast such as *Saccharomyces cerevisiae*]). Thus, for example, transformation of *Mortierella alpina* (which is commercially used for production of ARA) with any of the present Δ9 elongase genes under the control of inducible or regulated promoters could yield a transformant organism capable of synthesizing increased quantities of EDA; this could be converted to increased quantities of DGLA if a Δ8 desaturase gene was co-expressed. The method of transformation of *M. alpina* is described by Mackenzie et al. (*Appl. Environ. Microbiol.,* 66:4655 (2000)). Similarly, methods for transformation of Thraustochytriales microorganisms are disclosed in U.S. Pat. No. 7,001,772.

Based on the teachings described above, in one embodiment this invention is drawn to a method of producing either EDA or ETrA, respectively, comprising:

a) providing an oleaginous yeast comprising:
   (i) a first recombinant DNA construct comprising an isolated polynucleotide encoding a Δ9 elongase polypeptide, operably linked to at least one regulatory sequence; and,
   (ii) a source of elongase substrate consisting of either LA or ALA, respectively; and,
b) growing the yeast of step (a) in the presence of a suitable fermentable carbon source wherein the gene encoding a Δ9 elongase polypeptide is expressed and LA is converted to EDA or ALA is converted to ETrA, respectively; and,
c) optionally recovering the EDA or ETrA, respectively, of step (b).

Substrate feeding may be required.

In some preferred embodiments, the nucleotide sequence of the gene encoding a Δ9 elongase is selected from the group consisting of SEQ ID NO:1 and SEQ ID NO:4. In alternate preferred embodiments, the nucleotide sequence of the gene encoding a Δ9 elongase polypeptide is set forth in SEQ ID NO:3 (wherein at least 106 codons have been optimized for expression in *Yarrowia* relative to SEQ ID NO:1). And, in other preferred embodiments, the nucleotide sequence of the gene encoding a Δ9 elongase polypeptide is set forth in SEQ ID NO:6 (wherein at least 113 codons have been optimized for expression in *Yarrowia* relative to SEQ ID NO:4).

Of course, since naturally produced PUFAs in oleaginous yeast are limited to 18:2 fatty acids (i.e., LA), and less commonly, 18:3 fatty acids (i.e., ALA), in more preferred embodiments of the present invention the oleaginous yeast will be genetically engineered to express multiple enzymes necessary for long-chain PUFA biosynthesis (thereby enabling production of e.g., ARA, EPA, DPA and DHA), in addition to the Δ9 elongases described herein.

Specifically, in one embodiment this invention concerns an oleaginous yeast comprising:

a) a first recombinant DNA construct comprising an isolated polynucleotide encoding a Δ9 elongase polypeptide, operably linked to at least one regulatory sequence; and, b) at least one additional recombinant DNA construct comprising an isolated polynucleotide, operably linked to at least one regulatory sequence, encoding a polypeptide selected from the group consisting of: a Δ4 desaturase, a Δ5 desaturase, Δ6 desaturase, a Δ9 desaturase, a Δ12 desaturase, a Δ15 desaturase, a Δ17 desaturase, a Δ8 desaturase, a $C_{14/16}$ elongase, a $C_{16/18}$ elongase, a $C_{18/20}$ elongase and a $C_{20/22}$ elongase.

In particularly preferred embodiments, the at least one additional recombinant DNA construct encodes a polypeptide having Δ8 desaturase activity, e.g., the Δ8 desaturase isolated and/or derived from *Euglena gracilis* and set forth in SEQ ID NOs:61 and 69.

Metabolic Engineering of ω-3 and/or ω-6 Fatty Acid Biosynthesis in Microbes

Methods for manipulating biochemical pathways are well known to those skilled in the art; and, it is expected that numerous manipulations will be possible to maximize ω-3 and/or ω-6 fatty acid biosynthesis in oleaginous yeasts, and particularly, in *Yarrowia lipolytica*. This may require metabolic engineering directly within the PUFA biosynthetic pathway or additional coordinated manipulation of various other metabolic pathways.

In the case of manipulations within the PUFA biosynthetic pathway, it may be desirable to increase the production of LA to enable increased production of ω-6 and/or ω-3 fatty acids. Introducing and/or amplifying genes encoding Δ9 desaturases and/or Δ12 desaturases may accomplish this. To maximize production of ω-6 unsaturated fatty acids, it is well known to one skilled in the art that production is favored in a host microorganism that is substantially free of ALA; thus, preferably, the host is selected or obtained by removing or inhibiting Δ15 or ω-3 type desaturase activity that permits conversion of LA to ALA. The endogenous desaturase activity can be reduced or eliminated by, for example: (1) providing a cassette for transcription of antisense sequences to the Δ15 desaturase transcription product; (2) disrupting the Δ15 desaturase gene through insertion, substitution and/or deletion of all or part of the target gene; or (3) using a host cell which naturally has [or has been mutated to have] low or no Δ15 desaturase activity. Inhibition of undesired desaturase pathways can also be accomplished through the use of specific desaturase inhibitors such as those described in U.S. Pat. No. 4,778,630.

Alternatively, it may be desirable to maximize production of ω-3 fatty acids (and minimize synthesis of ω-6 fatty acids). In this example, one could utilize a host microorganism wherein the Δ12 desaturase activity that permits conversion of oleic acid to LA is removed or inhibited; subsequently, appropriate expression cassettes would be introduced into the host, along with appropriate substrates (e.g., ALA) for conversion to ω-3 fatty acid derivatives of ALA (e.g., STA, ETrA, ETA, EPA, DPA, DHA).

In alternate embodiments, biochemical pathways competing with the ω-3 and/or ω-6 fatty acid biosynthetic pathways for energy or carbon, or native PUFA biosynthetic pathway enzymes that interfere with production of a particular PUFA end-product, may be eliminated by gene disruption or down-regulated by other means (e.g., antisense mRNA).

Detailed discussion of manipulations within the PUFA biosynthetic pathway as a means to increase ARA, EPA or DHA (and associated techniques thereof) are presented in PCT Publication No. WO 2006/055322 [U.S. Patent Publication No. 2006-0094092-A1], PCT Publication No. WO 2006/052870 [U.S. Patent Publication No. 2006-0115881-A1] and PCT Publication No. WO 2006/052871 [U.S. Patent Publication No. 2006-0110806-A1], respectively, as are desirable manipulations in the TAG biosynthetic pathway and the TAG degradation pathway (and associated techniques thereof).

Within the context of the present invention, it may be useful to modulate the expression of the fatty acid biosynthetic pathway by any one of the strategies described above. For example, the present invention provides methods whereby genes encoding key enzymes in the Δ9 elongase/Δ8 desaturase biosynthetic pathway are introduced into oleaginous yeasts for the production of ω-3 and/or ω-6 fatty acids. It will be particularly useful to express the present Δ9 elongase genes in oleaginous yeasts that do not naturally possess ω-3 and/or ω-6 fatty acid biosynthetic pathways and coordinate the expression of these genes, to maximize production of preferred PUFA products using various means for metabolic engineering of the host organism.

Microbial Fermentation Processes for PUFA Production

The transformed microbial host cell is grown under conditions that optimize expression of chimeric desaturase and elongase genes and produce the greatest and the most economical yield of desired PUFAs. In general, media conditions that may be optimized include the type and amount of carbon source, the type and amount of nitrogen source, the carbon-to-nitrogen ratio, the oxygen level, growth temperature, pH, length of the biomass production phase, length of the oil accumulation phase and the time and method of cell harvest. Microorganisms of interest, such as oleaginous yeast (e.g., *Yarrowia lipolytica*) are generally grown in complex media (e.g., yeast extract-peptone-dextrose broth (YPD)) or a defined minimal media that lacks a component necessary for growth and thereby forces selection of the desired expression cassettes (e.g., Yeast Nitrogen Base (DIFCO Laboratories, Detroit, Mich.)).

Fermentation media in the present invention must contain a suitable carbon source. Suitable carbon sources may include, but are not limited to: monosaccharides (e.g., glucose, fructose), disaccharides (e.g., lactose, sucrose), oligosaccharides, polysaccharides (e.g., starch, cellulose or mixtures thereof), sugar alcohols (e.g., glycerol) or mixtures from renewable feedstocks (e.g., cheese whey permeate, cornsteep liquor, sugar beet molasses, barley malt). Additionally, carbon sources may include alkanes, fatty acids, esters of fatty acids, monoglycerides, diglycerides, triglycerides, phospholipids and various commercial sources of fatty acids including vegetable oils (e.g., soybean oil) and animal fats. The carbon source may include one-carbon sources (e.g., carbon dioxide, methanol, formaldehyde, formate and carbon-containing amines) for which metabolic conversion into key biochemical intermediates has been demonstrated. Hence it is contemplated that the source of carbon utilized in the present invention may encompass a wide variety of carbon-containing sources and will only be limited by the choice of the host organism. Preferred carbon sources are sugars, glycerol, and/or fatty acids. Most preferred is glucose and/or fatty acids containing between 10-22 carbons.

Nitrogen may be supplied from an inorganic (e.g., $(NH_4)_2SO_4$) or organic (e.g., urea or glutamate) source. In addition to appropriate carbon and nitrogen sources, the fermentation media must also contain suitable minerals, salts, cofactors, buffers, vitamins and other components known to those skilled in the art suitable for the growth of the oleaginous host and promotion of the enzymatic pathways necessary for PUFA production. Particular attention is given to several metal ions (e.g., $Mn^{+2}$, $Co^{+2}$, $Zn^{+2}$, $Mg^{+2}$) that promote synthesis of lipids and PUFAs (Nakahara, T. et al., *Ind. Appl. Single Cell Oils*, D. J. Kyle and R. Colin, eds. pp 61-97 (1992)).

Preferred growth media in the present invention are common commercially prepared media, such as Yeast Nitrogen Base (DIFCO Laboratories, Detroit, Mich.). Other defined or synthetic growth media may also be used and the appropriate medium for growth of the transformant host cells will be known by one skilled in the art of microbiology or fermentation science. A suitable pH range for the fermentation is typically between about pH 4.0 to pH 8.0, wherein pH 5.5 to pH 7.5 is preferred as the range for the initial growth conditions. The fermentation may be conducted under aerobic or anaerobic conditions, wherein microaerobic conditions are preferred.

Typically, accumulation of high levels of PUFAs in oleaginous yeast cells requires a two-stage process, since the metabolic state must be "balanced" between growth and synthesis/storage of fats. Thus, most preferably, a two-stage fermentation process is necessary for the production of PUFAs in oleaginous yeast (e.g., *Yarrowia lipolytica*). This approach is described in PCT Publication No. WO 2004/101757, as are various suitable fermentation process designs (i.e., batch, fed-batch and continuous) and considerations during growth.

Purification and Processing of PUFA Oils

PUFAs may be found in the host microorganisms and plants as free fatty acids or in esterified forms such as acylglycerols, phospholipids, sulfolipids or glycolipids, and may be extracted from the host cells through a variety of means well-known in the art. One review of extraction techniques, quality analysis and acceptability standards for yeast lipids is that of Z. Jacobs (*Critical Reviews in Biotechnology,* 12(5/6): 463-491 (1992)). A brief review of downstream processing is also available by A. Singh and O. Ward (*Adv. Appl. Microbiol.,* 45:271-312 (1997)).

In general, means for the purification of PUFAs may include extraction with organic solvents, sonication, supercritical fluid extraction (e.g., using carbon dioxide), saponification and physical means such as presses, or combinations thereof. One is referred to the teachings of PCT Publication No. WO 2004/101757 for additional details.

Methods of isolating seed oils are well known in the art (Young et al., Processing of Fats and Oils, In *The Lipid Handbook*, Gunstone et al., eds., Chapter 5, pp 253-257; Chapman & Hall: London (1994)). For example, soybean oil is produced using a series of steps involving the extraction and purification of an edible oil product from the oil-bearing seed. Soybean oils and soybean byproducts are produced using the generalized steps shown in the Table below.

TABLE 5

Generalized Steps for Soybean Oil and Byproduct Production

| Process Step | Process | Impurities Removed and/or By-Products Obtained |
|---|---|---|
| #1 | Soybean seed | |
| #2 | Oil extraction | Meal |
| #3 | Degumming | Lecithin |
| #4 | Alkali or physical refining | Gums, free fatty acids, pigments |
| #5 | Water washing | Soap |
| #6 | Bleaching | Color, soap, metal |
| #7 | (Hydrogenation) | |
| #8 | (Winterization) | Stearine |
| #9 | Deodorization | Free fatty acids, tocopherols, sterols, volatiles |
| #10 | Oil products | |

More specifically, soybean seeds are cleaned, tempered, dehulled and flaked, thereby increasing the efficiency of oil extraction. Oil extraction is usually accomplished by solvent (e.g., hexane) extraction but can also be achieved by a combination of physical pressure and/or solvent extraction. The resulting oil is called crude oil. The crude oil may be degummed by hydrating phospholipids and other polar and neutral lipid complexes that facilitate their separation from the nonhydrating, triglyceride fraction (soybean oil). The resulting lecithin gums may be further processed to make commercially important lecithin products used in a variety of food and industrial products as emulsification and release (i.e., anti-sticking) agents. Degummed oil may be further refined for the removal of impurities (primarily free fatty acids, pigments and residual gums). Refining is accomplished by the addition of a caustic agent that reacts with free fatty acid to form soap and hydrates phosphatides and proteins in the crude oil. Water is used to wash out traces of soap formed during refining. The soapstock byproduct may be used directly in animal feeds or acidulated to recover the free fatty acids. Color is removed through adsorption with a bleaching earth that removes most of the chlorophyll and carotenoid compounds. The refined oil can be hydrogenated, thereby resulting in fats with various melting properties and textures. Winterization (fractionation) may be used to remove stearine from the hydrogenated oil through crystallization under carefully controlled cooling conditions. Deodorization (principally via steam distillation under vacuum) is the last step and is designed to remove compounds which impart odor or flavor to the oil. Other valuable byproducts such as tocopherols and sterols may be removed during the deodorization process. Deodorized distillate containing these byproducts may be sold for production of natural vitamin E and other high-value pharmaceutical products. Refined, bleached, (hydrogenated, fractionated) and deodorized oils and fats may be packaged and sold directly or further processed into more specialized products. A more detailed reference to soybean seed processing, soybean oil production and byproduct utilization can be found in Erickson, Practical Handbook of Soybean Processing and Utilization, The American Oil Chemists' Society and United Soybean Board (1995). Soybean oil is liquid at room temperature because it is relatively low in saturated fatty acids when compared with oils such as coconut, palm, palm kernel and cocoa butter.

Plant and microbial oils containing PUFAs that have been refined and/or purified can be hydrogenated, to thereby result in fats with various melting properties and textures. Many processed fats (including spreads, confectionery fats, hard butters, margarines, baking shortenings, etc.) require varying degrees of solidity at room temperature and can only be produced through alteration of the source oil's physical properties. This is most commonly achieved through catalytic hydrogenation.

Hydrogenation is a chemical reaction in which hydrogen is added to the unsaturated fatty acid double bonds with the aid of a catalyst such as nickel. For example, high oleic soybean oil contains unsaturated oleic, LA and linolenic fatty acids and each of these can be hydrogenated. Hydrogenation has two primary effects. First, the oxidative stability of the oil is increased as a result of the reduction of the unsaturated fatty acid content. Second, the physical properties of the oil are changed because the fatty acid modifications increase the melting point resulting in a semi-liquid or solid fat at room temperature.

There are many variables which affect the hydrogenation reaction, which, in turn, alter the composition of the final product. Operating conditions including pressure, temperature, catalyst type and concentration, agitation and reactor design are among the more important parameters that can be controlled. Selective hydrogenation conditions can be used to hydrogenate the more unsaturated fatty acids in preference to the less unsaturated ones. Very light or brush hydrogenation is often employed to increase stability of liquid oils. Further hydrogenation converts a liquid oil to a physically solid fat. The degree of hydrogenation depends on the desired performance and melting characteristics designed for the particular end product. Liquid shortenings (used in the manufacture of baking products, solid fats and shortenings used for commercial frying and roasting operations) and base stocks for margarine manufacture are among the myriad of possible oil and fat products achieved through hydrogenation. A more detailed description of hydrogenation and hydrogenated products can be found in Patterson, H. B. W., Hydrogenation of Fats and Oils: Theory and Practice. The American Oil Chemists' Society (1994).

Hydrogenated oils have become somewhat controversial due to the presence of trans-fatty acid isomers that result from the hydrogenation process. Ingestion of large amounts of trans-isomers has been linked with detrimental health effects including increased ratios of low density to high density lipoproteins in the blood plasma and increased risk of coronary heart disease.

PUFA-Containing Oils for Use in Foodstuffs

The market place currently supports a large variety of food and feed products, incorporating ω-3 and/or ω-6 fatty acids (particularly ARA, EPA and DHA). It is contemplated that the plant/seed oils, altered seeds and microbial oils of the invention comprising PUFAs will function in food and feed products to impart the health benefits of current formulations. Compared to other vegetable oils, the oils of the invention are believed to function similarly to other oils in food applications from a physical standpoint (for example, partially hydrogenated oils such as soybean oil are widely used as ingredients for soft spreads, margarine and shortenings for baking and frying).

Plant/seed oils, altered seeds and microbial oils containing ω-3 and/or ω-6 fatty acids described herein will be suitable for use in a variety of food and feed products including, but not limited to: food analogs, meat products, cereal products, snack foods, baked foods and dairy products. Additionally, the present plant/seed oils, altered seeds and microbial oils may be used in formulations to impart health benefit in medical foods including medical nutritionals, dietary supplements, infant formula as well as pharmaceutical products. One of skill in the art of food processing and food formulation will understand how the amount and composition of the plant and microbial oils may be added to the food or feed product. Such an amount will be referred to herein as an "effective" amount and will depend on the food or feed product, the diet that the product is intended to supplement or the medical condition that the medical food or medical nutritional is intended to correct or treat.

Food analogs can be made using processes well known to those skilled in the art. There can be mentioned meat analogs, cheese analogs, milk analogs and the like. Meat analogs made from soybeans contain soy protein or tofu and other ingredients mixed together to simulate various kinds of meats. These meat alternatives are sold as frozen, canned or dried foods. Usually, they can be used the same way as the foods they replace. Meat alternatives made from soybeans are excellent sources of protein, iron and B vitamins. Examples of meat analogs include, but are not limited to: ham analogs, sausage analogs, bacon analogs, and the like.

Food analogs can be classified as imitation or substitutes depending on their functional and compositional characteristics. For example, an imitation cheese need only resemble the cheese it is designed to replace. However, a product can generally be called a substitute cheese only if it is nutritionally equivalent to the cheese it is replacing and meets the minimum compositional requirements for that cheese. Thus, substitute cheese will often have higher protein levels than imitation cheeses and be fortified with vitamins and minerals.

Milk analogs or nondairy food products include, but are not limited to: imitation milk and nondairy frozen desserts (e.g., those made from soybeans and/or soy protein products).

Meat products encompass a broad variety of products. In the United States "meat" includes "red meats" produced from cattle, hogs and sheep. In addition to the red meats there are poultry items which include chickens, turkeys, geese, guineas, ducks and the fish and shellfish. There is a wide assortment of seasoned and processes meat products: fresh, cured and fried, and cured and cooked. Sausages and hot dogs are examples of processed meat products. Thus, the term "meat products" as used herein includes, but is not limited to, processed meat products.

A cereal food product is a food product derived from the processing of a cereal grain. A cereal grain includes any plant from the grass family that yields an edible grain (seed). The most popular grains are barley, corn, millet, oats, quinoa, rice, rye, sorghum, triticale, wheat and wild rice. Examples of a cereal food product include, but are not limited to: whole grain, crushed grain, grits, flour, bran, germ, breakfast cereals, extruded foods, pastas, and the like.

A baked goods product comprises any of the cereal food products mentioned above and has been baked or processed in a manner comparable to baking, i.e., to dry or harden by subjecting to heat. Examples of a baked good product include, but are not limited to: bread, cakes, doughnuts, bars, pastas, bread crumbs, baked snacks, mini-biscuits, mini-crackers, mini-cookies and mini-pretzels. As was mentioned above, oils of the invention can be used as an ingredient.

A snack food product comprises any of the above or below described food products.

A fried food product comprises any of the above or below described food products that has been fried.

A health food product is any food product that imparts a health benefit. Many oilseed-derived food products may be considered as health foods.

A beverage can be in a liquid or in a dry powdered form.

For example, there can be mentioned non-carbonated drinks; fruit juices, fresh, frozen, canned or concentrate; flavored or plain milk drinks, etc. Adult and infant nutritional formulas are well known in the art and commercially available (e.g., Similac®, Ensure®, Jevity®, and Alimentum® from Ross Products Division, Abbott Laboratories).

Infant formulas are liquids or reconstituted powders fed to infants and young children. "Infant formula" is defined herein as an enteral nutritional product which can be substituted for human breast milk in feeding infants and typically is composed of a desired percentage of fat mixed with desired percentages of carbohydrates and proteins in an aqueous solution (e.g., see U.S. Pat. No. 4,670,285). Based on worldwide composition studies, as well as levels specified by expert groups, average human breast milk typically contains about 0.20% to 0.40% of total fatty acids (assuming about 50% of calories from fat); and, generally the ratio of DHA to ARA would range from about 1:1 to 1:2 (see, e.g., formulations of Enfamil LIPIL™ [Mead Johnson & Company] and Similac Advance™ [Ross Products Division, Abbott Laboratories]). Infant formulas have a special role to play in the diets of infants because they are often the only source of nutrients for infants; and, although breast-feeding is still the best nourishment for infants, infant formula is a close enough second that babies not only survive but thrive.

A dairy product is a product derived from milk. A milk analog or nondairy product is derived from a source other than milk, for example, soymilk as was discussed above. These products include, but are not limited to: whole milk, skim milk, fermented milk products such as yoghurt or sour milk, cream, butter, condensed milk, dehydrated milk, coffee whitener, coffee creamer, ice cream, cheese, etc.

Additional food products into which the PUFA-containing oils of the invention could be included are, for example: chewing gums, confections and frostings, gelatins and puddings, hard and soft candies, jams and jellies, white granulated sugar, sugar substitutes, sweet sauces, toppings and syrups, and dry-blended powder mixes.

PUFA-Containing Oils for Use in Health Food Products and Pharmaceuticals

A health food product is any food product that imparts a health benefit and includes functional foods, medical foods, medical nutritionals, infant formulas and dietary supplements. Additionally, plant/seed oils, altered seeds and microbial oils of the invention may be used in standard pharmaceutical compositions. For example, the oils of the invention could readily be incorporated into the any of the above mentioned food products, to thereby produce, e.g., a functional or medical food. More concentrated formulations comprising PUFAs include capsules, powders, tablets, softgels, gelcaps, liquid concentrates and emulsions which can be used as a dietary supplement in humans or animals other than humans.

PUFA-Containing Oils for Use in Animal Feeds

Animal feeds are generically defined herein as products intended for use as feed or for mixing in feed for animals other than humans. The plant/seed oils, altered seeds and microbial oils of the invention can be used as an ingredient in various animal feeds.

More specifically, although not limited herein, it is expected that the oils of the invention can be used within pet food products, ruminant and poultry food products and aquacultural food products. Pet food products are those products intended to be fed to a pet [e.g., a dog, cat, bird, reptile, rodent]; these products can include the cereal and health food products above, as well as meat and meat byproducts, soy protein products and grass and hay products (e.g., alfalfa, timothy, oat or brome grass, vegetables). Ruminant and poultry food products are those wherein the product is intended to be fed to e.g., turkeys, chickens, cattle and swine. As with the pet foods above, these products can include cereal and health food products, soy protein products, meat and meat byproducts, and grass and hay products as listed above. Aquacultural food products (or "aquafeeds") are those products intended to be used in aquafarming, i.e., which concerns the propagation, cultivation or farming of aquatic organisms, animals and/or plants in fresh or marine waters.

EXAMPLES

The present invention is further defined in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

General Methods

Standard recombinant DNA and molecular cloning techniques used in the Examples are well known in the art and are described by:

1) Sambrook, J., Fritsch, E. F. and Maniatis, T. *Molecular Cloning: A Laboratory Manual*; Cold Spring Harbor Laboratory: Cold Spring Harbor, N.Y. (1989) (Maniatis); 2) T. J. Silhavy, M. L. Bennan, and L. W. Enquist, Experiments with Gene Fusions; Cold Spring Harbor Laboratory: Cold Spring Harbor, N.Y. (1984); and 3) Ausubel, F. M. et al., Current Protocols in Molecular Biology, published by Greene Publishing Assoc. and Wiley-Interscience (1987).

Materials and methods suitable for the maintenance and growth of microbial cultures are well known in the art. Techniques suitable for use in the following examples may be found as set out in Manual of Methods for General Bacteriology (Phillipp Gerhardt, R. G. E. Murray, Ralph N. Costilow, Eugene W. Nester, Willis A. Wood, Noel R. Krieg and G. Briggs Phillips, Eds), American Society for Microbiology: Washington, D.C. (1994)); or by Thomas D. Brock in Biotechnology: A Textbook of Industrial Microbiology, 2nd ed., Sinauer Associates: Sunderland, Mass. (1989). All reagents, restriction enzymes and materials used for the growth and maintenance of microbial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.), unless otherwise specified. *E. coli* strains were typically grown at 37° C. on Luria Bertani (LB) plates.

General molecular cloning was performed according to standard methods (Sambrook et al., supra). DNA sequence was generated on an ABI Automatic sequencer using dye terminator technology (U.S. Pat. No. 5,366,860; EP 272,007) using a combination of vector and insert-specific primers. Sequence editing was performed in Sequencer (Gene Codes Corporation, Ann Arbor, Mich.). All sequences represent coverage at least two times in both directions. Comparisons of genetic sequences were accomplished using DNASTAR software (DNASTAR Inc., Madison, Wis.).

The meaning of abbreviations is as follows: "sec" means second(s), "min" means minute(s), "h" means hour(s), "d" means day(s), "μl" means microliter(s), "mL" means milliliter(s), "L" means liter(s), "μM" means micromolar, "mM" means millimolar, "M" means molar, "mmol" means millimole(s), "μmole" mean micromole(s), "g" means gram(s), "μg" means microgram(s), "ng" means nanogram(s), "U" means unit(s), "bp" means base pair(s) and "kB" means kilobase(s).

Transformation and Cultivation of *Yarrowia lipolytica*

*Yarrowia lipolytica* strains with ATCC Accession Nos. #20362, #76982 and #90812 were purchased from the American Type Culture Collection (Rockville, Md.). *Y. lipolytica* strains were typically grown at 28° C. on YPD agar (1% yeast extract, 2% bactopeptone, 2% glucose, 2% agar).

Transformation of *Y. lipolytica* was performed according to the method of Chen, D. C. et al. (*Appl. Microbiol. Biotechnol.*, 48(2):232-235 (1997)), unless otherwise noted. Briefly, *Yarrowia* was streaked onto a YPD plate and grown at 30° C. for approximately 18 h. Several large loopfuls of cells were scraped from the plate and resuspended in 1 mL of transformation buffer containing: 2.25 mL of 50% PEG, average MW 3350; 0.125 mL of 2 M Li acetate, pH 6.0; 0.125 mL of 2 M DTT; and 50 μg sheared salmon sperm DNA. Then, approximately 500 ng of linearized plasmid DNA was incubated in 100 μL of resuspended cells, and maintained at 39° C. for 1 h with vortex mixing at 15 min intervals. The cells were plated onto selection media plates and maintained at 30° C. for 2 to 3 days.

For selection of transformants, minimal medium ("MM") was generally used; the composition of MM is as follows: 0.17% yeast nitrogen base (Difco Laboratories, Detroit, Mich.) without ammonium sulfate or amino acids, 2% glucose, 0.1% proline, pH 6.1). Supplements of uracil were added as appropriate to a final concentration of 0.01% (thereby producing "MMU" selection media, prepared with 20 g/L agar).

Alternatively, transformants were selected on 5-fluoroorotic acid ("FOA"; also 5-fluorouracil-6-carboxylic acid monohydrate) selection media, comprising: 0.17% yeast nitrogen base (Difco Laboratories, Detroit, Mich.) without ammonium sulfate or amino acids, 2% glucose, 0.1% proline, 75 mg/L uracil, 75 mg/L uridine, 900 mg/L FOA (Zymo Research Corp., Orange, Calif.) and 20 g/L agar.

Fatty Acid Analysis of *Yarrowia lipolytica*

For fatty acid analysis, cells were collected by centrifugation and lipids were extracted as described in Bligh, E. G. & Dyer, W. J. (*Can. J. Biochem. Physiol.*, 37:911-917 (1959)). Fatty acid methyl esters were prepared by transesterification of the lipid extract with sodium methoxide (Roughan, G., and Nishida I., *Arch Biochem Biophys.*, 276(1):38-46 (1990)) and subsequently analyzed with a Hewlett-Packard 6890 GC fitted with a 30 m×0.25 mm (i.d.) HP-INNOWAX (Hewlett-Packard) column. The oven temperature was from 170° C. (25 min hold) to 185° C. at 3.5° C./min.

For direct base transesterification, *Yarrowia* culture (3 mL) was harvested, washed once in distilled water, and dried under vacuum in a Speed-Vac for 5-10 min. Sodium methoxide (100 μL of 1%) was added to the sample, and then the sample was vortexed and rocked for 20 min. After adding 3 drops of 1 M NaCl and 400 μL hexane, the sample was vortexed and spun. The upper layer was removed and analyzed by GC as described above.

Example 1

*Euglena gracilis* Growth Conditions, Lipid Profile and mRNA Isolation

The present Example describes the growth of *Euglena gracilis*, culture lipid analysis and mRNA isolation.

Growth and Lipid Analysis

*Euglena gracilis* was obtained from Dr. Richard Triemer's lab at Michigan State University (East Lansing, Mich.). From 10 mL of actively growing culture, a 1 mL aliquot was transferred into 250 mL of *Euglena gracilis* (Eg) Medium in a 500 mL glass bottle. Eg medium was made by combining 1 g of sodium acetate, 1 g of beef extract (Catalog No. U126-01, Difco Laboratories, Detroit, Mich.), 2 g of Bacto® tryptone (Catalog No. 0123-17-3, Difco Laboratories), 2 g of Bacto® yeast extract (Catalog No. 0127-17-9, Difco Laboratories) in 970 mL of water. After filter sterilizing, 30 mL of soil-water supernatant (Catalog No. 15-3790, Carolina Biological Supply Company, Burlington, N.C.) was aseptically added to produce the final Eg medium. *Euglena gracilis* cultures were grown at 23° C. with a 16 h light, 8 h dark cycle for 2 weeks with no agitation.

Figure 3:
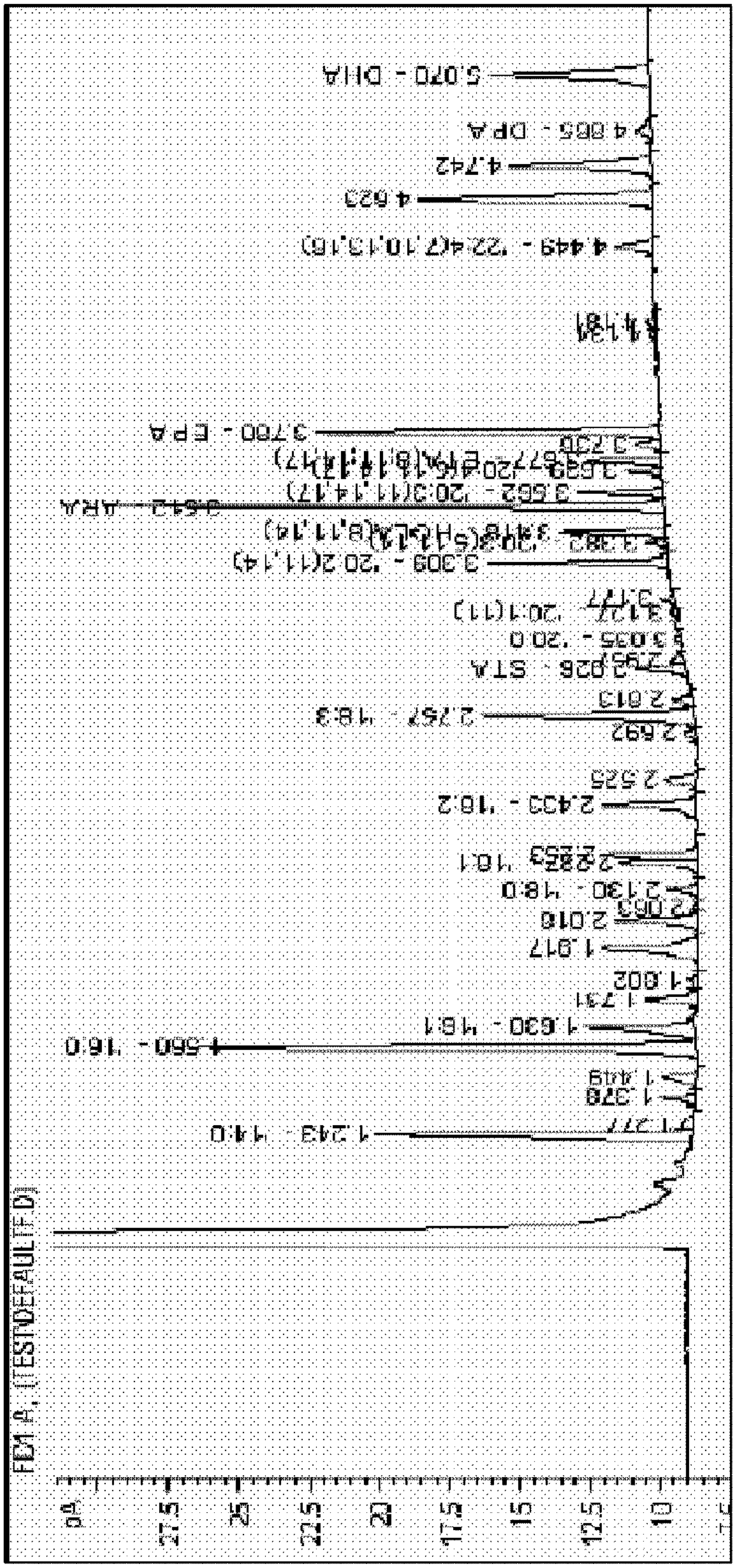
FIG. 3 shows a chromatogram of the lipid profile of an *Euglena gracilis* cell extract (Example 1).

After 2 weeks, 10 mL of culture was removed for lipid analysis and centrifuged at 1,800×g for 5 min. The pellet was washed once with water and re-centrifuged. The resulting pellet was dried for 5 min under vacuum, resuspended in 100 μL of trimethylsulfonium hydroxide (TMSH) and incubated at room temperature for 15 min with shaking. After this, 0.5 mL of hexane was added and the vials were incubated for 15 min at room temperature with shaking. Fatty acid methyl esters (5 μL injected from hexane layer) were separated and quantified using a Hewlett-Packard 6890 Gas Chromatograph fitted with an Omegawax 320 fused silica capillary column (Catalog No. 24152, Supelco Inc.). The oven temperature was programmed to hold at 220° C. for 2.7 min, increase to 240° C. at 20° C./min and then hold for an additional 2.3 min. Carrier gas was supplied by a Whatman hydrogen generator. Retention times were compared to those for methyl esters of standards commercially available (Catalog No. U-99-A, Nu-Chek Prep, Inc.) and the resulting chromatogram is shown in FIG. 3.

Preparation of mRNA from *Euglena Gracilis*

The remaining 2 week culture (240 mL) was pelleted by centrifugation at 1,800×g for 10 min, washed once with water and re-centrifuged. Total RNA was extracted from the resulting pellet using the RNA STAT-60™ reagent (TEL-TEST, Inc., Friendswood, Tex.) and following the manufacturer's protocol provided (use 5 mL of reagent, dissolved RNA in 0.5 mL of water). In this way, 1 mg of total RNA (2 mg/mL) was obtained from the pellet. The mRNA was isolated from 1 mg of total RNA using the mRNA Purification Kit (Amersham Biosciences, Piscataway, N.J.) following the manufacturer's protocol provided. In this way, 85 μg of mRNA was obtained.

Example 2

*Euglena gracilis* cDNA Synthesis, Library Construction and Sequencing

A cDNA library was generated using the Cloneminer™ cDNA Library Construction Kit (Catalog No. 18249-029, Invitrogen Corporation, Carlsbad, Calif.) and following the manufacturer's protocol provided (Version B, 25-0608). Using the non-radiolabeling method, cDNA was synthesized from 3.2 μg of mRNA (Example 1) using the Biotin-attB2-Oligo(dT) primer. After synthesis of the first and second strand, the attB1 adapter was added, ligated and the cDNA was size fractionated using column chromatography. DNA from fractions 7 and 8 (size ranging from ~800-1500 bp) was concentrated, recombined into pDONR™222 and transformed into *E. coli* ElectroMAX™ DH10B™ T1 Phage-Resistant cells (Invitrogen Corporation). The *Euglena gracilis* library was named "eeg1c".

For sequencing, clones first were recovered from archived glycerol cultures grown/frozen in 384-well freezing media plates, and replicated with a sterile 384 pin replicator (Genetix, Boston, Mass.) in 384-well microtiter plates containing LB+75 μg/mL kanamycin (replicated plates). Plasmids then were isolated, using the Templiphi DNA sequencing template amplification kit method (Amersham Biosciences) following the manufacturer's protocol. Briefly, the Templiphi method uses bacteriophage ϕ29 DNA polymerase to amplify circular single-stranded or double-stranded DNA by isothermal rolling circle amplification (Dean et al., *Genome Res.,* 11:1095-1099 (2001); Nelson et al., *Biotechniques,* 32:S44-S47 (2002)). After growing 20 h at 37° C., cells from the replicated plate were added to 5 μL of dilution buffer and denatured at 95° C. for 3 min to partially lyse cells and release the denatured template. Templiphi premix (5 μL) was then added to each sample and the resulting reaction mixture was incubated at 30° C. for 16 h, then at 65° C. for 10 min to inactivate the ϕ29 DNA polymerase activity. DNA quantification with the PicoGreen® dsDNA Quantitation Reagent (Molecular Probes) was performed after diluting the amplified samples 1:3 in distilled water.

The amplified products then were denatured at 95° C. for 10 min and end-sequenced in 384-well plates, using the M13F universal primer (SEQ ID NO:18), and the ABI BigDye version 3.1 Prism Sequencing Kit. For the sequencing reaction, 100-200 ng of templates and 6.4 pmol of primers were used, and the following reaction conditions were repeated 25 times: 96° C. for 10 sec, 50° C. for 5 sec and 60° C. for 4 min. After ethanol-based cleanup, cycle sequencing reaction products were resolved and detected on Perkin-Elmer ABI 3730xl automated sequencers.

Example 3

Identification of Δ9 Elongase Enzyme Homologs from *Euglena gracilis* cDNA Library eeg1c cDNA clones encoding long-chain polyunsaturated fatty acid elongation enzyme homologs (i.e., LC-PUFA ELO homologs or Δ9 elongases) were identified by conducting BLAST (Basic Local Alignment Search Tool; Altschul et al., *J. Mol. Biol.,* 215:403-410 (1993)) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL and DDBJ databases). The cDNA sequences obtained in Example 2 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States, *Nat. Genet.,* 3:266-272 (1993)) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

The BLASTX search using the nucleotide sequences from clone eeg1c.pk001.n5.f revealed similarity of the protein encoded by the cDNA to IgD9e (i.e., the long-chain PUFA elongation enzyme from *Isochrysis galbana* set forth herein as SEQ ID NO:8; NCBI Accession No. AAL37626 (GI 17226123), locus AAL37626, CDS AF390174; Qi et al., *FEBS Lett.* 510(3):159-165 (2002)). The sequence of a portion of the cDNA insert from clone eeg1c.pk001.n5.f is shown in SEQ ID NO:10 (5' end of cDNA insert).

Additional sequence was obtained from the 3' end of the cDNA insert of eeg1c.pk001.n5.1 as described above, but using the poly(A) tail-primed WobbleT oligonucleotides. Briefly, the WobbleT primer is an equimolar mix of 21 mer poly(T)A, poly(T)C, and poly(T)G, used to sequence the 3' end of cDNA clones. The 3' end sequence is shown in SEQ ID NO:11.

Both the 5' and 3' sequences were aligned using Sequencher™ (Version 4.2, Gene Codes Corporation, Ann Arbor, Mich.) and the resulting sequence for the cDNA is shown in SEQ ID NO:12. Sequence for the coding sequence from the cDNA in eeg1c.pk001.n5.f and the corresponding deduced amino acid sequence is shown in SEQ ID NO:1 and SEQ ID NO:2, respectively. On the basis of the homologies reported above, the *Euglena gracilis* gene product of the cDNA insert of eeg1c.pk001.n5.1 was hypothesized to encode a Δ9 elongase and was thus designated as "EgD9e".

The amino acid sequence set forth in SEQ ID NO:2 (i.e., EgD9e) was evaluated by BLASTP, yielding a pLog value of 38.70 (E value of 2e-39) versus IgD9e (SEQ ID NO:8). EgD9e is 39.4% identical to IgD9e using the Jotun Hein method. Sequence percent identity calculations performed by the Jotun Hein method (Hein, J. J., *Meth. Enz.,* 183:626-645 (1990)) were done using the MegAlign™ v6.1 program of the LASERGENE bioinformatics computing suite (DNASTAR Inc., Madison, Wis.) with the default parameters for pairwise alignment (KTUPLE=2). EgD9e (SEQ ID NO:2) is 31.8% identical to IgD9e (SEQ ID NO:8) using the Clustal V method (FIG. 4). Sequence percent identity calculations performed by the Clustal V method (Higgins, D. G. and Sharp, P. M., *Comput. Appl. Biosci.,* 5:151-153 (1989); Higgins et al., *Comput. Appl. Biosci.,* 8:189-191 (1992)) were done using the MegAlign™ v6.1 program of the LASERGENE bioinformatics computing suite with the default parameters for pairwise alignment (KTUPLE=1, GAP PENALTY=3, WINDOW=5, DIAGONALS SAVED=5 and GAP LENGTH PENALTY=10).

BLAST scores and probabilities indicated that the instant nucleic acid fragment (SEQ ID NO:12) encoded an entire *Euglena gracilis* A9 elongase.

Example 4

Functional Analysis of the *Euglena gracilis* Δ9 Elongase (EgD9e) in *Saccharomyces cerevisiae*

The present Example describes functional analysis of EgD9e in *Saccharomyces cerevisiae*. This required: (2) cloning of EgD9e into yeast expression vector pY-75 to produce pY119; (2) comparison of lipid profiles within transformant organisms comprising pY-75 and pY119, after substrate feeding; and (3) comparison of lipid profiles within transformant organisms comprising pY-75 and pY119, after no substrate feeding.

Construction of Plasmids pY-75 (Control) and DY119, Comprising EgD9e

Figure 5:
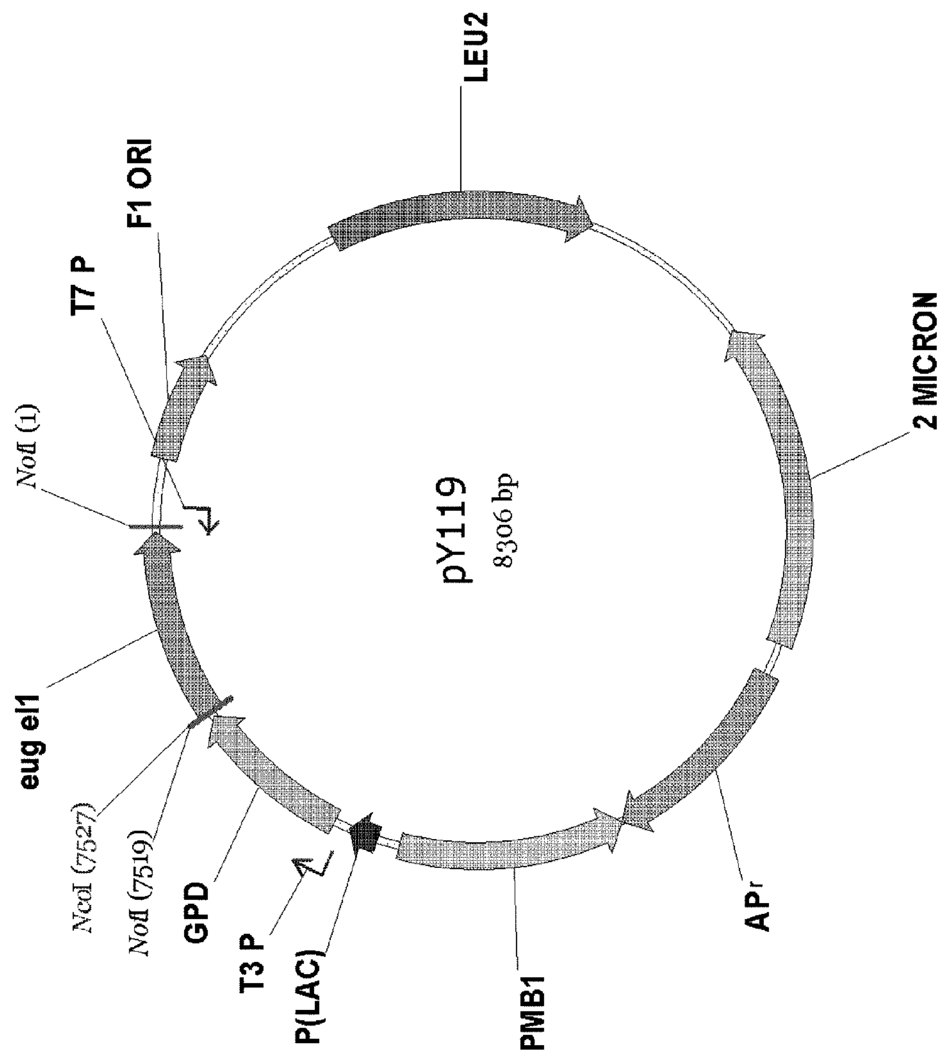
FIG. 5 is a map of plasmid pY119.

The yeast episomal plasmid (YEp)-type vector pRS425 (Christianson et al., *Gene,* 110:119-122 (1992)) contains sequences from the *Saccharomyces cerevisiae* 2μ endogenous plasmid, a LEU2 selectable marker and sequences based on the backbone of a multifunctional phagemid, pBluescript II SK(+). The *Saccharomyces cerevisiae* strong, constitutive glyceraldehyde-3-phosphate dehydrogenase (GPD) promoter was cloned between the SacII and SpeI sites of pRS425 in the same way as described by Jia et al. (*Physiol. Genomics,* 3:83-92 (2000)) to produce pGPD-425. A Not1 site was introduced into the BamHI site of pGPD-425, thus producing a NotI site flanked by BamHI sites, and this plasmid was called pY-75. EgD9e was amplified from eeg1c.pk001.n5.f with oligonucleotide primers oEugEL1-1 (SEQ ID NO:19) and oEugEL1-2 (SEQ ID NO:20) using the VentR® DNA Polymerase (Catalog No. M0254S, New England Biolabs Inc., Beverly, Mass.) following the manufacturer's protocol. The resulting DNA fragment was cloned into the pCR-Blunt® cloning vector using the Zero Blunt® PCR Cloning Kit (Invitrogen Corporation), following the manufacturer's protocol, to produce pKR906. EgD9e was released from pKR906 by digestion with NotI and cloned into the NotI site of pY-75 to produce pY119 (SEQ ID NO:21; FIG. 5). EgD9e is labeled as "eug el1" in FIG. 5.

Functional Analysis of EgD9e Elongase Activity by Substrate Feeding

Plasmids pY119 and pY-75 were transformed into *Saccharomyces cerevisiae* INVSC1 (Invitrogen Corporation) using standard lithium acetate transformation procedures. Transformants were selected on DOBA media supplemented with CSM-leu (Qbiogene, Carlsbad, Calif.). Transformants from each plate were inoculated into 2 mL of DOB medium supplemented with CSM-leu (Qbiogene) and 0.2% tergitol. Cells were grown for 1 day at 30° C. after which 0.1 mL was transferred to 3 mL of the same medium supplemented with either LA [18:2(9,12)], ALA [18:3(9, 12, 15)], GLA [18:3(6, 9, 12)], STA [18:4(6, 9, 12, 15)], ARA [20:4(5, 8, 11, 14)] or EPA [20:5(5, 8, 11, 14, 17)] to 0.175 mM. These were incubated for 16 h at 30° C., 250 rpm and then pellets were obtained by centrifugation. Cells were washed once with water, pelleted by centrifugation and air dried. Pellets were transesterified (Roughan, G., and Nishida I., *Arch Biochem Biophys.,* 276(1):38-46 (1990)) with 500 μL of 1% sodium methoxide for 30 min at 50° C. after which 500 μL of 1 M sodium chloride and 100 μL of heptane were added. After thorough mixing and centrifugation, fatty acid methyl esters (FAMEs) were analyzed by GC as described in Example 1.

Results for feeding cells containing pY75 (vector control) or pY119 (3 independent transformants, designated as pY119-5, pY119-6 and pY119-8) are shown in FIG. 6. Fatty acids are identified as 16:0 (palmitate), 16:1(9) (palmitoleic acid), 18:0, 18:1(9) (oleic acid), LA, GLA, ALA, STA, EDA, DGLA, ARA, ETrA, ETA, EPA, 22:2(13,16) (docosadienoic acid), 22:4(7, 10, 13, 16) (adrenic acid), DPA and 24:1 (nervonic acid). The elongation efficiency ("% Elo") was calculated for each fatty acid ("FA") fed as: [% $FA_{product}$/(% $FA_{product}$+% $FA_{substrate}$)*100].

The data in FIG. 6 demonstrated that the cloned EgD9e efficiently elongated LA and ALA to EDA and ETrA, respectively.

Functional Analysis of EgD9e Elongase Activity without Substrate Feeding

Additionally, FAMEs from cells where no fatty acid had been fed were analyzed by GC using slightly different temperature profiles in order to achieve separation of oleic acid [OA-18:1(9)] and vaccenic acid [VA-18:1(11)], the product of palmitoleic acid [PA-16:1(9)] elongation. Fatty acid methyl esters (3 μL injected from hexane layer) were separated and quantified using a Hewlett-Packard 6890 Gas Chromatograph fitted with an Omegawax 320 fused silica capillary column (Supelco Inc., Catalog No. 24152). The oven temperature was programmed to hold at 200° C. for 2.7 min, increase to 240° C. at 20° C./min and then hold for an additional 2.3 min. Results are shown in Table 6.

TABLE 6

Lipid Profiles Having No Exogenous Fatty Acid Added

| Sample Name | 16:0 | 16:1 (9) | 18:0 | 18:1 (9) | 18:1 (11) | % Elo 16:0 | % Elo 16:1 |
|---|---|---|---|---|---|---|---|
| pY75 | 13.1 | 54.7 | 3.5 | 27.6 | 1.2 | 20.9 | 2.1 |
| pY119-5 | 12.9 | 55.6 | 3.6 | 26.0 | 1.8 | 21.6 | 3.2 |
| pY119-6 | 13.4 | 54.0 | 3.6 | 27.3 | 1.6 | 21.2 | 3.0 |
| pY119-8 | 12.7 | 53.3 | 3.5 | 29.0 | 1.5 | 21.7 | 2.8 |

Based on the results shown above, EgD9e may act as both a $C_{16/18}$ elongase and a $C_{18/20}$ elongase, in addition to its primary role as a Δ9 elongase that is capable of catalyzing the elongation of LA and ALA to EDA and ETrA, respectively.

Example 5

Construction of *Yarrowia lipolytica* Expression Vector pY115, Comprising a Synthetic Δ9 Elongase Gene (Derived from *Isochrysis galbana*), Codon-Optimized for Expression in *Yarrowia lipolytica* (IgD9eS)

The present Example describes the construction of *Yarrowia lipolytica* expression vector pY115, comprising a chimeric FBAINm::IgD9eS::Pex20 gene, wherein IgD9eS is a synthetic Δ9 elongase derived from *Isochrysis galbana* and codon-optimized for expression in *Yarrowia lipolytica*. Plasmid pY115 indirectly enabled the Δ9 elongase activity of IgD9eS to be compared to the Δ9 elongase activity of EgD9e, as described in Examples 6 and 7, infra.

Figure 8:
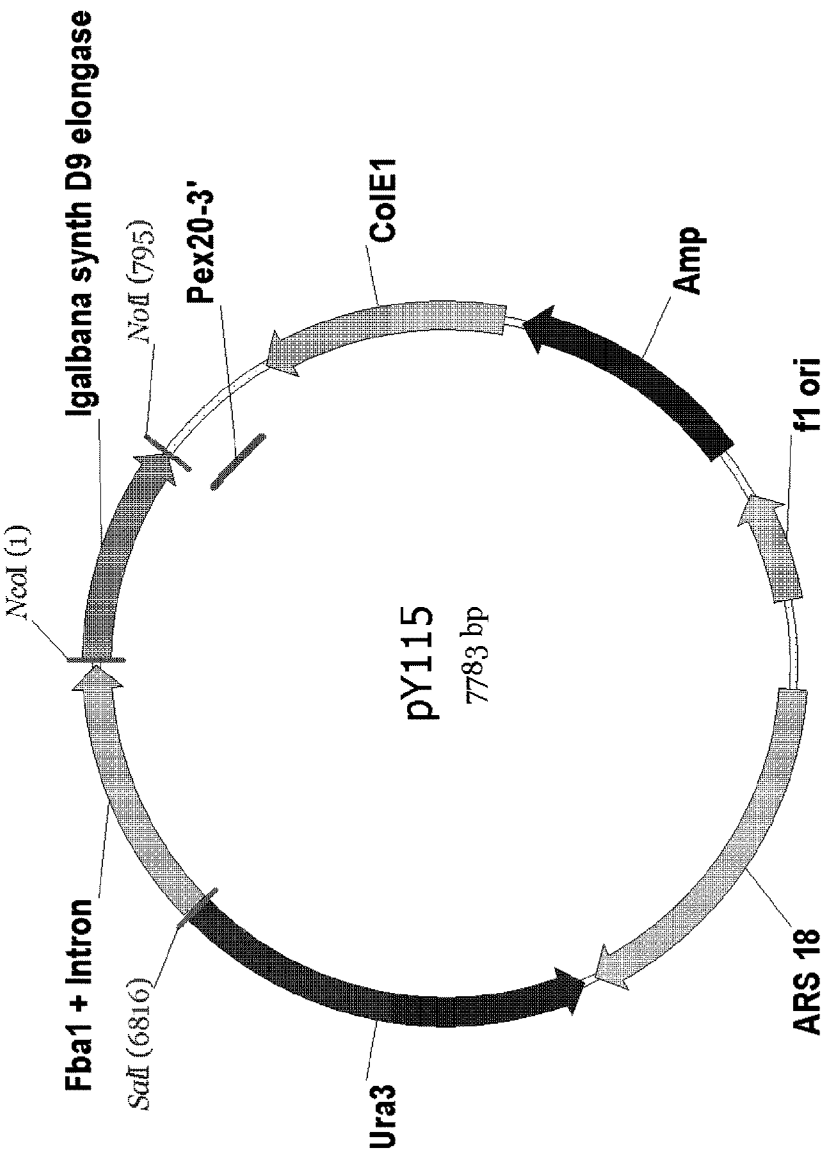
FIG. 8 is a map of plasmid pY115.

Construction of plasmid pY115 (SEQ ID NO:45; FIG. 8) required: (1) construction of pDMW263; (2) synthesis of IgD9eS and creation of plasmid pDMW237; and (3) ligation of fragments from plasmids pDMW263 and pDMW237.

Construction of pDMW263

Plasmid pY5-30 (FIG. 7A; previously described in PCT Publication No. WO 05/003310 [the contents of which are hereby incorporated by reference]) is a shuttle plasmid that can replicate both in *E. coli* and *Yarrowia lipolytica*. Plasmid pY5-30 contains the following: a *Yarrowia* autonomous replication sequence (ARS18); a ColE1 plasmid origin of replication; an ampicillin-resistance gene (AmpR), for selection in *E. coli*; a *Yarrowia* LEU2 gene, for selection in *Yarrowia*; and a chimeric TEF::GUS::XPR gene.

Figure 7:
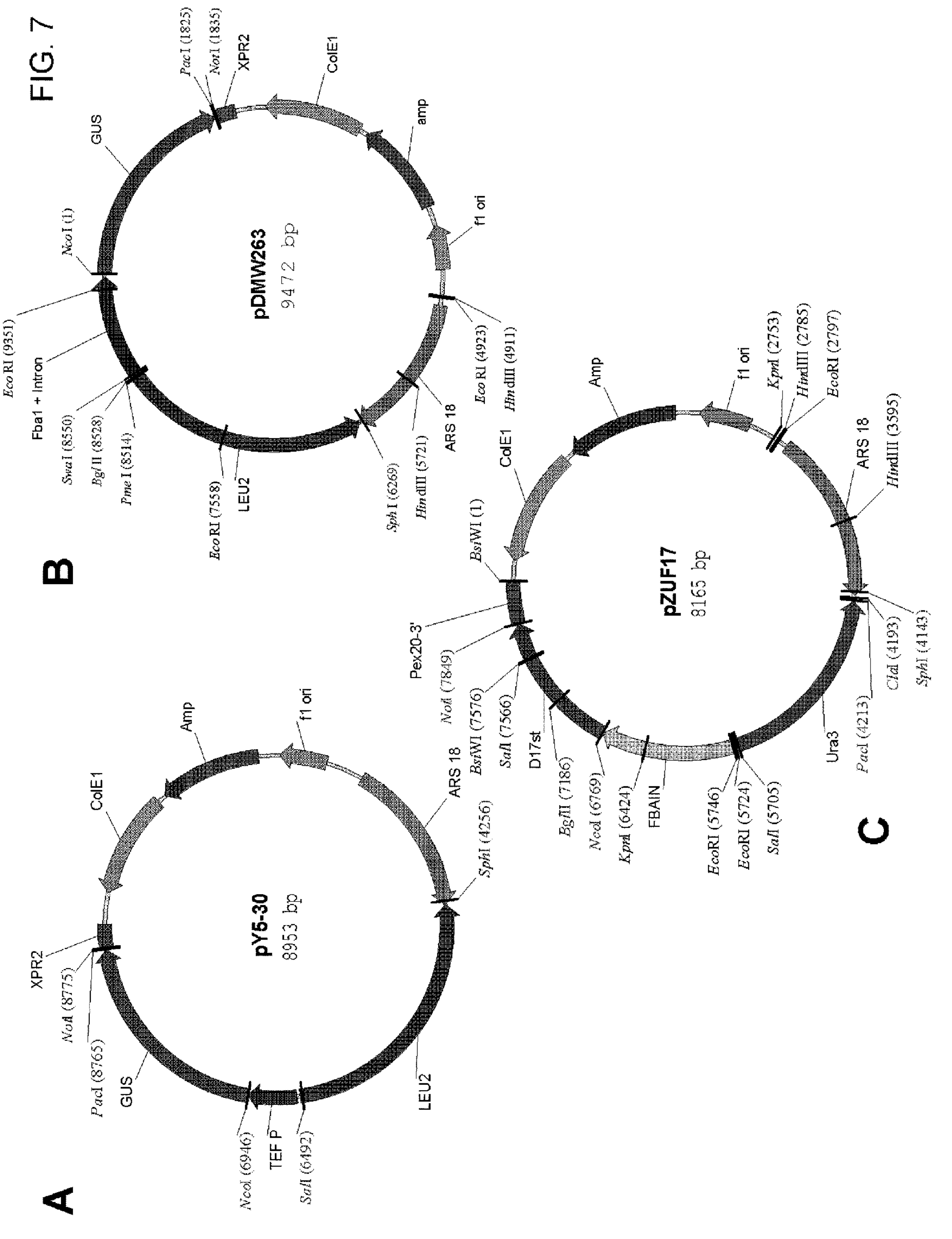
FIG. 7A is a map of plasmid pY5-30.
FIG. 7B is a map of plasmid pDMW263.
FIG. 7C is a plasmid map of pZUF17.

Plasmid pDMW263 (SEQ ID NO:22; FIG. 7B) was created from pY5-30, by replacing the TEF promoter with the *Yarrowia lipolytica* FBAINm promoter (PCT Publication No. WO 05/049805) using techniques well known to one skilled in the art. Briefly, this promoter refers to a modified promoter which is located in the 5' upstream untranslated region in front of the 'ATG' translation initiation codon of the fructose-bisphosphate aldolase enzyme (E.G. 4.1.2.13) encoded by the fba1 gene and that is necessary for expression, plus a portion of 5' coding region that has an intron, wherein FBAINm has a 52 bp deletion between the ATG translation initiation codon and the intron of the FBAIN promoter (thereby including only 22 amino acids of the N-terminus) and a new translation consensus motif after the intron. Table 7 summarizes the components of pDMW263.

TABLE 7

| Components of Plasmid pDMW263 (SEQ ID NO: 22) | |
|---|---|
| RE Sites and Nucleotides Within SEQ ID NO: 22 | Description of Fragment and Chimeric Gene Components |
| 4992-4296 | ARS18 sequence (GenBank Accession No. A17608) |
| SalI/SacII (8505-2014) | FBAINm::GUS::XPR, comprising:<br>FBAINm: FBAINm promoter (PCT Publication No. WO 2005/049805; labeled as "Fba1 + intron" in FIG. 7B)<br>GUS: *E. coli* gene encoding β-glucuronidase (Jefferson, R. A. Nature. 14: 342: 837-838 (1989)<br>XPR: ~100 bp of the 3' region of the *Yarrowia* Xpr gene (GenBank Accession No. M17741) |
| 6303-8505 | *Yarrowia* Leu2 gene (GenBank Accession No. AF260230) |

In Vitro Synthesis of IgD9eS

The codon usage of the Δ9 elongase gene of *Isochrysis galbana* (IgD9e; SEQ ID NOs:7 and 8) was optimized for expression in *Yarrowia lipolytica*, in a manner similar to that described in PCT Publication No. WO 2004/101753 (US-2004-0253621-A1) and as described in PCT Publication No. WO 2006/052870 (US-2006-0115881-A1), each incorporated by reference in their entirety herein. Specifically, a codon-optimized Δ9 elongase gene (designated "IgD9eS"; SEQ ID NO:9) was designed, based on the coding sequence of IgD9e (SEQ ID NO:7), according to the *Yarrowia* codon usage pattern, the consensus sequence around the ATG translation initiation codon, and the general rules of RNA stability (Guhaniyogi, G. and J. Brewer, *Gene,* 265(1-2):11-23 (2001)). In addition to modification of the translation initiation site, 127 bp of the 792 bp coding region were modified (16.0%), and 122 codons were optimized. None of the modifications in the codon-optimized gene changed the amino acid sequence of the encoded protein (SEQ ID NO:8).

More specifically, eight pairs of oligonucleotides were designed to extend the entire length of IgD9eS (e.g., IL3-1A, IL3-1B, IL3-2A, IL3-2B, IL3-3A, IL3-3B, IL3-4A, IL3-4B, IL3-5A, IL3-5B, IL3-6A, IL3-6B, IL3-7A, IL3-7B, IL3-8A and IL3-8B, corresponding to SEQ ID NOs:23-38). Each pair of sense (A) and anti-sense (B) oligonucleotides were complementary, with the exception of a 4 bp overhang at each 5'-end. Additionally, primers IL3-1F, IL3-4R, IL3-5F and IL3-8R (SEQ ID NOs:39-42) also introduced NcoI, PstI, PstI and Not1 restriction sites, respectively, for subsequent subcloning.

Each oligonucleotide (100 ng) was phosphorylated at 37° C. for 1 h in a volume of 20 μL containing 50 mM Tris-HCl (pH 7.5), 10 mM $MgCl_2$, 10 mM DTT, 0.5 mM spermidine, 0.5 mM ATP and 10 U of T4 polynucleotide kinase. Each pair of sense and antisense oligonucleotides was mixed and annealed in a thermocycler using the following parameters: 95° C. (2 min), 85° C. (2 min), 65° C. (15 min), 37° C. (15 min), 24° C. (15 min) and 4° C. (15 min). Thus, IL3-1A (SEQ ID NO:23) was annealed to IL3-1B (SEQ ID NO:24) to produce the double-stranded product "IL3-1AB". Similarly, IL3-2A (SEQ ID NO:25) was annealed to IL3-2B (SEQ ID NO:26) to produce the double-stranded product "IL3-2AB", etc.

Two separate pools of annealed, double-stranded oligonucleotides were then ligated together, as shown below: Pool 1 (comprising IL3-1AB, IL3-2AB, IL3-3AB and IL3-4AB); and Pool 2 (comprising IL3-5AB, IL3-6AB, IL3-7AB and IL3-8AB). Each pool of annealed oligonucleotides was mixed in a volume of 20 μL with 10 U of T4 DNA ligase and the ligation reaction was incubated overnight at 16° C.

The product of each ligation reaction was then used as template to amplify the designed DNA fragment by PCR. Specifically, using the ligated "Pool 1" mixture (e.g., IL3-1AB, IL3-2AB, IL3-3AB and IL3-4AB) as template, and oligonucleotides IL3-1F and IL3-4R (SEQ ID NOs:39 and 40) as primers, the first portion of IgD9eS was amplified by PCR. The 417 bp PCR fragment was subcloned into the pGEM-T easy vector (Promega) to generate pT9(1-4) (SEQ ID NO:43).

Using the ligated "Pool 2" mixture (e.g., IL3-5AB, IL3-6AB, IL3-7AB and IL3-8AB) as the template, and oligonucleotides IL3-5F and IL3-8R (SEQ ID NOs:41 and 42) as primers, the second portion of IgD9eS was amplified similarly by PCR and cloned into the pGEM-T-easy vector to generate pT9(5-8) (SEQ ID NO:44).

*E. coli* was transformed separately with pT9(1-4) (SEQ ID NO:43) and pT9(5-8) (SEQ ID NO:44) and the plasmid DNA was isolated from ampicillin-resistant transformants. Plasmid DNA was purified and digested with the appropriate restriction endonucleases to liberate the 417 bp NcoI/PstI fragment of pT9(1-4) and the 377 bp PstI/NotI fragment of pT9(5-8). These two fragments were then combined and directionally ligated together with Nco1/Not1 digested pZUF17 (SEQ ID NO:121; FIG. 7C) to generate pDMW237 (SEQ ID NO:46). Thus, the synthetically produced IgD9eS gene was flanked by a FBAIN promoter and *Yarrowia* Pex20 terminator within expression vector pDMW237.

Final Construction of *Yarrowia lipolytica* Expression Vector pY115

The NcoI/SalI DNA fragment from pDMW263 (containing the *Yarrowia lipolytica* FBAINm promoter) was cloned into the NcoI/SalI DNA fragment of pDMW237 (containing IgD9eS), to produce pY115 (SEQ ID NO:45; FIG. 8), comprising a chimeric FBAINm::IgD9eS::Pex20 gene. FBAINm is labeled as "Fba1+Intron" and IgD9eS is labeled as "I galbana synth D9 elongas" in FIG. 8.

Example 6

Construction of *Yarrowia lipolytica* Expression Vectors pBY2 (Comprising EgD9e) and pBY1-FAE (Comprising IgD9eS)

The present Example describes synthesis of *Yarrowia lipolytica* expression vectors pBY2 (comprising a chimeric FBAINm::EgD9e::Pex20 gene) and pBY1-FAE (comprising a chimeric FBAINm::IgD9eS::Pex20 gene). Delta-9 elongase activity of IgD9eS was compared to that of EgD9e when expressed in *Yarrowia lipolytica*, as described in Example 7 (infra).

Construction of *Yarrowia lipolytica* Expression Vector pBY2

Figure 9:
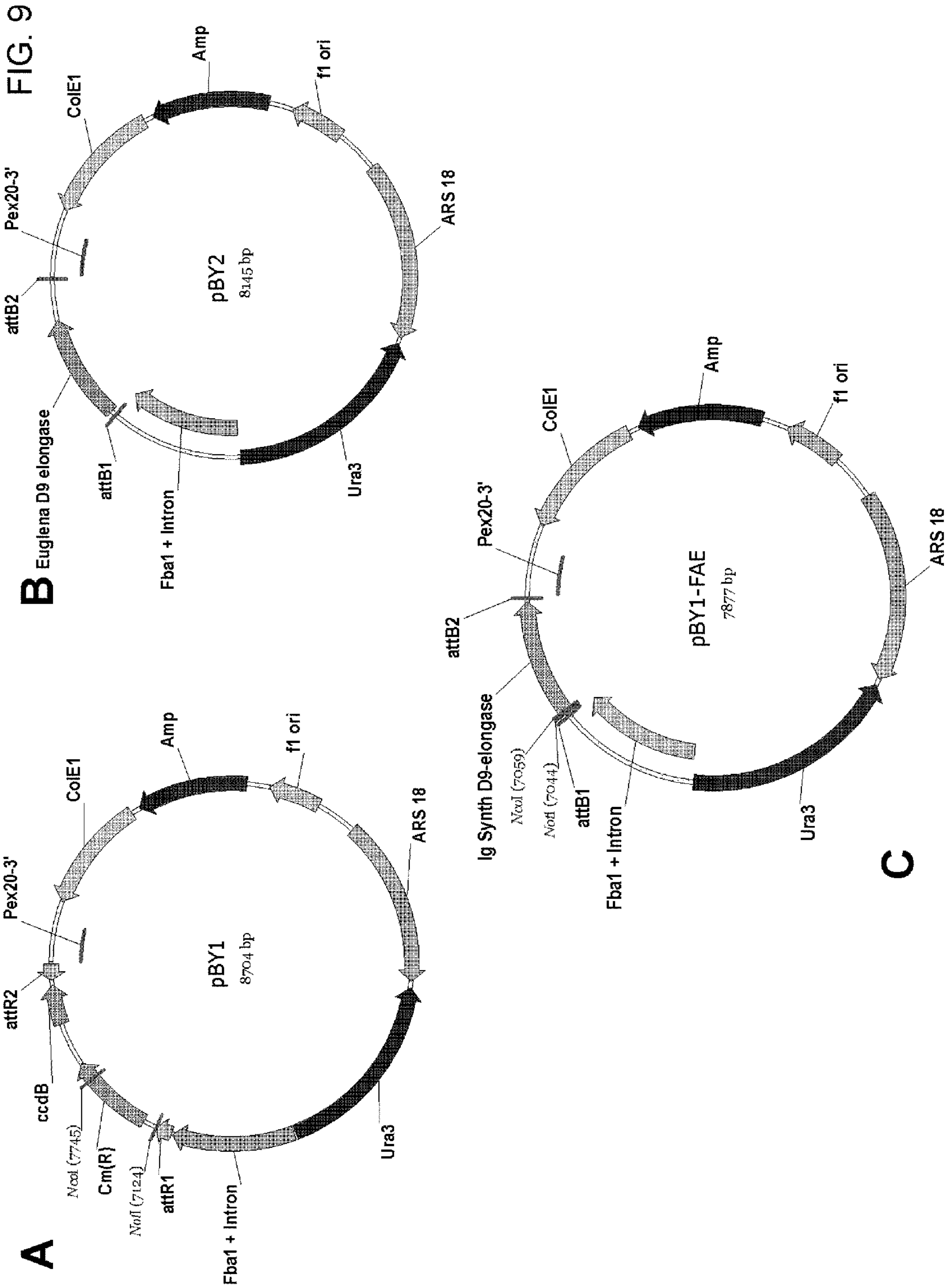
FIG. 9A is a map of *Yarrowia lipolytica* Gateway® destination vector pBY1.
FIG. 9B is a map of plasmid pBY2.
FIG. 9C is a map of plasmid pBY1-FAE.

Plasmid pY115 (SEQ ID NO:45; Example 5) was digested with NcoI/NotI and the resulting DNA ends were filled using Klenow. After filling to form blunt ends, the DNA fragments were treated with calf intestinal alkaline phosphatase and separated using agarose gel electrophoresis. The 6989 bp fragment containing the *Yarrowia lipolytica* FBAINm promoter was excised from the agarose gel and purified using the QIAquick® Gel Extraction Kit (Qiagen Inc., Valencia, Calif.) following the manufacturer's protocol. The purified 6989 bp fragment was ligated with cassette rfA using the Gateway Vector Conversion System (Catalog No. 11823-029, Invitrogen Corporation) following the manufacturer's protocol to form *Yarrowia lipolytica* Gateway® destination vector pBY1 (SEQ ID NO:47; FIG. 9A).

Plasmid was purified from *Euglena gracilis* clone eeg1c.pk001.n5.f (Examples 2 and 3) using the QIAprep®

Spin Miniprep Kit (Qiagen Inc., Valencia, Calif.) following the manufacturer's protocol. Using the Gateway® LR Clonase™ II enzyme mix (Catalog No. 11791-020, Invitrogen Corporation) and following the manufacturer's protocol, the cDNA from eeg1c.pk001.n5.f was transferred to pBY1 to form pBY2 (SEQ ID NO:48; FIG. 9B). Since sequencing was performed with the WobbleT primer, the full sequence of the 3' end of eeg1c.pk001.n5.f (i.e., containing the polyA tail) was not known. Based on restriction digest and agarose gel analysis, the poly A tail appeared to be less than 100 bp long.

Construction of *Yarrowia lipolytica* Expression Vector pBY1-FAE

IgD9eS was amplified from pY115 (SEQ ID NO:45; Example 5) with oligonucleotide primers ig-s (SEQ ID NO:49) and ig-as (SEQ ID NO:50) using AccuPrime™ Taq Polymerase High Fidelity (Catalog No. 12346-086, Invitrogen Corporation) following the manufacturer's protocol. The resulting DNA fragment was cloned into pENTR™/D-TOPO® using the pENTR™ Directional TOPO® Cloning Kit (Invitrogen Corporation), following the manufacturer's protocol, to produce pENTR-FAE. Plasmid pENTR-FAE was purified using the QIAprep® Spin Miniprep Kit (Qiagen Inc., Valencia, Calif.) following the manufacturer's protocol as above. Using the Gateway® LR Clonase™ II enzyme mix (Catalog No. 11791-020, Invitrogen Corporation) and following the manufacturer's protocol, the CDS for IgD9eS was transferred to pBY1 to form pBY1-FAE (SEQ ID NO:51; FIG. 9C).

Vector Transformation into *Escherichia coli*

Following creation of pBY2 and pBY1-FAE, each vector was transformed into *E. coli* DH10B™ (Invitrogen Corporation) cells. The transformant cells were grown and pBY2 and pBY1-FAE were isolated using the QIAprep® Spin Miniprep Kit (Qiagen Inc., Valencia, Calif.).

Example 7

Functional Analysis of EgD9e in *Yarrowia lipolytica* Strain Y2224

The present Example describes functional analysis of EgD9e in *Yarrowia lipolytica* strain Y2224. This required: (1) construction of strain Y2224 (i.e., a FOA resistant mutant from an autonomous mutation of the Ura3 gene of wildtype *Yarrowia* strain ATCC #20362); and, (2) comparison of lipid profiles within transformant organisms of *Yarrowia lipolytica* strain Y2224 that were comprising either pBY2 (expressing EgD9e) or pBY1-FAE (expressing IgD9eS).

Generation of *Yarrowia lipolytica* Strain Y2224

Strain Y2224 was isolated in the following manner: *Yarrowia lipolytica* ATCC #20362 cells from a YPD agar plate were streaked onto a minimal medium plate (75 mg/L each of uracil and uridine, 6.7 g/L YNB with ammonia sulfate, without amino acid, 20 g/L glucose) containing 250 mg/L 5-FOA (Zymo Research). Plates were incubated at 28° C. and four of the resulting colonies were patched separately onto minimal medium plates containing 200 mg/mL 5-FOA and minimal medium plates lacking uracil and uridine to confirm uracil Ura3 auxotrophy. Subsequently, *Yarrowia lipolytica* strain Y2224 was grown at 28° C. on YPD agar.

Functional Analysis of *Yarrowia lipolytica* Transformants Comprising pBY1-FAE and pBY2 pBY1-FAE (comprising a chimeric FBAINm::IgD9eS::Pex20 gene) and pBY2 (comprising a chimeric FBAINm::EgD9e::Pex20 gene) were transformed into *Yarrowia lipolytica* strain Y2224 as described in the General Methods. The cells were plated onto minimal media plates lacking uracil and maintained at 30° C. for 2 to 3 days.

Single colonies of transformants were then grown in 3 mL minimal medium lacking uracil at 30° C. to an $OD_{600}$~1.0. As a control, Y2224 was also grown in a similar way on minimal media supplemented with uracil. Cells were subsequently washed with water, collected by centrifugation and lipids transesterified as described supra. FAMEs from cells containing pBY1-FAE, pBY2 or no expression vector were analyzed by GC, using the methodology described in Example 4 (i.e., for *S. cerevisiae* cells containing pY119). Results for the average of three replications of each are shown in Table 8. Fatty acids are identified as 16:0 (palmitate), 16:1(9) (palmitoleic acid), 17:1(9), 18:0, 18:1(9) (oleic acid), LA and EDA. Elongation Efficiency ("% Elo LA") was calculated as described in Example 4.

TABLE 8

Comparison Of Lipid Profiles Of *Yarrowia* Expressing EgD9e And IgD9eS

| Sample Name | Δ9 Elongase | 16:0 | 16:1 (9) | 17:1 (9) | 18:0 | 18:1 (9) | LA | EDA | % Elo LA |
|---|---|---|---|---|---|---|---|---|---|
| Y2224-1 | None | 13.4 | 12.6 | 0.8 | 2.8 | 43.1 | 27.2 | 0.1 | 0.2 |
| Y2224-2 | None | 12.2 | 12.3 | 0.8 | 2.3 | 46.1 | 26.2 | 0.1 | 0.2 |
| Y2224-3 | None | 11.7 | 10.8 | 1.1 | 2.8 | 48.4 | 25.0 | 0.1 | 0.2 |
| pBY1-FAE-1 | IgD9eS | 11.9 | 11.9 | 0.8 | 3.1 | 50.6 | 20.2 | 1.6 | 7.5 |
| pBY1-FAE-2 | IgD9eS | 12.9 | 11.4 | 0.9 | 3.6 | 46.7 | 23.0 | 1.4 | 5.9 |
| pBY1-FAE-3 | IgD9eS | 12.1 | 12.5 | 0.8 | 3.2 | 50.0 | 19.8 | 1.6 | 7.4 |
| pBY2-1 | EgD9e | 12.3 | 11.7 | 0.8 | 3.4 | 48.4 | 21.1 | 2.2 | 9.5 |
| pBY2-2 | EgD9e | 12.1 | 12.5 | 0.8 | 3.2 | 50.1 | 19.1 | 2.3 | 10.6 |
| pBY2-3 | EgD9e | 12.1 | 12.2 | 0.8 | 3.3 | 50.0 | 19.4 | 2.1 | 9.9 |

As shown in Table 8, the results demonstrated that EgD9e functioned with greater substrate conversion efficiency than IgD9eS, when converting LA to EDA.

Example 8

Construction and Functional Analysis of *Yarrowia lipolytica* Expression Vector pZuFmEgD9ES, Comprising a Synthetic Δ9 Elongase Gene (Derived from *Euglena gracilis*), Codon-Optimized for Expression in *Yarrowia lipolytica* (EgD9eS)

The present Example describes the expression of *Yarrowia lipolytica* vector pZuFmEgD9ES, comprising a chimeric FBAINm::EgD9ES::Pex20 gene, wherein EgD9eS is a synthetic Δ9 elongase derived from *Euglena gracilis* and codon-optimized for expression in *Yarrowia*. This analysis therefore required: (1) synthesis of EgD9eS; (2) construction and transformation of pZuFmEgD9ES into *Yarrowia lipolytica* strain Y2224; and (3) analysis of lipid profiles within transformant organisms of *Yarrowia lipolytica* strain Y2224 that were comprising pZuFmEgD9ES (expressing EgD9eS).

Synthesis of EgD9eS

The codon usage of the Δ9 elongase gene of *Euglena gracilis* (EgD9e; SEQ ID NOs:1 and 2) was optimized for expression in *Yarrowia lipolytica*, in a manner similar to that described in Example 5 and PCT Publication No. WO 2004/101753. Specifically, a codon-optimized Δ9 elongase gene (designated "EgD9eS"; SEQ ID NO:3) was designed, based on the coding sequence of EgD9e (i.e., from clone eeg1c.pk001.n5.f), according to the *Yarrowia* codon usage pattern (PCT Publication No. WO 2004/101753), the consensus sequence around the 'ATG' translation initiation codon, and the general rules of RNA stability (Guhaniyogi, G. and J. Brewer, *Gene,* 265(1-2):11-23 (2001)). In addition to modification of the translation initiation site, 117 bp of the 777 bp coding region were modified (15.1%) and 106 codons were optimized. FIG. 10 shows a comparison of the nucleotide sequences of EgD9e and EgD9eS. None of the modifications in the codon-optimized gene changed the amino acid sequence of the encoded protein (SEQ ID NO:2). The designed EgD9eS gene was synthesized by GenScript Corporation (Piscataway, N.J.) and cloned into pUC57 (GenBank Accession No. Y14837) to generate pEgD9S.

Generation of Construct pZuFmEgD9E (Comprising EgD9E) and pZuFmEgD9ES (Comprising EgD9ES)

Plasmid pZuFmEgD9ES (SEQ ID NO:53), comprising a chimeric FBAINm::EgD9ES::Pex20 gene, was constructed by replacing the Nco I/Not I fragment of pZUF17 (FIG. 7C; SEQ ID NO:121) with the Nco I/Not I fragment from pEgD9S comprising EgD9eS. The product of this ligation was auto-replicating expression vector pZuFmEgD9ES, which thereby contained the following components:

TABLE 9

Components of Plasmid pZuFmEgD9ES (SEQ ID NO: 53)

| RE Sites and Nucleotides Within SEQ ID NO: 53 | Description of Fragment and Chimeric Gene Components |
|---|---|
| Swa I/BsiW I (6067-318) | FBAINm::EgD9eS::Pex20, comprising: FBAINm: *Yarrowia lipolytica* FBAINm promoter (PCT Publication No. WO 2005/049805) EgD9eS: codon-optimized Δ9 elongase (SEQ ID NO: 3, described herein as EgD9eS), derived from *Euglena gracilis* Pex20: Pex20 terminator sequence of *Yarrowia* Pex20 gene (GenBank Accession No. AF054613) |
| 1354-474 | ColE1 plasmid origin of replication |
| 2284-1424 | Ampicillin-resistance gene ($Amp^R$) for selection in *E. coli* |
| 3183-4487 | *Yarrowia* autonomous replication sequence (ARS18; GenBank Accession No. A17608) |
| 6020-4533 | *Yarrowia* Ura 3 gene (GenBank Accession No. AJ306421) |

Plasmid pZuFmEgD9E (SEQ ID NO:52), comprising a chimeric FBAINm::EgD9E::Pex20 gene, was synthesized in a similar manner using the pZUF17 plasmid backbone.

Functional Analysis of *Yarrowia lipolytica* Transformants Comprising pZuFmEgD9E and pZuFmEgD9ES Plasmid pZuFmEgD9E and pZuFmEgD9ES (comprising a chimeric FBAINm::EgD9e::Pex20 gene and FBAINm::EgD9eS::Pex20 gene, respectively) were transformed into strain Y2224 (the FOA resistant mutant from an autonomous mutation of the Ura3 gene of wildtype *Yarrowia* strain ATCC #20362; Example 7), as described in the General Methods. The transformants were selected on MM plates. After 2 days growth at 30° C., 3 transformants grown on the MM plates were picked and re-streaked onto fresh MM plates. Once grown, these strains were individually inoculated into 3 mL liquid MM at 30° C. and shaken at 250 rpm/min for 2 days. The cells were collected by centrifugation, lipids were extracted, and fatty acid methyl esters were prepared by trans-esterification, and subsequently analyzed with a Hewlett-Packard 6890 GC.

GC analyses showed that there were about 3.2% EDA (C20:2) of total lipids produced in all seven transformants with pZuFmEgD9E, wherein the average conversion efficiency of LA (C18:2) to EDA in these seven strains was determined to be about 18.3% (average; calculated as described in Example 4).

In contrast, GC analyses showed that there were about 3.6% EDA (C20:2) of total lipids produced in all seven transformants with pZuFmEgD9ES, wherein the average conversion efficiency of LA (C18:2) to EDA in these seven strains was determined to be about 20.1% (average). Thus, the experimental data demonstrated that the synthetic *Euglena gracilis* Δ9 elongase codon-optimized for expression in *Yarrowia lipolytica* (i.e., EgD9eS; SEQ ID NO:3) was about 16.2% more efficient elongating LA to EDA than the wild-type EgD9e gene (i.e., SEQ ID NO:1).

Example 9

Construction of *Yarrowia lipolytica* Expression Vector pY120 for Expression of the *Euglena gracilis* Δ9 Elongase (EgD9e)

The present Example describes construction of *Yarrowia lipolytica* vector pY120 for expression of EgD9e. Specifically, the NcoI/NotI DNA fragment from pKR906 (comprising EgD9e; from Example 4) was cloned into the NcoI/NotI DNA fragment from pY115 (FIG. 8; Example 5; comprising the *Yarrowia lipolytica* FBAINm promoter) to produce pY120 (SEQ ID NO:54; FIG. 11A). In this Figure, EgD9e is labeled as "eug el1".

Example 10

Construction of Soybean Expression Vector pKR912 for Expression of the *Euglena gracilis* Δ9 Elongase (EgD9e)

The present Example describes construction of soybean vector pKR912 for expression of EgD9e.

A starting plasmid pKR72 (ATCC Accession No. PTA-6019; SEQ ID NO:55), a derivative of pKS123 which was previously described in PCT Publication No. WO 02/008269 (the contents of which are hereby incorporated by reference), contains the hygromycin B phosphotransferase gene (HPT) (Gritz, L. and Davies, J., *Gene,* 25:179-188 (1983)), flanked by the T7 promoter and transcription terminator (T7prom/HPT/T7term cassette), and a bacterial origin of replication (ori) for selection and replication in bacteria (e.g., *E. coli*). In addition, pKR72 also contains the HPT gene, flanked by the 35S promoter (Odell et al., *Nature,* 313:810-812 (1985)) and NOS 3' transcription terminator (Depicker et al., *J. Mol. Appl. Genet.,* 1:561-570 (1982)) (35S/HPT/NOS3' cassette) for selection in plants such as soybean. pKR72 also contains a NotI restriction site, flanked by the promoter for the α' subunit of β-conglycinin ("BCON Pro"; Beachy et al., *EMBO J.,* 4:3047-3053 (1985)) and the 3' transcription termination region of the phaseolin gene (Doyle et al., *J. Biol. Chem.,*

261:9228-9238 (1986)), thus allowing for strong tissue-specific expression in the seeds of soybean of genes cloned into the NotI site.

EgD9e was released from pKR906 (Example 4) by digestion with NotI and cloned into the NotI site of pKR72 to produce pKR912 (SEQ ID NO:56). A schematic depiction of pKR912 is shown in FIG. 11B; EgD9e is labeled as "eug el1" therein.

Example 11

Construction of Soybean Intermediate Cloning Vector pKR911 for Expression of the *Euglena gracilis* Δ9 Elongase (EgD9e)

The present Example describes construction of soybean vector pKR911 for expression of EgD9e.

Vector pKS102 (SEQ ID NO:57), previously described in PCT Publication No. WO 02/00905 (the contents of which are hereby incorporated by reference), contains a T7prom/HPT/T7term cassette (described in Example 10), and a bacterial origin of replication (ori) for selection and replication in bacteria (e.g., *E. coli*).

Vector pKR197 (SEQ ID NO:58), previously described in PCT Publication No. WO 04/071467 (the contents of which are hereby incorporated by reference), was constructed by combining the AscI fragment from plasmid pKS102 (SEQ ID NO:57), containing the T7prom/HPT/T7term cassette and bacterial ori, with the AscI fragment of plasmid pKR72 (described in Example 10), containing the βcon/NotI/Phas cassette.

EgD9e was released from pKR906 (Example 4) by digestion with NotI and cloned into the NotI site of pKR197 to produce intermediate cloning vector pKR911 (SEQ ID NO:59). A schematic depiction of pKR911 is shown in FIG. 12A; EgD9e is labeled as "eug el1" therein.

Example 12 cDNA Synthesis and PCR of *Euglena gracilis* Δ8 Desaturase (EgD8)

The present Example describes the isolation of a Δ8 desaturase (designated as "EgD8") from *Euglena gracilis*, as disclosed in U.S. patent application Ser. No. 11/166,003 and Ser. No. 11/166,993 (corresponding with PCT Publications No. WO 06/012325 and No. WO 06/012326 [the contents of which are hereby incorporated by reference]). The isolation of this gene was desirable to enable co-expression of EgD9e and EgD8, to thereby permit expression of a Δ9 elongase/Δ8 desaturase pathway and enable accumulation of DGLA and/or ETA from LA and/or ALA.

*Euglena gracilis* cDNA was synthesized from 765 ng of mRNA (Example 1) using the SuperScript™ Choice System for cDNA synthesis (Invitrogen™ Life Technologies, Carlsbad, Calif.) with the provided oligo(dT) primer according to the manufacturer's protocol. The synthesized cDNA was dissolved in 20 μL of water.

The *Euglena gracilis* Δ8 desaturase was amplified from cDNA using the conditions described below. Specifically, cDNA (1 μL) was combined with 50 pmol of Eg5-1 (SEQ ID NO:62), 50 pmol of Eg3-3 (SEQ ID NO:63), 1 μL of PCR nucleotide mix (10 mM, Promega, Madison, Wis.), 5 μL of 10×PCR buffer (Invitrogen Corporation), 1.5 μL of $MgCl_2$ (50 mM, Invitrogen Corporation), 0.5 μL of Taq polymerase (Invitrogen Corporation) and water to 50 μL. The reaction conditions were 94° C. for 3 min followed by 35 cycles of 94° C. for 45 sec, 55° C. for 45 sec and 72° C. for 1 min. The PCR was finished at 72° C. for 7 min and then held at 4° C. The PCR reaction was analyzed by agarose gel electrophoresis on 5 μL and a DNA band with molecular weight around 1.3 kB was observed. The remaining 45 μL of product was separated by agarose gel electrophoresis and the DNA band was purified using the Zymoclean™ Gel DNA Recovery Kit (Zymo Research, Orange, Calif.) following the manufacturer's protocol. The resulting DNA was cloned into the pGEM®-T Easy Vector (Promega) following the manufacturer's protocol. Multiple clones were sequenced using T7 (SEQ ID NO:64), M13-28Rev (SEQ ID NO:65), Eg3-2 (SEQ ID NO:66) and Eg5-2 (SEQ ID NO:67).

Thus, a DNA sequence for the *Euglena gracilis* Δ8 desaturase (i.e., Eg5) was obtained (SEQ ID NO:60). Translation of Eg5 gave rise to the protein sequence set forth in SEQ ID NO:61. For the purposes herein, "Eg5" is referred to throughout the remainder of this specification as "EgD8".

Although not detailed herein, a synthetic version of EgD8 was also created that was codon-optimized for expression in *Yarrowia lipolytica* (as disclosed in U.S. patent application Ser. No. 11/166,003 and Ser. No. 11/166,993 (corresponding with PCT Publications No. WO 06/012325 and No. WO 06/012326)), using the methodology described in Example 5, supra. This gene, designated as EgD8S, is described herein as SEQ ID NOs:68 and 69.

Example 13

Construction of Soybean Expression Vector pKR913 for Co-Expression of EgD9e and EgD8

The present Example describes construction of soybean vector pKR913 for co-expression of EgD9e and EgD8.

Vector pKS121 (SEQ ID NO:70), which was previously described in PCT Publication No. WO 02/00904 (the contents of which are hereby incorporated by reference), contains a NotI site flanked by the Kunitz soybean Trypsin Inhibitor (KTi) promoter (Jofuku et al., *Plant Cell,* 1:1079-1093 (1989)) and the KTi 3' termination region, the isolation of which is described in U.S. Pat. No. 6,372,965 (KTi/NotI/KTi3' cassette).

Vector pKR457 (SEQ ID NO:71), which was previously described in PCT Publication No. WO 05/047479 (the contents of which are hereby incorporated by reference), is a derivative of pKS121 where the restriction sites upstream and downstream of the KTi/NotI/KTi3' cassette have been altered through a number of subcloning steps. Vector pKR457 also contains the soy albumin transcription terminator (GM-ALB TERM), which was previously described in PCT Publication No. WO 04/071467 (the contents of which are hereby incorporated by reference), downstream of the KTi terminator to lengthen and strengthen termination of transcription. In pKR457, the BamHI site upstream of the KTi promoter in the KTi/NotI/KTi3' cassette was removed and a new sequence (SEQ ID NO:72) was added containing a BsiWI, SalI, SbfI and HindIII site with the BsiWI site being closest to the 5' end of the KTi promoter.

In addition, the SalI site downstream of the KTi terminator in the KTi/NotI/KTi3' cassette from pKS121 was removed and a new sequence (SEQ ID NO:73) added containing an XbaI (closest to 3' end of KTi terminator), a BamHI site, the soy albumin transcription terminator sequence, a BsiWI site and another BamHI site. The albumin transcription terminator had been previously amplified from soy genomic DNA using primer oSalb-12 (SEQ ID NO:74), designed to introduce a BsiWI site at the 3' end of the terminator, and primer oSalb-13 (SEQ ID NO:75), designed to introduce a BamHI site at the 5' end of the terminator.

EgD8 (SEQ ID NO:60) was released from the pGEM®-T Easy Vector described in Example 12 by digestion with NotI and cloned into the NotI site of pKR457 to produce pKR680 (SEQ ID NO:76). Plasmid pKR680 was then digested with BsiWI and the fragment containing EgD8 was cloned into the BsiWI site of pKR911 (SEQ ID NO:59; Example 11) to produce pKR913 (SEQ ID NO:77). A schematic depiction of pKR913 is shown in FIG. 12B. EgD9e is labeled as "eug el1" and EgD8 is labeled as eug d8-sq5 therein.

Example 14

Construction of a Soybean Expression Vector for Co-Expression of EgD9e and EgD8

The present Example describes construction of a soybean vector for co-expression of EgD9e and EgD8. Specifically, plasmid pKR680 (SEQ ID NO:76; Example 13) is digested with BsiWI and the fragment containing EgD8 (SEQ ID NO:60) is cloned into the BsiWI site of pKR912 (SEQ ID NO:56; Example 10). In this way, EgD8 is co-expressed with EgD9e behind strong, seed-specific promoters.

Example 15

Construction of a Vector for Co-Expression of EgD9e and EgD8 with the *Mortierella alpina* Δ5 Desaturase (Mad5)

The present Example describes construction of a soybean vector for co-expression of EgD9e and EgD8, in addition with other PUFA genes (i.e., a Δ5 desaturase).

A soybean expression vector containing EgD8 (SEQ ID NO:60), EgD9e (SEQ ID NO:1) and the *Mortierella alpina* Δ5 desaturase (SEQ ID NO:78; "Mad5"), which is described in U.S. Pat. No. 6,075,183 and PCT Publication Nos. WO 04/071467 and WO 05/0479479 (the contents of which are hereby incorporated by reference), all under the control of strong seed-specific promoters, is constructed in the following way.

Through a number of sub-cloning steps, a sequence of DNA (SEQ ID NO:80) is effectively added into the SmaI site of vector pKR287 (which is described in PCT Publication No. WO 04/071467, the contents of which are hereby incorporated by reference), to produce pKR767 (SEQ ID NO:81). In this way, a SbfI restriction site is added to the 3' end of the leg1A transcription terminator of the Gy1/Mad5/legA2 cassette, which is described in PCT Publication Nos. WO 04/071467 and WO 05/0479479.

The Gy1/Mad5/legA2 cassette is released from pKR767 by digestion with SbfI and the resulting fragment is cloned into the SbfI site of the vector described in Example 14 to produce a new vector that co-expresses all three genes (i.e., EgD9e, EgD8 and Mad5) under control of strong seed-specific promoters.

Example 16

Co-Expressing a Soybean Expression Vector Comprising EgD9e, EgD8 and Mad5 with the *Saprolegnia diclina* Δ17 Desaturase (SdD17)

The present Example describes a means of co-transforming the soybean expression vector described in Example 15 (expressing EgD9e, EgD8 and Mad5), along with other vectors expressing multiple different seed-specific promoter/long chain PUFA-biosynthetic gene combinations (e.g., expressing a Δ17 desaturase). Whole plasmids, or purified AscI fragments from the plasmids containing the appropriate gene combinations, are used (as could any combination of either fragment of plasmid).

For instance, the vector described in Example 15 could be co-transformed with pKR328 (SEQ ID NO:82, described in PCT Publication No. WO 04/071467) containing the *Saprolegnia diclina* Δ17 desaturase (SdD17) under control of the annexin promoter and having a hygromycin resistance gene for selection in plants.

Similarly, the vector described in Example 15, could be co-transformed with pKR886 or pKR886r (FIG. 13A and FIG. 13B, respectively), two vectors similar to pKR328 but having the SAMS/ALS/ALS3' cassette (which is described in PCT Publication No. WO 04/071467) for selection in plants. Specifically, vectors pKR886 (SEQ ID NO:83) and pKR886r (SEQ ID NO:84) are made by cloning the PstI fragment, containing the Ann/Sdd17/BD30 cassette from pKR271 (SEQ ID NO:85, which is described in PCT Publication No. WO 04/071467) into the SbfI site of pKR226 (SEQ ID NO:86, which is described in PCT Publication No. WO 04/071467).

Example 17

Co-Expressing a Soybean Expression Vector Comprising EgD9e, EgD8 and Mad5 with SdD17 and *Arabidopsis* Fad3

The present Example describes a means of co-transforming the soybean expression vector described in Example 15 (expressing EgD9e, EgD8 and Mad5), along with other vectors expressing multiple different seed-specific promoter/long chain PUFA-biosynthetic gene combinations (e.g., expressing a Δ17 desaturase and Fad3).

The vector described in Example 15 could be co-transformed into soybeans with either pKR275 (SEQ ID NO:87, which is described in PCT Publication No. WO 04/071467 and has ATCC Accession Number PTA-4989) or pKR329 (SEQ ID NO:88, which is described in PCT Publication No. WO 04/07146). Plasmids pKR275 and pKR329 have ALS or hygromycin selection, respectively, and contain the KTi/Fad3/KTi3' gene cassette (which is described in PCT Publication No. WO 04/071467) in addition to the Ann/Sdd17/BD30 cassette. In this way, the *Arabidopsis* Fad3 gene could be co-expressed with the *Saprolegnia diclina* Δ17 desaturase (SdD17) behind strong, seed-specific promoters.

Example 18

Co-Expressing a Soybean Expression Vector Comprising EgD9e, EgD8 and Mad5 with SdD17 and *Fusarium moniliforme* ω15 Desaturase (Fmd15)

The present Example describes a means of co-transforming the soybean expression vector described in Example 15 (expressing EgD9e, EgD8 and Mad5), along with other vectors expressing multiple different seed-specific promoter/long chain PUFA-biosynthetic gene combinations (e.g., expressing a Δ17 desaturase and a Δ15 desaturase).

The vector described in Example 15 could be co-transformed into soybeans with pKR585 (SEQ ID NO:89, which is described in PCT Publication No. WO 05/0479479 and has ATCC Accession No. PTA-6019), having hygromycin selection and containing the *Fusarium moniliforme* ω15 desaturase (FmD15) under control of the KTi promoter.

The vector described in Example 15 could also be co-transformed into soybeans with pKR669, having ALS selection and containing the *Fusarium moniliforme* ω15 desaturase under control of the KTi promoter in addition to the Ann/Sdd17/BD30 cassette. Plasmid pKR669 is produced in the following way. The KTi promoter:FmD15:KTi terminator cassette is released from plasmid pKR578 (SEQ ID NO:90, which is described in PCT Publication No. WO 05/0479479 and has ATCC Accession No. PTA-6280) by digestion with BsiWI and is cloned into the BsiWI site of plasmid pKR226 (SEQ ID NO:86, which is described in PCT Publication No. WO 04/071467), containing the ALS gene for selection, the T7prom/HPT/T7term cassette and the bacterial on region, to produce pKR667 (SEQ ID NO:91). Plasmid pKR271 (SEQ ID NO:85, which is described in PCT Publication No. WO 04/071467) is digested with PstI and the fragment containing the *Saprolegnia diclina* Δ17 desaturase is cloned into the SbfI site of pKR667 to produce pKR669. In this way, the *Fusarium moniliforme* ω15 desaturase could be co-expressed with the *Saprolegnia diclina* Δ17 desaturase behind strong, seed-specific promoters. A schematic depiction of pKR669 is shown in FIG. 14A.

The vector described in Example 15 could also be co-transformed into soybeans with pKR873 (SEQ ID NO:92), having ALS selection and containing the *Fusarium moniliforme* ω15 desaturase (FmD15) under control of the soy albumin promoter (which is described in PCT Publication No. WO 04/071467) in addition to the Ann/Sdd17/BD30 cassette. Specifically, plasmid pKR873 is produced in the following way. The SA/NotI/SA3' cassette is amplified from plasmid pKR132 (SEQ ID NO:93, which is described in PCT Publication No. WO 04/071467) using PCR. Primer oSAlb-9 (SEQ ID NO:94) is designed to introduce XbaI and BsiWI sites at the 5' end of the promoter and primer oSAlb-2 (SEQ ID NO:95) is designed to introduce BsiWI and XbaI sites at the 3' end of the terminator. The resulting PCR fragment is subsequently cloned into pCR-Script AMP SK(+) (Stratagene Company, San Diego, Calif.) to produce pKR160 (SEQ ID NO:96). Plasmid pKR160 is then digested with BsiWI and the SA/NotI/SA3' cassette ligated into the BsiWI site of pKR124 (SEQ ID NO:97, which is described in PCT Publication No. WO 05/0479479) to produce pKR163 (SEQ ID NO:98). The NotI fragment from pY34 (SEQ ID NO:99, which is described in PCT Publication No. WO 05/0479479), containing the *Fusarium moniliforme* ω15 desaturase, is cloned into the NotI site of pKR163 (SEQ ID NO:98) to produce pKR863 (SEQ ID NO:100). The SA/FmD15/SA3' cassette is released from plasmid pKR863 by digestion with BsiWI and is cloned into the BsiWI site of plasmid pKR226 (SEQ ID NO:86, which is described in PCT Publication No. WO 04/071467), containing the ALS gene for selection, the T7prom/HPT/T7term cassette and the bacterial on region, to produce pKR869 (SEQ ID NO:101). Plasmid pKR271 (SEQ ID NO:85, which is described in PCT Publication No. WO 04/071467) is digested with PstI and the fragment containing the *Saprolegnia diclina* Δ17 desaturase is cloned into the SbfI site of pKR869 (SEQ ID NO:101) to thereby produce pKR873 (SEQ ID NO:92). In this way, the *Fusarium moniliforme* ω15 desaturase could be co-expressed with the *Saprolegnia diclina* Δ17 desaturase behind strong, seed-specific promoters. A schematic depiction of pKR873 is shown in FIG. 14B.

Example 19

Co-Expressing a Soybean Expression Vector Comprising EgD9e, EgD8 and Mad5 with SdD17 and *Mortierella alpina* Elongase (MaELO)

The present Example describes a means of co-transforming the soybean expression vector described in Example 15 (expressing EgD9e, EgD8 and Mad5), along with other vectors expressing multiple different seed-specific promoter/long chain PUFA-biosynthetic gene combinations (e.g., expressing a Δ17 desaturase and an elongase).

The vector described in Example 15 could also be co-transformed into soybeans with a vector having ALS selection and containing the *Mortierella alpina* elongase (which is described in PCT Publication Nos. WO 04/071467 and WO 00/12720) under control of the soy albumin promoter (which is described in PCT Publication No. WO 04/071467) in addition to the Ann/Sdd17/BD30 cassette. This plasmid could be produced in a similar way as described supra. For instance, the NotI fragment from pKR270 (SEQ ID NO:102, which is described in PCT Publication No. WO 04/071467), containing the *Mortierella alpina* elongase ("Maelo"), could be cloned into the NotI site of pKR163 (SEQ ID NO:98) to produce a vector having the SA/Maelo/SA3' cassette. The SA/Maelo/SA3' cassette could be released from that plasmid by digestion with BsiWI and could be cloned into the BsiWI site of plasmid pKR226 (SEQ ID NO:86, which is described in PCT Publication No. WO 04/071467), containing the ALS gene for selection, the T7prom/HPT/T7term cassette and the bacterial on region, to produce a new plasmid. Plasmid pKR271 (SEQ ID NO:85, which is described in PCT Publication No. WO 04/071467) could then be digested with PstI and the fragment containing the *Saprolegnia diclina* Δ17 desaturase could be cloned into the SbfI site of the new plasmid containing the SA/Maelo/SA3' cassette. In this way, the *Mortierella alpina* elongase could be co-expressed with the *Saprolegnia diclina* Δ17 desaturase behind strong, seed-specific promoters.

Example 20

Co-Expressing a Soybean Expression Vector Comprising EgD9e, EgD8 and Mad5 with $C_{20/22}$ Elongases and Δ4 Desaturases The present Example describes a means of co-transforming the soybean expression vector described in Example 15 (expressing EgD9e, EgD8 and Mad5), along with other vectors expressing multiple different seed-specific promoter/long chain PUFA-biosynthetic gene combinations (e.g., expressing $C_{20/22}$ elongases and Δ4 desaturases).

$C_{20/22}$ elongases (also identified as Δ5 elongases and/or EPA elongases) and/or Δ4 desaturases can also be co-expressed in soybean expression vectors similar to those described herein. For instance, a Δ4 desaturase from *Schizochytrium aggregatum* (described in PCT Publication No. WO 02/090493) or a Δ5 elongase from *Pavlova* (described in PCT Publication No. WO 04/071467), can be cloned into suitable soybean expression vectors such as those described in PCT Publication No. WO 04/071467. PCR primers designed to introduce NotI sites at the 5' and 3' ends of the Δ4 desaturase or Δ5 elongase can be used to amplify the gene. The resulting PCR product can then be digested with NotI and can be cloned into a suitable soybean expression vector containing a NotI site flanked by a strong seed-specific promoter and a transcription terminator. Further sub-cloning into other vectors such as those described herein, or in PCT Publication No. WO 04/071467 or PCT Publication No. WO 05/047479, but not limited to these, should yield vectors suitable for expression and co-expression of the Δ4 desaturase and or Δ5 elongase in soybean.

Example 21

Preparation of *Eutreptiella* sp. CCMP389 Genomic DNA, RNA and cDNA

The present Example describes the preparation of genomic DNA, RNA and cDNA from *Eutreptiella* sp. CCMP389, which had been purchased from The Provasoli-Guillard National Center for Culture of Marine Phytoplankton (CGMP) (Bigelow Laboratory for Ocean Sciences, West Boothbay Harbor, Me.).

Preparation of RNA and Genomic DNA from *Eutreptiella* sp. CCMP389

Total RNA and genomic DNA were isolated from 1 liter of culture using Trizol reagent (Invitrogen, Carlsbad, Calif.), according to the manufacturer's protocol. Specifically, the cell pellet was resuspended in 0.75 mL of Trizol reagent, mixed with 0.5 mL of 0.5 mm glass beads, and homogenized in a Biospec mini beadbeater (Bartlesville, Okla.) at the highest setting for 3 min. The mixtures were centrifuged in an Eppendorf centrifuge for 30 sec at 14,000 rpm to remove debris and glass beads. The supernatant was extracted with 150 μl of 24:1 chloroform:isoamyl alcohol (Invitrogen). The upper aqueous phase was used for RNA isolation and the lower organic phase was used for DNA isolation.

For RNA isolation, the aqueous phase was mixed with 0.375 mL of isopropyl alcohol and allowed to incubate at room temperature for 5 min. Precipitated RNA was collected by centrifugation at 8,000 rpm and 4° C. for 5 min. The pellet was washed once with 0.7 mL of 80% ethanol and air-dried. In this way, 360 μg of total RNA were obtained.

For genomic DNA isolation, the lower organic phase was mixed with 75 μl of ethanol and incubated at room temperature for 5 min. The sample was then centrifuged at 5,000 rpm for 2 min in an Eppendorf centrifuge. The pellet was washed with 0.75 mL of 0.1 M sodium citrate:10% ethanol twice. Each time, the sample was incubated for 15 min at room temperature in the wash solution, followed by centrifugation at 5,000 rpm for 5 min at 4° C. The pellet was air-dried and re-dissolved in 300 μl of 8 mM NaOH. The pH of the sample was adjusted to 7.5 with 1 M HEPES. The genomic DNA was then further purified with a Qiagen PCR purification kit (Valencia, Calif.) exactly as described in the manufacturer's protocol. Thus, 40 μg of genomic DNA was isolated.

Preparation of cDNA from *Eutreptiella* sp. CCMP389

Double-stranded cDNA was generated, using the Creator™ SMART™ cDNA Library Construction Kit from BD Bioscience Clontech (Palo Alto, Calif.). Specifically, for first strand cDNA synthesis, 1 μl of the total RNA sample (1.2 μg) was mixed individually with 1 μl of SMART™ IV oligonucleotide (SEQ ID NO:103), 1 μl CDSIII/3' PCR primer (SEQ ID NO:104) and 2 μl of water. The mixture was heated to 75° C. for 5 min and cooled on ice for 5 min. To the sample was added 2 μl of 5× first strand buffer, 1 μl 20 mM DTT, 1 μl of dNTP mix (10 mM each of dATP, dCTP, dGTP and dTTP) and 1 μl of PowerScript reverse transcriptase. The sample was incubated at 42° C. for 1 hr.

The first strand cDNA synthesis mixture was used as template for amplification. Specifically, the reaction mixture contained 2 μl of the above first strand cDNA sample, 80 μl of water, 10 μl of 10× Advantage 2 PCR buffer, 2 μl 50×dNTP mix (10 mM each of dATP, dCTP, dGTP and dTTP), 2 μl of 5'-PCR primer (SEQ ID NO:105), 2 μl CDSIII/3'-PCR primer (SEQ ID NO:104) and 2 μl 50× Advantage 2 polymerase mix. PCR amplification was performed using the following conditions: 95° C. for 1 min, followed by 20 cycles of 95° C. for 10 sec and 68° C. for 6 min. Amplification products were purified with a Qiagen PCR purification kit following the manufacturer's protocol exactly. Purified products were eluted with 50 μl of water.

Example 22

Isolation of the Full-Length Δ9 Elongase from *Eutreptiella* sp. CCMP389

The present Example describes the identification of a partial cDNA fragment encoding a Δ9 elongase from *Eutreptiella* sp. CCMP389, by use of primers derived from conserved regions of the *Euglena gracilis* (EgD9e; Example 3) and *I. galbana* (IgD9e) Δ9 elongase sequences. Then, based on the sequence of the partial cDNA fragment, the 5' and 3' ends of the gene were isolated. This enabled assembly of a contig (SEQ ID NO:17), extending 51 bases upstream of the *Eutreptiella* sp. CCMP389 Δ9 elongase translation initiation 'ATG' codon and 662 bp beyond the Δ9 elongase termination codon.

Identification of a cDNA Fragment Encoding a Partial Δ9 Elongase from *Eutreptiella* sp. CCMP389

*Eutreptiella* sp. CCMP389 was analyzed for the presence of a Δ9 elongase. Design of degenerate primers suitable to isolate the *Eutreptiella* sp. CCMP389 Δ9 elongase was based on the identification of several stretches of conserved amino acid sequences common to both EgD9e (SEQ ID NO:2) and IgD9e (SEQ ID NO:8), when an alignment of the two elongases was produced using the method of Clustal W (slow, accurate, Gonnet option; Thompson et al., *Nucleic Acids Res.*, 22:4673-4680 (1994)) of the MegAlign™ program of DNASTAR software (Clustal W alignment not shown herein, in lieu of Clustal V alignment of EgD9e and IgD9e provided as FIG. 4).

Based on this alignment, the following set of degenerate oligonucleotides were designed to amplify a portion of the coding region of the Δ9 elongase gene from *Eutreptiella* sp. CCMP389, as shown in Table 10.

TABLE 10

Degenerate Oligonucleotides Used To Amplify The Δ9 Elongase Gene From *Eutreptiella* sp. CCMP389

| Primer | Nucleotide Sequence | Amino Acid Sequence | Position Within SEQ ID NO: 2 (EgD9e) |
|---|---|---|---|
| EuEF3 | YTNCARTTYTTYCAYCA YTT (SEQ ID NO: 106) | LQFFHHL (SEQ ID NO: 107) | 150-156 |

TABLE 10-continued

Degenerate Oligonucleotides Used To Amplify The Δ9 Elongase Gene From *Eutreptiella* sp. CCMP389

| Primer | Nucleotide Sequence | Amino Acid Sequence | Position Within SEQ ID NO: 2 (EgD9e) |
|---|---|---|---|
| EuER3 | TTRAAYTGDATDATYTG CAT (SEQ ID NO: 108) | MQIIQFN (SEQ ID NO: 109) | 210-216 |

[Note:
The nucleic acid degeneracy code used for SEQ ID NOs: 106 and 108 was as follows: R = A/G; Y = C/T; D = G/A/T; and N = A/C/T/G.]

The reaction mixture contained 1 μl of 1:20 diluted cDNA, 5 μl each of the forward and reverse primers (20 μM), 14 μl water and 25 μl of TaKaRa ExTaq 2× premix (TaKaRa Bio, Mountain View, Calif.). PCR amplification was performed using the following parameters: 94° C. for 1 min, then 35 cycles of 94° C. for 20 sec, 55° C. for 20 sec, and 72° C. for 1 min, followed by a final elongation cycle at 72° C. for 5 min.

Agarose gel analysis of the PCR products showed that a ~200 bp fragment was obtained. The fragments were purified with a Qiagen PCR purification kit, cloned into pCR2.1-TOPO (Invitrogen) and sequenced. The resultant sequence (SEQ ID NO:13), when translated, had homology with the known Δ9 elongase from *Isochrysis galbana* (IgD9e; SEQ ID NO:8), based on BLAST program analysis (Basic Local Alignment Search Tool; Altschul, S. F., et al., *J. Mol. Biol.,* 215:403-410 (1993); Example 3).

Isolation of the 5'-End Sequence of the *Eutreptiella* sp. CCMP389 Δ9 Elongase

Double-stranded cDNA of *Eutreptiella* sp. CCMP389 (Example 21) was used as template in two separate rounds of PCR amplification. In the first round of PCR amplification, the oligonucleotide primers consisted of a gene specific oligonucleotide (i.e., 389Elo-5-1 [SEQ ID NO:110]) and the generic oligonucleotide 5'-PCR primer (SEQ ID NO:105) from the BD-Clontech Creator™ SMART™ cDNA Library Kit. The PCR amplifications were carried out in a 50 μl total volume, comprising: 1 μl of 1:10 diluted *Eutreptiella* sp. CCMP389 cDNA as template, 1 μl of each primer (20 μM), 22 μl water and 25 μl TaKaRa ExTaq 2× premix. Amplification was carried out at 94° C. for 90 sec, then 30 cycles of 94° C. for 30 sec, 55° C. for 30 sec and 72° C. for 1 min, followed by a final elongation cycle at 72° C. for 7 min.

The second round of PCR amplification used 1 μl of diluted product (1:50) from the first round PCR reaction as template. Primers consisted of a gene specific oligonucleotide (i.e., 389Elo-5-2 (SEQ ID NO:111)) and the oligonucleotide DNR CDS 5'-2 (SEQ ID NO:112). Amplification was conducted as described above.

The products of the second round PCR reaction were electrophoresed in 1% (w/v) agarose and appeared as a diffused band spanning the size range of 200 to 800 bp. Products between 400 bp to 600 bp were isolated using a Qiagen Gel purification kit according to the manufacturer's protocol, cloned into pCR2.1-TOPO (Invitrogen), and transformed into *E. coli*. Transformants were selected on LB agar containing ampicillin (100 μg/mL).

Sequence analysis of the plasmid DNA from one transformant comprising the 5' region of the putative Δ9 elongase cDNA revealed a fragment of 406 bp (i.e., 5'-cDNA fragment 1; SEQ ID NO:14). This fragment extended to near the gene's 'ATG' translation initiation codon, but neither the start codon nor the first 20 to 30 amino acids were included in SEQ ID NO:14.

An additional oligonucleotide (i.e., 389Elo-5-4 (SEQ ID NO:113)) was then designed to obtain the complete 5' end of the gene by PCR, based on the sequence of 5'-cDNA fragment 1 (SEQ ID NO:14). The reaction mixture and amplification conditions were identical to those used for the second round of PCR above, except that primer 389Elo-5-2 was replaced with 389Elo-5-4. When analyzed by agarose gel electrophoresis, PCR products again appeared as a diffused band between 200 and 800 bp and fragments with a size of 200 to 500 bp were isolated, cloned and transformed as described above.

Sequence analysis of the plasmid DNA from one transformant comprising the 5' region of the putative Δ9 elongase cDNA revealed a fragment of 197 bp (5'-cDNA fragment 2; SEQ ID NO:15). This included the 5'-end of the cDNA and 51 bp of upstream untranslated region.

Isolation of the 3'-End of the *Eutreptiella* sp. CCMP389 Δ9 Elongase

The 3' end of the putative Δ9 delta elongase was also isolated by PCR amplification using cDNA as template. The methodology was as described above for isolation of the 5' end; however, the primers used on both the first and second round of PCR amplification were as shown below in Table 11 and were 10 μM instead of 20 μM. Additionally, the final elongation cycle at 72° C. was decreased from 7 min to 5 min.

TABLE 11

Oligonucleotide Primers Used For 3' cDNA Isolation

| PCR Amplification | Gene Specific Oligonucleotide | Generic Oligonucleotide |
|---|---|---|
| 1st Round | 389Elo-3-1 (SEQ ID NO: 114) | CDSIII/3' PCR primer (SEQ ID NO: 104) |
| 2nd Round | 389Elo-3-2 (SEQ ID NO: 115) | CDSIII/3' PCR primer (SEQ ID NO: 104) |

* CDSIII/3' PCR primer was supplied in Clontech's Creator ™ SMART ™ cDNA Library Construction Kit.

A ~1 kB DNA fragment was generated from the 2nd round PCR amplification, which was purified with a Qiagen PCR purification kit, cloned into pCR2.1-TOPO, transformed and sequenced. Sequence analysis of several clones showed that the ~1 kB DNA fragment contained the 3'-region of the putative Δ9 elongase cDNA, including the polyA tail. The 920 bp assembled contig sequence of the 3'-region is shown as SEQ ID NO:16.

Assembly of the Full-Length Δ9 Elongase Sequence from *Eutreptiella* sp. CCMP389

Assembly of the original partial cDNA fragment (SEQ ID NO:13), the two 5' cDNA fragments (SEQ ID NOs:14 and 15) and 3'-cDNA fragment (SEQ ID NO:16) resulted in the complete sequence of the Δ9 elongase from *Eutreptiella* sp. CCMP389, plus 51 bp of 5' untranslated region and 662 bp of 3' untranslated region (SEQ ID NO:17; 1504 bp). The coding region is 792 bp long and encodes a protein of 263 amino acids (SEQ ID NO:5). SEQ ID NO:4 is the nucleotide sequence of the coding sequence of *Eutreptiella* sp. CCMP389 A9 elongase (designated herein as E389D9e).

Comparison of the Δ9 Elongase Sequence of *Eutreptiella* sp. CCMP389 (E389D9e) to Known Δ9 Elongases Identity of SEQ ID NO:5 (i.e., E389D9e) was determined by conducting BLAST searches for similarity to sequences contained in the BLAST "nr" database (Example 3). The results of the BLAST comparison summarizing the sequence to which SEQ ID NO:5 has the most similarity are reported according to the % identity, % similarity, and Expectation value. "% Identity" is defined as the percentage of amino acids that are identical between the two proteins. "% Similarity" is defined as the percentage of amino acids that are identical or conserved between the two proteins. "Expectation value" estimates the statistical significance of the match, specifying the number of matches, with a given score, that are expected in a search of a database of this size absolutely by chance.

Thus, the amino acid fragment described herein as SEQ ID NO:5 shared 38% identity and 56% similarity with IgD9e, the Δ9 elongase of *Isochrysis galbana* (SEQ ID NO:8), with an expectation value of 2E-43. Similarly, E389D9e is 33.1% identical to IgD9e using the Clustal V method and E389D9e is 65.1% identical to EgD9e using the Clustal V method (FIG. 2). Sequence percent identity calculations performed by the Clustal V method (Higgins, D. G. and Sharp, P. M., *Comput. Appl. Biosci.,* 5:151-153 (1989); Higgins et al., *Comput. Appl. Biosci.,* 8:189-191 (1992)) were done using the MegAlign™ v6.1 program of the LASERGENE bioinformatics computing suite with the default parameters for pairwise alignment (KTUPLE=1, GAP PENALTY=3, WINDOW=5, DIAGONALS SAVED=5 and GAP LENGTH PENALTY=10).

Example 23

Construction and Functional Analysis of *Yarrowia lipolytica* Expression Vector pFBAIN-389Elo (Comprising the *Eutreptiella* sp. CCMP389 Δ9 Elongase (E389D9e)) in *Yarrowia lipolytica* Strain Y2224

The present Example describes synthesis of *Yarrowia lipolytica* expression vector pFBAIN-389Elo (comprising a chimeric FBAINm::E389D9e::Pex20 gene). Delta-9 elongase activity of E389D9e when expressed in *Yarrowia lipolytica* strain Y2224 was subsequently determined.

Construction of *Yarrowia lipolytica* Expression Vector pFBAIN-389Elo

Oligonucleotides 389Elo-F and 389Elo-R1 (SEQ ID NOs: 116 and 117, respectively) were used as primers to amplify the full length cDNA of E389D9e (SEQ ID NO:4). The PCR reactions, with *Eutreptiella* sp. CCMP389 cDNA (Example 21) as template, were individually carried out in a 50 μl total volume comprising: 1 μl each of 20 μM forward and reverse primers, 1 μl cDNA, 10 μl 5×PCR buffer, 1 μl dNTP mix (10 μM each), 35 μl water and 1 μl Phusion polymerase (New England Biolabs, Inc., Ipswich, Mass.). Amplification was carried out at 98° C. for 1 min, then 30 cycles of 98° C. for 10 sec, 55° C. for 10 sec, and 72° C. for 30 sec, followed by a final elongation cycle at 72° C. for 5 min. The PCR product was digested with NcoI and EarI to generate a ~210 bp fragment that contained the 5' region of the Δ9 elongase cDNA. It was also digested with EarI and NotI to generate a ~600 bp fragment that contained the 3' region of the cDNA. The NcoI/EarI and the EarI/NotI digested fragments were purified following gel electrophoresis in 1% (w/v) agarose.

The NcoI/EarI and the EarI/NotI Δ9 elongase digested fragments were directionally ligated with NcoI/NotI digested pFBAIN-MOD-1 (SEQ ID NO:118), such that the E389D9e gene was under the control of the *Y. lipolytica* FBAINm promoter and the PEX20-3' terminator region. Specifically, the ligation reaction contained: 10 μl 2× ligation buffer, 1 μl T4 DNA ligase (Promega), 4 μl each of the ~210 bp and the ~600 bp fragment (~300 ng each), and 1 μl pFBAIN-MOD-1 (~150 ng). The reaction mixture was incubated at room temperature for 2 hrs and used to transform *E. coli* Top10 competent cells (Invitrogen). Plasmid DNA from transformants was recovered using a Qiagen Miniprep kit. Correct clones were identified by restriction mapping and the final construct was designated "pFBAIN-389Elo".

Thus, pFBAIN-389Elo (FIG. 15A; SEQ ID NO:119) thereby contained the following components:

TABLE 12

Components of Plasmid pFBAIN-389Elo (SEQ ID NO: 119)

| RE Sites and Nucleotides Within SEQ ID NO: 119 | Description of Fragment and Chimeric Gene Components |
|---|---|
| BglII-BsiWI (6040-301) | FBAINm::E389D9e::Pex20, comprising:<br>FBAINm: *Yarrowia lipolytica* FBAINm promoter (PCT Publication No. WO 2005/049805)<br>E389D9e: *Eutreptiella* sp. CCMP389 Δ9 elongase (SEQ ID NO: 4 described herein)<br>Pex20: Pex20 terminator sequence of *Yarrowia* Pex20 gene (GenBank Accession No. AF054613) |
| PacI-BglII (4533-6040) | *Yarrowia* Ura 3 gene (GenBank Accession No. AJ306421) |
| (3123-4487) | *Yarrowia* autonomous replication sequence (ARS18; GenBank Accession No. A17608) |
| (2464-2864) | f1 origin |
| (1424-2284) | Ampicillin-resistance gene ($Amp^R$) for selection in *E. coli* |
| (474-1354) | ColE1 plasmid origin of replication |

Functional Analysis of *Yarrowia lipolytica* Transformants Comprising pFBAIN-389Elo Five (5) individual clones of pFBAIN-389Elo (comprising E389D9e) and control plasmid pFBAIN-MOD-1 were transformed into *Yarrowia lipolytica* strain Y2224 (Example 7) as described in the General Methods. The cells were plated onto MM plates lacking uracil and maintained at 30° C. for 2 to 3 days. Then, cells from each plate were scraped off, lipids were extracted, and fatty acid methyl esters were prepared by trans-esterification, and subsequently analyzed with a Hewlett-Packard 6890 GC.

GC analyses showed that EDA was produced in all five of the transformants comprising pFBAIN-389Elo, while no EDA was produced in the control strain (Table 13). Fatty acids are identified as 18:2 (LA) and 20:2 (EDA); and the composition of each is presented as a % of the total fatty acids. The conversion efficiency was calculated according to the following formula: ([product]/[substrate+product])*100, where 'product' includes the immediate product and all products in the pathway derived from it.

TABLE 13

Lipid Composition in *Yarrowia lipolytica* Strain Y2224 Engineered To Over-Express *Eutreptiella* sp. CCMP389 Δ9 Elongase (E389D9e)

| Plasmid | Clone | C18:2 | C20:2 | Conversion Efficiency |
|---|---|---|---|---|
| pFBAIN-MOD-1 | 1 | 17.4 | 0 | 0 |
| pFBAIN-389Elo | 1 | 13.49 | 2.16 | 13.80 |
| | 2 | 13.16 | 1.79 | 11.97 |
| | 3 | 14.11 | 1.92 | 11.98 |
| | 4 | 15.55 | 0.78 | 4.78 |
| | 5 | 13.24 | 1.79 | 11.91 |

The results shown above confirmed that the cloned cDNA from *Eutreptiella* sp. CCMP389, described herein as SEQ ID NOs:4 and 5, efficiently desaturated LA to EDA and thus functioned as a Δ9 elongase.

Example 24

Construction and Functional Analysis of *Yarrowia lipolytica* Expression Vector pZUFE389S, Comprising a Synthetic Δ9 Elongase Gene (Derived from *Eutreptiella* sp. CCMP389), Codon-Optimized for Expression in *Yarrowia lipolytica* (E389D9eS)

The present Example describes the functional expression of *Yarrowia lipolytica* vector pZUFE389S, comprising a chimeric FBAIN::E389D9eS::Pex20 gene, wherein E389D9eS is a synthetic Δ9 elongase derived from *Eutreptiella* sp. CCMP389 and codon-optimized for expression in *Yarrowia*. This analysis therefore required: (1) synthesis of E389D9eS; (2) construction and transformation of pZUFE389S into *Yarrowia lipolytica* strain Y2224; and (3) analysis of lipid profiles within transformant organisms of *Yarrowia lipolytica* strain Y2224 that were comprising pZUFE389S (expressing E389D9eS).

Synthesis of E389D9eS

The codon usage of the Δ9 elongase gene of *Eutreptiella* sp. CCMP389 (E389D9e; SEQ ID NOs:4 and 5) was optimized for expression in *Yarrowia lipolytica*, in a manner similar to that described in Example 5, Example 8 and PCT Publication No. WO 2004/101753. Specifically, a codon-optimized Δ9 elongase gene (designated “E389D9eS”, SEQ ID NO:6) was designed, based on the coding sequence of E389D9e (SEQ ID NO:4), according to the *Yarrowia* codon usage pattern (PCT Publication No. WO 2004/101753), the consensus sequence around the ‘ATG’ translation initiation codon, and the general rules of RNA stability (Guhaniyogi, G. and J. Brewer, *Gene,* 265(1-2):11-23 (2001)). In addition to modification of the translation initiation site, 128 bp of the 792 bp coding region (including the stop codon) were modified (16.2%) and 113 codons were optimized. The GC content was increased from 45.7% within the wildtype gene (i.e., E389D9e) to 50.1% within the synthetic gene (i.e., E389D9eS). A NcoI site and NotI sites were incorporated around the translation initiation codon and after the stop codon of E389D9eS, respectively. FIG. 16 shows a comparison of the nucleotide sequences of E389D9e and E389D9eS. None of the modifications in the codon-optimized gene changed the amino acid sequence of the encoded protein (SEQ ID NO:5).

The designed E389D9eS gene (SEQ ID NO:6) was synthesized by GenScript Corporation (Piscataway, N.J.) and cloned into pUC57 (GenBank Accession No. Y14837) to generate pE389S (SEQ ID NO:120).

Generation of Construct pZUFE389S, Comprising E389D9eS

Plasmid pZUFE389S (FIG. 15B; SEQ ID NO:122) was constructed by replacing the Nco I/Not I fragment of pZUF17 (FIG. 7C; SEQ ID NO:121) with the Nco I/Not I fragment from pE389S (SEQ ID NO:120) comprising E389D9eS. The product of this ligation was pZUFE389S, which thereby contained the following components:

TABLE 14

Components of Plasmid pZUFE389S (SEQ ID NO: 122)

| RE Sites and Nucleotides Within SEQ ID NO: 122 | Description of Fragment and Chimeric Gene Components |
|---|---|
| EcoR I/BsiW I (6857-1112) | FBAIN::E389d9eS::Pex20, comprising: FBAIN: *Yarrowia lipolytica* FBAIN promoter (PCT Publication No. WO 2005/049805) E389D9eS: codon-optimized Δ9 elongase (SEQ ID NO: 6), derived from *Eutreptiella* sp. CCMP389 Pex20: Pex20 terminator sequence of *Yarrowia* Pex20 gene (GenBank Accession No. AF054613) |
| 2148-1268 | ColE1 plasmid origin of replication |
| 3078-2218 | Ampicillin-resistance gene ($Amp^R$) for selection in *E. coli* |
| 3977-5281 | *Yarrowia* autonomous replication sequence (ARS18; GenBank Accession No. A17608) |
| 6835-5324 | *Yarrowia* Ura 3 gene (GenBank Accession No. AJ306421) |

Functional Analysis of *Yarrowia lipolytica* Transformants Comprising pZUFE389S

Plasmid pZUFE389S was transformed into strain Y2224 (the FOA resistant mutant from an autonomous mutation of the Ura3 gene of wildtype *Yarrowia* strain ATCC #20362; Example 7), as described in the General Methods. The transformants were selected on MM plates. After 2 days growth at 30° C., transformants were picked and re-streaked onto fresh MM plates. Once grown, these strains were individually inoculated into 3 mL liquid MM at 30° C. and shaken at 250 rpm/min for 2 days. The cells were collected by centrifugation, lipids were extracted, and fatty acid methyl esters were prepared by trans-esterification, and subsequently analyzed with a Hewlett-Packard 6890 GC.

GC analyses showed that there were about 2.2% C20:2 (EDA) of total lipids produced in all 12 transformants, wherein the conversion efficiency of C18:2 to C20:2 in these 12 strains was determined to be about 12% (average; calculated as described in Example 23).

Example 25

Construction of Alternate Soybean Expression Vectors for Expression of *Euglena gracilis* (EgD9e or EgD9eS) and/or *Eutreptiella* sp. CCMP389 (E389D9e or E389D9eS) Δ9 Elongases It will be appreciated by the skilled person that the above Examples are intended to be illustrative but are not limiting. For example, any of the soybean expression vectors created above in Examples 10, 11 and 13-15 for expression of EgD9e could be readily modified to instead enable expression (or co-expression) of EgD9eS, E389D9e and/or E389D9eS using methods similar to, but not limited to, the methods described herein. PCR primers designed to introduce NotI sites at the 5' and 3' ends of the Δ9 elongase can be used to amplify the gene. The resulting PCR product can then be digested with NotI and can be cloned into a suitable soybean expression vector containing a NotI site flanked by a strong seed-specific promoter and a transcription terminator. Further sub-cloning into other vectors such as those described herein, or in PCT Publication Nos. WO 2004/071467 or WO 2005/047479 (but not limited to these), would yield vectors suitable for expression of Δ9 elongases in soybean.

Furthermore, in addition to the genes, promoters, terminators and gene cassettes described herein, one skilled in the art can appreciate that other promoter/gene/terminator cassette combinations can be synthesized in a way similar to, but not limited to, that described herein for expression of EgD9e, EgD9eS, E389D9e and/or E389D9eS. Similarly, it may be desirable to express other PUFA genes (such as those described below in Table 17), for co-expression with any of the Δ9 elongases of the present invention.

For instance, PCT Publication Nos. WO 2004/071467 and WO 2004/071178 describe the isolation of a number of promoter and transcription terminator sequences for use in embryo-specific expression in soybean. Furthermore, PCT Publication Nos. WO 2004/071467, WO 2005/047479 and WO 2006/012325 describe the synthesis of multiple promoter/gene/terminator cassette combinations by ligating individual promoters, genes and transcription terminators together in unique combinations. Generally, a NotI site flanked by the suitable promoter (such as those listed in, but not limited to, Table 15) and a transcription terminator (such as those listed in, but not limited to, Table 16) is used to clone the desired gene. NotI sites can be added to a gene of interest such as those listed in, but not limited to, Table 17 using PCR amplification with oligonucleotides designed to introduce NotI sites at the 5' and 3' ends of the gene. The resulting PCR product is then digested with NotI and cloned into a suitable promoter/NotI/terminator cassette.

In addition, PCT Publication Nos. WO 2004/071467, WO 2005/047479 and WO 2006/012325 describe the further linking together of individual gene cassettes in unique combinations (along with suitable selectable marker cassettes), in order to obtain the desired phenotypic expression. Although this is done mainly using different restriction enzymes sites, one skilled in the art can appreciate that a number of techniques can be utilized to achieve the desired promoter/gene/transcription terminator combination. In so doing, any combination of embryo-specific promoter/gene/transcription terminator cassettes can be achieved. One skilled in the art can also appreciate that these cassettes can be located on individual DNA fragments or on multiple fragments where co-expression of genes is the outcome of co-transformation of multiple DNA fragments.

TABLE 15

Seed-specific Promoters

| Promoter | Organism | Promoter Reference |
|---|---|---|
| Beta-conglycinin α'-subunit | soybean | Beachy et al., EMBO J., 4: 3047-3053 (1985) |
| kunitz trypsin inhibitor | soybean | Jofuku et al., Plant Cell, 1: 1079-1093 (1989) |
| Annexin | soybean | WO 2004/071467 |
| glycinin Gy1 | soybean | WO 2004/071467 |
| albumin 2S | soybean | U.S. Pat. No. 6,177,613 |
| legumin A1 | pea | Rerie et al., Mol. Gen. Genet., 225: 148-157 (1991) |
| β-conglycinin β-subunit | soybean | WO 2004/071467 |
| BD30 (also called P34) | soybean | WO 2004/071467 |
| legumin A2 | pea | Rerie et al., Mol. Gen. Genet., 225: 148-157 (1991) |

TABLE 16

Transcription Terminators

| Transcription Terminator | Organism | Reference |
|---|---|---|
| phaseolin 3' | bean | WO 2004/071467 |
| kunitz trypsin inhibitor 3' | soybean | WO 2004/071467 |
| BD30 (also called P34) 3' | soybean | WO 2004/071467 |
| legumin A2 3' | pea | WO 2004/071467 |
| albumin 2S 3' | soybean | WO 2004/071467 |

TABLE 17

PUFA Biosynthetic Pathway Genes

| Gene | Organism | Reference |
|---|---|---|
| Δ6 desaturase | *Saprolegnia diclina* | WO 2002/081668 |
| Δ6 desaturase | *Mortierella alpina* | U.S. Pat. No. 5,968,809 |
| elongase | *Mortierella alpina* | WO 2000/12720; U.S. Pat. No. 6,403,349 |
| Δ5 desaturase | *Mortierella alpina* | U.S. Pat. No. 6,075,183 |
| Δ5 desaturase | *Saprolegnia diclina* | WO 2002/081668 |
| Δ15 desaturase | *Fusarium moniliforme* | WO 2005/047479 |
| Δ17 desaturase | *Saprolegnia diclina* | WO 2002/081668 |
| elongase | *Thraustochytrium aureum* | WO 2002/08401; U.S. Pat. No. 6,677,145 |
| elongase | *Pavlova* sp. | Pereira et al., Biochem. J., 384: 357-366 (2004) |
| Δ4 desaturase | *Schizochytrium aggregatum* | WO 2002/090493 |
| Δ9 elongase | *Isochrysis galbana* | WO 2002/077213 |
| Δ8 desaturase | *Euglena gracilis* | WO 2000/34439; U.S. Pat. No. 6,825,017; WO 2004/057001; WO 2006/012325 |
| Δ8 desaturase | *Acanthamoeba castellanii* | Sayanova et al., FEBS Lett., 580: 1946-1952 (2006) |
| Δ8 desaturase | *Pavlova salina* | WO 2005/103253 |
| Δ8 desaturase | *Pavlova lutheri* | U.S. Provisional Application No. 60/795,810 |
| Δ8 desaturase | *Tetruetreptia pomquetensis* CCMP1491 | U.S. Provisional Application No. 60/853,563 |
| Δ8 desaturase | *Eutreptiella* sp. CCMP389 | U.S. Provisional Application No. 60/853,563 |
| Δ8 desaturase | *Eutreptiella cf_gymnastica* CCMP1594 | U.S. Provisional Application No. 60/853,563 |

Example 26

Transformation of Somatic Soybean Embryo Cultures

Culture Conditions:

Soybean embryogenic suspension cultures (cv. Jack) can be maintained in 35 mL liquid medium SB196 (see recipes below) on rotary shaker, 150 rpm, 26° C. with cool white fluorescent lights on 16:8 h day/night photoperiod at light intensity of 60-85 μE/m2/s. Cultures are subcultured every seven days to two weeks by inoculating approximately 35 mg of tissue into 35 mL of fresh liquid SB196 (the preferred subculture interval is every seven days).

Soybean embryogenic suspension cultures can be transformed with the plasmids and DNA fragments described earlier by the method of particle gun bombardment (Klein et al., *Nature* (London), 327:70-73 (1987); U.S. Pat. No. 4,945,050). A DuPont Biolistic™ PDS1000/HE instrument (helium retrofit) would be used for all transformations.

Soybean Embryogenic Suspension Culture Initiation:

Soybean cultures are initiated twice each month with five-seven days between each initiation. Pods with immature seeds from available soybean plants 45-55 days after planting are picked, removed from their shells and placed into a sterilized magenta box. The soybean seeds are sterilized by shaking them for 15 min in a 5% Clorox solution with 1 drop of ivory soap (i.e., 95 mL of autoclaved distilled water plus 5 mL Clorox and 1 drop of soap, mixed well). Seeds are rinsed using 2 1-liter bottles of sterile distilled water and those less than 4 mm are placed on individual microscope slides. The small end of the seed is cut and the cotyledons pressed out of the seed coat. Cotyledons are transferred to plates containing SB1 medium (25-30 cotyledons per plate). Plates are wrapped with fiber tape and stored for eight weeks. After this time, secondary embryos are cut and placed into SB196 liquid media for seven days.

Preparation of DNA for Bombardment:

Either an intact plasmid or a DNA plasmid fragment containing the genes of interest and the selectable marker gene can be used for bombardment. Fragments from plasmids such pKR274 (ATCC Accession No. PTA-4988), pKR685 (ATCC Accession No. PTA-6047) or pKR681 (ATCC Accession No. PTA-6046) and/or other expression plasmids can be obtained by gel isolation of digested plasmids. In each case, 100 μg of plasmid DNA can be used in 0.5 mL of the specific enzyme mix described below. Plasmids could be digested with AscI (100 units) in NEBuffer 4 (20 mM Tris-acetate, 10 mM magnesium acetate, 50 mM potassium acetate, 1 mM dithiothreitol, pH 7.9), 100 μg/mL BSA, and 5 mM beta-mercaptoethanol at 37° C. for 1.5 h. The resulting DNA fragments could be separated by gel electrophoresis on 1% SeaPlaque® GTG agarose (BioWhitaker Molecular Applications) and the DNA fragments containing PUFA biosynthetic genes could be cut from the agarose gel. DNA can be purified from the agarose using the GELase® digesting enzyme following the manufacturer's protocol. Alternatively, whole plasmids or a combination of whole plasmid with fragment could be used.

A 50 μL aliquot of sterile distilled water containing 3 mg of gold particles (3 mg gold) can be added to 5 μL of a 1 μg/μL DNA solution (either intact plasmid or DNA fragment prepared as described above), 50 μL 2.5 M $CaCl_2$ and 20 μL of 0.1 M spermidine. The mixture is shaken 3 min on level 3 of a vortex shaker and spun for 10 sec in a bench microfuge. After a wash with 400 μL 100% ethanol, the pellet is suspended by sonication in 40 μL of 100% ethanol. Five μL of DNA suspension is dispensed to each flying disk of the Biolistic PDS1000/HE instrument disk. Each 5 μL aliquot contained approximately 0.375 mg gold per bombardment (e.g., per disk).

Tissue Preparation and Bombardment with DNA:

Approximately 150-200 mg of seven day old embryonic suspension cultures are placed in an empty, sterile 60×15 mm petri dish and the dish is covered with plastic mesh. Tissue is bombarded one or two shots per plate with the membrane rupture pressure set at 1100 PSI and the chamber evacuated to a vacuum of 27-28 inches of mercury. Tissue is placed approximately 3.5 inches from the retaining/stopping screen.

Selection of Transformed Embryos:

Transformed embryos are selected either using hygromycin (i.e., when the hygromycin B phosphotransferase (HPT) gene was used as the selectable marker) or chlorsulfuron (i.e., when the acetolactate synthase (ALS) gene was used as the selectable marker).

Hygromycin (HPT) Selection:

Following bombardment, the tissue is placed into fresh SB196 media and cultured as described above. Six days post-bombardment, the SB196 is exchanged with fresh SB196 containing a selection agent of 30 mg/L hygromycin. The selection media is refreshed weekly. Four to six weeks post selection, green, transformed tissue may be observed growing from untransformed, necrotic embryogenic clusters. Isolated, green tissue is removed and inoculated into multiwell plates to generate new, clonally propagated, transformed embryogenic suspension cultures.

Chlorsulfuron (ALS) Selection:

Following bombardment, the tissue is divided between two flasks with fresh SB196 media and cultured as described above. Six to seven days post-bombardment, the SB196 is exchanged with fresh SB196 containing selection agent of 100 ng/mL chlorsulfuron. The selection media is refreshed weekly. Four to six weeks post selection, green, transformed tissue may be observed growing from untransformed, necrotic embryogenic clusters. Isolated, green tissue is removed and inoculated into multiwell plates containing SB196 to generate new, clonally propagated, transformed embryogenic suspension cultures.

Regeneration of Soybean Somatic Embryos into Plants:

In order to obtain whole plants from embryogenic suspension cultures, the tissue needs to be regenerated.

Embryo Maturation:

Transformed embryogenic clusters from production transformation were cultured for four-six weeks (one-three weeks for model system) in multiwell plates as described above at 26° C. in SB196 under cool white fluorescent (Phillips cool white Econowatt F40/CW/RS/EW) and Agro (Phillips F40 Agro) bulbs (40 watt) on a 16:8 hr photoperiod with light intensity of 90-120 $\mu E/m^2s$. After this time embryo clusters were removed to a solid agar media, SB166, for one-two weeks (1 week for model system) and then subcultured to SB103 medium for 3-4 weeks to mature embryos. After maturation on plates in SB103, individual embryos were removed from the clusters, dried and screened for alterations in their fatty acid compositions as described supra. When desired, plants were obtained from some events as described below.

Alternatively, in some model system experiments, embryos were matured in soybean histodifferentiation and maturation liquid medium (SHaM liquid media; Schmidt et al., *Cell Biology and Morphogenesis* 24:393 (2005)) using a modified procedure. Briefly, after 4 weeks of selection in SB196 as described above, embryo clusters were removed to 35 mL of SB228 (SHaM liquid media) in a 250 mL Erlenmeyer flask. Tissue was maintained in SHaM liquid media on a rotary shaker at 130 rpm and 26° C. with cool white fluorescent lights on a 16:8 hr day/night photoperiod at a light intensity of 60-85 μE/m2/s for 2-3 weeks as embryos matured. Embryos grown for 2-3 weeks in SHaM liquid media were equivalent in size and fatty acid content to embryos cultured on SB166/SB103 for 5-8 weeks.

After maturation in SHaM liquid media, individual embryos were removed from the clusters, dried and screened for alterations in their fatty acid compositions as described supra. When desired, plants were obtained from some events as described below.

Embryo Desiccation and Germination:

Matured individual embryos can be desiccated by placing them into an empty, small petri dish (35×10 mm) for approximately four-seven days. The plates are sealed with fiber tape (creating a small humidity chamber). Desiccated embryos can be planted into SB71-4 medium where they are left to germinate under the same culture conditions described above. Germinated plantlets are removed from germination medium and rinsed thoroughly with water and then planted in Redi-Earth in a 24-cell pack tray, covered with clear plastic dome.

After two weeks the dome is removed and plants hardened off for a further week. If plantlets look hardy, they are transplanted to a 10 inch pot of Redi-Earth with up to 3 plantlets per pot. After ten to sixteen weeks, mature seeds can be harvested, chipped and analyzed for fatty acids as described above.

Media Recipes:

SB 196-FN Lite Liquid Proliferation Medium (Per Liter)

| | | |
|---|---|---|
| MS FeEDTA - 100x Stock 1 | 10 | mL |
| MS Sulfate - 100x Stock 2 | 10 | mL |
| FN Lite Halides - 100x Stock 3 | 10 | mL |
| FN Lite P, B, Mo - 100x Stock 4 | 10 | mL |
| B5 vitamins (1 mL/L) | 1.0 | mL |
| 2,4-D (10 mg/L final concentration) | 1.0 | mL |
| $KNO_3$ | 2.83 | gm |
| $(NH_4)_2SO_4$ | 0.463 | gm |
| asparagine | 1.0 | gm |
| sucrose (1%) | 10 | gm |

pH 5.8

FN Lite Stock Solutions

| Stock Number | 1000 mL | 500 mL |
|---|---|---|
| 1 - MS Fe EDTA 100x Stock | | |
| $Na_2$ EDTA* | 3.724 g | 1.862 g |
| $FeSO_4$—$7H_2O$ | 2.784 g | 1.392 g |
| 2 - MS Sulfate 100x stock | | |
| $MgSO_4$—$7H_2O$ | 37.0 g | 18.5 g |
| $MnSO_4$—$H_2O$ | 1.69 g | 0.845 g |
| $ZnSO_4$—$7H_2O$ | 0.86 g | 0.43 g |
| $CuSO_4$—$5H_2O$ | 0.0025 g | 0.00125 g |
| 3 - FN Lite Halides 100x Stock | | |
| $CaCl_2$—$2H_2O$ | 30.0 g | 15.0 g |
| KI | 0.083 g | 0.0715 g |
| $CoCl_2$—$6H_2O$ | 0.0025 g | 0.00125 g |
| 4 - FN Lite P, B, Mo 100x Stock | | |
| $KH_2PO_4$ | 18.5 g | 9.25 g |
| $H_3BO_3$ | 0.62 g | 0.31 g |
| $Na_2MoO_4$—$2H_2O$ | 0.025 g | 0.0125 g |

*Add first, dissolve in dark bottle while stirring

SB1 Solid Medium (per liter): 1 package MS salts (Gibco/BRL—Cat. No. 11117-066), 1 mL B5 vitamins 1000× stock, 31.5 g sucrose, 2 mL 2,4-D (20 mg/L final concentration), pH 5.7, 8 g TC agar SB 166 Solid Medium (per liter): 1 package MS salts (Gibco/BRL—Cat. No. 11117-066), 1 mL B5 vitamins 1000× stock, 60 g maltose, 750 mg $MgCl_2$ hexahydrate, 5 g activated charcoal, pH 5.7, 2 g gelrite SB 103 Solid Medium (per liter): 1 package MS salts (Gibco/BRL—Cat. No. 11117-066), 1 mL B5 vitamins 1000× stock, 60 g maltose, 750 mg MgCl2 hexahydrate, pH 5.7, 2 g gelrite SB 71-4 Solid Medium (per liter): 1 bottle Gamborg's B5 salts w/sucrose (Gibco/BRL—Cat. No. 21153-036), pH 5.7, 5 g TC agar 2,4-D Stock: Obtain premade from Phytotech Cat. No. D 295—concentration 1 mg/mL B5 Vitamins Stock (per 100 mL): 10 g myo-inositol, 100 mg nicotinic acid, 100 mg pyridoxine HCl, 1 g thiamine. Store aliquots at −20° C.; if the solution does not dissolve quickly enough, apply a low level of heat via the hot stir plate.

Chlorsulfuron Stock: 1 mg/mL in 0.01 N Ammonium Hydroxide

To induce somatic embryos, cotyledons, 3-5 mm in length dissected from surface sterilized, immature seeds of the soybean cultivar A2872, can be cultured in the light or dark at 26° C. on an appropriate agar medium for six-ten weeks. Somatic embryos, which produce secondary embryos, are then excised and placed into a suitable liquid medium. After repeated selection for clusters of somatic embryos which multiplied as early, globular staged embryos, the suspensions are maintained as described below.

Soybean embryogenic suspension cultures can be maintained in 35 mL liquid media on a rotary shaker, 150 rpm, at 26° C. with florescent lights on a 16:8 h day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al., *Nature* (London), 327:70-73, U.S. Pat. No. 4,945,050). A DuPont Biolistic™ PDS1000/HE instrument (helium retrofit) can be used for these transformations.

A selectable marker gene which can be used to facilitate soybean transformation is a recombinant DNA construct composed of the 35S promoter from Cauliflower Mosaic Virus (Odell et al., *Nature,* 313:810-812 (1985)), the hygromycin B phosphotransferase gene from plasmid pJR225 (from *E. coli*; Gritz et al., *Gene,* 25:179-188 (1983)) and the 3' region of the nopaline synthase gene from the T-DNA of the Ti plasmid of *Agrobacterium tumefaciens*. The seed expression cassette comprising the phaseolin 5' region, the fragment encoding the instant polypeptide and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μL spermidine (0.1 M), and 50 μL $CaCl_2$ (2.5 M). The particle preparation is then agitated for three minutes, spun in a microfuge for 10 sec and the supernatant removed. The DNA-coated particles are then washed once in 400 μL 70% ethanol and resuspended in 40 μL of anhydrous ethanol. The DNA/particle suspension can be sonicated three times for one sec each. Five μL of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately five-ten plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

What is claimed is:

1. A microbial oil comprising at least one omega-3 fatty acid having at least twenty carbon atoms and five or more double bonds, said oil produced by a transformed host cell comprising an isolated polynucleotide selected from the group consisting of:

(a) an isolated nucleic acid sequence comprising a nucleotide sequence encoding a polypeptide having Δ9 elongase activity, wherein the polypeptide has at least 95% amino acid identity, based on the Clustal V method of alignment, when compared to an amino acid sequence as set forth in SEQ ID NO:2 or SEQ ID NO:5;

(b) an isolated nucleic acid sequence comprising a nucleotide sequence encoding a polypeptide having Δ9 elongase activity, wherein the nucleotide sequence has at least 95% sequence identity, based on the BLASTN method of alignment, when compared to a nucleotide sequence as set forth in SEQ ID NO:1, SEQ ID NO:3, SEQ ID NO:4 or SEQ ID NO:6;

(c) an isolated nucleic acid sequence comprising a nucleotide sequence encoding a polypeptide having Δ9 elongase activity, wherein the nucleotide sequence hybridizes with the nucleotide sequence as set forth in SEQ ID NO:1, SEQ ID NO:3, SEQ ID NO:4 or SEQ ID NO:6 under the following stringent hybridization conditions: 0.1×SSC, 0.1% SDS, 65° C. and washed with 2×SSC, 0.1% SDS followed by 0.1×SSC, 0.1% SDS; or (d) a complement of the nucleotide sequence of (a), (b) or (c), wherein the complement and the nucleotide sequence consist of the same number of nucleotides and are 100% complementary;

wherein said transformed host cell is an oleaginous yeast which produces at least 25% of its dry cell weight as oil.

2. The microbial oil of claim 1, wherein said oil is incorporated into a product selected from the group consisting of: a food product, an animal feed, a medical food, a dietary supplement, an infant formula and a pharmaceutical.

3. The microbial oil of claim 2, wherein said oil is incorporated into a food product selected from the group consisting of a food analogue, a meat product, a cereal product, a baked food, a snack food and a dairy product.

4. The microbial oil of claim 2, wherein said oil is incorporated into an animal feed selected from the group consisting of a pet feed, a ruminant feed, a poultry feed and an aquacultural feed.

* * * * *

SEQUENCE LISTING

```
<160> NUMBER OF SEQ ID NOS: 129

<210> SEQ ID NO 1
<211> LENGTH: 777
<212> TYPE: DNA
<213> ORGANISM: Euglena gracilis

<400> SEQUENCE: 1

atggaggtgg tgaatgaaat agtctcaatt gggcaggaag ttttacccaa agttgattat      60

gcccaactct ggagtgatgc cagtcactgt gaggtgcttt acttgtccat cgcatttgtc     120

atcttgaagt tcactcttgg ccccccttggt ccaaaaggtc agtctcgtat gaagtttgtt    180

ttcaccaatt acaaccttct catgtccatt tattcgttgg gatcattcct ctcaatggca     240

tatgccatgt acaccatcgg tgttatgtct gacaactgcg agaaggcttt tgacaacaac     300

gtcttcagga tcaccacgca gttgttctat ttgagcaagt tcctggagta tattgactcc     360

ttctatttgc cactgatggg caagcctctg acctggttgc aattcttcca tcatttgggg     420

gcaccgatgg atatgtggct gttctataat taccgaaatg aagctgtttg gatttttgtg     480

ctgttgaatg gtttcatcca ctggatcatg tacggttatt attggaccag attgatcaag     540

ctgaagttcc ccatgccaaa atccctgatt acatcaatgc agatcattca attcaatgtt     600

ggtttctaca ttgtctggaa gtacaggaac attccctgtt atcgccaaga tgggatgagg     660

atgtttggct ggttcttcaa ttacttttat gttggcacag tcttgtgttt gttcttgaat     720

ttctatgtgc aaacgtatat cgtcaggaag cacaagggag ccaaaaagat tcagtga        777


<210> SEQ ID NO 2
<211> LENGTH: 258
<212> TYPE: PRT
<213> ORGANISM: Euglena gracilis
<220> FEATURE:
<221> NAME/KEY: MISC_FEATURE
<222> LOCATION: (1)..(258)
<223> OTHER INFORMATION: delta-9 elongase (EgD9e)

<400> SEQUENCE: 2

Met Glu Val Val Asn Glu Ile Val Ser Ile Gly Gln Glu Val Leu Pro
1               5                   10                  15

Lys Val Asp Tyr Ala Gln Leu Trp Ser Asp Ala Ser His Cys Glu Val
            20                  25                  30

Leu Tyr Leu Ser Ile Ala Phe Val Ile Leu Lys Phe Thr Leu Gly Pro
        35                  40                  45

Leu Gly Pro Lys Gly Gln Ser Arg Met Lys Phe Val Phe Thr Asn Tyr
    50                  55                  60

Asn Leu Leu Met Ser Ile Tyr Ser Leu Gly Ser Phe Leu Ser Met Ala
65                  70                  75                  80

Tyr Ala Met Tyr Thr Ile Gly Val Met Ser Asp Asn Cys Glu Lys Ala
                85                  90                  95

Phe Asp Asn Asn Val Phe Arg Ile Thr Thr Gln Leu Phe Tyr Leu Ser
            100                 105                 110

Lys Phe Leu Glu Tyr Ile Asp Ser Phe Tyr Leu Pro Leu Met Gly Lys
        115                 120                 125

Pro Leu Thr Trp Leu Gln Phe Phe His His Leu Gly Ala Pro Met Asp
    130                 135                 140
```

```
Met Trp Leu Phe Tyr Asn Tyr Arg Asn Glu Ala Val Trp Ile Phe Val
145                 150                 155                 160

Leu Leu Asn Gly Phe Ile His Trp Ile Met Tyr Gly Tyr Tyr Trp Thr
                165                 170                 175

Arg Leu Ile Lys Leu Lys Phe Pro Met Pro Lys Ser Leu Ile Thr Ser
            180                 185                 190

Met Gln Ile Ile Gln Phe Asn Val Gly Phe Tyr Ile Val Trp Lys Tyr
        195                 200                 205

Arg Asn Ile Pro Cys Tyr Arg Gln Asp Gly Met Arg Met Phe Gly Trp
    210                 215                 220

Phe Phe Asn Tyr Phe Tyr Val Gly Thr Val Leu Cys Leu Phe Leu Asn
225                 230                 235                 240

Phe Tyr Val Gln Thr Tyr Ile Val Arg Lys His Lys Gly Ala Lys Lys
                245                 250                 255

Ile Gln


<210> SEQ ID NO 3
<211> LENGTH: 777
<212> TYPE: DNA
<213> ORGANISM: Artificial Sequence
<220> FEATURE:
<223> OTHER INFORMATION: EgD9eS: synthetic delta-9 elongase derived from
      Euglena gracilis and codon-optimized for expression in Yarrowia
      lipolytica

<400> SEQUENCE: 3

atggaggtcg tgaacgaaat cgtctccatt ggccaggagg ttcttcccaa ggtcgactat      60

gctcagctct ggtctgatgc ctcgcactgc gaggtgctgt acctctccat cgccttcgtc     120

atcctgaagt tcacccttgg tcctctcgga cccaagggtc agtctcgaat gaagtttgtg     180

ttcaccaact acaacctgct catgtccatc tactcgctgg gctccttcct ctctatggcc     240

tacgccatgt acaccattgg tgtcatgtcc gacaactgcg agaaggcttt cgacaacaat     300

gtcttccgaa tcaccactca gctgttctac ctcagcaagt tcctcgagta cattgactcc     360

ttctatctgc ccctcatggg caagcctctg acctggttgc agttctttca ccatctcgga     420

gctcctatgg acatgtggct gttctacaac taccgaaacg aagccgtttg gatctttgtg     480

ctgctcaacg gcttcattca ctggatcatg tacggctact attggacccg actgatcaag     540

ctcaagttcc ctatgcccaa gtccctgatt acttctatgc agatcattca gttcaacgtt     600

ggcttctaca tcgtctggaa gtaccggaac attccctgct accgacaaga tggaatgaga     660

atgtttggct ggtttttcaa ctacttctac gttggtactg tcctgtgtct gttcctcaac     720

ttctacgtgc agacctacat cgtccgaaag cacaagggag ccaaaaagat tcagtga        777


<210> SEQ ID NO 4
<211> LENGTH: 792
<212> TYPE: DNA
<213> ORGANISM: Eutreptiella sp. CCMP389

<400> SEQUENCE: 4

atggctgcgg tgatagaggt cgccaacgag tttgtagcca tcacggcaga aacgctcccc      60

aaagttgact atcaacgact atggcgagac atttacagtt gtgagctact gtatttctcc     120

attgccttcg tgatcttgaa gtttacgttg ggcgagttga gcgacagcgg aaaaaagatt     180

ttgagagtgt tgttcaagtg gtacaatctc ttcatgtccg tgttctcctt ggtgtctttc     240

ctttgcatgg gctatgccat ttataccgtg ggcctatact ctaacgaatg cgacagggct     300

ttcgacaact cgttgttccg ctttgcaaca aaggtgttct actacagtaa gtttttggag     360
```

```
tacatcgact ctttttatct tccgctcatg gccaagccgc tgtctttcct gcaattcttc    420

catcacttgg gagcccccat ggacatgtgg ctctttgtcc aatattctgg ggaatctatt    480

tggatctttg tgtttttgaa tgggttcatt cactttgtta tgtacgggta ctactggact    540

cggctgatga agttcaattt cccaatgccc aagcagttga ttaccgcgat gcagatcacg    600

cagttcaacg ttggtttcta cctcgtgtgg tggtacaaag atattccctg ctaccgaaag    660

gatcccatgc gaatgttggc ctggatcttc aattactggt atgttgggac tgtcttgctg    720

ctgttcatta atttcttcgt caaatcctat gtgttcccaa agccgaagac tgcagataaa    780

aaggtccaat ag                                                        792


<210> SEQ ID NO 5
<211> LENGTH: 263
<212> TYPE: PRT
<213> ORGANISM: Eutreptiella sp. CCMP389
<220> FEATURE:
<221> NAME/KEY: MISC_FEATURE
<222> LOCATION: (1)..(263)
<223> OTHER INFORMATION: delta-9 elongase (E389D9e)

<400> SEQUENCE: 5

Met Ala Ala Val Ile Glu Val Ala Asn Glu Phe Val Ala Ile Thr Ala
1               5                   10                  15

Glu Thr Leu Pro Lys Val Asp Tyr Gln Arg Leu Trp Arg Asp Ile Tyr
            20                  25                  30

Ser Cys Glu Leu Leu Tyr Phe Ser Ile Ala Phe Val Ile Leu Lys Phe
        35                  40                  45

Thr Leu Gly Glu Leu Ser Asp Ser Gly Lys Lys Ile Leu Arg Val Leu
    50                  55                  60

Phe Lys Trp Tyr Asn Leu Phe Met Ser Val Phe Ser Leu Val Ser Phe
65                  70                  75                  80

Leu Cys Met Gly Tyr Ala Ile Tyr Thr Val Gly Leu Tyr Ser Asn Glu
                85                  90                  95

Cys Asp Arg Ala Phe Asp Asn Ser Leu Phe Arg Phe Ala Thr Lys Val
            100                 105                 110

Phe Tyr Tyr Ser Lys Phe Leu Glu Tyr Ile Asp Ser Phe Tyr Leu Pro
        115                 120                 125

Leu Met Ala Lys Pro Leu Ser Phe Leu Gln Phe Phe His His Leu Gly
    130                 135                 140

Ala Pro Met Asp Met Trp Leu Phe Val Gln Tyr Ser Gly Glu Ser Ile
145                 150                 155                 160

Trp Ile Phe Val Phe Leu Asn Gly Phe Ile His Phe Val Met Tyr Gly
                165                 170                 175

Tyr Tyr Trp Thr Arg Leu Met Lys Phe Asn Phe Pro Met Pro Lys Gln
            180                 185                 190

Leu Ile Thr Ala Met Gln Ile Thr Gln Phe Asn Val Gly Phe Tyr Leu
        195                 200                 205

Val Trp Trp Tyr Lys Asp Ile Pro Cys Tyr Arg Lys Asp Pro Met Arg
    210                 215                 220

Met Leu Ala Trp Ile Phe Asn Tyr Trp Tyr Val Gly Thr Val Leu Leu
225                 230                 235                 240

Leu Phe Ile Asn Phe Phe Val Lys Ser Tyr Val Phe Pro Lys Pro Lys
                245                 250                 255

Thr Ala Asp Lys Lys Val Gln
            260
```

<210> SEQ ID NO 6
<211> LENGTH: 792
<212> TYPE: DNA
<213> ORGANISM: Artificial Sequence
<220> FEATURE:
<223> OTHER INFORMATION: E389D9eS: synthetic delta-9 elongase derived from Eutreptiella sp. CCMP389 and codon-optimized for expression in Yarrowia lipolytica

<400> SEQUENCE: 6

```
atggctgccg tcatcgaggt ggccaacgag ttcgtcgcta tcactgccga gacccttccc      60

aaggtggact atcagcgact ctggcgagac atctactcct gcgagctcct gtacttctcc     120

attgctttcg tcatcctcaa gtttaccctt ggcgagctct cggattctgg caaaaagatt     180

ctgcgagtgc tgttcaagtg gtacaacctc ttcatgtccg tcttttcgct ggtgtccttc     240

ctctgtatgg gttacgccat ctacaccgtt ggactgtact ccaacgaatg cgacagagct     300

ttcgacaaca gcttgttccg atttgccacc aaggtcttct actattccaa gtttctggag     360

tacatcgact ctttctacct tcccctcatg gccaagcctc tgtcctttct gcagttcttt     420

catcacttgg gagctcctat ggacatgtgg ctcttcgtgc agtactctgg cgaatccatt     480

tggatctttg tgttcctgaa cggattcatt cactttgtca tgtacggcta ctattggaca     540

cggctgatga agttcaactt tcccatgccc aagcagctca ttaccgcaat gcagatcacc     600

cagttcaacg ttggcttcta cctcgtgtgg tggtacaagg acattccctg ttaccgaaag     660

gatcccatgc gaatgctggc ctggatcttc aactactggt acgtcggtac cgttcttctg     720

ctcttcatca acttctttgt caagtcctac gtgtttccca agcctaagac tgccgacaaa     780

aaggtccagt ag                                                         792
```

<210> SEQ ID NO 7
<211> LENGTH: 1064
<212> TYPE: DNA
<213> ORGANISM: Isochrysis galbana (GenBank Accession No. AF390174)
<220> FEATURE:
<221> NAME/KEY: CDS
<222> LOCATION: (2)..(793)
<223> OTHER INFORMATION: delta-9 elongase (IgD9e)

<400> SEQUENCE: 7

```
g atg gcc ctc gca aac gac gcg gga gag cgc atc tgg gcg gct gtg acc      49
  Met Ala Leu Ala Asn Asp Ala Gly Glu Arg Ile Trp Ala Ala Val Thr
  1               5                   10                  15

gac ccg gaa atc ctc att ggc acc ttc tcg tac ttg cta ctc aaa ccg       97
Asp Pro Glu Ile Leu Ile Gly Thr Phe Ser Tyr Leu Leu Leu Lys Pro
            20                  25                  30

ctg ctc cgc aat tcc ggg ctg gtg gat gag aag aag ggc gca tac agg      145
Leu Leu Arg Asn Ser Gly Leu Val Asp Glu Lys Lys Gly Ala Tyr Arg
        35                  40                  45

acg tcc atg atc tgg tac aac gtt ctg ctg gcg ctc ttc tct gcg ctg      193
Thr Ser Met Ile Trp Tyr Asn Val Leu Leu Ala Leu Phe Ser Ala Leu
    50                  55                  60

agc ttc tac gtg acg gcg acc gcc ctc ggc tgg gac tat ggt acg ggc      241
Ser Phe Tyr Val Thr Ala Thr Ala Leu Gly Trp Asp Tyr Gly Thr Gly
65                  70                  75                  80

gcg tgg ctg cgc agg caa acc ggc gac aca ccg cag ccg ctc ttc cag      289
Ala Trp Leu Arg Arg Gln Thr Gly Asp Thr Pro Gln Pro Leu Phe Gln
                85                  90                  95

tgc ccg tcc ccg gtt tgg gac tcg aag ctc ttc aca tgg acc gcc aag      337
Cys Pro Ser Pro Val Trp Asp Ser Lys Leu Phe Thr Trp Thr Ala Lys
            100                 105                 110
```

```
gca ttc tat tac tcc aag tac gtg gag tac ctc gac acg gcc tgg ctg      385
Ala Phe Tyr Tyr Ser Lys Tyr Val Glu Tyr Leu Asp Thr Ala Trp Leu
        115                 120                 125

gtg ctc aag ggc aag agg gtc tcc ttt ctc cag gcc ttc cac cac ttt      433
Val Leu Lys Gly Lys Arg Val Ser Phe Leu Gln Ala Phe His His Phe
    130                 135                 140

ggc gcg ccg tgg gat gtg tac ctc ggc att cgg ctg cac aac gag ggc      481
Gly Ala Pro Trp Asp Val Tyr Leu Gly Ile Arg Leu His Asn Glu Gly
145                 150                 155                 160

gta tgg atc ttc atg ttt ttc aac tcg ttc att cac acc atc atg tac      529
Val Trp Ile Phe Met Phe Phe Asn Ser Phe Ile His Thr Ile Met Tyr
                165                 170                 175

acc tac tac ggc ctc acc gcc gcc ggg tat aag ttc aag gcc aag ccg      577
Thr Tyr Tyr Gly Leu Thr Ala Ala Gly Tyr Lys Phe Lys Ala Lys Pro
            180                 185                 190

ctc atc acc gcg atg cag atc tgc cag ttc gtg ggc ggc ttc ctg ttg      625
Leu Ile Thr Ala Met Gln Ile Cys Gln Phe Val Gly Gly Phe Leu Leu
        195                 200                 205

gtc tgg gac tac atc aac gtc ccc tgc ttc aac tcg gac aaa ggg aag      673
Val Trp Asp Tyr Ile Asn Val Pro Cys Phe Asn Ser Asp Lys Gly Lys
    210                 215                 220

ttg ttc agc tgg gct ttc aac tat gca tac gtc ggc tcg gtc ttc ttg      721
Leu Phe Ser Trp Ala Phe Asn Tyr Ala Tyr Val Gly Ser Val Phe Leu
225                 230                 235                 240

ctc ttc tgc cac ttt ttc tac cag gac aac ttg gca acg aag aaa tcg      769
Leu Phe Cys His Phe Phe Tyr Gln Asp Asn Leu Ala Thr Lys Lys Ser
                245                 250                 255

gcc aag gcg ggc aag cag ctc tag gcctcgagcc ggctcgcggg ttcaaggagg     823
Ala Lys Ala Gly Lys Gln Leu
            260

gcgacacggg ggtgggacgt ttgcatggag atggattgtg gatgtcctta cgccttactc    883

atcaatgtcc tcccatctct cccctctaga ccttctacta gccatctaga agggcagctc    943

agagacggat accgttcccc ctccccttcc ttttcgtctt tgctttgcca ttgtttgttt   1003

gtctctattt tttaaactat tgacgctaac gcgttacgct cgcaaaaaaa aaaaaaaaaa   1063

a                                                                   1064


<210> SEQ ID NO 8
<211> LENGTH: 263
<212> TYPE: PRT
<213> ORGANISM: Isochrysis galbana (GenBank Accession No. AF390174)

<400> SEQUENCE: 8

Met Ala Leu Ala Asn Asp Ala Gly Glu Arg Ile Trp Ala Ala Val Thr
1               5                   10                  15

Asp Pro Glu Ile Leu Ile Gly Thr Phe Ser Tyr Leu Leu Leu Lys Pro
            20                  25                  30

Leu Leu Arg Asn Ser Gly Leu Val Asp Glu Lys Lys Gly Ala Tyr Arg
        35                  40                  45

Thr Ser Met Ile Trp Tyr Asn Val Leu Leu Ala Leu Phe Ser Ala Leu
    50                  55                  60

Ser Phe Tyr Val Thr Ala Thr Ala Leu Gly Trp Asp Tyr Gly Thr Gly
65                  70                  75                  80

Ala Trp Leu Arg Arg Gln Thr Gly Asp Thr Pro Gln Pro Leu Phe Gln
                85                  90                  95

Cys Pro Ser Pro Val Trp Asp Ser Lys Leu Phe Thr Trp Thr Ala Lys
            100                 105                 110

Ala Phe Tyr Tyr Ser Lys Tyr Val Glu Tyr Leu Asp Thr Ala Trp Leu
```

```
        115                 120                 125

Val Leu Lys Gly Lys Arg Val Ser Phe Leu Gln Ala Phe His His Phe
    130                 135                 140

Gly Ala Pro Trp Asp Val Tyr Leu Gly Ile Arg Leu His Asn Glu Gly
145                 150                 155                 160

Val Trp Ile Phe Met Phe Phe Asn Ser Phe Ile His Thr Ile Met Tyr
                165                 170                 175

Thr Tyr Tyr Gly Leu Thr Ala Ala Gly Tyr Lys Phe Lys Ala Lys Pro
            180                 185                 190

Leu Ile Thr Ala Met Gln Ile Cys Gln Phe Val Gly Gly Phe Leu Leu
        195                 200                 205

Val Trp Asp Tyr Ile Asn Val Pro Cys Phe Asn Ser Asp Lys Gly Lys
    210                 215                 220

Leu Phe Ser Trp Ala Phe Asn Tyr Ala Tyr Val Gly Ser Val Phe Leu
225                 230                 235                 240

Leu Phe Cys His Phe Phe Tyr Gln Asp Asn Leu Ala Thr Lys Lys Ser
                245                 250                 255

Ala Lys Ala Gly Lys Gln Leu
            260


<210> SEQ ID NO 9
<211> LENGTH: 792
<212> TYPE: DNA
<213> ORGANISM: Artificial Sequence
<220> FEATURE:
<223> OTHER INFORMATION: IgD9eS: synthetic delta-9 elongase derived
      from Isochrysis galbana and codon-optimized for expression in
      Yarrowia lipolytica

<400> SEQUENCE: 9

atggctctgg ccaacgacgc tggcgagcga atctgggctg ccgtcaccga tcccgaaatc      60

ctcattggca ccttctccta cctgctcctg aagcctctcc tgcgaaactc tggtctcgtg     120

gacgagaaga aaggagccta ccgaacctcc atgatctggt acaacgtcct cctggctctc     180

ttctctgccc tgtccttcta cgtgactgcc accgctctcg gctgggacta cggtactgga     240

gcctggctgc gaagacagac cggtgatact ccccagcctc tctttcagtg tccctctcct     300

gtctgggact ccaagctgtt cacctggact gccaaggcct tctactattc taagtacgtg     360

gagtacctcg acaccgcttg gctggtcctc aagggcaagc gagtgtcctt tctgcaggcc     420

ttccatcact ttggagctcc ctgggacgtc tacctcggca ttcgactgca caacgagggt     480

gtgtggatct tcatgttctt taactcgttc attcacacca tcatgtacac ctactatgga     540

ctgactgccg ctggctacaa gttcaaggcc aagcctctga tcactgccat gcagatttgc     600

cagttcgtcg gtggcttttct cctggtctgg gactacatca acgttccctg cttcaactct     660

gacaagggca agctgttctc ctgggctttc aactacgcct acgtcggatc tgtctttctc     720

ctgttctgtc acttctttta ccaggacaac ctggccacca agaaatccgc taaggctggt     780

aagcagcttt ag                                                          792


<210> SEQ ID NO 10
<211> LENGTH: 757
<212> TYPE: DNA
<213> ORGANISM: Euglena gracilis
<220> FEATURE:
<221> NAME/KEY: misc_feature
<222> LOCATION: (677)..(677)
<223> OTHER INFORMATION: n is a, c, g, or t

<400> SEQUENCE: 10
```

```
ttttttttcg aacacttaat ggaggtggtg aatgaaatag tctcaattgg gcaggaagtt     60

ttacccaaag ttgattatgc ccaactctgg agtgatgcca gtcactgtga ggtgctttac    120

ttgtccatcg catttgtcat cttgaagttc actcttggcc cccttggtcc aaaaggtcag    180

tctcgtatga agtttgtttt caccaattac aaccttctca tgtccattta ttcgttggga    240

tcattcctct caatggcata tgccatgtac accatcggtg ttatgtctga caactgcgag    300

aaggcttttg acaacaacgt cttcaggatc accacgcagt tgttctattt gagcaagttc    360

ctggagtata ttgactcctt ctatttgcca ctgatgggca agcctctgac ctggttgcaa    420

ttcttccatc atttgggggc accgatggat atgtggctgt tctataatta ccgaaatgaa    480

gctgtttgga tttttgtgct gttgaatggt ttcatccact ggatcatgta cggttattat    540

tggaccagat tgatcaagct gaagttcccc atgccaaaat ccctgattac atcaatgcag    600

atcattcaat tcaatgttgg tttctacatt gtctggaagt acaggaacat tccctgttat    660

cgccaagatg ggatgangat gtttggctgg ttcttcaatt acttttatgt tggcacagtc    720

ttgtgtttgt tcttgaattt ctatgtgcaa acgtata                             757
```

<210> SEQ ID NO 11
<211> LENGTH: 774
<212> TYPE: DNA
<213> ORGANISM: Euglena gracilis
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (82)..(82)
<223> OTHER INFORMATION: n is a, c, g, or t
<220> FEATURE:
<221> NAME/KEY: misc_feature
<222> LOCATION: (112)..(112)
<223> OTHER INFORMATION: n is a, c, g, or t
<220> FEATURE:
<221> NAME/KEY: misc_feature
<222> LOCATION: (218)..(220)
<223> OTHER INFORMATION: n is a, c, g, or t
<220> FEATURE:
<221> NAME/KEY: misc_feature
<222> LOCATION: (707)..(709)
<223> OTHER INFORMATION: n is a, c, g, or t
<220> FEATURE:
<221> NAME/KEY: misc_feature
<222> LOCATION: (711)..(711)
<223> OTHER INFORMATION: n is a, c, g, or t

<400> SEQUENCE: 11

```
tcaggatcac cacgcagttg ttctatttga gcangttcct ggagtatatt gactccttct     60

atttgccant gatgggcaag cntctgacct ggttgcaatt cttccatcat tngggggcac    120

cgatggatat gtggctgttc tataattacc gaaatgaagc tgtttggatt tttgtgctgt    180

tgaatggttt catccactgg atcatgtacg gttattannn gaccagattg atcaagctga    240

agttccccat gccaaaatcc ctgattacat caatgcagat cattcaattc aatgttggtt    300

tctacattgt ctggaagtac aggaacattc cctgttatcg ccaagatggg atgaggatgt    360

ttggctggtt cttcaattac ttttatgttg gcacagtctt gtgtttgttc ttgaatttct    420

atgtgcaaac gtatatcgtc aggaagcaca agggagccaa aaagattcag tgatatttcc    480

tcctctgcgg tggcctcttt tgacctcccc ttgacaccta taatgtggag gtgtcgggct    540
```

ctctccgtct caccagcact tgactctgca ggtgctcact tttatttttt acccatcttt 600
gcttgttgac cattcacctc tcccacttcc acatagtcca ttctaactgt tgcagactgc 660
ggtccatttt ttccagagct cccaatgacc atacgcgaca ccttgtnnnc ncccagccca 720
ttgtgcacaa ttcatagtgg catcgttttg ccttgatacg tgtgcatcca gcgg 774

<210> SEQ ID NO 12
<211> LENGTH: 1201
<212> TYPE: DNA
<213> ORGANISM: Euglena gracilis
<220> FEATURE:
<221> NAME/KEY: misc_feature
<222> LOCATION: (1134)..(1136)
<223> OTHER INFORMATION: n is a, c, g, or t
<220> FEATURE:
<221> NAME/KEY: misc_feature
<222> LOCATION: (1138)..(1138)
<223> OTHER INFORMATION: n is a, c, g, or t

<400> SEQUENCE: 12
gacatggcaa ctatgatttt attttgactg atagtgacct gttcgttgca acaaattgat 60
gagcaatgct tttttataat gccaactttg tacaaaaaag ttggattttt tttcgaacac 120
ttaatggagg tggtgaatga aatagtctca attgggcagg aagttttacc caaagttgat 180
tatgcccaac tctggagtga tgccagtcac tgtgaggtgc tttacttgtc catcgcattt 240
gtcatcttga agttcactct tggcccccttt ggtccaaaag gtcagtctcg tatgaagttt 300
gttttcacca attacaacct tctcatgtcc atttattcgt tgggatcatt cctctcaatg 360
gcatatgcca tgtacaccat cggtgttatg tctgacaact gcgagaaggc ttttgacaac 420
aacgtcttca ggatcaccac gcagttgttc tatttgagca agttcctgga gtatattgac 480
tccttctatt tgccactgat gggcaagcct ctgacctggt tgcaattctt ccatcatttg 540
ggggcaccga tggatatgtg gctgttctat aattaccgaa atgaagctgt ttggattttt 600
gtgctgttga atggtttcat ccactggatc atgtacggtt attattggac cagattgatc 660
aagctgaagt tccccatgcc aaaatccctg attacatcaa tgcagatcat tcaattcaat 720
gttggtttct acattgtctg gaagtacagg aacattccct gttatcgcca agatgggatg 780
aggatgtttg gctggttctt caattacttt tatgttggca cagtcttgtg tttgttcttg 840
aatttctatg tgcaaacgta tatcgtcagg aagcacaagg gagccaaaaa gattcagtga 900
tatttcctcc tctgcggtgg cctcttttga cctccccttg acacctataa tgtggaggtg 960
tcgggctctc tccgtctcac cagcacttga ctctgcaggt gctcactttt atttttttacc 1020 catctttgct tgttgaccat tcacctctcc cacttccaca tagtccattc taactgttgc 1080
agactgcggt ccatttttc cagagctccc aatgaccata cgcgacacct tgtnnncncc 1140
cagcccattg tgcacaattc atagtggcat cgttttgcct tgatacgtgt gcatccagcg 1200
g 1201

<210> SEQ ID NO 13
<211> LENGTH: 200
<212> TYPE: DNA
<213> ORGANISM: Eutreptiella sp. CCMP389

<400> SEQUENCE: 13
ttacagttct tccaccactt gggagccccc atggacatgt ggctctttgt ccaatattct 60
ggggaatcta tttggatctt tgtgtttttg aatgggttca ttcactttgt tatgtacggg 120
tactactgga ctcggctgat gaagttcaat ttcccaatgc ccaagcagtt gattaccgcg 180
atgcagatca tccaattcaa 200

<210> SEQ ID NO 14
<211> LENGTH: 406
<212> TYPE: DNA
<213> ORGANISM: Eutreptiella sp. CCMP389

<400> SEQUENCE: 14
atggcgagac atttacagtt gtgagctact gtatttctcc attgccttcg tgatcttgaa 60
gtttacgttg ggcgagttga gcgacagcgg aaaaaagatt ttgagagtgt tgttcaagtg 120
gtacaatctc ttcatgtccg tgttctcctt ggtgtctttc ctttgcatgg gctatgccat 180
ttataccgtg ggcctatact ctaacgaatg cgacagggct ttcgacaact cgttgttccg 240
ctttgcaaca aaggtgttct actacagtaa gtttttggag tacatcgact ctttttatct 300
tccgctcatg gccaagccgc tgtctttcct gcaattcttc catcacttgg gagcccccat 360
ggacatgtgg ctctttgtcc aatattctgg ggaatctatt tggatc 406

<210> SEQ ID NO 15
<211> LENGTH: 197
<212> TYPE: DNA
<213> ORGANISM: Eutreptiella sp. CCMP389

<400> SEQUENCE: 15
tccatttcgc ccgtcaagcc agagtggcca ttacggctgg tcggacacaa catggctgcg 60
gtgatagagg tcgccaacga gtttgtagcc atcacggcag aaacgctccc caaagttgac 120
tatcaacgac tatggcgaga catttacagt tgtgagctac tgtatttctc cattgccttc 180
gtgatcttga agtttac 197

<210> SEQ ID NO 16
<211> LENGTH: 920
<212> TYPE: DNA
<213> ORGANISM: Eutreptiella sp. CCMP389

<400> SEQUENCE: 16
ctggactcgg ctgatgaagt tcaatttccc aatgcccaag cagttgatta ccgcgatgca 60
gatcacgcag ttcaacgttg gtttctacct cgtgtggtgg tacaaagata ttccctgcta 120
ccgaaaggat cccatgcgaa tgttggcctg gatcttcaat tactggtatg ttgggactgt 180
cttgctgctg ttcattaatt tcttcgtcaa atcctatgtg ttcccaaagc cgaagactgc 240
agataaaaag gtccaatagc tgcacacaca caattatgca gctccccacc actttctccc 300
caaaacagcc agccagcccc cttcccatga aacaagaacc taccccctcc ctgctcctct 360 tttttaatc tcttattcca ccatacactt gatgacaaca gttgccgtgc agtggagcta 420
tgtggtgcat gctgcaatgc actggggcat catattaaga ttattgttat tagtggtgcc 480
cttgcttctc tgctttgtgc ccctggtacc agggtgcacc catgatgcag tacacaagtt 540
gttcaatgtg tgcactgtgg tattctctga attccttgag gagccattta gtttaaccaa 600
gcatgactcg gctggattgg ctcgaggtca ttgcggaagc aaaagttttg cgaggcagct 660
gccgaaggtg ctgctaagtt cggcttcaaa ctggcctttg cacacccagg tacccaggga 720
ttccaagtct catggctggc atattttagg tttcatgcat ccgcagtggc gtttatgcaa 780
ggcacagacg tttatattta tggatatgcg agtgaaggtt ggcttgccag cattggcatc 840
gcctgcctgc atactgagtt ttgttgtaaa agtacaaact cagtatcaac aatacaattt 900
ttktttgaaa aaaaaaaaaa 920

<210> SEQ ID NO 17
<211> LENGTH: 1504
<212> TYPE: DNA
<213> ORGANISM: Eutreptiella sp. CCMP389
<220> FEATURE:
<221> NAME/KEY: misc_feature
<222> LOCATION: (1487)..(1487)
<223> OTHER INFORMATION: n is a, c, g, or t

<400> SEQUENCE: 17
tccatttcgc ccgtcaagcc agagtggcca ttacggctgg tcggacacaa catggctgcg 60
gtgatagagg tcgccaacga gtttgtagcc atcacggcag aaacgctccc caaagttgac 120
tatcaacgac tatggcgaga catttacagt tgtgagctac tgtatttctc cattgccttc 180
gtgatcttga agtttacgtt gggcgagttg agcgacagcg gaaaaaagat tttgagagtg 240
ttgttcaagt ggtacaatct cttcatgtcc gtgttctcct tggtgtcttt cctttgcatg 300
ggctatgcca tttataccgt gggcctatac tctaacgaat gcgacagggc tttcgacaac 360
tcgttgttcc gctttgcaac aaaggtgttc tactacagta agtttttgga gtacatcgac 420
tctttttatc ttccgctcat ggccaagccg ctgtctttcc tgcaattctt ccatcacttg 480
ggagccccca tggacatgtg gctctttgtc caatattctg gggaatctat ttggatcttt 540
gtgtttttga atgggttcat tcactttgtt atgtacgggt actactggac tcggctgatg 600
aagttcaatt tcccaatgcc caagcagttg attaccgcga tgcagatcac gcagttcaac 660
gttggtttct acctcgtgtg gtggtacaaa gatattccct gctaccgaaa ggatcccatg 720
cgaatgttgg cctggatctt caattactgg tatgttggga ctgtcttgct gctgttcatt 780
aatttcttcg tcaaatccta tgtgttccca aagccgaaga ctgcagataa aaaggtccaa 840
tagctgcaca cacacaatta tgcagctccc caccactttc tccccaaaac agccagccag 900 ccccccttccc atgaaacaag aacctacccc ctccctgctc ctcttttttt aatctcttat 960
tccaccatac acttgatgac aacagttgcc gtgcagtgga gctatgtggt gcatgctgca 1020
atgcactggg gcatcatatt aagattattg ttattagtgg tgcccttgct tctctgcttt 1080
gtgcccctgg taccagggtg cacccatgat gcagtacaca agttgttcaa tgtgtgcact 1140
gtggtattct ctgaattcct tgaggagcca tttagtttaa ccaagcatga ctcggctgga 1200
ttggctcgag gtcattgcgg aagcaaaagt tttgcgaggc agctgccgaa ggtgctgcta 1260
agttcggctt caaactggcc tttgcacacc caggtaccca gggattccaa gtctcatggc 1320
tggcatattt taggtttcat gcatccgcag tggcgtttat gcaaggcaca gacgtttata 1380
tttatggata tgcgagtgaa ggttggcttg ccagcattgg catcgcctgc ctgcatactg 1440
agttttgttg taaaagtaca aactcagtat caacaataca atttttnttt gaaaaaaaaa 1500
aaaa 1504

<210> SEQ ID NO 18
<211> LENGTH: 18
<212> TYPE: DNA
<213> ORGANISM: Artificial Sequence
<220> FEATURE:
<223> OTHER INFORMATION: M13F universal primer

<400> SEQUENCE: 18
tgtaaaacga cggccagt 18

<210> SEQ ID NO 19
<211> LENGTH: 30

<212> TYPE: DNA
<213> ORGANISM: Artificial Sequence
<220> FEATURE:
<223> OTHER INFORMATION: Primer oEugEL1-1

<400> SEQUENCE: 19
agcggccgca ccatggaggt ggtgaatgaa 30

<210> SEQ ID NO 20
<211> LENGTH: 30
<212> TYPE: DNA
<213> ORGANISM: Artificial Sequence
<220> FEATURE:
<223> OTHER INFORMATION: Primer oEugEL1-2

<400> SEQUENCE: 20
tgcggccgct cactgaatct ttttggctcc 30

<210> SEQ ID NO 21
<211> LENGTH: 8306
<212> TYPE: DNA
<213> ORGANISM: Artificial Sequence
<220> FEATURE:
<223> OTHER INFORMATION: Plasmid pY119

<400> SEQUENCE: 21
ggccgcaggg cggatccccc gggctgcagg aattcgatat caagcttatc gataccgtcg 60
acctcgaggg ggggcccggt acccaattcg ccctatagtg agtcgtatta cgcgcgctca 120
ctggccgtcg ttttacaacg tcgtgactgg gaaaaccctg gcgttaccca acttaatcgc 180
cttgcagcac atcccccttt cgccagctgg cgtaatagcg aagaggcccg caccgatcgc 240
ccttcccaac agttgcgcag cctgaatggc gaatggcgcg acgcgccctg tagcggcgca 300
ttaagcgcgg cgggtgtggt ggttacgcgc agcgtgaccg ctacacttgc cagcgcccta 360
gcgcccgctc ctttcgcttt cttcccttcc tttctcgcca cgttcgccgg ctttccccgt 420
caagctctaa atcgggggct ccctttaggg ttccgattta gtgctttacg gcacctcgac 480
cccaaaaaac ttgattaggg tgatggttca cgtagtgggc catcgccctg atagacggtt 540
tttcgccctt tgacgttgga gtccacgttc tttaatagtg gactcttgtt ccaaactgga 600
acaacactca accctatctc ggtctattct tttgatttat aagggatttt gccgatttcg 660
gcctattggt taaaaaatga gctgatttaa caaaaattta acgcgaattt taacaaaata 720
ttaacgttta caatttcctg atgcggtatt ttctccttac gcatctgtgc ggtatttcac 780
accgcatatc gacggtcgag gagaacttct agtatatcca catacctaat attattgcct 840
tattaaaaat ggaatcccaa caattacatc aaaatccaca ttctcttcaa aatcaattgt 900
cctgtacttc cttgttcatg tgtgttcaaa aacgttatat ttataggata attatactct 960
atttctcaac aagtaattgg ttgtttggcc gagcggtcta aggcgcctga ttcaagaaat 1020
atcttgaccg cagttaactg tgggaatact caggtatcgt aagatgcaag agttcgaatc 1080
tcttagcaac cattattttt ttcctcaaca taacgagaac acacaggggc gctatcgcac 1140
agaatcaaat tcgatgactg gaaatttttt gttaatttca gaggtcgcct gacgcatata 1200
cctttttcaa ctgaaaaatt gggagaaaaa ggaaaggtga gaggccggaa ccggcttttc 1260
atatagaata gagaagcgtt catgactaaa tgcttgcatc acaatacttg aagttgacaa 1320
tattatttaa ggacctattg ttttttccaa taggtggtta gcaatcgtct tactttctaa 1380
cttttcttac cttttacatt tcagcaatat atatatatat ttcaaggata taccattcta 1440
atgtctgccc ctatgtctgc ccctaagaag atcgtcgttt tgccaggtga ccacgttggt 1500
caagaaatca cagccgaagc cattaaggtt cttaaagcta tttctgatgt tcgttccaat 1560
gtcaagttcg atttcgaaaa tcatttaatt ggtggtgctg ctatcgatgc tacaggtgtc 1620
ccacttccag atgaggcgct ggaagcctcc aagaaggttg atgccgtttt gttaggtgct 1680
gtggctggtc ctaaatgggg taccggtagt gttagacctg aacaaggttt actaaaaatc 1740
cgtaaagaac ttcaattgta cgccaactta agaccatgta actttgcatc cgactctctt 1800
ttagacttat ctccaatcaa gccacaattt gctaaaggta ctgacttcgt tgttgtcaga 1860
gaattagtgg gaggtattta ctttggtaag agaaaggaag acgatggtga tggtgtcgct 1920
tgggatagtg aacaatacac cgttccagaa gtgcaaagaa tcacaagaat ggccgctttc 1980
atggccctac aacatgagcc accattgcct atttggtcct tggataaagc taatcttttg 2040
gcctcttcaa gattatggag aaaaactgtg gaggaaacca tcaagaacga attccctaca 2100
ttgaaggttc aacatcaatt gattgattct gccgccatga tcctagttaa gaacccaacc 2160
cacctaaatg gtattataat caccagcaac atgtttggtg atatcatctc cgatgaagcc 2220
tccgttatcc caggttcctt gggtttgttg ccatctgcgt ccttggcctc tttgccagac 2280
aagaacaccg catttggttt gtacgaacca tgccacggtt ctgctccaga tttgccaaag 2340
aataaggttg accctatcgc cactatcttg tctgctgcaa tgatgttgaa attgtcattg 2400
aacttgcctg aagaaggtaa ggccattgaa gatgcagtta aaaaggtttt ggatgcaggt 2460
atcagaactg gtgatttagg tggttccaac agtaccaccg aagtcggtga tgctgtcgcc 2520
gaagaagtta agaaaatcct tgcttaaaaa gattctcttt ttttatgata tttgtacata 2580
aactttataa atgaaattca taatagaaac gacacgaaat tacaaaatgg aatatgttca 2640
tagggtagac gaaactatat acgcaatcta catacattta tcaagaagga gaaaaaggag 2700
gatagtaaag gaatacaggt aagcaaattg atactaatgg ctcaacgtga taaggaaaaa 2760
gaattgcact ttaacattaa tattgacaag gaggagggca ccacacaaaa agttaggtgt 2820
aacagaaaat catgaaacta cgattcctaa tttgatattg gaggattttc tctaaaaaaa 2880
aaaaaataca acaaataaaa aacactcaat gacctgacca tttgatggag tttaagtcaa 2940
taccttcttg aagcatttcc cataatggtg aaagttccct caagaatttt actctgtcag 3000
aaacggcctt acgacgtagt cgatatggtg cactctcagt acaatctgct ctgatgccgc 3060
atagttaagc cagccccgac acccgccaac acccgctgac gcgccctgac gggcttgtct 3120
gctcccggca tccgcttaca gacaagctgt gaccgtctcc gggagctgca tgtgtcagag 3180
gttttcaccg tcatcaccga aacgcgcgag acgaaagggc ctcgtgatac gcctattttt 3240
ataggttaat gtcatgataa taatggtttc ttagtatgat ccaatatcaa aggaaatgat 3300
agcattgaag gatgagacta atccaattga ggagtggcag catatagaac agctaaaggg 3360
tagtgctgaa ggaagcatac gataccccgc atggaatggg ataatatcac aggaggtact 3420
agactacctt tcatcctaca taaatagacg catataagta cgcatttaag cataaacacg 3480
cactatgccg ttcttctcat gtatatatat atacaggcaa cacgcagata taggtgcgac 3540
gtgaacagtg agctgtatgt gcgcagctcg cgttgcattt tcggaagcgc tcgttttcgg 3600
aaacgctttg aagttcctat tccgaagttc ctattctcta gaaagtatag gaacttcaga 3660
gcgcttttga aaaccaaaag cgctctgaag acgcactttc aaaaaaccaa aaacgcaccg 3720
gactgtaacg agctactaaa atattgcgaa taccgcttcc acaaacattg ctcaaaagta 3780
tctctttgct atatatctct gtgctatatc cctatataac ctacccatcc acctttcgct 3840
ccttgaactt gcatctaaac tcgacctcta catttttat gtttatctct agtattactc 3900
tttagacaaa aaaattgtag taagaactat tcatagagtg aatcgaaaac aatacgaaaa 3960
tgtaaacatt tcctatacgt agtatataga gacaaaatag aagaaaccgt tcataatttt 4020
ctgaccaatg aagaatcatc aacgctatca ctttctgttc acaaagtatg cgcaatccac 4080
atcggtatag aatataatcg ggatgccttt tatcttgaaa aaatgcaccc gcagcttcgc 4140
tagtaatcag taaacgcggg aagtggagtc aggctttttt tatggaagag aaaatagaca 4200
ccaaagtagc cttcttctaa ccttaacgga cctacagtgc aaaaagttat caagagactg 4260
cattatagag cgcacaaagg agaaaaaaag taatctaaga tgctttgtta gaaaaatagc 4320
gctctcggga tgcatttttg tagaacaaaa aagaagtata gattctttgt tggtaaaata 4380
gcgctctcgc gttgcatttc tgttctgtaa aaatgcagct cagattcttt gtttgaaaaa 4440
ttagcgctct cgcgttgcat ttttgtttta caaaaatgaa gcacagattc ttcgttggta 4500
aaatagcgct ttcgcgttgc atttctgttc tgtaaaaatg cagctcagat tctttgtttg 4560
aaaaattagc gctctcgcgt tgcatttttg ttctacaaaa tgaagcacag atgcttcgtt 4620
caggtggcac ttttcgggga aatgtgcgcg gaacccctat ttgtttattt ttctaaatac 4680
attcaaatat gtatccgctc atgagacaat aaccctgata aatgcttcaa taatattgaa 4740
aaaggaagag tatgagtatt caacatttcc gtgtcgccct tattcccttt tttgcggcat 4800
tttgccttcc tgtttttgct cacccagaaa cgctggtgaa agtaaaagat gctgaagatc 4860
agttgggtgc acgagtgggt tacatcgaac tggatctcaa cagcggtaag atccttgaga 4920
gttttcgccc cgaagaacgt tttccaatga tgagcacttt taaagttctg ctatgtggcg 4980
cggtattatc ccgtattgac gccgggcaag agcaactcgg tcgccgcata cactattctc 5040
agaatgactt ggttgagtac tcaccagtca cagaaaagca tcttacggat ggcatgacag 5100
taagagaatt atgcagtgct gccataacca tgagtgataa cactgcggcc aacttacttc 5160
tgacaacgat cggaggaccg aaggagctaa ccgctttttt gcacaacatg ggggatcatg 5220
taactcgcct tgatcgttgg gaaccggagc tgaatgaagc cataccaaac gacgagcgtg 5280
acaccacgat gcctgtagca atggcaacaa cgttgcgcaa actattaact ggcgaactac 5340
ttactctagc ttcccggcaa caattaatag actggatgga ggcggataaa gttgcaggac 5400
cacttctgcg ctcggccctt ccggctggct ggtttattgc tgataaatct ggagccggtg 5460
agcgtgggtc tcgcggtatc attgcagcac tggggccaga tggtaagccc tcccgtatcg 5520
tagttatcta cacgacgggg agtcaggcaa ctatggatga acgaaataga cagatcgctg 5580
agataggtgc ctcactgatt aagcattggt aactgtcaga ccaagtttac tcatatatac 5640
tttagattga tttaaaactt catttttaat ttaaaaggat ctaggtgaag atcctttttg 5700
ataatctcat gaccaaaatc ccttaacgtg agttttcgtt ccactgagcg tcagaccccg 5760
tagaaaagat caaaggatct tcttgagatc ctttttttct gcgcgtaatc tgctgcttgc 5820
aaacaaaaaa accaccgcta ccagcggtgg tttgtttgcc ggatcaagag ctaccaactc 5880
tttttccgaa ggtaactggc ttcagcagag cgcagatacc aaatactgtc cttctagtgt 5940
agccgtagtt aggccaccac ttcaagaact ctgtagcacc gcctacatac ctcgctctgc 6000
taatcctgtt accagtggct gctgccagtg gcgataagtc gtgtcttacc gggttggact 6060
caagacgata gttaccggat aaggcgcagc ggtcgggctg aacggggggt tcgtgcacac 6120
agcccagctt ggagcgaacg acctacaccg aactgagata cctacagcgt gagctatgag 6180
aaagcgccac gcttcccgaa gggagaaagg cggacaggta tccggtaagc ggcagggtcg 6240
gaacaggaga gcgcacgagg gagcttccag ggggaaacgc ctggtatctt tatagtcctg 6300
tcgggtttcg ccacctctga cttgagcgtc gatttttgtg atgctcgtca ggggggcgga 6360
gcctatggaa aaacgccagc aacgcggcct ttttacggtt cctggccttt tgctggcctt 6420
ttgctcacat gttctttcct gcgttatccc ctgattctgt ggataaccgt attaccgcct 6480
ttgagtgagc tgataccgct cgccgcagcc gaacgaccga gcgcagcgag tcagtgagcg 6540
aggaagcgga agagcgccca atacgcaaac cgcctctccc cgcgcgttgg ccgattcatt 6600
aatgcagctg gcacgacagg tttcccgact ggaaagcggg cagtgagcgc aacgcaatta 6660
atgtgagtta cctcactcat taggcacccc aggctttaca ctttatgctt ccggctccta 6720
tgttgtgtgg aattgtgagc ggataacaat ttcacacagg aaacagctat gaccatgatt 6780
acgccaagcg cgcaattaac cctcactaaa gggaacaaaa gctggagctc caccgcggga 6840
tttcgaaact aagttcttgg tgttttaaaa ctaaaaaaaa gactaactat aaaagtagaa 6900
tttaagaagt ttaagaaata gatttacaga attacaatca atacctaccg tctttatata 6960
cttattagtc aagtagggga ataatttcag ggaactggtt tcaacctttt ttttcagctt 7020
tttccaaatc agagagagca gaaggtaata gaaggtgtaa gaaaatgaga tagatacatg 7080
cgtgggtcaa ttgccttgtg tcatcattta ctccaggcag gttgcatcac tccattgagg 7140
ttgtgcccgt tttttgcctg tttgtgcccc tgttctctgt agttgcgcta agagaatgga 7200
cctatgaact gatggttggt gaagaaaaca atattttggt gctgggattc tttttttttc 7260
tggatgccag cttaaaaagc gggctccatt atatttagtg gatgccagga ataaactgtt 7320
cacccagaca cctacgatgt tatatattct gtgtaacccg cccccctattt tgggcatgta 7380 cgggttacag cagaattaaa aggctaattt tttgactaaa taaagttagg aaaatcacta 7440
ctattaatta tttacgtatt ctttgaaatg gcagtattga taatgataaa ctcgaaatca 7500
ctagtggatc cgcccagcgg ccgcaccatg gaggtggtga atgaaatagt ctcaattggg 7560
caggaagttt tacccaaagt tgattatgcc caactctgga gtgatgccag tcactgtgag 7620
gtgctttact tgtccatcgc atttgtcatc ttgaagttca ctcttggccc ccttggtcca 7680
aaaggtcagt ctcgtatgaa gtttgttttc accaattaca accttctcat gtccatttat 7740
tcgttgggat cattcctctc aatggcatat gccatgtaca ccatcggtgt tatgtctgac 7800
aactgcgaga aggcttttga caacaacgtc ttcaggatca ccacgcagtt gttctatttg 7860
agcaagttcc tggagtatat tgactccttc tatttgccac tgatgggcaa gcctctgacc 7920
tggttgcaat tcttccatca tttgggggca ccgatggata tgtggctgtt ctataattac 7980
cgaaatgaag ctgtttggat ttttgtgctg ttgaatggtt tcatccactg gatcatgtac 8040
ggttattatt ggaccagatt gatcaagctg aagttcccca tgccaaaatc cctgattaca 8100
tcaatgcaga tcattcaatt caatgttggt ttctacattg tctggaagta caggaacatt 8160
ccctgttatc gccaagatgg gatgaggatg tttggctggt tcttcaatta cttttatgtt 8220
ggcacagtct tgtgtttgtt cttgaatttc tatgtgcaaa cgtatatcgt caggaagcac 8280
aagggagcca aaaagattca gtgagc 8306

<210> SEQ ID NO 22
<211> LENGTH: 9472
<212> TYPE: DNA
<213> ORGANISM: Artificial Sequence
<220> FEATURE:
<223> OTHER INFORMATION: Plasmid pDMW263

<400> SEQUENCE: 22
catggcatgg atggtacgtc ctgtagaaac cccaacccgt gaaatcaaaa aactcgacgg 60
cctgtgggca ttcagtctgg atcgcgaaaa ctgtggaatt gatcagcgtt ggtgggaaag 120
cgcgttacaa gaaagccggg caattgctgt gccaggcagt tttaacgatc agttcgccga 180
tgcagatatt cgtaattatg cgggcaacgt ctggtatcag cgcgaagtct ttataccgaa 240
aggttgggca ggccagcgta tcgtgctgcg tttcgatgcg gtcactcatt acggcaaagt 300
gtgggtcaat aatcaggaag tgatggagca tcagggcggc tatacgccat ttgaagccga 360
tgtcacgccg tatgttattg ccgggaaaag tgtacgtatc accgtttgtg tgaacaacga 420
actgaactgg cagactatcc cgccgggaat ggtgattacc gacgaaaacg gcaagaaaaa 480
gcagtcttac ttccatgatt tctttaacta tgccgggatc catcgcagcg taatgctcta 540
caccacgccg aacacctggg tggacgatat caccgtggtg acgcatgtcg cgcaagactg 600
taaccacgcg tctgttgact ggcaggtggt ggccaatggt gatgtcagcg ttgaactgcg 660
tgatgcggat caacaggtgg ttgcaactgg acaaggcact agcgggactt tgcaagtggt 720
gaatccgcac ctctggcaac cgggtgaagg ttatctctat gaactgtgcg tcacagccaa 780
aagccagaca gagtgtgata tctacccgct tcgcgtcggc atccggtcag tggcagtgaa 840
gggcgaacag ttcctgatta accacaaacc gttctacttt actggctttg gtcgtcatga 900
agatgcggac ttacgtggca aaggattcga taacgtgctg atggtgcacg accacgcatt 960
aatggactgg attggggcca actcctaccg tacctcgcat taccottacg ctgaagagat 1020
gctcgactgg gcagatgaac atggcatcgt ggtgattgat gaaactgctg ctgtcggctt 1080
taacctctct ttaggcattg gtttcgaagc gggcaacaag ccgaaagaac tgtacagcga 1140
agaggcagtc aacggggaaa ctcagcaagc gcacttacag gcgattaaag agctgatagc 1200
gcgtgacaaa aaccacccaa gcgtggtgat gtggagtatt gccaacgaac cggatacccg 1260
tccgcaagtg cacgggaata tttcgccact ggcggaagca acgcgtaaac tcgacccgac 1320
gcgtccgatc acctgcgtca atgtaatgtt ctgcgacgct cacaccgata ccatcagcga 1380
tctctttgat gtgctgtgcc tgaaccgtta ttacggatgg tatgtccaaa gcggcgattt 1440
ggaaacggca gagaaggtac tggaaaaaga acttctggcc tggcaggaga aactgcatca 1500
gccgattatc atcaccgaat acggcgtgga tacgttagcc gggctgcact caatgtacac 1560
cgacatgtgg agtgaagagt atcagtgtgc atggctggat atgtatcacc gcgtctttga 1620
tcgcgtcagc gccgtcgtcg gtgaacaggt atggaatttc gccgattttg cgacctcgca 1680
aggcatattg cgcgttggcg gtaacaagaa agggatcttc actcgcgacc gcaaaccgaa 1740
gtcggcggct tttctgctgc aaaaacgctg gactggcatg aacttcggtg aaaaaccgca 1800
gcagggaggc aaacaatgat taattaacta gagcggccgc caccgcggcc cgagattccg 1860
gcctcttcgg ccgccaagcg acccgggtgg acgtctagag gtacctagca attaacagat 1920
agtttgccgg tgataattct cttaacctcc cacactcctt tgacataacg atttatgtaa 1980
cgaaactgaa atttgaccag atattgtgtc cgcggtggag ctccagcttt tgttcccttt 2040
agtgagggtt aatttcgagc ttggcgtaat catggtcata gctgtttcct gtgtgaaatt 2100
gttatccgct cacaattcca cacaacatac gagccggaag cataaagtgt aaagcctggg 2160
gtgcctaatg agtgagctaa ctcacattaa ttgcgttgcg ctcactgccc gctttccagt 2220
cgggaaacct gtcgtgccag ctgcattaat gaatcggcca acgcgcgggg agaggcggtt 2280
tgcgtattgg gcgctcttcc gcttcctcgc tcactgactc gctgcgctcg gtcgttcggc 2340
tgcggcgagc ggtatcagct cactcaaagg cggtaatacg gttatccaca gaatcagggg 2400
ataacgcagg aaagaacatg tgagcaaaag gccagcaaaa ggccaggaac cgtaaaaagg 2460

```
ccgcgttgct ggcgtttttc cataggctcc gcccccctga cgagcatcac aaaaatcgac   2520
gctcaagtca gaggtggcga aacccgacag gactataaag ataccaggcg tttccccctg   2580
gaagctccct cgtgcgctct cctgttccga ccctgccgct taccggatac ctgtccgcct   2640
ttctcccttc gggaagcgtg gcgctttctc atagctcacg ctgtaggtat ctcagttcgg   2700
tgtaggtcgt tcgctccaag ctgggctgtg tgcacgaacc ccccgttcag cccgaccgct   2760
gcgccttatc cggtaactat cgtcttgagt ccaacccggt aagacacgac ttatcgccac   2820
tggcagcagc cactggtaac aggattagca gagcgaggta tgtaggcggt gctacagagt   2880
tcttgaagtg gtggcctaac tacggctaca ctagaaggac agtatttggt atctgcgctc   2940
tgctgaagcc agttaccttc ggaaaaagag ttggtagctc ttgatccggc aaacaaacca   3000
ccgctggtag cggtggtttt tttgtttgca agcagcagat tacgcgcaga aaaaaaggat   3060
ctcaagaaga tcctttgatc ttttctacgg ggtctgacgc tcagtggaac gaaaactcac   3120
gttaagggat tttggtcatg agattatcaa aaaggatctt cacctagatc cttttaaatt   3180
aaaaatgaag ttttaaatca atctaaagta tatatgagta aacttggtct gacagttacc   3240
aatgcttaat cagtgaggca cctatctcag cgatctgtct atttcgttca tccatagttg   3300
cctgactccc cgtcgtgtag ataactacga tacgggaggg cttaccatct ggccccagtg   3360
ctgcaatgat accgcgagac ccacgctcac cggctccaga tttatcagca ataaaccagc   3420
cagccggaag ggccgagcgc agaagtggtc ctgcaacttt atccgcctcc atccagtcta   3480
ttaattgttg ccgggaagct agagtaagta gttcgccagt taatagtttg cgcaacgttg   3540
ttgccattgc tacaggcatc gtggtgtcac gctcgtcgtt tggtatggct tcattcagct   3600
ccggttccca acgatcaagg cgagttacat gatcccccat gttgtgcaaa aaagcggtta   3660
gctccttcgg tcctccgatc gttgtcagaa gtaagttggc cgcagtgtta tcactcatgg   3720
ttatggcagc actgcataat tctcttactg tcatgccatc cgtaagatgc ttttctgtga   3780
ctggtgagta ctcaaccaag tcattctgag aatagtgtat gcggcgaccg agttgctctt   3840
gcccggcgtc aatacgggat aataccgcgc cacatagcag aactttaaaa gtgctcatca   3900
ttggaaaacg ttcttcgggg cgaaaactct caaggatctt accgctgttg agatccagtt   3960
cgatgtaacc cactcgtgca cccaactgat cttcagcatc ttttactttc accagcgttt   4020
ctgggtgagc aaaaacagga aggcaaaatg ccgcaaaaaa gggaataagg gcgacacgga   4080
aatgttgaat actcatactc ttcctttttc aatattattg aagcatttat cagggttatt   4140
gtctcatgag cggatacata tttgaatgta tttagaaaaa taaacaaata ggggttccgc   4200
gcacatttcc ccgaaaagtg ccacctgacg cgccctgtag cggcgcatta agcgcggcgg   4260
gtgtggtggt tacgcgcagc gtgaccgcta cacttgccag cgccctagcg cccgctcctt   4320
tcgctttctt cccttccttt ctcgccacgt tcgccggctt tccccgtcaa gctctaaatc   4380
gggggctccc tttagggttc cgatttagtg ctttacggca cctcgacccc aaaaaacttg   4440
attagggtga tggttcacgt agtgggccat cgccctgata gacggttttt cgccctttga   4500
cgttggagtc cacgttcttt aatagtggac tcttgttcca aactggaaca acactcaacc   4560
ctatctcggt ctattctttt gatttataag ggattttgcc gatttcggcc tattggttaa   4620
aaaatgagct gatttaacaa aaatttaacg cgaattttaa caaaatatta acgcttacaa   4680
tttccattcg ccattcaggc tgcgcaactg ttgggaaggg cgatcggtgc gggcctcttc   4740
gctattacgc cagctggcga aagggggatg tgctgcaagg cgattaagtt gggtaacgcc   4800
agggttttcc cagtcacgac gttgtaaaac gacggccagt gaattgtaat acgactcact   4860
```

```
atagggcgaa ttgggtaccg ggccccccct cgaggtcgat ggtgtcgata agcttgatat   4920
cgaattcatg tcacacaaac cgatcttcgc ctcaaggaaa cctaattcta catccgagag   4980
actgccgaga tccagtctac actgattaat tttcgggcca ataatttaaa aaaatcgtgt   5040
tatataatat tatatgtatt atatatatac atcatgatga tactgacagt catgtcccat   5100
tgctaaatag acagactcca tctgccgcct ccaactgatg ttctcaatat ttaaggggtc   5160
atctcgcatt gtttaataat aaacagactc catctaccgc ctccaaatga tgttctcaaa   5220
atatattgta tgaacttatt tttattactt agtattatta gacaacttac ttgctttatg   5280
aaaaacactt cctatttagg aaacaattta taatggcagt tcgttcattt aacaatttat   5340
gtagaataaa tgttataaat gcgtatggga aatcttaaat atggatagca taaatgatat   5400
ctgcattgcc taattcgaaa tcaacagcaa cgaaaaaaat cccttgtaca acataaatag   5460
tcatcgagaa atatcaacta tcaaagaaca gctattcaca cgttactatt gagattatta   5520
ttggacgaga atcacacact caactgtctt tctctcttct agaaatacag gtacaagtat   5580
gtactattct cattgttcat acttctagtc atttcatccc acatattcct tggatttctc   5640
tccaatgaat gacattctat cttgcaaatt caacaattat aataagatat accaaagtag   5700
cggtatagtg gcaatcaaaa agcttctctg gtgtgcttct cgtatttatt tttattctaa   5760
tgatccatta aaggtatata tttatttctt gttatataat ccttttgttt attacatggg   5820
ctggatacat aaaggtattt tgatttaatt ttttgcttaa attcaatccc ccctcgttca   5880
gtgtcaactg taatggtagg aaattaccat acttttgaag aagcaaaaaa aatgaaagaa   5940
aaaaaaaatc gtatttccag gttagacgtt ccgcagaatc tagaatgcgg tatgcggtac   6000
attgttcttc gaacgtaaaa gttgcgctcc ctgagatatt gtacattttt gcttttacaa   6060
gtacaagtac atcgtacaac tatgtactac tgttgatgca tccacaacag tttgttttgt   6120
tttttttgt ttttttttt tctaatgatt cattaccgct atgtatacct acttgtactt   6180
gtagtaagcc gggttattgg cgttcaatta atcatagact tatgaatctg cacggtgtgc   6240
gctgcgagtt acttttagct tatgcatgct acttgggtgt aatattggga tctgttcgga   6300
aatcaacgga tgctcaaccg atttcgacag taataatttg aatcgaatcg gagcctaaaa   6360
tgaacccgag tatatctcat aaaattctcg gtgagaggtc tgtgactgtc agtacaaggt   6420
gccttcatta tgccctcaac cttaccatac ctcactgaat gtagtgtacc tctaaaaatg   6480
aaatacagtg ccaaaagcca aggcactgag ctcgtctaac ggacttgata tacaaccaat   6540
taaaacaaat gaaaagaaat acagttcttt gtatcatttg taacaattac cctgtacaaa   6600
ctaaggtatt gaaatcccac aatattccca aagtccaccc ctttccaaat tgtcatgcct   6660
acaactcata taccaagcac taacctacca aacaccacta aaaccccaca aaatatatct   6720
taccgaatat acagtaacaa gctaccacca cactcgttgg gtgcagtcgc cagcttaaag   6780
atatctatcc acatcagcca caactccctt cctttaataa accgactaca cccttggcta   6840
ttgaggttat gagtgaatat actgtagaca agacactttc aagaagactg tttccaaaac   6900
gtaccactgt cctccactac aaacacaccc aatctgcttc ttctagtcaa ggttgctaca   6960
ccggtaaatt ataaatcatc atttcattag cagggcaggg cccttttttat agagtcttat   7020
acactagcgg accctgccgg tagaccaacc cgcaggcgcg tcagtttgct ccttccatca   7080
atgcgtcgta gaaacgactt actccttctt gagcagctcc ttgaccttgt tggcaacaag   7140
tctccgacct cggaggtgga ggaagagcct ccgatatcgg cggtagtgat accagcctcg   7200
acggactcct tgacggcagc ctcaacagcg tcaccggcgg gcttcatgtt aagagagaac   7260
```

```
ttgagcatca tggcggcaga cagaatggtg gcaatggggt tgaccttctg cttgccgaga   7320
tcgggggcag atccgtgaca gggctcgtac agaccgaacg cctcgttggt gtcgggcaga   7380
gaagccagag aggcggaggg cagcagaccc agagaaccgg ggatgacgga ggcctcgtcg   7440
gagatgatat cgccaaacat gttggtggtg atgatgatac cattcatctt ggagggctgc   7500
ttgatgagga tcatggcggc cgagtcgatc agctggtggt tgagctcgag ctggggggaat  7560
tcgtccttga ggactcgagt gacagtcttt cgccaaagtc gagaggaggc cagcacgttg   7620
gccttgtcaa gagaccacac gggaagaggg gggttgtgct gaagggccag gaaggcggcc   7680
attcgggcaa ttcgctcaac ctcaggaacg gagtaggtct cggtgtcgga agcgacgcca   7740
gatccgtcat cctcctttcg ctctccaaag tagatacctc cgacgagctc tcggacaatg   7800
atgaagtcgg tgccctcaac gtttcggatg ggggagagat cggcgagctt gggcgacagc   7860
agctggcagg gtcgcaggtt ggcgtacagg ttcaggtcct ttcgcagctt gaggagaccc   7920
tgctcgggtc gcacgtcggt tcgtccgtcg ggagtggtcc atacggtgtt ggcagcgcct   7980
ccgacagcac cgagcataat agagtcagcc tttcggcaga tgtcgagagt agcgtcggtg   8040
atgggctcgc cctccttctc aatggcagct cctccaatga gtcggtcctc aaacacaaac   8100
tcggtgccgg aggcctcagc aacagacttg agcaccttga cggcctcggc aatcacctcg   8160
gggccacaga agtcgccgcc gagaagaaca atcttcttgg agtcagtctt ggtcttctta   8220
gtttcgggtt ccattgtgga tgtgtgtggt tgtatgtgtg atgtggtgtg tggagtgaaa   8280
atctgtggct ggcaaacgct cttgtatata tacgcacttt tgcccgtgct atgtggaaga   8340
ctaaacctcc gaagattgtg actcaggtag tgcggtatcg gctagggacc caaaccttgt   8400
cgatgccgat agcgctatcg aacgtacccc agccggccgg gagtatgtcg gaggggacat   8460
acgagatcgt caagggtttg tggccaactg gtaaataaat gatgtcgacg tttaaacagt   8520
gtacgcagat ctactataga ggaacattta aattgccccg gagaagacgg ccaggccgcc   8580
tagatgacaa attcaacaac tcacagctga ctttctgcca ttgccactag gggggggcct   8640
ttttatatgg ccaagccaag ctctccacgt cggttgggct gcacccaaca ataaatgggt   8700
agggttgcac caacaaaggg atgggatggg gggtagaaga tacgaggata acggggctca   8760
atggcacaaa taagaacgaa tactgccatt aagactcgtg atccagcgac tgacaccatt   8820
gcatcatcta agggcctcaa aactacctcg gaactgctgc gctgatctgg acaccacaga   8880
ggttccgagc actttaggtt gcaccaaatg tcccaccagg tgcaggcaga aaacgctgga   8940
acagcgtgta cagtttgtct taacaaaaag tgagggcgct gaggtcgagc agggtggtgt   9000
gacttgttat agcctttaga gctgcgaaag cgcgtatgga tttggctcat caggccagat   9060
tgagggtctg tggacacatg tcatgttagt gtacttcaat cgccccctgg atatagcccc   9120
gacaataggc cgtggcctca ttttttttgcc ttccgcacat ttccattgct cgatacccac  9180
accttgcttc tcctgcactt gccaacctta atactggttt acattgacca acatcttaca   9240
agcggggggc ttgtctaggg tatatataaa cagtggctct cccaatcggt tgccagtctc   9300
ttttttcctt tctttcccca cagattcgaa atctaaacta cacatcacag aattccgagc   9360
cgtgagtatc cacgacaaga tcagtgtcga gacgacgcgt tttgtgtaat gacacaatcc   9420
gaaagtcgct agcaacacac actctctaca caaactaacc cagctctggt ac           9472
```

<210> SEQ ID NO 23
<211> LENGTH: 101
<212> TYPE: DNA
<213> ORGANISM: Artificial Sequence
<220> FEATURE:
<223> OTHER INFORMATION: Primer IL3-1A

<400> SEQUENCE: 23
gccaacgacg ctggcgagcg aatctgggct gccgtcaccg atcccgaaat cctcattggc 60
accttctcct acctgctcct gaagcctctc ctgcgaaact c 101

<210> SEQ ID NO 24
<211> LENGTH: 101
<212> TYPE: DNA
<213> ORGANISM: Artificial Sequence
<220> FEATURE:
<223> OTHER INFORMATION: Primer IL3-1B

<400> SEQUENCE: 24
accagagttt cgcaggagag gcttcaggag caggtaggag aaggtgccaa tgaggatttc 60
gggatcggtg acggcagccc agattcgctc gccagcgtcg t 101

<210> SEQ ID NO 25
<211> LENGTH: 100
<212> TYPE: DNA
<213> ORGANISM: Artificial Sequence
<220> FEATURE:
<223> OTHER INFORMATION: Primer IL3-2A

<400> SEQUENCE: 25
tggtctcgtg gacgagaaga aaggagccta ccgaacctcc atgatctggt acaacgtcct 60
cctggctctc ttctctgccc tgtccttcta cgtgactgcc 100

<210> SEQ ID NO 26
<211> LENGTH: 100
<212> TYPE: DNA
<213> ORGANISM: Artificial Sequence
<220> FEATURE:
<223> OTHER INFORMATION: Primer IL3-2B

<400> SEQUENCE: 26
cggtggcagt cacgtagaag gacagggcag agaagagagc caggaggacg ttgtaccaga 60
tcatggaggt tcggtaggct cctttcttct cgtccacgag 100

<210> SEQ ID NO 27
<211> LENGTH: 100
<212> TYPE: DNA
<213> ORGANISM: Artificial Sequence
<220> FEATURE:
<223> OTHER INFORMATION: Primer IL3-3A

<400> SEQUENCE: 27
accgctctcg gctgggacta cggtactgga gcctggctgc gaagacagac cggtgatact 60
ccccagcctc tctttcagtg tccctctcct gtctgggact 100

<210> SEQ ID NO 28
<211> LENGTH: 100
<212> TYPE: DNA
<213> ORGANISM: Artificial Sequence
<220> FEATURE:
<223> OTHER INFORMATION: Primer IL3-3B

<400> SEQUENCE: 28
ttggagtccc agacaggaga gggacactga aagagaggct ggggagtatc accggtctgt 60
cttcgcagcc aggctccagt accgtagtcc cagccgagag 100

-continued

<210> SEQ ID NO 29
<211> LENGTH: 100
<212> TYPE: DNA
<213> ORGANISM: Artificial Sequence
<220> FEATURE:
<223> OTHER INFORMATION: Primer IL3-4A

<400> SEQUENCE: 29
ccaagctgtt cacctggact gccaaggcct tctactattc taagtacgtg gagtacctcg 60
acaccgcttg gctggtcctc aagggcaagc gagtgtcctt 100

<210> SEQ ID NO 30
<211> LENGTH: 100
<212> TYPE: DNA
<213> ORGANISM: Artificial Sequence
<220> FEATURE:
<223> OTHER INFORMATION: Primer IL3-4B

<400> SEQUENCE: 30
cagaaaggac actcgcttgc ccttgaggac cagccaagcg gtgtcgaggt actccacgta 60
cttagaatag tagaaggcct tggcagtcca ggtgaacagc 100

<210> SEQ ID NO 31
<211> LENGTH: 89
<212> TYPE: DNA
<213> ORGANISM: Artificial Sequence
<220> FEATURE:
<223> OTHER INFORMATION: Primer IL3-5A

<400> SEQUENCE: 31
ttccatcact ttggagctcc ctgggacgtc tacctcggca ttcgactgca caacgagggt 60
gtgtggatct tcatgttctt taactcgtt 89

<210> SEQ ID NO 32
<211> LENGTH: 89
<212> TYPE: DNA
<213> ORGANISM: Artificial Sequence
<220> FEATURE:
<223> OTHER INFORMATION: Primer IL3-5B

<400> SEQUENCE: 32
aatgaacgag ttaaagaaca tgaagatcca cacaccctcg ttgtgcagtc gaatgccgag 60
gtagacgtcc cagggagctc caaagtgat 89

<210> SEQ ID NO 33
<211> LENGTH: 91
<212> TYPE: DNA
<213> ORGANISM: Artificial Sequence
<220> FEATURE:
<223> OTHER INFORMATION: Primer IL3-6A

<400> SEQUENCE: 33
cattcacacc atcatgtaca cctactatgg actgactgcc gctggctaca agttcaaggc 60
caagcctctg atcactgcca tgcagatttg c 91

<210> SEQ ID NO 34
<211> LENGTH: 91
<212> TYPE: DNA
<213> ORGANISM: Artificial Sequence
<220> FEATURE:
<223> OTHER INFORMATION: Primer IL3-6B

<400> SEQUENCE: 34
actggcaaat ctgcatggca gtgatcagag gcttggcctt gaacttgtag ccagcggcag 60
tcagtccata gtaggtgtac atgatggtgt g 91

<210> SEQ ID NO 35
<211> LENGTH: 94
<212> TYPE: DNA
<213> ORGANISM: Artificial Sequence
<220> FEATURE:
<223> OTHER INFORMATION: Primer IL3-7A

<400> SEQUENCE: 35
cagttcgtcg gtggctttct cctggtctgg gactacatca acgttccctg cttcaactct 60
gacaagggca agctgttctc ctgggctttc aact 94

<210> SEQ ID NO 36
<211> LENGTH: 94
<212> TYPE: DNA
<213> ORGANISM: Artificial Sequence
<220> FEATURE:
<223> OTHER INFORMATION: Primer IL3-7B

<400> SEQUENCE: 36
gcgtagttga aagcccagga gaacagcttg cccttgtcag agttgaagca gggaacgttg 60
atgtagtccc agaccaggag aaagccaccg acga 94

<210> SEQ ID NO 37
<211> LENGTH: 91
<212> TYPE: DNA
<213> ORGANISM: Artificial Sequence
<220> FEATURE:
<223> OTHER INFORMATION: Primer IL3-8A

<400> SEQUENCE: 37
acgcctacgt cggatctgtc tttctcctgt tctgtcactt cttttaccag gacaacctgg 60
ccaccaagaa atccgctaag gctggtaagc a 91

<210> SEQ ID NO 38
<211> LENGTH: 91
<212> TYPE: DNA
<213> ORGANISM: Artificial Sequence
<220> FEATURE:
<223> OTHER INFORMATION: Primer IL3-8B

<400> SEQUENCE: 38
aagctgctta ccagccttag cggatttctt ggtggccagg ttgtcctggt aaaagaagtg 60
acagaacagg agaaagacag atccgacgta g 91

<210> SEQ ID NO 39
<211> LENGTH: 41
<212> TYPE: DNA
<213> ORGANISM: Artificial Sequence
<220> FEATURE:
<223> OTHER INFORMATION: Primer IL3-1F

<400> SEQUENCE: 39
tttccatggc tctggccaac gacgctggcg agcgaatctg g 41

<210> SEQ ID NO 40
<211> LENGTH: 36
<212> TYPE: DNA
<213> ORGANISM: Artificial Sequence
<220> FEATURE:
<223> OTHER INFORMATION: Primer IL3-4R

<400> SEQUENCE: 40

-continued tttctgcaga aaggacactc gcttgccctt gaggac 36

<210> SEQ ID NO 41
<211> LENGTH: 41
<212> TYPE: DNA
<213> ORGANISM: Artificial Sequence
<220> FEATURE:
<223> OTHER INFORMATION: Primer IL3-5F

<400> SEQUENCE: 41
tttctgcagg ccttccatca ctttggagct ccctgggacg t 41

<210> SEQ ID NO 42
<211> LENGTH: 42
<212> TYPE: DNA
<213> ORGANISM: Artificial Sequence
<220> FEATURE:
<223> OTHER INFORMATION: Primer IL3-8R

<400> SEQUENCE: 42
tttgcggccg ctaaagctgc ttaccagcct tagcggattt ct 42

<210> SEQ ID NO 43
<211> LENGTH: 417
<212> TYPE: DNA
<213> ORGANISM: Artificial Sequence
<220> FEATURE:
<223> OTHER INFORMATION: 417 bp NcoI/PstI fragment pT9(1-4)

<400> SEQUENCE: 43
catggctctg gccaacgacg ctggcgagcg aatctgggct gccgtcaccg atcccgaaat 60
cctcattggc accttctcct acctgctcct gaagcctctc ctgcgaaact ctggtctcgt 120
ggacgagaag aaaggagcct accgaacctc catgatctgg tacaacgtcc tcctggctct 180
cttctctgcc ctgtccttct acgtgactgc caccgctctc ggctgggact acggtactgg 240
agcctggctg cgaagacaga ccggtgatac tccccagcct ctctttcagt gtccctctcc 300
tgtctgggac tccaagctgt tcacctggac tgccaaggcc ttctactatt ctaagtacgt 360
ggagtacctc gacaccgctt ggctggtcct caagggcaag cgagtgtcct ttctgca 417

<210> SEQ ID NO 44
<211> LENGTH: 377
<212> TYPE: DNA
<213> ORGANISM: Artificial Sequence
<220> FEATURE:
<223> OTHER INFORMATION: 377 bp PstI/Not1 fragment pT9(5-8)

<400> SEQUENCE: 44
ggccttccat cactttggag ctccctggga cgtctacctc ggcattcgac tgcacaacga 60
gggtgtgtgg atcttcatgt tctttaactc gttcattcac accatcatgt acacctacta 120
tggactgact gccgctggct acaagttcaa ggccaagcct ctgatcactg ccatgcagat 180
ttgccagttc gtcggtggct ttctcctggt ctgggactac atcaacgttc cctgcttcaa 240
ctctgacaag ggcaagctgt tctcctgggc tttcaactac gcctacgtcg gatctgtctt 300
tctcctgttc tgtcacttct tttaccagga caacctggcc accaagaaat ccgctaaggc 360
tggtaagcag ctttagc 377

<210> SEQ ID NO 45
<211> LENGTH: 7783
<212> TYPE: DNA
<213> ORGANISM: Artificial Sequence
<220> FEATURE:
<223> OTHER INFORMATION: Plasmid pY115

<400> SEQUENCE: 45

```
catggctctg gccaacgacg ctggcgagcg aatctgggct gccgtcaccg atcccgaaat     60
cctcattggc accttctcct acctgctcct gaagcctctc ctgcgaaact ctggtctcgt    120
ggacgagaag aaaggagcct accgaacctc catgatctgg tacaacgtcc tcctggctct    180
cttctctgcc ctgtccttct acgtgactgc caccgctctc ggctgggact acggtactgg    240
agcctggctg cgaagacaga ccggtgatac tccccagcct ctctttcagt gtccctctcc    300
tgtctgggac tccaagctgt tcacctggac tgccaaggcc ttctactatt ctaagtacgt    360
ggagtacctc gacaccgctt ggctggtcct caagggcaag cgagtgtcct ttctgcaggc    420
cttccatcac tttggagctc cctgggacgt ctacctcggc attcgactgc acaacgaggg    480
tgtgtggatc ttcatgttct ttaactcgtt cattcacacc atcatgtaca cctactatgg    540
actgactgcc gctggctaca agttcaaggc caagcctctg atcactgcca tgcagatttg    600
ccagttcgtc ggtggctttc tcctggtctg ggactacatc aacgttccct gcttcaactc    660
tgacaagggc aagctgttct cctgggcttt caactacgcc tacgtcggat ctgtctttct    720
cctgttctgt cacttctttt accaggacaa cctggccacc aagaaatccg ctaaggctgg    780
taagcagctt tagcggccgc aagtgtggat ggggaagtga gtgcccggtt ctgtgtgcac    840
aattggcaat ccaagatgga tggattcaac acagggatat agcgagctac gtggtggtgc    900
gaggatatag caacggatat ttatgtttga cacttgagaa tgtacgatac aagcactgtc    960
caagtacaat actaaacata ctgtacatac tcatactcgt acccgggcaa cggtttcact   1020
tgagtgcagt ggctagtgct cttactcgta cagtgtgcaa tactgcgtat catagtcttt   1080
gatgtatatc gtattcattc atgttagttg cgtacgagcc ggaagcataa agtgtaaagc   1140
ctggggtgcc taatgagtga gctaactcac attaattgcg ttgcgctcac tgcccgcttt   1200
ccagtcggga aacctgtcgt gccagctgca ttaatgaatc ggccaacgcg cggggagagg   1260
cggtttgcgt attgggcgct cttccgcttc ctcgctcact gactcgctgc gctcggtcgt   1320
tcggctgcgg cgagcggtat cagctcactc aaaggcggta atacggttat ccacagaatc   1380
aggggataac gcaggaaaga acatgtgagc aaaaggccag caaaaggcca ggaaccgtaa   1440
aaaggccgcg ttgctggcgt ttttccatag gctccgcccc cctgacgagc atcacaaaaa   1500
tcgacgctca agtcagaggt ggcgaaaccc gacaggacta taaagatacc aggcgtttcc   1560
ccctggaagc tccctcgtgc gctctcctgt tccgaccctg ccgcttaccg gatacctgtc   1620
cgcctttctc ccttcgggaa gcgtggcgct ttctcatagc tcacgctgta ggtatctcag   1680
ttcggtgtag gtcgttcgct ccaagctggg ctgtgtgcac gaaccccccg ttcagcccga   1740
ccgctgcgcc ttatccggta actatcgtct tgagtccaac ccggtaagac acgacttatc   1800
gccactggca gcagccactg gtaacaggat tagcagagcg aggtatgtag gcggtgctac   1860
agagttcttg aagtggtggc ctaactacgg ctacactaga aggacagtat ttggtatctg   1920
cgctctgctg aagccagtta ccttcggaaa aagagttggt agctcttgat ccggcaaaca   1980
aaccaccgct ggtagcggtg gtttttttgt ttgcaagcag cagattacgc gcagaaaaaa   2040
aggatctcaa gaagatcctt tgatcttttc tacggggtct gacgctcagt ggaacgaaaa   2100
ctcacgttaa gggattttgg tcatgagatt atcaaaaagg atcttcacct agatcctttt   2160
aaattaaaaa tgaagtttta aatcaatcta aagtatatat gagtaaactt ggtctgacag   2220
ttaccaatgc ttaatcagtg aggcacctat ctcagcgatc tgtctatttc gttcatccat   2280
```

-continued

```
agttgcctga ctccccgtcg tgtagataac tacgatacgg gagggcttac catctggccc   2340
cagtgctgca atgataccgc gagacccacg ctcaccggct ccagatttat cagcaataaa   2400
ccagccagcc ggaagggccg agcgcagaag tggtcctgca actttatccg cctccatcca   2460
gtctattaat tgttgccggg aagctagagt aagtagttcg ccagttaata gtttgcgcaa   2520
cgttgttgcc attgctacag gcatcgtggt gtcacgctcg tcgtttggta tggcttcatt   2580
cagctccggt tcccaacgat caaggcgagt tacatgatcc cccatgttgt gcaaaaaagc   2640
ggttagctcc ttcggtcctc cgatcgttgt cagaagtaag ttggccgcag tgttatcact   2700
catggttatg gcagcactgc ataattctct tactgtcatg ccatccgtaa gatgcttttc   2760
tgtgactggt gagtactcaa ccaagtcatt ctgagaatag tgtatgcggc gaccgagttg   2820
ctcttgcccg gcgtcaatac gggataatac cgcgccacat agcagaactt taaaagtgct   2880
catcattgga aaacgttctt cggggcgaaa actctcaagg atcttaccgc tgttgagatc   2940
cagttcgatg taacccactc gtgcacccaa ctgatcttca gcatctttta ctttcaccag   3000
cgtttctggg tgagcaaaaa caggaaggca aaatgccgca aaaaagggaa taagggcgac   3060
acggaaatgt tgaatactca tactcttcct ttttcaatat tattgaagca tttatcaggg   3120
ttattgtctc atgagcggat acatatttga atgtatttag aaaaataaac aaataggggt   3180
tccgcgcaca tttccccgaa aagtgccacc tgacgcgccc tgtagcggcg cattaagcgc   3240
ggcgggtgtg gtggttacgc gcagcgtgac cgctacactt gccagcgccc tagcgcccgc   3300
tcctttcgct ttcttccctt cctttctcgc cacgttcgcc ggctttcccc gtcaagctct   3360
aaatcggggg ctccctttag ggttccgatt tagtgcttta cggcacctcg accccaaaaa   3420
acttgattag ggtgatggtt cacgtagtgg gccatcgccc tgatagacgg tttttcgccc   3480
tttgacgttg gagtccacgt tctttaatag tggactcttg ttccaaactg gaacaacact   3540
caaccctatc tcggtctatt cttttgattt ataagggatt ttgccgattt cggcctattg   3600
gttaaaaaat gagctgattt aacaaaaatt taacgcgaat tttaacaaaa tattaacgct   3660
tacaatttcc attcgccatt caggctgcgc aactgttggg aagggcgatc ggtgcgggcc   3720
tcttcgctat tacgccagct ggcgaaaggg ggatgtgctg caaggcgatt aagttgggta   3780
acgccagggt tttcccagtc acgacgttgt aaaacgacgg ccagtgaatt gtaatacgac   3840
tcactatagg gcgaattggg taccgggccc cccctcgagg tcgatggtgt cgataagctt   3900
gatatcgaat tcatgtcaca caaaccgatc ttcgcctcaa ggaaacctaa ttctacatcc   3960
gagagactgc cgagatccag tctacactga ttaattttcg ggccaataat ttaaaaaaat   4020
cgtgttatat aatattatat gtattatata tatacatcat gatgatactg acagtcatgt   4080
cccattgcta aatagacaga ctccatctgc cgcctccaac tgatgttctc aatatttaag   4140
gggtcatctc gcattgttta ataataaaca gactccatct accgcctcca aatgatgttc   4200
tcaaaatata ttgtatgaac ttatttttat tacttagtat tattagacaa cttacttgct   4260
ttatgaaaaa cacttcctat ttaggaaaca atttataatg gcagttcgtt catttaacaa   4320
tttatgtaga ataaatgtta taaatgcgta tgggaaatct taaatatgga tagcataaat   4380
gatatctgca ttgcctaatt cgaaatcaac agcaacgaaa aaaatccctt gtacaacata   4440
aatagtcatc gagaaatatc aactatcaaa gaacagctat tcacacgtta ctattgagat   4500
tattattgga cgagaatcac acactcaact gtctttctct cttctagaaa tacaggtaca   4560
agtatgtact attctcattg ttcatacttc tagtcatttc atcccacata ttccttggat   4620
ttctctccaa tgaatgacat tctatcttgc aaattcaaca attataataa gatataccaa   4680
```

-continued

```
agtagcggta tagtggcaat caaaaagctt ctctggtgtg cttctcgtat ttatttttat   4740
tctaatgatc cattaaaggt atatatttat ttcttgttat ataatccttt tgtttattac   4800
atgggctgga tacataaagg tattttgatt taatttttttg cttaaattca atccccccctc   4860
gttcagtgtc aactgtaatg gtaggaaatt accatacttt tgaagaagca aaaaaaatga   4920
aagaaaaaaa aaatcgtatt tccaggttag acgttccgca gaatctagaa tgcggtatgc   4980
ggtacattgt tcttcgaacg taaaagttgc gctccctgag atattgtaca tttttgcttt   5040
tacaagtaca agtacatcgt acaactatgt actactgttg atgcatccac aacagtttgt   5100
tttgtttttt tttgtttttt ttttttctaa tgattcatta ccgctatgta tacctacttg   5160
tacttgtagt aagccgggtt attggcgttc aattaatcat agacttatga atctgcacgg   5220
tgtgcgctgc gagttacttt tagcttatgc atgctacttg ggtgtaatat tgggatctgt   5280
tcggaaatca acggatgctc aatcgatttc gacagtaatt aattaagtca tacacaagtc   5340
agctttcttc gagcctcata taagtataag tagttcaacg tattagcact gtacccagca   5400
tctccgtatc gagaaacaca acaacatgcc ccattggaca gatcatgcgg atacacaggt   5460
tgtgcagtat catacatact cgatcagaca ggtcgtctga ccatcataca agctgaacaa   5520
gcgctccata cttgcacgct ctctatatac acagttaaat tacatatcca tagtctaacc   5580
tctaacagtt aatcttctgg taagcctccc agccagcctt ctggtatcgc ttggcctcct   5640
caataggatc tcggttctgg ccgtacagac ctcggccgac aattatgata tccgttccgg   5700
tagacatgac atcctcaaca gttcggtact gctgtccgag agcgtctccc ttgtcgtcaa   5760
gacccacccc gggggtcaga ataagccagt cctcagagtc gcccttaggt cggttctggg   5820
caatgaagcc aaccacaaac tcggggtcgg atcgggcaag ctcaatggtc tgcttggagt   5880
actcgccagt ggccagagag cccttgcaag acagctcggc cagcatgagc agacctctgg   5940
ccagcttctc gttgggagag gggactagga actccttgta ctgggagttc tcgtagtcag   6000
agacgtcctc cttcttctgt tcagagacag tttcctcggc accagctcgc aggccagcaa   6060
tgattccggt tccgggtaca ccgtgggcgt tggtgatatc ggaccactcg gcgattcggt   6120
gacaccggta ctggtgcttg acagtgttgc caatatctgc gaactttctg tcctcgaaca   6180
ggaagaaacc gtgcttaaga gcaagttcct tgagggggag cacagtgccg gcgtaggtga   6240
agtcgtcaat gatgtcgata tgggttttga tcatgcacac ataaggtccg accttatcgg   6300
caagctcaat gagctccttg gtggtggtaa catccagaga agcacacagg ttggttttct   6360
tggctgccac gagcttgagc actcgagcgg caaaggcgga cttgtggacg ttagctcgag   6420
cttcgtagga gggcattttg gtggtgaaga ggagactgaa ataaatttag tctgcagaac   6480
tttttatcgg aaccttatct ggggcagtga agtatatgtt atggtaatag ttacgagtta   6540
gttgaactta tagatagact ggactatacg gctatcggtc caaattagaa agaacgtcaa   6600
tggctctctg ggcgtcgcct ttgccgacaa aaatgtgatc atgatgaaag ccagcaatga   6660
cgttgcagct gatattgttg tcggccaacc gcgccgaaaa cgcagctgtc agacccacag   6720
cctccaacga agaatgtatc gtcaaagtga tccaagcaca ctcatagttg gagtcgtact   6780
ccaaaggcgg caatgacgag tcagacagat actcgtcgac gtttaaacag tgtacgcaga   6840
tctactatag aggaacattt aaattgcccc ggagaagacg gccaggccgc ctagatgaca   6900
aattcaacaa ctcacagctg actttctgcc attgccacta ggggggggcc tttttatatg   6960
gccaagccaa gctctccacg tcggttgggc tgcacccaac aataaatggg tagggttgca   7020
ccaacaaagg gatgggatgg ggggtagaag atacgaggat aacggggctc aatggcacaa   7080
```

ataagaacga atactgccat taagactcgt gatccagcga ctgacaccat tgcatcatct 7140
aagggcctca aaactacctc ggaactgctg cgctgatctg gacaccacag aggttccgag 7200
cactttaggt tgcaccaaat gtcccaccag gtgcaggcag aaaacgctgg aacagcgtgt 7260
acagtttgtc ttaacaaaaa gtgagggcgc tgaggtcgag cagggtggtg tgacttgtta 7320
tagcctttag agctgcgaaa gcgcgtatgg atttggctca tcaggccaga ttgagggtct 7380
gtggacacat gtcatgttag tgtacttcaa tcgccccctg gatatagccc cgacaatagg 7440
ccgtggcctc atttttttgc cttccgcaca tttccattgc tcgataccca caccttgctt 7500
ctcctgcact tgccaacctt aatactggtt tacattgacc aacatcttac aagcgggggg 7560
cttgtctagg gtatatataa acagtggctc tcccaatcgg ttgccagtct cttttttcct 7620
ttctttcccc acagattcga aatctaaact acacatcaca gaattccgag ccgtgagtat 7680
ccacgacaag atcagtgtcg agacgacgcg ttttgtgtaa tgacacaatc cgaaagtcgc 7740
tagcaacaca cactctctac acaaactaac ccagctctgg tac 7783

<210> SEQ ID NO 46
<211> LENGTH: 7879
<212> TYPE: DNA
<213> ORGANISM: Artificial Sequence
<220> FEATURE:
<223> OTHER INFORMATION: Plasmid pDMW237

<400> SEQUENCE: 46
ggccgcaagt gtggatgggg aagtgagtgc ccggttctgt gtgcacaatt ggcaatccaa 60
gatggatgga ttcaacacag ggatatagcg agctacgtgg tggtgcgagg atatagcaac 120
ggatatttat gtttgacact tgagaatgta cgatacaagc actgtccaag tacaatacta 180
aacatactgt acatactcat actcgtaccc gggcaacggt ttcacttgag tgcagtggct 240
agtgctctta ctcgtacagt gtgcaatact gcgtatcata gtctttgatg tatatcgtat 300
tcattcatgt tagttgcgta cgagccggaa gcataaagtg taaagcctgg ggtgcctaat 360
gagtgagcta actcacatta attgcgttgc gctcactgcc cgctttccag tcgggaaacc 420
tgtcgtgcca gctgcattaa tgaatcggcc aacgcgcggg gagaggcggt ttgcgtattg 480
ggcgctcttc cgcttcctcg ctcactgact cgctgcgctc ggtcgttcgg ctgcggcgag 540
cggtatcagc tcactcaaag gcggtaatac ggttatccac agaatcaggg gataacgcag 600
gaaagaacat gtgagcaaaa ggccagcaaa aggccaggaa ccgtaaaaag gccgcgttgc 660
tggcgttttt ccataggctc cgcccccctg acgagcatca caaaaatcga cgctcaagtc 720
agaggtggcg aaacccgaca ggactataaa gataccaggc gtttccccct ggaagctccc 780
tcgtgcgctc tcctgttccg accctgccgc ttaccggata cctgtccgcc tttctccctt 840
cgggaagcgt ggcgctttct catagctcac gctgtaggta tctcagttcg gtgtaggtcg 900
ttcgctccaa gctgggctgt gtgcacgaac cccccgttca gcccgaccgc tgcgccttat 960
ccggtaacta tcgtcttgag tccaacccgg taagacacga cttatcgcca ctggcagcag 1020
ccactggtaa caggattagc agagcgaggt atgtaggcgg tgctacagag ttcttgaagt 1080
ggtggcctaa ctacggctac actagaagga cagtatttgg tatctgcgct ctgctgaagc 1140
cagttacctt cggaaaaaga gttggtagct cttgatccgg caaacaaacc accgctggta 1200
gcggtggttt ttttgtttgc aagcagcaga ttacgcgcag aaaaaaagga tctcaagaag 1260
atcctttgat cttttctacg gggtctgacg ctcagtggaa cgaaaactca cgttaaggga 1320
ttttggtcat gagattatca aaaaggatct tcacctagat ccttttaaat taaaaatgaa 1380

-continued

```
gttttaaatc aatctaaagt atatatgagt aaacttggtc tgacagttac caatgcttaa   1440
tcagtgaggc acctatctca gcgatctgtc tatttcgttc atccatagtt gcctgactcc   1500
ccgtcgtgta gataactacg atacgggagg gcttaccatc tggccccagt gctgcaatga   1560
taccgcgaga cccacgctca ccggctccag atttatcagc aataaaccag ccagccggaa   1620
gggccgagcg cagaagtggt cctgcaactt tatccgcctc catccagtct attaattgtt   1680
gccgggaagc tagagtaagt agttcgccag ttaatagttt gcgcaacgtt gttgccattg   1740
ctacaggcat cgtggtgtca cgctcgtcgt ttggtatggc ttcattcagc tccggttccc   1800
aacgatcaag gcgagttaca tgatccccca tgttgtgcaa aaaagcggtt agctccttcg   1860
gtcctccgat cgttgtcaga agtaagttgg ccgcagtgtt atcactcatg gttatggcag   1920
cactgcataa ttctcttact gtcatgccat ccgtaagatg cttttctgtg actggtgagt   1980
actcaaccaa gtcattctga gaatagtgta tgcggcgacc gagttgctct tgcccggcgt   2040
caatacggga taataccgcg ccacatagca gaactttaaa agtgctcatc attggaaaac   2100
gttcttcggg gcgaaaactc tcaaggatct taccgctgtt gagatccagt tcgatgtaac   2160
ccactcgtgc acccaactga tcttcagcat cttttacttt caccagcgtt tctgggtgag   2220
caaaaacagg aaggcaaaat gccgcaaaaa agggaataag ggcgacacgg aaatgttgaa   2280
tactcatact cttccttttt caatattatt gaagcattta tcagggttat tgtctcatga   2340
gcggatacat atttgaatgt atttagaaaa ataaacaaat aggggttccg cgcacatttc   2400
cccgaaaagt gccacctgac gcgccctgta gcggcgcatt aagcgcggcg ggtgtggtgg   2460
ttacgcgcag cgtgaccgct acacttgcca gcgccctagc gcccgctcct ttcgctttct   2520
tcccttcctt tctcgccacg ttcgccggct ttccccgtca agctctaaat cgggggctcc   2580
ctttagggtt ccgatttagt gctttacggc acctcgaccc caaaaaactt gattagggtg   2640
atggttcacg tagtgggcca tcgccctgat agacggtttt tcgccctttg acgttggagt   2700
ccacgttctt taatagtgga ctcttgttcc aaactggaac aacactcaac cctatctcgg   2760
tctattcttt tgatttataa gggattttgc cgatttcggc ctattggtta aaaaatgagc   2820
tgatttaaca aaaatttaac gcgaatttta acaaaatatt aacgcttaca atttccattc   2880
gccattcagg ctgcgcaact gttgggaagg gcgatcggtg cgggcctctt cgctattacg   2940
ccagctggcg aaagggggat gtgctgcaag gcgattaagt tgggtaacgc cagggttttc   3000
ccagtcacga cgttgtaaaa cgacggccag tgaattgtaa tacgactcac tatagggcga   3060
attgggtacc gggccccccc tcgaggtcga tggtgtcgat aagcttgata tcgaattcat   3120
gtcacacaaa ccgatcttcg cctcaaggaa acctaattct acatccgaga gactgccgag   3180
atccagtcta cactgattaa ttttcgggcc aataatttaa aaaaatcgtg ttatataata   3240
ttatatgtat tatatatata catcatgatg atactgacag tcatgtccca ttgctaaata   3300
gacagactcc atctgccgcc tccaactgat gttctcaata tttaaggggt catctcgcat   3360
tgtttaataa taaacagact ccatctaccg cctccaaatg atgttctcaa aatatattgt   3420
atgaacttat ttttattact tagtattatt agacaactta cttgctttat gaaaaacact   3480
tcctatttag gaaacaattt ataatggcag ttcgttcatt taacaattta tgtagaataa   3540
atgttataaa tgcgtatggg aaatcttaaa tatggatagc ataaatgata tctgcattgc   3600
ctaattcgaa atcaacagca acgaaaaaaa tcccttgtac aacataaata gtcatcgaga   3660
aatatcaact atcaaagaac agctattcac acgttactat tgagattatt attggacgag   3720
aatcacacac tcaactgtct ttctctcttc tagaaataca ggtacaagta tgtactattc   3780
```

```
tcattgttca tacttctagt catttcatcc cacatattcc ttggatttct ctccaatgaa   3840
tgacattcta tcttgcaaat tcaacaatta taataagata taccaaagta gcggtatagt   3900
ggcaatcaaa aagcttctct ggtgtgcttc tcgtatttat ttttattcta atgatccatt   3960
aaaggtatat atttatttct tgttatataa tccttttgtt tattacatgg gctggataca   4020
taaaggtatt ttgatttaat tttttgctta aattcaatcc cccctcgttc agtgtcaact   4080
gtaatggtag gaaattacca tacttttgaa gaagcaaaaa aaatgaaaga aaaaaaaaat   4140
cgtatttcca ggttagacgt tccgcagaat ctagaatgcg gtatgcggta cattgttctt   4200
cgaacgtaaa agttgcgctc cctgagatat tgtacatttt tgcttttaca agtacaagta   4260
catcgtacaa ctatgtacta ctgttgatgc atccacaaca gtttgttttg tttttttttg   4320
tttttttttt ttctaatgat tcattaccgc tatgtatacc tacttgtact tgtagtaagc   4380
cgggttattg gcgttcaatt aatcatagac ttatgaatct gcacggtgtg cgctgcgagt   4440
tacttttagc ttatgcatgc tacttgggtg taatattggg atctgttcgg aaatcaacgg   4500
atgctcaatc gatttcgaca gtaattaatt aagtcataca caagtcagct ttcttcgagc   4560
ctcatataag tataagtagt tcaacgtatt agcactgtac ccagcatctc cgtatcgaga   4620
aacacaacaa catgccccat tggacagatc atgcggatac acaggttgtg cagtatcata   4680
catactcgat cagacaggtc gtctgaccat catacaagct gaacaagcgc tccatacttg   4740
cacgctctct atatacacag ttaaattaca tatccatagt ctaacctcta acagttaatc   4800
ttctggtaag cctcccagcc agccttctgg tatcgcttgg cctcctcaat aggatctcgg   4860
ttctggccgt acagacctcg gccgacaatt atgatatccg ttccggtaga catgacatcc   4920
tcaacagttc ggtactgctg tccgagagcg tctcccttgt cgtcaagacc caccccgggg   4980
gtcagaataa gccagtcctc agagtcgccc ttaggtcggt tctgggcaat gaagccaacc   5040
acaaactcgg ggtcggatcg ggcaagctca atggtctgct tggagtactc gccagtggcc   5100
agagagccct tgcaagacag ctcggccagc atgagcagac ctctggccag cttctcgttg   5160
ggagagggga ctaggaactc cttgtactgg gagttctcgt agtcagagac gtcctccttc   5220
ttctgttcag agacagtttc ctcggcacca gctcgcaggc cagcaatgat tccggttccg   5280
ggtacaccgt gggcgttggt gatatcggac cactcggcga ttcggtgaca ccggtactgg   5340
tgcttgacag tgttgccaat atctgcgaac tttctgtcct cgaacaggaa gaaaccgtgc   5400
ttaagagcaa gttccttgag ggggagcaca gtgccggcgt aggtgaagtc gtcaatgatg   5460
tcgatatggg ttttgatcat gcacacataa ggtccgacct tatcggcaag ctcaatgagc   5520
tccttggtgg tggtaacatc cagagaagca cacaggttgg ttttcttggc tgccacgagc   5580
ttgagcactc gagcggcaaa ggcggacttg tggacgttag ctcgagcttc gtaggagggc   5640
atttggtgg tgaagaggag actgaaataa atttagtctg cagaactttt tatcggaacc   5700
ttatctgggg cagtgaagta tatgttatgg taatagttac gagttagttg aacttataga   5760
tagactggac tatacggcta tcggtccaaa ttagaaagaa cgtcaatggc tctctgggcg   5820
tcgcctttgc cgacaaaaat gtgatcatga tgaaagccag caatgacgtt gcagctgata   5880
ttgttgtcgg ccaaccgcgc cgaaaacgca gctgtcagac ccacagcctc caacgaagaa   5940
tgtatcgtca aagtgatcca agcacactca tagttggagt cgtactccaa aggcggcaat   6000
gacgagtcag acagatactc gtcgactcag gcgacgacgg aattcctgca gcccatctgc   6060
agaattcagg agagaccggg ttggcggcgt atttgtgtcc caaaaaacag ccccaattgc   6120
cccggagaag acggccaggc cgcctagatg acaaattcaa caactcacag ctgactttct   6180
```

gccattgcca ctagggggg gcctttttat atggccaagc caagctctcc acgtcggttg 6240
ggctgcaccc aacaataaat gggtagggtt gcaccaacaa agggatggga tggggggtag 6300
aagatacgag gataacgggg ctcaatggca caaataagaa cgaatactgc cattaagact 6360
cgtgatccag cgactgacac cattgcatca tctaagggcc tcaaaactac ctcggaactg 6420
ctgcgctgat ctggacacca cagaggttcc gagcacttta ggttgcacca aatgtcccac 6480
caggtgcagg cagaaaacgc tggaacagcg tgtacagttt gtcttaacaa aaagtgaggg 6540
cgctgaggtc gagcagggtg gtgtgacttg ttatagcctt tagagctgcg aaagcgcgta 6600
tggatttggc tcatcaggcc agattgaggg tctgtggaca catgtcatgt tagtgtactt 6660
caatcgcccc ctggatatag ccccgacaat aggccgtggc ctcatttttt tgccttccgc 6720
acatttccat tgctcggtac ccacaccttg cttctcctgc acttgccaac cttaatactg 6780
gtttacattg accaacatct tacaagcggg gggcttgtct agggtatata taaacagtgg 6840
ctctcccaat cggttgccag tctctttttt cctttctttc cccacagatt cgaaatctaa 6900
actacacatc acacaatgcc tgttactgac gtccttaagc gaaagtccgg tgtcatcgtc 6960
ggcgacgatg tccgagccgt gagtatccac gacaagatca gtgtcgagac gacgcgtttt 7020
gtgtaatgac acaatccgaa agtcgctagc aacacacact ctctacacaa actaacccag 7080
ctctccatgg ctctggccaa cgacgctggc gagcgaatct gggctgccgt caccgatccc 7140
gaaatcctca ttggcacctt ctcctacctg ctcctgaagc ctctcctgcg aaactctggt 7200
ctcgtggacg agaagaaagg agcctaccga acctccatga tctggtacaa cgtcctcctg 7260
gctctcttct ctgccctgtc cttctacgtg actgccaccg ctctcggctg ggactacggt 7320
actggagcct ggctgcgaag acagaccggt gatactcccc agcctctctt tcagtgtccc 7380
tctcctgtct gggactccaa gctgttcacc tggactgcca aggccttcta ctattctaag 7440
tacgtggagt acctcgacac cgcttggctg gtcctcaagg gcaagcgagt gtcctttctg 7500
caggccttcc atcactttgg agctccctgg gacgtctacc tcggcattcg actgcacaac 7560
gagggtgtgt ggatcttcat gttctttaac tcgttcattc acaccatcat gtacacctac 7620
tatggactga ctgccgctgg ctacaagttc aaggccaagc ctctgatcac tgccatgcag 7680
atttgccagt tcgtcggtgg ctttctcctg gtctgggact acatcaacgt tccctgcttc 7740
aactctgaca agggcaagct gttctcctgg gctttcaact acgcctacgt cggatctgtc 7800
tttctcctgt tctgtcactt cttttaccag gacaacctgg ccaccaagaa atccgctaag 7860
gctggtaagc agctttagc 7879

<210> SEQ ID NO 47
<211> LENGTH: 8704
<212> TYPE: DNA
<213> ORGANISM: Artificial Sequence
<220> FEATURE:
<223> OTHER INFORMATION: Plasmid pBY1

<400> SEQUENCE: 47
ggccgcaagt gtggatgggg aagtgagtgc ccggttctgt gtgcacaatt ggcaatccaa 60
gatggatgga ttcaacacag ggatatagcg agctacgtgg tggtgcgagg atatagcaac 120
ggatatttat gtttgacact tgagaatgta cgatacaagc actgtccaag tacaatacta 180
aacatactgt acatactcat actcgtaccc gggcaacggt ttcacttgag tgcagtggct 240
agtgctctta ctcgtacagt gtgcaatact gcgtatcata gtctttgatg tatatcgtat 300
tcattcatgt tagttgcgta cgagccggaa gcataaagtg taaagcctgg ggtgcctaat 360

-continued

```
gagtgagcta actcacatta attgcgttgc gctcactgcc cgctttccag tcgggaaacc    420
tgtcgtgcca gctgcattaa tgaatcggcc aacgcgcggg gagaggcggt ttgcgtattg    480
ggcgctcttc cgcttcctcg ctcactgact cgctgcgctc ggtcgttcgg ctgcggcgag    540
cggtatcagc tcactcaaag gcggtaatac ggttatccac agaatcaggg gataacgcag    600
gaaagaacat gtgagcaaaa ggccagcaaa aggccaggaa ccgtaaaaag gccgcgttgc    660
tggcgttttt ccataggctc cgcccccctg acgagcatca caaaaatcga cgctcaagtc    720
agaggtggcg aaacccgaca ggactataaa gataccaggc gtttccccct ggaagctccc    780
tcgtgcgctc tcctgttccg accctgccgc ttaccggata cctgtccgcc tttctccctt    840
cgggaagcgt ggcgctttct catagctcac gctgtaggta tctcagttcg gtgtaggtcg    900
ttcgctccaa gctgggctgt gtgcacgaac cccccgttca gcccgaccgc tgcgccttat    960
ccggtaacta tcgtcttgag tccaacccgg taagacacga cttatcgcca ctggcagcag   1020
ccactggtaa caggattagc agagcgaggt atgtaggcgg tgctacagag ttcttgaagt   1080
ggtggcctaa ctacggctac actagaagga cagtatttgg tatctgcgct ctgctgaagc   1140
cagttacctt cggaaaaaga gttggtagct cttgatccgg caaacaaacc accgctggta   1200
gcggtggttt ttttgtttgc aagcagcaga ttacgcgcag aaaaaaagga tctcaagaag   1260
atcctttgat cttttctacg gggtctgacg ctcagtggaa cgaaaactca cgttaaggga   1320
ttttggtcat gagattatca aaaaggatct tcacctagat ccttttaaat taaaaatgaa   1380
gttttaaatc aatctaaagt atatatgagt aaacttggtc tgacagttac caatgcttaa   1440
tcagtgaggc acctatctca gcgatctgtc tatttcgttc atccatagtt gcctgactcc   1500
ccgtcgtgta gataactacg atacgggagg gcttaccatc tggccccagt gctgcaatga   1560
taccgcgaga cccacgctca ccggctccag atttatcagc aataaaccag ccagccggaa   1620
gggccgagcg cagaagtggt cctgcaactt tatccgcctc catccagtct attaattgtt   1680
gccgggaagc tagagtaagt agttcgccag ttaatagttt gcgcaacgtt gttgccattg   1740
ctacaggcat cgtggtgtca cgctcgtcgt ttggtatggc ttcattcagc tccggttccc   1800
aacgatcaag gcgagttaca tgatccccca tgttgtgcaa aaaagcggtt agctccttcg   1860
gtcctccgat cgttgtcaga agtaagttgg ccgcagtgtt atcactcatg gttatggcag   1920
cactgcataa ttctcttact gtcatgccat ccgtaagatg cttttctgtg actggtgagt   1980
actcaaccaa gtcattctga gaatagtgta tgcggcgacc gagttgctct tgcccggcgt   2040
caatacggga taataccgcg ccacatagca gaactttaaa agtgctcatc attggaaaac   2100
gttcttcggg gcgaaaactc tcaaggatct taccgctgtt gagatccagt tcgatgtaac   2160
ccactcgtgc acccaactga tcttcagcat cttttacttt caccagcgtt tctgggtgag   2220
caaaaacagg aaggcaaaat gccgcaaaaa agggaataag ggcgacacgg aaatgttgaa   2280
tactcatact cttccttttt caatattatt gaagcattta tcagggttat tgtctcatga   2340
gcggatacat atttgaatgt atttagaaaa ataaacaaat aggggttccg cgcacatttc   2400
cccgaaaagt gccacctgac gcgccctgta gcggcgcatt aagcgcggcg ggtgtggtgg   2460
ttacgcgcag cgtgaccgct acacttgcca gcgccctagc gcccgctcct ttcgctttct   2520
tcccttcctt tctcgccacg ttcgccggct ttccccgtca agctctaaat cgggggctcc   2580
ctttagggtt ccgatttagt gctttacggc acctcgaccc caaaaaactt gattagggtg   2640
atggttcacg tagtgggcca tcgccctgat agacggtttt tcgccctttg acgttggagt   2700
ccacgttctt taatagtgga ctcttgttcc aaactggaac aacactcaac cctatctcgg   2760
```

tctattcttt tgatttataa gggattttgc cgatttcggc ctattggtta aaaaatgagc 2820
tgatttaaca aaaatttaac gcgaatttta acaaaatatt aacgcttaca atttccattc 2880
gccattcagg ctgcgcaact gttgggaagg gcgatcggtg cgggcctctt cgctattacg 2940
ccagctggcg aaagggggat gtgctgcaag gcgattaagt tgggtaacgc cagggttttc 3000
ccagtcacga cgttgtaaaa cgacggccag tgaattgtaa tacgactcac tatagggcga 3060
attgggtacc gggccccccc tcgaggtcga tggtgtcgat aagcttgata tcgaattcat 3120
gtcacacaaa ccgatcttcg cctcaaggaa acctaattct acatccgaga gactgccgag 3180
atccagtcta cactgattaa ttttcgggcc aataatttaa aaaaatcgtg ttatataata 3240
ttatatgtat tatatatata catcatgatg atactgacag tcatgtccca ttgctaaata 3300
gacagactcc atctgccgcc tccaactgat gttctcaata tttaaggggt catctcgcat 3360
tgtttaataa taaacagact ccatctaccg cctccaaatg atgttctcaa aatatattgt 3420
atgaacttat ttttattact tagtattatt agacaactta cttgctttat gaaaaacact 3480
tcctatttag gaaacaattt ataatggcag ttcgttcatt taacaattta tgtagaataa 3540
atgttataaa tgcgtatggg aaatcttaaa tatggatagc ataaatgata tctgcattgc 3600
ctaattcgaa atcaacagca acgaaaaaaa tcccttgtac aacataaata gtcatcgaga 3660
aatatcaact atcaaagaac agctattcac acgttactat tgagattatt attggacgag 3720
aatcacacac tcaactgtct ttctctcttc tagaaataca ggtacaagta tgtactattc 3780
tcattgttca tacttctagt catttcatcc cacatattcc ttggatttct ctccaatgaa 3840
tgacattcta tcttgcaaat tcaacaatta taataagata taccaaagta gcggtatagt 3900
ggcaatcaaa aagcttctct ggtgtgcttc tcgtatttat ttttattcta atgatccatt 3960
aaaggtatat atttatttct tgttatataa tccttttgtt tattacatgg gctggataca 4020
taaaggtatt ttgatttaat tttttgctta aattcaatcc cccctcgttc agtgtcaact 4080
gtaatggtag gaaattacca tacttttgaa gaagcaaaaa aaatgaaaga aaaaaaaaat 4140
cgtatttcca ggttagacgt tccgcagaat ctagaatgcg gtatgcggta cattgttctt 4200
cgaacgtaaa agttgcgctc cctgagatat tgtacatttt tgcttttaca agtacaagta 4260
catcgtacaa ctatgtacta ctgttgatgc atccacaaca gtttgttttg ttttttttg 4320 ttttttttt ttctaatgat tcattaccgc tatgtatacc tacttgtact tgtagtaagc 4380
cgggttattg gcgttcaatt aatcatagac ttatgaatct gcacggtgtg cgctgcgagt 4440
tacttttagc ttatgcatgc tacttgggtg taatattggg atctgttcgg aaatcaacgg 4500
atgctcaatc gatttcgaca gtaattaatt aagtcataca caagtcagct ttcttcgagc 4560
ctcatataag tataagtagt tcaacgtatt agcactgtac ccagcatctc cgtatcgaga 4620
aacacaacaa catgccccat tggacagatc atgcggatac acaggttgtg cagtatcata 4680
catactcgat cagacaggtc gtctgaccat catacaagct gaacaagcgc tccatacttg 4740
cacgctctct atatacacag ttaaattaca tatccatagt ctaacctcta acagttaatc 4800
ttctggtaag cctcccagcc agccttctgg tatcgcttgg cctcctcaat aggatctcgg 4860
ttctggccgt acagacctcg gccgacaatt atgatatccg ttccggtaga catgacatcc 4920
tcaacagttc ggtactgctg tccgagagcg tctcccttgt cgtcaagacc caccccgggg 4980
gtcagaataa gccagtcctc agagtcgccc ttaggtcggt tctgggcaat gaagccaacc 5040
acaaactcgg ggtcggatcg ggcaagctca atggtctgct tggagtactc gccagtggcc 5100
agagagccct tgcaagacag ctcggccagc atgagcagac ctctggccag cttctcgttg 5160

-continued

```
ggagagggga ctaggaactc cttgtactgg gagttctcgt agtcagagac gtcctccttc   5220
ttctgttcag agacagtttc ctcggcacca gctcgcaggc cagcaatgat tccggttccg   5280
ggtacaccgt gggcgttggt gatatcggac cactcggcga ttcggtgaca ccggtactgg   5340
tgcttgacag tgttgccaat atctgcgaac tttctgtcct cgaacaggaa gaaaccgtgc   5400
ttaagagcaa gttccttgag ggggagcaca gtgccggcgt aggtgaagtc gtcaatgatg   5460
tcgatatggg ttttgatcat gcacacataa ggtccgacct tatcggcaag ctcaatgagc   5520
tccttggtgg tggtaacatc cagagaagca cacaggttgg ttttcttggc tgccacgagc   5580
ttgagcactc gagcggcaaa ggcggacttg tggacgttag ctcgagcttc gtaggagggc   5640
atttggtgg tgaagaggag actgaaataa atttagtctg cagaactttt tatcggaacc    5700
ttatctgggg cagtgaagta tatgttatgg taatagttac gagttagttg aacttataga   5760
tagactggac tatacggcta tcggtccaaa ttagaaagaa cgtcaatggc tctctgggcg   5820
tcgcctttgc cgacaaaaat gtgatcatga tgaaagccag caatgacgtt gcagctgata   5880
ttgttgtcgg ccaaccgcgc cgaaaacgca gctgtcagac ccacagcctc caacgaagaa   5940
tgtatcgtca aagtgatcca agcacactca tagttggagt cgtactccaa aggcggcaat   6000
gacgagtcag acagatactc gtcgacgttt aaacagtgta cgcagatcta ctatagagga   6060
acatttaaat tgccccggag aagacggcca ggccgcctag atgacaaatt caacaactca   6120
cagctgactt tctgccattg ccactagggg ggggcctttt tatatggcca agccaagctc   6180
tccacgtcgg ttgggctgca cccaacaata aatgggtagg gttgcaccaa caaagggatg   6240
ggatgggggg tagaagatac gaggataacg gggctcaatg gcacaaataa gaacgaatac   6300
tgccattaag actcgtgatc cagcgactga caccattgca tcatctaagg gcctcaaaac   6360
tacctcggaa ctgctgcgct gatctggaca ccacagaggt tccgagcact ttaggttgca   6420
ccaaatgtcc caccaggtgc aggcagaaaa cgctggaaca gcgtgtacag tttgtcttaa   6480
caaaaagtga gggcgctgag gtcgagcagg gtggtgtgac ttgttatagc ctttagagct   6540
gcgaaagcgc gtatggattt ggctcatcag gccagattga gggtctgtgg acacatgtca   6600
tgttagtgta cttcaatcgc cccctggata tagccccgac aataggccgt ggcctcattt   6660
ttttgccttc cgcacatttc cattgctcga tacccacacc ttgcttctcc tgcacttgcc   6720
aaccttaata ctggtttaca ttgaccaaca tcttacaagc ggggggcttg tctagggtat   6780
atataaacag tggctctccc aatcggttgc cagtctcttt tttcctttct ttccccacag   6840
attcgaaatc taaactacac atcacagaat tccgagccgt gagtatccac gacaagatca   6900
gtgtcgagac gacgcgtttt gtgtaatgac acaatccgaa agtcgctagc aacacacact   6960
ctctacacaa actaacccag ctctggtacc atgatcacaa gtttgtacaa aaaagctgaa   7020
cgagaaacgt aaaatgatat aaatatcaat atattaaatt agattttgca taaaaaacag   7080
actacataat actgtaaaac acaacatatc cagtcatatt ggcggccgca ttaggcaccc   7140
caggctttac actttatgct tccggctcgt ataatgtgtg gattttgagt taggatccgt   7200
cgagattttc aggagctaag gaagctaaaa tggagaaaaa aatcactgga tataccaccg   7260
ttgatatatc ccaatggcat cgtaaagaac attttgaggc atttcagtca gttgctcaat   7320
gtacctataa ccagaccgtt cagctggata ttacggcctt tttaaagacc gtaaagaaaa   7380
ataagcacaa gttttatccg gcctttattc acattcttgc ccgcctgatg aatgctcatc   7440
cggaattccg tatggcaatg aaagacggtg agctggtgat atgggatagt gttcaccctt   7500
gttacaccgt tttccatgag caaactgaaa cgttttcatc gctctggagt gaataccacg   7560
```

acgatttccg gcagtttcta cacatatatt cgcaagatgt ggcgtgttac ggtgaaaacc 7620
tggcctattt ccctaaaggg tttattgaga atatgttttt cgtctcagcc aatccctggg 7680
tgagtttcac cagttttgat ttaaacgtgg ccaatatgga caacttcttc gcccccgttt 7740
tcaccatggg caaatattat acgcaaggcg acaaggtgct gatgccgctg gcgattcagg 7800
ttcatcatgc cgtttgtgat ggcttccatg tcggcagaat gcttaatgaa ttacaacagt 7860
actgcgatga gtggcagggc ggggcgtaaa cgcgtggatc cggcttacta aaagccagat 7920
aacagtatgc gtatttgcgc gctgattttt gcggtataag aatatatact gatatgtata 7980
cccgaagtat gtcaaaaaga ggtatgctat gaagcagcgt attacagtga cagttgacag 8040
cgacagctat cagttgctca aggcatatat gatgtcaata tctccggtct ggtaagcaca 8100
accatgcaga atgaagcccg tcgtctgcgt gccgaacgct ggaaagcgga aaatcaggaa 8160
gggatggctg aggtcgcccg gtttattgaa atgaacggct cttttgctga cgagaacagg 8220
ggctggtgaa atgcagttta aggtttacac ctataaaaga gagagccgtt atcgtctgtt 8280
tgtggatgta cagagtgata ttattgacac gcccgggcga cggatggtga tccccctggc 8340
cagtgcacgt ctgctgtcag ataaagtctc ccgtgaactt tacccggtgg tgcatatcgg 8400
ggatgaaagc tggcgcatga tgaccaccga tatggccagt gtgccggtct ccgttatcgg 8460
ggaagaagtg gctgatctca gccaccgcga aaatgacatc aaaaacgcca ttaacctgat 8520
gttctgggga atataaatgt caggctccct tatacacagc cagtctgcag gtcgaccata 8580
gtgactggat atgttgtgtt ttacagcatt atgtagtctg tttttatgc aaaatctaat 8640 ttaatatatt gatatttata tcattttacg tttctcgttc agctttcttg tacaaagtgg 8700
tgat 8704

<210> SEQ ID NO 48
<211> LENGTH: 8145
<212> TYPE: DNA
<213> ORGANISM: Artificial Sequence
<220> FEATURE:
<223> OTHER INFORMATION: Plasmid pBY2
<220> FEATURE:
<221> NAME/KEY: misc_feature
<222> LOCATION: (8028)..(8031)
<223> OTHER INFORMATION: n is a, c, g, or t
<220> FEATURE:
<221> NAME/KEY: misc_feature
<222> LOCATION: (8063)..(8065)
<223> OTHER INFORMATION: n is a, c, g, or t
<220> FEATURE:
<221> NAME/KEY: misc_feature
<222> LOCATION: (8067)..(8069)
<223> OTHER INFORMATION: n is a, c, g, or t
<220> FEATURE:
<221> NAME/KEY: misc_feature
<222> LOCATION: (8071)..(8073)
<223> OTHER INFORMATION: n is a, c, g, or t
<220> FEATURE:
<221> NAME/KEY: misc_feature
<222> LOCATION: (8075)..(8075)
<223> OTHER INFORMATION: n is a, c, g, or t
<220> FEATURE:
<221> NAME/KEY: misc_feature
<222> LOCATION: (8126)..(8135)
<223> OTHER INFORMATION: n is a, c, g, or t

<400> SEQUENCE: 48
cttgtacaaa gtggtgatgg ccgcaagtgt ggatggggaa gtgagtgccc ggttctgtgt 60
gcacaattgg caatccaaga tggatggatt caacacaggg atatagcgag ctacgtggtg 120
gtgcgaggat atagcaacgg atatttatgt ttgacacttg agaatgtacg atacaagcac 180
tgtccaagta caatactaaa catactgtac atactcatac tcgtacccgg gcaacggttt 240
cacttgagtg cagtggctag tgctcttact cgtacagtgt gcaatactgc gtatcatagt 300
ctttgatgta tatcgtattc attcatgtta gttgcgtacg agccggaagc ataaagtgta 360
aagcctgggg tgcctaatga gtgagctaac tcacattaat tgcgttgcgc tcactgcccg 420
ctttccagtc gggaaacctg tcgtgccagc tgcattaatg aatcggccaa cgcgcgggga 480
gaggcggttt gcgtattggg cgctcttccg cttcctcgct cactgactcg ctgcgctcgg 540
tcgttcggct gcggcgagcg gtatcagctc actcaaaggc ggtaatacgg ttatccacag 600
aatcagggga taacgcagga aagaacatgt gagcaaaagg ccagcaaaag gccaggaacc 660
gtaaaaaggc cgcgttgctg gcgtttttcc ataggctccg cccccctgac gagcatcaca 720
aaaatcgacg ctcaagtcag aggtggcgaa acccgacagg actataaaga taccaggcgt 780
ttccccctgg aagctccctc gtgcgctctc ctgttccgac cctgccgctt accggatacc 840
tgtccgcctt tctcccttcg ggaagcgtgg cgctttctca tagctcacgc tgtaggtatc 900
tcagttcggt gtaggtcgtt cgctccaagc tgggctgtgt gcacgaaccc cccgttcagc 960
ccgaccgctg cgccttatcc ggtaactatc gtcttgagtc caacccggta agacacgact 1020
tatcgccact ggcagcagcc actggtaaca ggattagcag agcgaggtat gtaggcggtg 1080
ctacagagtt cttgaagtgg tggcctaact acggctacac tagaaggaca gtatttggta 1140
tctgcgctct gctgaagcca gttaccttcg gaaaaagagt tggtagctct tgatccggca 1200
aacaaaccac cgctggtagc ggtggttttt ttgtttgcaa gcagcagatt acgcgcagaa 1260
aaaaaggatc tcaagaagat cctttgatct tttctacggg gtctgacgct cagtggaacg 1320
aaaactcacg ttaagggatt ttggtcatga gattatcaaa aaggatcttc acctagatcc 1380
ttttaaatta aaaatgaagt tttaaatcaa tctaaagtat atatgagtaa acttggtctg 1440
acagttacca atgcttaatc agtgaggcac ctatctcagc gatctgtcta tttcgttcat 1500
ccatagttgc ctgactcccc gtcgtgtaga taactacgat acgggagggc ttaccatctg 1560
gccccagtgc tgcaatgata ccgcgagacc cacgctcacc ggctccagat ttatcagcaa 1620
taaaccagcc agccggaagg gccgagcgca gaagtggtcc tgcaacttta tccgcctcca 1680
tccagtctat taattgttgc cgggaagcta gagtaagtag ttcgccagtt aatagtttgc 1740
gcaacgttgt tgccattgct acaggcatcg tggtgtcacg ctcgtcgttt ggtatggctt 1800
cattcagctc cggttcccaa cgatcaaggc gagttacatg atcccccatg ttgtgcaaaa 1860
aagcggttag ctccttcggt cctccgatcg ttgtcagaag taagttggcc gcagtgttat 1920
cactcatggt tatggcagca ctgcataatt ctcttactgt catgccatcc gtaagatgct 1980
tttctgtgac tggtgagtac tcaaccaagt cattctgaga atagtgtatg cggcgaccga 2040
gttgctcttg cccggcgtca atacgggata ataccgcgcc acatagcaga actttaaaag 2100
tgctcatcat tggaaaacgt tcttcggggc gaaaactctc aaggatctta ccgctgttga 2160
gatccagttc gatgtaaccc actcgtgcac ccaactgatc ttcagcatct tttactttca 2220
ccagcgtttc tgggtgagca aaaacaggaa ggcaaaatgc cgcaaaaaag ggaataaggg 2280
cgacacggaa atgttgaata ctcatactct tcctttttca atattattga agcatttatc 2340
agggttattg tctcatgagc ggatacatat ttgaatgtat ttagaaaaat aaacaaatag 2400
gggttccgcg cacatttccc cgaaaagtgc cacctgacgc gccctgtagc ggcgcattaa 2460
gcgcggcggg tgtggtggtt acgcgcagcg tgaccgctac acttgccagc gccctagcgc 2520
ccgctccttt cgctttcttc ccttcctttc tcgccacgtt cgccggcttt ccccgtcaag 2580

```
ctctaaatcg ggggctccct ttagggttcc gatttagtgc tttacggcac ctcgacccca   2640
aaaaacttga ttagggtgat ggttcacgta gtgggccatc gccctgatag acggtttttc   2700
gccctttgac gttggagtcc acgttcttta atagtggact cttgttccaa actggaacaa   2760
cactcaaccc tatctcggtc tattcttttg atttataagg gattttgccg atttcggcct   2820
attggttaaa aaatgagctg atttaacaaa aatttaacgc gaattttaac aaaatattaa   2880
cgcttacaat ttccattcgc cattcaggct gcgcaactgt tgggaagggc gatcggtgcg   2940
ggcctcttcg ctattacgcc agctggcgaa agggggatgt gctgcaaggc gattaagttg   3000
ggtaacgcca gggttttccc agtcacgacg ttgtaaaacg acggccagtg aattgtaata   3060
cgactcacta tagggcgaat tgggtaccgg gccccccctc gaggtcgatg gtgtcgataa   3120
gcttgatatc gaattcatgt cacacaaacc gatcttcgcc tcaaggaaac ctaattctac   3180
atccgagaga ctgccgagat ccagtctaca ctgattaatt ttcgggccaa taatttaaaa   3240
aaatcgtgtt atataatatt atatgtatta tatatataca tcatgatgat actgacagtc   3300
atgtcccatt gctaaataga cagactccat ctgccgcctc caactgatgt tctcaatatt   3360
taaggggtca tctcgcattg tttaataata aacagactcc atctaccgcc tccaaatgat   3420
gttctcaaaa tatattgtat gaacttattt ttattactta gtattattag acaacttact   3480
tgctttatga aaaacacttc ctatttagga aacaatttat aatggcagtt cgttcattta   3540
acaatttatg tagaataaat gttataaatg cgtatgggaa atcttaaata tggatagcat   3600
aaatgatatc tgcattgcct aattcgaaat caacagcaac gaaaaaaatc ccttgtacaa   3660
cataaatagt catcgagaaa tatcaactat caaagaacag ctattcacac gttactattg   3720
agattattat tggacgagaa tcacacactc aactgtcttt ctctcttcta gaaatacagg   3780
tacaagtatg tactattctc attgttcata cttctagtca tttcatccca catattcctt   3840
ggatttctct ccaatgaatg acattctatc ttgcaaattc aacaattata ataagatata   3900
ccaaagtagc ggtatagtgg caatcaaaaa gcttctctgg tgtgcttctc gtatttattt   3960
ttattctaat gatccattaa aggtatatat ttatttcttg ttatataatc cttttgttta   4020
ttacatgggc tggatacata aaggtatttt gatttaattt tttgcttaaa ttcaatcccc   4080
cctcgttcag tgtcaactgt aatggtagga aattaccata cttttgaaga agcaaaaaaa   4140
atgaaagaaa aaaaaaatcg tatttccagg ttagacgttc cgcagaatct agaatgcggt   4200
atgcggtaca ttgttcttcg aacgtaaaag ttgcgctccc tgagatattg tacatttttg   4260
cttttacaag tacaagtaca tcgtacaact atgtactact gttgatgcat ccacaacagt   4320
ttgttttgtt ttttttgtt ttttttttt ctaatgattc attaccgcta tgtataccta   4380
cttgtacttg tagtaagccg ggttattggc gttcaattaa tcatagactt atgaatctgc   4440
acggtgtgcg ctgcgagtta cttttagctt atgcatgcta cttgggtgta atattgggat   4500
ctgttcggaa atcaacggat gctcaatcga tttcgacagt aattaattaa gtcatacaca   4560
agtcagcttt cttcgagcct catataagta taagtagttc aacgtattag cactgtaccc   4620
agcatctccg tatcgagaaa cacaacaaca tgccccattg gacagatcat gcggatacac   4680
aggttgtgca gtatcataca tactcgatca gacaggtcgt ctgaccatca tacaagctga   4740
acaagcgctc catacttgca cgctctctat atacacagtt aaattacata tccatagtct   4800
aacctctaac agttaatctt ctggtaagcc tcccagccag ccttctggta tcgcttggcc   4860
tcctcaatag gatctcggtt ctggccgtac agacctcggc cgacaattat gatatccgtt   4920
ccggtagaca tgacatcctc aacagttcgg tactgctgtc cgagagcgtc tcccttgtcg   4980
```

-continued

```
tcaagaccca ccccgggggt cagaataagc cagtcctcag agtcgccctt aggtcggttc   5040
tgggcaatga agccaaccac aaactcgggg tcggatcggg caagctcaat ggtctgcttg   5100
gagtactcgc cagtggccag agagcccttg caagacagct cggccagcat gagcagacct   5160
ctggccagct tctcgttggg agaggggact aggaactcct tgtactggga gttctcgtag   5220
tcagagacgt cctccttctt ctgttcagag acagtttcct cggcaccagc tcgcaggcca   5280
gcaatgattc cggttccggg tacaccgtgg gcgttggtga tatcggacca ctcggcgatt   5340
cggtgacacc ggtactggtg cttgacagtg ttgccaatat ctgcgaactt tctgtcctcg   5400
aacaggaaga aaccgtgctt aagagcaagt tccttgaggg ggagcacagt gccggcgtag   5460
gtgaagtcgt caatgatgtc gatatgggtt ttgatcatgc acacataagg tccgacctta   5520
tcggcaagct caatgagctc cttggtggtg gtaacatcca gagaagcaca caggttggtt   5580
ttcttggctg ccacgagctt gagcactcga gcggcaaagg cggacttgtg gacgttagct   5640
cgagcttcgt aggagggcat tttggtggtg aagaggagac tgaaataaat ttagtctgca   5700
gaacttttta tcggaacctt atctggggca gtgaagtata tgttatggta atagttacga   5760
gttagttgaa cttatagata gactggacta tacggctatc ggtccaaatt agaaagaacg   5820
tcaatggctc tctgggcgtc gcctttgccg acaaaaatgt gatcatgatg aaagccagca   5880
atgacgttgc agctgatatt gttgtcggcc aaccgcgccg aaaacgcagc tgtcagaccc   5940
acagcctcca acgaagaatg tatcgtcaaa gtgatccaag cacactcata gttggagtcg   6000
tactccaaag gcggcaatga cgagtcagac agatactcgt cgacgtttaa acagtgtacg   6060
cagatctact atagaggaac atttaaattg ccccggagaa gacggccagg ccgcctagat   6120
gacaaattca acaactcaca gctgactttc tgccattgcc actagggggg ggccttttta   6180
tatggccaag ccaagctctc cacgtcggtt gggctgcacc caacaataaa tgggtagggt   6240
tgcaccaaca aagggatggg atgggggta gaagatacga ggataacggg gctcaatggc   6300
acaaataaga acgaatactg ccattaagac tcgtgatcca gcgactgaca ccattgcatc   6360
atctaagggc ctcaaaacta cctcggaact gctgcgctga tctggacacc acagaggttc   6420
cgagcacttt aggttgcacc aaatgtccca ccaggtgcag gcagaaaacg ctggaacagc   6480
gtgtacagtt tgtcttaaca aaaagtgagg gcgctgaggt cgagcagggt ggtgtgactt   6540
gttatagcct ttagagctgc gaaagcgcgt atggatttgg ctcatcaggc cagattgagg   6600
gtctgtggac acatgtcatg ttagtgtact tcaatcgccc cctggatata gccccgacaa   6660
taggccgtgg cctcattttt ttgccttccg cacatttcca ttgctcgata cccacacctt   6720
gcttctcctg cacttgccaa ccttaatact ggtttacatt gaccaacatc ttacaagcgg   6780
ggggcttgtc tagggtatat ataaacagtg gctctcccaa tcggttgcca gtctcttttt   6840
tcctttcttt ccccacagat tcgaaatcta aactacacat cacagaattc cgagccgtga   6900
gtatccacga caagatcagt gtcgagacga cgcgttttgt gtaatgacac aatccgaaag   6960
tcgctagcaa cacacactct ctacacaaac taacccagct ctggtaccat gatcacaagt   7020
ttgtacaaaa aagttggatt ttttttcgaa cacttaatgg aggtggtgaa tgaaatagtc   7080
tcaattgggc aggaagtttt acccaaagtt gattatgccc aactctggag tgatgccagt   7140
cactgtgagg tgctttactt gtccatcgca tttgtcatct tgaagttcac tcttggcccc   7200
cttggtccaa aaggtcagtc tcgtatgaag tttgttttca ccaattacaa ccttctcatg   7260
tccatttatt cgttgggatc attcctctca atggcatatg ccatgtacac catcggtgtt   7320
atgtctgaca actgcgagaa ggcttttgac aacaacgtct tcaggatcac cacgcagttg   7380
```

ttctatttga gcaagttcct ggagtatatt gactccttct atttgccact gatgggcaag 7440
cctctgacct ggttgcaatt cttccatcat ttgggggcac cgatggatat gtggctgttc 7500
tataattacc gaaatgaagc tgtttggatt tttgtgctgt tgaatggttt catccactgg 7560
atcatgtacg gttattattg gaccagattg atcaagctga agttccccat gccaaaatcc 7620
ctgattacat caatgcagat cattcaattc aatgttggtt tctacattgt ctggaagtac 7680
aggaacattc cctgttatcg ccaagatggg atgaggatgt ttggctggtt cttcaattac 7740
ttttatgttg gcacagtctt gtgtttgttc ttgaatttct atgtgcaaac gtatatcgtc 7800
aggaagcaca agggagccaa aaagattcag tgatatttcc tcctctgcgg tggcctcttt 7860
tgacctcccc ttgacaccta taatgtggag gtgtcgggct ctctccgtct caccagcact 7920
tgactctgca ggtgctcact tttatttttt acccatcttt gcttgttgac cattcacctc 7980
tcccacttcc acatagtcca ttctaactgt tgcagactgc ggtccatnnn ntccagagct 8040
cccaatgacc atacgcgaca ccnnntnnna nnncngccca ttgtgcacaa ttcatagtgg 8100
catcgttttg ccttgatacg tgtgcnnnnn nnnnnaccca acttt 8145

<210> SEQ ID NO 49
<211> LENGTH: 31
<212> TYPE: DNA
<213> ORGANISM: Artificial Sequence
<220> FEATURE:
<223> OTHER INFORMATION: Primer ig-s

<400> SEQUENCE: 49
caccatggct ctggccaacg acgctggcga g 31

<210> SEQ ID NO 50
<211> LENGTH: 26
<212> TYPE: DNA
<213> ORGANISM: Artificial Sequence
<220> FEATURE:
<223> OTHER INFORMATION: Primer ig-as

<400> SEQUENCE: 50
ctaaagctgc ttaccagcct tagcgg 26

<210> SEQ ID NO 51
<211> LENGTH: 7877
<212> TYPE: DNA
<213> ORGANISM: Artificial Sequence
<220> FEATURE:
<223> OTHER INFORMATION: Plasmid pBY1-FAE

<400> SEQUENCE: 51
cttgtacaaa gtggtgatgg ccgcaagtgt ggatggggaa gtgagtgccc ggttctgtgt 60
gcacaattgg caatccaaga tggatggatt caacacaggg atatagcgag ctacgtggtg 120
gtgcgaggat atagcaacgg atatttatgt ttgacacttg agaatgtacg atacaagcac 180
tgtccaagta caatactaaa catactgtac atactcatac tcgtacccgg gcaacggttt 240
cacttgagtg cagtggctag tgctcttact cgtacagtgt gcaatactgc gtatcatagt 300
ctttgatgta tatcgtattc attcatgtta gttgcgtacg agccggaagc ataaagtgta 360
aagcctgggg tgcctaatga gtgagctaac tcacattaat tgcgttgcgc tcactgcccg 420
ctttccagtc gggaaacctg tcgtgccagc tgcattaatg aatcggccaa cgcgcgggga 480
gaggcggttt gcgtattggg cgctcttccg cttcctcgct cactgactcg ctgcgctcgg 540
tcgttcggct gcggcgagcg gtatcagctc actcaaaggc ggtaatacgg ttatccacag 600
aatcagggga taacgcagga aagaacatgt gagcaaaagg ccagcaaaag gccaggaacc 660
gtaaaaaggc cgcgttgctg gcgtttttcc ataggctccg cccccctgac gagcatcaca 720
aaaatcgacg ctcaagtcag aggtggcgaa acccgacagg actataaaga taccaggcgt 780
ttccccctgg aagctccctc gtgcgctctc ctgttccgac cctgccgctt accggatacc 840
tgtccgcctt tctcccttcg ggaagcgtgg cgctttctca tagctcacgc tgtaggtatc 900
tcagttcggt gtaggtcgtt cgctccaagc tgggctgtgt gcacgaaccc cccgttcagc 960
ccgaccgctg cgccttatcc ggtaactatc gtcttgagtc caacccggta agacacgact 1020
tatcgccact ggcagcagcc actggtaaca ggattagcag agcgaggtat gtaggcggtg 1080
ctacagagtt cttgaagtgg tggcctaact acggctacac tagaaggaca gtatttggta 1140
tctgcgctct gctgaagcca gttaccttcg gaaaaagagt tggtagctct tgatccggca 1200
aacaaaccac cgctggtagc ggtggttttt ttgtttgcaa gcagcagatt acgcgcagaa 1260
aaaaaggatc tcaagaagat cctttgatct tttctacggg gtctgacgct cagtggaacg 1320
aaaactcacg ttaagggatt ttggtcatga gattatcaaa aaggatcttc acctagatcc 1380
ttttaaatta aaaatgaagt tttaaatcaa tctaaagtat atatgagtaa acttggtctg 1440
acagttacca atgcttaatc agtgaggcac ctatctcagc gatctgtcta tttcgttcat 1500
ccatagttgc ctgactcccc gtcgtgtaga taactacgat acgggagggc ttaccatctg 1560
gccccagtgc tgcaatgata ccgcgagacc cacgctcacc ggctccagat ttatcagcaa 1620
taaaccagcc agccggaagg gccgagcgca gaagtggtcc tgcaacttta tccgcctcca 1680
tccagtctat taattgttgc cgggaagcta gagtaagtag ttcgccagtt aatagtttgc 1740
gcaacgttgt tgccattgct acaggcatcg tggtgtcacg ctcgtcgttt ggtatggctt 1800
cattcagctc cggttcccaa cgatcaaggc gagttacatg atcccccatg ttgtgcaaaa 1860
aagcggttag ctccttcggt cctccgatcg ttgtcagaag taagttggcc gcagtgttat 1920
cactcatggt tatggcagca ctgcataatt ctcttactgt catgccatcc gtaagatgct 1980
tttctgtgac tggtgagtac tcaaccaagt cattctgaga atagtgtatg cggcgaccga 2040
gttgctcttg cccggcgtca atacgggata ataccgcgcc acatagcaga actttaaaag 2100
tgctcatcat tggaaaacgt tcttcggggc gaaaactctc aaggatctta ccgctgttga 2160
gatccagttc gatgtaaccc actcgtgcac ccaactgatc ttcagcatct tttactttca 2220
ccagcgtttc tgggtgagca aaaacaggaa ggcaaaatgc cgcaaaaaag ggaataaggg 2280
cgacacggaa atgttgaata ctcatactct tcctttttca atattattga agcatttatc 2340
agggttattg tctcatgagc ggatacatat ttgaatgtat ttagaaaaat aaacaaatag 2400
gggttccgcg cacatttccc cgaaaagtgc cacctgacgc gccctgtagc ggcgcattaa 2460
gcgcggcggg tgtggtggtt acgcgcagcg tgaccgctac acttgccagc gccctagcgc 2520
ccgctccttt cgctttcttc ccttcctttc tcgccacgtt cgccggcttt ccccgtcaag 2580
ctctaaatcg ggggctccct ttagggttcc gatttagtgc tttacggcac ctcgacccca 2640
aaaaacttga ttagggtgat ggttcacgta gtgggccatc gccctgatag acggtttttc 2700
gccctttgac gttggagtcc acgttcttta atagtggact cttgttccaa actggaacaa 2760
cactcaaccc tatctcggtc tattcttttg atttataagg gattttgccg atttcggcct 2820
attggttaaa aaatgagctg atttaacaaa aatttaacgc gaattttaac aaaatattaa 2880
cgcttacaat ttccattcgc cattcaggct gcgcaactgt tgggaagggc gatcggtgcg 2940
ggcctcttcg ctattacgcc agctggcgaa agggggatgt gctgcaaggc gattaagttg 3000
ggtaacgcca gggttttccc agtcacgacg ttgtaaaacg acggccagtg aattgtaata 3060
cgactcacta tagggcgaat tgggtaccgg gccccccctc gaggtcgatg gtgtcgataa 3120
gcttgatatc gaattcatgt cacacaaacc gatcttcgcc tcaaggaaac ctaattctac 3180
atccgagaga ctgccgagat ccagtctaca ctgattaatt ttcgggccaa taatttaaaa 3240
aaatcgtgtt atataatatt atatgtatta tatatataca tcatgatgat actgacagtc 3300
atgtcccatt gctaaataga cagactccat ctgccgcctc caactgatgt tctcaatatt 3360
taaggggtca tctcgcattg tttaataata aacagactcc atctaccgcc tccaaatgat 3420
gttctcaaaa tatattgtat gaacttattt ttattactta gtattattag acaacttact 3480
tgctttatga aaaacacttc ctatttagga aacaatttat aatggcagtt cgttcattta 3540
acaatttatg tagaataaat gttataaatg cgtatgggaa atcttaaata tggatagcat 3600
aaatgatatc tgcattgcct aattcgaaat caacagcaac gaaaaaaatc ccttgtacaa 3660
cataaatagt catcgagaaa tatcaactat caaagaacag ctattcacac gttactattg 3720
agattattat tggacgagaa tcacacactc aactgtcttt ctctcttcta gaaatacagg 3780
tacaagtatg tactattctc attgttcata cttctagtca tttcatccca catattcctt 3840
ggatttctct ccaatgaatg acattctatc ttgcaaattc aacaattata ataagatata 3900
ccaaagtagc ggtatagtgg caatcaaaaa gcttctctgg tgtgcttctc gtatttattt 3960
ttattctaat gatccattaa aggtatatat ttatttcttg ttatataatc cttttgttta 4020
ttacatgggc tggatacata aaggtatttt gatttaattt tttgcttaaa ttcaatcccc 4080
cctcgttcag tgtcaactgt aatggtagga aattaccata cttttgaaga agcaaaaaaa 4140
atgaaagaaa aaaaaaatcg tatttccagg ttagacgttc cgcagaatct agaatgcggt 4200
atgcggtaca ttgttcttcg aacgtaaaag ttgcgctccc tgagatattg tacatttttg 4260
cttttacaag tacaagtaca tcgtacaact atgtactact gttgatgcat ccacaacagt 4320
ttgttttgtt ttttttgtt ttttttttt ctaatgattc attaccgcta tgtataccta 4380
cttgtacttg tagtaagccg ggttattggc gttcaattaa tcatagactt atgaatctgc 4440
acggtgtgcg ctgcgagtta cttttagctt atgcatgcta cttgggtgta atattgggat 4500
ctgttcggaa atcaacggat gctcaatcga tttcgacagt aattaattaa gtcatacaca 4560
agtcagcttt cttcgagcct catataagta taagtagttc aacgtattag cactgtaccc 4620
agcatctccg tatcgagaaa cacaacaaca tgccccattg gacagatcat gcggatacac 4680
aggttgtgca gtatcataca tactcgatca gacaggtcgt ctgaccatca tacaagctga 4740
acaagcgctc catacttgca cgctctctat atacacagtt aaattacata tccatagtct 4800
aacctctaac agttaatctt ctggtaagcc tcccagccag ccttctggta tcgcttggcc 4860
tcctcaatag gatctcggtt ctggccgtac agacctcggc cgacaattat gatatccgtt 4920
ccggtagaca tgacatcctc aacagttcgg tactgctgtc cgagagcgtc tcccttgtcg 4980
tcaagaccca ccccgggggt cagaataagc cagtcctcag agtcgccctt aggtcggttc 5040
tgggcaatga agccaaccac aaactcgggg tcggatcggg caagctcaat ggtctgcttg 5100
gagtactcgc cagtggccag agagcccttg caagacagct cggccagcat gagcagacct 5160
ctggccagct tctcgttggg agaggggact aggaactcct tgtactggga gttctcgtag 5220
tcagagacgt cctccttctt ctgttcagag acagtttcct cggcaccagc tcgcaggcca 5280
gcaatgattc cggttccggg tacaccgtgg gcgttggtga tatcggacca ctcggcgatt 5340
cggtgacacc ggtactggtg cttgacagtg ttgccaatat ctgcgaactt tctgtcctcg 5400
aacaggaaga aaccgtgctt aagagcaagt tccttgaggg ggagcacagt gccggcgtag 5460
gtgaagtcgt caatgatgtc gatatgggtt ttgatcatgc acacataagg tccgacctta 5520
tcggcaagct caatgagctc cttggtggtg gtaacatcca gagaagcaca caggttggtt 5580
ttcttggctg ccacgagctt gagcactcga gcggcaaagg cggacttgtg gacgttagct 5640
cgagcttcgt aggagggcat tttggtggtg aagaggagac tgaaataaat ttagtctgca 5700
gaacttttta tcggaacctt atctggggca gtgaagtata tgttatggta atagttacga 5760
gttagttgaa cttatagata gactggacta tacggctatc ggtccaaatt agaaagaacg 5820
tcaatggctc tctgggcgtc gcctttgccg acaaaaatgt gatcatgatg aaagccagca 5880
atgacgttgc agctgatatt gttgtcggcc aaccgcgccg aaaacgcagc tgtcagaccc 5940
acagcctcca acgaagaatg tatcgtcaaa gtgatccaag cacactcata gttggagtcg 6000
tactccaaag gcggcaatga cgagtcagac agatactcgt cgacgtttaa acagtgtacg 6060
cagatctact atagaggaac atttaaattg ccccggagaa gacggccagg ccgcctagat 6120
gacaaattca acaactcaca gctgactttc tgccattgcc actagggggg ggccttttta 6180
tatggccaag ccaagctctc cacgtcggtt gggctgcacc caacaataaa tgggtagggt 6240
tgcaccaaca aagggatggg atgggggta gaagatacga ggataacggg gctcaatggc 6300
acaaataaga acgaatactg ccattaagac tcgtgatcca gcgactgaca ccattgcatc 6360
atctaagggc ctcaaaacta cctcggaact gctgcgctga tctggacacc acagaggttc 6420
cgagcacttt aggttgcacc aaatgtccca ccaggtgcag gcagaaaacg ctggaacagc 6480
gtgtacagtt tgtcttaaca aaaagtgagg gcgctgaggt cgagcagggt ggtgtgactt 6540
gttatagcct ttagagctgc gaaagcgcgt atggatttgg ctcatcaggc cagattgagg 6600
gtctgtggac acatgtcatg ttagtgtact tcaatcgccc cctggatata gccccgacaa 6660
taggccgtgg cctcattttt ttgccttccg cacatttcca ttgctcgata cccacacctt 6720
gcttctcctg cacttgccaa ccttaatact ggtttacatt gaccaacatc ttacaagcgg 6780
ggggcttgtc tagggtatat ataaacagtg gctctcccaa tcggttgcca gtctcttttt 6840
tcctttcttt ccccacagat tcgaaatcta aactacacat cacagaattc cgagccgtga 6900
gtatccacga caagatcagt gtcgagacga cgcgttttgt gtaatgacac aatccgaaag 6960
tcgctagcaa cacacactct ctacacaaac taacccagct ctggtaccat gatcacaagt 7020
ttgtacaaaa aagcaggctc cgcggccgcc cccttcacca tggctctggc caacgacgct 7080
ggcgagcgaa tctgggctgc cgtcaccgat cccgaaatcc tcattggcac cttctcctac 7140
ctgctcctga agcctctcct gcgaaactct ggtctcgtgg acgagaagaa aggagcctac 7200
cgaacctcca tgatctggta caacgtcctc ctggctctct tctctgccct gtccttctac 7260
gtgactgcca ccgctctcgg ctgggactac ggtactggag cctggctgcg aagacagacc 7320
ggtgatactc cccagcctct ctttcagtgt ccctctcctg tctgggactc caagctgttc 7380
acctggactg ccaaggcctt ctactattct aagtacgtgg agtacctcga caccgcttgg 7440
ctggtcctca agggcaagcg agtgtccttt ctgcaggcct tccatcactt tggagctccc 7500
tgggacgtct acctcggcat tcgactgcac aacgagggtg tgtggatctt catgttcttt 7560
aactcgttca ttcacaccat catgtacacc tactatggac tgactgccgc tggctacaag 7620
ttcaaggcca agcctctgat cactgccatg cagatttgcc agttcgtcgg tggctttctc 7680
ctggtctggg actacatcaa cgttccctgc ttcaactctg acaagggcaa gctgttctcc 7740
tgggctttca actacgccta cgtcggatct gtctttctcc tgttctgtca cttcttttac 7800
caggacaacc tggccaccaa gaaatccgct aaggctggta agcagcttta gaagggtggg 7860
cgcgccgacc cagcttt 7877

<210> SEQ ID NO 52
<211> LENGTH: 7771
<212> TYPE: DNA
<213> ORGANISM: Artificial Sequence
<220> FEATURE:
<223> OTHER INFORMATION: Plasmid pZUFmEgD9e

<400> SEQUENCE: 52
catggaggtg gtgaatgaaa tagtctcaat tgggcaggaa gttttaccca accagttgat 60
tatgcccaac tctggagtga tgccagtcac tgtgaggtgc tttacttgtc catcgcattt 120
gtcatcttga agttcactct tggcccccctt ggtccaaaag gtcagtctcg tatgaagttt 180
gttttcacca attacaacct tctcatgtcc atttattcgt tgggatcatt cctctcaatg 240
gcatatgcca tgtacaccat cggtgttatg tctgacaact gcgagaaggc ttttgacaac 300
aacgtcttca ggatcaccac gcagttgttc tatttgagca agttcctgga gtatattgac 360
tccttctatt tgccactgat gggcaagcct ctgacctggt tgcaattctt ccatcatttg 420
ggggcaccga tggatatgtg gctgttctat aattaccgaa atgaagctgt ttggattttt 480
gtgctgttga atggtttcat ccactggatc atgtacggtt attattggac cagattgatc 540
aagctgaagt tccccatgcc aaaatccctg attacatcaa tgcagatcat tcaattcaat 600
gttggtttct acattgtctg gaagtacagg aacattccct gttatcgcca agatgggatg 660
aggatgtttg gctggttctt caattacttt tatgttggca cagtcttgtg tttgttcttg 720
aatttctatg tgcaaacgta tatcgtcagg aagcacaagg gagccaaaaa gattcagtga 780
gcggccgcaa gtgtggatgg ggaagtgagt gcccggttct gtgtgcacaa ttggcaatcc 840
aagatggatg gattcaacac agggatatag cgagctacgt ggtggtgcga ggatatagca 900
acggatattt atgtttgaca cttgagaatg tacgatacaa gcactgtcca agtacaatac 960
taaacatact gtacatactc atactcgtac ccgggcaacg gtttcacttg agtgcagtgg 1020
ctagtgctct tactcgtaca gtgtgcaata ctgcgtatca tagtctttga tgtatatcgt 1080
attcattcat gttagttgcg tacgagccgg aagcataaag tgtaaagcct ggggtgccta 1140
atgagtgagc taactcacat taattgcgtt gcgctcactg cccgctttcc agtcgggaaa 1200
cctgtcgtgc cagctgcatt aatgaatcgg ccaacgcgcg gggagaggcg gtttgcgtat 1260
tgggcgctct tccgcttcct cgctcactga ctcgctgcgc tcggtcgttc ggctgcggcg 1320
agcggtatca gctcactcaa aggcggtaat acggttatcc acagaatcag gggataacgc 1380
aggaaagaac atgtgagcaa aaggccagca aaaggccagg aaccgtaaaa aggccgcgtt 1440
gctggcgttt ttccataggc tccgcccccc tgacgagcat cacaaaaatc gacgctcaag 1500
tcagaggtgg cgaaacccga caggactata aagataccag gcgtttcccc ctggaagctc 1560
cctcgtgcgc tctcctgttc cgaccctgcc gcttaccgga tacctgtccg cctttctccc 1620
ttcgggaagc gtggcgcttt ctcatagctc acgctgtagg tatctcagtt cggtgtaggt 1680
cgttcgctcc aagctgggct gtgtgcacga accccccgtt cagcccgacc gctgcgcctt 1740
atccggtaac tatcgtcttg agtccaaccc ggtaagacac gacttatcgc cactggcagc 1800
agccactggt aacaggatta gcagagcgag gtatgtaggc ggtgctacag agttcttgaa 1860
gtggtggcct aactacggct acactagaag gacagtattt ggtatctgcg ctctgctgaa 1920
gccagttacc ttcggaaaaa gagttggtag ctcttgatcc ggcaaacaaa ccaccgctgg 1980

```
tagcggtggt ttttttgttt gcaagcagca gattacgcgc agaaaaaaag gatctcaaga   2040
agatcctttg atcttttcta cggggtctga cgctcagtgg aacgaaaact cacgttaagg   2100
gattttggtc atgagattat caaaaaggat cttcacctag atccttttaa attaaaaatg   2160
aagttttaaa tcaatctaaa gtatatatga gtaaacttgg tctgacagtt accaatgctt   2220
aatcagtgag gcacctatct cagcgatctg tctatttcgt tcatccatag ttgcctgact   2280
ccccgtcgtg tagataacta cgatacggga gggcttacca tctggcccca gtgctgcaat   2340
gataccgcga gacccacgct caccggctcc agatttatca gcaataaacc agccagccgg   2400
aagggccgag cgcagaagtg gtcctgcaac tttatccgcc tccatccagt ctattaattg   2460
ttgccgggaa gctagagtaa gtagttcgcc agttaatagt ttgcgcaacg ttgttgccat   2520
tgctacaggc atcgtggtgt cacgctcgtc gtttggtatg gcttcattca gctccggttc   2580
ccaacgatca aggcgagtta catgatcccc catgttgtgc aaaaaagcgg ttagctcctt   2640
cggtcctccg atcgttgtca gaagtaagtt ggccgcagtg ttatcactca tggttatggc   2700
agcactgcat aattctctta ctgtcatgcc atccgtaaga tgcttttctg tgactggtga   2760
gtactcaacc aagtcattct gagaatagtg tatgcggcga ccgagttgct cttgcccggc   2820
gtcaatacgg gataataccg cgccacatag cagaacttta aaagtgctca tcattggaaa   2880
acgttcttcg gggcgaaaac tctcaaggat cttaccgctg ttgagatcca gttcgatgta   2940
acccactcgt gcacccaact gatcttcagc atcttttact ttcaccagcg tttctgggtg   3000
agcaaaaaca ggaaggcaaa atgccgcaaa aaagggaata agggcgacac ggaaatgttg   3060
aatactcata ctcttccttt ttcaatatta ttgaagcatt tatcagggtt attgtctcat   3120
gagcggatac atatttgaat gtatttagaa aaataaacaa ataggggttc cgcgcacatt   3180
tccccgaaaa gtgccacctg acgcgccctg tagcggcgca ttaagcgcgg cgggtgtggt   3240
ggttacgcgc agcgtgaccg ctacacttgc cagcgcccta gcgcccgctc ctttcgcttt   3300
cttcccttcc tttctcgcca cgttcgccgg ctttccccgt caagctctaa atcgggggct   3360
ccctttaggg ttccgattta gtgctttacg gcacctcgac cccaaaaaac ttgattaggg   3420
tgatggttca cgtagtgggc catcgccctg atagacggtt tttcgccctt tgacgttgga   3480
gtccacgttc tttaatagtg gactcttgtt ccaaactgga acaacactca accctatctc   3540
ggtctattct tttgatttat aagggatttt gccgatttcg gcctattggt taaaaaatga   3600
gctgatttaa caaaaattta acgcgaattt taacaaaata ttaacgctta caatttccat   3660
tcgccattca ggctgcgcaa ctgttgggaa gggcgatcgg tgcgggcctc ttcgctatta   3720
cgccagctgg cgaaaggggg atgtgctgca aggcgattaa gttgggtaac gccagggttt   3780
tcccagtcac gacgttgtaa aacgacggcc agtgaattgt aatacgactc actatagggc   3840
gaattgggta ccgggccccc cctcgaggtc gatggtgtcg ataagcttga tatcgaattc   3900
atgtcacaca aaccgatctt cgcctcaagg aaacctaatt ctacatccga gagactgccg   3960
agatccagtc tacactgatt aattttcggg ccaataattt aaaaaaatcg tgttatataa   4020
tattatatgt attatatata tacatcatga tgatactgac agtcatgtcc cattgctaaa   4080
tagacagact ccatctgccg cctccaactg atgttctcaa tatttaaggg gtcatctcgc   4140
attgtttaat aataaacaga ctccatctac cgcctccaaa tgatgttctc aaaatatatt   4200
gtatgaactt atttttatta cttagtatta ttagacaact tacttgcttt atgaaaaaca   4260
cttcctattt aggaaacaat ttataatggc agttcgttca tttaacaatt tatgtagaat   4320
aaatgttata aatgcgtatg ggaaatctta aatatggata gcataaatga tatctgcatt   4380
```

```
gcctaattcg aaatcaacag caacgaaaaa aatcccttgt acaacataaa tagtcatcga   4440
gaaatatcaa ctatcaaaga acagctattc acacgttact attgagatta ttattggacg   4500
agaatcacac actcaactgt ctttctctct tctagaaata caggtacaag tatgtactat   4560
tctcattgtt catacttcta gtcatttcat cccacatatt ccttggattt ctctccaatg   4620
aatgacattc tatcttgcaa attcaacaat tataataaga tataccaaag tagcggtata   4680
gtggcaatca aaaagcttct ctggtgtgct tctcgtattt atttttattc taatgatcca   4740
ttaaaggtat atatttattt cttgttatat aatccttttg tttattacat gggctggata   4800
cataaaggta ttttgattta attttttgct taaattcaat ccccccctcgt tcagtgtcaa   4860
ctgtaatggt aggaaattac catacttttg aagaagcaaa aaaaatgaaa gaaaaaaaaa   4920
atcgtatttc caggttagac gttccgcaga atctagaatg cggtatgcgg tacattgttc   4980
ttcgaacgta aaagttgcgc tccctgagat attgtacatt tttgctttta caagtacaag   5040
tacatcgtac aactatgtac tactgttgat gcatccacaa cagtttgttt tgttttttttt   5100
tgtttttttt ttttctaatg attcattacc gctatgtata cctacttgta cttgtagtaa   5160
gccgggttat tggcgttcaa ttaatcatag acttatgaat ctgcacggtg tgcgctgcga   5220
gttactttta gcttatgcat gctacttggg tgtaatattg ggatctgttc ggaaatcaac   5280
ggatgctcaa tcgatttcga cagtaattaa ttaagtcata cacaagtcag ctttcttcga   5340
gcctcatata agtataagta gttcaacgta ttagcactgt acccagcatc tccgtatcga   5400
gaaacacaac aacatgcccc attggacaga tcatgcggat acacaggttg tgcagtatca   5460
tacatactcg atcagacagg tcgtctgacc atcatacaag ctgaacaagc gctccatact   5520
tgcacgctct ctatatacac agttaaatta catatccata gtctaacctc taacagttaa   5580
tcttctggta agcctcccag ccagccttct ggtatcgctt ggcctcctca ataggatctc   5640
ggttctggcc gtacagacct cggccgacaa ttatgatatc cgttccggta gacatgacat   5700
cctcaacagt tcggtactgc tgtccgagag cgtctccctt gtcgtcaaga cccaccccgg   5760
gggtcagaat aagccagtcc tcagagtcgc ccttaggtcg gttctgggca atgaagccaa   5820
ccacaaactc ggggtcggat cgggcaagct caatggtctg cttggagtac tcgccagtgg   5880
ccagagagcc cttgcaagac agctcggcca gcatgagcag acctctggcc agcttctcgt   5940
tgggagaggg gactaggaac tccttgtact gggagttctc gtagtcagag acgtcctcct   6000
tcttctgttc agagacagtt tcctcggcac cagctcgcag gccagcaatg attccggttc   6060
cgggtacacc gtgggcgttg gtgatatcgg accactcggc gattcggtga caccggtact   6120
ggtgcttgac agtgttgcca atatctgcga actttctgtc ctcgaacagg aagaaaccgt   6180
gcttaagagc aagttccttg agggggagca cagtgccggc gtaggtgaag tcgtcaatga   6240
tgtcgatatg ggttttgatc atgcacacat aaggtccgac cttatcggca agctcaatga   6300
gctccttggt ggtggtaaca tccagagaag cacacaggtt ggttttcttg gctgccacga   6360
gcttgagcac tcgagcggca aaggcggact tgtggacgtt agctcgagct tcgtaggagg   6420
gcattttggt ggtgaagagg agactgaaat aaatttagtc tgcagaactt tttatcggaa   6480
ccttatctgg ggcagtgaag tatatgttat ggtaatagtt acgagttagt tgaacttata   6540
gatagactgg actatacggc tatcggtcca aattagaaag aacgtcaatg gctctctggg   6600
cgtcgccttt gccgacaaaa atgtgatcat gatgaaagcc agcaatgacg ttgcagctga   6660
tattgttgtc ggccaaccgc gccgaaaacg cagctgtcag acccacagcc tccaacgaag   6720
aatgtatcgt caaagtgatc caagcacact catagttgga gtcgtactcc aaaggcggca   6780
```

atgacgagtc agacagatac tcgtcgacgt ttaaacagtg tacgcagatc tactatagag 6840
gaacatttaa attgccccgg agaagacggc caggccgcct agatgacaaa ttcaacaact 6900
cacagctgac tttctgccat tgccactagg ggggggcctt tttatatggc caagccaagc 6960
tctccacgtc ggttgggctg cacccaacaa taaatgggta gggttgcacc aacaaaggga 7020
tgggatgggg ggtagaagat acgaggataa cggggctcaa tggcacaaat aagaacgaat 7080
actgccatta agactcgtga tccagcgact gacaccattg catcatctaa gggcctcaaa 7140
actacctcgg aactgctgcg ctgatctgga caccacagag gttccgagca ctttaggttg 7200
caccaaatgt cccaccaggt gcaggcagaa aacgctggaa cagcgtgtac agtttgtctt 7260
aacaaaaagt gagggcgctg aggtcgagca gggtggtgtg acttgttata gcctttagag 7320
ctgcgaaagc gcgtatggat ttggctcatc aggccagatt gagggtctgt ggacacatgt 7380
catgttagtg tacttcaatc gccccctgga tatagccccg acaataggcc gtggcctcat 7440 tttttgcct tccgcacatt tccattgctc gatacccaca ccttgcttct cctgcacttg 7500
ccaaccttaa tactggttta cattgaccaa catcttacaa gcggggggct tgtctagggt 7560
atatataaac agtggctctc ccaatcggtt gccagtctct tttttccttt ctttccccac 7620
agattcgaaa tctaaactac acatcacaga attccgagcc gtgagtatcc acgacaagat 7680
cagtgtcgag acgacgcgtt ttgtgtaatg acacaatccg aaagtcgcta gcaacacaca 7740
ctctctacac aaactaaccc agctctggta c 7771

<210> SEQ ID NO 53
<211> LENGTH: 7769
<212> TYPE: DNA
<213> ORGANISM: Artificial Sequence
<220> FEATURE:
<223> OTHER INFORMATION: Plasmid pZUFmEgD9eS

<400> SEQUENCE: 53
ggccgcaagt gtggatgggg aagtgagtgc ccggttctgt gtgcacaatt ggcaatccaa 60
gatggatgga ttcaacacag ggatatagcg agctacgtgg tggtgcgagg atatagcaac 120
ggatatttat gtttgacact tgagaatgta cgatacaagc actgtccaag tacaatacta 180
aacatactgt acatactcat actcgtaccc gggcaacggt ttcacttgag tgcagtggct 240
agtgctctta ctcgtacagt gtgcaatact gcgtatcata gtctttgatg tatatcgtat 300
tcattcatgt tagttgcgta cgagccggaa gcataaagtg taaagcctgg ggtgcctaat 360
gagtgagcta actcacatta attgcgttgc gctcactgcc cgctttccag tcgggaaacc 420
tgtcgtgcca gctgcattaa tgaatcggcc aacgcgcggg gagaggcggt ttgcgtattg 480
ggcgctcttc cgcttcctcg ctcactgact cgctgcgctc ggtcgttcgg ctgcggcgag 540
cggtatcagc tcactcaaag gcggtaatac ggttatccac agaatcaggg gataacgcag 600
gaaagaacat gtgagcaaaa ggccagcaaa aggccaggaa ccgtaaaaag gccgcgttgc 660
tggcgttttt ccataggctc cgcccccctg acgagcatca caaaaatcga cgctcaagtc 720
agaggtggcg aaacccgaca ggactataaa gataccaggc gtttccccct ggaagctccc 780
tcgtgcgctc tcctgttccg accctgccgc ttaccggata cctgtccgcc tttctccctt 840
cgggaagcgt ggcgctttct catagctcac gctgtaggta tctcagttcg gtgtaggtcg 900
ttcgctccaa gctgggctgt gtgcacgaac cccccgttca gcccgaccgc tgcgccttat 960
ccggtaacta tcgtcttgag tccaacccgg taagacacga cttatcgcca ctggcagcag 1020
ccactggtaa caggattagc agagcgaggt atgtaggcgg tgctacagag ttcttgaagt 1080
ggtggcctaa ctacggctac actagaagga cagtatttgg tatctgcgct ctgctgaagc 1140
cagttacctt cggaaaaaga gttggtagct cttgatccgg caaacaaacc accgctggta 1200
gcggtggttt ttttgtttgc aagcagcaga ttacgcgcag aaaaaaagga tctcaagaag 1260
atcctttgat cttttctacg gggtctgacg ctcagtggaa cgaaaactca cgttaaggga 1320
ttttggtcat gagattatca aaaaggatct tcacctagat ccttttaaat taaaaatgaa 1380
gttttaaatc aatctaaagt atatatgagt aaacttggtc tgacagttac caatgcttaa 1440
tcagtgaggc acctatctca gcgatctgtc tatttcgttc atccatagtt gcctgactcc 1500
ccgtcgtgta gataactacg atacgggagg gcttaccatc tggccccagt gctgcaatga 1560
taccgcgaga cccacgctca ccggctccag atttatcagc aataaaccag ccagccggaa 1620
gggccgagcg cagaagtggt cctgcaactt tatccgcctc catccagtct attaattgtt 1680
gccgggaagc tagagtaagt agttcgccag ttaatagttt gcgcaacgtt gttgccattg 1740
ctacaggcat cgtggtgtca cgctcgtcgt ttggtatggc ttcattcagc tccggttccc 1800
aacgatcaag gcgagttaca tgatccccca tgttgtgcaa aaaagcggtt agctccttcg 1860
gtcctccgat cgttgtcaga agtaagttgg ccgcagtgtt atcactcatg gttatggcag 1920
cactgcataa ttctcttact gtcatgccat ccgtaagatg cttttctgtg actggtgagt 1980
actcaaccaa gtcattctga gaatagtgta tgcggcgacc gagttgctct tgcccggcgt 2040
caatacggga taataccgcg ccacatagca gaactttaaa agtgctcatc attggaaaac 2100
gttcttcggg gcgaaaactc tcaaggatct taccgctgtt gagatccagt tcgatgtaac 2160
ccactcgtgc acccaactga tcttcagcat cttttacttt caccagcgtt tctgggtgag 2220
caaaaacagg aaggcaaaat gccgcaaaaa agggaataag ggcgacacgg aaatgttgaa 2280
tactcatact cttccttttt caatattatt gaagcattta tcagggttat tgtctcatga 2340
gcggatacat atttgaatgt atttagaaaa ataaacaaat aggggttccg cgcacatttc 2400
cccgaaaagt gccacctgac gcgccctgta gcggcgcatt aagcgcggcg ggtgtggtgg 2460
ttacgcgcag cgtgaccgct acacttgcca gcgccctagc gcccgctcct ttcgctttct 2520
tcccttcctt tctcgccacg ttcgccggct ttccccgtca agctctaaat cgggggctcc 2580
ctttagggtt ccgatttagt gctttacggc acctcgaccc caaaaaactt gattagggtg 2640
atggttcacg tagtgggcca tcgccctgat agacggtttt tcgccctttg acgttggagt 2700
ccacgttctt taatagtgga ctcttgttcc aaactggaac aacactcaac cctatctcgg 2760
tctattcttt tgatttataa gggattttgc cgatttcggc ctattggtta aaaaatgagc 2820
tgatttaaca aaaatttaac gcgaatttta acaaaatatt aacgcttaca atttccattc 2880
gccattcagg ctgcgcaact gttgggaagg gcgatcggtg cgggcctctt cgctattacg 2940
ccagctggcg aaagggggat gtgctgcaag gcgattaagt tgggtaacgc cagggttttc 3000
ccagtcacga cgttgtaaaa cgacggccag tgaattgtaa tacgactcac tatagggcga 3060
attgggtacc gggccccccc tcgaggtcga tggtgtcgat aagcttgata tcgaattcat 3120
gtcacacaaa ccgatcttcg cctcaaggaa acctaattct acatccgaga gactgccgag 3180
atccagtcta cactgattaa ttttcgggcc aataatttaa aaaaatcgtg ttatataata 3240
ttatatgtat tatatatata catcatgatg atactgacag tcatgtccca ttgctaaata 3300
gacagactcc atctgccgcc tccaactgat gttctcaata tttaaggggt catctcgcat 3360
tgtttaataa taaacagact ccatctaccg cctccaaatg atgttctcaa aatatattgt 3420
atgaacttat ttttattact tagtattatt agacaactta cttgctttat gaaaaacact 3480
tcctatttag gaaacaattt ataatggcag ttcgttcatt taacaattta tgtagaataa 3540
atgttataaa tgcgtatggg aaatcttaaa tatggatagc ataaatgata tctgcattgc 3600
ctaattcgaa atcaacagca acgaaaaaaa tcccttgtac aacataaata gtcatcgaga 3660
aatatcaact atcaaagaac agctattcac acgttactat tgagattatt attggacgag 3720
aatcacacac tcaactgtct ttctctcttc tagaaataca ggtacaagta tgtactattc 3780
tcattgttca tacttctagt catttcatcc cacatattcc ttggatttct ctccaatgaa 3840
tgacattcta tcttgcaaat tcaacaatta taataagata taccaaagta gcggtatagt 3900
ggcaatcaaa aagcttctct ggtgtgcttc tcgtatttat ttttattcta atgatccatt 3960
aaaggtatat atttatttct tgttatataa tccttttgtt tattacatgg gctggataca 4020
taaaggtatt ttgatttaat tttttgctta aattcaatcc cccctcgttc agtgtcaact 4080
gtaatggtag gaaattacca tacttttgaa gaagcaaaaa aaatgaaaga aaaaaaaaat 4140
cgtatttcca ggttagacgt tccgcagaat ctagaatgcg gtatgcggta cattgttctt 4200
cgaacgtaaa agttgcgctc cctgagatat tgtacatttt tgcttttaca agtacaagta 4260
catcgtacaa ctatgtacta ctgttgatgc atccacaaca gtttgttttg tttttttttg 4320
tttttttttt ttctaatgat tcattaccgc tatgtatacc tacttgtact tgtagtaagc 4380
cgggttattg gcgttcaatt aatcatagac ttatgaatct gcacggtgtg cgctgcgagt 4440
tacttttagc ttatgcatgc tacttgggtg taatattggg atctgttcgg aaatcaacgg 4500
atgctcaatc gatttcgaca gtaattaatt aagtcataca caagtcagct ttcttcgagc 4560
ctcatataag tataagtagt tcaacgtatt agcactgtac ccagcatctc cgtatcgaga 4620
aacacaacaa catgccccat tggacagatc atgcggatac acaggttgtg cagtatcata 4680
catactcgat cagacaggtc gtctgaccat catacaagct gaacaagcgc tccatacttg 4740
cacgctctct atatacacag ttaaattaca tatccatagt ctaacctcta acagttaatc 4800
ttctggtaag cctcccagcc agccttctgg tatcgcttgg cctcctcaat aggatctcgg 4860
ttctggccgt acagacctcg gccgacaatt atgatatccg ttccggtaga catgacatcc 4920
tcaacagttc ggtactgctg tccgagagcg tctcccttgt cgtcaagacc caccccgggg 4980
gtcagaataa gccagtcctc agagtcgccc ttaggtcggt tctgggcaat gaagccaacc 5040
acaaactcgg ggtcggatcg ggcaagctca atggtctgct tggagtactc gccagtggcc 5100
agagagccct tgcaagacag ctcggccagc atgagcagac ctctggccag cttctcgttg 5160
ggagagggga ctaggaactc cttgtactgg gagttctcgt agtcagagac gtcctccttc 5220
ttctgttcag agacagtttc ctcggcacca gctcgcaggc cagcaatgat tccggttccg 5280
ggtacaccgt gggcgttggt gatatcggac cactcggcga ttcggtgaca ccggtactgg 5340
tgcttgacag tgttgccaat atctgcgaac tttctgtcct cgaacaggaa gaaaccgtgc 5400
ttaagagcaa gttccttgag ggggagcaca gtgccggcgt aggtgaagtc gtcaatgatg 5460
tcgatatggg ttttgatcat gcacacataa ggtccgacct tatcggcaag ctcaatgagc 5520
tccttggtgg tggtaacatc cagagaagca cacaggttgg ttttcttggc tgccacgagc 5580
ttgagcactc gagcggcaaa ggcggacttg tggacgttag ctcgagcttc gtaggagggc 5640
attttggtgg tgaagaggag actgaaataa atttagtctg cagaactttt tatcggaacc 5700
ttatctgggg cagtgaagta tatgttatgg taatagttac gagttagttg aacttataga 5760
tagactggac tatacggcta tcggtccaaa ttagaaagaa cgtcaatggc tctctgggcg 5820
tcgcctttgc cgacaaaaat gtgatcatga tgaaagccag caatgacgtt gcagctgata 5880
ttgttgtcgg ccaaccgcgc cgaaaacgca gctgtcagac ccacagcctc caacgaagaa 5940
tgtatcgtca aagtgatcca agcacactca tagttggagt cgtactccaa aggcggcaat 6000
gacgagtcag acagatactc gtcgacgttt aaacagtgta cgcagatcta ctatagagga 6060
acatttaaat tgccccggag aagacggcca ggccgcctag atgacaaatt caacaactca 6120
cagctgactt tctgccattg ccactagggg ggggcctttt tatatggcca agccaagctc 6180
tccacgtcgg ttgggctgca cccaacaata aatgggtagg gttgcaccaa caaagggatg 6240
ggatgggggg tagaagatac gaggataacg gggctcaatg gcacaaataa gaacgaatac 6300
tgccattaag actcgtgatc cagcgactga caccattgca tcatctaagg gcctcaaaac 6360
tacctcggaa ctgctgcgct gatctggaca ccacagaggt tccgagcact ttaggttgca 6420
ccaaatgtcc caccaggtgc aggcagaaaa cgctggaaca gcgtgtacag tttgtcttaa 6480
caaaaagtga gggcgctgag gtcgagcagg gtggtgtgac ttgttatagc ctttagagct 6540
gcgaaagcgc gtatggattt ggctcatcag gccagattga gggtctgtgg acacatgtca 6600
tgttagtgta cttcaatcgc cccctggata tagccccgac aataggccgt ggcctcattt 6660
ttttgccttc cgcacatttc cattgctcga tacccacacc ttgcttctcc tgcacttgcc 6720
aaccttaata ctggtttaca ttgaccaaca tcttacaagc ggggggcttg tctagggtat 6780
atataaacag tggctctccc aatcggttgc cagtctcttt tttcctttct ttccccacag 6840
attcgaaatc taaactacac atcacagaat tccgagccgt gagtatccac gacaagatca 6900
gtgtcgagac gacgcgtttt gtgtaatgac acaatccgaa agtcgctagc aacacacact 6960
ctctacacaa actaacccag ctctggtacc atggaggtcg tgaacgaaat cgtctccatt 7020
ggccaggagg ttcttcccaa ggtcgactat gctcagctct ggtctgatgc ctcgcactgc 7080
gaggtgctgt acctctccat cgccttcgtc atcctgaagt tcacccttgg tcctctcgga 7140
cccaagggtc agtctcgaat gaagtttgtg ttcaccaact acaacctgct catgtccatc 7200
tactcgctgg gctccttcct ctctatggcc tacgccatgt acaccattgg tgtcatgtcc 7260
gacaactgcg agaaggcttt cgacaacaat gtcttccgaa tcaccactca gctgttctac 7320
ctcagcaagt tcctcgagta cattgactcc ttctatctgc cctcatgggg caagcctctg 7380
acctggttgc agttctttca ccatctcgga gctcctatgg acatgtggct gttctacaac 7440
taccgaaacg aagccgtttg gatctttgtg ctgctcaacg gcttcattca ctggatcatg 7500
tacggctact attggacccg actgatcaag ctcaagttcc ctatgcccaa gtccctgatt 7560
acttctatgc agatcattca gttcaacgtt ggcttctaca tcgtctggaa gtaccggaac 7620
attccctgct accgacaaga tggaatgaga atgtttggct ggtttttcaa ctacttctac 7680
gttggtactg tcctgtgtct gttcctcaac ttctacgtgc agacctacat cgtccgaaag 7740
cacaagggag ccaaaaagat tcagtgagc 7769

<210> SEQ ID NO 54
<211> LENGTH: 7769
<212> TYPE: DNA
<213> ORGANISM: Artificial Sequence
<220> FEATURE:
<223> OTHER INFORMATION: Plasmid pY120

<400> SEQUENCE: 54
ggccgcaagt gtggatgggg aagtgagtgc ccggttctgt gtgcacaatt ggcaatccaa 60
gatggatgga ttcaacacag ggatatagcg agctacgtgg tggtgcgagg atatagcaac 120
ggatatttat gtttgacact tgagaatgta cgatacaagc actgtccaag tacaatacta 180

```
aacatactgt acatactcat actcgtaccc gggcaacggt ttcacttgag tgcagtggct    240
agtgctctta ctcgtacagt gtgcaatact gcgtatcata gtctttgatg tatatcgtat    300
tcattcatgt tagttgcgta cgagccggaa gcataaagtg taaagcctgg ggtgcctaat    360
gagtgagcta actcacatta attgcgttgc gctcactgcc cgctttccag tcgggaaacc    420
tgtcgtgcca gctgcattaa tgaatcggcc aacgcgcggg gagaggcggt ttgcgtattg    480
ggcgctcttc cgcttcctcg ctcactgact cgctgcgctc ggtcgttcgg ctgcggcgag    540
cggtatcagc tcactcaaag gcggtaatac ggttatccac agaatcaggg gataacgcag    600
gaaagaacat gtgagcaaaa ggccagcaaa aggccaggaa ccgtaaaaag gccgcgttgc    660
tggcgttttt ccataggctc cgcccccctg acgagcatca caaaaatcga cgctcaagtc    720
agaggtggcg aaacccgaca ggactataaa gataccaggc gtttccccct ggaagctccc    780
tcgtgcgctc tcctgttccg accctgccgc ttaccggata cctgtccgcc tttctccctt    840
cgggaagcgt ggcgctttct catagctcac gctgtaggta tctcagttcg gtgtaggtcg    900
ttcgctccaa gctgggctgt gtgcacgaac cccccgttca gcccgaccgc tgcgccttat    960
ccggtaacta tcgtcttgag tccaacccgg taagacacga cttatcgcca ctggcagcag   1020
ccactggtaa caggattagc agagcgaggt atgtaggcgg tgctacagag ttcttgaagt   1080
ggtggcctaa ctacggctac actagaagga cagtatttgg tatctgcgct ctgctgaagc   1140
cagttacctt cggaaaaaga gttggtagct cttgatccgg caaacaaacc accgctggta   1200
gcggtggttt ttttgtttgc aagcagcaga ttacgcgcag aaaaaaagga tctcaagaag   1260
atcctttgat cttttctacg gggtctgacg ctcagtggaa cgaaaactca cgttaaggga   1320
ttttggtcat gagattatca aaaaggatct tcacctagat ccttttaaat taaaaatgaa   1380
gttttaaatc aatctaaagt atatatgagt aaacttggtc tgacagttac caatgcttaa   1440
tcagtgaggc acctatctca gcgatctgtc tatttcgttc atccatagtt gcctgactcc   1500
ccgtcgtgta gataactacg atacgggagg gcttaccatc tggccccagt gctgcaatga   1560
taccgcgaga cccacgctca ccggctccag atttatcagc aataaaccag ccagccggaa   1620
gggccgagcg cagaagtggt cctgcaactt tatccgcctc catccagtct attaattgtt   1680
gccgggaagc tagagtaagt agttcgccag ttaatagttt gcgcaacgtt gttgccattg   1740
ctacaggcat cgtggtgtca cgctcgtcgt ttggtatggc ttcattcagc tccggttccc   1800
aacgatcaag gcgagttaca tgatccccca tgttgtgcaa aaaagcggtt agctccttcg   1860
gtcctccgat cgttgtcaga agtaagttgg ccgcagtgtt atcactcatg gttatggcag   1920
cactgcataa ttctcttact gtcatgccat ccgtaagatg cttttctgtg actggtgagt   1980
actcaaccaa gtcattctga gaatagtgta tgcggcgacc gagttgctct tgcccggcgt   2040
caatacggga taataccgcg ccacatagca gaactttaaa agtgctcatc attggaaaac   2100
gttcttcggg gcgaaaactc tcaaggatct taccgctgtt gagatccagt tcgatgtaac   2160
ccactcgtgc acccaactga tcttcagcat cttttacttt caccagcgtt tctgggtgag   2220
caaaaacagg aaggcaaaat gccgcaaaaa agggaataag ggcgacacgg aaatgttgaa   2280
tactcatact cttccttttt caatattatt gaagcattta tcagggttat tgtctcatga   2340
gcggatacat atttgaatgt atttagaaaa ataaacaaat aggggttccg cgcacatttc   2400
cccgaaaagt gccacctgac gcgccctgta gcggcgcatt aagcgcggcg ggtgtggtgg   2460
ttacgcgcag cgtgaccgct acacttgcca gcgccctagc gcccgctcct ttcgctttct   2520
tcccttcctt tctcgccacg ttcgccggct ttccccgtca agctctaaat cgggggctcc   2580
```

```
ctttagggtt ccgatttagt gctttacggc acctcgaccc caaaaaactt gattagggtg   2640
atggttcacg tagtgggcca tcgccctgat agacggtttt tcgccctttg acgttggagt   2700
ccacgttctt taatagtgga ctcttgttcc aaactggaac aacactcaac cctatctcgg   2760
tctattcttt tgatttataa gggattttgc cgatttcggc ctattggtta aaaaatgagc   2820
tgatttaaca aaaatttaac gcgaatttta acaaaatatt aacgcttaca atttccattc   2880
gccattcagg ctgcgcaact gttgggaagg gcgatcggtg cgggcctctt cgctattacg   2940
ccagctggcg aaagggggat gtgctgcaag gcgattaagt tgggtaacgc cagggttttc   3000
ccagtcacga cgttgtaaaa cgacggccag tgaattgtaa tacgactcac tatagggcga   3060
attgggtacc gggccccccc tcgaggtcga tggtgtcgat aagcttgata tcgaattcat   3120
gtcacacaaa ccgatcttcg cctcaaggaa acctaattct acatccgaga gactgccgag   3180
atccagtcta cactgattaa ttttcgggcc aataatttaa aaaaatcgtg ttatataata   3240
ttatatgtat tatatatata catcatgatg atactgacag tcatgtccca ttgctaaata   3300
gacagactcc atctgccgcc tccaactgat gttctcaata tttaaggggt catctcgcat   3360
tgtttaataa taaacagact ccatctaccg cctccaaatg atgttctcaa aatatattgt   3420
atgaacttat ttttattact tagtattatt agacaactta cttgctttat gaaaaacact   3480
tcctatttag gaaacaattt ataatggcag ttcgttcatt taacaattta tgtagaataa   3540
atgttataaa tgcgtatggg aaatcttaaa tatggatagc ataaatgata tctgcattgc   3600
ctaattcgaa atcaacagca acgaaaaaaa tcccttgtac aacataaata gtcatcgaga   3660
aatatcaact atcaaagaac agctattcac acgttactat tgagattatt attggacgag   3720
aatcacacac tcaactgtct ttctctcttc tagaaataca ggtacaagta tgtactattc   3780
tcattgttca tacttctagt catttcatcc cacatattcc ttggatttct ctccaatgaa   3840
tgacattcta tcttgcaaat tcaacaatta taataagata taccaaagta gcggtatagt   3900
ggcaatcaaa aagcttctct ggtgtgcttc tcgtatttat ttttattcta atgatccatt   3960
aaaggtatat atttatttct tgttatataa tccttttgtt tattacatgg gctggataca   4020
taaaggtatt ttgatttaat tttttgctta aattcaatcc cccctcgttc agtgtcaact   4080
gtaatggtag gaaattacca tacttttgaa gaagcaaaaa aaatgaaaga aaaaaaaaat   4140
cgtatttcca ggttagacgt tccgcagaat ctagaatgcg gtatgcggta cattgttctt   4200
cgaacgtaaa agttgcgctc cctgagatat tgtacatttt tgcttttaca agtacaagta   4260
catcgtacaa ctatgtacta ctgttgatgc atccacaaca gtttgttttg tttttttttg   4320
tttttttttt ttctaatgat tcattaccgc tatgtatacc tacttgtact tgtagtaagc   4380
cgggttattg gcgttcaatt aatcatagac ttatgaatct gcacggtgtg cgctgcgagt   4440
tacttttagc ttatgcatgc tacttgggtg taatattggg atctgttcgg aaatcaacgg   4500
atgctcaatc gatttcgaca gtaattaatt aagtcataca caagtcagct ttcttcgagc   4560
ctcatataag tataagtagt tcaacgtatt agcactgtac ccagcatctc cgtatcgaga   4620
aacacaacaa catgccccat tggacagatc atgcggatac acaggttgtg cagtatcata   4680
catactcgat cagacaggtc gtctgaccat catacaagct gaacaagcgc tccatacttg   4740
cacgctctct atatacacag ttaaattaca tatccatagt ctaacctcta acagttaatc   4800
ttctggtaag cctcccagcc agccttctgg tatcgcttgg cctcctcaat aggatctcgg   4860
ttctggccgt acagacctcg gccgacaatt atgatatccg ttccggtaga catgacatcc   4920
tcaacagttc ggtactgctg tccgagagcg tctcccttgt cgtcaagacc caccccgggg   4980
```

gtcagaataa gccagtcctc agagtcgccc ttaggtcggt tctgggcaat gaagccaacc 5040
acaaactcgg ggtcggatcg ggcaagctca atggtctgct tggagtactc gccagtggcc 5100
agagagccct tgcaagacag ctcggccagc atgagcagac ctctggccag cttctcgttg 5160
ggagagggga ctaggaactc cttgtactgg gagttctcgt agtcagagac gtcctccttc 5220
ttctgttcag agacagtttc ctcggcacca gctcgcaggc cagcaatgat tccggttccg 5280
ggtacaccgt gggcgttggt gatatcggac cactcggcga ttcggtgaca ccggtactgg 5340
tgcttgacag tgttgccaat atctgcgaac tttctgtcct cgaacaggaa gaaaccgtgc 5400
ttaagagcaa gttccttgag ggggagcaca gtgccggcgt aggtgaagtc gtcaatgatg 5460
tcgatatggg ttttgatcat gcacacataa ggtccgacct tatcggcaag ctcaatgagc 5520
tccttggtgg tggtaacatc cagagaagca cacaggttgg ttttcttggc tgccacgagc 5580
ttgagcactc gagcggcaaa ggcggacttg tggacgttag ctcgagcttc gtaggagggc 5640 atttggtgg tgaagaggag actgaaataa atttagtctg cagaactttt tatcggaacc 5700
ttatctgggg cagtgaagta tatgttatgg taatagttac gagttagttg aacttataga 5760
tagactggac tatacggcta tcggtccaaa ttagaaagaa cgtcaatggc tctctgggcg 5820
tcgcctttgc cgacaaaaat gtgatcatga tgaaagccag caatgacgtt gcagctgata 5880
ttgttgtcgg ccaaccgcgc cgaaaacgca gctgtcagac ccacagcctc caacgaagaa 5940
tgtatcgtca aagtgatcca agcacactca tagttggagt cgtactccaa aggcggcaat 6000
gacgagtcag acagatactc gtcgacgttt aaacagtgta cgcagatcta ctatagagga 6060
acatttaaat tgccccggag aagacggcca ggccgcctag atgacaaatt caacaactca 6120
cagctgactt tctgccattg ccactagggg ggggcctttt tatatggcca agccaagctc 6180
tccacgtcgg ttgggctgca cccaacaata aatgggtagg gttgcaccaa caaagggatg 6240
ggatgggggg tagaagatac gaggataacg gggctcaatg gcacaaataa gaacgaatac 6300
tgccattaag actcgtgatc cagcgactga caccattgca tcatctaagg gcctcaaaac 6360
tacctcggaa ctgctgcgct gatctggaca ccacagaggt tccgagcact ttaggttgca 6420
ccaaatgtcc caccaggtgc aggcagaaaa cgctggaaca gcgtgtacag tttgtcttaa 6480
caaaaagtga gggcgctgag gtcgagcagg gtggtgtgac ttgttatagc ctttagagct 6540
gcgaaagcgc gtatggattt ggctcatcag gccagattga gggtctgtgg acacatgtca 6600
tgttagtgta cttcaatcgc cccctggata tagccccgac aataggccgt ggcctcattt 6660
ttttgccttc cgcacatttc cattgctcga tacccacacc ttgcttctcc tgcacttgcc 6720
aaccttaata ctggtttaca ttgaccaaca tcttacaagc ggggggcttg tctagggtat 6780
atataaacag tggctctccc aatcggttgc cagtctcttt tttcctttct ttccccacag 6840
attcgaaatc taaactacac atcacagaat tccgagccgt gagtatccac gacaagatca 6900
gtgtcgagac gacgcgtttt gtgtaatgac acaatccgaa agtcgctagc aacacacact 6960
ctctacacaa actaacccag ctctggtacc atggaggtgg tgaatgaaat agtctcaatt 7020
gggcaggaag ttttacccaa agttgattat gcccaactct ggagtgatgc cagtcactgt 7080
gaggtgcttt acttgtccat cgcatttgtc atcttgaagt tcactcttgg ccccccttggt 7140 ccaaaaggtc agtctcgtat gaagtttgtt ttcaccaatt acaaccttct catgtccatt 7200
tattcgttgg gatcattcct ctcaatggca tatgccatgt acaccatcgg tgttatgtct 7260
gacaactgcg agaaggcttt tgacaacaac gtcttcagga tcaccacgca gttgttctat 7320
ttgagcaagt tcctggagta tattgactcc ttctatttgc cactgatggg caagcctctg 7380
acctggttgc aattcttcca tcatttgggg gcaccgatgg atatgtggct gttctataat 7440
taccgaaatg aagctgtttg gatttttgtg ctgttgaatg gtttcatcca ctggatcatg 7500
tacggttatt attggaccag attgatcaag ctgaagttcc ccatgccaaa atccctgatt 7560
acatcaatgc agatcattca attcaatgtt ggtttctaca ttgtctggaa gtacaggaac 7620
attccctgtt atcgccaaga tgggatgagg atgtttggct ggttcttcaa ttacttttat 7680
gttggcacag tcttgtgttt gttcttgaat ttctatgtgc aaacgtatat cgtcaggaag 7740
cacaagggag ccaaaaagat tcagtgagc 7769

<210> SEQ ID NO 55
<211> LENGTH: 7085
<212> TYPE: DNA
<213> ORGANISM: Artificial Sequence
<220> FEATURE:
<223> OTHER INFORMATION: Plasmid pKR72

<400> SEQUENCE: 55
gtacggatcc gtcgacggcg cgcccgatca tccggatata gttcctcctt tcagcaaaaa 60
acccctcaag acccgtttag aggccccaag gggttatgct agttattgct cagcggtggc 120
agcagccaac tcagcttcct ttcgggcttt gttagcagcc ggatcgatcc aagctgtacc 180
tcactattcc tttgccctcg gacgagtgct ggggcgtcgg tttccactat cggcgagtac 240
ttctacacag ccatcggtcc agacggccgc gcttctgcgg gcgatttgtg tacgcccgac 300
agtcccggct ccggatcgga cgattgcgtc gcatcgaccc tgcgcccaag ctgcatcatc 360
gaaattgccg tcaaccaagc tctgatagag ttggtcaaga ccaatgcgga gcatatacgc 420
ccggagccgc ggcgatcctg caagctccgg atgcctccgc tcgaagtagc gcgtctgctg 480
ctccatacaa gccaaccacg gcctccagaa gaagatgttg gcgacctcgt attgggaatc 540
cccgaacatc gcctcgctcc agtcaatgac cgctgttatg cggccattgt ccgtcaggac 600
attgttggag ccgaaatccg cgtgcacgag gtgccggact tcggggcagt cctcggccca 660
aagcatcagc tcatcgagag cctgcgcgac ggacgcactg acggtgtcgt ccatcacagt 720
ttgccagtga tacacatggg gatcagcaat cgcgcatatg aaatcacgcc atgtagtgta 780
ttgaccgatt ccttgcggtc cgaatgggcc gaacccgctc gtctggctaa gatcggccgc 840
agcgatcgca tccatagcct ccgcgaccgg ctgcagaaca gcgggcagtt cggtttcagg 900
caggtcttgc aacgtgacac cctgtgcacg gcgggagatg caataggtca ggctctcgct 960
gaattcccca atgtcaagca cttccggaat cgggagcgcg gccgatgcaa agtgccgata 1020
aacataacga tctttgtaga aaccatcggc gcagctattt acccgcagga catatccacg 1080
ccctcctaca tcgaagctga aagcacgaga ttcttcgccc tccgagagct gcatcaggtc 1140
ggagacgctg tcgaactttt cgatcagaaa cttctcgaca gacgtcgcgg tgagttcagg 1200
cttttccatg ggtatatctc cttcttaaag ttaaacaaaa ttatttctag agggaaaccg 1260
ttgtggtctc cctatagtga gtcgtattaa tttcgcggga tcgagatcga tccaattcca 1320
atcccacaaa aatctgagct taacagcaca gttgctcctc tcagagcaga atcgggtatt 1380
caacaccctc atatcaacta ctacgttgtg tataacggtc cacatgccgg tatatacgat 1440
gactggggtt gtacaaaggc ggcaacaaac ggcgttcccg gagttgcaca caagaaattt 1500
gccactatta cagaggcaag agcagcagct gacgcgtaca caacaagtca gcaaacagac 1560
aggttgaact tcatccccaa aggagaagct caactcaagc ccaagagctt tgctaaggcc 1620
ctaacaagcc caccaaagca aaaagcccac tggctcacgc taggaaccaa aaggcccagc 1680
agtgatccag ccccaaaaga gatctccttt gccccggaga ttacaatgga cgatttcctc 1740
tatctttacg atctaggaag gaagttcgaa ggtgaaggtg acgacactat gttcaccact 1800
gataatgaga aggttagcct cttcaatttc agaaagaatg ctgacccaca gatggttaga 1860
gaggcctacg cagcaggtct catcaagacg atctacccga gtaacaatct ccaggagatc 1920
aaataccttc ccaagaaggt taaagatgca gtcaaaagat tcaggactaa ttgcatcaag 1980
aacacagaga aagacatatt tctcaagatc agaagtacta ttccagtatg gacgattcaa 2040
ggcttgcttc ataaaccaag gcaagtaata gagattggag tctctaaaaa ggtagttcct 2100
actgaatcta aggccatgca tggagtctaa gattcaaatc gaggatctaa cagaactcgc 2160
cgtgaagact ggcgaacagt tcatacagag tcttttacga ctcaatgaca agaagaaaat 2220
cttcgtcaac atggtggagc acgacactct ggtctactcc aaaaatgtca aagatacagt 2280
ctcagaagac caaagggcta ttgagacttt tcaacaaagg ataatttcgg gaaacctcct 2340
cggattccat tgcccagcta tctgtcactt catcgaaagg acagtagaaa aggaaggtgg 2400
ctcctacaaa tgccatcatt gcgataaagg aaaggctatc attcaagatg cctctgccga 2460
cagtggtccc aaagatggac ccccacccac gaggagcatc gtggaaaaag aagacgttcc 2520
aaccacgtct tcaaagcaag tggattgatg tgacatctcc actgacgtaa gggatgacgc 2580
acaatcccac tatccttcgc aagacccttc ctctatataa ggaagttcat ttcatttgga 2640
gaggacacgc tcgagctcat ttctctatta cttcagccat aacaaaagaa ctcttttctc 2700
ttcttattaa accatgaaaa agcctgaact caccgcgacg tctgtcgaga agtttctgat 2760
cgaaaagttc gacagcgtct ccgacctgat gcagctctcg gagggcgaag aatctcgtgc 2820
tttcagcttc gatgtaggag ggcgtggata tgtcctgcgg gtaaatagct gcgccgatgg 2880
tttctacaaa gatcgttatg tttatcggca ctttgcatcg gccgcgctcc cgattccgga 2940
agtgcttgac attggggaat tcagcgagag cctgacctat tgcatctccc gccgtgcaca 3000
gggtgtcacg ttgcaagacc tgcctgaaac cgaactgccc gctgttctgc agccggtcgc 3060
ggaggccatg gatgcgatcg ctgcggccga tcttagccag acgagcgggt tcggcccatt 3120
cggaccgcaa ggaatcggtc aatacactac atggcgtgat ttcatatgcg cgattgctga 3180
tccccatgtg tatcactggc aaactgtgat ggacgacacc gtcagtgcgt ccgtcgcgca 3240
ggctctcgat gagctgatgc tttgggccga ggactgcccc gaagtccggc acctcgtgca 3300
cgcggatttc ggctccaaca atgtcctgac ggacaatggc cgcataacag cggtcattga 3360
ctggagcgag gcgatgttcg gggattccca atacgaggtc gccaacatct tcttctggag 3420
gccgtggttg gcttgtatgg agcagcagac gcgctacttc gagcggaggc atccggagct 3480
tgcaggatcg ccgcggctcc gggcgtatat gctccgcatt ggtcttgacc aactctatca 3540
gagcttggtt gacggcaatt tcgatgatgc agcttgggcg cagggtcgat gcgacgcaat 3600
cgtccgatcc ggagccggga ctgtcgggcg tacacaaatc gcccgcagaa gcgcggccgt 3660
ctggaccgat ggctgtgtag aagtactcgc cgatagtgga aaccgacgcc ccagcactcg 3720
tccgagggca aaggaatagt gaggtaccta aagaaggagt gcgtcgaagc agatcgttca 3780
aacatttggc aataaagttt cttaagattg aatcctgttg ccggtcttgc gatgattatc 3840
atataatttc tgttgaatta cgttaagcat gtaataatta acatgtaatg catgacgtta 3900
tttatgagat gggtttttat gattagagtc ccgcaattat acatttaata cgcgatagaa 3960
aacaaaatat agcgcgcaaa ctaggataaa ttatcgcgcg cggtgtcatc tatgttacta 4020
gatcgatgtc gaatcgatca acctgcatta atgaatcggc caacgcgcgg ggagaggcgg 4080

```
tttgcgtatt gggcgctctt ccgcttcctc gctcactgac tcgctgcgct cggtcgttcg   4140
gctgcggcga gcggtatcag ctcactcaaa ggcggtaata cggttatcca cagaatcagg   4200
ggataacgca ggaaagaaca tgtgagcaaa aggccagcaa aaggccagga accgtaaaaa   4260
ggccgcgttg ctggcgtttt tccataggct ccgcccccct gacgagcatc acaaaaatcg   4320
acgctcaagt cagaggtggc gaaacccgac aggactataa agataccagg cgtttccccc   4380
tggaagctcc ctcgtgcgct ctcctgttcc gaccctgccg cttaccggat acctgtccgc   4440
ctttctccct tcgggaagcg tggcgctttc tcaatgctca cgctgtaggt atctcagttc   4500
ggtgtaggtc gttcgctcca agctgggctg tgtgcacgaa ccccccgttc agcccgaccg   4560
ctgcgcctta tccggtaact atcgtcttga gtccaacccg gtaagacacg acttatcgcc   4620
actggcagca gccactggta acaggattag cagagcgagg tatgtaggcg gtgctacaga   4680
gttcttgaag tggtggccta actacggcta cactagaagg acagtatttg gtatctgcgc   4740
tctgctgaag ccagttacct tcggaaaaag agttggtagc tcttgatccg gcaaacaaac   4800
caccgctggt agcggtggtt tttttgtttg caagcagcag attacgcgca gaaaaaaagg   4860
atctcaagaa gatcctttga tcttttctac ggggtctgac gctcagtgga acgaaaactc   4920
acgttaaggg attttggtca tgacattaac ctataaaaat aggcgtatca cgaggccctt   4980
tcgtctcgcg cgtttcggtg atgacggtga aaacctctga cacatgcagc tcccggagac   5040
ggtcacagct tgtctgtaag cggatgccgg gagcagacaa gcccgtcagg gcgcgtcagc   5100
gggtgttggc gggtgtcggg gctggcttaa ctatgcggca tcagagcaga ttgtactgag   5160
agtgcaccat atggacatat tgtcgttaga acgcggctac aattaataca taaccttatg   5220
tatcatacac atacgattta ggtgacacta tagaacggcg cgccaagctt gttgaaacat   5280
ccctgaagtg tctcatttta ttttatttat tctttgctga taaaaaaata aaataaaaga   5340
agctaagcac acggtcaacc attgctctac tgctaaaagg gttatgtgta gtgttttact   5400
gcataaatta tgcagcaaac aagacaactc aaattaaaaa atttcctttg cttgtttttt   5460
tgttgtctct gacttgactt tcttgtggaa gttggttgta taaggattgg gacaccattg   5520
tccttcttaa tttaatttta ttctttgctg ataaaaaaaa aaatttcata tagtgttaaa   5580
taataatttg ttaaataacc aaaaagtcaa atatgtttac tctcgtttaa ataattgaga   5640
ttcgtccagc aaggctaaac gattgtatag atttatgaca atatttactt ttttatagat   5700
aaatgttata ttataataaa tttatataca tatattatat gttatttatt attattttaa   5760
atccttcaat attttatcaa accaactcat aatttttttt ttatctgtaa gaagcaataa   5820
aattaaatag acccacttta aggatgatcc aacctttata cagagtaaga gagttcaaat   5880
agtacccttt catatacata tcaactaaaa tattagaaat atcatggatc aaaccttata   5940
aagacattaa ataagtggat aagtataata tataaatggg tagtatataa tatataaatg   6000
gatacaaact tctctcttta taattgttat gtctccttaa catcctaata taatacataa   6060
gtgggtaata tataatatat aaatggagac aaacttcttc cattataatt gttatgtctt   6120
cttaacactt atgtctcgtt cacaatgcta aggttagaat tgtttagaaa gtcttatagt   6180
acacatttgt ttttgtacta tttgaagcat tccataagcc gtcacgattc agatgattta   6240
taataataag aggaaattta tcatagaaca ataaggtgca tagatagagt gttaatatat   6300
cataacatcc tttgtttatt catagaagaa gtgagatgga gctcagttat tatactgtta   6360
catggtcgga tacaatattc catgctctcc atgagctctt acacctacat gcattttagt   6420
tcatacttgc ggccgcagta tatcttaaat tctttaatac ggtgtactag gatattgaac   6480
```

tggttcttga tgatgaaaac ctgggccgag attgcagcta tttatagtca taggtcttgt 6540
taacatgcat ggacatttgg ccacggggtg gcatgcagtt tgacgggtgt tgaaataaac 6600
aaaaatgagg tggcggaaga gaatacgagt ttgaggttgg gttagaaaca acaaatgtga 6660
gggctcatga tgggttgagt tggtgaatgt tttgggctgc tcgattgaca cctttgtgag 6720
tacgtgttgt tgtgcatggc ttttggggtc cagttttttt ttcttgacgc ggcgatcctg 6780
atcagctagt ggataagtga tgtccactgt gtgtgattgc gtttttgttt gaattttatg 6840
aacttagaca ttgctatgca aaggatactc tcattgtgtt ttgtcttctt ttgttccttg 6900
gctttttctt atgatccaag agactagtca gtgttgtggc attcgagact accaagatta 6960
attatgatgg gggaaggata agtaactgat tagtacggac tgttaccaaa ttaattaata 7020
agcggcaaat gaagggcatg gatcaaaagc ttggatctcc tgcaggatct ggccggccgg 7080
atctc 7085

<210> SEQ ID NO 56
<211> LENGTH: 7873
<212> TYPE: DNA
<213> ORGANISM: Artificial Sequence
<220> FEATURE:
<223> OTHER INFORMATION: Plasmid pKR912

<400> SEQUENCE: 56
ggccgcaagt atgaactaaa atgcatgtag gtgtaagagc tcatggagag catggaatat 60
tgtatccgac catgtaacag tataataact gagctccatc tcacttcttc tatgaataaa 120
caaaggatgt tatgatatat taacactcta tctatgcacc ttattgttct atgataaatt 180
tcctcttatt attataaatc atctgaatcg tgacggctta tggaatgctt caaatagtac 240
aaaaacaaat gtgtactata agactttcta aacaattcta accttagcat tgtgaacgag 300
acataagtgt taagaagaca taacaattat aatggaagaa gtttgtctcc atttatatat 360
tatatattac ccacttatgt attatattag gatgttaagg agacataaca attataaaga 420
gagaagtttg tatccattta tatattatat actacccatt tatatattat acttatccac 480
ttatttaatg tctttataag gtttgatcca tgatatttct aatattttag ttgatatgta 540
tatgaaaggg tactatttga actctcttac tctgtataaa ggttggatca tccttaaagt 600
gggtctattt aattttattg cttcttacag ataaaaaaaa aattatgagt tggtttgata 660
aaatattgaa ggatttaaaa taataataaa taacatataa tatatgtata taaatttatt 720
ataatataac atttatctat aaaaaagtaa atattgtcat aaatctatac aatcgtttag 780
ccttgctgga cgaatctcaa ttatttaaac gagagtaaac atatttgact tttggttat 840 ttaacaaatt attatttaac actatatgaa attttttttt ttatcagcaa agaataaaat 900
taaattaaga aggacaatgg tgtcccaatc cttatacaac caacttccac aagaaagtca 960
agtcagagac aacaaaaaaa caagcaaagg aaatttttta atttgagttg tcttgtttgc 1020
tgcataattt atgcagtaaa acactacaca taaccctttt agcagtagag caatggttga 1080
ccgtgtgctt agcttctttt attttatttt tttatcagca aagaataaat aaaataaaat 1140
gagacacttc agggatgttt caacaagctt ggcgcgccgt tctatagtgt cacctaaatc 1200
gtatgtgtat gatacataag gttatgtatt aattgtagcc gcgttctaac gacaatatgt 1260
ccatatggtg cactctcagt acaatctgct ctgatgccgc atagttaagc cagccccgac 1320
acccgccaac acccgctgac gcgccctgac gggcttgtct gctcccggca tccgcttaca 1380
gacaagctgt gaccgtctcc gggagctgca tgtgtcagag gttttcaccg tcatcaccga 1440

-continued aacgcgcgag acgaaagggc ctcgtgatac gcctattttt ataggttaat gtcatgacca 1500
aaatccctta acgtgagttt tcgttccact gagcgtcaga ccccgtagaa aagatcaaag 1560
gatcttcttg agatcctttt tttctgcgcg taatctgctg cttgcaaaca aaaaaaccac 1620
cgctaccagc ggtggtttgt ttgccggatc aagagctacc aactcttttt ccgaaggtaa 1680
ctggcttcag cagagcgcag ataccaaata ctgtccttct agtgtagccg tagttaggcc 1740
accacttcaa gaactctgta gcaccgccta catacctcgc tctgctaatc ctgttaccag 1800
tggctgctgc cagtggcgat aagtcgtgtc ttaccgggtt ggactcaaga cgatagttac 1860
cggataaggc gcagcggtcg ggctgaacgg ggggttcgtg cacacagccc agcttggagc 1920
gaacgaccta caccgaactg agatacctac agcgtgagca ttgagaaagc gccacgcttc 1980
ccgaagggag aaaggcggac aggtatccgg taagcggcag ggtcggaaca ggagagcgca 2040
cgagggagct tccaggggga aacgcctggt atctttatag tcctgtcggg tttcgccacc 2100
tctgacttga gcgtcgattt ttgtgatgct cgtcaggggg gcggagccta tggaaaaacg 2160
ccagcaacgc ggccttttta cggttcctgg ccttttgctg gccttttgct cacatgttct 2220
ttcctgcgtt atcccctgat tctgtggata accgtattac cgcctttgag tgagctgata 2280
ccgctcgccg cagccgaacg accgagcgca gcgagtcagt gagcgaggaa gcggaagagc 2340
gcccaatacg caaaccgcct ctccccgcgc gttggccgat tcattaatgc aggttgatcg 2400
attcgacatc gatctagtaa catagatgac accgcgcgcg ataatttatc ctagtttgcg 2460
cgctatattt tgttttctat cgcgtattaa atgtataatt gcgggactct aatcataaaa 2520
acccatctca taaataacgt catgcattac atgttaatta ttacatgctt aacgtaattc 2580
aacagaaatt atatgataat catcgcaaga ccggcaacag gattcaatct taagaaactt 2640
tattgccaaa tgtttgaacg atctgcttcg acgcactcct tctttaggta cctcactatt 2700
cctttgccct cggacgagtg ctggggcgtc ggtttccact atcggcgagt acttctacac 2760
agccatcggt ccagacggcc gcgcttctgc gggcgatttg tgtacgcccg acagtcccgg 2820
ctccggatcg gacgattgcg tcgcatcgac cctgcgccca agctgcatca tcgaaattgc 2880
cgtcaaccaa gctctgatag agttggtcaa gaccaatgcg gagcatatac gcccggagcc 2940
gcggcgatcc tgcaagctcc ggatgcctcc gctcgaagta gcgcgtctgc tgctccatac 3000
aagccaacca cggcctccag aagaagatgt tggcgacctc gtattgggaa tccccgaaca 3060
tcgcctcgct ccagtcaatg accgctgtta tgcggccatt gtccgtcagg acattgttgg 3120
agccgaaatc cgcgtgcacg aggtgccgga cttcggggca gtcctcggcc caaagcatca 3180
gctcatcgag agcctgcgcg acggacgcac tgacggtgtc gtccatcaca gtttgccagt 3240
gatacacatg gggatcagca atcgcgcata tgaaatcacg ccatgtagtg tattgaccga 3300
ttccttgcgg tccgaatggg ccgaacccgc tcgtctggct aagatcggcc gcagcgatcg 3360
catccatggc ctccgcgacc ggctgcagaa cagcgggcag ttcggtttca ggcaggtctt 3420
gcaacgtgac accctgtgca cggcgggaga tgcaataggt caggctctcg ctgaattccc 3480
caatgtcaag cacttccgga atcgggagcg cggccgatgc aaagtgccga taaacataac 3540
gatctttgta gaaaccatcg gcgcagctat ttacccgcag gacatatcca cgccctccta 3600
catcgaagct gaaagcacga gattcttcgc cctccgagag ctgcatcagg tcggagacgc 3660
tgtcgaactt ttcgatcaga aacttctcga cagacgtcgc ggtgagttca ggctttttca 3720
tggtttaata agaagagaaa agagttcttt tgttatggct gaagtaatag agaaatgagc 3780
tcgagcgtgt cctctccaaa tgaaatgaac ttccttatat agaggaaggg tcttgcgaag 3840
gatagtggga ttgtgcgtca tcccttacgt cagtggagat gtcacatcaa tccacttgct 3900
ttgaagacgt ggttggaacg tcttcttttt ccacgatgct cctcgtgggt gggggtccat 3960
ctttgggacc actgtcggca gaggcatctt gaatgatagc ctttccttta tcgcaatgat 4020
ggcatttgta ggagccacct tccttttcta ctgtcctttc gatgaagtga cagatagctg 4080
ggcaatggaa tccgaggagg tttcccgaaa ttatcctttg ttgaaaagtc tcaatagccc 4140
tttggtcttc tgagactgta tctttgacat ttttggagta gaccagagtg tcgtgctcca 4200
ccatgttgac gaagattttc ttcttgtcat tgagtcgtaa aagactctgt atgaactgtt 4260
cgccagtctt cacggcgagt tctgttagat cctcgatttg aatcttagac tccatgcatg 4320
gccttagatt cagtaggaac taccttttta gagactccaa tctctattac ttgccttggt 4380
ttatgaagca agccttgaat cgtccatact ggaatagtac ttctgatctt gagaaatatg 4440
tctttctctg tgttcttgat gcaattagtc ctgaatcttt tgactgcatc tttaaccttc 4500
ttgggaaggt atttgatctc ctggagattg ttactcgggt agatcgtctt gatgagacct 4560
gctgcgtagg cctctctaac catctgtggg tcagcattct ttctgaaatt gaagaggcta 4620
accttctcat tatcagtggt gaacatagtg tcgtcacctt caccttcgaa cttccttcct 4680
agatcgtaaa gatagaggaa atcgtccatt gtaatctccg gggcaaagga gatctctttt 4740
ggggctggat cactgctggg ccttttggtt cctagcgtga gccagtgggc tttttgcttt 4800
ggtgggcttg ttagggcctt agcaaagctc ttgggcttga gttgagcttc tcctttgggg 4860
atgaagttca acctgtctgt ttgctgactt gttgtgtacg cgtcagctgc tgctcttgcc 4920
tctgtaatag tggcaaattt cttgtgtgca actccgggaa cgccgtttgt tgccgccttt 4980
gtacaacccc agtcatcgta tataccggca tgtggaccgt tatacacaac gtagtagttg 5040
atatgagggt gttgaatacc cgattctgct ctgagaggag caactgtgct gttaagctca 5100
gatttttgtg ggattggaat tggatcgatc tcgatcccgc gaaattaata cgactcacta 5160
tagggagacc acaacggttt ccctctagaa ataattttgt ttaactttaa gaaggagata 5220
tacccatgga aaagcctgaa ctcaccgcga cgtctgtcga gaagtttctg atcgaaaagt 5280
tcgacagcgt ctccgacctg atgcagctct cggagggcga agaatctcgt gctttcagct 5340
tcgatgtagg agggcgtgga tatgtcctgc gggtaaatag ctgcgccgat ggtttctaca 5400
aagatcgtta tgtttatcgg cactttgcat cggccgcgct cccgattccg gaagtgcttg 5460
acattgggga attcagcgag agcctgacct attgcatctc ccgccgtgca cagggtgtca 5520
cgttgcaaga cctgcctgaa accgaactgc ccgctgttct gcagccggtc gcggaggcta 5580
tggatgcgat cgctgcggcc gatcttagcc agacgagcgg gttcggccca ttcggaccgc 5640
aaggaatcgg tcaatacact acatggcgtg atttcatatg cgcgattgct gatccccatg 5700
tgtatcactg gcaaactgtg atggacgaca ccgtcagtgc gtccgtcgcg caggctctcg 5760
atgagctgat gctttgggcc gaggactgcc ccgaagtccg gcacctcgtg cacgcggatt 5820
tcggctccaa caatgtcctg acggacaatg gccgcataac agcggtcatt gactggagcg 5880
aggcgatgtt cggggattcc caatacgagg tcgccaacat cttcttctgg aggccgtggt 5940
tggcttgtat ggagcagcag acgcgctact tcgagcggag gcatccggag cttgcaggat 6000
cgccgcggct ccgggcgtat atgctccgca ttggtcttga ccaactctat cagagcttgg 6060
ttgacggcaa tttcgatgat gcagcttggg cgcagggtcg atgcgacgca atcgtccgat 6120
ccggagccgg gactgtcggg cgtacacaaa tcgcccgcag aagcgcggcc gtctggaccg 6180
atggctgtgt agaagtactc gccgatagtg gaaaccgacg ccccagcact cgtccgaggg 6240

```
caaaggaata gtgaggtaca gcttggatcg atccggctgc taacaaagcc cgaaaggaag   6300
ctgagttggc tgctgccacc gctgagcaat aactagcata accccttggg gcctctaaac   6360
gggtcttgag gggttttttg ctgaaaggag gaactatatc cggatgatcg ggcgcgccgt   6420
cgacggatcc gtacgagatc cggccggcca gatcctgcag gagatccaag cttttgatcc   6480
atgcccttca tttgccgctt attaattaat ttggtaacag tccgtactaa tcagttactt   6540
atccttcccc catcataatt aatcttggta gtctcgaatg ccacaacact gactagtctc   6600
ttggatcata agaaaaagcc aaggaacaaa agaagacaaa acacaatgag agtatccttt   6660
gcatagcaat gtctaagttc ataaaattca aacaaaaacg caatcacaca cagtggacat   6720
cacttatcca ctagctgatc aggatcgccg cgtcaagaaa aaaaaactgg accccaaaag   6780
ccatgcacaa caacacgtac tcacaaaggt gtcaatcgag cagcccaaaa cattcaccaa   6840
ctcaacccat catgagccct cacatttgtt gtttctaacc caacctcaaa ctcgtattct   6900
cttccgccac ctcatttttg tttatttcaa cacccgtcaa actgcatgcc accccgtggc   6960
caaatgtcca tgcatgttaa caagacctat gactataaat agctgcaatc tcggcccagg   7020
ttttcatcat caagaaccag ttcaatatcc tagtacaccg tattaaagaa tttaagatat   7080
actgcggccg caccatggag gtggtgaatg aaatagtctc aattgggcag gaagttttac   7140
ccaaagttga ttatgcccaa ctctggagtg atgccagtca ctgtgaggtg ctttacttgt   7200
ccatcgcatt tgtcatcttg aagttcactc ttggcccccct tggtccaaaa ggtcagtctc   7260
gtatgaagtt tgttttcacc aattacaacc ttctcatgtc catttattcg ttgggatcat   7320
tcctctcaat ggcatatgcc atgtacacca tcggtgttat gtctgacaac tgcgagaagg   7380
cttttgacaa caacgtcttc aggatcacca cgcagttgtt ctatttgagc aagttcctgg   7440
agtatattga ctccttctat ttgccactga tgggcaagcc tctgacctgg ttgcaattct   7500
tccatcattt gggggcaccg atggatatgt ggctgttcta taattaccga aatgaagctg   7560
tttggatttt tgtgctgttg aatggtttca tccactggat catgtacggt tattattgga   7620
ccagattgat caagctgaag ttccccatgc caaaatccct gattacatca atgcagatca   7680
ttcaattcaa tgttggtttc tacattgtct ggaagtacag gaacattccc tgttatcgcc   7740
aagatgggat gaggatgttt ggctggttct tcaattactt ttatgttggc acagtcttgt   7800
gtttgttctt gaatttctat gtgcaaacgt atatcgtcag gaagcacaag ggagccaaaa   7860
agattcagtg agc                                                      7873
```

<210> SEQ ID NO 57
<211> LENGTH: 2540
<212> TYPE: DNA
<213> ORGANISM: Artificial Sequence
<220> FEATURE:
<223> OTHER INFORMATION: Plasmid pKS102

<400> SEQUENCE: 57

```
cgatcatccg gatatagttc ctcctttcag caaaaaaccc ctcaagaccc gtttagaggc     60
cccaaggggt tatgctagtt attgctcagc ggtggcagca gccaactcag cttcctttcg    120
ggctttgtta gcagccggat cgatccaagc tgtacctcac tattcctttg ccctcggacg    180
agtgctgggg cgtcggtttc cactatcggc gagtacttct acacagccat cggtccagac    240
ggccgcgctt ctgcgggcga tttgtgtacg cccgacagtc ccggctccgg atcggacgat    300
tgcgtcgcat cgaccctgcg cccaagctgc atcatcgaaa ttgccgtcaa ccaagctctg    360
atagagttgg tcaagaccaa tgcggagcat atacgcccgg agccgcggcg atcctgcaag    420
```

```
ctccggatgc ctccgctcga agtagcgcgt ctgctgctcc atacaagcca accacggcct    480
ccagaagaag atgttggcga cctcgtattg ggaatccccg aacatcgcct cgctccagtc    540
aatgaccgct gttatgcggc cattgtccgt caggacattg ttggagccga aatccgcgtg    600
cacgaggtgc cggacttcgg ggcagtcctc ggcccaaagc atcagctcat cgagagcctg    660
cgcgacggac gcactgacgg tgtcgtccat cacagtttgc cagtgataca catggggatc    720
agcaatcgcg catatgaaat cacgccatgt agtgtattga ccgattcctt gcggtccgaa    780
tgggccgaac ccgctcgtct ggctaagatc ggccgcagcg atcgcatcca tagcctccgc    840
gaccggctgc agaacagcgg gcagttcggt ttcaggcagg tcttgcaacg tgacaccctg    900
tgcacggcgg gagatgcaat aggtcaggct ctcgctgaat tccccaatgt caagcacttc    960
cggaatcggg agcgcggccg atgcaaagtg ccgataaaca taacgatctt tgtagaaacc   1020
atcggcgcag ctatttaccc gcaggacata tccacgccct cctacatcga agctgaaagc   1080
acgagattct tcgccctccg agagctgcat caggtcggag acgctgtcga acttttcgat   1140
cagaaacttc tcgacagacg tcgcggtgag ttcaggcttt tccatgggta tatctccttc   1200
ttaaagttaa acaaaattat ttctagaggg aaaccgttgt ggtctcccta tagtgagtcg   1260
tattaatttc gcgggatcga gatctgatca acctgcatta atgaatcggc caacgcgcgg   1320
ggagaggcgg tttgcgtatt gggcgctctt ccgcttcctc gctcactgac tcgctgcgct   1380
cggtcgttcg gctgcggcga gcggtatcag ctcactcaaa ggcggtaata cggttatcca   1440
cagaatcagg ggataacgca ggaaagaaca tgtgagcaaa aggccagcaa aaggccagga   1500
accgtaaaaa ggccgcgttg ctggcgtttt tccataggct ccgcccccct gacgagcatc   1560
acaaaaatcg acgctcaagt cagaggtggc gaaacccgac aggactataa agataccagg   1620
cgtttccccc tggaagctcc ctcgtgcgct ctcctgttcc gaccctgccg cttaccggat   1680
acctgtccgc ctttctccct tcgggaagcg tggcgctttc tcaatgctca cgctgtaggt   1740
atctcagttc ggtgtaggtc gttcgctcca agctgggctg tgtgcacgaa ccccccgttc   1800
agcccgaccg ctgcgcctta tccggtaact atcgtcttga gtccaacccg gtaagacacg   1860
acttatcgcc actggcagca gccactggta acaggattag cagagcgagg tatgtaggcg   1920
gtgctacaga gttcttgaag tggtggccta actacggcta cactagaagg acagtatttg   1980
gtatctgcgc tctgctgaag ccagttacct tcggaaaaag agttggtagc tcttgatccg   2040
gcaaacaaac caccgctggt agcggtggtt tttttgtttg caagcagcag attacgcgca   2100
gaaaaaaagg atctcaagaa gatcctttga tcttttctac ggggtctgac gctcagtgga   2160
acgaaaactc acgttaaggg attttggtca tgacattaac ctataaaaat aggcgtatca   2220
cgaggccctt tcgtctcgcg cgtttcggtg atgacggtga aaacctctga cacatgcagc   2280
tcccggagac ggtcacagct tgtctgtaag cggatgccgg gagcagacaa gcccgtcagg   2340
gcgcgtcagc gggtgttggc gggtgtcggg gctggcttaa ctatgcggca tcagagcaga   2400
ttgtactgag agtgcaccat atggacatat tgtcgttaga acgcggctac aattaataca   2460
taaccttatg tatcatacac atacgattta ggtgacacta tagaacggcg cgccaagctt   2520
ggatccgtcg acggcgcgcc                                                2540
```

<210> SEQ ID NO 58
<211> LENGTH: 4359
<212> TYPE: DNA
<213> ORGANISM: Artificial Sequence
<220> FEATURE:
<223> OTHER INFORMATION: Plasmid pKR197

<400> SEQUENCE: 58
cgcgcccgat catccggata tagttcctcc tttcagcaaa aaacccctca agacccgttt 60
agaggcccca aggggttatg ctagttattg ctcagcggtg gcagcagcca actcagcttc 120
ctttcgggct ttgttagcag ccggatcgat ccaagctgta cctcactatt cctttgccct 180
cggacgagtg ctggggcgtc ggtttccact atcggcgagt acttctacac agccatcggt 240
ccagacggcc gcgcttctgc gggcgatttg tgtacgcccg acagtcccgg ctccggatcg 300
gacgattgcg tcgcatcgac cctgcgccca agctgcatca tcgaaattgc cgtcaaccaa 360
gctctgatag agttggtcaa gaccaatgcg gagcatatac gcccggagcc gcggcgatcc 420
tgcaagctcc ggatgcctcc gctcgaagta gcgcgtctgc tgctccatac aagccaacca 480
cggcctccag aagaagatgt tggcgacctc gtattgggaa tccccgaaca tcgcctcgct 540
ccagtcaatg accgctgtta tgcggccatt gtccgtcagg acattgttgg agccgaaatc 600
cgcgtgcacg aggtgccgga cttcggggca gtcctcggcc caaagcatca gctcatcgag 660
agcctgcgcg acggacgcac tgacggtgtc gtccatcaca gtttgccagt gatacacatg 720
gggatcagca atcgcgcata tgaaatcacg ccatgtagtg tattgaccga ttccttgcgg 780
tccgaatggg ccgaacccgc tcgtctggct aagatcggcc gcagcgatcg catccatagc 840
ctccgcgacc ggctgcagaa cagcgggcag ttcggtttca ggcaggtctt gcaacgtgac 900
accctgtgca cggcgggaga tgcaataggt caggctctcg ctgaattccc caatgtcaag 960
cacttccgga atcgggagcg cggccgatgc aaagtgccga taaacataac gatctttgta 1020
gaaaccatcg gcgcagctat ttacccgcag gacatatcca cgccctccta catcgaagct 1080
gaaagcacga gattcttcgc cctccgagag ctgcatcagg tcggagacgc tgtcgaactt 1140
ttcgatcaga aacttctcga cagacgtcgc ggtgagttca ggctttttcca tgggtatatc 1200
tccttcttaa agttaaacaa aattatttct agagggaaac cgttgtggtc tccctatagt 1260
gagtcgtatt aatttcgcgg gatcgagatc tgatcaacct gcattaatga atcggccaac 1320
gcgcggggag aggcggtttg cgtattgggc gctcttccgc ttcctcgctc actgactcgc 1380
tgcgctcggt cgttcggctg cggcgagcgg tatcagctca ctcaaaggcg gtaatacggt 1440
tatccacaga atcaggggat aacgcaggaa agaacatgtg agcaaaaggc cagcaaaagg 1500
ccaggaaccg taaaaaggcc gcgttgctgg cgtttttcca taggctccgc ccccctgacg 1560
agcatcacaa aaatcgacgc tcaagtcaga ggtggcgaaa cccgacagga ctataaagat 1620
accaggcgtt tccccctgga agctccctcg tgcgctctcc tgttccgacc ctgccgctta 1680
ccggatacct gtccgccttt ctcccttcgg gaagcgtggc gctttctcaa tgctcacgct 1740
gtaggtatct cagttcggtg taggtcgttc gctccaagct gggctgtgtg cacgaacccc 1800
ccgttcagcc cgaccgctgc gccttatccg gtaactatcg tcttgagtcc aacccggtaa 1860
gacacgactt atcgccactg gcagcagcca ctggtaacag gattagcaga gcgaggtatg 1920
taggcggtgc tacagagttc ttgaagtggt ggcctaacta cggctacact agaaggacag 1980
tatttggtat ctgcgctctg ctgaagccag ttaccttcgg aaaaagagtt ggtagctctt 2040
gatccggcaa acaaaccacc gctggtagcg gtggtttttt tgtttgcaag cagcagatta 2100
cgcgcagaaa aaaaggatct caagaagatc ctttgatctt ttctacgggg tctgacgctc 2160
agtggaacga aaactcacgt taagggattt tggtcatgac attaacctat aaaaataggc 2220
gtatcacgag gccctttcgt ctcgcgcgtt tcggtgatga cggtgaaaac ctctgacaca 2280
tgcagctccc ggagacggtc acagcttgtc tgtaagcgga tgccgggagc agacaagccc 2340

```
gtcagggcgc gtcagcgggt gttggcgggt gtcggggctg gcttaactat gcggcatcag   2400
agcagattgt actgagagtg caccatatgg acatattgtc gttagaacgc ggctacaatt   2460
aatacataac cttatgtatc atacacatac gatttaggtg acactataga acggcgcgcc   2520
aagcttgttg aaacatccct gaagtgtctc attttatttt atttattctt tgctgataaa   2580
aaaataaaat aaaagaagct aagcacacgg tcaaccattg ctctactgct aaaagggtta   2640
tgtgtagtgt tttactgcat aaattatgca gcaaacaaga caactcaaat taaaaaattt   2700
cctttgcttg ttttttttgtt gtctctgact tgactttctt gtggaagttg gttgtataag   2760
gattgggaca ccattgtcct tcttaattta attttattct ttgctgataa aaaaaaaaat   2820
ttcatatagt gttaaataat aatttgttaa ataaccaaaa agtcaaatat gtttactctc   2880
gtttaaataa ttgagattcg tccagcaagg ctaaacgatt gtatagattt atgacaatat   2940
ttactttttt atagataaat gttatattat aataaattta tatacatata ttatatgtta   3000
tttattatta ttttaaatcc ttcaatattt tatcaaacca actcataatt ttttttttat   3060
ctgtaagaag caataaaatt aaatagaccc actttaagga tgatccaacc tttatacaga   3120
gtaagagagt tcaaatagta ccctttcata tacatatcaa ctaaaatatt agaaatatca   3180
tggatcaaac cttataaaga cattaaataa gtggataagt ataatatata aatgggtagt   3240
atataatata taaatggata caaacttctc tctttataat tgttatgtct ccttaacatc   3300
ctaatataat acataagtgg gtaatatata atatataaat ggagacaaac ttcttccatt   3360
ataattgtta tgtcttctta acacttatgt ctcgttcaca atgctaaggt tagaattgtt   3420
tagaaagtct tatagtacac atttgttttt gtactatttg aagcattcca taagccgtca   3480
cgattcagat gatttataat aataagagga aatttatcat agaacaataa ggtgcataga   3540
tagagtgtta atatatcata acatcctttg tttattcata gaagaagtga gatggagctc   3600
agttattata ctgttacatg gtcggataca atattccatg ctctccatga gctcttacac   3660
ctacatgcat tttagttcat acttgcggcc gcagtatatc ttaaattctt taatacggtg   3720
tactaggata ttgaactggt tcttgatgat gaaaacctgg gccgagattg cagctattta   3780
tagtcatagg tcttgttaac atgcatggac atttggccac ggggtggcat gcagtttgac   3840
gggtgttgaa ataaacaaaa atgaggtggc ggaagagaat acgagtttga ggttgggtta   3900
gaaacaacaa atgtgagggc tcatgatggg ttgagttggt gaatgttttg ggctgctcga   3960
ttgacacctt tgtgagtacg tgttgttgtg catggctttt ggggtccagt tttttttttct   4020
tgacgcggcg atcctgatca gctagtggat aagtgatgtc cactgtgtgt gattgcgttt   4080
ttgtttgaat tttatgaact tagacattgc tatgcaaagg atactctcat tgtgttttgt   4140
cttcttttgt tccttggctt tttcttatga tccaagagac tagtcagtgt tgtggcattc   4200
gagactacca agattaatta tgatgggga aggataagta actgattagt acggactgtt   4260
accaaattaa ttaataagcg gcaaatgaag ggcatggatc aaaagcttgg atctcctgca   4320
ggatctggcc ggccggatct cgtacggatc cgtcgacgg                          4359
```

```
<210> SEQ ID NO 59
<211> LENGTH: 5147
<212> TYPE: DNA
<213> ORGANISM: Artificial Sequence
<220> FEATURE:
<223> OTHER INFORMATION: Plasmid pKR911

<400> SEQUENCE: 59

ggccgcaagt atgaactaaa atgcatgtag gtgtaagagc tcatggagag catggaatat     60
```

```
tgtatccgac catgtaacag tataataact gagctccatc tcacttcttc tatgaataaa    120
caaaggatgt tatgatatat taacactcta tctatgcacc ttattgttct atgataaatt    180
tcctcttatt attataaatc atctgaatcg tgacggctta tggaatgctt caaatagtac    240
aaaaacaaat gtgtactata agactttcta aacaattcta accttagcat tgtgaacgag    300
acataagtgt taagaagaca taacaattat aatggaagaa gtttgtctcc atttatatat    360
tatatattac ccacttatgt attatattag gatgttaagg agacataaca attataaaga    420
gagaagtttg tatccattta tatattatat actacccatt tatatattat acttatccac    480
ttatttaatg tctttataag gtttgatcca tgatatttct aatattttag ttgatatgta    540
tatgaaaggg tactatttga actctcttac tctgtataaa ggttggatca tccttaaagt    600
gggtctattt aattttattg cttcttacag ataaaaaaaa aattatgagt tggtttgata    660
aaatattgaa ggatttaaaa taataataaa taacatataa tatatgtata taaatttatt    720
ataatataac atttatctat aaaaaagtaa atattgtcat aaatctatac aatcgtttag    780
ccttgctgga cgaatctcaa ttatttaaac gagagtaaac atatttgact ttttggttat    840
ttaacaaatt attatttaac actatatgaa attttttttt ttatcagcaa agaataaaat    900
taaattaaga aggacaatgg tgtcccaatc cttatacaac caacttccac aagaaagtca    960
agtcagagac aacaaaaaaa caagcaaagg aaatttttta atttgagttg tcttgtttgc   1020
tgcataattt atgcagtaaa acactacaca taaccctttt agcagtagag caatggttga   1080
ccgtgtgctt agcttctttt attttatttt tttatcagca aagaataaat aaaataaaat   1140
gagacacttc agggatgttt caacaagctt ggcgcgccgt tctatagtgt cacctaaatc   1200
gtatgtgtat gatacataag gttatgtatt aattgtagcc gcgttctaac gacaatatgt   1260
ccatatggtg cactctcagt acaatctgct ctgatgccgc atagttaagc cagccccgac   1320
acccgccaac acccgctgac gcgccctgac gggcttgtct gctcccggca tccgcttaca   1380
gacaagctgt gaccgtctcc gggagctgca tgtgtcagag gttttcaccg tcatcaccga   1440
aacgcgcgag acgaaagggc ctcgtgatac gcctattttt ataggttaat gtcatgacca   1500
aaatccctta acgtgagttt tcgttccact gagcgtcaga ccccgtagaa aagatcaaag   1560
gatcttcttg agatcctttt tttctgcgcg taatctgctg cttgcaaaca aaaaaaccac   1620
cgctaccagc ggtggtttgt ttgccggatc aagagctacc aactcttttt ccgaaggtaa   1680
ctggcttcag cagagcgcag ataccaaata ctgtccttct agtgtagccg tagttaggcc   1740
accacttcaa gaactctgta gcaccgccta catacctcgc tctgctaatc ctgttaccag   1800
tggctgctgc cagtggcgat aagtcgtgtc ttaccgggtt ggactcaaga cgatagttac   1860
cggataaggc gcagcggtcg ggctgaacgg ggggttcgtg cacacagccc agcttggagc   1920
gaacgaccta caccgaactg agatacctac agcgtgagca ttgagaaagc gccacgcttc   1980
ccgaagggag aaaggcggac aggtatccgg taagcggcag ggtcggaaca ggagagcgca   2040
cgagggagct tccaggggga aacgcctggt atctttatag tcctgtcggg tttcgccacc   2100
tctgacttga gcgtcgattt ttgtgatgct cgtcaggggg gcggagccta tggaaaaacg   2160
ccagcaacgc ggccttttta cggttcctgg ccttttgctg gccttttgct cacatgttct   2220
ttcctgcgtt atcccctgat tctgtggata accgtattac cgcctttgag tgagctgata   2280
ccgctcgccg cagccgaacg accgagcgca gcgagtcagt gagcgaggaa gcggaagagc   2340
gcccaatacg caaaccgcct ctccccgcgc gttggccgat tcattaatgc aggttgatca   2400
gatctcgatc ccgcgaaatt aatacgactc actataggga gaccacaacg gtttccctct   2460
```

-continued agaaataatt ttgtttaact ttaagaagga gatataccca tggaaaagcc tgaactcacc 2520
gcgacgtctg tcgagaagtt tctgatcgaa aagttcgaca gcgtctccga cctgatgcag 2580
ctctcggagg gcgaagaatc tcgtgctttc agcttcgatg taggagggcg tggatatgtc 2640
ctgcgggtaa atagctgcgc cgatggtttc tacaaagatc gttatgttta tcggcacttt 2700
gcatcggccg cgctcccgat tccggaagtg cttgacattg gggaattcag cgagagcctg 2760
acctattgca tctcccgccg tgcacagggt gtcacgttgc aagacctgcc tgaaaccgaa 2820
ctgcccgctg ttctgcagcc ggtcgcggag gctatggatg cgatcgctgc ggccgatctt 2880
agccagacga gcgggttcgg cccattcgga ccgcaaggaa tcggtcaata cactacatgg 2940
cgtgatttca tatgcgcgat tgctgatccc catgtgtatc actggcaaac tgtgatggac 3000
gacaccgtca gtgcgtccgt cgcgcaggct ctcgatgagc tgatgctttg ggccgaggac 3060
tgccccgaag tccggcacct cgtgcacgcg gatttcggct ccaacaatgt cctgacggac 3120
aatggccgca taacagcggt cattgactgg agcgaggcga tgttcgggga ttcccaatac 3180
gaggtcgcca acatcttctt ctggaggccg tggttggctt gtatggagca gcagacgcgc 3240
tacttcgagc ggaggcatcc ggagcttgca ggatcgccgc ggctccgggc gtatatgctc 3300
cgcattggtc ttgaccaact ctatcagagc ttggttgacg gcaatttcga tgatgcagct 3360
tgggcgcagg gtcgatgcga cgcaatcgtc cgatccggag ccgggactgt cgggcgtaca 3420
caaatcgccc gcagaagcgc ggccgtctgg accgatggct gtgtagaagt actcgccgat 3480
agtggaaacc gacgccccag cactcgtccg agggcaaagg aatagtgagg tacagcttgg 3540
atcgatccgg ctgctaacaa agcccgaaag gaagctgagt tggctgctgc caccgctgag 3600
caataactag cataacccct tggggcctct aaacgggtct tgaggggttt tttgctgaaa 3660
ggaggaacta tatccggatg atcgggcgcg ccgtcgacgg atccgtacga gatccggccg 3720
gccagatcct gcaggagatc caagcttttg atccatgccc ttcatttgcc gcttattaat 3780
taatttggta acagtccgta ctaatcagtt acttatcctt cccccatcat aattaatctt 3840
ggtagtctcg aatgccacaa cactgactag tctcttggat cataagaaaa agccaaggaa 3900
caaaagaaga caaaacacaa tgagagtatc ctttgcatag caatgtctaa gttcataaaa 3960
ttcaaacaaa aacgcaatca cacacagtgg acatcactta tccactagct gatcaggatc 4020
gccgcgtcaa gaaaaaaaaa ctggacccca aaagccatgc acaacaacac gtactcacaa 4080
aggtgtcaat cgagcagccc aaaacattca ccaactcaac ccatcatgag ccctcacatt 4140
tgttgtttct aacccaacct caaactcgta ttctcttccg ccacctcatt tttgtttatt 4200
tcaacacccg tcaaactgca tgccaccccg tggccaaatg tccatgcatg ttaacaagac 4260
ctatgactat aaatagctgc aatctcggcc caggttttca tcatcaagaa ccagttcaat 4320
atcctagtac accgtattaa agaatttaag atatactgcg gccgcaccat ggaggtggtg 4380
aatgaaatag tctcaattgg gcaggaagtt ttacccaaag ttgattatgc ccaactctgg 4440
agtgatgcca gtcactgtga ggtgctttac ttgtccatcg catttgtcat cttgaagttc 4500
actcttggcc cccttggtcc aaaaggtcag tctcgtatga agtttgtttt caccaattac 4560
aaccttctca tgtccattta ttcgttggga tcattcctct caatggcata tgccatgtac 4620
accatcggtg ttatgtctga caactgcgag aaggcttttg acaacaacgt cttcaggatc 4680
accacgcagt tgttctattt gagcaagttc ctggagtata ttgactcctt ctatttgcca 4740
ctgatgggca agcctctgac ctggttgcaa ttcttccatc atttgggggc accgatggat 4800
atgtggctgt tctataatta ccgaaatgaa gctgtttgga tttttgtgct gttgaatggt 4860

```
ttcatccact ggatcatgta cggttattat tggaccagat tgatcaagct gaagttcccc   4920

atgccaaaat ccctgattac atcaatgcag atcattcaat tcaatgttgg tttctacatt   4980

gtctggaagt acaggaacat tccctgttat cgccaagatg ggatgaggat gtttggctgg   5040

ttcttcaatt acttttatgt tggcacagtc ttgtgtttgt tcttgaattt ctatgtgcaa   5100

acgtatatcg tcaggaagca caagggagcc aaaaagattc agtgagc                 5147


<210> SEQ ID NO 60
<211> LENGTH: 1266
<212> TYPE: DNA
<213> ORGANISM: Euglena gracilis

<400> SEQUENCE: 60

atgaagtcaa agcgccaagc gcttcccctt acaattgatg gaacaacata tgatgtgtct     60

gcctgggtca atttccaccc tggtggtgcg gaaattatag agaattacca aggaagggat    120

gccactgatg ccttcatggt tatgcactct caagaagcct tcgacaagct caagcgcatg    180

cccaaaatca atcccagttc tgagttgcca ccccaggctg cagtgaatga agctcaagag    240

gatttccgga agctccgaga agagttgatc gcaactggca tgtttgatgc ctccccccctc    300

tggtactcat acaaaatcag caccacactg ggccttggag tgctgggtta tttcctgatg    360

gttcagtatc agatgtattt cattggggca gtgttgcttg ggatgcacta tcaacagatg    420

ggctggcttt ctcatgacat ttgccaccac cagactttca agaaccggaa ctggaacaac    480

ctcgtgggac tggtatttgg caatggtctg caaggttttt ccgtgacatg gtggaaggac    540

agacacaatg cacatcattc ggcaaccaat gttcaagggc acgaccctga tattgacaac    600

ctcccccctct tagcctggtc tgaggatgac gtcacacggg cgtcaccgat ttcccgcaag    660

ctcattcagt tccagcagta ctatttcttg gtcatctgta tcttgttgcg gttcatttgg    720

tgtttccaga gcgtgttgac cgtgcgcagt ttgaaggaca gagataacca attctatcgc    780

tctcagtata agaaggaggc cattggcctc gccctgcact ggaccttgaa gaccctgttc    840

cacttattct ttatgcccag catcctcaca tcgctgttgg tgtttttcgt ttcggagctg    900

gttggcggct tcggcattgc gatcgtggtg ttcatgaacc actacccact ggagaagatc    960

ggggactcag tctgggatgg ccatggattc tcggttggcc agatccatga gaccatgaac   1020

attcggcgag ggattatcac agattggttt ttcggaggct tgaattacca gattgagcac   1080

catttgtggc cgaccctccc tcgccacaac ctgacagcgg ttagctacca ggtggaacag   1140

ctgtgccaga agcacaacct gccgtatcgg aacccgctgc cccatgaagg gttggtcatc   1200

ctgctgcgct atctggcggt gttcgcccgg atggcggaga agcaacccgc ggggaaggct   1260

ctataa                                                              1266


<210> SEQ ID NO 61
<211> LENGTH: 421
<212> TYPE: PRT
<213> ORGANISM: Euglena gracilis
<220> FEATURE:
<221> NAME/KEY: MISC_FEATURE
<223> OTHER INFORMATION: delta-8 desaturase ("Eg5" or "EgD8")
<300> PUBLICATION INFORMATION:
<302> TITLE: DELTA-8 DESATURASE AND ITS USE IN MAKING POLYUNSATURATED
      FATTY ACIDS
<310> PATENT DOCUMENT NUMBER: WO 2006/012325 and WO 2006/012326
<311> PATENT FILING DATE: 2005-06-24
<312> PUBLICATION DATE: 2006-02-02
<313> RELEVANT RESIDUES IN SEQ ID NO: (1)..(421)
<300> PUBLICATION INFORMATION:
<302> TITLE: DELTA-8 DESATURASE AND ITS USE IN MAKING POLYUNSATURATED
```

FATTY ACIDS
<310> PATENT DOCUMENT NUMBER: US_2005-0287652-A1
<311> PATENT FILING DATE: 2005-06-24
<312> PUBLICATION DATE: 2005-12-29
<313> RELEVANT RESIDUES IN SEQ ID NO: (1)..(421)

<400> SEQUENCE: 61

```
Met Lys Ser Lys Arg Gln Ala Leu Pro Leu Thr Ile Asp Gly Thr Thr
1               5                   10                  15

Tyr Asp Val Ser Ala Trp Val Asn Phe His Pro Gly Gly Ala Glu Ile
            20                  25                  30

Ile Glu Asn Tyr Gln Gly Arg Asp Ala Thr Asp Ala Phe Met Val Met
        35                  40                  45

His Ser Gln Glu Ala Phe Asp Lys Leu Lys Arg Met Pro Lys Ile Asn
    50                  55                  60

Pro Ser Ser Glu Leu Pro Pro Gln Ala Ala Val Asn Glu Ala Gln Glu
65                  70                  75                  80

Asp Phe Arg Lys Leu Arg Glu Glu Leu Ile Ala Thr Gly Met Phe Asp
                85                  90                  95

Ala Ser Pro Leu Trp Tyr Ser Tyr Lys Ile Ser Thr Thr Leu Gly Leu
            100                 105                 110

Gly Val Leu Gly Tyr Phe Leu Met Val Gln Tyr Gln Met Tyr Phe Ile
        115                 120                 125

Gly Ala Val Leu Leu Gly Met His Tyr Gln Gln Met Gly Trp Leu Ser
    130                 135                 140

His Asp Ile Cys His His Gln Thr Phe Lys Asn Arg Asn Trp Asn Asn
145                 150                 155                 160

Leu Val Gly Leu Val Phe Gly Asn Gly Leu Gln Gly Phe Ser Val Thr
                165                 170                 175

Trp Trp Lys Asp Arg His Asn Ala His His Ser Ala Thr Asn Val Gln
            180                 185                 190

Gly His Asp Pro Asp Ile Asp Asn Leu Pro Leu Leu Ala Trp Ser Glu
        195                 200                 205

Asp Asp Val Thr Arg Ala Ser Pro Ile Ser Arg Lys Leu Ile Gln Phe
    210                 215                 220

Gln Gln Tyr Tyr Phe Leu Val Ile Cys Ile Leu Leu Arg Phe Ile Trp
225                 230                 235                 240

Cys Phe Gln Ser Val Leu Thr Val Arg Ser Leu Lys Asp Arg Asp Asn
                245                 250                 255

Gln Phe Tyr Arg Ser Gln Tyr Lys Lys Glu Ala Ile Gly Leu Ala Leu
            260                 265                 270

His Trp Thr Leu Lys Thr Leu Phe His Leu Phe Phe Met Pro Ser Ile
        275                 280                 285

Leu Thr Ser Leu Leu Val Phe Phe Val Ser Glu Leu Val Gly Gly Phe
    290                 295                 300

Gly Ile Ala Ile Val Val Phe Met Asn His Tyr Pro Leu Glu Lys Ile
305                 310                 315                 320

Gly Asp Ser Val Trp Asp Gly His Gly Phe Ser Val Gly Gln Ile His
                325                 330                 335

Glu Thr Met Asn Ile Arg Arg Gly Ile Ile Thr Asp Trp Phe Phe Gly
            340                 345                 350

Gly Leu Asn Tyr Gln Ile Glu His His Leu Trp Pro Thr Leu Pro Arg
        355                 360                 365

His Asn Leu Thr Ala Val Ser Tyr Gln Val Glu Gln Leu Cys Gln Lys
    370                 375                 380
```

-continued

His Asn Leu Pro Tyr Arg Asn Pro Leu Pro His Glu Gly Leu Val Ile
385 390 395 400

Leu Leu Arg Tyr Leu Ala Val Phe Ala Arg Met Ala Glu Lys Gln Pro
405 410 415

Ala Gly Lys Ala Leu
420

<210> SEQ ID NO 62
<211> LENGTH: 19
<212> TYPE: DNA
<213> ORGANISM: Artificial Sequence
<220> FEATURE:
<223> OTHER INFORMATION: Primer Eg5-1

<400> SEQUENCE: 62
gaaatgaagt caaagcgcc 19

<210> SEQ ID NO 63
<211> LENGTH: 19
<212> TYPE: DNA
<213> ORGANISM: Artificial Sequence
<220> FEATURE:
<223> OTHER INFORMATION: Primer Eg3-3

<400> SEQUENCE: 63
ccttatagag ccttccccg 19

<210> SEQ ID NO 64
<211> LENGTH: 19
<212> TYPE: DNA
<213> ORGANISM: Artificial Sequence
<220> FEATURE:
<223> OTHER INFORMATION: T7 primer

<400> SEQUENCE: 64
ggaaacagct atgaccatg 19

<210> SEQ ID NO 65
<211> LENGTH: 22
<212> TYPE: DNA
<213> ORGANISM: Artificial Sequence
<220> FEATURE:
<223> OTHER INFORMATION: Primer M13-28Rev

<400> SEQUENCE: 65
gtaatacgac tcactatagg gc 22

<210> SEQ ID NO 66
<211> LENGTH: 19
<212> TYPE: DNA
<213> ORGANISM: Artificial Sequence
<220> FEATURE:
<223> OTHER INFORMATION: Primer Eg3-2

<400> SEQUENCE: 66
aatgttcatg gtctcatgg 19

<210> SEQ ID NO 67
<211> LENGTH: 19
<212> TYPE: DNA
<213> ORGANISM: Artificial Sequence
<220> FEATURE:
<223> OTHER INFORMATION: Primer Eg5-2

<400> SEQUENCE: 67
ttggcaatgg tctgcaagg 19

<210> SEQ ID NO 68
<211> LENGTH: 1272
<212> TYPE: DNA
<213> ORGANISM: Euglena gracilis
<220> FEATURE:
<221> NAME/KEY: misc_feature
<222> LOCATION: (2)..(1270)
<223> OTHER INFORMATION: synthetic delta-8 desaturase CDS, codon-optimized for expression in Yarrowia lipolytica ("D8SF" or "EgD8S")
<300> PUBLICATION INFORMATION:
<302> TITLE: DELTA-8 DESATURASE AND ITS USE IN MAKING POLYUNSATURATED FATTY ACIDS
<310> PATENT DOCUMENT NUMBER: WO 2006/012325 and WO 2006/012326
<311> PATENT FILING DATE: 2005-06-24
<312> PUBLICATION DATE: 2006-02-02
<313> RELEVANT RESIDUES IN SEQ ID NO: (1)..(1272)
<300> PUBLICATION INFORMATION:
<302> TITLE: DELTA-8 DESATURASE AND ITS USE IN MAKING POLYUNSATURATED FATTY ACIDS
<310> PATENT DOCUMENT NUMBER: US-2005-0287652-A1
<311> PATENT FILING DATE: 2005-06-24
<312> PUBLICATION DATE: 2005-12-29
<313> RELEVANT RESIDUES IN SEQ ID NO: (1)..(1272)

<400> SEQUENCE: 68
catggtgaag tccaagcgac aggctctgcc cctcaccatc gacggaacta cctacgacgt 60
ctccgcttgg gtgaacttcc accctggtgg agctgaaatc attgagaact accagggacg 120
agatgctact gacgccttca tggttatgca ctctcaggaa gccttcgaca agctcaagcg 180
aatgcccaag atcaacccct cctccgagct gcctccccag gctgccgtca acgaagctca 240
ggaggatttc cgaaagctcc gagaagagct gatcgccact ggcatgtttg acgcctctcc 300
cctctggtac tcgtacaaga tctccaccac cctgggtctt ggcgtgcttg gatacttcct 360
gatggtccag taccagatgt acttcattgg tgctgtgctg ctcggtatgc actaccagca 420
aatgggatgg ctgtctcatg acatctgcca ccaccagacc ttcaagaacc gaaactggaa 480
taacctcgtg ggtctggtct ttggcaacgg actccagggc ttctccgtga cctggtggaa 540
ggacagacac aacgcccatc attctgctac caacgttcag ggtcacgatc ccgacattga 600
taacctgcct ctgctcgcct ggtccgagga cgatgtcact cgagcttctc ccatctcccg 660
aaagctcatt cagttccaac agtactattt cctggtcatc tgtattctcc tgcgattcat 720
ctggtgtttc cagtctgtgc tgaccgttcg atccctcaag gaccgagaca accagttcta 780
ccgatctcag tacaagaaag aggccattgg actcgctctg cactggactc tcaagaccct 840
gttccacctc ttctttatgc cctccatcct gacctcgctc ctggtgttct ttgtttccga 900
gctcgtcggt ggcttcggaa ttgccatcgt ggtcttcatg aaccactacc ctctggagaa 960
gatcggtgat tccgtctggg acggacatgg cttctctgtg ggtcagatcc atgagaccat 1020
gaacattcga cgaggcatca ttactgactg gttctttgga ggcctgaact accagatcga 1080
gcaccatctc tggcccaccc tgcctcgaca caacctcact gccgtttcct accaggtgga 1140
acagctgtgc cagaagcaca acctccccta ccgaaaccct ctgccccatg aaggtctcgt 1200
catcctgctc cgatacctgg ccgtgttcgc tcgaatggcc gagaagcagc ccgctggcaa 1260
ggctctctaa gc 1272

<210> SEQ ID NO 69
<211> LENGTH: 422
<212> TYPE: PRT
<213> ORGANISM: Euglena gracilis
<220> FEATURE:
<221> NAME/KEY: MISC_FEATURE
<223> OTHER INFORMATION: synthetic delta-8 desaturase codon-optimized
      for expression in Yarrowia lipolytica ("D8SF" or "EgD8S")
<300> PUBLICATION INFORMATION:
<302> TITLE: DELTA-8 DESATURASE AND ITS USE IN MAKING POLYUNSATURATED
      FATTY ACIDS
<310> PATENT DOCUMENT NUMBER: WO 2006/012325 and WO 2006/012326
<311> PATENT FILING DATE: 2005-06-24
<312> PUBLICATION DATE: 2006-02-02
<313> RELEVANT RESIDUES IN SEQ ID NO: (1)..(422)
<300> PUBLICATION INFORMATION:
<302> TITLE: DELTA-8 DESATURASE AND ITS USE IN MAKING POLYUNSATURATED
      FATTY ACIDS
<310> PATENT DOCUMENT NUMBER: US-2005-0287652-A1
<311> PATENT FILING DATE: 2005-06-24
<312> PUBLICATION DATE: 2005-12-29
<313> RELEVANT RESIDUES IN SEQ ID NO: (1)..(422)

<400> SEQUENCE: 69

```
Met Val Lys Ser Lys Arg Gln Ala Leu Pro Leu Thr Ile Asp Gly Thr
1               5                   10                  15

Thr Tyr Asp Val Ser Ala Trp Val Asn Phe His Pro Gly Gly Ala Glu
            20                  25                  30

Ile Ile Glu Asn Tyr Gln Gly Arg Asp Ala Thr Asp Ala Phe Met Val
        35                  40                  45

Met His Ser Gln Glu Ala Phe Asp Lys Leu Lys Arg Met Pro Lys Ile
    50                  55                  60

Asn Pro Ser Ser Glu Leu Pro Pro Gln Ala Ala Val Asn Glu Ala Gln
65                  70                  75                  80

Glu Asp Phe Arg Lys Leu Arg Glu Glu Leu Ile Ala Thr Gly Met Phe
                85                  90                  95

Asp Ala Ser Pro Leu Trp Tyr Ser Tyr Lys Ile Ser Thr Thr Leu Gly
            100                 105                 110

Leu Gly Val Leu Gly Tyr Phe Leu Met Val Gln Tyr Gln Met Tyr Phe
        115                 120                 125

Ile Gly Ala Val Leu Leu Gly Met His Tyr Gln Gln Met Gly Trp Leu
    130                 135                 140

Ser His Asp Ile Cys His His Gln Thr Phe Lys Asn Arg Asn Trp Asn
145                 150                 155                 160

Asn Leu Val Gly Leu Val Phe Gly Asn Gly Leu Gln Gly Phe Ser Val
                165                 170                 175

Thr Trp Trp Lys Asp Arg His Asn Ala His His Ser Ala Thr Asn Val
            180                 185                 190

Gln Gly His Asp Pro Asp Ile Asp Asn Leu Pro Leu Leu Ala Trp Ser
        195                 200                 205

Glu Asp Asp Val Thr Arg Ala Ser Pro Ile Ser Arg Lys Leu Ile Gln
    210                 215                 220

Phe Gln Gln Tyr Tyr Phe Leu Val Ile Cys Ile Leu Leu Arg Phe Ile
225                 230                 235                 240

Trp Cys Phe Gln Ser Val Leu Thr Val Arg Ser Leu Lys Asp Arg Asp
                245                 250                 255

Asn Gln Phe Tyr Arg Ser Gln Tyr Lys Lys Glu Ala Ile Gly Leu Ala
            260                 265                 270

Leu His Trp Thr Leu Lys Thr Leu Phe His Leu Phe Phe Met Pro Ser
        275                 280                 285

Ile Leu Thr Ser Leu Leu Val Phe Phe Val Ser Glu Leu Val Gly Gly
    290                 295                 300

Phe Gly Ile Ala Ile Val Val Phe Met Asn His Tyr Pro Leu Glu Lys
305                 310                 315                 320

Ile Gly Asp Ser Val Trp Asp Gly His Gly Phe Ser Val Gly Gln Ile
```

```
                325                 330                 335

His Glu Thr Met Asn Ile Arg Arg Gly Ile Ile Thr Asp Trp Phe Phe
            340                 345                 350

Gly Gly Leu Asn Tyr Gln Ile Glu His His Leu Trp Pro Thr Leu Pro
        355                 360                 365

Arg His Asn Leu Thr Ala Val Ser Tyr Gln Val Glu Gln Leu Cys Gln
    370                 375                 380

Lys His Asn Leu Pro Tyr Arg Asn Pro Leu Pro His Glu Gly Leu Val
385                 390                 395                 400

Ile Leu Leu Arg Tyr Leu Ala Val Phe Ala Arg Met Ala Glu Lys Gln
                405                 410                 415

Pro Ala Gly Lys Ala Leu
            420


<210> SEQ ID NO 70
<211> LENGTH: 4826
<212> TYPE: DNA
<213> ORGANISM: Artificial Sequence
<220> FEATURE:
<223> OTHER INFORMATION: Plasmid pKS121
<220> FEATURE:
<221> NAME/KEY: misc_feature
<222> LOCATION: (3711)..(3711)
<223> OTHER INFORMATION: n is a, c, g, or t

<400> SEQUENCE: 70

tcgacggcgc gcccgatcat ccggatatag ttcctccttt cagcaaaaaa cccctcaaga     60

cccgtttaga ggccccaagg ggttatgcta gttattgctc agcggtggca gcagccaact    120

cagcttcctt tcgggctttg ttagcagccg gatcgatcca agctgtacct cactattcct    180

ttgccctcgg acgagtgctg gggcgtcggt ttccactatc ggcgagtact tctacacagc    240

catcggtcca gacggccgcg cttctgcggg cgatttgtgt acgcccgaca gtcccggctc    300

cggatcggac gattgcgtcg catcgaccct gcgcccaagc tgcatcatcg aaattgccgt    360

caaccaagct ctgatagagt tggtcaagac caatgcggag catatacgcc cggagccgcg    420

gcgatcctgc aagctccgga tgcctccgct cgaagtagcg cgtctgctgc tccatacaag    480

ccaaccacgg cctccagaag aagatgttgg cgacctcgta ttgggaatcc ccgaacatcg    540

cctcgctcca gtcaatgacc gctgttatgc ggccattgtc cgtcaggaca ttgttggagc    600

cgaaatccgc gtgcacgagg tgccggactt cggggcagtc ctcggcccaa agcatcagct    660

catcgagagc ctgcgcgacg gacgcactga cggtgtcgtc catcacagtt tgccagtgat    720

acacatgggg atcagcaatc gcgcatatga aatcacgcca tgtagtgtat tgaccgattc    780

cttgcggtcc gaatgggccg aacccgctcg tctggctaag atcggccgca gcgatcgcat    840

ccatagcctc cgcgaccggc tgcagaacag cgggcagttc ggtttcaggc aggtcttgca    900

acgtgacacc ctgtgcacgg cgggagatgc aataggtcag gctctcgctg aattccccaa    960

tgtcaagcac ttccggaatc gggagcgcgg ccgatgcaaa gtgccgataa acataacgat   1020

ctttgtagaa accatcggcg cagctattta cccgcaggac atatccacgc cctcctacat   1080

cgaagctgaa agcacgagat tcttcgccct ccgagagctg catcaggtcg gagacgctgt   1140

cgaacttttc gatcagaaac ttctcgacag acgtcgcggt gagttcaggc ttttccatgg   1200

gtatatctcc ttcttaaagt taaacaaaat tatttctaga gggaaaccgt tgtggtctcc   1260

ctatagtgag tcgtattaat ttcgcgggat cgagatctga tcaacctgca ttaatgaatc   1320

ggccaacgcg cggggagagg cggtttgcgt attgggcgct cttccgcttc ctcgctcact   1380
```

-continued

```
gactcgctgc gctcggtcgt tcggctgcgg cgagcggtat cagctcactc aaaggcggta   1440
atacggttat ccacagaatc aggggataac gcaggaaaga acatgtgagc aaaaggccag   1500
caaaaggcca ggaaccgtaa aaaggccgcg ttgctggcgt ttttccatag gctccgcccc   1560
cctgacgagc atcacaaaaa tcgacgctca agtcagaggt ggcgaaaccc gacaggacta   1620
taaagatacc aggcgtttcc ccctggaagc tccctcgtgc gctctcctgt tccgaccctg   1680
ccgcttaccg gatacctgtc cgcctttctc ccttcgggaa gcgtggcgct ttctcaatgc   1740
tcacgctgta ggtatctcag ttcggtgtag gtcgttcgct ccaagctggg ctgtgtgcac   1800
gaaccccccg ttcagcccga ccgctgcgcc ttatccggta actatcgtct tgagtccaac   1860
ccggtaagac acgacttatc gccactggca gcagccactg gtaacaggat tagcagagcg   1920
aggtatgtag gcggtgctac agagttcttg aagtggtggc ctaactacgg ctacactaga   1980
aggacagtat ttggtatctg cgctctgctg aagccagtta ccttcggaaa aagagttggt   2040
agctcttgat ccggcaaaca aaccaccgct ggtagcggtg gtttttttgt ttgcaagcag   2100
cagattacgc gcagaaaaaa aggatctcaa gaagatcctt tgatcttttc tacggggtct   2160
gacgctcagt ggaacgaaaa ctcacgttaa gggattttgg tcatgacatt aacctataaa   2220
aataggcgta tcacgaggcc ctttcgtctc gcgcgtttcg gtgatgacgg tgaaaacctc   2280
tgacacatgc agctcccgga gacggtcaca gcttgtctgt aagcggatgc cgggagcaga   2340
caagcccgtc agggcgcgtc agcgggtgtt ggcgggtgtc ggggctggct taactatgcg   2400
gcatcagagc agattgtact gagagtgcac catatggaca tattgtcgtt agaacgcggc   2460
tacaattaat acataacctt atgtatcata cacatacgat ttaggtgaca ctatagaacg   2520
gcgcgccaag cttggatcct cgaagagaag ggttaataac acatttttta acatttttaa   2580
cacaaatttt agttatttaa aaatttatta aaaaatttaa aataagaaga ggaactcttt   2640
aaataaatct aacttacaaa atttatgatt tttaataagt tttcaccaat aaaaaatgtc   2700
ataaaaatat gttaaaaagt atattatcaa tattctcttt atgataaata aaaagaaaaa   2760
aaaaataaaa gttaagtgaa aatgagattg aagtgacttt aggtgtgtat aaatatatca   2820
accccgccaa caatttattt aatccaaata tattgaagta tattattcca tagcctttat   2880
ttatttatat atttattata taaaagcttt atttgttcta ggttgttcat gaaatatttt   2940
tttggtttta tctccgttgt aagaaaatca tgtgctttgt gtcgccactc actattgcag   3000
ctttttcatg cattggtcag attgacggtt gattgtattt ttgtttttta tggttttgtg   3060
ttatgactta agtcttcatc tctttatctc ttcatcaggt ttgatggtta cctaatatgg   3120
tccatgggta catgcatggt taaattaggt ggccaacttt gttgtgaacg atagaatttt   3180
ttttatatta agtaaactat ttttatatta tgaaataata ataaaaaaaa tattttatca   3240
ttattaacaa aatcatatta gttaatttgt taactctata ataaaagaaa tactgtaaca   3300
ttcacattac atggtaacat ctttccaccc tttcatttgt tttttgtttg atgacttttt   3360
ttcttgttta aatttatttc ccttctttta aatttggaat acattatcat catatataaa   3420
ctaaaatact aaaaacagga ttacacaaat gataaataat aacacaaata tttataaatc   3480
tagctgcaat atatttaaac tagctatatc gatattgtaa aataaaacta gctgcattga   3540
tactgataaa aaaatatcat gtgctttctg gactgatgat gcagtatact tttgacattg   3600
cctttatttt atttttcaga aaagctttct tagttctggg ttcttcatta tttgtttccc   3660
atctccattg tgaattgaat catttgcttc gtgtcacaaa tacaatttag ntaggtacat   3720
gcattggtca gattcacggt ttattatgtc atgacttaag ttcatggtag tacattacct   3780
```

gccacgcatg cattatattg gttagatttg ataggcaaat ttggttgtca acaatataaa 3840
tataaataat gtttttatat tacgaaataa cagtgatcaa aacaaacagt tttatcttta 3900
ttaacaagat tttgtttttg tttgatgacg ttttttaatg tttacgcttt ccccttctt 3960 ttgaatttag aacactttat catcataaaa tcaaatacta aaaaaattac atatttcata 4020
aataataaca caaatatttt taaaaaatct gaaataataa tgaacaatat tacatattat 4080
cacgaaaatt cattaataaa aatattatat aaataaaatg taatagtagt tatatgtagg 4140
aaaaaagtac tgcacgcata atatatacaa aaagattaaa atgaactatt ataaataata 4200
acactaaatt aatggtgaat catatcaaaa taatgaaaaa gtaaataaaa tttgtaatta 4260
acttctatat gtattacaca cacaaataat aaataatagt aaaaaaaatt atgataaata 4320
tttaccatct cataagatat ttaaaataat gataaaaata tagattattt tttatgcaac 4380
tagctagcca aaaagagaac acgggtatat ataaaaagag tacctttaaa ttctactgta 4440
cttcctttat tcctgacgtt tttatatcaa gtggacatac gtgaagattt taattatcag 4500
tctaaatatt tcattagcac ttaatacttt tctgttttat tcctatccta taagtagtcc 4560
cgattctccc aacattgctt attcacacaa ctaactaaga aagtcttcca tagcccccca 4620
agcggccgcg acacaagtgt gagagtacta aataaatgct ttggttgtac gaaatcatta 4680
cactaaataa aataatcaaa gcttatatat gccttccgct aaggccgaat gcaaagaaat 4740
tggttctttc tcgttatctt ttgccacttt tactagtacg tattaattac tacttaatca 4800
tctttgttta cggctcatta tatccg 4826

<210> SEQ ID NO 71
<211> LENGTH: 5252
<212> TYPE: DNA
<213> ORGANISM: Artificial Sequence
<220> FEATURE:
<223> OTHER INFORMATION: Plasmid pKR457
<220> FEATURE:
<221> NAME/KEY: misc_feature
<222> LOCATION: (3872)..(3872)
<223> OTHER INFORMATION: n is a, c, g, or t

<400> SEQUENCE: 71
gtacgtgggc ggatccccg ggctgcagga attcactggc cgtcgtttta caacgtcgtg 60
actgggaaaa ccctggcgtt acccaactta atcgccttgc agcacatccc cctttcgcca 120
gctggcgtaa tagcgaagag gcccgcaccg atcgcccttc ccaacagttg cgcagcctga 180
atggcgaatg gcgcctgatg cggtattttc tccttacgca tctgtgcggt atttcacacc 240
gcatatggtg cactctcagt acaatctgct ctgatgccgc atagttaagc cagccccgac 300
acccgccaac acccgctgac gcgccctgac gggcttgtct gctcccggca tccgcttaca 360
gacaagctgt gaccgtctcc gggagctgca tgtgtcagag gttttcaccg tcatcaccga 420
aacgcgcgag acgaaagggc ctcgtgatac gcctattttt ataggttaat gtcatgataa 480
taatggtttc ttagacgtca ggtggcactt ttcggggaaa tgtgcgcgga acccctattt 540
gtttattttt ctaaatacat tcaaatatgt atccgctcat gagacaataa ccctgataaa 600
tgcttcaata atattgaaaa aggaagagta tgagtattca acatttccgt gtcgccctta 660
ttcccttttt tgcggcattt tgccttcctg tttttgctca cccagaaacg ctggtgaaag 720
taaaagatgc tgaagatcag ttgggtgcac gagtgggtta catcgaactg gatctcaaca 780
gcggtaagat ccttgagagt tttcgccccg aagaacgttt tccaatgatg agcactttta 840
aagttctgct atgtggcgcg gtattatccc gtattgacgc cgggcaagag caactcggtc 900
gccgcataca ctattctcag aatgacttgg ttgagtactc accagtcaca gaaaagcatc 960
ttacggatgg catgacagta agagaattat gcagtgctgc cataaccatg agtgataaca 1020
ctgcggccaa cttacttctg acaacgatcg gaggaccgaa ggagctaacc gcttttttgc 1080
acaacatggg ggatcatgta actcgccttg atcgttggga accggagctg aatgaagcca 1140
taccaaacga cgagcgtgac accacgatgc ctgtagcaat ggcaacaacg ttgcgcaaac 1200
tattaactgg cgaactactt actctagctt cccggcaaca attaatagac tggatggagg 1260
cggataaagt tgcaggacca cttctgcgct cggcccttcc ggctggctgg tttattgctg 1320
ataaatctgg agccggtgag cgtgggtctc gcggtatcat tgcagcactg gggccagatg 1380
gtaagccctc ccgtatcgta gttatctaca cgacggggag tcaggcaact atggatgaac 1440
gaaatagaca gatcgctgag ataggtgcct cactgattaa gcattggtaa ctgtcagacc 1500
aagtttactc atatatactt tagattgatt taaaacttca tttttaattt aaaaggatct 1560
aggtgaagat cctttttgat aatctcatga ccaaaatccc ttaacgtgag ttttcgttcc 1620
actgagcgtc agaccccgta gaaaagatca aaggatcttc ttgagatcct ttttttctgc 1680
gcgtaatctg ctgcttgcaa acaaaaaaac caccgctacc agcggtggtt tgtttgccgg 1740
atcaagagct accaactctt tttccgaagg taactggctt cagcagagcg cagataccaa 1800
atactgtcct tctagtgtag ccgtagttag gccaccactt caagaactct gtagcaccgc 1860
ctacatacct cgctctgcta atcctgttac cagtggctgc tgccagtggc gataagtcgt 1920
gtcttaccgg gttggactca agacgatagt taccggataa ggcgcagcgg tcgggctgaa 1980
cggggggttc gtgcacacag cccagcttgg agcgaacgac ctacaccgaa ctgagatacc 2040
tacagcgtga gctatgagaa agcgccacgc ttcccgaagg gagaaaggcg gacaggtatc 2100
cggtaagcgg cagggtcgga acaggagagc gcacgaggga gcttccaggg ggaaacgcct 2160
ggtatcttta tagtcctgtc gggtttcgcc acctctgact tgagcgtcga tttttgtgat 2220
gctcgtcagg ggggcggagc ctatggaaaa acgccagcaa cgcggccttt ttacggttcc 2280
tggccttttg ctggcctttt gctcacatgt tctttcctgc gttatcccct gattctgtgg 2340
ataaccgtat taccgccttt gagtgagctg ataccgctcg ccgcagccga acgaccgagc 2400
gcagcgagtc agtgagcgag gaagcggaag agcgcccaat acgcaaaccg cctctccccg 2460
cgcgttggcc gattcattaa tgcagctggc acgacaggtt tcccgactgg aaagcgggca 2520
gtgagcgcaa cgcaattaat gtgagttagc tcactcatta ggcaccccag gctttacact 2580
ttatgcttcc ggctcgtatg ttgtgtggaa ttgtgagcgg ataacaattt cacacaggaa 2640
acagctatga ccatgattac gccaagcttg catgcctgca ggtcgactcg acgtacgtcc 2700
tcgaagagaa gggttaataa cacatttttt aacattttta acacaaattt tagttattta 2760
aaaatttatt aaaaaattta aaataagaag aggaactctt taaataaatc taacttacaa 2820
aatttatgat ttttaataag ttttcaccaa taaaaaatgt cataaaaata tgttaaaaag 2880
tatattatca atattctctt tatgataaat aaaaagaaaa aaaaaataaa agttaagtga 2940
aaatgagatt gaagtgactt taggtgtgta taaatatatc aaccccgcca acaatttatt 3000
taatccaaat atattgaagt atattattcc atagccttta tttatttata tatttattat 3060
ataaaagctt tatttgttct aggttgttca tgaaatattt ttttggtttt atctccgttg 3120
taagaaaatc atgtgctttg tgtcgccact cactattgca gctttttcat gcattggtca 3180
gattgacggt tgattgtatt tttgtttttt atggttttgt gttatgactt aagtcttcat 3240
ctctttatct cttcatcagg tttgatggtt acctaatatg gtccatgggt acatgcatgg 3300

-continued

```
ttaaattagg tggccaactt tgttgtgaac gatagaattt tttttatatt aagtaaacta   3360

tttttatatt atgaaataat aataaaaaaa atattttatc attattaaca aaatcatatt   3420

agttaatttg ttaactctat aataaaagaa atactgtaac attcacatta catggtaaca   3480

tctttccacc ctttcatttg ttttttgttt gatgactttt tttcttgttt aaatttattt   3540

cccttctttt aaatttggaa tacattatca tcatatataa actaaaatac taaaaacagg   3600

attacacaaa tgataaataa taacacaaat atttataaat ctagctgcaa tatatttaaa   3660

ctagctatat cgatattgta aaataaaact agctgcattg atactgataa aaaaatatca   3720

tgtgctttct ggactgatga tgcagtatac ttttgacatt gcctttattt tatttttcag   3780

aaaagctttc ttagttctgg gttcttcatt atttgtttcc catctccatt gtgaattgaa   3840

tcatttgctt cgtgtcacaa atacaattta gntaggtaca tgcattggtc agattcacgg   3900

tttattatgt catgacttaa gttcatggta gtacattacc tgccacgcat gcattatatt   3960

ggttagattt gataggcaaa tttggttgtc aacaatataa atataaataa tgtttttata   4020

ttacgaaata acagtgatca aaacaaacag ttttatcttt attaacaaga ttttgttttt   4080

gtttgatgac gtttttaat gtttacgctt tccccttct tttgaattta gaacacttta   4140

tcatcataaa atcaaatact aaaaaaatta catatttcat aaataataac acaaatattt   4200

ttaaaaaatc tgaaataata atgaacaata ttacatatta tcacgaaaat tcattaataa   4260

aaatattata taaataaaat gtaatagtag ttatatgtag gaaaaaagta ctgcacgcat   4320

aatatataca aaaagattaa aatgaactat tataaataat aacactaaat taatggtgaa   4380

tcatatcaaa ataatgaaaa agtaaataaa atttgtaatt aacttctata tgtattacac   4440

acacaaataa taaataatag taaaaaaaat tatgataaat atttaccatc tcataagata   4500

tttaaaataa tgataaaaat atagattatt ttttatgcaa ctagctagcc aaaaagagaa   4560

cacgggtata tataaaaaga gtacctttaa attctactgt acttccttta ttcctgacgt   4620

ttttatatca agtggacata cgtgaagatt ttaattatca gtctaaatat ttcattagca   4680

cttaatactt ttctgtttta ttcctatcct ataagtagtc ccgattctcc caacattgct   4740

tattcacaca actaactaag aaagtcttcc atagcccccc aagcggccgc gacacaagtg   4800

tgagagtact aaataaatgc tttggttgta cgaaatcatt acactaaata aaataatcaa   4860

agcttatata tgccttccgc taaggccgaa tgcaaagaaa ttggttcttt ctcgttatct   4920

tttgccactt ttactagtac gtattaatta ctacttaatc atctttgttt acggctcatt   4980

atatccggtc tagaggatcc aaggccgcga agttaaaagc aatgttgtca cttgtcgtac   5040

taacacatga tgtgatagtt tatgctagct agctataaca taagctgtct ctgagtgtgt   5100

tgtatattaa taaagatcat cactggtgaa tggtgatcgt gtacgtaccc tacttagtag   5160

gcaatggaag cacttagagt gtgctttgtg catggccttg cctctgtttt gagacttttg   5220

taatgtttc gagtttaaat ctttgccttt gc                                   5252
```

<210> SEQ ID NO 72
<211> LENGTH: 37
<212> TYPE: DNA
<213> ORGANISM: Artificial Sequence
<220> FEATURE:
<223> OTHER INFORMATION: KTi cassette 5' end MCS for pKR457

<400> SEQUENCE: 72

```
aagcttgcat gcctgcaggt cgactcgacg tacgtcc                              37
```

<210> SEQ ID NO 73

```
<211> LENGTH: 282
<212> TYPE: DNA
<213> ORGANISM: Artificial Sequence
<220> FEATURE:
<223> OTHER INFORMATION: KTi cassette 3' end MCS for pKR457 including
      the soy albumin transcription 3' terminator

<400> SEQUENCE: 73

ggtctagagg atccaaggcc gcgaagttaa aagcaatgtt gtcacttgtc gtactaacac     60

atgatgtgat agtttatgct agctagctat aacataagct gtctctgagt gtgttgtata    120

ttaataaaga tcatcactgg tgaatggtga tcgtgtacgt accctactta gtaggcaatg    180

gaagcactta gagtgtgctt tgtgcatggc cttgcctctg ttttgagact tttgtaatgt    240

tttcgagttt aaatctttgc ctttgcgtac gtgggcggat cc                        282


<210> SEQ ID NO 74
<211> LENGTH: 32
<212> TYPE: DNA
<213> ORGANISM: Artificial Sequence
<220> FEATURE:
<223> OTHER INFORMATION: Primer oSalb-12

<400> SEQUENCE: 74

tttggatcct ctagacgtac gcaaaggcaa ag                                    32


<210> SEQ ID NO 75
<211> LENGTH: 36
<212> TYPE: DNA
<213> ORGANISM: Artificial Sequence
<220> FEATURE:
<223> OTHER INFORMATION: Primer oSalb-13

<400> SEQUENCE: 75

aaaggatcca aggccgcgaa gttaaaagca atgttg                                36


<210> SEQ ID NO 76
<211> LENGTH: 6559
<212> TYPE: DNA
<213> ORGANISM: Artificial Sequence
<220> FEATURE:
<223> OTHER INFORMATION: Plasmid pKR680
<220> FEATURE:
<221> NAME/KEY: misc_feature
<222> LOCATION: (4340)..(4340)
<223> OTHER INFORMATION: n is a, c, g, or t

<400> SEQUENCE: 76

ggccgcgaca caagtgtgag agtactaaat aaatgctttg gttgtacgaa atcattacac     60

taaataaaat aatcaaagct tatatatgcc ttccgctaag gccgaatgca aagaaattgg    120

ttctttctcg ttatcttttg ccacttttac tagtacgtat taattactac ttaatcatct    180

ttgtttacgg ctcattatat ccggtctaga ggatccaagg ccgcgaagtt aaaagcaatg    240

ttgtcacttg tcgtactaac acatgatgtg atagtttatg ctagctagct ataacataag    300

ctgtctctga gtgtgttgta tattaataaa gatcatcact ggtgaatggt gatcgtgtac    360

gtaccctact tagtaggcaa tggaagcact tagagtgtgc tttgtgcatg gccttgcctc    420

tgttttgaga cttttgtaat gttttcgagt ttaaatcttt gcctttgcgt acgtgggcgg    480

atcccccggg ctgcaggaat tcactggccg tcgttttaca acgtcgtgac tgggaaaacc    540

ctggcgttac ccaacttaat cgccttgcag cacatccccc tttcgccagc tggcgtaata    600

gcgaagaggc ccgcaccgat cgcccttccc aacagttgcg cagcctgaat ggcgaatggc    660

gcctgatgcg gtattttctc cttacgcatc tgtgcggtat ttcacaccgc atatggtgca    720
```

ctctcagtac aatctgctct gatgccgcat agttaagcca gccccgacac ccgccaacac 780
ccgctgacgc gccctgacgg gcttgtctgc tcccggcatc cgcttacaga caagctgtga 840
ccgtctccgg gagctgcatg tgtcagaggt tttcaccgtc atcaccgaaa cgcgcgagac 900
gaaagggcct cgtgatacgc ctatttttat aggttaatgt catgataata atggtttctt 960
agacgtcagg tggcactttt cggggaaatg tgcgcggaac ccctatttgt ttatttttct 1020
aaatacattc aaatatgtat ccgctcatga gacaataacc ctgataaatg cttcaataat 1080
attgaaaaag gaagagtatg agtattcaac atttccgtgt cgcccttatt cccttttttg 1140
cggcattttg ccttcctgtt tttgctcacc cagaaacgct ggtgaaagta aaagatgctg 1200
aagatcagtt gggtgcacga gtgggttaca tcgaactgga tctcaacagc ggtaagatcc 1260
ttgagagttt tcgccccgaa gaacgttttc caatgatgag cacttttaaa gttctgctat 1320
gtggcgcggt attatcccgt attgacgccg ggcaagagca actcggtcgc cgcatacact 1380
attctcagaa tgacttggtt gagtactcac cagtcacaga aaagcatctt acggatggca 1440
tgacagtaag agaattatgc agtgctgcca taaccatgag tgataacact gcggccaact 1500
tacttctgac aacgatcgga ggaccgaagg agctaaccgc ttttttgcac aacatggggg 1560
atcatgtaac tcgccttgat cgttgggaac cggagctgaa tgaagccata ccaaacgacg 1620
agcgtgacac cacgatgcct gtagcaatgg caacaacgtt gcgcaaacta ttaactggcg 1680
aactacttac tctagcttcc cggcaacaat taatagactg gatggaggcg gataaagttg 1740
caggaccact tctgcgctcg gcccttccgg ctggctggtt tattgctgat aaatctggag 1800
ccggtgagcg tgggtctcgc ggtatcattg cagcactggg gccagatggt aagccctccc 1860
gtatcgtagt tatctacacg acggggagtc aggcaactat ggatgaacga aatagacaga 1920
tcgctgagat aggtgcctca ctgattaagc attggtaact gtcagaccaa gtttactcat 1980
atatacttta gattgattta aaacttcatt tttaatttaa aaggatctag gtgaagatcc 2040
tttttgataa tctcatgacc aaaatccctt aacgtgagtt ttcgttccac tgagcgtcag 2100
accccgtaga aaagatcaaa ggatcttctt gagatccttt ttttctgcgc gtaatctgct 2160
gcttgcaaac aaaaaaacca ccgctaccag cggtggtttg tttgccggat caagagctac 2220
caactctttt tccgaaggta actggcttca gcagagcgca gataccaaat actgtccttc 2280
tagtgtagcc gtagttaggc caccacttca agaactctgt agcaccgcct acatacctcg 2340
ctctgctaat cctgttacca gtggctgctg ccagtggcga taagtcgtgt cttaccgggt 2400
tggactcaag acgatagtta ccggataagg cgcagcggtc gggctgaacg gggggttcgt 2460
gcacacagcc cagcttggag cgaacgacct acaccgaact gagataccta cagcgtgagc 2520
tatgagaaag cgccacgctt cccgaaggga gaaaggcgga caggtatccg gtaagcggca 2580
gggtcggaac aggagagcgc acgagggagc ttccaggggg aaacgcctgg tatctttata 2640
gtcctgtcgg gtttcgccac ctctgacttg agcgtcgatt tttgtgatgc tcgtcagggg 2700
ggcggagcct atggaaaaac gccagcaacg cggccttttt acggttcctg gccttttgct 2760
ggccttttgc tcacatgttc tttcctgcgt tatcccctga ttctgtggat aaccgtatta 2820
ccgcctttga gtgagctgat accgctcgcc gcagccgaac gaccgagcgc agcgagtcag 2880
tgagcgagga agcggaagag cgcccaatac gcaaaccgcc tctccccgcg cgttggccga 2940
ttcattaatg cagctggcac gacaggtttc ccgactggaa agcgggcagt gagcgcaacg 3000
caattaatgt gagttagctc actcattagg caccccaggc tttacacttt atgcttccgg 3060
ctcgtatgtt gtgtggaatt gtgagcggat aacaatttca cacaggaaac agctatgacc 3120
atgattacgc caagcttgca tgcctgcagg tcgactcgac gtacgtcctc gaagagaagg 3180
gttaataaca catttttaa catttttaac acaaatttta gttatttaaa aatttattaa 3240
aaaatttaaa ataagaagag gaactcttta aataaatcta acttacaaaa tttatgattt 3300
ttaataagtt ttcaccaata aaaaatgtca taaaaatatg ttaaaaagta tattatcaat 3360
attctcttta tgataaataa aaagaaaaaa aaaataaaag ttaagtgaaa atgagattga 3420
agtgacttta ggtgtgtata aatatatcaa ccccgccaac aatttattta atccaaatat 3480
attgaagtat attattccat agcctttatt tatttatata tttattatat aaaagcttta 3540
tttgttctag gttgttcatg aaatattttt ttggttttat ctccgttgta agaaaatcat 3600
gtgctttgtg tcgccactca ctattgcagc tttttcatgc attggtcaga ttgacggttg 3660
attgtatttt tgtttttat ggttttgtgt tatgacttaa gtcttcatct ctttatctct 3720
tcatcaggtt tgatggttac ctaatatggt ccatgggtac atgcatggtt aaattaggtg 3780
gccaactttg ttgtgaacga tagaattttt tttatattaa gtaaactatt tttatattat 3840
gaaataataa taaaaaaaat attttatcat tattaacaaa atcatattag ttaatttgtt 3900
aactctataa taaaagaaat actgtaacat tcacattaca tggtaacatc tttccaccct 3960
ttcatttgtt ttttgtttga tgactttttt tcttgtttaa atttatttcc cttcttttaa 4020
atttggaata cattatcatc atatataaac taaaatacta aaaacaggat tacacaaatg 4080
ataaataata acacaaatat ttataaatct agctgcaata tatttaaact agctatatcg 4140
atattgtaaa ataaaactag ctgcattgat actgataaaa aaatatcatg tgctttctgg 4200
actgatgatg cagtatactt ttgacattgc ctttatttta tttttcagaa aagctttctt 4260
agttctgggt tcttcattat ttgtttccca tctccattgt gaattgaatc atttgcttcg 4320
tgtcacaaat acaatttagn taggtacatg cattggtcag attcacggtt tattatgtca 4380
tgacttaagt tcatggtagt acattacctg ccacgcatgc attatattgg ttagatttga 4440
taggcaaatt tggttgtcaa caatataaat ataaataatg tttttatatt acgaaataac 4500
agtgatcaaa acaaacagtt ttatctttat taacaagatt ttgtttttgt ttgatgacgt 4560
tttttaatgt ttacgctttc cccctttcttt tgaatttaga acactttatc atcataaaat 4620
caaatactaa aaaaattaca tatttcataa ataataacac aaatattttt aaaaaatctg 4680
aaataataat gaacaatatt acatattatc acgaaaattc attaataaaa atattatata 4740
aataaaatgt aatagtagtt atatgtagga aaaaagtact gcacgcataa tatatacaaa 4800
aagattaaaa tgaactatta taaataataa cactaaatta atggtgaatc atatcaaaat 4860
aatgaaaaag taaataaaat ttgtaattaa cttctatatg tattacacac acaaataata 4920
aataatagta aaaaaaatta tgataaatat ttaccatctc ataagatatt taaaataatg 4980
ataaaaatat agattatttt ttatgcaact agctagccaa aaagagaaca cgggtatata 5040
taaaaagagt acctttaaat tctactgtac ttcctttatt cctgacgttt ttatatcaag 5100
tggacatacg tgaagatttt aattatcagt ctaaatattt cattagcact taatactttt 5160
ctgttttatt cctatcctat aagtagtccc gattctccca acattgctta ttcacacaac 5220
taactaagaa agtcttccat agccccccaa gcggccgcgg gaattcgatt gaaatgaagt 5280
caaagcgcca agcgcttccc cttacaattg atggaacaac atatgatgtg tctgcctggg 5340
tcaatttcca ccctggtggt gcggaaatta tagagaatta ccaaggaagg gatgccactg 5400
atgccttcat ggttatgcac tctcaagaag ccttcgacaa gctcaagcgc atgcccaaaa 5460
tcaatcccag ttctgagttg ccaccccagg ctgcagtgaa tgaagctcaa gaggatttcc 5520

```
ggaagctccg agaagagttg atcgcaactg gcatgtttga tgcctccccc ctctggtact   5580
catacaaaat cagcaccaca ctgggccttg gagtgctggg ttatttcctg atggttcagt   5640
atcagatgta tttcattggg gcagtgttgc ttgggatgca ctatcaacag atgggctggc   5700
tttctcatga catttgccac caccagactt tcaagaaccg gaactggaac aacctcgtgg   5760
gactggtatt tggcaatggt ctgcaaggtt tttccgtgac atggtggaag gacagacaca   5820
atgcacatca ttcggcaacc aatgttcaag ggcacgaccc tgatattgac aacctccccc   5880
tcttagcctg gtctgaggat gacgtcacac gggcgtcacc gatttcccgc aagctcattc   5940
agttccagca gtactatttc ttggtcatct gtatcttgtt gcggttcatt tggtgtttcc   6000
agagcgtgtt gaccgtgcgc agtttgaagg acagagataa ccaattctat cgctctcagt   6060
ataagaagga ggccattggc ctcgccctgc actggacctt gaagaccctg ttccacttat   6120
tctttatgcc cagcatcctc acatcgctgt tggtgttttt cgtttcggag ctggttggcg   6180
gcttcggcat tgcgatcgtg gtgttcatga accactaccc actggagaag atcggggact   6240
cagtctggga tggccatgga ttctcggttg gccagatcca tgagaccatg aacattcggc   6300
gagggattat cacagattgg tttttcggag gcttgaatta ccagattgag caccatttgt   6360
ggccgaccct ccctcgccac aacctgacag cggttagcta ccaggtggaa cagctgtgcc   6420
agaagcacaa cctgccgtat cggaacccgc tgccccatga agggttggtc atcctgctgc   6480
gctatctggc ggtgttcgcc cggatggcgg agaagcaacc cgcggggaag gctctataag   6540
gaatcactag tgaattcgc                                                6559
```

<210> SEQ ID NO 77
<211> LENGTH: 9014
<212> TYPE: DNA
<213> ORGANISM: Artificial Sequence
<220> FEATURE:
<223> OTHER INFORMATION: Plasmid pKR913
<220> FEATURE:
<221> NAME/KEY: misc_feature
<222> LOCATION: (7839)..(7839)
<223> OTHER INFORMATION: n is a, c, g, or t

<400> SEQUENCE: 77

```
gtacgagatc cggccggcca gatcctgcag gagatccaag cttttgatcc atgcccttca     60
tttgccgctt attaattaat ttggtaacag tccgtactaa tcagttactt atccttcccc    120
catcataatt aatcttggta gtctcgaatg ccacaacact gactagtctc ttggatcata    180
agaaaaagcc aaggaacaaa agaagacaaa acacaatgag agtatccttt gcatagcaat    240
gtctaagttc ataaaattca aacaaaaacg caatcacaca cagtggacat cacttatcca    300
ctagctgatc aggatcgccg cgtcaagaaa aaaaaactgg accccaaaag ccatgcacaa    360
caacacgtac tcacaaaggt gtcaatcgag cagcccaaaa cattcaccaa ctcaacccat    420
catgagccct cacatttgtt gtttctaacc caacctcaaa ctcgtattct cttccgccac    480
ctcatttttg tttatttcaa cacccgtcaa actgcatgcc accccgtggc caaatgtcca    540
tgcatgttaa caagacctat gactataaat agctgcaatc tcggcccagg ttttcatcat    600
caagaaccag ttcaatatcc tagtacaccg tattaaagaa tttaagatat actgcggccg    660
caccatggag gtggtgaatg aaatagtctc aattgggcag gaagttttac ccaaagttga    720
ttatgcccaa ctctggagtg atgccagtca ctgtgaggtg ctttacttgt ccatcgcatt    780
tgtcatcttg aagttcactc ttggccccct tggtccaaaa ggtcagtctc gtatgaagtt    840
tgttttcacc aattacaacc ttctcatgtc catttattcg ttgggatcat tcctctcaat    900
```

ggcatatgcc atgtacacca tcggtgttat gtctgacaac tgcgagaagg cttttgacaa 960
caacgtcttc aggatcacca cgcagttgtt ctatttgagc aagttcctgg agtatattga 1020
ctccttctat ttgccactga tgggcaagcc tctgacctgg ttgcaattct tccatcattt 1080
gggggcaccg atggatatgt ggctgttcta taattaccga aatgaagctg tttggatttt 1140
tgtgctgttg aatggtttca tccactggat catgtacggt tattattgga ccagattgat 1200
caagctgaag ttccccatgc caaaatccct gattacatca atgcagatca ttcaattcaa 1260
tgttggtttc tacattgtct ggaagtacag gaacattccc tgttatcgcc aagatgggat 1320
gaggatgttt ggctggttct tcaattactt ttatgttggc acagtcttgt gtttgttctt 1380
gaatttctat gtgcaaacgt atatcgtcag gaagcacaag ggagccaaaa agattcagtg 1440
agcggccgca agtatgaact aaaatgcatg taggtgtaag agctcatgga gagcatggaa 1500
tattgtatcc gaccatgtaa cagtataata actgagctcc atctcacttc ttctatgaat 1560
aaacaaagga tgttatgata tattaacact ctatctatgc accttattgt tctatgataa 1620
atttcctctt attattataa atcatctgaa tcgtgacggc ttatggaatg cttcaaatag 1680
tacaaaaaca aatgtgtact ataagacttt ctaaacaatt ctaaccttag cattgtgaac 1740
gagacataag tgttaagaag acataacaat tataatggaa gaagtttgtc tccatttata 1800
tattatatat tacccactta tgtattatat taggatgtta aggagacata acaattataa 1860
agagagaagt ttgtatccat ttatatatta tatactaccc atttatatat tatacttatc 1920
cacttattta atgtctttat aaggtttgat ccatgatatt tctaatattt tagttgatat 1980
gtatatgaaa gggtactatt tgaactctct tactctgtat aaaggttgga tcatccttaa 2040
agtgggtcta tttaatttta ttgcttctta cagataaaaa aaaaattatg agttggtttg 2100
ataaaatatt gaaggattta aaataataat aaataacata taatatatgt atataaattt 2160
attataatat aacatttatc tataaaaaag taaatattgt cataaatcta tacaatcgtt 2220
tagccttgct ggacgaatct caattattta aacgagagta aacatatttg actttttggt 2280
tatttaacaa attattattt aacactatat gaaatttttt tttttatcag caaagaataa 2340
aattaaatta agaaggacaa tggtgtccca atccttatac aaccaacttc cacaagaaag 2400
tcaagtcaga gacaacaaaa aaacaagcaa aggaaatttt ttaatttgag ttgtcttgtt 2460
tgctgcataa tttatgcagt aaaacactac acataaccct tttagcagta gagcaatggt 2520
tgaccgtgtg cttagcttct tttattttat ttttttatca gcaaagaata aataaaataa 2580
aatgagacac ttcagggatg tttcaacaag cttggcgcgc cgttctatag tgtcacctaa 2640
atcgtatgtg tatgatacat aaggttatgt attaattgta gccgcgttct aacgacaata 2700
tgtccatatg gtgcactctc agtacaatct gctctgatgc cgcatagtta agccagcccc 2760
gacacccgcc aacacccgct gacgcgccct gacgggcttg tctgctcccg gcatccgctt 2820
acagacaagc tgtgaccgtc tccgggagct gcatgtgtca gaggttttca ccgtcatcac 2880
cgaaacgcgc gagacgaaag ggcctcgtga tacgcctatt tttataggtt aatgtcatga 2940
ccaaaatccc ttaacgtgag ttttcgttcc actgagcgtc agaccccgta gaaaagatca 3000
aaggatcttc ttgagatcct ttttttctgc gcgtaatctg ctgcttgcaa acaaaaaaac 3060
caccgctacc agcggtggtt tgtttgccgg atcaagagct accaactctt tttccgaagg 3120
taactggctt cagcagagcg cagataccaa atactgtcct tctagtgtag ccgtagttag 3180
gccaccactt caagaactct gtagcaccgc ctacatacct cgctctgcta atcctgttac 3240
cagtggctgc tgccagtggc gataagtcgt gtcttaccgg gttggactca agacgatagt 3300

```
taccggataa ggcgcagcgg tcgggctgaa cggggggttc gtgcacacag cccagcttgg   3360
agcgaacgac ctacaccgaa ctgagatacc tacagcgtga gcattgagaa agcgccacgc   3420
ttcccgaagg gagaaaggcg gacaggtatc cggtaagcgg cagggtcgga acaggagagc   3480
gcacgaggga gcttccaggg ggaaacgcct ggtatcttta tagtcctgtc gggtttcgcc   3540
acctctgact tgagcgtcga tttttgtgat gctcgtcagg ggggcggagc ctatggaaaa   3600
acgccagcaa cgcggccttt ttacggttcc tggccttttg ctggcctttt gctcacatgt   3660
tctttcctgc gttatcccct gattctgtgg ataaccgtat taccgccttt gagtgagctg   3720
ataccgctcg ccgcagccga acgaccgagc gcagcgagtc agtgagcgag gaagcggaag   3780
agcgcccaat acgcaaaccg cctctccccg cgcgttggcc gattcattaa tgcaggttga   3840
tcagatctcg atcccgcgaa attaatacga ctcactatag ggagaccaca acggtttccc   3900
tctagaaata attttgttta actttaagaa ggagatatac ccatggaaaa gcctgaactc   3960
accgcgacgt ctgtcgagaa gtttctgatc gaaaagttcg acagcgtctc cgacctgatg   4020
cagctctcgg agggcgaaga atctcgtgct ttcagcttcg atgtaggagg gcgtggatat   4080
gtcctgcggg taaatagctg cgccgatggt ttctacaaag atcgttatgt ttatcggcac   4140
tttgcatcgg ccgcgctccc gattccggaa gtgcttgaca ttggggaatt cagcgagagc   4200
ctgacctatt gcatctcccg ccgtgcacag ggtgtcacgt tgcaagacct gcctgaaacc   4260
gaactgcccg ctgttctgca gccggtcgcg gaggctatgg atgcgatcgc tgcggccgat   4320
cttagccaga cgagcgggtt cggcccattc ggaccgcaag gaatcggtca atacactaca   4380
tggcgtgatt tcatatgcgc gattgctgat ccccatgtgt atcactggca aactgtgatg   4440
gacgacaccg tcagtgcgtc cgtcgcgcag gctctcgatg agctgatgct ttgggccgag   4500
gactgccccg aagtccggca cctcgtgcac gcggatttcg gctccaacaa tgtcctgacg   4560
gacaatggcc gcataacagc ggtcattgac tggagcgagg cgatgttcgg ggattcccaa   4620
tacgaggtcg ccaacatctt cttctggagg ccgtggttgg cttgtatgga gcagcagacg   4680
cgctacttcg agcggaggca tccggagctt gcaggatcgc cgcggctccg ggcgtatatg   4740
ctccgcattg gtcttgacca actctatcag agcttggttg acggcaattt cgatgatgca   4800
gcttgggcgc agggtcgatg cgacgcaatc gtccgatccg gagccgggac tgtcgggcgt   4860
acacaaatcg cccgcagaag cgcggccgtc tggaccgatg gctgtgtaga agtactcgcc   4920
gatagtggaa accgacgccc cagcactcgt ccgagggcaa aggaatagtg aggtacagct   4980
tggatcgatc cggctgctaa caaagcccga aaggaagctg agttggctgc tgccaccgct   5040
gagcaataac tagcataacc ccttggggcc tctaaacggg tcttgagggg ttttttgctg   5100
aaaggaggaa ctatatccgg atgatcgggc gcgccgtcga cggatccgta cgcaaaggca   5160
aagatttaaa ctcgaaaaca ttacaaaagt ctcaaaacag aggcaaggcc atgcacaaag   5220
cacactctaa gtgcttccat tgcctactaa gtagggtacg tacacgatca ccattcacca   5280
gtgatgatct ttattaatat acaacacact cagagacagc ttatgttata gctagctagc   5340
ataaactatc acatcatgtg ttagtacgac aagtgacaac attgctttta acttcgcggc   5400
cttggatcct ctagaccgga tataatgagc cgtaaacaaa gatgattaag tagtaattaa   5460
tacgtactag taaaagtggc aaaagataac gagaaagaac caatttcttt gcattcggcc   5520
ttagcggaag gcatatataa gctttgatta ttttatttag tgtaatgatt tcgtacaacc   5580
aaagcattta tttagtactc tcacacttgt gtcgcggccg cgaattcact agtgattcct   5640
tatagagcct tccccgcggg ttgcttctcc gccatccggg cgaacaccgc cagatagcgc   5700
```

agcaggatga ccaacccttc atggggcagc gggttccgat acggcaggtt gtgcttctgg 5760
cacagctgtt ccacctggta gctaaccgct gtcaggttgt ggcgagggag ggtcggccac 5820
aaatggtgct caatctggta attcaagcct ccgaaaaacc aatctgtgat aatccctcgc 5880
cgaatgttca tggtctcatg gatctggcca accgagaatc catggccatc ccagactgag 5940
tccccgatct tctccagtgg gtagtggttc atgaacacca cgatcgcaat gccgaagccg 6000
ccaaccagct ccgaaacgaa aaacaccaac agcgatgtga ggatgctggg cataaagaat 6060
aagtggaaca gggtcttcaa ggtccagtgc agggcgaggc caatggcctc cttcttatac 6120
tgagagcgat agaattggtt atctctgtcc ttcaaactgc gcacggtcaa cacgctctgg 6180
aaacaccaaa tgaaccgcaa caagatacag atgaccaaga aatagtactg ctggaactga 6240
atgagcttgc gggaaatcgg tgacgcccgt gtgacgtcat cctcagacca ggctaagagg 6300
gggaggttgt caatatcagg gtcgtgccct tgaacattgg ttgccgaatg atgtgcattg 6360
tgtctgtcct tccaccatgt cacggaaaaa ccttgcagac cattgccaaa taccagtccc 6420
acgaggttgt tccagttccg gttcttgaaa gtctggtggt ggcaaatgtc atgagaaagc 6480
cagcccatct gttgatagtg catcccaagc aacactgccc caatgaaata catctgatac 6540
tgaaccatca ggaaataacc cagcactcca aggcccagtg tggtgctgat tttgtatgag 6600
taccagaggg gggaggcatc aaacatgcca gttgcgatca actcttctcg gagcttccgg 6660
aaatcctctt gagcttcatt cactgcagcc tggggtggca actcagaact gggattgatt 6720
ttgggcatgc gcttgagctt gtcgaaggct tcttgagagt gcataaccat gaaggcatca 6780
gtggcatccc ttccttggta attctctata atttccgcac caccagggtg gaaattgacc 6840
caggcagaca catcatatgt tgttccatca attgtaaggg gaagcgcttg gcgctttgac 6900
ttcatttcaa tcgaattccc gcggccgctt ggggggctat ggaagacttt cttagttagt 6960
tgtgtgaata agcaatgttg ggagaatcgg gactacttat aggataggaa taaaacagaa 7020
aagtattaag tgctaatgaa atatttagac tgataattaa aatcttcacg tatgtccact 7080
tgatataaaa acgtcaggaa taaaggaagt acagtagaat ttaaaggtac tctttttata 7140
tatacccgtg ttctcttttt ggctagctag ttgcataaaa aataatctat atttttatca 7200
ttattttaaa tatcttatga gatggtaaat atttatcata attttttttta ctattattta 7260
ttatttgtgt gtgtaataca tatagaagtt aattacaaat tttatttact ttttcattat 7320
tttgatatga ttcaccatta atttagtgtt attatttata atagttcatt ttaatctttt 7380
tgtatatatt atgcgtgcag tactttttttc ctacatataa ctactattac attttattta 7440
tataatattt ttattaatga attttcgtga taatatgtaa tattgttcat tattatttca 7500
gattttttaa aaatatttgt gttattattt atgaaatatg taattttttt agtatttgat 7560
tttatgatga taaagtgttc taaattcaaa agaaggggga aagcgtaaac attaaaaaac 7620
gtcatcaaac aaaaacaaaa tcttgttaat aaagataaaa ctgtttgttt tgatcactgt 7680
tatttcgtaa tataaaaaca ttatttatat ttatattgtt gacaaccaaa tttgcctatc 7740
aaatctaacc aatataatgc atgcgtggca ggtaatgtac taccatgaac ttaagtcatg 7800
acataataaa ccgtgaatct gaccaatgca tgtacctanc taaattgtat ttgtgacacg 7860
aagcaaatga ttcaattcac aatggagatg ggaaacaaat aatgaagaac ccagaactaa 7920
gaaagctttt ctgaaaaata aaataaaggc aatgtcaaaa gtatactgca tcatcagtcc 7980
agaaagcaca tgatattttt ttatcagtat caatgcagct agttttattt tacaatatcg 8040
atatagctag tttaaatata ttgcagctag atttataaat atttgtgtta ttatttatca 8100

```
tttgtgtaat cctgttttta gtattttagt ttatatatga tgataatgta ttccaaattt   8160

aaaagaaggg aaataaattt aaacaagaaa aaaagtcatc aaacaaaaaa caaatgaaag   8220

ggtggaaaga tgttaccatg taatgtgaat gttacagtat ttcttttatt atagagttaa   8280

caaattaact aatatgattt tgttaataat gataaaatat ttttttttatt attatttcat   8340

aatataaaaa tagtttactt aatataaaaa aaattctatc gttcacaaca aagttggcca   8400

cctaatttaa ccatgcatgt acccatggac catattaggt aaccatcaaa cctgatgaag   8460

agataaagag atgaagactt aagtcataac acaaaaccat aaaaaacaaa aatacaatca   8520

accgtcaatc tgaccaatgc atgaaaaagc tgcaatagtg agtggcgaca caaagcacat   8580

gattttctta caacggagat aaaaccaaaa aaatatttca tgaacaacct agaacaaata   8640

aagcttttat ataataaata tataaataaa taaaggctat ggaataatat acttcaatat   8700

atttggatta aataaattgt tggcggggtt gatatattta tacacaccta aagtcacttc   8760

aatctcattt tcacttaact tttatttttt ttttcttttt atttatcata aagagaatat   8820

tgataatata ctttttaaca tatttttatg acattttttta ttggtgaaaa cttattaaaa   8880

atcataaatt ttgtaagtta gatttattta aagagttcct cttcttattt taaatttttt   8940

aataaatttt taaataacta aaatttgtgt taaaaatgtt aaaaaatgtg ttattaaccc   9000

ttctcttcga ggac                                                      9014


<210> SEQ ID NO 78
<211> LENGTH: 1482
<212> TYPE: DNA
<213> ORGANISM: Mortierella alpina
<220> FEATURE:
<221> NAME/KEY: CDS
<222> LOCATION: (59)..(1399)
<223> OTHER INFORMATION: delta-5 desaturase

<400> SEQUENCE: 78

gcttcctcca gttcatcctc catttcgcca cctgcattct ttacgaccgt taagcaag       58

atg gga acg gac caa gga aaa acc ttc acc tgg gaa gag ctg gcg gcc      106
Met Gly Thr Asp Gln Gly Lys Thr Phe Thr Trp Glu Glu Leu Ala Ala
1               5                   10                  15

cat aac acc aag gac gac cta ctc ttg gcc atc cgc ggc agg gtg tac      154
His Asn Thr Lys Asp Asp Leu Leu Leu Ala Ile Arg Gly Arg Val Tyr
            20                  25                  30

gat gtc aca aag ttc ttg agc cgc cat cct ggt gga gtg gac act ctc      202
Asp Val Thr Lys Phe Leu Ser Arg His Pro Gly Gly Val Asp Thr Leu
        35                  40                  45

ctg ctc gga gct ggc cga gat gtt act ccg gtc ttt gag atg tat cac      250
Leu Leu Gly Ala Gly Arg Asp Val Thr Pro Val Phe Glu Met Tyr His
    50                  55                  60

gcg ttt ggg gct gca gat gcc att atg aag aag tac tat gtc ggt aca      298
Ala Phe Gly Ala Ala Asp Ala Ile Met Lys Lys Tyr Tyr Val Gly Thr
65                  70                  75                  80

ctg gtc tcg aat gag ctg ccc atc ttc ccg gag cca acg gtg ttc cac      346
Leu Val Ser Asn Glu Leu Pro Ile Phe Pro Glu Pro Thr Val Phe His
                85                  90                  95

aaa acc atc aag acg aga gtc gag ggc tac ttt acg gat cgg aac att      394
Lys Thr Ile Lys Thr Arg Val Glu Gly Tyr Phe Thr Asp Arg Asn Ile
            100                 105                 110

gat ccc aag aat aga cca gag atc tgg gga cga tac gct ctt atc ttt      442
Asp Pro Lys Asn Arg Pro Glu Ile Trp Gly Arg Tyr Ala Leu Ile Phe
        115                 120                 125

gga tcc ttg atc gct tcc tac tac gcg cag ctc ttt gtg cct ttc gtt      490
```

```
Gly Ser Leu Ile Ala Ser Tyr Tyr Ala Gln Leu Phe Val Pro Phe Val
    130                 135                 140

gtc gaa cgc aca tgg ctt cag gtg gtg ttt gca atc atc atg gga ttt      538
Val Glu Arg Thr Trp Leu Gln Val Val Phe Ala Ile Ile Met Gly Phe
145                 150                 155                 160

gcg tgc gca caa gtc gga ctc aac cct ctt cat gat gcg tct cac ttt      586
Ala Cys Ala Gln Val Gly Leu Asn Pro Leu His Asp Ala Ser His Phe
                165                 170                 175

tca gtg acc cac aac ccc act gtc tgg aag att ctg gga gcc acg cac      634
Ser Val Thr His Asn Pro Thr Val Trp Lys Ile Leu Gly Ala Thr His
            180                 185                 190

gac ttt ttc aac gga gca tcg tac ctg gtg tgg atg tac caa cat atg      682
Asp Phe Phe Asn Gly Ala Ser Tyr Leu Val Trp Met Tyr Gln His Met
        195                 200                 205

ctc ggc cat cac ccc tac acc aac att gct gga gca gat ccc gac gtg      730
Leu Gly His His Pro Tyr Thr Asn Ile Ala Gly Ala Asp Pro Asp Val
    210                 215                 220

tcg acg tct gag ccc gat gtt cgt cgt atc aag ccc aac caa aag tgg      778
Ser Thr Ser Glu Pro Asp Val Arg Arg Ile Lys Pro Asn Gln Lys Trp
225                 230                 235                 240

ttt gtc aac cac atc aac cag cac atg ttt gtt cct ttc ctg tac gga      826
Phe Val Asn His Ile Asn Gln His Met Phe Val Pro Phe Leu Tyr Gly
                245                 250                 255

ctg ctg gcg ttc aag gtg cgc att cag gac atc aac att ttg tac ttt      874
Leu Leu Ala Phe Lys Val Arg Ile Gln Asp Ile Asn Ile Leu Tyr Phe
            260                 265                 270

gtc aag acc aat gac gct att cgt gtc aat ccc atc tcg aca tgg cac      922
Val Lys Thr Asn Asp Ala Ile Arg Val Asn Pro Ile Ser Thr Trp His
        275                 280                 285

act gtg atg ttc tgg ggc ggc aag gct ttc ttt gtc tgg tat cgc ctg      970
Thr Val Met Phe Trp Gly Gly Lys Ala Phe Phe Val Trp Tyr Arg Leu
    290                 295                 300

att gtt ccc ctg cag tat ctg ccc ctg ggc aag gtg ctg ctc ttg ttc     1018
Ile Val Pro Leu Gln Tyr Leu Pro Leu Gly Lys Val Leu Leu Leu Phe
305                 310                 315                 320

acg gtc gcg gac atg gtg tcg tct tac tgg ctg gcg ctg acc ttc cag     1066
Thr Val Ala Asp Met Val Ser Ser Tyr Trp Leu Ala Leu Thr Phe Gln
                325                 330                 335

gcg aac cac gtt gtt gag gaa gtt cag tgg ccg ttg cct gac gag aac     1114
Ala Asn His Val Val Glu Glu Val Gln Trp Pro Leu Pro Asp Glu Asn
            340                 345                 350

ggg atc atc caa aag gac tgg gca gct atg cag gtc gag act acg cag     1162
Gly Ile Ile Gln Lys Asp Trp Ala Ala Met Gln Val Glu Thr Thr Gln
        355                 360                 365

gat tac gca cac gat tcg cac ctc tgg acc agc atc act ggc agc ttg     1210
Asp Tyr Ala His Asp Ser His Leu Trp Thr Ser Ile Thr Gly Ser Leu
    370                 375                 380

aac tac cag gct gtg cac cat ctg ttc ccc aac gtg tcg cag cac cat     1258
Asn Tyr Gln Ala Val His His Leu Phe Pro Asn Val Ser Gln His His
385                 390                 395                 400

tat ccc gat att ctg gcc atc atc aag aac acc tgc agc gag tac aag     1306
Tyr Pro Asp Ile Leu Ala Ile Ile Lys Asn Thr Cys Ser Glu Tyr Lys
                405                 410                 415

gtt cca tac ctt gtc aag gat acg ttt tgg caa gca ttt gct tca cat     1354
Val Pro Tyr Leu Val Lys Asp Thr Phe Trp Gln Ala Phe Ala Ser His
            420                 425                 430

ttg gag cac ttg cgt gtt ctt gga ctc cgt ccc aag gaa gag tag         1399
Leu Glu His Leu Arg Val Leu Gly Leu Arg Pro Lys Glu Glu
        435                 440                 445

aagaaaaaaa gcgccgaatg aagtattgcc ccctttttct ccaagaatgg caaaaggaga   1459
```

tcaagtggac attctctatg aag 1482

<210> SEQ ID NO 79
<211> LENGTH: 446
<212> TYPE: PRT
<213> ORGANISM: Mortierella alpina

<400> SEQUENCE: 79

Met Gly Thr Asp Gln Gly Lys Thr Phe Thr Trp Glu Glu Leu Ala Ala
1 5 10 15

His Asn Thr Lys Asp Asp Leu Leu Leu Ala Ile Arg Gly Arg Val Tyr
20 25 30

Asp Val Thr Lys Phe Leu Ser Arg His Pro Gly Gly Val Asp Thr Leu
35 40 45

Leu Leu Gly Ala Gly Arg Asp Val Thr Pro Val Phe Glu Met Tyr His
50 55 60

Ala Phe Gly Ala Ala Asp Ala Ile Met Lys Lys Tyr Tyr Val Gly Thr
65 70 75 80

Leu Val Ser Asn Glu Leu Pro Ile Phe Pro Glu Pro Thr Val Phe His
85 90 95

Lys Thr Ile Lys Thr Arg Val Glu Gly Tyr Phe Thr Asp Arg Asn Ile
100 105 110

Asp Pro Lys Asn Arg Pro Glu Ile Trp Gly Arg Tyr Ala Leu Ile Phe
115 120 125

Gly Ser Leu Ile Ala Ser Tyr Tyr Ala Gln Leu Phe Val Pro Phe Val
130 135 140

Val Glu Arg Thr Trp Leu Gln Val Val Phe Ala Ile Ile Met Gly Phe
145 150 155 160

Ala Cys Ala Gln Val Gly Leu Asn Pro Leu His Asp Ala Ser His Phe
165 170 175

Ser Val Thr His Asn Pro Thr Val Trp Lys Ile Leu Gly Ala Thr His
180 185 190

Asp Phe Phe Asn Gly Ala Ser Tyr Leu Val Trp Met Tyr Gln His Met
195 200 205

Leu Gly His His Pro Tyr Thr Asn Ile Ala Gly Ala Asp Pro Asp Val
210 215 220

Ser Thr Ser Glu Pro Asp Val Arg Arg Ile Lys Pro Asn Gln Lys Trp
225 230 235 240

Phe Val Asn His Ile Asn Gln His Met Phe Val Pro Phe Leu Tyr Gly
245 250 255

Leu Leu Ala Phe Lys Val Arg Ile Gln Asp Ile Asn Ile Leu Tyr Phe
260 265 270

Val Lys Thr Asn Asp Ala Ile Arg Val Asn Pro Ile Ser Thr Trp His
275 280 285

Thr Val Met Phe Trp Gly Gly Lys Ala Phe Phe Val Trp Tyr Arg Leu
290 295 300

Ile Val Pro Leu Gln Tyr Leu Pro Leu Gly Lys Val Leu Leu Leu Phe
305 310 315 320

Thr Val Ala Asp Met Val Ser Ser Tyr Trp Leu Ala Leu Thr Phe Gln
325 330 335

Ala Asn His Val Val Glu Glu Val Gln Trp Pro Leu Pro Asp Glu Asn
340 345 350

Gly Ile Ile Gln Lys Asp Trp Ala Ala Met Gln Val Glu Thr Thr Gln
355 360 365

Asp Tyr Ala His Asp Ser His Leu Trp Thr Ser Ile Thr Gly Ser Leu
370 375 380

Asn Tyr Gln Ala Val His His Leu Phe Pro Asn Val Ser Gln His His
385 390 395 400

Tyr Pro Asp Ile Leu Ala Ile Ile Lys Asn Thr Cys Ser Glu Tyr Lys
405 410 415

Val Pro Tyr Leu Val Lys Asp Thr Phe Trp Gln Ala Phe Ala Ser His
420 425 430

Leu Glu His Leu Arg Val Leu Gly Leu Arg Pro Lys Glu Glu
435 440 445

<210> SEQ ID NO 80
<211> LENGTH: 69
<212> TYPE: DNA
<213> ORGANISM: Artificial Sequence
<220> FEATURE:
<223> OTHER INFORMATION: Restriction enzyme sites added to pKR287 to produce pKR767

<400> SEQUENCE: 80
ccatggtcaa tcaatgagac gccaacttct taatctattg agacctgcag gtctagaagg 60
gcggatccc 69

<210> SEQ ID NO 81
<211> LENGTH: 5561
<212> TYPE: DNA
<213> ORGANISM: Artificial Sequence
<220> FEATURE:
<223> OTHER INFORMATION: Plasmid pKR767

<400> SEQUENCE: 81
catggtcaat caatgagacg ccaacttctt aatctattga gacctgcagg tctagaaggg 60
cggatccccg ggtaccgagc tcgaattcac tggccgtcgt tttacaacgt cgtgactggg 120
aaaaccctgg cgttacccaa cttaatcgcc ttgcagcaca tccccctttc gccagctggc 180
gtaatagcga agaggcccgc accgatcgcc cttcccaaca gttgcgcagc ctgaatggcg 240
aatggcgcct gatgcggtat tttctcctta cgcatctgtg cggtatttca caccgcatat 300
ggtgcactct cagtacaatc tgctctgatg ccgcatagtt aagccagccc cgacacccgc 360
caacacccgc tgacgcgccc tgacgggctt gtctgctccc ggcatccgct tacagacaag 420
ctgtgaccgt ctccgggagc tgcatgtgtc agaggttttc accgtcatca ccgaaacgcg 480
cgagacgaaa gggcctcgtg atacgcctat ttttataggt taatgtcatg ataataatgg 540
tttcttagac gtcaggtggc acttttcggg gaaatgtgcg cggaacccct atttgtttat 600
ttttctaaat acattcaaat atgtatccgc tcatgagaca ataaccctga taaatgcttc 660
aataatattg aaaaaggaag agtatgagta ttcaacattt ccgtgtcgcc cttattccct 720
tttttgcggc attttgcctt cctgtttttg ctcacccaga aacgctggtg aaagtaaaag 780
atgctgaaga tcagttgggt gcacgagtgg gttacatcga actggatctc aacagcggta 840
agatccttga gagttttcgc cccgaagaac gttttccaat gatgagcact tttaaagttc 900
tgctatgtgg cgcggtatta tcccgtattg acgccgggca agagcaactc ggtcgccgca 960
tacactattc tcagaatgac ttggttgagt actcaccagt cacagaaaag catcttacgg 1020
atggcatgac agtaagagaa ttatgcagtg ctgccataac catgagtgat aacactgcgg 1080
ccaacttact tctgacaacg atcggaggac cgaaggagct aaccgctttt ttgcacaaca 1140
tgggggatca tgtaactcgc cttgatcgtt gggaaccgga gctgaatgaa gccataccaa 1200

-continued

```
acgacgagcg tgacaccacg atgcctgtag caatggcaac aacgttgcgc aaactattaa   1260
ctggcgaact acttactcta gcttcccggc aacaattaat agactggatg gaggcggata   1320
aagttgcagg accacttctg cgctcggccc ttccggctgg ctggtttatt gctgataaat   1380
ctggagccgg tgagcgtggg tctcgcggta tcattgcagc actggggcca gatggtaagc   1440
cctcccgtat cgtagttatc tacacgacgg ggagtcaggc aactatggat gaacgaaata   1500
gacagatcgc tgagataggt gcctcactga ttaagcattg gtaactgtca gaccaagttt   1560
actcatatat actttagatt gatttaaaac ttcattttta atttaaaagg atctaggtga   1620
agatcctttt tgataatctc atgaccaaaa tcccttaacg tgagttttcg ttccactgag   1680
cgtcagaccc cgtagaaaag atcaaaggat cttcttgaga tccttttttt ctgcgcgtaa   1740
tctgctgctt gcaaacaaaa aaaccaccgc taccagcggt ggtttgtttg ccggatcaag   1800
agctaccaac tctttttccg aaggtaactg gcttcagcag agcgcagata ccaaatactg   1860
tccttctagt gtagccgtag ttaggccacc acttcaagaa ctctgtagca ccgcctacat   1920
acctcgctct gctaatcctg ttaccagtgg ctgctgccag tggcgataag tcgtgtctta   1980
ccgggttgga ctcaagacga tagttaccgg ataaggcgca gcggtcgggc tgaacggggg   2040
gttcgtgcac acagcccagc ttggagcgaa cgacctacac cgaactgaga tacctacagc   2100
gtgagctatg agaaagcgcc acgcttcccg aagggagaaa ggcggacagg tatccggtaa   2160
gcggcagggt cggaacagga gagcgcacga gggagcttcc agggggaaac gcctggtatc   2220
tttatagtcc tgtcgggttt cgccacctct gacttgagcg tcgatttttg tgatgctcgt   2280
caggggggcg gagcctatgg aaaaacgcca gcaacgcggc ctttttacgg ttcctggcct   2340
tttgctggcc ttttgctcac atgttctttc ctgcgttatc ccctgattct gtggataacc   2400
gtattaccgc ctttgagtga gctgataccg ctcgccgcag ccgaacgacc gagcgcagcg   2460
agtcagtgag cgaggaagcg gaagagcgcc caatacgcaa accgcctctc cccgcgcgtt   2520
ggccgattca ttaatgcagc tggcacgaca ggtttcccga ctggaaagcg ggcagtgagc   2580
gcaacgcaat taatgtgagt tagctcactc attaggcacc ccaggcttta cactttatgc   2640
ttccggctcg tatgttgtgt ggaattgtga gcggataaca atttcacaca ggaaacagct   2700
atgaccatga ttacgccaag cttgcatgcc tgcaggctag cctaagtacg tactcaaaat   2760
gccaacaaat aaaaaaaaag ttgctttaat aatgccaaaa caaattaata aaacacttac   2820
aacaccggat ttttttaat taaaatgtgc catttaggat aaatagttaa tatttttaat   2880
aattatttaa aaagccgtat ctactaaaat gatttttatt tggttgaaaa tattaatatg   2940
tttaaatcaa cacaatctat caaaattaaa ctaaaaaaaa aataagtgta cgtggttaac   3000
attagtacag taatataaga ggaaaatgag aaattaagaa attgaaagcg agtctaattt   3060
ttaaattatg aacctgcata tataaaagga aagaaagaat ccaggaagaa aagaaatgaa   3120
accatgcatg gtcccctcgt catcacgagt ttctgccatt tgcaatagaa acactgaaac   3180
acctttctct ttgtcactta attgagatgc cgaagccacc tcacaccatg aacttcatga   3240
ggtgtagcac ccaaggcttc catagccatg catactgaag aatgtctcaa gctcagcacc   3300
ctacttctgt gacgtgtccc tcattcacct tcctctcttc cctataaata accacgcctc   3360
aggttctccg cttcacaact caaacattct ctccattggt ccttaaacac tcatcagtca   3420
tcaccgcggc cgcatgggaa cggaccaagg aaaaaccttc acctgggaag agctggcggc   3480
ccataacacc aaggacgacc tactcttggc catccgcggc agggtgtacg atgtcacaaa   3540
gttcttgagc cgccatcctg gtggagtgga cactctcctg ctcggagctg gccgagatgt   3600
```

```
tactccggtc tttgagatgt atcacgcgtt tggggctgca gatgccatta tgaagaagta   3660
ctatgtcggt acactggtct cgaatgagct gcccatcttc ccggagccaa cggtgttcca   3720
caaaaccatc aagacgagag tcgagggcta ctttacggat cggaacattg atcccaagaa   3780
tagaccagag atctggggac gatacgctct tatctttgga tccttgatcg cttcctacta   3840
cgcgcagctc tttgtgcctt tcgttgtcga acgcacatgg cttcaggtgg tgtttgcaat   3900
catcatggga tttgcgtgcg cacaagtcgg actcaaccct cttcatgatg cgtctcactt   3960
ttcagtgacc cacaacccca ctgtctggaa gattctggga gccacgcacg actttttcaa   4020
cggagcatcg tacctggtgt ggatgtacca acatatgctc ggccatcacc cctacaccaa   4080
cattgctgga gcagatcccg acgtgtcgac gtctgagccc gatgttcgtc gtatcaagcc   4140
caaccaaaag tggtttgtca accacatcaa ccagcacatg tttgttcctt tcctgtacgg   4200
actgctggcg ttcaaggtgc gcattcagga catcaacatt ttgtactttg tcaagaccaa   4260
tgacgctatt cgtgtcaatc ccatctcgac atggcacact gtgatgttct ggggcggcaa   4320
ggctttcttt gtctggtatc gcctgattgt tcccctgcag tatctgcccc tgggcaaggt   4380
gctgctcttg ttcacggtcg cggacatggt gtcgtcttac tggctggcgc tgaccttcca   4440
ggcgaaccac gttgttgagg aagttcagtg gccgttgcct gacgagaacg ggatcatcca   4500
aaaggactgg gcagctatgc aggtcgagac tacgcaggat tacgcacacg attcgcacct   4560
ctggaccagc atcactggca gcttgaacta ccaggctgtg caccatctgt tccccaacgt   4620
gtcgcagcac cattatcccg atattctggc catcatcaag aacacctgca gcgagtacaa   4680
ggttccatac cttgtcaagg atacgttttg gcaagcattt gcttcacatt tggagcactt   4740
gcgtgttctt ggactccgtc ccaaggaaga gtaggcggcc gcatttcgca ccaaatcaat   4800
gaaagtaata atgaaaagtc tgaataagaa tacttaggct tagatgcctt tgttacttgt   4860
gtaaaataac ttgagtcatg tacctttggc ggaaacagaa taaataaaag gtgaaattcc   4920
aatgctctat gtataagtta gtaatactta atgtgttcta cggttgtttc aatatcatca   4980
aactctaatt gaaactttag aaccacaaat ctcaatcttt tcttaatgaa atgaaaaatc   5040
ttaattgtac catgtttatg ttaaacacct tacaattggt tggagaggag gaccaaccga   5100
tgggacaaca ttgggagaaa gagattcaat ggagatttgg ataggagaac aacattcttt   5160
ttcacttcaa tacaagatga gtgcaacact aaggatatgt atgagacttt cagaagctac   5220
gacaacatag atgagtgagg tggtgattcc tagcaagaaa gacattagag gaagccaaaa   5280
tcgaacaagg aagacatcaa gggcaagaga caggaccatc catctcagga aaaggagctt   5340
tgggatagtc cgagaagttg tacaagaaat tttttggagg gtgagtgatg cattgctggt   5400
gactttaact caatcaaaat tgagaaagaa agaaaaggga gggggctcac atgtgaatag   5460
aagggaaacg ggagaatttt acagttttga tctaatgggc atcccagcta gtggtaacat   5520
attcaccatg tttaaccttc acgtacgtct agaggatccc c                        5561
```

<210> SEQ ID NO 82
<211> LENGTH: 8671
<212> TYPE: DNA
<213> ORGANISM: Artificial Sequence
<220> FEATURE:
<223> OTHER INFORMATION: Plasmid pKR328

<400> SEQUENCE: 82

```
ggatctggcc ggccggatct cgtacggatc cgtcgacggc gcgcccgatc atccggatat     60
agttcctcct ttcagcaaaa aacccctcaa gacccgttta gaggccccaa ggggttatgc    120
```

-continued tagttattgc tcagcggtgg cagcagccaa ctcagcttcc tttcgggctt tgttagcagc 180
cggatcgatc caagctgtac ctcactattc ctttgccctc ggacgagtgc tggggcgtcg 240
gtttccacta tcggcgagta cttctacaca gccatcggtc cagacggccg cgcttctgcg 300
ggcgatttgt gtacgcccga cagtcccggc tccggatcgg acgattgcgt cgcatcgacc 360
ctgcgcccaa gctgcatcat cgaaattgcc gtcaaccaag ctctgataga gttggtcaag 420
accaatgcgg agcatatacg cccggagccg cggcgatcct gcaagctccg gatgcctccg 480
ctcgaagtag cgcgtctgct gctccataca agccaaccac ggcctccaga agaagatgtt 540
ggcgacctcg tattgggaat ccccgaacat cgcctcgctc cagtcaatga ccgctgttat 600
gcggccattg tccgtcagga cattgttgga gccgaaatcc gcgtgcacga ggtgccggac 660
ttcggggcag tcctcggccc aaagcatcag ctcatcgaga gcctgcgcga cggacgcact 720
gacggtgtcg tccatcacag tttgccagtg atacacatgg ggatcagcaa tcgcgcatat 780
gaaatcacgc catgtagtgt attgaccgat tccttgcggt ccgaatgggc cgaacccgct 840
cgtctggcta agatcggccg cagcgatcgc atccatagcc tccgcgaccg gctgcagaac 900
agcgggcagt tcggtttcag gcaggtcttg caacgtgaca ccctgtgcac ggcgggagat 960
gcaataggtc aggctctcgc tgaattcccc aatgtcaagc acttccggaa tcgggagcgc 1020
ggccgatgca aagtgccgat aaacataacg atctttgtag aaaccatcgg cgcagctatt 1080
tacccgcagg acatatccac gccctcctac atcgaagctg aaagcacgag attcttcgcc 1140
ctccgagagc tgcatcaggt cggagacgct gtcgaacttt tcgatcagaa acttctcgac 1200
agacgtcgcg gtgagttcag gcttttccat gggtatatct ccttcttaaa gttaaacaaa 1260
attatttcta gagggaaacc gttgtggtct ccctatagtg agtcgtatta atttcgcggg 1320
atcgagatcg atccaattcc aatcccacaa aaatctgagc ttaacagcac agttgctcct 1380
ctcagagcag aatcgggtat tcaacaccct catatcaact actacgttgt gtataacggt 1440
ccacatgccg gtatatacga tgactggggt tgtacaaagg cggcaacaaa cggcgttccc 1500
ggagttgcac acaagaaatt tgccactatt acagaggcaa gagcagcagc tgacgcgtac 1560
acaacaagtc agcaaacaga caggttgaac ttcatcccca aaggagaagc tcaactcaag 1620
cccaagagct ttgctaaggc cctaacaagc ccaccaaagc aaaaagccca ctggctcacg 1680
ctaggaacca aaaggcccag cagtgatcca gccccaaaag agatctcctt tgccccggag 1740
attacaatgg acgatttcct ctatctttac gatctaggaa ggaagttcga aggtgaaggt 1800
gacgacacta tgttcaccac tgataatgag aaggttagcc tcttcaattt cagaaagaat 1860
gctgacccac agatggttag agaggcctac gcagcaggtc tcatcaagac gatctacccg 1920
agtaacaatc tccaggagat caaatacctt cccaagaagg ttaaagatgc agtcaaaaga 1980
ttcaggacta attgcatcaa gaacacagag aaagacatat ttctcaagat cagaagtact 2040
attccagtat ggacgattca aggcttgctt cataaaccaa ggcaagtaat agagattgga 2100
gtctctaaaa aggtagttcc tactgaatct aaggccatgc atggagtcta agattcaaat 2160
cgaggatcta acagaactcg ccgtgaagac tggcgaacag ttcatacaga gtcttttacg 2220
actcaatgac aagaagaaaa tcttcgtcaa catggtggag cacgacactc tggtctactc 2280
caaaaatgtc aaagatacag tctcagaaga ccaaagggct attgagactt ttcaacaaag 2340
gataatttcg ggaaacctcc tcggattcca ttgcccagct atctgtcact tcatcgaaag 2400
gacagtagaa aaggaaggtg gctcctacaa atgccatcat tgcgataaag gaaaggctat 2460
cattcaagat gcctctgccg acagtggtcc caaagatgga cccccaccca cgaggagcat 2520

-continued

```
cgtggaaaaa gaagacgttc caaccacgtc ttcaaagcaa gtggattgat gtgacatctc   2580
cactgacgta agggatgacg cacaatccca ctatccttcg caagaccctt cctctatata   2640
aggaagttca tttcatttgg agaggacacg ctcgagctca tttctctatt acttcagcca   2700
taacaaaaga actcttttct cttcttatta aaccatgaaa aagcctgaac tcaccgcgac   2760
gtctgtcgag aagtttctga tcgaaaagtt cgacagcgtc tccgacctga tgcagctctc   2820
ggagggcgaa gaatctcgtg ctttcagctt cgatgtagga gggcgtggat atgtcctgcg   2880
ggtaaatagc tgcgccgatg gtttctacaa agatcgttat gtttatcggc actttgcatc   2940
ggccgcgctc ccgattccgg aagtgcttga cattggggaa ttcagcgaga gcctgaccta   3000
ttgcatctcc cgccgtgcac agggtgtcac gttgcaagac ctgcctgaaa ccgaactgcc   3060
cgctgttctg cagccggtcg cggaggccat ggatgcgatc gctgcggccg atcttagcca   3120
gacgagcggg ttcggcccat tcggaccgca aggaatcggt caatacacta catggcgtga   3180
tttcatatgc gcgattgctg atccccatgt gtatcactgg caaactgtga tggacgacac   3240
cgtcagtgcg tccgtcgcgc aggctctcga tgagctgatg ctttgggccg aggactgccc   3300
cgaagtccgg cacctcgtgc acgcggattt cggctccaac aatgtcctga cggacaatgg   3360
ccgcataaca gcggtcattg actggagcga ggcgatgttc ggggattccc aatacgaggt   3420
cgccaacatc ttcttctgga ggccgtggtt ggcttgtatg gagcagcaga cgcgctactt   3480
cgagcggagg catccggagc ttgcaggatc gccgcggctc cgggcgtata tgctccgcat   3540
tggtcttgac caactctatc agagcttggt tgacggcaat ttcgatgatg cagcttgggc   3600
gcagggtcga tgcgacgcaa tcgtccgatc cggagccggg actgtcgggc gtacacaaat   3660
cgcccgcaga agcgcggccg tctggaccga tggctgtgta gaagtactcg ccgatagtgg   3720
aaaccgacgc cccagcactc gtccgagggc aaaggaatag tgaggtacct aaagaaggag   3780
tgcgtcgaag cagatcgttc aaacatttgg caataaagtt tcttaagatt gaatcctgtt   3840
gccggtcttg cgatgattat catataattt ctgttgaatt acgttaagca tgtaataatt   3900
aacatgtaat gcatgacgtt atttatgaga tgggttttta tgattagagt cccgcaatta   3960
tacatttaat acgcgataga aaacaaaata tagcgcgcaa actaggataa attatcgcgc   4020
gcggtgtcat ctatgttact agatcgatgt cgaatcgatc aacctgcatt aatgaatcgg   4080
ccaacgcgcg gggagaggcg gtttgcgtat tgggcgctct tccgcttcct cgctcactga   4140
ctcgctgcgc tcggtcgttc ggctgcggcg agcggtatca gctcactcaa aggcggtaat   4200
acggttatcc acagaatcag gggataacgc aggaaagaac atgtgagcaa aaggccagca   4260
aaaggccagg aaccgtaaaa aggccgcgtt gctggcgttt ttccataggc tccgcccccc   4320
tgacgagcat cacaaaaatc gacgctcaag tcagaggtgg cgaaacccga caggactata   4380
aagataccag gcgtttcccc ctggaagctc cctcgtgcgc tctcctgttc cgaccctgcc   4440
gcttaccgga tacctgtccg cctttctccc ttcgggaagc gtggcgcttt ctcaatgctc   4500
acgctgtagg tatctcagtt cggtgtaggt cgttcgctcc aagctgggct gtgtgcacga   4560
accccccgtt cagcccgacc gctgcgcctt atccggtaac tatcgtcttg agtccaaccc   4620
ggtaagacac gacttatcgc cactggcagc agccactggt aacaggatta gcagagcgag   4680
gtatgtaggc ggtgctacag agttcttgaa gtggtggcct aactacggct acactagaag   4740
gacagtattt ggtatctgcg ctctgctgaa gccagttacc ttcggaaaaa gagttggtag   4800
ctcttgatcc ggcaaacaaa ccaccgctgg tagcggtggt ttttttgttt gcaagcagca   4860
gattacgcgc agaaaaaaag gatctcaaga agatcctttg atcttttcta cggggtctga   4920
```

```
cgctcagtgg aacgaaaact cacgttaagg gattttggtc atgacattaa cctataaaaa   4980
taggcgtatc acgaggccct ttcgtctcgc gcgtttcggt gatgacggtg aaaacctctg   5040
acacatgcag ctcccggaga cggtcacagc ttgtctgtaa gcggatgccg ggagcagaca   5100
agcccgtcag ggcgcgtcag cgggtgttgg cgggtgtcgg ggctggctta actatgcggc   5160
atcagagcag attgtactga gagtgcacca tatggacata ttgtcgttag aacgcggcta   5220
caattaatac ataaccttat gtatcataca catacgattt aggtgacact atagaacggc   5280
gcgccaagct tggatctcct gcagcccggg ggatccgccc acgtacggta ccatctgcta   5340
atattttaaa tcacatgcaa gagaggaggc atggttccat tttctacctt cacattattt   5400
gagaaaaacg aacttgttct gtgttttatt tttgcccttc acattagtac aacgtggaag   5460
actcatggtt acacagaatc atacataagt acaatgcttg tccctaagaa aacaagcact   5520
cgttgtattg aacctttacg gctcatgcgg ccgcgaattc actagtgatt gaattcgcgg   5580
ccgcttagtc cgacttggcc ttggcggccg cggccgactc tttgagcgtg aagatctgcg   5640
ccgtctcggg cacagcgccg tagttgacaa agaggtgcgc ggtcttgaag aaggccgtga   5700
tgatgggctc gtcgttcctg cgcacgaggt gcgggtacgc ggccgcaaag tgcttggtgg   5760
cttcgttgag cttgtagtgc ggaatgatcg ggaacaagtg gtggacctgg tgcgtgccaa   5820
tgtggtggct caggttgtcc acgaacgcgc cgtacgagcg gtcgacgctc gagaggttgc   5880
ccttgacgta cgtccactcc gagtcgccgt accacggcgt cgcttcgtcg ttgtggtgca   5940
agaaggtcgt aatgacgagg aacgaagcaa agacaaagag cggcgcatag tagtagaggc   6000
ccatgacggc aaagccgagc gagtatgtga ggtacgcgta cgcggcgaag aaggcggccc   6060
agacgccgag cgacacgatg acggccgacg cgcggcgaag gaggagcggg tcccacgggt   6120
caaagtggct catcgtgcgc ggggcatacc cgaccttcaa gtagacaaac cacgcaccgc   6180
cgagcgtgta gacccattgg cgcacgtcct ggaggtcctt gaccgaccgg tgcgggtaaa   6240
agatctcgtc cttatcaatg ttgcccgtgt tcttgtggtg gtggcggtgc gtcacgcgcc   6300
agctctcgaa cggcgtcaaa atcgcagagt gcatgatgca gccgatgata aagttgacgc   6360
tgtggtagcg cgagaaggcc gagtggccgc agtcgtggcc gaccgtgaag aagccccaga   6420
agatgacgcc ctgcacgtag atgtaggtgg cgcaaacgag cgcgtggagc agaacgttat   6480
cggcaatgaa cggcgtcgag cgcgccgcgt agagcagcgc cgccgaggcc gacgcgttga   6540
agatcgcgcg ggccgtgtag tagagcgaga ggccgaggtt cgactcaaag cacgcgttcg   6600
ggatcgagtg cttgagctcc gtgagcgtcg ggaactcgac cttcgtctta tcctcagtca   6660
tgcggccgct gaagtattgc ttcttagtta acctttcctt tctctctcag ctatgtgaat   6720
tcattttgct ttcgtcacaa tttatatagt gaaattggat ctttggagtt aacgccttca   6780
caggattatc gtgttagaac aatgcttttt catgttctaa ttagtagtac attacaaatg   6840
tgcactctat tcaataagca tcttttggca cgttaataaa tcatgtgaaa aaaaaatact   6900
actatttcaa agaaagtgtt gtaaaaagaa acggaaagag agctggcttc agttgttgag   6960
acttgtttgc tagtaaaaat ggtgtgaaga gtgattcatg gtgaggtggt ttttcgtccc   7020
tttctgtttg catgaaaaac aaatggcaag agatgacgta ggattccttc ccttaacgat   7080
tatctgtttt taatttcaaa tatacatata ggaatttatg aattactaag gttgtaaaat   7140
atgctggtca tttatttatg gctaaaatat ttttttttct cgtaaatata aaaatattta   7200
aaatttattt ttatcatatt ttttatcctt ataaaattat gtgtacaacc tatataaaaa   7260
aatatcatat ttaatattga ttatatgttt aatcaatata aaaaatcatt atcatatatt   7320
```

tagatttatt cgaatataca tctaaacaaa aaataacata ttttaatttt atgaagaaaa 7380
aaaaatattt tatcctttat ttatttaaga ttaattaata gttatgtatt gtggaaagac 7440
ttttacacat gcaatagata tactgaatca attagatgcc aatgctgagt tggaaatcac 7500
ttgaggaggg gaggagactt gccaatgctt ttcagtttca tttaaatgat ttagtggagg 7560
agatagagta gtgataaagg catgccccaa ttttggagtg tatatatgag tggaaataag 7620
agagggatag agagaaaaaa taaagagagt aaaaataatt aatgtgaaat gatatgataa 7680
aaaaataaag aaagagataa agagaaaaat gaaatgagag atagatgaaa tagagagtag 7740
atacatgttt gtttaggttt tttttaggaa ataacacatt tttttctcat cacttattac 7800
tcactgtcaa tttcctctct ttcaatcata atgatatgat ttgtttaaca aaaatgtgaa 7860
aaaacatata aagtaaaata tttttataaa ttgataaata aaaatttaca aaatttattt 7920
cttattaaat tgaatagaaa atgaaagaaa agaaaagaaa aagtatatat aaaatgatat 7980
agctttaaaa agaataaatt tttcatatca gtcttttttt aataatttag aaatatttaa 8040
gtatatagca aaaatataat gtactttaca tatgcataaa taataatttg aaaatagaac 8100
taatagaata gagaaaaaag taatataata attaactata tgaaaattta gaagggacaa 8160
tatttttaat taagaatata aacaatattt cttttcatgt aatgagggac ggatgtacgg 8220
ggccagtgtt ggagtcaaag ccaaaatagt cacggggaaa ttaatgcact gcatgactat 8280
tcgaaaaaat tcactagcct tacttagatg ttagattaat agctaggggg tgcagataat 8340
tttgaaaggc atgaaaaaca ttaatttgta cattgcaagc ttttgatgac aagctttgca 8400
attgttcaca ctaccttatg ccatttataa atagagtgat tggcatatga aggaaatcat 8460
gagagtcgaa gcgaaaaaca aagcttgaga gtgtaggaaa aatacagttt ttttggtaaa 8520
aatacagtat ttgaatagga gcgaaaaata tcctttcaaa atgatccttt tctttttttt 8580
ttttttcttt gttgttcttg gtcagttatt caaaggaaaa gggattgaaa taaaaacttg 8640
catgtgggat cgtacgtcga gtcgacctgc a 8671

<210> SEQ ID NO 83
<211> LENGTH: 9892
<212> TYPE: DNA
<213> ORGANISM: Artificial Sequence
<220> FEATURE:
<223> OTHER INFORMATION: Plasmid pKR886

<400> SEQUENCE: 83
ggtcgactcg acgtacgtct agaggatccg tcgacggcgc gcccgatcat ccggatatag 60
ttcctccttt cagcaaaaaa cccctcaaga cccgtttaga ggccccaagg ggttatgcta 120
gttattgctc agcggtggca gcagccaact cagcttcctt tcgggctttg ttagcagccg 180
gatcgatcca agctgtacct cactattcct ttgccctcgg acgagtgctg gggcgtcggt 240
ttccactatc ggcgagtact tctacacagc catcggtcca gacggccgcg cttctgcggg 300
cgatttgtgt acgcccgaca gtcccggctc cggatcggac gattgcgtcg catcgaccct 360
gcgcccaagc tgcatcatcg aaattgccgt caaccaagct ctgatagagt tggtcaagac 420
caatgcggag catatacgcc cggagccgcg gcgatcctgc aagctccgga tgcctccgct 480
cgaagtagcg cgtctgctgc tccatacaag ccaaccacgg cctccagaag aagatgttgg 540
cgacctcgta ttgggaatcc ccgaacatcg cctcgctcca gtcaatgacc gctgttatgc 600
ggccattgtc cgtcaggaca ttgttggagc cgaaatccgc gtgcacgagg tgccggactt 660
cggggcagtc ctcggcccaa agcatcagct catcgagagc ctgcgcgacg gacgcactga 720

-continued

```
cggtgtcgtc catcacagtt tgccagtgat acacatgggg atcagcaatc gcgcatatga    780
aatcacgcca tgtagtgtat tgaccgattc cttgcggtcc gaatgggccg aacccgctcg    840
tctggctaag atcggccgca gcgatcgcat ccatagcctc cgcgaccggc tgcagaacag    900
cgggcagttc ggtttcaggc aggtcttgca acgtgacacc ctgtgcacgg cgggagatgc    960
aataggtcag gctctcgctg aattccccaa tgtcaagcac ttccggaatc gggagcgcgg   1020
ccgatgcaaa gtgccgataa acataacgat ctttgtagaa accatcggcg cagctattta   1080
cccgcaggac atatccacgc cctcctacat cgaagctgaa agcacgagat tcttcgccct   1140
ccgagagctg catcaggtcg gagacgctgt cgaacttttc gatcagaaac ttctcgacag   1200
acgtcgcggt gagttcaggc ttttccatgg gtatatctcc ttcttaaagt taaacaaaat   1260
tatttctaga gggaaaccgt tgtggtctcc ctatagtgag tcgtattaat ttcgcgggat   1320
cgagatctga tcaacctgca ttaatgaatc ggccaacgcg cggggagagg cggtttgcgt   1380
attgggcgct cttccgcttc ctcgctcact gactcgctgc gctcggtcgt tcggctgcgg   1440
cgagcggtat cagctcactc aaaggcggta atacggttat ccacagaatc aggggataac   1500
gcaggaaaga acatgtgagc aaaaggccag caaaaggcca ggaaccgtaa aaaggccgcg   1560
ttgctggcgt ttttccatag gctccgcccc cctgacgagc atcacaaaaa tcgacgctca   1620
agtcagaggt ggcgaaaccc gacaggacta taaagatacc aggcgtttcc ccctggaagc   1680
tccctcgtgc gctctcctgt tccgaccctg ccgcttaccg gatacctgtc cgcctttctc   1740
ccttcgggaa gcgtggcgct ttctcaatgc tcacgctgta ggtatctcag ttcggtgtag   1800
gtcgttcgct ccaagctggg ctgtgtgcac gaaccccccg ttcagcccga ccgctgcgcc   1860
ttatccggta actatcgtct tgagtccaac ccggtaagac acgacttatc gccactggca   1920
gcagccactg gtaacaggat tagcagagcg aggtatgtag gcggtgctac agagttcttg   1980
aagtggtggc ctaactacgg ctacactaga aggacagtat ttggtatctg cgctctgctg   2040
aagccagtta ccttcggaaa aagagttggt agctcttgat ccggcaaaca aaccaccgct   2100
ggtagcggtg gtttttttgt ttgcaagcag cagattacgc gcagaaaaaa aggatctcaa   2160
gaagatcctt tgatcttttc tacggggtct gacgctcagt ggaacgaaaa ctcacgttaa   2220
gggattttgg tcatgacatt aacctataaa aataggcgta tcacgaggcc ctttcgtctc   2280
gcgcgtttcg gtgatgacgg tgaaaacctc tgacacatgc agctcccgga gacggtcaca   2340
gcttgtctgt aagcggatgc cgggagcaga caagcccgtc agggcgcgtc agcgggtgtt   2400
ggcgggtgtc ggggctggct taactatgcg gcatcagagc agattgtact gagagtgcac   2460
catatggaca tattgtcgtt agaacgcggc tacaattaat acataacctt atgtatcata   2520
cacatacgat ttaggtgaca ctatagaacg gcgcgccaag ctgggtctag aactagaaac   2580
gtgatgccac ttgttattga agtcgattac agcatctatt ctgttttact atttataact   2640
ttgccatttc tgacttttga aaactatctc tggatttcgg tatcgctttg tgaagatcga   2700
gcaaaagaga cgttttgtgg acgcaatggt ccaaatccgt tctacatgaa caaattggtc   2760
acaatttcca ctaaaagtaa ataaatggca agttaaaaaa ggaatatgca ttttactgat   2820
tgcctaggtg agctccaaga gaagttgaat ctacacgtct accaaccgct aaaaaaagaa   2880
aaacattgat atgtaacctg attccattag cttttgactt cttcaacaga ttctctactt   2940
agatttctaa cagaaatatt attactagca catcattttc agtctcacta cagcaaaaaa   3000
tccaacggca caatacagac aacaggagat atcagactac agagatagat agatgctact   3060
gcatgtagta agttaaataa aaggaaaata aaatgtcttg ctaccaaaac tactacagac   3120
```

-continued

```
tatgatgctc accacaggcc aaatcctgca actaggacag cattatctta tatatattgt   3180
acaaaacaag catcaaggaa catttggtct aggcaatcag tacctcgttc taccatcacc   3240
ctcagttatc acatccttga aggatccatt actgggaatc atcggcaaca catgctcctg   3300
atggggcaca atgacatcaa gaaggtaggg gccaggggtg tccaacattc tctgaattgc   3360
cgctctaagc tcttccttct tcgtcactcg cgctgccggt atcccacaag catcagcaaa   3420
cttgagcatg tttgggaata tctcgctctc gctagacgga tctccaagat aggtgtgagc   3480
tctattggac ttgtagaacc tatcctccaa ctgaaccacc atacccaaat gctgattgtt   3540
caacaacaat atcttaactg ggagattctc cactcttata gtggccaact cctgaacatt   3600
catgatgaaa ctaccatccc catcaatgtc aaccacaaca gccccagggt tagcaacagc   3660
agcaccaata gccgcaggca atccaaaacc catggctcca agacccccctg aggtcaacca   3720
ctgcctcggt ctcttgtact tgtaaaactg cgcagcccac atttgatgct gcccaacccc   3780
agtactaaca atagcatctc cattagtcaa ctcatcaaga acctcgatag catgctgcgg   3840
agaaatcgcg tcctggaatg tcttgtaacc caatggaaac ttgtgtttct gcacattaat   3900
ctcttctctc caacctccaa gatcaaactt accctccact cctttctcct ccaaaatcat   3960
attaattccc ttcaaggcca acttcaaatc cgcgcaaacc gacacgtgcg cctgcttgtt   4020
cttcccaatc tcggcagaat caatatcaat gtgaacaatc ttagccctac tagcaaaagc   4080
ctcaagcttc ccagtaacac ggtcatcaaa ccttacccca aaggcaagca acaaatcact   4140
attgtcaaca gcatagttag cataaacagt accatgcata cccagcatct gaagggaata   4200
ttcatcacca ataggaaaag ttccaagacc cattaaagtg ctagcaacgg gaataccagt   4260
gagttcaaca aagcgcctca attcagcact ggaattcaaa ctgccaccgc cgacgtagag   4320
aacgggcttt tgggcctcca tgatgagtct gacaatgtgt tccaattggg cctcggcggg   4380
gggcctgggc agcctggcga ggtaaccggg gaggttaacg ggctcgtccc aattaggcac   4440
ggcgagttgc tgctgaacgt ctttgggaat gtcgatgagg accggaccgg ggcggccgga   4500
ggtggcgacg aagaaagcct cggcgacgac gcgggggatg tcgtcgacgt cgaggatgag   4560
gtagttgtgc ttcgtgatgg atctgctcac ctccacgatc ggggtttctt ggaaggcgtc   4620
ggtgccgatc atccggcggg cgacctggcc ggtgatggcg acgactggga cgctgtccat   4680
taaagcgtcg gcgaggccgc tcacgaggtt ggtggcgccg gggccggagg tggcaatgca   4740
gacgccgggg aggccggagg aacgcgcgta gccttcggcg gcgaagacgc cgccctgctc   4800
gtggcgcggg agcacgttgc ggatggcggc ggagcgcgtg agcgcctggt ggatctccat   4860
cgacgcaccg ccggggtacg cgaacaccgt cgtcacgccc tgcctctcca gcgcctccac   4920
aaggatgtcc gcgcccttgc gaggttcgcc ggaggcgaac cgtgacacga agggctccgt   4980
ggtcggcgct tccttggtga agggcgccgc cgtgggggt ttggagatgg aacatttgat   5040
tttgagagcg tggttgggtt tggtgagggt ttgatgagag agagggaggg tggatctagt   5100
aatgcgtttg gggaaggtgg ggtgtgaaga ggaagaagag aatcgggtgg ttctggaagc   5160
ggtggccgcc attgtgttgt gtggcatggt tatacttcaa aaactgcaca acaagcctag   5220
agttagtacc taaacagtaa atttacaaca gagagcaaag acacatgcaa aaatttcagc   5280
cataaaaaaa gttataatag aatttaaagc aaaagtttca ttttttaaac atatatacaa   5340
acaaactgga tttgaaggaa gggattaatt cccctgctca aagtttgaat tcctattgtg   5400
acctatactc gaataaaatt gaagcctaag gaatgtatga gaaacaagaa aacaaaacaa   5460
aactacagac aaacaagtac aattacaaaa ttcgctaaaa ttctgtaatc accaaacccc   5520
```

-continued

```
atctcagtca gcacaaggcc caaggtttat tttgaaataa aaaaaaagtg attttatttc   5580
tcataagcta aaagaaagaa aggcaattat gaaatgattt cgactagatc tgaaagtcca   5640
acgcgtattc cgcagatatt aaagaaagag tagagtttca catggatcct agatggaccc   5700
agttgaggaa aaagcaaggc aaagcaaacc agaagtgcaa gatccgaaat tgaaccacgg   5760
aatctaggat ttggtagagg gagaagaaaa gtaccttgag aggtagaaga gaagagaaga   5820
gcagagagat atatgaacga gtgtgtcttg gtctcaactc tgaagcgata cgagtttaga   5880
ggggagcatt gagttccaat ttatagggaa accgggtggc aggggtgagt taatgacgga   5940
aaagccccta agtaacgaga ttggattgtg ggttagattc aaccgtttgc atccgcggct   6000
tagattgggg aagtcagagt gaatctcaac cgttgactga gttgaaaatt gaatgtagca   6060
accaattgag ccaaccccag cctttgccct ttgattttga tttgtttgtt gcatactttt   6120
tatttgtctt ctggttctga ctctctttct ctcgtttcaa tgccaggttg cctactccca   6180
caccactcac aagaagattc tactgttagt attaaatatt ttttaatgta ttaaatgatg   6240
aatgcttttg taaacagaac aagactatgt ctaataagtg tcttgcaaca tttttaaga   6300
aattaaaaaa aatatattta ttatcaaaat caaatgtatg aaaaatcatg aataatataa   6360
ttttatacat ttttttaaaa aatcttttaa tttcttaatt aatatcttaa aaataatgat   6420
taatatttaa cccaaaataa ttagtatgat tggtaaggaa gatatccatg ttatgtttgg   6480
atgtgagttt gatctagagc aaagcttact agagtcgacc tgcaggtcga ctcgacgtac   6540
gatcccacat gcaagttttt atttcaatcc cttttccttt gaataactga ccaagaacaa   6600
caagaaaaaa aaaaaaaaag aaaaggatca ttttgaaagg atatttttcg ctcctattca   6660
aatactgtat ttttaccaaa aaaactgtat ttttcctaca ctctcaagct ttgtttttcg   6720
cttcgactct catgatttcc ttcatatgcc aatcactcta tttataaatg gcataaggta   6780
gtgtgaacaa ttgcaaagct tgtcatcaaa agcttgcaat gtacaaatta atgtttttca   6840
tgcctttcaa aattatctgc accccctagc tattaatcta acatctaagt aaggctagtg   6900
aattttttcg aatagtcatg cagtgcatta atttccccgt gactattttg gctttgactc   6960
caacactggc cccgtacatc cgtccctcat tacatgaaaa gaaatattgt ttatattctt   7020
aattaaaaat attgtccctt ctaaattttc atatagttaa ttattatatt actttttct   7080
ctattctatt agttctattt tcaaattatt atttatgcat atgtaaagta cattatattt   7140
ttgctatata cttaaatatt tctaaattat taaaaaaaga ctgatatgaa aaatttattc   7200
tttttaaagc tatatcattt tatatatact ttttcttttc ttttctttca ttttctattc   7260
aatttaataa gaaataaatt ttgtaaattt ttatttatca atttataaaa atattttact   7320
ttatatgttt tttcacattt ttgttaaaca aatcatatca ttatgattga aagagaggaa   7380
attgacagtg agtaataagt gatgagaaaa aaatgtgtta tttcctaaaa aaaacctaaa   7440
caaacatgta tctactctct atttcatcta tctctcattt cattttctc tttatctctt   7500
tctttatttt tttatcatat catttcacat taattatttt tactctcttt atttttctc   7560
tctatccctc tcttatttcc actcatatat acactccaaa attggggcat gcctttatca   7620
ctactctatc tcctccacta aatcatttaa atgaaactga aaagcattgg caagtctcct   7680
cccctcctca agtgatttcc aactcagcat tggcatctaa ttgattcagt atatctattg   7740
catgtgtaaa agtctttcca caatacataa ctattaatta atcttaaata aataaaggat   7800
aaaatatttt tttttcttca taaaattaaa atatgttatt ttttgtttag atgtatattc   7860
gaataaatct aaatatatga taatgatttt ttatattgat taaacatata atcaatatta   7920
```

aatatgatat tttttatat aggttgtaca cataatttta taaggataaa aaatatgata 7980
aaaataaatt ttaaatattt ttatatttac gagaaaaaaa aatattttag ccataaataa 8040
atgaccagca tattttacaa ccttagtaat tcataaattc ctatatgtat atttgaaatt 8100
aaaaacagat aatcgttaag ggaaggaatc ctacgtcatc tcttgccatt tgtttttcat 8160
gcaaacagaa agggacgaaa aaccacctca ccatgaatca ctcttcacac catttttact 8220
agcaaacaag tctcaacaac tgaagccagc tctctttccg tttcttttta caacactttc 8280
tttgaaatag tagtattttt ttttcacatg atttattaac gtgccaaaag atgcttattg 8340
aatagagtgc acatttgtaa tgtactacta attagaacat gaaaaagcat tgttctaaca 8400
cgataatcct gtgaaggcgt taactccaaa gatccaattt cactatataa attgtgacga 8460
aagcaaaatg aattcacata gctgagagag aaaggaaagg ttaactaaga agcaatactt 8520
cagcggccgc atgactgagg ataagacgaa ggtcgagttc ccgacgctca cggagctcaa 8580
gcactcgatc ccgaacgcgt gctttgagtc gaacctcggc ctctcgctct actacacggc 8640
ccgcgcgatc ttcaacgcgt cggcctcggc ggcgctgctc tacgcggcgc gctcgacgcc 8700
gttcattgcc gataacgttc tgctccacgc gctcgtttgc gccacctaca tctacgtgca 8760
gggcgtcatc ttctggggct tcttcacggt cggccacgac tgcggccact cggccttctc 8820
gcgctaccac agcgtcaact ttatcatcgg ctgcatcatg cactctgcga ttttgacgcc 8880
gttcgagagc tggcgcgtga cgcaccgcca ccaccacaag aacacgggca acattgataa 8940
ggacgagatc ttttacccgc accggtcggt caaggacctc caggacgtgc gccaatgggt 9000
ctacacgctc ggcggtgcgt ggtttgtcta cttgaaggtc gggtatgccc cgcgcacgat 9060
gagccacttt gacccgtggg acccgctcct ccttcgccgc gcgtcggccg tcatcgtgtc 9120
gctcggcgtc tgggccgcct tcttcgccgc gtacgcgtac ctcacatact cgctcggctt 9180
tgccgtcatg ggcctctact actatgcgcc gctctttgtc tttgcttcgt tcctcgtcat 9240
tacgaccttc ttgcaccaca acgacgaagc gacgccgtgg tacggcgact cggagtggac 9300
gtacgtcaag ggcaacctct cgagcgtcga ccgctcgtac ggcgcgttcg tggacaacct 9360
gagccaccac attggcacgc accaggtcca ccacttgttc ccgatcattc cgcactacaa 9420
gctcaacgaa gccaccaagc actttgcggc cgcgtacccg cacctcgtgc gcaggaacga 9480
cgagcccatc atcacggcct tcttcaagac cgcgcacctc tttgtcaact acggcgctgt 9540
gcccgagacg gcgcagatct tcacgctcaa agagtcggcc gcggccgcca aggccaagtc 9600
ggactaagcg gccgcgaatt caatcactag tgaattcgcg gccgcatgag ccgtaaaggt 9660
tcaatacaac gagtgcttgt ttcttaggg acaagcattg tacttatgta tgattctgtg 9720
taaccatgag tcttccacgt tgtactaatg tgaagggcaa aaataaaaca cagaacaagt 9780
tcgtttttct caaataatgt gaaggtagaa aatggaacca tgcctcctct cttgcatgtg 9840
atttaaaata ttagcagatg gtaccgtacg tgggcggatc ccccgggctg ca 9892

<210> SEQ ID NO 84
<211> LENGTH: 9892
<212> TYPE: DNA
<213> ORGANISM: Artificial Sequence
<220> FEATURE:
<223> OTHER INFORMATION: Plasmid pKR886r

<400> SEQUENCE: 84
ggtcgactcg acgtacgtct agaggatccg tcgacggcgc gcccgatcat ccggatatag 60
ttcctccttt cagcaaaaaa cccctcaaga cccgtttaga ggccccaagg ggttatgcta 120

-continued

```
gttattgctc agcggtggca gcagccaact cagcttcctt tcgggctttg ttagcagccg    180
gatcgatcca agctgtacct cactattcct ttgccctcgg acgagtgctg gggcgtcggt    240
ttccactatc ggcgagtact tctacacagc catcggtcca gacggccgcg cttctgcggg    300
cgatttgtgt acgcccgaca gtcccggctc cggatcggac gattgcgtcg catcgaccct    360
gcgcccaagc tgcatcatcg aaattgccgt caaccaagct ctgatagagt tggtcaagac    420
caatgcggag catatacgcc cggagccgcg gcgatcctgc aagctccgga tgcctccgct    480
cgaagtagcg cgtctgctgc tccatacaag ccaaccacgg cctccagaag aagatgttgg    540
cgacctcgta ttgggaatcc ccgaacatcg cctcgctcca gtcaatgacc gctgttatgc    600
ggccattgtc cgtcaggaca ttgttggagc cgaaatccgc gtgcacgagg tgccggactt    660
cggggcagtc ctcggcccaa agcatcagct catcgagagc ctgcgcgacg gacgcactga    720
cggtgtcgtc catcacagtt tgccagtgat acacatgggg atcagcaatc gcgcatatga    780
aatcacgcca tgtagtgtat tgaccgattc cttgcggtcc gaatgggccg aacccgctcg    840
tctggctaag atcggccgca gcgatcgcat ccatagcctc cgcgaccggc tgcagaacag    900
cgggcagttc ggtttcaggc aggtcttgca acgtgacacc ctgtgcacgg cgggagatgc    960
aataggtcag gctctcgctg aattccccaa tgtcaagcac ttccggaatc gggagcgcgg   1020
ccgatgcaaa gtgccgataa acataacgat ctttgtagaa accatcggcg cagctattta   1080
cccgcaggac atatccacgc cctcctacat cgaagctgaa agcacgagat tcttcgccct   1140
ccgagagctg catcaggtcg gagacgctgt cgaacttttc gatcagaaac ttctcgacag   1200
acgtcgcggt gagttcaggc ttttccatgg gtatatctcc ttcttaaagt taaacaaaat   1260
tatttctaga gggaaaccgt tgtggtctcc ctatagtgag tcgtattaat ttcgcgggat   1320
cgagatctga tcaacctgca ttaatgaatc ggccaacgcg cggggagagg cggtttgcgt   1380
attgggcgct cttccgcttc ctcgctcact gactcgctgc gctcggtcgt tcggctgcgg   1440
cgagcggtat cagctcactc aaaggcggta atacggttat ccacagaatc aggggataac   1500
gcaggaaaga acatgtgagc aaaaggccag caaaaggcca ggaaccgtaa aaaggccgcg   1560
ttgctggcgt ttttccatag gctccgcccc cctgacgagc atcacaaaaa tcgacgctca   1620
agtcagaggt ggcgaaaccc gacaggacta taaagatacc aggcgtttcc ccctggaagc   1680
tccctcgtgc gctctcctgt tccgaccctg ccgcttaccg gatacctgtc cgcctttctc   1740
ccttcgggaa gcgtggcgct ttctcaatgc tcacgctgta ggtatctcag ttcggtgtag   1800
gtcgttcgct ccaagctggg ctgtgtgcac gaacccccg ttcagcccga ccgctgcgcc   1860
ttatccggta actatcgtct tgagtccaac ccggtaagac acgacttatc gccactggca   1920
gcagccactg gtaacaggat tagcagagcg aggtatgtag gcggtgctac agagttcttg   1980
aagtggtggc ctaactacgg ctacactaga aggacagtat ttggtatctg cgctctgctg   2040
aagccagtta ccttcggaaa aagagttggt agctcttgat ccggcaaaca aaccaccgct   2100
ggtagcggtg gtttttttgt ttgcaagcag cagattacgc gcagaaaaaa aggatctcaa   2160
gaagatcctt tgatcttttc tacggggtct gacgctcagt ggaacgaaaa ctcacgttaa   2220
gggattttgg tcatgacatt aacctataaa aataggcgta tcacgaggcc ctttcgtctc   2280
gcgcgtttcg gtgatgacgg tgaaaacctc tgacacatgc agctcccgga gacggtcaca   2340
gcttgtctgt aagcggatgc cgggagcaga caagcccgtc agggcgcgtc agcgggtgtt   2400
ggcgggtgtc ggggctggct taactatgcg gcatcagagc agattgtact gagagtgcac   2460
catatggaca tattgtcgtt agaacgcggc tacaattaat acataacctt atgtatcata   2520
```

-continued

```
cacatacgat ttaggtgaca ctatagaacg gcgcgccaag ctgggtctag aactagaaac   2580
gtgatgccac ttgttattga agtcgattac agcatctatt ctgttttact atttataact   2640
ttgccatttc tgacttttga aaactatctc tggatttcgg tatcgctttg tgaagatcga   2700
gcaaaagaga cgttttgtgg acgcaatggt ccaaatccgt tctacatgaa caaattggtc   2760
acaatttcca ctaaaagtaa ataaatggca agttaaaaaa ggaatatgca ttttactgat   2820
tgcctaggtg agctccaaga gaagttgaat ctacacgtct accaaccgct aaaaaaagaa   2880
aaacattgat atgtaacctg attccattag cttttgactt cttcaacaga ttctctactt   2940
agatttctaa cagaaatatt attactagca catcattttc agtctcacta cagcaaaaaa   3000
tccaacggca caatacagac aacaggagat atcagactac agagatagat agatgctact   3060
gcatgtagta agttaaataa aaggaaaata aaatgtcttg ctaccaaaac tactacagac   3120
tatgatgctc accacaggcc aaatcctgca actaggacag cattatctta tatatattgt   3180
acaaaacaag catcaaggaa catttggtct aggcaatcag tacctcgttc taccatcacc   3240
ctcagttatc acatccttga aggatccatt actgggaatc atcggcaaca catgctcctg   3300
atggggcaca atgacatcaa gaaggtaggg gccaggggtg tccaacattc tctgaattgc   3360
cgctctaagc tcttccttct tcgtcactcg cgctgccggt atcccacaag catcagcaaa   3420
cttgagcatg tttgggaata tctcgctctc gctagacgga tctccaagat aggtgtgagc   3480
tctattggac ttgtagaacc tatcctccaa ctgaaccacc atacccaaat gctgattgtt   3540
caacaacaat atcttaactg ggagattctc cactcttata gtggccaact cctgaacatt   3600
catgatgaaa ctaccatccc catcaatgtc aaccacaaca gccccagggt tagcaacagc   3660
agcaccaata gccgcaggca atccaaaacc catggctcca agacccccctg aggtcaacca   3720
ctgcctcggt ctcttgtact tgtaaaactg cgcagcccac atttgatgct gcccaacccc   3780
agtactaaca atagcatctc cattagtcaa ctcatcaaga acctcgatag catgctgcgg   3840
agaaatcgcg tcctggaatg tcttgtaacc caatggaaac ttgtgtttct gcacattaat   3900
ctcttctctc caacctccaa gatcaaactt accctccact cctttctcct ccaaaatcat   3960
attaattccc ttcaaggcca acttcaaatc cgcgcaaacc gacacgtgcg cctgcttgtt   4020
cttcccaatc tcggcagaat caatatcaat gtgaacaatc ttagccctac tagcaaaagc   4080
ctcaagcttc ccagtaacac ggtcatcaaa ccttacccca aaggcaagca acaaatcact   4140
attgtcaaca gcatagttag cataaacagt accatgcata cccagcatct gaagggaata   4200
ttcatcacca ataggaaaag ttccaagacc cattaaagtg ctagcaacgg gaataccagt   4260
gagttcaaca aagcgcctca attcagcact ggaattcaaa ctgccaccgc cgacgtagag   4320
aacgggcttt tgggcctcca tgatgagtct gacaatgtgt tccaattggg cctcggcggg   4380
gggcctgggc agcctggcga ggtaaccggg gaggttaacg ggctcgtccc aattaggcac   4440
ggcgagttgc tgctgaacgt ctttgggaat gtcgatgagg accggaccgg ggcggccgga   4500
ggtggcgacg aagaaagcct cggcgacgac gcgggggatg tcgtcgacgt cgaggatgag   4560
gtagttgtgc ttcgtgatgg atctgctcac ctccacgatc ggggtttctt ggaaggcgtc   4620
ggtgccgatc atccggcggg cgacctggcc ggtgatggcg acgactggga cgctgtccat   4680
taaagcgtcg gcgaggccgc tcacgaggtt ggtggcgccg gggccggagg tggcaatgca   4740
gacgccgggg aggccggagg aacgcgcgta gccttcggcg gcgaagacgc cgccctgctc   4800
gtggcgcggg agcacgttgc ggatggcggc ggagcgcgtg agcgcctggt ggatctccat   4860
cgacgcaccg ccggggtacg cgaacaccgt cgtcacgccc tgcctctcca gcgcctccac   4920
```

```
aaggatgtcc gcgcccttgc gaggttcgcc ggaggcgaac cgtgacacga agggctccgt    4980

ggtcggcgct tccttggtga agggcgccgc cgtgggggt ttggagatgg aacatttgat     5040

tttgagagcg tggttgggtt tggtgagggt ttgatgagag agagggaggg tggatctagt    5100

aatgcgtttg gggaaggtgg ggtgtgaaga ggaagaagag aatcgggtgg ttctggaagc    5160

ggtggccgcc attgtgttgt gtggcatggt tatacttcaa aaactgcaca acaagcctag    5220

agttagtacc taaacagtaa atttacaaca gagagcaaag acacatgcaa aaatttcagc    5280

cataaaaaaa gttataatag aatttaaagc aaaagtttca ttttttaaac atatatacaa    5340

acaaactgga tttgaaggaa gggattaatt cccctgctca aagtttgaat tcctattgtg    5400

acctatactc gaataaaatt gaagcctaag gaatgtatga gaaacaagaa aacaaaacaa    5460

aactacagac aaacaagtac aattacaaaa ttcgctaaaa ttctgtaatc accaaacccc    5520

atctcagtca gcacaaggcc caaggtttat tttgaaataa aaaaaaagtg attttatttc    5580

tcataagcta aaagaaagaa aggcaattat gaaatgattt cgactagatc tgaaagtcca    5640

acgcgtattc cgcagatatt aaagaaagag tagagtttca catggatcct agatggaccc    5700

agttgaggaa aaagcaaggc aaagcaaacc agaagtgcaa gatccgaaat tgaaccacgg    5760

aatctaggat ttggtagagg gagaagaaaa gtaccttgag aggtagaaga aagagaaga    5820

gcagagagat atatgaacga gtgtgtcttg gtctcaactc tgaagcgata cgagtttaga    5880

ggggagcatt gagttccaat ttatagggaa accgggtggc aggggtgagt taatgacgga    5940

aaagccccta agtaacgaga ttggattgtg ggttagattc aaccgtttgc atccgcggct    6000

tagattgggg aagtcagagt gaatctcaac cgttgactga gttgaaaatt gaatgtagca    6060

accaattgag ccaaccccag cctttgccct ttgattttga tttgtttgtt gcatactttt    6120

tatttgtctt ctggttctga ctctctttct ctcgtttcaa tgccaggttg cctactccca    6180

caccactcac aagaagattc tactgttagt attaaatatt ttttaatgta ttaaatgatg    6240

aatgcttttg taaacagaac aagactatgt ctaataagtg tcttgcaaca ttttttaaga    6300

aattaaaaaa aatatattta ttatcaaaat caaatgtatg aaaaatcatg aataatataa    6360

ttttatacat ttttttaaaa aatcttttaa tttcttaatt aatatcttaa aaataatgat    6420

taatatttaa cccaaaataa ttagtatgat tggtaaggaa gatatccatg ttatgtttgg    6480

atgtgagttt gatctagagc aaagcttact agagtcgacc tgcagcccgg gggatccgcc    6540

cacgtacggt accatctgct aatattttaa atcacatgca agagaggagg catggttcca    6600

ttttctacct tcacattatt tgagaaaaac gaacttgttc tgtgttttat ttttgccctt    6660

cacattagta caacgtggaa gactcatggt tacacagaat catacataag tacaatgctt    6720

gtccctaaga aaacaagcac tcgttgtatt gaacctttac ggctcatgcg gccgcgaatt    6780

cactagtgat tgaattcgcg gccgcttagt ccgacttggc cttggcggcc gcggccgact    6840

ctttgagcgt gaagatctgc gccgtctcgg gcacagcgcc gtagttgaca aagaggtgcg    6900

cggtcttgaa gaaggccgtg atgatgggct cgtcgttcct gcgcacgagg tgcgggtacg    6960

cggccgcaaa gtgcttggtg gcttcgttga gcttgtagtg cggaatgatc gggaacaagt    7020

ggtggacctg gtgcgtgcca atgtggtggc tcaggttgtc cacgaacgcg ccgtacgagc    7080

ggtcgacgct cgagaggttg cccttgacgt acgtccactc cgagtcgccg taccacggcg    7140

tcgcttcgtc gttgtggtgc aagaaggtcg taatgacgag gaacgaagca aagacaaaga    7200

gcggcgcata gtagtagagg cccatgacgg caaagccgag cgagtatgtg aggtacgcgt    7260

acgcggcgaa gaaggcggcc cagacgccga gcgacacgat gacggccgac gcgcggcgaa    7320
```

```
ggaggagcgg gtcccacggg tcaaagtggc tcatcgtgcg cggggcatac ccgaccttca   7380
agtagacaaa ccacgcaccg ccgagcgtgt agacccattg gcgcacgtcc tggaggtcct   7440
tgaccgaccg gtgcgggtaa aagatctcgt ccttatcaat gttgcccgtg ttcttgtggt   7500
ggtggcggtg cgtcacgcgc cagctctcga acggcgtcaa aatcgcagag tgcatgatgc   7560
agccgatgat aaagttgacg ctgtggtagc gcgagaaggc cgagtggccg cagtcgtggc   7620
cgaccgtgaa gaagccccag aagatgacgc cctgcacgta gatgtaggtg gcgcaaacga   7680
gcgcgtggag cagaacgtta tcggcaatga acggcgtcga gcgcgccgcg tagagcagcg   7740
ccgccgaggc cgacgcgttg aagatcgcgc gggccgtgta gtagagcgag aggccgaggt   7800
tcgactcaaa gcacgcgttc gggatcgagt gcttgagctc cgtgagcgtc gggaactcga   7860
ccttcgtctt atcctcagtc atgcggccgc tgaagtattg cttcttagtt aacctttcct   7920
ttctctctca gctatgtgaa ttcattttgc tttcgtcaca atttatatag tgaaattgga   7980
tctttggagt taacgccttc acaggattat cgtgttagaa caatgctttt tcatgttcta   8040
attagtagta cattacaaat gtgcactcta ttcaataagc atcttttggc acgttaataa   8100
atcatgtgaa aaaaaaatac tactatttca aagaaagtgt tgtaaaaaga aacggaaaga   8160
gagctggctt cagttgttga gacttgtttg ctagtaaaaa tggtgtgaag agtgattcat   8220
ggtgaggtgg tttttcgtcc ctttctgttt gcatgaaaaa caaatggcaa gagatgacgt   8280
aggattcctt cccttaacga ttatctgttt ttaatttcaa atatacatat aggaatttat   8340
gaattactaa ggttgtaaaa tatgctggtc atttatttat ggctaaaata tttttttttc   8400
tcgtaaatat aaaaatattt aaaatttatt tttatcatat tttttatcct tataaaatta   8460
tgtgtacaac ctatataaaa aaatatcata tttaatattg attatatgtt taatcaatat   8520
aaaaaatcat tatcatatat ttagatttat tcgaatatac atctaaacaa aaaataacat   8580
attttaattt tatgaagaaa aaaaaatatt ttatccttta tttatttaag attaattaat   8640
agttatgtat tgtggaaaga cttttacaca tgcaatagat atactgaatc aattagatgc   8700
caatgctgag ttggaaatca cttgaggagg ggaggagact tgccaatgct tttcagtttc   8760
atttaaatga tttagtggag gagatagagt agtgataaag gcatgcccca attttggagt   8820
gtatatatga gtggaaataa gagagggata gagagaaaaa ataaagagag taaaaataat   8880
taatgtgaaa tgatatgata aaaaaataaa gaaagagata aagagaaaaa tgaaatgaga   8940
gatagatgaa atagagagta gatacatgtt tgtttaggtt ttttttagga aataacacat   9000
tttttctca tcacttatta ctcactgtca atttcctctc tttcaatcat aatgatatga   9060
tttgtttaac aaaaaatgtga aaaaacatat aaagtaaaat atttttataa attgataaat   9120
aaaaatttac aaaatttatt tcttattaaa ttgaatagaa aatgaaagaa aagaaaagaa   9180
aaagtatata taaaatgata tagctttaaa aagaataaat ttttcatatc agtctttttt   9240
taataattta gaaatattta agtatatagc aaaaatataa tgtactttac atatgcataa   9300
ataataattt gaaaatagaa ctaatagaat agagaaaaaa gtaatataat aattaactat   9360
atgaaaattt agaagggaca atatttttaa ttaagaatat aaacaatatt tcttttcatg   9420
taatgaggga cggatgtacg gggccagtgt tggagtcaaa gccaaaatag tcacggggaa   9480
attaatgcac tgcatgacta ttcgaaaaaa ttcactagcc ttacttagat gttagattaa   9540
tagctagggg gtgcagataa ttttgaaagg catgaaaaac attaatttgt acattgcaag   9600
cttttgatga caagctttgc aattgttcac actaccttat gccatttata aatagagtga   9660
ttggcatatg aaggaaatca tgagagtcga agcgaaaaac aaagcttgag agtgtaggaa   9720
```

-continued

```
aaatacagtt tttttggtaa aaatacagta tttgaatagg agcgaaaaat atcctttcaa   9780

aatgatcctt ttcttttttt tttttttttct tgttgttctt ggtcagttat tcaaaggaaa   9840

agggattgaa ataaaaactt gcatgtggga tcgtacgtcg agtcgacctg ca           9892
```

<210> SEQ ID NO 85
<211> LENGTH: 6021
<212> TYPE: DNA
<213> ORGANISM: Artificial Sequence
<220> FEATURE:
<223> OTHER INFORMATION: Plasmid pKR271

<400> SEQUENCE: 85

```
ggccgcgaat tcaatcacta gtgaattcgc ggccgcatga gccgtaaagg ttcaatacaa     60

cgagtgcttg ttttcttagg gacaagcatt gtacttatgt atgattctgt gtaaccatga    120

gtcttccacg ttgtactaat gtgaagggca aaaataaaac acagaacaag ttcgtttttc    180

tcaaataatg tgaaggtaga aaatggaacc atgcctcctc tcttgcatgt gatttaaaat    240

attagcagat ggtaccgtac gtgggcggat cccccgggct gcaggaattc actggccgtc    300

gttttacaac gtcgtgactg ggaaaaccct ggcgttaccc aacttaatcg ccttgcagca    360

catccccctt tcgccagctg gcgtaatagc gaagaggccc gcaccgatcg cccttcccaa    420

cagttgcgca gcctgaatgg cgaatggcgc ctgatgcggt attttctcct tacgcatctg    480

tgcggtattt cacaccgcat atggtgcact ctcagtacaa tctgctctga tgccgcatag    540

ttaagccagc cccgacaccc gccaacaccc gctgacgcgc cctgacgggc ttgtctgctc    600

ccggcatccg cttacagaca agctgtgacc gtctccggga gctgcatgtg tcagaggttt    660

tcaccgtcat caccgaaacg cgcgagacga aagggcctcg tgatacgcct atttttatag    720

gttaatgtca tgataataat ggtttcttag acgtcaggtg gcacttttcg gggaaatgtg    780

cgcggaaccc ctatttgttt atttttctaa atacattcaa atatgtatcc gctcatgaga    840

caataaccct gataaatgct tcaataatat tgaaaaagga agagtatgag tattcaacat    900

ttccgtgtcg cccttattcc cttttttgcg gcattttgcc ttcctgtttt tgctcaccca    960

gaaacgctgg tgaaagtaaa agatgctgaa gatcagttgg gtgcacgagt gggttacatc   1020

gaactggatc tcaacagcgg taagatcctt gagagttttc gccccgaaga acgttttcca   1080

atgatgagca cttttaaagt tctgctatgt ggcgcggtat tatcccgtat tgacgccggg   1140

caagagcaac tcggtcgccg catacactat tctcagaatg acttggttga gtactcacca   1200

gtcacagaaa agcatcttac ggatggcatg acagtaagag aattatgcag tgctgccata   1260

accatgagtg ataacactgc ggccaactta cttctgacaa cgatcggagg accgaaggag   1320

ctaaccgctt ttttgcacaa catgggggat catgtaactc gccttgatcg ttgggaaccg   1380

gagctgaatg aagccatacc aaacgacgag cgtgacacca cgatgcctgt agcaatggca   1440

acaacgttgc gcaaactatt aactggcgaa ctacttactc tagcttcccg gcaacaatta   1500

atagactgga tggaggcgga taaagttgca ggaccacttc tgcgctcggc ccttccggct   1560

ggctggttta ttgctgataa atctggagcc ggtgagcgtg ggtctcgcgg tatcattgca   1620

gcactggggc cagatggtaa gccctcccgt atcgtagtta tctacacgac ggggagtcag   1680

gcaactatgg atgaacgaaa tagacagatc gctgagatag gtgcctcact gattaagcat   1740

tggtaactgt cagaccaagt ttactcatat atactttaga ttgatttaaa acttcatttt   1800

taatttaaaa ggatctaggt gaagatcctt tttgataatc tcatgaccaa aatcccttaa   1860

cgtgagtttt cgttccactg agcgtcagac cccgtagaaa agatcaaagg atcttcttga   1920
```

-continued

```
gatccttttt ttctgcgcgt aatctgctgc ttgcaaacaa aaaaaccacc gctaccagcg   1980
gtggtttgtt tgccggatca agagctacca actctttttc cgaaggtaac tggcttcagc   2040
agagcgcaga taccaaatac tgtccttcta gtgtagccgt agttaggcca ccacttcaag   2100
aactctgtag caccgcctac atacctcgct ctgctaatcc tgttaccagt ggctgctgcc   2160
agtggcgata agtcgtgtct taccgggttg gactcaagac gatagttacc ggataaggcg   2220
cagcggtcgg gctgaacggg gggttcgtgc acacagccca gcttggagcg aacgacctac   2280
accgaactga gatacctaca gcgtgagcta tgagaaagcg ccacgcttcc cgaagggaga   2340
aaggcggaca ggtatccggt aagcggcagg gtcggaacag gagagcgcac gagggagctt   2400
ccagggggaa acgcctggta tctttatagt cctgtcgggt ttcgccacct ctgacttgag   2460
cgtcgatttt tgtgatgctc gtcagggggg cggagcctat ggaaaaacgc cagcaacgcg   2520
gcctttttac ggttcctggc cttttgctgg ccttttgctc acatgttctt tcctgcgtta   2580
tcccctgatt ctgtggataa ccgtattacc gcctttgagt gagctgatac cgctcgccgc   2640
agccgaacga ccgagcgcag cgagtcagtg agcgaggaag cggaagagcg cccaatacgc   2700
aaaccgcctc tccccgcgcg ttggccgatt cattaatgca gctggcacga caggtttccc   2760
gactggaaag cgggcagtga gcgcaacgca attaatgtga gttagctcac tcattaggca   2820
ccccaggctt tacactttat gcttccggct cgtatgttgt gtggaattgt gagcggataa   2880
caatttcaca caggaaacag ctatgaccat gattacgcca agcttgcatg cctgcaggtc   2940
gactcgacgt acgatcccac atgcaagttt ttatttcaat ccctttcct ttgaataact   3000
gaccaagaac aacaagaaaa aaaaaaaaaa agaaaaggat cattttgaaa ggatattttt   3060
cgctcctatt caaatactgt atttttacca aaaaaactgt atttttccta cactctcaag   3120
ctttgttttt cgcttcgact ctcatgattt ccttcatatg ccaatcactc tatttataaa   3180
tggcataagg tagtgtgaac aattgcaaag cttgtcatca aaagcttgca atgtacaaat   3240
taatgttttt catgcctttc aaaattatct gcacccccta gctattaatc taacatctaa   3300
gtaaggctag tgaatttttt cgaatagtca tgcagtgcat taatttcccc gtgactattt   3360
tggctttgac tccaacactg gccccgtaca tccgtccctc attacatgaa aagaaatatt   3420
gtttatattc ttaattaaaa atattgtccc ttctaaattt tcatatagtt aattattata   3480
ttactttttt ctctattcta ttagttctat tttcaaatta ttatttatgc atatgtaaag   3540
tacattatat ttttgctata tacttaaata tttctaaatt attaaaaaaa gactgatatg   3600
aaaaatttat tctttttaaa gctatatcat tttatatata ctttttcttt tcttttcttt   3660
cattttctat tcaatttaat aagaaataaa ttttgtaaat ttttatttat caatttataa   3720
aaatatttta ctttatatgt tttttcacat ttttgttaaa caaatcatat cattatgatt   3780
gaaagagagg aaattgacag tgagtaataa gtgatgagaa aaaaatgtgt tatttcctaa   3840
aaaaaaccta aacaaacatg tatctactct ctatttcatc tatctctcat ttcatttttc   3900
tctttatctc tttctttatt tttttatcat atcatttcac attaattatt tttactctct   3960
ttattttttc tctctatccc tctcttattt ccactcatat atacactcca aaattggggc   4020
atgcctttat cactactcta tctcctccac taaatcattt aaatgaaact gaaaagcatt   4080
ggcaagtctc ctcccctcct caagtgattt ccaactcagc attggcatct aattgattca   4140
gtatatctat tgcatgtgta aaagtctttc cacaatacat aactattaat taatcttaaa   4200
taaataaagg ataaaatatt ttttttcttt cataaaatta aaatatgtta ttttttgttt   4260
agatgtatat tcgaataaat ctaaatatat gataatgatt ttttatattg attaaacata   4320
```

taatcaatat taaatatgat attttttat ataggttgta cacataattt tataaggata 4380
aaaaatatga taaaaataaa ttttaaatat ttttatattt acgagaaaaa aaaatatttt 4440
agccataaat aaatgaccag catattttac aaccttagta attcataaat tcctatatgt 4500
atatttgaaa ttaaaaacag ataatcgtta agggaaggaa tcctacgtca tctcttgcca 4560
tttgtttttc atgcaaacag aaagggacga aaaaccacct caccatgaat cactcttcac 4620
accattttta ctagcaaaca agtctcaaca actgaagcca gctctctttc cgtttctttt 4680
tacaacactt tctttgaaat agtagtattt tttttcaca tgatttatta acgtgccaaa 4740
agatgcttat tgaatagagt gcacatttgt aatgtactac taattagaac atgaaaaagc 4800
attgttctaa cacgataatc ctgtgaaggc gttaactcca aagatccaat ttcactatat 4860
aaattgtgac gaaagcaaaa tgaattcaca tagctgagag agaaaggaaa ggttaactaa 4920
gaagcaatac ttcagcggcc gcatgactga ggataagacg aaggtcgagt tcccgacgct 4980
cacggagctc aagcactcga tcccgaacgc gtgctttgag tcgaacctcg gcctctcgct 5040
ctactacacg gcccgcgcga tcttcaacgc gtcggcctcg gcggcgctgc tctacgcggc 5100
gcgctcgacg ccgttcattg ccgataacgt tctgctccac gcgctcgttt gcgccaccta 5160
catctacgtg cagggcgtca tcttctgggg cttcttcacg gtcggccacg actgcggcca 5220
ctcggccttc tcgcgctacc acagcgtcaa ctttatcatc ggctgcatca tgcactctgc 5280
gattttgacg ccgttcgaga gctggcgcgt gacgcaccgc caccaccaca agaacacggg 5340
caacattgat aaggacgaga tcttttaccc gcaccggtcg gtcaaggacc tccaggacgt 5400
gcgccaatgg gtctacacgc tcggcggtgc gtggtttgtc tacttgaagg tcgggtatgc 5460
cccgcgcacg atgagccact ttgacccgtg ggacccgctc ctccttcgcc gcgcgtcggc 5520
cgtcatcgtg tcgctcggcg tctgggccgc cttcttcgcc gcgtacgcgt acctcacata 5580
ctcgctcggc tttgccgtca tgggcctcta ctactatgcg ccgctctttg tctttgcttc 5640
gttcctcgtc attacgacct tcttgcacca caacgacgaa gcgacgccgt ggtacggcga 5700
ctcggagtgg acgtacgtca agggcaacct ctcgagcgtc gaccgctcgt acggcgcgtt 5760
cgtggacaac ctgagccacc acattggcac gcaccaggtc caccacttgt tcccgatcat 5820
tccgcactac aagctcaacg aagccaccaa gcactttgcg gccgcgtacc cgcacctcgt 5880
gcgcaggaac gacgagccca tcatcacggc cttcttcaag accgcgcacc tctttgtcaa 5940
ctacggcgct gtgcccgaga cggcgcagat cttcacgctc aaagagtcgg ccgcggccgc 6000
caaggccaag tcggactaag c 6021

<210> SEQ ID NO 86
<211> LENGTH: 6524
<212> TYPE: DNA
<213> ORGANISM: Artificial Sequence
<220> FEATURE:
<223> OTHER INFORMATION: Plasmid pKR226

<400> SEQUENCE: 86
gtacgtctag aggatccgtc gacggcgcgc ccgatcatcc ggatatagtt cctcctttca 60
gcaaaaaacc cctcaagacc cgtttagagg ccccaagggg ttatgctagt tattgctcag 120
cggtggcagc agccaactca gcttcctttc gggctttgtt agcagccgga tcgatccaag 180
ctgtacctca ctattccttt gccctcggac gagtgctggg gcgtcggttt ccactatcgg 240
cgagtacttc tacacagcca tcggtccaga cggccgcgct tctgcgggcg atttgtgtac 300
gcccgacagt cccggctccg gatcggacga ttgcgtcgca tcgaccctgc gcccaagctg 360

```
catcatcgaa attgccgtca accaagctct gatagagttg gtcaagacca atgcggagca    420
tatacgcccg gagccgcggc gatcctgcaa gctccggatg cctccgctcg aagtagcgcg    480
tctgctgctc catacaagcc aaccacggcc tccagaagaa gatgttggcg acctcgtatt    540
gggaatcccc gaacatcgcc tcgctccagt caatgaccgc tgttatgcgg ccattgtccg    600
tcaggacatt gttggagccg aaatccgcgt gcacgaggtg ccggacttcg ggcagtcct    660
cggcccaaag catcagctca tcgagagcct gcgcgacgga cgcactgacg gtgtcgtcca    720
tcacagtttg ccagtgatac acatggggat cagcaatcgc gcatatgaaa tcacgccatg    780
tagtgtattg accgattcct tgcggtccga atgggccgaa cccgctcgtc tggctaagat    840
cggccgcagc gatcgcatcc atagcctccg cgaccggctg cagaacagcg ggcagttcgg    900
tttcaggcag gtcttgcaac gtgacaccct gtgcacggcg ggagatgcaa taggtcaggc    960
tctcgctgaa ttccccaatg tcaagcactt ccggaatcgg gagcgcggcc gatgcaaagt   1020
gccgataaac ataacgatct ttgtagaaac catcggcgca gctatttacc cgcaggacat   1080
atccacgccc tcctacatcg aagctgaaag cacgagattc ttcgccctcc gagagctgca   1140
tcaggtcgga gacgctgtcg aacttttcga tcagaaactt ctcgacagac gtcgcggtga   1200
gttcaggctt ttccatgggt atatctcctt cttaaagtta aacaaaatta tttctagagg   1260
gaaaccgttg tggtctccct atagtgagtc gtattaattt cgcgggatcg agatctgatc   1320
aacctgcatt aatgaatcgg ccaacgcgcg gggagaggcg gtttgcgtat tgggcgctct   1380
tccgcttcct cgctcactga ctcgctgcgc tcggtcgttc ggctgcggcg agcggtatca   1440
gctcactcaa aggcggtaat acggttatcc acagaatcag gggataacgc aggaaagaac   1500
atgtgagcaa aaggccagca aaaggccagg aaccgtaaaa aggccgcgtt gctggcgttt   1560
ttccataggc tccgcccccc tgacgagcat cacaaaaatc gacgctcaag tcagaggtgg   1620
cgaaacccga caggactata aagataccag gcgtttcccc ctggaagctc cctcgtgcgc   1680
tctcctgttc cgaccctgcc gcttaccgga tacctgtccg cctttctccc ttcgggaagc   1740
gtggcgcttt ctcaatgctc acgctgtagg tatctcagtt cggtgtaggt cgttcgctcc   1800
aagctgggct gtgtgcacga accccccgtt cagcccgacc gctgcgcctt atccggtaac   1860
tatcgtcttg agtccaaccc ggtaagacac gacttatcgc cactggcagc agccactggt   1920
aacaggatta gcagagcgag gtatgtaggc ggtgctacag agttcttgaa gtggtggcct   1980
aactacggct acactagaag gacagtattt ggtatctgcg ctctgctgaa gccagttacc   2040
ttcggaaaaa gagttggtag ctcttgatcc ggcaaacaaa ccaccgctgg tagcggtggt   2100
ttttttgttt gcaagcagca gattacgcgc agaaaaaaag gatctcaaga agatcctttg   2160
atcttttcta cggggtctga cgctcagtgg aacgaaaact cacgttaagg gattttggtc   2220
atgacattaa cctataaaaa taggcgtatc acgaggccct ttcgtctcgc gcgtttcggt   2280
gatgacggtg aaaacctctg acacatgcag ctcccggaga cggtcacagc ttgtctgtaa   2340
gcggatgccg ggagcagaca agcccgtcag ggcgcgtcag cgggtgttgg cgggtgtcgg   2400
ggctggctta actatgcggc atcagagcag attgtactga gagtgcacca tatggacata   2460
ttgtcgttag aacgcggcta caattaatac ataaccttat gtatcataca catacgattt   2520
aggtgacact atagaacggc gcgccaagct gggtctagaa ctagaaacgt gatgccactt   2580
gttattgaag tcgattacag catctattct gttttactat ttataacttt gccatttctg   2640
acttttgaaa actatctctg gatttcggta tcgctttgtg aagatcgagc aaaagagacg   2700
ttttgtggac gcaatggtcc aaatccgttc tacatgaaca aattggtcac aatttccact   2760
```

-continued

```
aaaagtaaat aaatggcaag ttaaaaaagg aatatgcatt ttactgattg cctaggtgag   2820
ctccaagaga agttgaatct acacgtctac caaccgctaa aaaaagaaaa acattgatat   2880
gtaacctgat tccattagct tttgacttct tcaacagatt ctctacttag atttctaaca   2940
gaaatattat tactagcaca tcattttcag tctcactaca gcaaaaaatc caacggcaca   3000
atacagacaa caggagatat cagactacag agatagatag atgctactgc atgtagtaag   3060
ttaaataaaa ggaaaataaa atgtcttgct accaaaacta ctacagacta tgatgctcac   3120
cacaggccaa atcctgcaac taggacagca ttatcttata tatattgtac aaaacaagca   3180
tcaaggaaca tttggtctag gcaatcagta cctcgttcta ccatcaccct cagttatcac   3240
atccttgaag gatccattac tgggaatcat cggcaacaca tgctcctgat ggggcacaat   3300
gacatcaaga aggtaggggc caggggtgtc caacattctc tgaattgccg ctctaagctc   3360
ttccttcttc gtcactcgcg ctgccggtat cccacaagca tcagcaaact tgagcatgtt   3420
tgggaatatc tcgctctcgc tagacggatc tccaagatag gtgtgagctc tattggactt   3480
gtagaaccta tcctccaact gaaccaccat acccaaatgc tgattgttca acaacaatat   3540
cttaactggg agattctcca ctcttatagt ggccaactcc tgaacattca tgatgaaact   3600
accatcccca tcaatgtcaa ccacaacagc cccagggtta gcaacagcag caccaatagc   3660
cgcaggcaat ccaaaaccca tggctccaag acccccctgag gtcaaccact gcctcggtct  3720
cttgtacttg taaaactgcg cagcccacat ttgatgctgc ccaaccccag tactaacaat   3780
agcatctcca ttagtcaact catcaagaac ctcgatagca tgctgcggag aaatcgcgtc   3840
ctggaatgtc ttgtaaccca atggaaactt gtgtttctgc acattaatct cttctctcca   3900
acctccaaga tcaaacttac cctccactcc tttctcctcc aaaatcatat taattccctt   3960
caaggccaac ttcaaatccg cgcaaaccga cacgtgcgcc tgcttgttct tcccaatctc   4020
ggcagaatca atatcaatgt gaacaatctt agccctacta gcaaaagcct caagcttccc   4080
agtaacacgg tcatcaaacc ttaccccaaa ggcaagcaac aaatcactat tgtcaacagc   4140
atagttagca taaacagtac catgcatacc cagcatctga agggaatatt catcaccaat   4200
aggaaaagtt ccaagaccca ttaaagtgct agcaacggga ataccagtga gttcaacaaa   4260
gcgcctcaat tcagcactgg aattcaaact gccaccgccg acgtagagaa cgggcttttg   4320
ggcctccatg atgagtctga caatgtgttc caattgggcc tcggcggggg gcctgggcag   4380
cctggcgagg taaccgggga ggttaacggg ctcgtcccaa ttaggcacgg cgagttgctg   4440
ctgaacgtct ttgggaatgt cgatgaggac cggaccgggg cggccggagg tggcgacgaa   4500
gaaagcctcg gcgacgacgc gggggatgtc gtcgacgtcg aggatgaggt agttgtgctt   4560
cgtgatggat ctgctcacct ccacgatcgg ggtttcttgg aaggcgtcgg tgccgatcat   4620
ccggcgggcg acctggccgg tgatggcgac gactgggacg ctgtccatta aagcgtcggc   4680
gaggccgctc acgaggttgg tggcgccggg gccggaggtg gcaatgcaga cgccggggag   4740
gccggaggaa cgcgcgtagc cttcggcggc gaagacgccg ccctgctcgt ggcgcgggag   4800
cacgttgcgg atggcggcgg agcgcgtgag cgcctggtgg atctccatcg acgcaccgcc   4860
ggggtacgcg aacaccgtcg tcacgccctg cctctccagc gcctccacaa ggatgtccgc   4920
gcccttgcga ggttcgccgg aggcgaaccg tgacacgaag ggctccgtgg tcggcgcttc   4980
cttggtgaag ggcgccgccg tggggggttt ggagatggaa catttgattt tgagagcgtg   5040
gttgggtttg gtgagggttt gatgagagag agggagggtg gatctagtaa tgcgtttggg   5100
gaaggtgggg tgtgaagagg aagaagagaa tcgggtggtt ctggaagcgg tggccgccat   5160
```

tgtgttgtgt ggcatggtta tacttcaaaa actgcacaac aagcctagag ttagtaccta 5220
aacagtaaat ttacaacaga gagcaaagac acatgcaaaa atttcagcca taaaaaaagt 5280
tataatagaa tttaaagcaa aagtttcatt ttttaaacat atatacaaac aaactggatt 5340
tgaaggaagg gattaattcc cctgctcaaa gtttgaattc ctattgtgac ctatactcga 5400
ataaaattga agcctaagga atgtatgaga aacaagaaaa caaaacaaaa ctacagacaa 5460
acaagtacaa ttacaaaatt cgctaaaatt ctgtaatcac caaaccccat ctcagtcagc 5520
acaaggccca aggtttattt tgaaataaaa aaaaagtgat tttatttctc ataagctaaa 5580
agaaagaaag gcaattatga aatgatttcg actagatctg aaagtccaac gcgtattccg 5640
cagatattaa agaaagagta gagtttcaca tggatcctag atggacccag ttgaggaaaa 5700
agcaaggcaa agcaaaccag aagtgcaaga tccgaaattg aaccacggaa tctaggattt 5760
ggtagaggga gaagaaaagt accttgagag gtagaagaga agagaagagc agagagatat 5820
atgaacgagt gtgtcttggt ctcaactctg aagcgatacg agtttagagg ggagcattga 5880
gttccaattt atagggaaac cgggtggcag gggtgagtta atgacggaaa agcccctaag 5940
taacgagatt ggattgtggg ttagattcaa ccgtttgcat ccgcggctta gattggggaa 6000
gtcagagtga atctcaaccg ttgactgagt tgaaaattga atgtagcaac caattgagcc 6060
aaccccagcc tttgcccttt gattttgatt tgtttgttgc atacttttta tttgtcttct 6120
ggttctgact ctctttctct cgtttcaatg ccaggttgcc tactcccaca ccactcacaa 6180
gaagattcta ctgttagtat taaatatttt ttaatgtatt aaatgatgaa tgcttttgta 6240
aacagaacaa gactatgtct aataagtgtc ttgcaacatt ttttaagaaa ttaaaaaaaa 6300
tatatttatt atcaaaatca aatgtatgaa aaatcatgaa taatataatt ttatacattt 6360
ttttaaaaaa tcttttaatt tcttaattaa tatcttaaaa ataatgatta atatttaacc 6420
caaaataatt agtatgattg gtaaggaaga tatccatgtt atgtttggat gtgagtttga 6480
tctagagcaa agcttactag agtcgacctg caggtcgact cgac 6524

<210> SEQ ID NO 87
<211> LENGTH: 13514
<212> TYPE: DNA
<213> ORGANISM: Artificial Sequence
<220> FEATURE:
<223> OTHER INFORMATION: Plasmid pKR275
<220> FEATURE:
<221> NAME/KEY: misc_feature
<222> LOCATION: (1192)..(1192)
<223> OTHER INFORMATION: n is a, c, g, or t
<220> FEATURE:
<221> NAME/KEY: misc_feature
<222> LOCATION: (2675)..(2675)
<223> OTHER INFORMATION: n is a, c, g, or t

<400> SEQUENCE: 87
ggtcgactcg acgtacgtcc tcgaagagaa gggttaataa cacatttttt aacattttta 60
acacaaattt tagttattta aaaatttatt aaaaaattta aaataagaag aggaactctt 120
taaataaatc taacttacaa aatttatgat tttaataag ttttcaccaa taaaaaatgt 180
cataaaaata tgttaaaaag tatattatca atattctctt tatgataaat aaaaagaaaa 240
aaaaaataaa agttaagtga aaatgagatt gaagtgactt taggtgtgta taaatatatc 300
aaccccgcca acaatttatt taatccaaat atattgaagt atattattcc atagccttta 360
tttatttata tatttattat ataaaagctt tatttgttct aggttgttca tgaaatattt 420
ttttggtttt atctccgttg taagaaaatc atgtgctttg tgtcgccact cactattgca 480

-continued

```
gctttttcat gcattggtca gattgacggt tgattgtatt tttgtttttt atggttttgt    540
gttatgactt aagtcttcat ctctttatct cttcatcagg tttgatggtt acctaatatg    600
gtccatgggt acatgcatgg ttaaattagg tggccaactt tgttgtgaac gatagaattt    660
tttttatatt aagtaaacta tttttatatt atgaaataat aataaaaaaa atattttatc    720
attattaaca aaatcatatt agttaatttg ttaactctat aataaaagaa atactgtaac    780
attcacatta catggtaaca tctttccacc ctttcatttg ttttttgttt gatgactttt    840
tttcttgttt aaatttattt cccttctttt aaatttggaa tacattatca tcatatataa    900
actaaaatac taaaaacagg attacacaaa tgataaataa taacacaaat atttataaat    960
ctagctgcaa tatatttaaa ctagctatat cgatattgta aaataaaact agctgcattg   1020
atactgataa aaaaatatca tgtgctttct ggactgatga tgcagtatac ttttgacatt   1080
gcctttattt tatttttcag aaaagctttc ttagttctgg gttcttcatt atttgtttcc   1140
catctccatt gtgaattgaa tcatttgctt cgtgtcacaa atacaattta gntaggtaca   1200
tgcattggtc agattcacgg tttattatgt catgacttaa gttcatggta gtacattacc   1260
tgccacgcat gcattatatt ggttagattt gataggcaaa tttggttgtc aacaatataa   1320
atataaataa tgtttttata ttacgaaata acagtgatca aaacaaacag ttttatcttt   1380
attaacaaga ttttgttttt gtttgatgac gtttttttaat gtttacgctt tccccccttct   1440
tttgaattta gaacacttta tcatcataaa atcaaatact aaaaaaaatta catatttcat   1500
aaataataac acaaatattt ttaaaaaatc tgaaataata atgaacaata ttacatatta   1560
tcacgaaaat tcattaataa aaatattata taaataaaat gtaatagtag ttatatgtag   1620
gaaaaaagta ctgcacgcat aatatataca aaaagattaa aatgaactat tataaataat   1680
aacactaaat taatggtgaa tcatatcaaa ataatgaaaa agtaaataaa atttgtaatt   1740
aacttctata tgtattacac acacaaataa taaataatag taaaaaaaat tatgataaat   1800
atttaccatc tcataagata tttaaaataa tgataaaaat atagattatt ttttatgcaa   1860
ctagctagcc aaaaagagaa cacgggtata tataaaaaga gtacctttaa attctactgt   1920
acttccttta ttcctgacgt ttttatatca agtggacata cgtgaagatt ttaattatca   1980
gtctaaatat ttcattagca cttaatactt ttctgtttta ttcctatcct ataagtagtc   2040
ccgattctcc caacattgct tattcacaca actaactaag aaagtcttcc atagcccccc   2100
aagcggccgc ctctctctct ctctcttctc tctttctctc cccctctctc cggcgatggt   2160
tgttgctatg gaccaacgca ccaatgtgaa cggagatccc ggcgccggag accggaagaa   2220
agaagaaagg tttgatccga gtgcacaacc accgttcaag atcggagata taagggcggc   2280
gattcctaag cactgttggg ttaagagtcc tttgagatca atgagttacg tcgtcagaga   2340
cattatcgcc gtcgcggctt tggccatcgc tgccgtgtat gttgatagct ggttcctttg   2400
gcctctttat tgggccgccc aaggaacact tttctgggcc atctttgttc tcggccacga   2460
ctgtggacat gggagtttct cagacattcc tctactgaat agtgtggttg gtcacattct   2520
tcattctttc atcctcgttc cttaccatgg ttggagaata agccaccgga cacaccacca   2580
gaaccatggc catgttgaaa acgacgagtc atgggttccg ttaccagaaa gggtgtacaa   2640
gaaattgccc cacagtactc ggatgctcag atacnctgtc cctctcccca tgctcgcata   2700
tcctctctat ttgtgctaca gaagtcctgg aaaagaagga tcacatttta acccatacag   2760
tagtttattt gctccaagcg agagaaagct tattgcaact tcaactactt gttggtccat   2820
aatgttcgtc agtcttatcg ctctatcttt cgtcttcggt ccactcgcgg ttcttaaagt   2880
```

-continued ctacggtgta ccgtacatta tctttgtgat gtggttggat gctgtcacgt atttgcatca 2940
tcatggtcac gatgagaagt tgccttggta tagaggcaag gaatggagtt atctacgtgg 3000
aggattaaca acaattgata gagattacgg aatctttaac aacattcatc acgacattgg 3060
aactcacgtg atccatcatc tcttcccaca aatccctcac tatcacttgg tcgacgccac 3120
gaaagcagct aaacatgtgt tgggaagata ctacagagaa ccaaagacgt caggagcaat 3180
accgatccac ttggtggaga gtttggtcgc aagtattaag aaagatcatt acgtcagcga 3240
cactggtgat attgtcttct acgagacaga tccagatctc tacgtttacg cttctgacaa 3300
atctaaaatc aattaatctc catttgttta gctctattag gaataaacca gcccactttt 3360
aaaattttta tttcttgttg tttttaagtt aaaagtgtac tcgtgaaact cttttttttt 3420
tctttttttt tattaatgta tttacattac aaggcgtaaa gcggccgcga cacaagtgtg 3480
agagtactaa ataaatgctt tggttgtacg aaatcattac actaaataaa ataatcaaag 3540
cttatatatg ccttccgcta aggccgaatg caaagaaatt ggttctttct cgttatcttt 3600
tgccactttt actagtacgt attaattact acttaatcat ctttgtttac ggctcattat 3660
atccgtacgt ctagaggatc cgtcgacggc gcgcccgatc atccggatat agttcctcct 3720
ttcagcaaaa aacccctcaa gacccgttta gaggccccaa ggggttatgc tagttattgc 3780
tcagcggtgg cagcagccaa ctcagcttcc tttcgggctt tgttagcagc cggatcgatc 3840
caagctgtac ctcactattc ctttgccctc ggacgagtgc tggggcgtcg gtttccacta 3900
tcggcgagta cttctacaca gccatcggtc cagacggccg cgcttctgcg ggcgatttgt 3960
gtacgcccga cagtcccggc tccggatcgg acgattgcgt cgcatcgacc ctgcgcccaa 4020
gctgcatcat cgaaattgcc gtcaaccaag ctctgataga gttggtcaag accaatgcgg 4080
agcatatacg cccggagccg cggcgatcct gcaagctccg gatgcctccg ctcgaagtag 4140
cgcgtctgct gctccataca agccaaccac ggcctccaga agaagatgtt ggcgacctcg 4200
tattgggaat ccccgaacat cgcctcgctc cagtcaatga ccgctgttat gcggccattg 4260
tccgtcagga cattgttgga gccgaaatcc gcgtgcacga ggtgccggac ttcggggcag 4320
tcctcggccc aaagcatcag ctcatcgaga gcctgcgcga cggacgcact gacggtgtcg 4380
tccatcacag tttgccagtg atacacatgg ggatcagcaa tcgcgcatat gaaatcacgc 4440
catgtagtgt attgaccgat tccttgcggt ccgaatgggc cgaacccgct cgtctggcta 4500
agatcggccg cagcgatcgc atccatagcc tccgcgaccg gctgcagaac agcgggcagt 4560
tcggtttcag gcaggtcttg caacgtgaca ccctgtgcac ggcgggagat gcaataggtc 4620
aggctctcgc tgaattcccc aatgtcaagc acttccggaa tcgggagcgc ggccgatgca 4680
aagtgccgat aaacataacg atctttgtag aaaccatcgg cgcagctatt tacccgcagg 4740
acatatccac gccctcctac atcgaagctg aaagcacgag attcttcgcc ctccgagagc 4800
tgcatcaggt cggagacgct gtcgaacttt tcgatcagaa acttctcgac agacgtcgcg 4860
gtgagttcag gcttttccat gggtatatct ccttcttaaa gttaaacaaa attatttcta 4920
gagggaaacc gttgtggtct ccctatagtg agtcgtatta atttcgcggg atcgagatct 4980
gatcaacctg cattaatgaa tcggccaacg cgcggggaga ggcggtttgc gtattgggcg 5040
ctcttccgct tcctcgctca ctgactcgct gcgctcggtc gttcggctgc ggcgagcggt 5100
atcagctcac tcaaaggcgg taatacggtt atccacagaa tcaggggata acgcaggaaa 5160
gaacatgtga gcaaaaggcc agcaaaaggc caggaaccgt aaaaaggccg cgttgctggc 5220
gtttttccat aggctccgcc cccctgacga gcatcacaaa aatcgacgct caagtcagag 5280

-continued

```
gtggcgaaac ccgacaggac tataaagata ccaggcgttt ccccctggaa gctccctcgt   5340
gcgctctcct gttccgaccc tgccgcttac cggatacctg tccgcctttc tcccttcggg   5400
aagcgtggcg ctttctcaat gctcacgctg taggtatctc agttcggtgt aggtcgttcg   5460
ctccaagctg ggctgtgtgc acgaaccccc cgttcagccc gaccgctgcg ccttatccgg   5520
taactatcgt cttgagtcca acccggtaag acacgactta tcgccactgg cagcagccac   5580
tggtaacagg attagcagag cgaggtatgt aggcggtgct acagagttct tgaagtggtg   5640
gcctaactac ggctacacta gaaggacagt atttggtatc tgcgctctgc tgaagccagt   5700
taccttcgga aaaagagttg gtagctcttg atccggcaaa caaaccaccg ctggtagcgg   5760
tggttttttt gtttgcaagc agcagattac gcgcagaaaa aaaggatctc aagaagatcc   5820
tttgatcttt tctacggggt ctgacgctca gtggaacgaa aactcacgtt aagggatttt   5880
ggtcatgaca ttaacctata aaaataggcg tatcacgagg ccctttcgtc tcgcgcgttt   5940
cggtgatgac ggtgaaaacc tctgacacat gcagctcccg gagacggtca cagcttgtct   6000
gtaagcggat gccgggagca gacaagcccg tcagggcgcg tcagcgggtg ttggcgggtg   6060
tcggggctgg cttaactatg cggcatcaga gcagattgta ctgagagtgc accatatgga   6120
catattgtcg ttagaacgcg gctacaatta atacataacc ttatgtatca tacacatacg   6180
atttaggtga cactatagaa cggcgcgcca agctgggtct agaactagaa acgtgatgcc   6240
acttgttatt gaagtcgatt acagcatcta ttctgtttta ctatttataa ctttgccatt   6300
tctgactttt gaaaactatc tctggatttc ggtatcgctt tgtgaagatc gagcaaaaga   6360
gacgttttgt ggacgcaatg gtccaaatcc gttctacatg aacaaattgg tcacaatttc   6420
cactaaaagt aaataaatgg caagttaaaa aaggaatatg cattttactg attgcctagg   6480
tgagctccaa gagaagttga atctacacgt ctaccaaccg ctaaaaaaag aaaaacattg   6540
atatgtaacc tgattccatt agcttttgac ttcttcaaca gattctctac ttagatttct   6600
aacagaaata ttattactag cacatcattt tcagtctcac tacagcaaaa aatccaacgg   6660
cacaatacag acaacaggag atatcagact acagagatag atagatgcta ctgcatgtag   6720
taagttaaat aaaaggaaaa taaaatgtct tgctaccaaa actactacag actatgatgc   6780
tcaccacagg ccaaatcctg caactaggac agcattatct tatatatatt gtacaaaaca   6840
agcatcaagg aacatttggt ctaggcaatc agtacctcgt tctaccatca ccctcagtta   6900
tcacatcctt gaaggatcca ttactgggaa tcatcggcaa cacatgctcc tgatggggca   6960
caatgacatc aagaaggtag gggccagggg tgtccaacat tctctgaatt gccgctctaa   7020
gctcttcctt cttcgtcact cgcgctgccg gtatcccaca agcatcagca aacttgagca   7080
tgtttgggaa tatctcgctc tcgctagacg gatctccaag ataggtgtga gctctattgg   7140
acttgtagaa cctatcctcc aactgaacca ccatacccaa atgctgattg ttcaacaaca   7200
atatcttaac tgggagattc tccactctta tagtggccaa ctcctgaaca ttcatgatga   7260
aactaccatc cccatcaatg tcaaccacaa cagccccagg gttagcaaca gcagcaccaa   7320
tagccgcagg caatccaaaa cccatggctc caagaccccc tgaggtcaac cactgcctcg   7380
gtctcttgta cttgtaaaac tgcgcagccc acatttgatg ctgcccaacc ccagtactaa   7440
caatagcatc tccattagtc aactcatcaa gaacctcgat agcatgctgc ggagaaatcg   7500
cgtcctggaa tgtcttgtaa cccaatggaa acttgtgttt ctgcacatta atctcttctc   7560
tccaacctcc aagatcaaac ttaccctcca ctcctttctc ctccaaaatc atattaattc   7620
ccttcaaggc caacttcaaa tccgcgcaaa ccgacacgtg cgcctgcttg ttcttcccaa   7680
```

```
tctcggcaga atcaatatca atgtgaacaa tcttagccct actagcaaaa gcctcaagct   7740
tcccagtaac acggtcatca aaccttaccc caaaggcaag caacaaatca ctattgtcaa   7800
cagcatagtt agcataaaca gtaccatgca tacccagcat ctgaagggaa tattcatcac   7860
caataggaaa agttccaaga cccattaaag tgctagcaac gggaatacca gtgagttcaa   7920
caaagcgcct caattcagca ctggaattca aactgccacc gccgacgtag agaacgggct   7980
tttgggcctc catgatgagt ctgacaatgt gttccaattg ggcctcggcg gggggcctgg   8040
gcagcctggc gaggtaaccg gggaggttaa cgggctcgtc ccaattaggc acggcgagtt   8100
gctgctgaac gtctttggga atgtcgatga ggaccggacc ggggcggccg gaggtggcga   8160
cgaagaaagc ctcggcgacg acgcggggga tgtcgtcgac gtcgaggatg aggtagttgt   8220
gcttcgtgat ggatctgctc acctccacga tcggggtttc ttggaaggcg tcggtgccga   8280
tcatccggcg ggcgacctgg ccggtgatgg cgacgactgg gacgctgtcc attaaagcgt   8340
cggcgaggcc gctcacgagg ttggtggcgc cggggccgga ggtggcaatg cagacgccgg   8400
ggaggccgga ggaacgcgcg tagccttcgg cggcgaagac gccgccctgc tcgtggcgcg   8460
ggagcacgtt gcggatggcg gcggagcgcg tgagcgcctg gtggatctcc atcgacgcac   8520
cgccggggta cgcgaacacc gtcgtcacgc cctgcctctc cagcgcctcc acaaggatgt   8580
ccgcgccctt gcgaggttcg ccggaggcga accgtgacac gaagggctcc gtggtcggcg   8640
cttccttggt gaagggcgcc gccgtggggg gtttggagat ggaacatttg attttgagag   8700
cgtggttggg tttggtgagg gtttgatgag agagagggag ggtggatcta gtaatgcgtt   8760
tggggaaggt ggggtgtgaa gaggaagaag agaatcgggt ggttctggaa gcggtggccg   8820
ccattgtgtt gtgtggcatg gttatacttc aaaaactgca caacaagcct agagttagta   8880
cctaaacagt aaatttacaa cagagagcaa agacacatgc aaaaatttca gccataaaaa   8940
aagttataat agaatttaaa gcaaaagttt catttttttaa acatatatac aaacaaactg   9000
gatttgaagg aagggattaa ttcccctgct caaagtttga attcctattg tgacctatac   9060
tcgaataaaa ttgaagccta aggaatgtat gagaaacaag aaaacaaaac aaaactacag   9120
acaaacaagt acaattacaa aattcgctaa aattctgtaa tcaccaaacc ccatctcagt   9180
cagcacaagg cccaaggttt attttgaaat aaaaaaaaag tgattttatt tctcataagc   9240
taaaagaaag aaaggcaatt atgaaatgat ttcgactaga tctgaaagtc caacgcgtat   9300
tccgcagata ttaaagaaag agtagagttt cacatggatc ctagatggac ccagttgagg   9360
aaaaagcaag gcaaagcaaa ccagaagtgc aagatccgaa attgaaccac ggaatctagg   9420
atttggtaga gggagaagaa aagtaccttg agaggtagaa gagaagagaa gagcagagag   9480
atatatgaac gagtgtgtct tggtctcaac tctgaagcga tacgagttta gaggggagca   9540
ttgagttcca atttataggg aaaccgggtg gcaggggtga gttaatgacg gaaaagcccc   9600
taagtaacga gattggattg tgggttagat tcaaccgttt gcatccgcgg cttagattgg   9660
ggaagtcaga gtgaatctca accgttgact gagttgaaaa ttgaatgtag caaccaattg   9720
agccaacccc agcctttgcc ctttgatttt gatttgtttg ttgcatactt tttatttgtc   9780
ttctggttct gactctcttt ctctcgtttc aatgccaggt tgcctactcc cacaccactc   9840
acaagaagat tctactgtta gtattaaata ttttttaatg tattaaatga tgaatgcttt   9900
tgtaaacaga acaagactat gtctaataag tgtcttgcaa catttttttaa gaaattaaaa   9960
aaaatatatt tattatcaaa atcaaatgta tgaaaaatca tgaataatat aattttatac  10020
attttttttaa aaaatctttt aatttcttaa ttaatatctt aaaaataatg attaatattt  10080
```

-continued

```
aacccaaaat aattagtatg attggtaagg aagatatcca tgttatgttt ggatgtgagt  10140
ttgatctaga gcaaagctta ctagagtcga cctgcaggtc gactcgacgt acgatcccac  10200
atgcaagttt ttatttcaat cccttttcct ttgaataact gaccaagaac aacaagaaaa  10260
aaaaaaaaaa agaaaaggat cattttgaaa ggatattttt cgctcctatt caaatactgt  10320
atttttacca aaaaaactgt atttttccta cactctcaag ctttgttttt cgcttcgact  10380
ctcatgattt ccttcatatg ccaatcactc tatttataaa tggcataagg tagtgtgaac  10440
aattgcaaag cttgtcatca aaagcttgca atgtacaaat taatgttttt catgcctttc  10500
aaaattatct gcacccccta gctattaatc taacatctaa gtaaggctag tgaatttttt  10560
cgaatagtca tgcagtgcat taatttcccc gtgactattt tggctttgac tccaacactg  10620
gccccgtaca tccgtccctc attacatgaa aagaaatatt gtttatattc ttaattaaaa  10680
atattgtccc ttctaaattt tcatatagtt aattattata ttactttttt ctctattcta  10740
ttagttctat tttcaaatta ttatttatgc atatgtaaag tacattatat ttttgctata  10800
tacttaaata tttctaaatt attaaaaaaa gactgatatg aaaaatttat tctttttaaa  10860
gctatatcat tttatatata cttttttcttt tcttttcttt cattttctat tcaatttaat  10920
aagaaataaa ttttgtaaat ttttatttat caatttataa aaatatttta ctttatatgt  10980
tttttcacat ttttgttaaa caaatcatat cattatgatt gaaagagagg aaattgacag  11040
tgagtaataa gtgatgagaa aaaaatgtgt tatttcctaa aaaaaaccta aacaaacatg  11100
tatctactct ctatttcatc tatctctcat ttcatttttc tctttatctc tttctttatt  11160
tttttatcat atcatttcac attaattatt tttactctct ttattttttc tctctatccc  11220
tctcttattt ccactcatat atacactcca aaattggggc atgcctttat cactactcta  11280
tctcctccac taaatcattt aaatgaaact gaaaagcatt ggcaagtctc ctcccctcct  11340
caagtgattt ccaactcagc attggcatct aattgattca gtatatctat tgcatgtgta  11400
aaagtctttc cacaatacat aactattaat taatcttaaa taaataaagg ataaaatatt  11460
tttttttctt cataaaatta aaatatgtta tttttttgttt agatgtatat tcgaataaat  11520
ctaaatatat gataatgatt ttttatattg attaaacata taatcaatat taaatatgat  11580
atttttttat ataggttgta cacataattt tataaggata aaaaatatga taaaaataaa  11640
ttttaaatat ttttatattt acgagaaaaa aaaatatttt agccataaat aaatgaccag  11700
catattttac aaccttagta attcataaat tcctatatgt atatttgaaa ttaaaaacag  11760
ataatcgtta agggaaggaa tcctacgtca tctcttgcca tttgtttttc atgcaaacag  11820
aaagggacga aaaaccacct caccatgaat cactcttcac accattttta ctagcaaaca  11880
agtctcaaca actgaagcca gctctctttc cgtttctttt tacaacactt tctttgaaat  11940
agtagtattt ttttttcaca tgatttatta acgtgccaaa agatgcttat tgaatagagt  12000
gcacatttgt aatgtactac taattagaac atgaaaaagc attgttctaa cacgataatc  12060
ctgtgaaggc gttaactcca aagatccaat ttcactatat aaattgtgac gaaagcaaaa  12120
tgaattcaca tagctgagag agaaaggaaa ggttaactaa gaagcaatac ttcagcggcc  12180
gcatgactga ggataagacg aaggtcgagt tcccgacgct cacggagctc aagcactcga  12240
tcccgaacgc gtgctttgag tcgaacctcg gcctctcgct ctactacacg gcccgcgcga  12300
tcttcaacgc gtcggcctcg gcggcgctgc tctacgcggc gcgctcgacg ccgttcattg  12360
ccgataacgt tctgctccac gcgctcgttt gcgccaccta catctacgtg cagggcgtca  12420
tcttctgggg cttcttcacg gtcggccacg actgcggcca ctcggccttc tcgcgctacc  12480
```

-continued acagcgtcaa ctttatcatc ggctgcatca tgcactctgc gattttgacg ccgttcgaga 12540
gctggcgcgt gacgcaccgc caccaccaca agaacacggg caacattgat aaggacgaga 12600
tcttttaccc gcaccggtcg gtcaaggacc tccaggacgt gcgccaatgg gtctacacgc 12660
tcggcggtgc gtggtttgtc tacttgaagg tcgggtatgc cccgcgcacg atgagccact 12720
ttgacccgtg ggacccgctc ctccttcgcc gcgcgtcggc cgtcatcgtg tcgctcggcg 12780
tctgggccgc cttcttcgcc gcgtacgcgt acctcacata ctcgctcggc tttgccgtca 12840
tgggcctcta ctactatgcg ccgctctttg tctttgcttc gttcctcgtc attacgacct 12900
tcttgcacca caacgacgaa gcgacgccgt ggtacggcga ctcggagtgg acgtacgtca 12960
agggcaacct ctcgagcgtc gaccgctcgt acggcgcgtt cgtggacaac ctgagccacc 13020
acattggcac gcaccaggtc caccacttgt tcccgatcat tccgcactac aagctcaacg 13080
aagccaccaa gcactttgcg gccgcgtacc cgcacctcgt gcgcaggaac gacgagccca 13140
tcatcacggc cttcttcaag accgcgcacc tctttgtcaa ctacggcgct gtgcccgaga 13200
cggcgcagat cttcacgctc aaagagtcgg ccgcggccgc caaggccaag tcggactaag 13260
cggccgcatg agccgtaaag gttcaataca acgagtgctt gttttcttag ggacaagcat 13320
tgtacttatg tatgattctg tgtaaccatg agtcttccac gttgtactaa tgtgaagggc 13380
aaaaataaaa cacagaacaa gttcgttttt ctcaaataat gtgaaggtag aaaatggaac 13440
catgcctcct ctcttgcatg tgatttaaaa tattagcaga tggtaccgta cgtgggcgga 13500
tcccccgggc tgca 13514

<210> SEQ ID NO 88
<211> LENGTH: 12323
<212> TYPE: DNA
<213> ORGANISM: Artificial Sequence
<220> FEATURE:
<223> OTHER INFORMATION: Plasmid pKR329
<220> FEATURE:
<221> NAME/KEY: misc_feature
<222> LOCATION: (1201)..(1201)
<223> OTHER INFORMATION: n is a, c, g, or t
<220> FEATURE:
<221> NAME/KEY: misc_feature
<222> LOCATION: (2684)..(2684)
<223> OTHER INFORMATION: n is a, c, g, or t

<400> SEQUENCE: 88
ggatctggcc ggccggatct cgtacgtcct cgaagagaag ggttaataac acatttttta 60
acatttttaa cacaaatttt agttatttaa aaatttatta aaaaatttaa aataagaaga 120
ggaactcttt aaataaatct aacttacaaa atttatgatt tttaataagt tttcaccaat 180
aaaaaatgtc ataaaaatat gttaaaaagt atattatcaa tattctcttt atgataaata 240
aaaagaaaaa aaaaataaaa gttaagtgaa aatgagattg aagtgacttt aggtgtgtat 300
aaatatatca accccgccaa caatttattt aatccaaata tattgaagta tattattcca 360
tagcctttat ttatttatat atttattata taaaagcttt atttgttcta ggttgttcat 420
gaaatatttt tttggtttta tctccgttgt aagaaaatca tgtgctttgt gtcgccactc 480
actattgcag ctttttcatg cattggtcag attgacggtt gattgtattt ttgtttttta 540
tggttttgtg ttatgactta agtcttcatc tctttatctc ttcatcaggt ttgatggtta 600
cctaatatgg tccatgggta catgcatggt taaattaggt ggccaacttt gttgtgaacg 660
atagaatttt ttttatatta agtaaactat ttttatatta tgaaataata ataaaaaaaa 720
tattttatca ttattaacaa aatcatatta gttaatttgt taactctata ataaaagaaa 780

-continued

```
tactgtaaca ttcacattac atggtaacat ctttccaccc tttcatttgt tttttgtttg    840
atgacttttt ttcttgttta aatttatttc ccttctttta aatttggaat acattatcat    900
catatataaa ctaaaatact aaaaacagga ttacacaaat gataaataat aacacaaata    960
tttataaatc tagctgcaat atatttaaac tagctatatc gatattgtaa aataaaacta   1020
gctgcattga tactgataaa aaaatatcat gtgctttctg gactgatgat gcagtatact   1080
tttgacattg cctttatttt atttttcaga aaagctttct tagttctggg ttcttcatta   1140
tttgtttccc atctccattg tgaattgaat catttgcttc gtgtcacaaa tacaatttag   1200
ntaggtacat gcattggtca gattcacggt ttattatgtc atgacttaag ttcatggtag   1260
tacattacct gccacgcatg cattatattg gttagatttg ataggcaaat ttggttgtca   1320
acaatataaa tataaataat gtttttatat tacgaaataa cagtgatcaa aacaaacagt   1380
tttatcttta ttaacaagat tttgtttttg tttgatgacg ttttttaatg tttacgcttt   1440
ccccccttctt ttgaatttag aacactttat catcataaaa tcaaatacta aaaaaattac   1500
atatttcata aataataaca caaatatttt taaaaaatct gaaataataa tgaacaatat   1560
tacatattat cacgaaaatt cattaataaa aatattatat aaataaaatg taatagtagt   1620
tatatgtagg aaaaaagtac tgcacgcata atatatacaa aaagattaaa atgaactatt   1680
ataaataata acactaaatt aatggtgaat catatcaaaa taatgaaaaa gtaaataaaa   1740
tttgtaatta acttctatat gtattacaca cacaaataat aaataatagt aaaaaaaatt   1800
atgataaata tttaccatct cataagatat ttaaaataat gataaaaata tagattattt   1860
tttatgcaac tagctagcca aaaagagaac acgggtatat ataaaaagag taccttttaaa  1920
ttctactgta cttcctttat tcctgacgtt tttatatcaa gtggacatac gtgaagattt   1980
taattatcag tctaaatatt tcattagcac ttaatacttt tctgttttat tcctatccta   2040
taagtagtcc cgattctccc aacattgctt attcacacaa ctaactaaga aagtcttcca   2100
tagcccccca agcggccgcc tctctctctc tctcttctct ctttctctcc ccctctctcc   2160
ggcgatggtt gttgctatgg accaacgcac caatgtgaac ggagatcccg gcgccggaga   2220
ccggaagaaa gaagaaaggt ttgatccgag tgcacaacca ccgttcaaga tcggagatat   2280
aagggcggcg attcctaagc actgttgggt taagagtcct ttgagatcaa tgagttacgt   2340
cgtcagagac attatcgccg tcgcggcttt ggccatcgct gccgtgtatg ttgatagctg   2400
gttcctttgg cctctttatt gggccgccca aggaacactt ttctgggcca tctttgttct   2460
cggccacgac tgtggacatg ggagtttctc agacattcct ctactgaata gtgtggttgg   2520
tcacattctt cattctttca tcctcgttcc ttaccatggt tggagaataa gccaccggac   2580
acaccaccag aaccatggcc atgttgaaaa cgacgagtca tgggttccgt taccagaaag   2640
ggtgtacaag aaattgcccc acagtactcg gatgctcaga tacnctgtcc ctctccccat   2700
gctcgcatat cctctctatt tgtgctacag aagtcctgga aaagaaggat cacattttaa   2760
cccatacagt agtttatttg ctccaagcga gagaaagctt attgcaactt caactacttg   2820
ttggtccata atgttcgtca gtcttatcgc tctatctttc gtcttcggtc cactcgcggt   2880
tcttaaagtc tacggtgtac cgtacattat ctttgtgatg tggttggatg ctgtcacgta   2940
tttgcatcat catggtcacg atgagaagtt gccttggtat agaggcaagg aatggagtta   3000
tctacgtgga ggattaacaa caattgatag agattacgga atctttaaca acattcatca   3060
cgacattgga actcacgtga tccatcatct cttcccacaa atccctcact atcacttggt   3120
cgacgccacg aaagcagcta aacatgtgtt gggaagatac tacagagaac caaagacgtc   3180
```

-continued

```
aggagcaata ccgatccact tggtggagag tttggtcgca agtattaaga aagatcatta   3240
cgtcagcgac actggtgata ttgtcttcta cgagacagat ccagatctct acgtttacgc   3300
ttctgacaaa tctaaaatca attaatctcc atttgtttag ctctattagg aataaaccag   3360
cccactttta aaatttttat ttcttgttgt ttttaagtta aaagtgtact cgtgaaactc   3420
ttttttttt cttttttttt attaatgtat ttacattaca aggcgtaaag cggccgcgac   3480
acaagtgtga gagtactaaa taaatgcttt ggttgtacga aatcattaca ctaaataaaa   3540
taatcaaagc ttatatatgc cttccgctaa ggccgaatgc aaagaaattg gttctttctc   3600
gttatctttt gccactttta ctagtacgta ttaattacta cttaatcatc tttgtttacg   3660
gctcattata tccgtacgga tccgtcgacg gcgcgcccga tcatccggat atagttcctc   3720
ctttcagcaa aaaacccctc aagacccgtt tagaggcccc aaggggttat gctagttatt   3780
gctcagcggt ggcagcagcc aactcagctt cctttcgggc tttgttagca gccggatcga   3840
tccaagctgt acctcactat tcctttgccc tcggacgagt gctggggcgt cggtttccac   3900
tatcggcgag tacttctaca cagccatcgg tccagacggc cgcgcttctg cgggcgattt   3960
gtgtacgccc gacagtcccg gctccggatc ggacgattgc gtcgcatcga ccctgcgccc   4020
aagctgcatc atcgaaattg ccgtcaacca agctctgata gagttggtca agaccaatgc   4080
ggagcatata cgcccggagc cgcggcgatc ctgcaagctc cggatgcctc cgctcgaagt   4140
agcgcgtctg ctgctccata caagccaacc acggcctcca gaagaagatg ttggcgacct   4200
cgtattggga atccccgaac atcgcctcgc tccagtcaat gaccgctgtt atgcggccat   4260
tgtccgtcag gacattgttg gagccgaaat ccgcgtgcac gaggtgccgg acttcggggc   4320
agtcctcggc ccaaagcatc agctcatcga gagcctgcgc gacggacgca ctgacggtgt   4380
cgtccatcac agtttgccag tgatacacat ggggatcagc aatcgcgcat atgaaatcac   4440
gccatgtagt gtattgaccg attccttgcg gtccgaatgg gccgaacccg ctcgtctggc   4500
taagatcggc cgcagcgatc gcatccatag cctccgcgac cggctgcaga acagcgggca   4560
gttcggtttc aggcaggtct tgcaacgtga caccctgtgc acggcgggag atgcaatagg   4620
tcaggctctc gctgaattcc ccaatgtcaa gcacttccgg aatcgggagc gcggccgatg   4680
caaagtgccg ataaacataa cgatctttgt agaaaccatc ggcgcagcta tttacccgca   4740
ggacatatcc acgccctcct acatcgaagc tgaaagcacg agattcttcg ccctccgaga   4800
gctgcatcag gtcggagacg ctgtcgaact tttcgatcag aaacttctcg acagacgtcg   4860
cggtgagttc aggctttttcc atgggtatat ctccttctta aagttaaaca aaattatttc   4920
tagagggaaa ccgttgtggt ctccctatag tgagtcgtat taatttcgcg ggatcgagat   4980
cgatccaatt ccaatcccac aaaaatctga gcttaacagc acagttgctc ctctcagagc   5040
agaatcgggt attcaacacc ctcatatcaa ctactacgtt gtgtataacg gtccacatgc   5100
cggtatatac gatgactggg gttgtacaaa ggcggcaaca aacggcgttc ccggagttgc   5160
acacaagaaa tttgccacta ttacagaggc aagagcagca gctgacgcgt acacaacaag   5220
tcagcaaaca gacaggttga acttcatccc caaaggagaa gctcaactca agcccaagag   5280
ctttgctaag gccctaacaa gcccaccaaa gcaaaaagcc cactggctca cgctaggaac   5340
caaaaggccc agcagtgatc cagccccaaa agagatctcc tttgccccgg agattacaat   5400
ggacgatttc ctctatcttt acgatctagg aaggaagttc gaaggtgaag gtgacgacac   5460
tatgttcacc actgataatg agaaggttag cctcttcaat ttcagaaaga atgctgaccc   5520
acagatggtt agagaggcct acgcagcagg tctcatcaag acgatctacc cgagtaacaa   5580
```

-continued

```
tctccaggag atcaaatacc ttcccaagaa ggttaaagat gcagtcaaaa gattcaggac   5640
taattgcatc aagaacacag agaaagacat atttctcaag atcagaagta ctattccagt   5700
atggacgatt caaggcttgc ttcataaacc aaggcaagta atagagattg gagtctctaa   5760
aaaggtagtt cctactgaat ctaaggccat gcatggagtc taagattcaa atcgaggatc   5820
taacagaact cgccgtgaag actggcgaac agttcataca gagtctttta cgactcaatg   5880
acaagaagaa aatcttcgtc aacatggtgg agcacgacac tctggtctac tccaaaaatg   5940
tcaaagatac agtctcagaa gaccaaaggg ctattgagac ttttcaacaa aggataattt   6000
cgggaaacct cctcggattc cattgcccag ctatctgtca cttcatcgaa aggacagtag   6060
aaaaggaagg tggctcctac aaatgccatc attgcgataa aggaaaggct atcattcaag   6120
atgcctctgc cgacagtggt cccaaagatg gacccccacc cacgaggagc atcgtggaaa   6180
aagaagacgt tccaaccacg tcttcaaagc aagtggattg atgtgacatc tccactgacg   6240
taagggatga cgcacaatcc cactatcctt cgcaagaccc ttcctctata taaggaagtt   6300
catttcattt ggagaggaca cgctcgagct catttctcta ttacttcagc cataacaaaa   6360
gaactctttt ctcttcttat taaaccatga aaaagcctga actcaccgcg acgtctgtcg   6420
agaagtttct gatcgaaaag ttcgacagcg tctccgacct gatgcagctc tcggagggcg   6480
aagaatctcg tgctttcagc ttcgatgtag gagggcgtgg atatgtcctg cgggtaaata   6540
gctgcgccga tggtttctac aaagatcgtt atgtttatcg gcactttgca tcggccgcgc   6600
tcccgattcc ggaagtgctt gacattgggg aattcagcga gagcctgacc tattgcatct   6660
cccgccgtgc acagggtgtc acgttgcaag acctgcctga aaccgaactg cccgctgttc   6720
tgcagccggt cgcggaggcc atggatgcga tcgctgcggc cgatcttagc cagacgagcg   6780
ggttcggccc attcggaccg caaggaatcg gtcaatacac tacatggcgt gatttcatat   6840
gcgcgattgc tgatccccat gtgtatcact ggcaaactgt gatggacgac accgtcagtg   6900
cgtccgtcgc gcaggctctc gatgagctga tgctttgggc cgaggactgc cccgaagtcc   6960
ggcacctcgt gcacgcggat ttcggctcca acaatgtcct gacggacaat ggccgcataa   7020
cagcggtcat tgactggagc gaggcgatgt tcggggattc ccaatacgag gtcgccaaca   7080
tcttcttctg gaggccgtgg ttggcttgta tggagcagca gacgcgctac ttcgagcgga   7140
ggcatccgga gcttgcagga tcgccgcggc tccgggcgta tatgctccgc attggtcttg   7200
accaactcta tcagagcttg gttgacggca atttcgatga tgcagcttgg gcgcagggtc   7260
gatgcgacgc aatcgtccga tccggagccg ggactgtcgg gcgtacacaa atcgcccgca   7320
gaagcgcggc cgtctggacc gatggctgtg tagaagtact cgccgatagt ggaaaccgac   7380
gccccagcac tcgtccgagg gcaaaggaat agtgaggtac ctaaagaagg agtgcgtcga   7440
agcagatcgt tcaaacattt ggcaataaag tttcttaaga ttgaatcctg ttgccggtct   7500
tgcgatgatt atcatataat ttctgttgaa ttacgttaag catgtaataa ttaacatgta   7560
atgcatgacg ttatttatga gatgggtttt tatgattaga gtcccgcaat tatacattta   7620
atacgcgata gaaaacaaaa tatagcgcgc aaactaggat aaattatcgc gcgcggtgtc   7680
atctatgtta ctagatcgat gtcgaatcga tcaacctgca ttaatgaatc ggccaacgcg   7740
cggggagagg cggtttgcgt attgggcgct cttccgcttc ctcgctcact gactcgctgc   7800
gctcggtcgt tcggctgcgg cgagcggtat cagctcactc aaaggcggta atacggttat   7860
ccacagaatc aggggataac gcaggaaaga acatgtgagc aaaaggccag caaaaggcca   7920
ggaaccgtaa aaaggccgcg ttgctggcgt ttttccatag gctccgcccc cctgacgagc   7980
```

atcacaaaaa tcgacgctca agtcagaggt ggcgaaaccc gacaggacta taaagatacc 8040
aggcgtttcc ccctggaagc tccctcgtgc gctctcctgt tccgaccctg ccgcttaccg 8100
gatacctgtc cgcctttctc ccttcgggaa gcgtggcgct ttctcaatgc tcacgctgta 8160
ggtatctcag ttcggtgtag gtcgttcgct ccaagctggg ctgtgtgcac gaaccccccg 8220
ttcagcccga ccgctgcgcc ttatccggta actatcgtct tgagtccaac ccggtaagac 8280
acgacttatc gccactggca gcagccactg gtaacaggat tagcagagcg aggtatgtag 8340
gcggtgctac agagttcttg aagtggtggc ctaactacgg ctacactaga aggacagtat 8400
ttggtatctg cgctctgctg aagccagtta ccttcggaaa aagagttggt agctcttgat 8460
ccggcaaaca aaccaccgct ggtagcggtg gtttttttgt ttgcaagcag cagattacgc 8520
gcagaaaaaa aggatctcaa gaagatcctt tgatcttttc tacggggtct gacgctcagt 8580
ggaacgaaaa ctcacgttaa gggattttgg tcatgacatt aacctataaa aataggcgta 8640
tcacgaggcc ctttcgtctc gcgcgtttcg gtgatgacgg tgaaaacctc tgacacatgc 8700
agctcccgga gacggtcaca gcttgtctgt aagcggatgc cgggagcaga caagcccgtc 8760
agggcgcgtc agcgggtgtt ggcgggtgtc ggggctggct taactatgcg gcatcagagc 8820
agattgtact gagagtgcac catatggaca tattgtcgtt agaacgcggc tacaattaat 8880
acataacctt atgtatcata cacatacgat ttaggtgaca ctatagaacg gcgcgccaag 8940
cttggatctc ctgcagcccg ggggatccgc ccacgtacgg taccatctgc taatatttta 9000
aatcacatgc aagagaggag gcatggttcc attttctacc ttcacattat ttgagaaaaa 9060
cgaacttgtt ctgtgtttta tttttgccct tcacattagt acaacgtgga agactcatgg 9120
ttacacagaa tcatacataa gtacaatgct tgtccctaag aaaacaagca ctcgttgtat 9180
tgaaccttta cggctcatgc ggccgcgaat tcactagtga ttgaattcgc ggccgcttag 9240
tccgacttgg ccttggcggc cgcggccgac tctttgagcg tgaagatctg cgccgtctcg 9300
ggcacagcgc cgtagttgac aaagaggtgc gcggtcttga agaaggccgt gatgatgggc 9360
tcgtcgttcc tgcgcacgag gtgcgggtac gcggccgcaa agtgcttggt ggcttcgttg 9420
agcttgtagt gcggaatgat cgggaacaag tggtggacct ggtgcgtgcc aatgtggtgg 9480
ctcaggttgt ccacgaacgc gccgtacgag cggtcgacgc tcgagaggtt gcccttgacg 9540
tacgtccact ccgagtcgcc gtaccacggc gtcgcttcgt cgttgtggtg caagaaggtc 9600
gtaatgacga ggaacgaagc aaagacaaag agcggcgcat agtagtagag gcccatgacg 9660
gcaaagccga gcgagtatgt gaggtacgcg tacgcggcga agaaggcggc ccagacgccg 9720
agcgacacga tgacggccga cgcgcggcga aggaggagcg ggtcccacgg gtcaaagtgg 9780
ctcatcgtgc gcggggcata cccgaccttc aagtagacaa accacgcacc gccgagcgtg 9840
tagacccatt ggcgcacgtc ctggaggtcc ttgaccgacc ggtgcgggta aaagatctcg 9900
tccttatcaa tgttgcccgt gttcttgtgg tggtggcggt gcgtcacgcg ccagctctcg 9960
aacggcgtca aaatcgcaga gtgcatgatg cagccgatga taaagttgac gctgtggtag 10020
cgcgagaagg ccgagtggcc gcagtcgtgg ccgaccgtga agaagcccca gaagatgacg 10080
ccctgcacgt agatgtaggt ggcgcaaacg agcgcgtgga gcagaacgtt atcggcaatg 10140
aacggcgtcg agcgcgccgc gtagagcagc gccgccgagg ccgacgcgtt gaagatcgcg 10200
cgggccgtgt agtagagcga gaggccgagg ttcgactcaa agcacgcgtt cgggatcgag 10260
tgcttgagct ccgtgagcgt cgggaactcg accttcgtct tatcctcagt catgcggccg 10320
ctgaagtatt gcttcttagt taacctttcc tttctctctc agctatgtga attcattttg 10380

-continued

```
ctttcgtcac aatttatata gtgaaattgg atctttggag ttaacgcctt cacaggatta  10440

tcgtgttaga acaatgcttt ttcatgttct aattagtagt acattacaaa tgtgcactct  10500

attcaataag catcttttgg cacgttaata aatcatgtga aaaaaaaata ctactatttc  10560

aaagaaagtg ttgtaaaaag aaacggaaag agagctggct tcagttgttg agacttgttt  10620

gctagtaaaa atggtgtgaa gagtgattca tggtgaggtg gtttttcgtc cctttctgtt  10680

tgcatgaaaa acaaatggca agagatgacg taggattcct tcccttaacg attatctgtt  10740

tttaatttca aatatacata taggaattta tgaattacta aggttgtaaa atatgctggt  10800

catttattta tggctaaaat attttttttt ctcgtaaata taaaaatatt taaaatttat  10860

ttttatcata tttttatcc ttataaaatt atgtgtacaa cctatataaa aaaatatcat  10920

atttaatatt gattatatgt ttaatcaata taaaaaatca ttatcatata tttagattta  10980

ttcgaatata catctaaaca aaaaataaca tattttaatt ttatgaagaa aaaaaaatat  11040

tttatccttt atttatttaa gattaattaa tagttatgta ttgtggaaag acttttacac  11100

atgcaataga tatactgaat caattagatg ccaatgctga gttggaaatc acttgaggag  11160

gggaggagac ttgccaatgc ttttcagttt catttaaatg atttagtgga ggagatagag  11220

tagtgataaa ggcatgcccc aattttggag tgtatatatg agtggaaata agagagggat  11280

agagagaaaa aataaagaga gtaaaaataa ttaatgtgaa atgatatgat aaaaaaataa  11340

agaaagagat aaagagaaaa atgaaatgag agatagatga aatagagagt agatacatgt  11400

ttgtttaggt ttttttagg aaataacaca tttttttctc atcacttatt actcactgtc  11460

aatttcctct ctttcaatca taatgatatg atttgtttaa caaaaatgtg aaaaaacata  11520

taaagtaaaa tatttttata aattgataaa taaaaattta caaaatttat ttcttattaa  11580

attgaataga aaatgaaaga aaagaaaaga aaaagtatat ataaaatgat atagctttaa  11640

aaagaataaa tttttcatat cagtcttttt ttaataattt agaaatattt aagtatatag  11700

caaaaatata atgtacttta catatgcata aataataatt tgaaaataga actaatagaa  11760

tagagaaaaa agtaatataa taattaacta tatgaaaatt tagaagggac aatattttta  11820

attaagaata taaacaatat ttcttttcat gtaatgaggg acggatgtac ggggccagtg  11880

ttggagtcaa agccaaaata gtcacgggga aattaatgca ctgcatgact attcgaaaaa  11940

attcactagc cttacttaga tgttagatta atagctaggg ggtgcagata attttgaaag  12000

gcatgaaaaa cattaatttg tacattgcaa gcttttgatg acaagctttg caattgttca  12060

cactacctta tgccatttat aaatagagtg attggcatat gaaggaaatc atgagagtcg  12120

aagcgaaaaa caaagcttga gagtgtagga aaaatacagt ttttttggta aaaatacagt  12180

atttgaatag gagcgaaaaa tatcctttca aaatgatcct tttctttttt tttttttttc  12240

ttgttgttct tggtcagtta ttcaaaggaa aagggattga aataaaaact tgcatgtggg  12300

atcgtacgtc gagtcgacct gca                                           12323
```

<210> SEQ ID NO 89
<211> LENGTH: 12456
<212> TYPE: DNA
<213> ORGANISM: Artificial Sequence
<220> FEATURE:
<223> OTHER INFORMATION: Plasmid pKR585
<220> FEATURE:
<221> NAME/KEY: misc_feature
<222> LOCATION: (1201)..(1201)
<223> OTHER INFORMATION: n is a, c, g, or t

<400> SEQUENCE: 89

```
ggatctggcc ggccggatct cgtacgtcct cgaagagaag ggttaataac acatttttta     60
acatttttaa cacaaatttt agttatttaa aaatttatta aaaaatttaa aataagaaga    120
ggaactcttt aaataaatct aacttacaaa atttatgatt tttaataagt tttcaccaat    180
aaaaaatgtc ataaaaatat gttaaaaagt atattatcaa tattctcttt atgataaata    240
aaaagaaaaa aaaaataaaa gttaagtgaa aatgagattg aagtgacttt aggtgtgtat    300
aaatatatca accccgccaa caatttattt aatccaaata tattgaagta tattattcca    360
tagcctttat ttatttatat atttattata taaaagcttt atttgttcta ggttgttcat    420
gaaatatttt tttggtttta tctccgttgt aagaaaatca tgtgctttgt gtcgccactc    480
actattgcag ctttttcatg cattggtcag attgacggtt gattgtattt ttgtttttta    540
tggttttgtg ttatgactta agtcttcatc tctttatctc ttcatcaggt ttgatggtta    600
cctaatatgg tccatgggta catgcatggt taaattaggt ggccaacttt gttgtgaacg    660
atagaatttt ttttatatta agtaaactat ttttatatta tgaaataata ataaaaaaaa    720
tattttatca ttattaacaa aatcatatta gttaatttgt taactctata ataaaagaaa    780
tactgtaaca ttcacattac atggtaacat ctttccaccc tttcatttgt tttttgtttg    840
atgacttttt ttcttgttta aatttatttc ccttctttta aatttggaat acattatcat    900
catatataaa ctaaaatact aaaaacagga ttacacaaat gataaataat aacacaaata    960
tttataaatc tagctgcaat atatttaaac tagctatatc gatattgtaa aataaaacta   1020
gctgcattga tactgataaa aaaatatcat gtgctttctg gactgatgat gcagtatact   1080
tttgacattg cctttatttt atttttcaga aaagctttct tagttctggg ttcttcatta   1140
tttgtttccc atctccattg tgaattgaat catttgcttc gtgtcacaaa tacaatttag   1200
ntaggtacat gcattggtca gattcacggt ttattatgtc atgacttaag ttcatggtag   1260
tacattacct gccacgcatg cattatattg gttagatttg ataggcaaat ttggttgtca   1320
acaatataaa tataaataat gtttttatat tacgaaataa cagtgatcaa aacaaacagt   1380
tttatcttta ttaacaagat tttgtttttg tttgatgacg ttttttaatg tttacgcttt   1440
ccccccttctt ttgaatttag aacactttat catcataaaa tcaaatacta aaaaaattac   1500
atatttcata aataataaca caaatatttt taaaaaatct gaaataataa tgaacaatat   1560
tacatattat cacgaaaatt cattaataaa aatattatat aaataaaatg taatagtagt   1620
tatatgtagg aaaaaagtac tgcacgcata atatatacaa aaagattaaa atgaactatt   1680
ataaataata acactaaatt aatggtgaat catatcaaaa taatgaaaaa gtaaataaaa   1740
tttgtaatta acttctatat gtattacaca cacaaataat aaataatagt aaaaaaaatt   1800
atgataaata tttaccatct cataagatat ttaaaataat gataaaaata tagattattt   1860
tttatgcaac tagctagcca aaaagagaac acgggtatat ataaaaagag tacctttaaa   1920
ttctactgta cttcctttat tcctgacgtt tttatatcaa gtggacatac gtgaagattt   1980
taattatcag tctaaatatt tcattagcac ttaatacttt tctgttttat tcctatccta   2040
taagtagtcc cgattctccc aacattgctt attcacacaa ctaactaaga aagtcttcca   2100
tagcccccca agcggccgca caatggcgac tcgacagcga actgccacca ctgttgtggt   2160
cgaggacctt cccaaggtca ctcttgaggc caagtctgaa cctgtgttcc ccgatatcaa   2220
gaccatcaag gatgccattc ccgcgcactg cttccagccc tcgctcgtca cctcattcta   2280
ctacgtcttc cgcgattttg ccatggtctc tgccctcgtc tgggctgctc tcacctacat   2340
ccccagcatc cccgaccaga ccctccgcgt cgcagcttgg atggtctacg gcttcgtcca   2400
```

-continued

```
gggtctgttc tgcaccggtg tctggattct cggccatgag tgcggccacg gtgctttctc   2460
tctccacgga aaggtcaaca atgtgaccgg ctggttcctc cactcgttcc tcctcgtccc   2520
ctacttcagc tggaagtact ctcaccaccg ccaccaccgc ttcaccggcc acatggatct   2580
cgacatggct ttcgtcccca agactgagcc caagccctcc aagtcgctca tgattgctgg   2640
cattgacgtc gccgagcttg ttgaggacac ccccgctgct cagatggtca agctcatctt   2700
ccaccagctt ttcggatggc aggcgtacct cttcttcaac gctagctctg gcaagggcag   2760
caagcagtgg gagcccaaga ctggcctctc caagtggttc cgagtcagtc acttcgagcc   2820
taccagcgct gtcttccgcc ccaacgaggc catcttcatc ctcatctccg atatcggtct   2880
tgctctaatg ggaactgctc tgtactttgc ttccaagcaa gttggtgttt cgaccattct   2940
cttcctctac cttgttccct acctgtgggt tcaccactgg ctcgttgcca ttacctacct   3000
ccaccaccac cacaccgagc tccctcacta caccgctgag ggctggacct acgtcaaggg   3060
agctctcgcc actgtcgacc gtgagtttgg cttcatcgga aagcacctct tccacggtat   3120
cattgagaag cacgttgttc accatctctt ccctaagatc cccttctaca aggctgacga   3180
ggccaccgag gccatcaagc ccgtcattgg cgaccactac tgccacgacg accgaagctt   3240
cctgggccag ctgtggacca tcttcggcac gctcaagtac gtcgagcacg accctgcccg   3300
acccggtgcc atgcgatgga acaaggacta ggctaggcgg ccgcgacaca agtgtgagag   3360
tactaaataa atgctttggt tgtacgaaat cattacacta aataaaataa tcaaagctta   3420
tatatgcctt ccgctaaggc cgaatgcaaa gaaattggtt ctttctcgtt atcttttgcc   3480
acttttacta gtacgtatta attactactt aatcatcttt gtttacggct cattatatcc   3540
ggtctagagg atccaaggcc gcgaagttaa aagcaatgtt gtcacttgtc gtactaacac   3600
atgatgtgat agtttatgct agctagctat aacataagct gtctctgagt gtgttgtata   3660
ttaataaaga tcatcactgg tgaatggtga tcgtgtacgt accctactta gtaggcaatg   3720
gaagcactta gagtgtgctt tgtgcatggc cttgcctctg ttttgagact tttgtaatgt   3780
tttcgagttt aaatctttgc ctttgcgtac ggatccgtcg acggcgcgcc cgatcatccg   3840
gatatagttc ctcctttcag caaaaaaccc ctcaagaccc gtttagaggc cccaaggggt   3900
tatgctagtt attgctcagc ggtggcagca gccaactcag cttcctttcg ggctttgtta   3960
gcagccggat cgatccaagc tgtacctcac tattcctttg ccctcggacg agtgctgggg   4020
cgtcggtttc cactatcggc gagtacttct acacagccat cggtccagac ggccgcgctt   4080
ctgcgggcga tttgtgtacg cccgacagtc ccggctccgg atcggacgat tgcgtcgcat   4140
cgaccctgcg cccaagctgc atcatcgaaa ttgccgtcaa ccaagctctg atagagttgg   4200
tcaagaccaa tgcggagcat atacgcccgg agccgcggcg atcctgcaag ctccggatgc   4260
ctccgctcga agtagcgcgt ctgctgctcc atacaagcca accacggcct ccagaagaag   4320
atgttggcga cctcgtattg ggaatccccg aacatcgcct cgctccagtc aatgaccgct   4380
gttatgcggc cattgtccgt caggacattg ttggagccga aatccgcgtg cacgaggtgc   4440
cggacttcgg ggcagtcctc ggcccaaagc atcagctcat cgagagcctg cgcgacggac   4500
gcactgacgg tgtcgtccat cacagtttgc cagtgataca catggggatc agcaatcgcg   4560
catatgaaat cacgccatgt agtgtattga ccgattcctt gcggtccgaa tgggccgaac   4620
ccgctcgtct ggctaagatc ggccgcagcg atcgcatcca tagcctccgc gaccggctgc   4680
agaacagcgg gcagttcggt ttcaggcagg tcttgcaacg tgacaccctg tgcacggcgg   4740
gagatgcaat aggtcaggct ctcgctgaat tccccaatgt caagcacttc cggaatcggg   4800
```

agcgcggccg atgcaaagtg ccgataaaca taacgatctt tgtagaaacc atcggcgcag 4860
ctatttaccc gcaggacata tccacgccct cctacatcga agctgaaagc acgagattct 4920
tcgccctccg agagctgcat caggtcggag acgctgtcga acttttcgat cagaaacttc 4980
tcgacagacg tcgcggtgag ttcaggcttt tccatgggta tatctccttc ttaaagttaa 5040
acaaaattat ttctagaggg aaaccgttgt ggtctcccta tagtgagtcg tattaatttc 5100
gcgggatcga gatcgatcca attccaatcc cacaaaaatc tgagcttaac agcacagttg 5160
ctcctctcag agcagaatcg ggtattcaac accctcatat caactactac gttgtgtata 5220
acggtccaca tgccggtata tacgatgact ggggttgtac aaaggcggca acaaacggcg 5280
ttcccggagt tgcacacaag aaatttgcca ctattacaga ggcaagagca gcagctgacg 5340
cgtacacaac aagtcagcaa acagacaggt tgaacttcat ccccaaagga gaagctcaac 5400
tcaagcccaa gagctttgct aaggccctaa caagcccacc aaagcaaaaa gcccactggc 5460
tcacgctagg aaccaaaagg cccagcagtg atccagcccc aaaagagatc tcctttgccc 5520
cggagattac aatggacgat ttcctctatc tttacgatct aggaaggaag ttcgaaggtg 5580
aaggtgacga cactatgttc accactgata atgagaaggt tagcctcttc aatttcagaa 5640
agaatgctga cccacagatg gttagagagg cctacgcagc aggtctcatc aagacgatct 5700
acccgagtaa caatctccag gagatcaaat accttcccaa gaaggttaaa gatgcagtca 5760
aaagattcag gactaattgc atcaagaaca cagagaaaga catatttctc aagatcagaa 5820
gtactattcc agtatggacg attcaaggct tgcttcataa accaaggcaa gtaatagaga 5880
ttggagtctc taaaaaggta gttcctactg aatctaaggc catgcatgga gtctaagatt 5940
caaatcgagg atctaacaga actcgccgtg aagactggcg aacagttcat acagagtctt 6000
ttacgactca atgacaagaa gaaaatcttc gtcaacatgg tggagcacga cactctggtc 6060
tactccaaaa atgtcaaaga tacagtctca gaagaccaaa gggctattga gacttttcaa 6120
caaaggataa tttcgggaaa cctcctcgga ttccattgcc cagctatctg tcacttcatc 6180
gaaaggacag tagaaaagga aggtggctcc tacaaatgcc atcattgcga taaaggaaag 6240
gctatcattc aagatgcctc tgccgacagt ggtcccaaag atggaccccc acccacgagg 6300
agcatcgtgg aaaaagaaga cgttccaacc acgtcttcaa agcaagtgga ttgatgtgac 6360
atctccactg acgtaaggga tgacgcacaa tcccactatc cttcgcaaga cccttcctct 6420
atataaggaa gttcatttca tttggagagg acacgctcga gctcatttct ctattacttc 6480
agccataaca aaagaactct tttctcttct tattaaacca tgaaaaagcc tgaactcacc 6540
gcgacgtctg tcgagaagtt tctgatcgaa aagttcgaca gcgtctccga cctgatgcag 6600
ctctcggagg gcgaagaatc tcgtgctttc agcttcgatg taggagggcg tggatatgtc 6660
ctgcgggtaa atagctgcgc cgatggtttc tacaaagatc gttatgttta tcggcacttt 6720
gcatcggccg cgctcccgat tccggaagtg cttgacattg gggaattcag cgagagcctg 6780
acctattgca tctcccgccg tgcacagggt gtcacgttgc aagacctgcc tgaaaccgaa 6840
ctgcccgctg ttctgcagcc ggtcgcggag gccatggatg cgatcgctgc ggccgatctt 6900
agccagacga gcgggttcgg cccattcgga ccgcaaggaa tcggtcaata cactacatgg 6960
cgtgatttca tatgcgcgat tgctgatccc catgtgtatc actggcaaac tgtgatggac 7020
gacaccgtca gtgcgtccgt cgcgcaggct ctcgatgagc tgatgctttg ggccgaggac 7080
tgccccgaag tccggcacct cgtgcacgcg gatttcggct ccaacaatgt cctgacggac 7140
aatggccgca taacagcggt cattgactgg agcgaggcga tgttcgggga ttcccaatac 7200
gaggtcgcca acatcttctt ctggaggccg tggttggctt gtatggagca gcagacgcgc 7260
tacttcgagc ggaggcatcc ggagcttgca ggatcgccgc ggctccgggc gtatatgctc 7320
cgcattggtc ttgaccaact ctatcagagc ttggttgacg gcaatttcga tgatgcagct 7380
tgggcgcagg gtcgatgcga cgcaatcgtc cgatccggag ccgggactgt cgggcgtaca 7440
caaatcgccc gcagaagcgc ggccgtctgg accgatggct gtgtagaagt actcgccgat 7500
agtggaaacc gacgccccag cactcgtccg agggcaaagg aatagtgagg tacctaaaga 7560
aggagtgcgt cgaagcagat cgttcaaaca tttggcaata aagtttctta agattgaatc 7620
ctgttgccgg tcttgcgatg attatcatat aatttctgtt gaattacgtt aagcatgtaa 7680
taattaacat gtaatgcatg acgttattta tgagatgggt ttttatgatt agagtcccgc 7740
aattatacat ttaatacgcg atagaaaaca aaatatagcg cgcaaactag gataaattat 7800
cgcgcgcggt gtcatctatg ttactagatc gatgtcgaat cgatcaacct gcattaatga 7860
atcggccaac gcgcggggag aggcggtttg cgtattgggc gctcttccgc ttcctcgctc 7920
actgactcgc tgcgctcggt cgttcggctg cggcgagcgg tatcagctca ctcaaaggcg 7980
gtaatacggt tatccacaga atcaggggat aacgcaggaa agaacatgtg agcaaaaggc 8040
cagcaaaagg ccaggaaccg taaaaaggcc gcgttgctgg cgtttttcca taggctccgc 8100
ccccctgacg agcatcacaa aaatcgacgc tcaagtcaga ggtggcgaaa cccgacagga 8160
ctataaagat accaggcgtt tccccctgga agctccctcg tgcgctctcc tgttccgacc 8220
ctgccgctta ccggatacct gtccgccttt ctcccttcgg gaagcgtggc gctttctcaa 8280
tgctcacgct gtaggtatct cagttcggtg taggtcgttc gctccaagct gggctgtgtg 8340
cacgaacccc ccgttcagcc cgaccgctgc gccttatccg gtaactatcg tcttgagtcc 8400
aacccggtaa gacacgactt atcgccactg gcagcagcca ctggtaacag gattagcaga 8460
gcgaggtatg taggcggtgc tacagagttc ttgaagtggt ggcctaacta cggctacact 8520
agaaggacag tatttggtat ctgcgctctg ctgaagccag ttaccttcgg aaaaagagtt 8580
ggtagctctt gatccggcaa acaaaccacc gctggtagcg gtggtttttt tgtttgcaag 8640
cagcagatta cgcgcagaaa aaaaggatct caagaagatc ctttgatctt ttctacgggg 8700
tctgacgctc agtggaacga aaactcacgt taagggattt tggtcatgac attaacctat 8760
aaaaataggc gtatcacgag gccctttcgt ctcgcgcgtt tcggtgatga cggtgaaaac 8820
ctctgacaca tgcagctccc ggagacggtc acagcttgtc tgtaagcgga tgccgggagc 8880
agacaagccc gtcagggcgc gtcagcgggt gttggcgggt gtcggggctg gcttaactat 8940
gcggcatcag agcagattgt actgagagtg caccatatgg acatattgtc gttagaacgc 9000
ggctacaatt aatacataac cttatgtatc atacacatac gatttaggtg acactataga 9060
acggcgcgcc aagcttggat ctcctgcagc ccgggggatc cgcccacgta cggtaccatc 9120
tgctaatatt ttaaatcaca tgcaagagag gaggcatggt tccattttct accttcacat 9180
tatttgagaa aaacgaactt gttctgtgtt ttatttttgc ccttcacatt agtacaacgt 9240
ggaagactca tggttacaca gaatcataca taagtacaat gcttgtccct aagaaaacaa 9300
gcactcgttg tattgaacct ttacggctca tgcggccgcg aattcactag tgattgaatt 9360
cgcggccgct tagtccgact tggccttggc ggccgcggcc gactctttga gcgtgaagat 9420
ctgcgccgtc tcgggcacag cgccgtagtt gacaaagagg tgcgcggtct tgaagaaggc 9480
cgtgatgatg ggctcgtcgt tcctgcgcac gaggtgcggg tacgcggccg caaagtgctt 9540
ggtggcttcg ttgagcttgt agtgcggaat gatcgggaac aagtggtgga cctggtgcgt 9600

```
gccaatgtgg tggctcaggt tgtccacgaa cgcgccgtac gagcggtcga cgctcgagag   9660
gttgcccttg acgtacgtcc actccgagtc gccgtaccac ggcgtcgctt cgtcgttgtg   9720
gtgcaagaag gtcgtaatga cgaggaacga agcaaagaca aagagcggcg catagtagta   9780
gaggcccatg acggcaaagc cgagcgagta tgtgaggtac gcgtacgcgg cgaagaaggc   9840
ggcccagacg ccgagcgaca cgatgacggc cgacgcgcgg cgaaggagga gcgggtccca   9900
cgggtcaaag tggctcatcg tgcgcggggc atacccgacc ttcaagtaga caaaccacgc   9960
accgccgagc gtgtagaccc attggcgcac gtcctggagg tccttgaccg accggtgcgg  10020
gtaaaagatc tcgtccttat caatgttgcc cgtgttcttg tggtggtggc ggtgcgtcac  10080
gcgccagctc tcgaacggcg tcaaaatcgc agagtgcatg atgcagccga tgataaagtt  10140
gacgctgtgg tagcgcgaga aggccgagtg gccgcagtcg tggccgaccg tgaagaagcc  10200
ccagaagatg acgccctgca cgtagatgta ggtggcgcaa acgagcgcgt ggagcagaac  10260
gttatcggca atgaacggcg tcgagcgcgc cgcgtagagc agcgccgccg aggccgacgc  10320
gttgaagatc gcgcgggccg tgtagtagag cgagaggccg aggttcgact caaagcacgc  10380
gttcgggatc gagtgcttga gctccgtgag cgtcgggaac tcgaccttcg tcttatcctc  10440
agtcatgcgg ccgctgaagt attgcttctt agttaacctt tcctttctct ctcagctatg  10500
tgaattcatt ttgctttcgt cacaatttat atagtgaaat tggatctttg gagttaacgc  10560
cttcacagga ttatcgtgtt agaacaatgc tttttcatgt tctaattagt agtacattac  10620
aaatgtgcac tctattcaat aagcatcttt tggcacgtta ataaatcatg tgaaaaaaaa  10680
atactactat ttcaaagaaa gtgttgtaaa aagaaacgga aagagagctg gcttcagttg  10740
ttgagacttg tttgctagta aaaatggtgt gaagagtgat tcatggtgag gtggtttttc  10800
gtccctttct gtttgcatga aaaacaaatg gcaagagatg acgtaggatt ccttccctta  10860
acgattatct gtttttaatt tcaaatatac atataggaat ttatgaatta ctaaggttgt  10920
aaaatatgct ggtcatttat ttatggctaa aatatttttt tttctcgtaa atataaaaat  10980
atttaaaatt tatttttatc atattttta tccttataaa attatgtgta caacctatat  11040
aaaaaaatat catatttaat attgattata tgtttaatca atataaaaaa tcattatcat  11100
atatttagat ttattcgaat atacatctaa acaaaaaata acatatttta attttatgaa  11160
gaaaaaaaaa tattttatcc tttatttatt taagattaat taatagttat gtattgtgga  11220
aagactttta cacatgcaat agatatactg aatcaattag atgccaatgc tgagttggaa  11280
atcacttgag gaggggagga gacttgccaa tgcttttcag tttcatttaa atgatttagt  11340
ggaggagata gagtagtgat aaaggcatgc cccaattttg gagtgtatat atgagtggaa  11400
ataagagagg gatagagaga aaaaataaag agagtaaaaa taattaatgt gaaatgatat  11460
gataaaaaaa taaagaaaga gataaagaga aaaatgaaat gagagataga tgaaatagag  11520
agtagataca tgtttgttta ggtttttttt aggaaataac acattttttt ctcatcactt  11580
attactcact gtcaatttcc tctctttcaa tcataatgat atgatttgtt taacaaaaat  11640
gtgaaaaaac atataaagta aaatattttt ataaattgat aaataaaaat ttacaaaatt  11700
tatttcttat taaattgaat agaaaatgaa agaaaagaaa agaaaaagta tatataaaat  11760
gatatagctt taaaaagaat aaatttttca tatcagtctt tttttaataa tttagaaata  11820
tttaagtata tagcaaaaat ataatgtact ttacatatgc ataaataata atttgaaaat  11880
agaactaata gaatagagaa aaaagtaata taataattaa ctatatgaaa atttagaagg  11940
gacaatattt ttaattaaga atataaacaa tatttctttt catgtaatga gggacggatg  12000
```

tacggggcca gtgttggagt caaagccaaa atagtcacgg ggaaattaat gcactgcatg 12060
actattcgaa aaaattcact agccttactt agatgttaga ttaatagcta gggggtgcag 12120
ataattttga aaggcatgaa aaacattaat ttgtacattg caagcttttg atgacaagct 12180
ttgcaattgt tcacactacc ttatgccatt tataaataga gtgattggca tatgaaggaa 12240
atcatgagag tcgaagcgaa aaacaaagct tgagagtgta ggaaaaaatac agttttttttg 12300 gtaaaaatac agtatttgaa taggagcgaa aaatatcctt tcaaaatgat ccttttcttt 12360
tttttttttt ttcttgttgt tcttggtcag ttattcaaag gaaaagggat tgaaataaaa 12420
acttgcatgt gggatcgtac gtcgagtcga cctgca 12456

<210> SEQ ID NO 90
<211> LENGTH: 9088
<212> TYPE: DNA
<213> ORGANISM: Artificial Sequence
<220> FEATURE:
<223> OTHER INFORMATION: Plasmid pKR578
<220> FEATURE:
<221> NAME/KEY: misc_feature
<222> LOCATION: (6951)..(6951)
<223> OTHER INFORMATION: n is a, c, g, or t

<400> SEQUENCE: 90
ggccgcgaca caagtgtgag agtactaaat aaatgctttg gttgtacgaa atcattacac 60
taaataaaat aatcaaagct tatatatgcc ttccgctaag gccgaatgca aagaaattgg 120
ttctttctcg ttatcttttg ccacttttac tagtacgtat taattactac ttaatcatct 180
ttgtttacgg ctcattatat ccggtctaga ggatccaagg ccgcgaagtt aaaagcaatg 240
ttgtcacttg tcgtactaac acatgatgtg atagtttatg ctagctagct ataacataag 300
ctgtctctga gtgtgttgta tattaataaa gatcatcact ggtgaatggt gatcgtgtac 360
gtaccctact tagtaggcaa tggaagcact tagagtgtgc tttgtgcatg gccttgcctc 420
tgttttgaga cttttgtaat gttttcgagt ttaaatcttt gcctttgcgt acggatccgt 480
cgacggcgcg cccgatcatc cggatatagt tcctcctttc agcaaaaaac ccctcaagac 540
ccgtttagag gccccaaggg gttatgctag ttattgctca gcggtggcag cagccaactc 600
agcttccttt cgggctttgt tagcagccgg atcgatccaa gctgtacctc actattcctt 660
tgccctcgga cgagtgctgg ggcgtcggtt tccactatcg gcgagtactt ctacacagcc 720
atcggtccag acggccgcgc ttctgcgggc gatttgtgta cgcccgacag tcccggctcc 780
ggatcggacg attgcgtcgc atcgaccctg cgcccaagct gcatcatcga aattgccgtc 840
aaccaagctc tgatagagtt ggtcaagacc aatgcggagc atatacgccc ggagccgcgg 900
cgatcctgca agctccggat gcctccgctc gaagtagcgc gtctgctgct ccatacaagc 960
caaccacggc ctccagaaga agatgttggc gacctcgtat tgggaatccc cgaacatcgc 1020
ctcgctccag tcaatgaccg ctgttatgcg gccattgtcc gtcaggacat tgttggagcc 1080
gaaatccgcg tgcacgaggt gccggacttc ggggcagtcc tcggcccaaa gcatcagctc 1140
atcgagagcc tgcgcgacgg acgcactgac ggtgtcgtcc atcacagttt gccagtgata 1200
cacatgggga tcagcaatcg cgcatatgaa atcacgccat gtagtgtatt gaccgattcc 1260
ttgcggtccg aatgggccga acccgctcgt ctggctaaga tcggccgcag cgatcgcatc 1320
catagcctcc gcgaccggct gcagaacagc gggcagttcg gtttcaggca ggtcttgcaa 1380
cgtgacaccc tgtgcacggc gggagatgca ataggtcagg ctctcgctga attccccaat 1440
gtcaagcact tccggaatcg ggagcgcggc cgatgcaaag tgccgataaa cataacgatc 1500

-continued

```
tttgtagaaa ccatcggcgc agctatttac ccgcaggaca tatccacgcc ctcctacatc   1560
gaagctgaaa gcacgagatt cttcgccctc cgagagctgc atcaggtcgg agacgctgtc   1620
gaacttttcg atcagaaact tctcgacaga cgtcgcggtg agttcaggct tttccatggg   1680
tatatctcct tcttaaagtt aaacaaaatt atttctagag ggaaaccgtt gtggtctccc   1740
tatagtgagt cgtattaatt tcgcgggatc gagatcgatc caattccaat cccacaaaaa   1800
tctgagctta acagcacagt tgctcctctc agagcagaat cgggtattca acaccctcat   1860
atcaactact acgttgtgta taacggtcca catgccggta tatacgatga ctggggttgt   1920
acaaaggcgg caacaaacgg cgttcccgga gttgcacaca agaaatttgc cactattaca   1980
gaggcaagag cagcagctga cgcgtacaca acaagtcagc aaacagacag gttgaacttc   2040
atccccaaag gagaagctca actcaagccc aagagctttg ctaaggccct aacaagccca   2100
ccaaagcaaa aagcccactg gctcacgcta ggaaccaaaa ggcccagcag tgatccagcc   2160
ccaaaagaga tctcctttgc cccggagatt acaatggacg atttcctcta tctttacgat   2220
ctaggaagga agttcgaagg tgaaggtgac gacactatgt tcaccactga taatgagaag   2280
gttagcctct tcaatttcag aaagaatgct gacccacaga tggttagaga ggcctacgca   2340
gcaggtctca tcaagacgat ctacccgagt aacaatctcc aggagatcaa ataccttccc   2400
aagaaggtta aagatgcagt caaaagattc aggactaatt gcatcaagaa cacagagaaa   2460
gacatatttc tcaagatcag aagtactatt ccagtatgga cgattcaagg cttgcttcat   2520
aaaccaaggc aagtaataga gattggagtc tctaaaaagg tagttcctac tgaatctaag   2580
gccatgcatg gagtctaaga ttcaaatcga ggatctaaca gaactcgccg tgaagactgg   2640
cgaacagttc atacagagtc ttttacgact caatgacaag aagaaaatct tcgtcaacat   2700
ggtggagcac gacactctgg tctactccaa aaatgtcaaa gatacagtct cagaagacca   2760
aagggctatt gagacttttc aacaaaggat aatttcggga aacctcctcg gattccattg   2820
cccagctatc tgtcacttca tcgaaaggac agtagaaaag gaaggtggct cctacaaatg   2880
ccatcattgc gataaaggaa aggctatcat tcaagatgcc tctgccgaca gtggtcccaa   2940
agatggaccc ccacccacga ggagcatcgt ggaaaaagaa gacgttccaa ccacgtcttc   3000
aaagcaagtg gattgatgtg acatctccac tgacgtaagg gatgacgcac aatcccacta   3060
tccttcgcaa gacccttcct ctatataagg aagttcattt catttggaga ggacacgctc   3120
gagctcattt ctctattact tcagccataa caaaagaact cttttctctt cttattaaac   3180
catgaaaaag cctgaactca ccgcgacgtc tgtcgagaag tttctgatcg aaaagttcga   3240
cagcgtctcc gacctgatgc agctctcgga gggcgaagaa tctcgtgctt tcagcttcga   3300
tgtaggaggg cgtggatatg tcctgcgggt aaatagctgc gccgatggtt tctacaaaga   3360
tcgttatgtt tatcggcact ttgcatcggc cgcgctcccg attccggaag tgcttgacat   3420
tggggaattc agcgagagcc tgacctattg catctcccgc cgtgcacagg gtgtcacgtt   3480
gcaagacctg cctgaaaccg aactgcccgc tgttctgcag ccggtcgcgg aggccatgga   3540
tgcgatcgct gcggccgatc ttagccagac gagcgggttc ggcccattcg gaccgcaagg   3600
aatcggtcaa tacactacat ggcgtgattt catatgcgcg attgctgatc cccatgtgta   3660
tcactggcaa actgtgatgg acgacaccgt cagtgcgtcc gtcgcgcagg ctctcgatga   3720
gctgatgctt tgggccgagg actgccccga agtccggcac ctcgtgcacg cggatttcgg   3780
ctccaacaat gtcctgacgg acaatggccg cataacagcg gtcattgact ggagcgaggc   3840
gatgttcggg gattcccaat acgaggtcgc caacatcttc ttctggaggc cgtggttggc   3900
```

-continued

```
ttgtatggag cagcagacgc gctacttcga gcggaggcat ccggagcttg caggatcgcc   3960
gcggctccgg gcgtatatgc tccgcattgg tcttgaccaa ctctatcaga gcttggttga   4020
cggcaatttc gatgatgcag cttgggcgca gggtcgatgc gacgcaatcg tccgatccgg   4080
agccgggact gtcgggcgta cacaaatcgc ccgcagaagc gcggccgtct ggaccgatgg   4140
ctgtgtagaa gtactcgccg atagtggaaa ccgacgcccc agcactcgtc cgagggcaaa   4200
ggaatagtga ggtacctaaa gaaggagtgc gtcgaagcag atcgttcaaa catttggcaa   4260
taaagtttct taagattgaa tcctgttgcc ggtcttgcga tgattatcat ataatttctg   4320
ttgaattacg ttaagcatgt aataattaac atgtaatgca tgacgttatt tatgagatgg   4380
gtttttatga ttagagtccc gcaattatac atttaatacg cgatagaaaa caaaatatag   4440
cgcgcaaact aggataaatt atcgcgcgcg gtgtcatcta tgttactaga tcgatgtcga   4500
atcgatcaac ctgcattaat gaatcggcca acgcgcgggg agaggcggtt tgcgtattgg   4560
gcgctcttcc gcttcctcgc tcactgactc gctgcgctcg gtcgttcggc tgcggcgagc   4620
ggtatcagct cactcaaagg cggtaatacg gttatccaca gaatcagggg ataacgcagg   4680
aaagaacatg tgagcaaaag gccagcaaaa ggccaggaac cgtaaaaagg ccgcgttgct   4740
ggcgtttttc cataggctcc gcccccctga cgagcatcac aaaaatcgac gctcaagtca   4800
gaggtggcga aacccgacag gactataaag ataccaggcg tttccccctg gaagctccct   4860
cgtgcgctct cctgttccga ccctgccgct taccggatac ctgtccgcct ttctcccttc   4920
gggaagcgtg gcgctttctc aatgctcacg ctgtaggtat ctcagttcgg tgtaggtcgt   4980
tcgctccaag ctgggctgtg tgcacgaacc ccccgttcag cccgaccgct gcgccttatc   5040
cggtaactat cgtcttgagt ccaacccggt aagacacgac ttatcgccac tggcagcagc   5100
cactggtaac aggattagca gagcgaggta tgtaggcggt gctacagagt tcttgaagtg   5160
gtggcctaac tacggctaca ctagaaggac agtatttggt atctgcgctc tgctgaagcc   5220
agttaccttc ggaaaaagag ttggtagctc ttgatccggc aaacaaacca ccgctggtag   5280
cggtggtttt tttgtttgca agcagcagat tacgcgcaga aaaaaaggat ctcaagaaga   5340
tcctttgatc ttttctacgg ggtctgacgc tcagtggaac gaaaactcac gttaagggat   5400
tttggtcatg acattaacct ataaaaatag gcgtatcacg aggccctttc gtctcgcgcg   5460
tttcggtgat gacggtgaaa acctctgaca catgcagctc ccggagacgg tcacagcttg   5520
tctgtaagcg gatgccggga gcagacaagc ccgtcagggc gcgtcagcgg gtgttggcgg   5580
gtgtcggggc tggcttaact atgcggcatc agagcagatt gtactgagag tgcaccatat   5640
ggacatattg tcgttagaac gcggctacaa ttaatacata accttatgta tcatacacat   5700
acgatttagg tgacactata gaacggcgcg ccaagcttgg atctcctgca ggatctggcc   5760
ggccggatct cgtacgtcct cgaagagaag ggttaataac acatttttta acatttttaa   5820
cacaaatttt agttatttaa aaatttatta aaaaatttaa aataagaaga ggaactcttt   5880
aaataaatct aacttacaaa atttatgatt tttaataagt tttcaccaat aaaaaatgtc   5940
ataaaaatat gttaaaaagt atattatcaa tattctcttt atgataaata aaaagaaaaa   6000
aaaaataaaa gttaagtgaa aatgagattg aagtgacttt aggtgtgtat aaatatatca   6060
accccgccaa caatttattt aatccaaata tattgaagta tattattcca tagcctttat   6120
ttatttatat atttattata taaaagcttt atttgttcta ggttgttcat gaaatatttt   6180
tttggtttta tctccgttgt aagaaaatca tgtgctttgt gtcgccactc actattgcag   6240
ctttttcatg cattggtcag attgacggtt gattgtattt ttgtttttta tggttttgtg   6300
```

```
ttatgactta agtcttcatc tctttatctc ttcatcaggt ttgatggtta cctaatatgg   6360
tccatgggta catgcatggt taaattaggt ggccaacttt gttgtgaacg atagaatttt   6420
ttttatatta agtaaactat ttttatatta tgaaataata ataaaaaaaa tattttatca   6480
ttattaacaa aatcatatta gttaatttgt taactctata ataaaagaaa tactgtaaca   6540
ttcacattac atggtaacat ctttccaccc tttcatttgt tttttgtttg atgacttttt   6600
ttcttgttta aatttatttc ccttctttta aatttggaat acattatcat catatataaa   6660
ctaaaatact aaaaacagga ttacacaaat gataaataat aacacaaata tttataaatc   6720
tagctgcaat atatttaaac tagctatatc gatattgtaa aataaaacta gctgcattga   6780
tactgataaa aaaatatcat gtgctttctg gactgatgat gcagtatact tttgacattg   6840
cctttatttt atttttcaga aaagctttct tagttctggg ttcttcatta tttgtttccc   6900
atctccattg tgaattgaat catttgcttc gtgtcacaaa tacaatttag ntaggtacat   6960
gcattggtca gattcacggt ttattatgtc atgacttaag ttcatggtag tacattacct   7020
gccacgcatg cattatattg gttagatttg ataggcaaat ttggttgtca acaatataaa   7080
tataaataat gtttttatat tacgaaataa cagtgatcaa aacaaacagt tttatcttta   7140
ttaacaagat tttgtttttg tttgatgacg ttttttaatg tttacgcttt ccccccttctt   7200
ttgaatttag aacactttat catcataaaa tcaaatacta aaaaaattac atatttcata   7260
aataataaca caaatatttt taaaaaatct gaaataataa tgaacaatat tacatattat   7320
cacgaaaatt cattaataaa aatattatat aaataaaatg taatagtagt tatatgtagg   7380
aaaaaagtac tgcacgcata atatatacaa aaagattaaa atgaactatt ataaataata   7440
acactaaatt aatggtgaat catatcaaaa taatgaaaaa gtaaataaaa tttgtaatta   7500
acttctatat gtattacaca cacaaataat aaataatagt aaaaaaaatt atgataaata   7560
tttaccatct cataagatat ttaaaataat gataaaaata tagattattt tttatgcaac   7620
tagctagcca aaaagagaac acgggtatat ataaaaagag tacctttaaa ttctactgta   7680
cttcctttat tcctgacgtt tttatatcaa gtggacatac gtgaagattt taattatcag   7740
tctaaatatt tcattagcac ttaatacttt tctgttttat tcctatccta taagtagtcc   7800
cgattctccc aacattgctt attcacacaa ctaactaaga aagtcttcca tagcccccca   7860
agcggccgca caatggcgac tcgacagcga actgccacca ctgttgtggt cgaggacctt   7920
cccaaggtca ctcttgaggc caagtctgaa cctgtgttcc ccgatatcaa gaccatcaag   7980
gatgccattc ccgcgcactg cttccagccc tcgctcgtca cctcattcta ctacgtcttc   8040
cgcgattttg ccatggtctc tgccctcgtc tgggctgctc tcacctacat ccccagcatc   8100
cccgaccaga ccctccgcgt cgcagcttgg atggtctacg gcttcgtcca gggtctgttc   8160
tgcaccggtg tctggattct cggccatgag tgcggccacg gtgctttctc tctccacgga   8220
aaggtcaaca atgtgaccgg ctggttcctc cactcgttcc tcctcgtccc ctacttcagc   8280
tggaagtact ctcaccaccg ccaccaccgc ttcaccggcc acatggatct cgacatggct   8340
ttcgtcccca agactgagcc caagccctcc aagtcgctca tgattgctgg cattgacgtc   8400
gccgagcttg ttgaggacac ccccgctgct cagatggtca agctcatctt ccaccagctt   8460
ttcggatggc aggcgtacct cttcttcaac gctagctctg gcaagggcag caagcagtgg   8520
gagcccaaga ctggcctctc caagtggttc cgagtcagtc acttcgagcc taccagcgct   8580
gtcttccgcc ccaacgaggc catcttcatc ctcatctccg atatcggtct tgctctaatg   8640
ggaactgctc tgtactttgc ttccaagcaa gttggtgttt cgaccattct cttcctctac   8700
```

-continued cttgttccct acctgtgggt tcaccactgg ctcgttgcca ttacctacct ccaccaccac 8760
cacaccgagc tccctcacta caccgctgag ggctggacct acgtcaaggg agctctcgcc 8820
actgtcgacc gtgagtttgg cttcatcgga aagcacctct tccacggtat cattgagaag 8880
cacgttgttc accatctctt ccctaagatc cccttctaca aggctgacga ggccaccgag 8940
gccatcaagc ccgtcattgg cgaccactac tgccacgacg accgaagctt cctgggccag 9000
ctgtggacca tcttcggcac gctcaagtac gtcgagcacg accctgcccg acccggtgcc 9060
atgcgatgga acaaggacta ggctaggc 9088

<210> SEQ ID NO 91
<211> LENGTH: 10309
<212> TYPE: DNA
<213> ORGANISM: Artificial Sequence
<220> FEATURE:
<223> OTHER INFORMATION: Plasmid pKR667
<220> FEATURE:
<221> NAME/KEY: misc_feature
<222> LOCATION: (7704)..(7704)
<223> OTHER INFORMATION: n is a, c, g, or t

<400> SEQUENCE: 91
gtacgtctag aggatccgtc gacggcgcgc ccgatcatcc ggatatagtt cctcctttca 60
gcaaaaaacc cctcaagacc cgtttagagg ccccaagggg ttatgctagt tattgctcag 120
cggtggcagc agccaactca gcttcctttc gggctttgtt agcagccgga tcgatccaag 180
ctgtacctca ctattccttt gccctcggac gagtgctggg gcgtcggttt ccactatcgg 240
cgagtacttc tacacagcca tcggtccaga cggccgcgct tctgcgggcg atttgtgtac 300
gcccgacagt cccggctccg gatcggacga ttgcgtcgca tcgaccctgc gcccaagctg 360
catcatcgaa attgccgtca accaagctct gatagagttg gtcaagacca atgcggagca 420
tatacgcccg gagccgcggc gatcctgcaa gctccggatg cctccgctcg aagtagcgcg 480
tctgctgctc catacaagcc aaccacggcc tccagaagaa gatgttggcg acctcgtatt 540
gggaatcccc gaacatcgcc tcgctccagt caatgaccgc tgttatgcgg ccattgtccg 600
tcaggacatt gttggagccg aaatccgcgt gcacgaggtg ccggacttcg gggcagtcct 660
cggcccaaag catcagctca tcgagagcct gcgcgacgga cgcactgacg gtgtcgtcca 720
tcacagtttg ccagtgatac acatggggat cagcaatcgc gcatatgaaa tcacgccatg 780
tagtgtattg accgattcct tgcggtccga atgggccgaa cccgctcgtc tggctaagat 840
cggccgcagc gatcgcatcc atagcctccg cgaccggctg cagaacagcg ggcagttcgg 900
tttcaggcag gtcttgcaac gtgacaccct gtgcacggcg ggagatgcaa taggtcaggc 960
tctcgctgaa ttccccaatg tcaagcactt ccggaatcgg gagcgcggcc gatgcaaagt 1020
gccgataaac ataacgatct ttgtagaaac catcggcgca gctatttacc cgcaggacat 1080
atccacgccc tcctacatcg aagctgaaag cacgagattc ttcgccctcc gagagctgca 1140
tcaggtcgga gacgctgtcg aacttttcga tcagaaactt ctcgacagac gtcgcggtga 1200
gttcaggctt ttccatgggt atatctcctt cttaaagtta aacaaaatta tttctagagg 1260
gaaaccgttg tggtctccct atagtgagtc gtattaattt cgcgggatcg agatctgatc 1320
aacctgcatt aatgaatcgg ccaacgcgcg gggagaggcg gtttgcgtat tgggcgctct 1380
tccgcttcct cgctcactga ctcgctgcgc tcggtcgttc ggctgcggcg agcggtatca 1440
gctcactcaa aggcggtaat acggttatcc acagaatcag gggataacgc aggaaagaac 1500
atgtgagcaa aaggccagca aaaggccagg aaccgtaaaa aggccgcgtt gctggcgttt 1560
ttccataggc tccgcccccc tgacgagcat cacaaaaatc gacgctcaag tcagaggtgg 1620
cgaaacccga caggactata aagataccag gcgtttcccc ctggaagctc cctcgtgcgc 1680
tctcctgttc cgaccctgcc gcttaccgga tacctgtccg cctttctccc ttcgggaagc 1740
gtggcgcttt ctcaatgctc acgctgtagg tatctcagtt cggtgtaggt cgttcgctcc 1800
aagctgggct gtgtgcacga accccccgtt cagcccgacc gctgcgcctt atccggtaac 1860
tatcgtcttg agtccaaccc ggtaagacac gacttatcgc cactggcagc agccactggt 1920
aacaggatta gcagagcgag gtatgtaggc ggtgctacag agttcttgaa gtggtggcct 1980
aactacggct acactagaag gacagtattt ggtatctgcg ctctgctgaa gccagttacc 2040
ttcggaaaaa gagttggtag ctcttgatcc ggcaaacaaa ccaccgctgg tagcggtggt 2100 tttttgttt gcaagcagca gattacgcgc agaaaaaaag gatctcaaga agatcctttg 2160
atcttttcta cggggtctga cgctcagtgg aacgaaaact cacgttaagg gattttggtc 2220
atgacattaa cctataaaaa taggcgtatc acgaggccct ttcgtctcgc gcgtttcggt 2280
gatgacggtg aaaacctctg acacatgcag ctcccggaga cggtcacagc ttgtctgtaa 2340
gcggatgccg ggagcagaca agcccgtcag ggcgcgtcag cgggtgttgg cgggtgtcgg 2400
ggctggctta actatgcggc atcagagcag attgtactga gagtgcacca tatggacata 2460
ttgtcgttag aacgcggcta caattaatac ataaccttat gtatcataca catacgattt 2520
aggtgacact atagaacggc gcgccaagct gggtctagaa ctagaaacgt gatgccactt 2580
gttattgaag tcgattacag catctattct gttttactat ttataacttt gccatttctg 2640
acttttgaaa actatctctg gatttcggta tcgctttgtg aagatcgagc aaaagagacg 2700
ttttgtggac gcaatggtcc aaatccgttc tacatgaaca aattggtcac aatttccact 2760
aaaagtaaat aaatggcaag ttaaaaaagg aatatgcatt ttactgattg cctaggtgag 2820
ctccaagaga agttgaatct acacgtctac caaccgctaa aaaaagaaaa acattgatat 2880
gtaacctgat tccattagct tttgacttct tcaacagatt ctctacttag atttctaaca 2940
gaaatattat tactagcaca tcattttcag tctcactaca gcaaaaaatc caacggcaca 3000
atacagacaa caggagatat cagactacag agatagatag atgctactgc atgtagtaag 3060
ttaaataaaa ggaaaataaa atgtcttgct accaaaacta ctacagacta tgatgctcac 3120
cacaggccaa atcctgcaac taggacagca ttatcttata tatattgtac aaaacaagca 3180
tcaaggaaca tttggtctag gcaatcagta cctcgttcta ccatcaccct cagttatcac 3240
atccttgaag gatccattac tgggaatcat cggcaacaca tgctcctgat ggggcacaat 3300
gacatcaaga aggtaggggc caggggtgtc caacattctc tgaattgccg ctctaagctc 3360
ttccttcttc gtcactcgcg ctgccggtat cccacaagca tcagcaaact tgagcatgtt 3420
tgggaatatc tcgctctcgc tagacggatc tccaagatag gtgtgagctc tattggactt 3480
gtagaaccta tcctccaact gaaccaccat acccaaatgc tgattgttca acaacaatat 3540
cttaactggg agattctcca ctcttatagt ggccaactcc tgaacattca tgatgaaact 3600
accatcccca tcaatgtcaa ccacaacagc cccagggtta gcaacagcag caccaatagc 3660
cgcaggcaat ccaaaaccca tggctccaag accccctgag gtcaaccact gcctcggtct 3720
cttgtacttg taaaactgcg cagcccacat ttgatgctgc ccaaccccag tactaacaat 3780
agcatctcca ttagtcaact catcaagaac ctcgatagca tgctgcggag aaatcgcgtc 3840
ctggaatgtc ttgtaaccca atggaaactt gtgtttctgc acattaatct cttctctcca 3900
acctccaaga tcaaacttac cctccactcc tttctcctcc aaaatcatat taattccctt 3960

-continued

```
caaggccaac ttcaaatccg cgcaaaccga cacgtgcgcc tgcttgttct tcccaatctc   4020
ggcagaatca atatcaatgt gaacaatctt agccctacta gcaaaagcct caagcttccc   4080
agtaacacgg tcatcaaacc ttaccccaaa ggcaagcaac aaatcactat tgtcaacagc   4140
atagttagca taaacagtac catgcatacc cagcatctga agggaatatt catcaccaat   4200
aggaaaagtt ccaagaccca ttaaagtgct agcaacggga ataccagtga gttcaacaaa   4260
gcgcctcaat tcagcactgg aattcaaact gccaccgccg acgtagagaa cgggcttttg   4320
ggcctccatg atgagtctga caatgtgttc caattgggcc tcggcggggg gcctgggcag   4380
cctggcgagg taaccgggga ggttaacggg ctcgtcccaa ttaggcacgg cgagttgctg   4440
ctgaacgtct ttgggaatgt cgatgaggac cggaccgggg cggccggagg tggcgacgaa   4500
gaaagcctcg gcgacgacgc gggggatgtc gtcgacgtcg aggatgaggt agttgtgctt   4560
cgtgatggat ctgctcacct ccacgatcgg ggtttcttgg aaggcgtcgg tgccgatcat   4620
ccggcgggcg acctggccgg tgatggcgac gactgggacg ctgtccatta aagcgtcggc   4680
gaggccgctc acgaggttgg tggcgccggg gccggaggtg gcaatgcaga cgccggggag   4740
gccggaggaa cgcgcgtagc cttcggcggc gaagacgccg ccctgctcgt ggcgcgggag   4800
cacgttgcgg atggcggcgg agcgcgtgag cgcctggtgg atctccatcg acgcaccgcc   4860
ggggtacgcg aacaccgtcg tcacgccctg cctctccagc gcctccacaa ggatgtccgc   4920
gcccttgcga ggttcgccgg aggcgaaccg tgacacgaag ggctccgtgg tcggcgcttc   4980
cttggtgaag ggcgccgccg tggggggttt ggagatggaa catttgattt tgagagcgtg   5040
gttgggtttg gtgagggttt gatgagagag agggagggtg gatctagtaa tgcgtttggg   5100
gaaggtgggg tgtgaagagg aagaagagaa tcgggtggtt ctggaagcgg tggccgccat   5160
tgtgttgtgt ggcatggtta tacttcaaaa actgcacaac aagcctagag ttagtaccta   5220
aacagtaaat ttacaacaga gagcaaagac acatgcaaaa atttcagcca taaaaaaagt   5280
tataatagaa tttaaagcaa aagtttcatt ttttaaacat atatacaaac aaactggatt   5340
tgaaggaagg gattaattcc cctgctcaaa gtttgaattc ctattgtgac ctatactcga   5400
ataaaattga agcctaagga atgtatgaga aacaagaaaa caaaacaaaa ctacagacaa   5460
acaagtacaa ttacaaaatt cgctaaaatt ctgtaatcac caaaccccat ctcagtcagc   5520
acaaggccca aggtttattt tgaaataaaa aaaaagtgat tttatttctc ataagctaaa   5580
agaaagaaag gcaattatga aatgatttcg actagatctg aaagtccaac gcgtattccg   5640
cagatattaa agaaagagta gagtttcaca tggatcctag atggacccag ttgaggaaaa   5700
agcaaggcaa agcaaaccag aagtgcaaga tccgaaattg aaccacggaa tctaggattt   5760
ggtagaggga gaagaaaagt accttgagag gtagaagaga agagaagagc agagagatat   5820
atgaacgagt gtgtcttggt ctcaactctg aagcgatacg agtttagagg ggagcattga   5880
gttccaattt atagggaaac cgggtggcag gggtgagtta atgacggaaa agcccctaag   5940
taacgagatt ggattgtggg ttagattcaa ccgtttgcat ccgcggctta gattggggaa   6000
gtcagagtga atctcaaccg ttgactgagt tgaaaattga atgtagcaac caattgagcc   6060
aaccccagcc tttgcccttt gattttgatt tgtttgttgc atacttttta tttgtcttct   6120
ggttctgact ctctttctct cgtttcaatg ccaggttgcc tactcccaca ccactcacaa   6180
gaagattcta ctgttagtat taaatatttt ttaatgtatt aaatgatgaa tgcttttgta   6240
aacagaacaa gactatgtct aataagtgtc ttgcaacatt ttttaagaaa ttaaaaaaaa   6300
tatatttatt atcaaaatca aatgtatgaa aaatcatgaa taatataatt ttatacattt   6360
```

-continued

```
ttttaaaaaa tcttttaatt tcttaattaa tatcttaaaa ataatgatta atatttaacc   6420
caaaataatt agtatgattg gtaaggaaga tatccatgtt atgtttggat gtgagtttga   6480
tctagagcaa agcttactag agtcgacctg caggtcgact cgacgtacgt cctcgaagag   6540
aagggttaat aacacatttt ttaacatttt taacacaaat tttagttatt taaaaattta   6600
ttaaaaaatt taaaataaga agaggaactc tttaaataaa tctaacttac aaaatttatg   6660
atttttaata agttttcacc aataaaaaat gtcataaaaa tatgttaaaa agtatattat   6720
caatattctc tttatgataa ataaaaagaa aaaaaaaata aaagttaagt gaaaatgaga   6780
ttgaagtgac tttaggtgtg tataaatata tcaaccccgc caacaattta tttaatccaa   6840
atatattgaa gtatattatt ccatagcctt tatttattta tatatttatt atataaaagc   6900
tttatttgtt ctaggttgtt catgaaatat ttttttggtt ttatctccgt tgtaagaaaa   6960
tcatgtgctt tgtgtcgcca ctcactattg cagctttttc atgcattggt cagattgacg   7020
gttgattgta tttttgtttt ttatggtttt gtgttatgac ttaagtcttc atctctttat   7080
ctcttcatca ggtttgatgg ttacctaata tggtccatgg gtacatgcat ggttaaatta   7140
ggtggccaac tttgttgtga acgatagaat tttttttata ttaagtaaac tatttttata   7200
ttatgaaata ataataaaaa aaatatttta tcattattaa caaaatcata ttagttaatt   7260
tgttaactct ataataaaag aaatactgta acattcacat tacatggtaa catctttcca   7320
ccctttcatt tgttttttgt ttgatgactt tttttcttgt ttaaatttat ttcccttctt   7380
ttaaatttgg aatacattat catcatatat aaactaaaat actaaaaaca ggattacaca   7440
aatgataaat aataacacaa atatttataa atctagctgc aatatattta aactagctat   7500
atcgatattg taaaataaaa ctagctgcat tgatactgat aaaaaaatat catgtgcttt   7560
ctggactgat gatgcagtat acttttgaca ttgcctttat tttatttttc agaaaagctt   7620
tcttagttct gggttcttca ttatttgttt cccatctcca ttgtgaattg aatcatttgc   7680
ttcgtgtcac aaatacaatt tagntaggta catgcattgg tcagattcac ggtttattat   7740
gtcatgactt aagttcatgg tagtacatta cctgccacgc atgcattata ttggttagat   7800
ttgataggca aatttggttg tcaacaatat aaatataaat aatgttttta tattacgaaa   7860
taacagtgat caaaacaaac agttttatct ttattaacaa gattttgttt ttgtttgatg   7920
acgtttttta atgtttacgc tttcccccttt cttttgaatt tagaacactt tatcatcata   7980
aaatcaaata ctaaaaaaat tacatatttc ataaataata acacaaatat ttttaaaaaa   8040
tctgaaataa taatgaacaa tattacatat tatcacgaaa attcattaat aaaaatatta   8100
tataaataaa atgtaatagt agttatatgt aggaaaaaag tactgcacgc ataatatata   8160
caaaaagatt aaaatgaact attataaata ataacactaa attaatggtg aatcatatca   8220
aaataatgaa aaagtaaata aaatttgtaa ttaacttcta tatgtattac acacacaaat   8280
aataaataat agtaaaaaaa attatgataa atatttacca tctcataaga tatttaaaat   8340
aatgataaaa atatagatta ttttttatgc aactagctag ccaaaaagag aacacgggta   8400
tatataaaaa gagtaccttt aaattctact gtacttcctt tattcctgac gtttttatat   8460
caagtggaca tacgtgaaga ttttaattat cagtctaaat atttcattag cacttaatac   8520
ttttctgttt tattcctatc ctataagtag tcccgattct cccaacattg cttattcaca   8580
caactaacta agaaagtctt ccatagcccc ccaagcggcc gcacaatggc gactcgacag   8640
cgaactgcca ccactgttgt ggtcgaggac cttcccaagg tcactcttga ggccaagtct   8700
gaacctgtgt tccccgatat caagaccatc aaggatgcca ttcccgcgca ctgcttccag   8760
```

ccctcgctcg tcacctcatt ctactacgtc ttccgcgatt ttgccatggt ctctgccctc 8820
gtctgggctg ctctcaccta catccccagc atccccgacc agaccctccg cgtcgcagct 8880
tggatggtct acggcttcgt ccagggtctg ttctgcaccg gtgtctggat tctcggccat 8940
gagtgcggcc acggtgcttt ctctctccac ggaaaggtca acaatgtgac cggctggttc 9000
ctccactcgt tcctcctcgt cccctacttc agctggaagt actctcacca ccgccaccac 9060
cgcttcaccg gccacatgga tctcgacatg gctttcgtcc ccaagactga gcccaagccc 9120
tccaagtcgc tcatgattgc tggcattgac gtcgccgagc ttgttgagga cacccccgct 9180
gctcagatgg tcaagctcat cttccaccag cttttcggat ggcaggcgta cctcttcttc 9240
aacgctagct ctggcaaggg cagcaagcag tgggagccca agactggcct ctccaagtgg 9300
ttccgagtca gtcacttcga gcctaccagc gctgtcttcc gccccaacga ggccatcttc 9360
atcctcatct ccgatatcgg tcttgctcta atgggaactg ctctgtactt tgcttccaag 9420
caagttggtg tttcgaccat tctcttcctc taccttgttc cctacctgtg ggttcaccac 9480
tggctcgttg ccattaccta cctccaccac caccacaccg agctccctca ctacaccgct 9540
gagggctgga cctacgtcaa gggagctctc gccactgtcg accgtgagtt tggcttcatc 9600
ggaaagcacc tcttccacgg tatcattgag aagcacgttg ttcaccatct cttccctaag 9660
atccccttct acaaggctga cgaggccacc gaggccatca agcccgtcat tggcgaccac 9720
tactgccacg acgaccgaag cttcctgggc cagctgtgga ccatcttcgg cacgctcaag 9780
tacgtcgagc acgaccctgc ccgacccggt gccatgcgat ggaacaagga ctaggctagg 9840
cggccgcgac acaagtgtga gagtactaaa taaatgcttt ggttgtacga aatcattaca 9900
ctaaataaaa taatcaaagc ttatatatgc cttccgctaa ggccgaatgc aaagaaattg 9960
gttctttctc gttatctttt gccactttta ctagtacgta ttaattacta cttaatcatc 10020
tttgtttacg gctcattata tccggtctag aggatccaag gccgcgaagt taaaagcaat 10080
gttgtcactt gtcgtactaa cacatgatgt gatagtttat gctagctagc tataacataa 10140
gctgtctctg agtgtgttgt atattaataa agatcatcac tggtgaatgg tgatcgtgta 10200
cgtaccctac ttagtaggca atggaagcac ttagagtgtg ctttgtgcat ggccttgcct 10260
ctgttttgag acttttgtaa tgttttcgag tttaaatctt tgcctttgc 10309

<210> SEQ ID NO 92
<211> LENGTH: 12403
<212> TYPE: DNA
<213> ORGANISM: Artificial Sequence
<220> FEATURE:
<223> OTHER INFORMATION: Plasmid pKR873

<400> SEQUENCE: 92
ggtcgactcg acgtacgaaa ccaactgcgt ttggggctcc agattaaacg acgccgtttc 60
gttcctttcg cttcacggct taacgatgtc gtttctgtct gtgcccaaaa aataaaggca 120
tttgttattt gcaccagata tttactaagt gcaccctagt ttgacaagta ggcgataatt 180
acaaatagat gcggtgcaaa taataaattt tgaaggaaat aattacaaaa gaacagaact 240
tatatttact ttattttaaa aaactaaaat gaaagaacaa aaaaagtaaa aaatacaaaa 300
aatgtgcttt aaccactttc attatttgtt acagaaagta tgattctact caaattgatc 360
tgttgtatct ggtgctgcct tgtcacactg gcgatttcaa tcccctaaag atatggtgca 420
aactgcgaag tgatcaatat ctgctcggtt aatttagatt aattaataat attcaacgtg 480
atgtaccaaa aaaagacaat tttttgctcc attgacaaat taaacctcat caaggtaatt 540

```
tccaaaccta taagcaaaaa aatttcacat taattggccc gcaatcctat tagtcttatt    600
atactagagt aggaaaaaaa acaattacac aacttgtctt attattctct atgctaatga    660
atatttttcc cttttgttag aaatcagtgt ttcctaattt attgagtatt aattccactc    720
accgcatata tttaccgttg aataagaaaa ttttacacat aattcttttt aagataaata    780
atttttttat actagatctt atatgattac gtgaagccaa gtgggttata ctaatgatat    840
ataatgtttg atagtaatca gtttataaac caaatgcatg gaaatgttac gtggaagcac    900
gtaaattaac aagcattgaa gcaaatgcag ccaccgcacc aaaaccaccc cacttcactt    960
ccacgtacca tattccatgc aactacaaca ccctaaaact tcaataaatg cccccacctt   1020
cacttcactt cacccatcaa tagcaagcgg ccgcacaatg gcgactcgac agcgaactgc   1080
caccactgtt gtggtcgagg accttcccaa ggtcactctt gaggccaagt ctgaacctgt   1140
gttccccgat atcaagacca tcaaggatgc cattcccgcg cactgcttcc agccctcgct   1200
cgtcacctca ttctactacg tcttccgcga ttttgccatg gtctctgccc tcgtctgggc   1260
tgctctcacc tacatcccca gcatccccga ccagaccctc cgcgtcgcag cttggatggt   1320
ctacggcttc gtccagggtc tgttctgcac cggtgtctgg attctcggcc atgagtgcgg   1380
ccacggtgct ttctctctcc acggaaaggt caacaatgtg accggctggt tcctccactc   1440
gttcctcctc gtcccctact tcagctggaa gtactctcac caccgccacc accgcttcac   1500
cggccacatg gatctcgaca tggctttcgt ccccaagact gagcccaagc cctccaagtc   1560
gctcatgatt gctggcattg acgtcgccga gcttgttgag gacacccccg ctgctcagat   1620
ggtcaagctc atcttccacc agcttttcgg atggcaggcg tacctcttct tcaacgctag   1680
ctctggcaag ggcagcaagc agtgggagcc caagactggc ctctccaagt ggttccgagt   1740
cagtcacttc gagcctacca gcgctgtctt ccgccccaac gaggccatct tcatcctcat   1800
ctccgatatc ggtcttgctc taatgggaac tgctctgtac tttgcttcca agcaagttgg   1860
tgtttcgacc attctcttcc tctaccttgt tccctacctg tgggttcacc actggctcgt   1920
tgccattacc tacctccacc accaccacac cgagctccct cactacaccg ctgagggctg   1980
gacctacgtc aagggagctc tcgccactgt cgaccgtgag tttggcttca tcggaaagca   2040
cctcttccac ggtatcattg agaagcacgt tgttcaccat ctcttcccta agatcccctt   2100
ctacaaggct gacgaggcca ccgaggccat caagcccgtc attggcgacc actactgcca   2160
cgacgaccga agcttcctgg gccagctgtg gaccatcttc ggcacgctca agtacgtcga   2220
gcacgaccct gcccgacccg gtgccatgcg atggaacaag gactaggcta ggcggccgcg   2280
aagttaaaag caatgttgtc acttgtcgta ctaacacatg atgtgatagt ttatgctagc   2340
tagctataac ataagctgtc tctgagtgtg ttgtatatta ataaagatca tcactggtga   2400
atggtgatcg tgtacgtacc ctacttagta ggcaatggaa gcacttagag tgtgctttgt   2460
gcatggcctt gcctctgttt tgagactttt gtaatgtttt cgagtttaaa tctttgcctt   2520
tgcgtacgtc tagaggatcc gtcgacggcg cgcccgatca tccggatata gttcctcctt   2580
tcagcaaaaa acccctcaag acccgtttag aggccccaag gggttatgct agttattgct   2640
cagcggtggc agcagccaac tcagcttcct ttcgggcttt gttagcagcc ggatcgatcc   2700
aagctgtacc tcactattcc tttgccctcg gacgagtgct ggggcgtcgg tttccactat   2760
cggcgagtac ttctacacag ccatcggtcc agacggccgc gcttctgcgg gcgatttgtg   2820
tacgcccgac agtcccggct ccggatcgga cgattgcgtc gcatcgaccc tgcgcccaag   2880
ctgcatcatc gaaattgccg tcaaccaagc tctgatagag ttggtcaaga ccaatgcgga   2940
```

```
gcatatacgc ccggagccgc ggcgatcctg caagctccgg atgcctccgc tcgaagtagc   3000
gcgtctgctg ctccatacaa gccaaccacg gcctccagaa gaagatgttg gcgacctcgt   3060
attgggaatc cccgaacatc gcctcgctcc agtcaatgac cgctgttatg cggccattgt   3120
ccgtcaggac attgttggag ccgaaatccg cgtgcacgag gtgccggact tcggggcagt   3180
cctcggccca aagcatcagc tcatcgagag cctgcgcgac ggacgcactg acggtgtcgt   3240
ccatcacagt ttgccagtga tacacatggg gatcagcaat cgcgcatatg aaatcacgcc   3300
atgtagtgta ttgaccgatt ccttgcggtc cgaatgggcc gaacccgctc gtctggctaa   3360
gatcggccgc agcgatcgca tccatagcct ccgcgaccgg ctgcagaaca gcgggcagtt   3420
cggtttcagg caggtcttgc aacgtgacac cctgtgcacg gcgggagatg caataggtca   3480
ggctctcgct gaattcccca atgtcaagca cttccggaat cgggagcgcg gccgatgcaa   3540
agtgccgata aacataacga tctttgtaga aaccatcggc gcagctattt acccgcagga   3600
catatccacg ccctcctaca tcgaagctga aagcacgaga ttcttcgccc tccgagagct   3660
gcatcaggtc ggagacgctg tcgaactttt cgatcagaaa cttctcgaca gacgtcgcgg   3720
tgagttcagg cttttccatg ggtatatctc cttcttaaag ttaaacaaaa ttatttctag   3780
agggaaaccg ttgtggtctc cctatagtga gtcgtattaa tttcgcggga tcgagatctg   3840
atcaacctgc attaatgaat cggccaacgc gcggggagag gcggtttgcg tattgggcgc   3900
tcttccgctt cctcgctcac tgactcgctg cgctcggtcg ttcggctgcg gcgagcggta   3960
tcagctcact caaaggcggt aatacggtta tccacagaat caggggataa cgcaggaaag   4020
aacatgtgag caaaaggcca gcaaaaggcc aggaaccgta aaaaggccgc gttgctggcg   4080
tttttccata ggctccgccc ccctgacgag catcacaaaa atcgacgctc aagtcagagg   4140
tggcgaaacc cgacaggact ataaagatac caggcgtttc cccctggaag ctccctcgtg   4200
cgctctcctg ttccgaccct gccgcttacc ggatacctgt ccgcctttct cccttcggga   4260
agcgtggcgc tttctcaatg ctcacgctgt aggtatctca gttcggtgta ggtcgttcgc   4320
tccaagctgg gctgtgtgca cgaacccccc gttcagcccg accgctgcgc cttatccggt   4380
aactatcgtc ttgagtccaa cccggtaaga cacgacttat cgccactggc agcagccact   4440
ggtaacagga ttagcagagc gaggtatgta ggcggtgcta cagagttctt gaagtggtgg   4500
cctaactacg gctacactag aaggacagta tttggtatct gcgctctgct gaagccagtt   4560
accttcggaa aaagagttgg tagctcttga tccggcaaac aaaccaccgc tggtagcggt   4620
ggtttttttg tttgcaagca gcagattacg cgcagaaaaa aaggatctca agaagatcct   4680
ttgatctttt ctacggggtc tgacgctcag tggaacgaaa actcacgtta agggattttg   4740
gtcatgacat taacctataa aaataggcgt atcacgaggc cctttcgtct cgcgcgtttc   4800
ggtgatgacg gtgaaaacct ctgacacatg cagctcccgg agacggtcac agcttgtctg   4860
taagcggatg ccgggagcag acaagcccgt cagggcgcgt cagcgggtgt tggcgggtgt   4920
cggggctggc ttaactatgc ggcatcagag cagattgtac tgagagtgca ccatatggac   4980
atattgtcgt tagaacgcgg ctacaattaa tacataacct tatgtatcat acacatacga   5040
tttaggtgac actatagaac ggcgcgccaa gctgggtcta gaactagaaa cgtgatgcca   5100
cttgttattg aagtcgatta cagcatctat tctgttttac tatttataac tttgccattt   5160
ctgacttttg aaaactatct ctggatttcg gtatcgcttt gtgaagatcg agcaaaagag   5220
acgttttgtg gacgcaatgg tccaaatccg ttctacatga acaaattggt cacaatttcc   5280
actaaaagta aataaatggc aagttaaaaa aggaatatgc attttactga ttgcctaggt   5340
```

-continued

```
gagctccaag agaagttgaa tctacacgtc taccaaccgc taaaaaaaga aaaacattga   5400
tatgtaacct gattccatta gcttttgact tcttcaacag attctctact tagatttcta   5460
acagaaatat tattactagc acatcatttt cagtctcact acagcaaaaa atccaacggc   5520
acaatacaga caacaggaga tatcagacta cagagataga tagatgctac tgcatgtagt   5580
aagttaaata aaaggaaaat aaaatgtctt gctaccaaaa ctactacaga ctatgatgct   5640
caccacaggc caaatcctgc aactaggaca gcattatctt atatatattg tacaaaacaa   5700
gcatcaagga acatttggtc taggcaatca gtacctcgtt ctaccatcac cctcagttat   5760
cacatccttg aaggatccat tactgggaat catcggcaac acatgctcct gatggggcac   5820
aatgacatca agaaggtagg ggccaggggt gtccaacatt ctctgaattg ccgctctaag   5880
ctcttccttc ttcgtcactc gcgctgccgg tatcccacaa gcatcagcaa acttgagcat   5940
gtttgggaat atctcgctct cgctagacgg atctccaaga taggtgtgag ctctattgga   6000
cttgtagaac ctatcctcca actgaaccac catacccaaa tgctgattgt tcaacaacaa   6060
tatcttaact gggagattct ccactcttat agtggccaac tcctgaacat tcatgatgaa   6120
actaccatcc ccatcaatgt caaccacaac agccccaggg ttagcaacag cagcaccaat   6180
agccgcaggc aatccaaaac ccatggctcc aagaccccct gaggtcaacc actgcctcgg   6240
tctcttgtac ttgtaaaact gcgcagccca catttgatgc tgcccaaccc cagtactaac   6300
aatagcatct ccattagtca actcatcaag aacctcgata gcatgctgcg gagaaatcgc   6360
gtcctggaat gtcttgtaac ccaatggaaa cttgtgtttc tgcacattaa tctcttctct   6420
ccaacctcca agatcaaact taccctccac tcctttctcc tccaaaatca tattaattcc   6480
cttcaaggcc aacttcaaat ccgcgcaaac cgacacgtgc gcctgcttgt tcttcccaat   6540
ctcggcagaa tcaatatcaa tgtgaacaat cttagcccta ctagcaaaag cctcaagctt   6600
cccagtaaca cggtcatcaa accttacccc aaaggcaagc aacaaatcac tattgtcaac   6660
agcatagtta gcataaacag taccatgcat acccagcatc tgaagggaat attcatcacc   6720
aataggaaaa gttccaagac ccattaaagt gctagcaacg ggaataccag tgagttcaac   6780
aaagcgcctc aattcagcac tggaattcaa actgccaccg ccgacgtaga gaacgggctt   6840
ttgggcctcc atgatgagtc tgacaatgtg ttccaattgg gcctcggcgg ggggcctggg   6900
cagcctggcg aggtaaccgg ggaggttaac gggctcgtcc caattaggca cggcgagttg   6960
ctgctgaacg tctttgggaa tgtcgatgag gaccggaccg gggcggccgg aggtggcgac   7020
gaagaaagcc tcggcgacga cgcgggggat gtcgtcgacg tcgaggatga ggtagttgtg   7080
cttcgtgatg gatctgctca cctccacgat cggggtttct tggaaggcgt cggtgccgat   7140
catccggcgg gcgacctggc cggtgatggc gacgactggg acgctgtcca ttaaagcgtc   7200
ggcgaggccg ctcacgaggt tggtggcgcc ggggccggag gtggcaatgc agacgccggg   7260
gaggccggag gaacgcgcgt agccttcggc ggcgaagacg ccgccctgct cgtggcgcgg   7320
gagcacgttg cggatggcgg cggagcgcgt gagcgcctgg tggatctcca tcgacgcacc   7380
gccggggtac gcgaacaccg tcgtcacgcc ctgcctctcc agcgcctcca caaggatgtc   7440
cgcgcccttg cgaggttcgc cggaggcgaa ccgtgacacg aagggctccg tggtcggcgc   7500
ttccttggtg aagggcgccg ccgtgggggg tttggagatg gaacatttga ttttgagagc   7560
gtggttgggt ttggtgaggg tttgatgaga gagagggagg gtggatctag taatgcgttt   7620
ggggaaggtg gggtgtgaag aggaagaaga gaatcgggtg gttctggaag cggtggccgc   7680
cattgtgttg tgtggcatgg ttatacttca aaaactgcac aacaagccta gagttagtac   7740
```

-continued

```
ctaaacagta aatttacaac agagagcaaa gacacatgca aaaatttcag ccataaaaaa   7800
agttataata gaatttaaag caaaagtttc atttttttaaa catatataca aacaaactgg   7860
atttgaagga agggattaat tcccctgctc aaagtttgaa ttcctattgt gacctatact   7920
cgaataaaat tgaagcctaa ggaatgtatg agaaacaaga aaacaaaaca aaactacaga   7980
caaacaagta caattacaaa attcgctaaa attctgtaat caccaaaccc catctcagtc   8040
agcacaaggc ccaaggttta ttttgaaata aaaaaaaagt gattttattt ctcataagct   8100
aaaagaaaga aaggcaatta tgaaatgatt tcgactagat ctgaaagtcc aacgcgtatt   8160
ccgcagatat taaagaaaga gtagagtttc acatggatcc tagatggacc cagttgagga   8220
aaaagcaagg caaagcaaac cagaagtgca agatccgaaa ttgaaccacg gaatctagga   8280
tttggtagag ggagaagaaa agtaccttga gaggtagaag agaagagaag agcagagaga   8340
tatatgaacg agtgtgtctt ggtctcaact ctgaagcgat acgagtttag aggggagcat   8400
tgagttccaa tttataggga aaccgggtgg caggggtgag ttaatgacgg aaaagcccct   8460
aagtaacgag attggattgt gggttagatt caaccgtttg catccgcggc ttagattggg   8520
gaagtcagag tgaatctcaa ccgttgactg agttgaaaat tgaatgtagc aaccaattga   8580
gccaacccca gcctttgccc tttgattttg atttgtttgt tgcatacttt ttatttgtct   8640
tctggttctg actctctttc tctcgtttca atgccaggtt gcctactccc acaccactca   8700
caagaagatt ctactgttag tattaaatat tttttaatgt attaaatgat gaatgctttt   8760
gtaaacagaa caagactatg tctaataagt gtcttgcaac attttttaag aaattaaaaa   8820
aaatatattt attatcaaaa tcaaatgtat gaaaaatcat gaataatata attttataca   8880
ttttttaaa aaatctttta atttcttaat taatatctta aaaataatga ttaatattta   8940
acccaaaata attagtatga ttggtaagga agatatccat gttatgtttg gatgtgagtt   9000
tgatctagag caaagcttac tagagtcgac ctgcagcccg gggggatccgc ccacgtacgg   9060
taccatctgc taatatttta aatcacatgc aagagaggag gcatggttcc attttctacc   9120
ttcacattat ttgagaaaaa cgaacttgtt ctgtgtttta tttttgccct tcacattagt   9180
acaacgtgga agactcatgg ttacacagaa tcatacataa gtacaatgct tgtccctaag   9240
aaaacaagca ctcgttgtat tgaacctttta cggctcatgc ggccgcgaat tcactagtga   9300
ttgaattcgc ggccgcttag tccgacttgg ccttggcggc cgcggccgac tctttgagcg   9360
tgaagatctg cgccgtctcg ggcacagcgc cgtagttgac aaagaggtgc gcggtcttga   9420
agaaggccgt gatgatgggc tcgtcgttcc tgcgcacgag gtgcgggtac gcggccgcaa   9480
agtgcttggt ggcttcgttg agcttgtagt gcggaatgat cgggaacaag tggtggacct   9540
ggtgcgtgcc aatgtggtgg ctcaggttgt ccacgaacgc gccgtacgag cggtcgacgc   9600
tcgagaggtt gcccttgacg tacgtccact ccgagtcgcc gtaccacggc gtcgcttcgt   9660
cgttgtggtg caagaaggtc gtaatgacga ggaacgaagc aaagacaaag agcggcgcat   9720
agtagtagag gcccatgacg gcaaagccga gcgagtatgt gaggtacgcg tacgcggcga   9780
agaaggcggc ccagacgccg agcgacacga tgacggccga cgcgcggcga aggaggagcg   9840
ggtcccacgg gtcaaagtgg ctcatcgtgc gcggggcata cccgaccttc aagtagacaa   9900
accacgcacc gccgagcgtg tagacccatt ggcgcacgtc ctggaggtcc ttgaccgacc   9960
ggtgcgggta aaagatctcg tccttatcaa tgttgcccgt gttcttgtgg tggtggcggt  10020
gcgtcacgcg ccagctctcg aacggcgtca aaatcgcaga gtgcatgatg cagccgatga  10080
taaagttgac gctgtggtag cgcgagaagg ccgagtggcc gcagtcgtgg ccgaccgtga  10140
```

agaagcccca gaagatgacg ccctgcacgt agatgtaggt ggcgcaaacg agcgcgtgga 10200
gcagaacgtt atcggcaatg aacggcgtcg agcgcgccgc gtagagcagc gccgccgagg 10260
ccgacgcgtt gaagatcgcg cgggccgtgt agtagagcga gaggccgagg ttcgactcaa 10320
agcacgcgtt cgggatcgag tgcttgagct ccgtgagcgt cgggaactcg accttcgtct 10380
tatcctcagt catgcggccg ctgaagtatt gcttcttagt taacctttcc tttctctctc 10440
agctatgtga attcattttg ctttcgtcac aatttatata gtgaaattgg atctttggag 10500
ttaacgcctt cacaggatta tcgtgttaga acaatgcttt ttcatgttct aattagtagt 10560
acattacaaa tgtgcactct attcaataag catcttttgg cacgttaata aatcatgtga 10620
aaaaaaaata ctactatttc aaagaaagtg ttgtaaaaag aaacggaaag agagctggct 10680
tcagttgttg agacttgttt gctagtaaaa atggtgtgaa gagtgattca tggtgaggtg 10740
gtttttcgtc cctttctgtt tgcatgaaaa acaaatggca agagatgacg taggattcct 10800
tcccttaacg attatctgtt tttaatttca aatatacata taggaattta tgaattacta 10860
aggttgtaaa atatgctggt catttattta tggctaaaat attttttttt ctcgtaaata 10920
taaaaatatt taaaatttat ttttatcata tttttttatcc ttataaaatt atgtgtacaa 10980
cctatataaa aaaatatcat atttaatatt gattatatgt ttaatcaata taaaaaatca 11040
ttatcatata tttagattta ttcgaatata catctaaaca aaaaataaca tattttaatt 11100
ttatgaagaa aaaaaaatat tttatccttt atttatttaa gattaattaa tagttatgta 11160
ttgtggaaag acttttacac atgcaataga tatactgaat caattagatg ccaatgctga 11220
gttggaaatc acttgaggag gggaggagac ttgccaatgc ttttcagttt catttaaatg 11280
atttagtgga ggagatagag tagtgataaa ggcatgcccc aattttggag tgtatatatg 11340
agtggaaata agagagggat agagagaaaa aataaagaga gtaaaaataa ttaatgtgaa 11400
atgatatgat aaaaaaataa agaaagagat aaagagaaaa atgaaatgag agatagatga 11460
aatagagagt agatacatgt ttgtttaggt tttttttagg aaataacaca ttttttttctc 11520 atcacttatt actcactgtc aatttcctct ctttcaatca taatgatatg atttgtttaa 11580
caaaaatgtg aaaaaacata taaagtaaaa tatttttata aattgataaa taaaaattta 11640
caaaatttat ttcttattaa attgaataga aaatgaaaga aaagaaaaga aaaagtatat 11700
ataaaatgat atagctttaa aaagaataaa tttttcatat cagtcttttt ttaataattt 11760
agaaatattt aagtatatag caaaaatata atgtacttta catatgcata aataataatt 11820
tgaaaataga actaatagaa tagagaaaaa agtaatataa taattaacta tatgaaaatt 11880
tagaagggac aatattttta attaagaata taaacaatat ttcttttcat gtaatgaggg 11940
acggatgtac ggggccagtg ttggagtcaa agccaaaata gtcacgggga aattaatgca 12000
ctgcatgact attcgaaaaa attcactagc cttacttaga tgttagatta atagctaggg 12060
ggtgcagata attttgaaag gcatgaaaaa cattaatttg tacattgcaa gcttttgatg 12120
acaagctttg caattgttca cactacctta tgccatttat aaatagagtg attggcatat 12180
gaaggaaatc atgagagtcg aagcgaaaaa caaagcttga gagtgtagga aaaatacagt 12240 tttttggta aaaatacagt atttgaatag gagcgaaaaa tatcctttca aaatgatcct 12300 tttcttttt tttttttttc ttgttgttct tggtcagtta ttcaaaggaa aagggattga 12360
aataaaaact tgcatgtggg atcgtacgtc gagtcgacct gca 12403

<210> SEQ ID NO 93
<211> LENGTH: 3983
<212> TYPE: DNA

<213> ORGANISM: Artificial Sequence
<220> FEATURE:
<223> OTHER INFORMATION: Plasmid pKR132

<400> SEQUENCE: 93
ctagagtcga cctgcaggca tgcaagcttg gcgtaatcat ggtcatagct gtttcctgtg 60
tgaaattgtt atccgctcac aattccacac aacatacgag ccggaagcat aaagtgtaaa 120
gcctggggtg cctaatgagt gagctaactc acattaattg cgttgcgctc actgcccgct 180
ttccagtcgg gaaacctgtc gtgccagctg cattaatgaa tcggccaacg cgcggggaga 240
ggcggtttgc gtattgggcg ctcttccgct tcctcgctca ctgactcgct gcgctcggtc 300
gttcggctgc ggcgagcggt atcagctcac tcaaaggcgg taatacggtt atccacagaa 360
tcaggggata acgcaggaaa gaacatgtga gcaaaaggcc agcaaaaggc caggaaccgt 420
aaaaaggccg cgttgctggc gtttttccat aggctccgcc cccctgacga gcatcacaaa 480
aatcgacgct caagtcagag gtggcgaaac ccgacaggac tataaagata ccaggcgttt 540
ccccctggaa gctccctcgt gcgctctcct gttccgaccc tgccgcttac cggatacctg 600
tccgcctttc tcccttcggg aagcgtggcg ctttctcata gctcacgctg taggtatctc 660
agttcggtgt aggtcgttcg ctccaagctg ggctgtgtgc acgaaccccc cgttcagccc 720
gaccgctgcg ccttatccgg taactatcgt cttgagtcca acccggtaag acacgactta 780
tcgccactgg cagcagccac tggtaacagg attagcagag cgaggtatgt aggcggtgct 840
acagagttct tgaagtggtg gcctaactac ggctacacta gaaggacagt atttggtatc 900
tgcgctctgc tgaagccagt taccttcgga aaaagagttg gtagctcttg atccggcaaa 960
caaaccaccg ctggtagcgg tggttttttt gtttgcaagc agcagattac gcgcagaaaa 1020
aaaggatctc aagaagatcc tttgatcttt tctacggggt ctgacgctca gtggaacgaa 1080
aactcacgtt aagggatttt ggtcatgaga ttatcaaaaa ggatcttcac ctagatcctt 1140
ttaaattaaa aatgaagttt taaatcaatc taaagtatat atgagtaaac ttggtctgac 1200
agttaccaat gcttaatcag tgaggcacct atctcagcga tctgtctatt tcgttcatcc 1260
atagttgcct gactccccgt cgtgtagata actacgatac gggagggctt accatctggc 1320
cccagtgctg caatgatacc gcgagaccca cgctcaccgg ctccagattt atcagcaata 1380
aaccagccag ccggaagggc cgagcgcaga agtggtcctg caactttatc cgcctccatc 1440
cagtctatta attgttgccg ggaagctaga gtaagtagtt cgccagttaa tagtttgcgc 1500
aacgttgttg ccattgctac aggcatcgtg gtgtcacgct cgtcgtttgg tatggcttca 1560
ttcagctccg gttcccaacg atcaaggcga gttacatgat cccccatgtt gtgcaaaaaa 1620
gcggttagct ccttcggtcc tccgatcgtt gtcagaagta agttggccgc agtgttatca 1680
ctcatggtta tggcagcact gcataattct cttactgtca tgccatccgt aagatgcttt 1740
tctgtgactg gtgagtactc aaccaagtca ttctgagaat agtgtatgcg gcgaccgagt 1800
tgctcttgcc cggcgtcaat acgggataat accgcgccac atagcagaac tttaaaagtg 1860
ctcatcattg gaaaacgttc ttcggggcga aaactctcaa ggatcttacc gctgttgaga 1920
tccagttcga tgtaacccac tcgtgcaccc aactgatctt cagcatcttt tactttcacc 1980
agcgtttctg ggtgagcaaa aacaggaagg caaaatgccg caaaaaaggg aataagggcg 2040
acacggaaat gttgaatact catactcttc ctttttcaat attattgaag catttatcag 2100
ggttattgtc tcatgagcgg atacatattt gaatgtattt agaaaaataa acaaataggg 2160
gttccgcgca catttccccg aaaagtgcca cctgacgtct aagaaaccat tattatcatg 2220
acattaacct ataaaaatag gcgtatcacg aggccctttc gtctcgcgcg tttcggtgat 2280
gacggtgaaa acctctgaca catgcagctc ccggagacgg tcacagcttg tctgtaagcg 2340
gatgccggga gcagacaagc ccgtcagggc gcgtcagcgg gtgttggcgg gtgtcggggc 2400
tggcttaact atgcggcatc agagcagatt gtactgagag tgcaccatat gcggtgtgaa 2460
ataccgcaca gatgcgtaag gagaaaatac cgcatcaggc gccattcgcc attcaggctg 2520
cgcaactgtt gggaagggcg atcggtgcgg gcctcttcgc tattacgcca gctggcgaaa 2580
gggggatgtg ctgcaaggcg attaagttgg gtaacgccag ggttttccca gtcacgacgt 2640
tgtaaaacga cggccagtga attcgagctc ggtacccggg gatcctctag acctgcaggc 2700
caactgcgtt tggggctcca gattaaacga cgccgtttcg ttcctttcgc ttcacggctt 2760
aacgatgtcg tttctgtctg tgcccaaaaa ataaaggcat ttgttatttg caccagatat 2820
ttactaagtg caccctagtt tgacaagtag gcgataatta caaatagatg cggtgcaaat 2880
aataaatttt gaaggaaata attacaaaag aacagaactt atatttactt tattttaaaa 2940
aactaaaatg aaagaacaaa aaaagtaaaa aatacaaaaa atgtgcttta accactttca 3000
ttatttgtta cagaaagtat gattctactc aaattgatct gttgtatctg gtgctgcctt 3060
gtcacactgg cgatttcaat cccctaaaga tatggtgcaa actgcgaagt gatcaatatc 3120
tgctcggtta atttagatta attaataata ttcaacgtga tgtaccaaaa aaagacaatt 3180
ttttgctcca ttgacaaatt aaacctcatc aaggtaattt ccaaacctat aagcaaaaaa 3240
atttcacatt aattggcccg caatcctatt agtcttatta tactagagta ggaaaaaaaa 3300
caattacaca acttgtctta ttattctcta tgctaatgaa tatttttccc ttttgttaga 3360
aatcagtgtt tcctaattta ttgagtatta attccactca ccgcatatat ttaccgttga 3420
ataagaaaat tttacacata attcttttta agataaataa ttttttttata ctagatctta 3480 tatgattacg tgaagccaag tgggttatac taatgatata taatgtttga tagtaatcag 3540
tttataaacc aaatgcatgg aaatgttacg tggaagcacg taaattaaca agcattgaag 3600
caaatgcagc caccgcacca aaaccacccc acttcacttc cacgtaccat attccatgca 3660
actacaacac cctaaaactt caataaatgc ccccaccttc acttcacttc acccatcaat 3720
agcaagcggc cgcgaagtta aaagcaatgt tgtcacttgt cgtactaaca catgatgtga 3780
tagtttatgc tagctagcta taacataagc tgtctctgag tgtgttgtat attaataaag 3840
atcatcactg gtgaatggtg atcgtgtacg taccctactt agtaggcaat ggaagcactt 3900
agagtgtgct ttgtgcatgg ccttgcctct gttttgagac ttttgtaatg ttttcgagtt 3960
taaatctttg cctttgcgta cgt 3983

<210> SEQ ID NO 94
<211> LENGTH: 33
<212> TYPE: DNA
<213> ORGANISM: Artificial Sequence
<220> FEATURE:
<223> OTHER INFORMATION: Primer oSAlb-9

<400> SEQUENCE: 94
ttctagacgt acgaaaccaa ctgcgtttgg ggc 33

<210> SEQ ID NO 95
<211> LENGTH: 35
<212> TYPE: DNA
<213> ORGANISM: Artificial Sequence
<220> FEATURE:
<223> OTHER INFORMATION: Primer oSAlb-2

<400> SEQUENCE: 95
aatctagacg tacgcaaagg caaagattta aactc 35

<210> SEQ ID NO 96
<211> LENGTH: 4268
<212> TYPE: DNA
<213> ORGANISM: Artificial Sequence
<220> FEATURE:
<223> OTHER INFORMATION: Plasmid pKR160

<400> SEQUENCE: 96
aatctagacg tacgcaaagg caaagattta aactcgaaaa cattacaaaa gtctcaaaac 60
agaggcaagg ccatgcacaa agcacactct aagtgcttcc attgcctact aagtagggta 120
cgtacacgat caccattcac cagtgatgat ctttattaat atacaacaca ctcagagaca 180
gcttatgtta tagctagcta gcataaacta tcacatcatg tgttagtacg acaagtgaca 240
acattgcttt taacttcgcg gccgcttgct attgatgggt gaagtgaagt gaaggtgggg 300
gcatttattg aagttttagg gtgttgtagt tgcatggaat atggtacgtg gaagtgaagt 360
ggggtggttt tggtgcggtg gctgcatttg cttcaatgct tgttaattta cgtgcttcca 420
cgtaacattt ccatgcattt ggtttataaa ctgattacta tcaaacatta tatatcatta 480
gtataaccca cttggcttca cgtaatcata taagatctag tataaaaaaa ttatttatct 540
taaaaagaat tatgtgtaaa attttcttat tcaacggtaa atatatgcgg tgagtggaat 600
taatactcaa taaattagga aacactgatt tctaacaaaa gggaaaaata ttcattagca 660
tagagaataa taagacaagt tgtgtaattg tttttttttcc tactctagta taataagact 720
aataggattg cgggccaatt aatgtgaaat ttttttgctt ataggtttgg aaattacctt 780
gatgaggttt aatttgtcaa tggagcaaaa aattgtcttt ttttggtaca tcacgttgaa 840
tattattaat taatctaaat taaccgagca gatattgatc acttcgcagt ttgcaccata 900
tctttagggg attgaaatcg ccagtgtgac aaggcagcac cagatacaac agatcaattt 960
gagtagaatc atactttctg taacaaataa tgaaagtggt taaagcacat tttttgtatt 1020
ttttactttt tttgttcttt cattttagtt ttttaaaata aagtaaatat aagttctgtt 1080
cttttgtaat tatttccttc aaaatttatt atttgcaccg catctatttg taattatcgc 1140
ctacttgtca aactagggtg cacttagtaa atatctggtg caaataacaa atgcctttat 1200
tttttgggca cagacagaaa cgacatcgtt aagccgtgaa gcgaaaggaa cgaaacggcg 1260
tcgtttaatc tggagcccca aacgcagttg gtttcgtacg tctagaaggg ctagagcggc 1320
cgccaccgcg gtggagctcc agcttttgtt ccctttagtg agggttaatt gcgcgcttgg 1380
cgtaatcatg gtcatagctg tttcctgtgt gaaattgtta tccgctcaca attccacaca 1440
acatacgagc cggaagcata aagtgtaaag cctggggtgc ctaatgagtg agctaactca 1500
cattaattgc gttgcgctca ctgcccgctt tccagtcggg aaacctgtcg tgccagctgc 1560
attaatgaat cggccaacgc gcggggagag gcggtttgcg tattgggcgc tcttccgctt 1620
cctcgctcac tgactcgctg cgctcggtcg ttcggctgcg gcgagcggta tcagctcact 1680
caaaggcggt aatacggtta tccacagaat caggggataa cgcaggaaag aacatgtgag 1740
caaaaggcca gcaaaaggcc aggaaccgta aaaaggccgc gttgctggcg tttttccata 1800
ggctccgccc ccctgacgag catcacaaaa atcgacgctc aagtcagagg tggcgaaacc 1860
cgacaggact ataaagatac caggcgtttc cccctggaag ctccctcgtg cgctctcctg 1920
ttccgaccct gccgcttacc ggatacctgt ccgcctttct cccttcggga agcgtggcgc 1980

```
tttctcatag ctcacgctgt aggtatctca gttcggtgta ggtcgttcgc tccaagctgg   2040
gctgtgtgca cgaacccccc gttcagcccg accgctgcgc cttatccggt aactatcgtc   2100
ttgagtccaa cccggtaaga cacgacttat cgccactggc agcagccact ggtaacagga   2160
ttagcagagc gaggtatgta ggcggtgcta cagagttctt gaagtggtgg cctaactacg   2220
gctacactag aaggacagta tttggtatct gcgctctgct gaagccagtt accttcggaa   2280
aaagagttgg tagctcttga tccggcaaac aaaccaccgc tggtagcggt ggtttttttg   2340
tttgcaagca gcagattacg cgcagaaaaa aaggatctca agaagatcct ttgatctttt   2400
ctacggggtc tgacgctcag tggaacgaaa actcacgtta agggattttg gtcatgagat   2460
tatcaaaaag gatcttcacc tagatccttt taaattaaaa atgaagtttt aaatcaatct   2520
aaagtatata tgagtaaact tggtctgaca gttaccaatg cttaatcagt gaggcaccta   2580
tctcagcgat ctgtctattt cgttcatcca tagttgcctg actccccgtc gtgtagataa   2640
ctacgatacg ggagggctta ccatctggcc ccagtgctgc aatgataccg cgagacccac   2700
gctcaccggc tccagattta tcagcaataa accagccagc cggaagggcc gagcgcagaa   2760
gtggtcctgc aactttatcc gcctccatcc agtctattaa ttgttgccgg gaagctagag   2820
taagtagttc gccagttaat agtttgcgca acgttgttgc cattgctaca ggcatcgtgg   2880
tgtcacgctc gtcgtttggt atggcttcat tcagctccgg ttcccaacga tcaaggcgag   2940
ttacatgatc ccccatgttg tgcaaaaaag cggttagctc cttcggtcct ccgatcgttg   3000
tcagaagtaa gttggccgca gtgttatcac tcatggttat ggcagcactg cataattctc   3060
ttactgtcat gccatccgta agatgctttt ctgtgactgg tgagtactca accaagtcat   3120
tctgagaata gtgtatgcgg cgaccgagtt gctcttgccc ggcgtcaata cgggataata   3180
ccgcgccaca tagcagaact ttaaaagtgc tcatcattgg aaaacgttct tcggggcgaa   3240
aactctcaag gatcttaccg ctgttgagat ccagttcgat gtaacccact cgtgcaccca   3300
actgatcttc agcatctttt actttcacca gcgtttctgg gtgagcaaaa acaggaaggc   3360
aaaatgccgc aaaaaaggga ataagggcga cacggaaatg ttgaatactc atactcttcc   3420
tttttcaata ttattgaagc atttatcagg gttattgtct catgagcgga tacatatttg   3480
aatgtattta gaaaaataaa caaatagggg ttccgcgcac atttccccga aaagtgccac   3540
ctaaattgta agcgttaata ttttgttaaa attcgcgtta aatttttgtt aaatcagctc   3600
atttttttaac caataggccg aaatcggcaa aatcccttat aaatcaaaag aatagaccga   3660
gatagggttg agtgttgttc cagtttggaa caagagtcca ctattaaaga acgtggactc   3720
caacgtcaaa gggcgaaaaa ccgtctatca gggcgatggc ccactacgtg aaccatcacc   3780
ctaatcaagt tttttggggt cgaggtgccg taaagcacta aatcggaacc ctaaagggag   3840
cccccgattt agagcttgac ggggaaagcc ggcgaacgtg gcgagaaagg aagggaagaa   3900
agcgaaagga gcgggcgcta gggcgctggc aagtgtagcg gtcacgctgc gcgtaaccac   3960
cacacccgcc gcgcttaatg cgccgctaca gggcgcgtcc cattcgccat tcaggctgcg   4020
caactgttgg gaagggcgat cggtgcgggc ctcttcgcta ttacgccagc tggcgaaagg   4080
gggatgtgct gcaaggcgat taagttgggt aacgccaggg ttttcccagt cacgacgttg   4140
taaaacgacg gccagtgagc gcgcgtaata cgactcacta tagggcgaat tgggtaccgg   4200
gccccccctc gaggtcgacg gtatcgataa gcttgatatc gaattcctgc agcccggggg   4260
atccgccc                                                            4268
```

<210> SEQ ID NO 97

<211> LENGTH: 4990
<212> TYPE: DNA
<213> ORGANISM: Artificial Sequence
<220> FEATURE:
<223> OTHER INFORMATION: Plasmid pKR124
<220> FEATURE:
<221> NAME/KEY: misc_feature
<222> LOCATION: (1186)..(1186)
<223> OTHER INFORMATION: n is a, c, g, or t

<400> SEQUENCE: 97

```
ctagacgtac gtcctcgaag agaagggtta ataacacatt ttttaacatt tttaacacaa     60

attttagtta tttaaaaatt tattaaaaaa tttaaaataa gaagaggaac tctttaaata    120

aatctaactt acaaaattta tgatttttaa taagttttca ccaataaaaa atgtcataaa    180

aatatgttaa aaagtatatt atcaatattc tctttatgat aaataaaaag aaaaaaaaaa    240

taaaagttaa gtgaaaatga gattgaagtg actttaggtg tgtataaata tatcaacccc    300

gccaacaatt tatttaatcc aaatatattg aagtatatta ttccatagcc tttatttatt    360

tatatattta ttatataaaa gctttatttg ttctaggttg ttcatgaaat atttttttgg    420

ttttatctcc gttgtaagaa aatcatgtgc tttgtgtcgc cactcactat tgcagctttt    480

tcatgcattg gtcagattga cggttgattg tatttttgtt ttttatggtt ttgtgttatg    540

acttaagtct tcatctcttt atctcttcat caggtttgat ggttacctaa tatggtccat    600

gggtacatgc atggttaaat taggtggcca actttgttgt gaacgataga atttttttta    660

tattaagtaa actattttta tattatgaaa taataataaa aaaaatattt tatcattatt    720

aacaaaatca tattagttaa tttgttaact ctataataaa agaaatactg taacattcac    780

attacatggt aacatctttc caccctttca tttgtttttt gtttgatgac ttttttttctt    840

gtttaaattt atttcccttc ttttaaattt ggaatacatt atcatcatat ataaactaaa    900

atactaaaaa caggattaca caaatgataa ataataacac aaatatttat aaatctagct    960

gcaatatatt taaactagct atatcgatat tgtaaaataa aactagctgc attgatactg   1020

ataaaaaaat atcatgtgct ttctggactg atgatgcagt atacttttga cattgccttt   1080

attttatttt tcagaaaagc tttcttagtt ctgggttctt cattatttgt ttcccatctc   1140

cattgtgaat tgaatcattt gcttcgtgtc acaaatacaa tttagntagg tacatgcatt   1200

ggtcagattc acggtttatt atgtcatgac ttaagttcat ggtagtacat tacctgccac   1260

gcatgcatta tattggttag atttgatagg caaatttggt tgtcaacaat ataaatataa   1320

ataatgtttt tatattacga aataacagtg atcaaaacaa acagttttat ctttattaac   1380

aagatttgt ttttgtttga tgacgttttt taatgtttac gctttccccc ttcttttgaa   1440

tttagaacac tttatcatca taaaatcaaa tactaaaaaa attacatatt tcataaataa   1500

taacacaaat atttttaaaa aatctgaaat aataatgaac aatattacat attatcacga   1560

aaattcatta ataaaaatat tatataaata aaatgtaata gtagttatat gtaggaaaaa   1620

agtactgcac gcataatata tacaaaaaga ttaaaatgaa ctattataaa taataacact   1680

aaattaatgg tgaatcatat caaaataatg aaaaagtaaa taaaatttgt aattaacttc   1740

tatatgtatt acacacacaa ataataaata atagtaaaaa aaattatgat aaatatttac   1800

catctcataa gatatttaaa ataatgataa aaatatagat tattttttat gcaactagct   1860

agccaaaaag agaacacggg tatatataaa aagagtacct ttaaattcta ctgtacttcc   1920

tttattcctg acgtttttat atcaagtgga catacgtgaa gattttaatt atcagtctaa   1980

atatttcatt agcacttaat acttttctgt tttattccta tcctataagt agtcccgatt   2040
```

```
ctcccaacat tgcttattca cacaactaac taagaaagtc ttccatagcc ccccaagcgg   2100
ccgcgacaca agtgtgagag tactaaataa atgctttggt tgtacgaaat cattacacta   2160
aataaaataa tcaaagctta tatatgcctt ccgctaaggc cgaatgcaaa gaaattggtt   2220
ctttctcgtt atcttttgcc acttttacta gtacgtatta attactactt aatcatcttt   2280
gtttacggct cattatatcc gtacgtcgag tcgacctgca ggcatgcaag cttggcgtaa   2340
tcatggtcat agctgtttcc tgtgtgaaat tgttatccgc tcacaattcc acacaacata   2400
cgagccggaa gcataaagtg taaagcctgg ggtgcctaat gagtgagcta actcacatta   2460
attgcgttgc gctcactgcc cgctttccag tcgggaaacc tgtcgtgcca gctgcattaa   2520
tgaatcggcc aacgcgcggg gagaggcggt ttgcgtattg ggcgctcttc cgcttcctcg   2580
ctcactgact cgctgcgctc ggtcgttcgg ctgcggcgag cggtatcagc tcactcaaag   2640
gcggtaatac ggttatccac agaatcaggg gataacgcag gaaagaacat gtgagcaaaa   2700
ggccagcaaa aggccaggaa ccgtaaaaag gccgcgttgc tggcgttttt ccataggctc   2760
cgcccccctg acgagcatca caaaaatcga cgctcaagtc agaggtggcg aaacccgaca   2820
ggactataaa gataccaggc gtttccccct ggaagctccc tcgtgcgctc tcctgttccg   2880
accctgccgc ttaccggata cctgtccgcc tttctccctt cgggaagcgt ggcgctttct   2940
catagctcac gctgtaggta tctcagttcg gtgtaggtcg ttcgctccaa gctgggctgt   3000
gtgcacgaac cccccgttca gcccgaccgc tgcgccttat ccggtaacta tcgtcttgag   3060
tccaacccgg taagacacga cttatcgcca ctggcagcag ccactggtaa caggattagc   3120
agagcgaggt atgtaggcgg tgctacagag ttcttgaagt ggtggcctaa ctacggctac   3180
actagaagga cagtatttgg tatctgcgct ctgctgaagc cagttacctt cggaaaaaga   3240
gttggtagct cttgatccgg caaacaaacc accgctggta gcggtggttt ttttgtttgc   3300
aagcagcaga ttacgcgcag aaaaaaagga tctcaagaag atcctttgat cttttctacg   3360
gggtctgacg ctcagtggaa cgaaaactca cgttaaggga ttttggtcat gagattatca   3420
aaaaggatct tcacctagat ccttttaaat taaaaatgaa gttttaaatc aatctaaagt   3480
atatatgagt aaacttggtc tgacagttac caatgcttaa tcagtgaggc acctatctca   3540
gcgatctgtc tatttcgttc atccatagtt gcctgactcc ccgtcgtgta gataactacg   3600
atacgggagg gcttaccatc tggccccagt gctgcaatga taccgcgaga cccacgctca   3660
ccggctccag atttatcagc aataaaccag ccagccggaa gggccgagcg cagaagtggt   3720
cctgcaactt tatccgcctc catccagtct attaattgtt gccgggaagc tagagtaagt   3780
agttcgccag ttaatagttt gcgcaacgtt gttgccattg ctacaggcat cgtggtgtca   3840
cgctcgtcgt ttggtatggc ttcattcagc tccggttccc aacgatcaag gcgagttaca   3900
tgatccccca tgttgtgcaa aaaagcggtt agctccttcg gtcctccgat cgttgtcaga   3960
agtaagttgg ccgcagtgtt atcactcatg gttatggcag cactgcataa ttctcttact   4020
gtcatgccat ccgtaagatg cttttctgtg actggtgagt actcaaccaa gtcattctga   4080
gaatagtgta tgcggcgacc gagttgctct tgcccggcgt caatacggga taataccgcg   4140
ccacatagca gaactttaaa agtgctcatc attggaaaac gttcttcggg gcgaaaactc   4200
tcaaggatct taccgctgtt gagatccagt tcgatgtaac ccactcgtgc acccaactga   4260
tcttcagcat cttttacttt caccagcgtt tctgggtgag caaaaacagg aaggcaaaat   4320
gccgcaaaaa agggaataag ggcgacacgg aaatgttgaa tactcatact cttccttttt   4380
caatattatt gaagcattta tcagggttat tgtctcatga gcggatacat atttgaatgt   4440
```

```
atttagaaaa ataaacaaat aggggttccg cgcacatttc cccgaaaagt gccacctgac   4500

gtctaagaaa ccattattat catgacatta acctataaaa ataggcgtat cacgaggccc   4560

tttcgtctcg cgcgtttcgg tgatgacggt gaaaacctct gacacatgca gctcccggag   4620

acggtcacag cttgtctgta agcggatgcc gggagcagac aagcccgtca gggcgcgtca   4680

gcgggtgttg gcgggtgtcg gggctggctt aactatgcgg catcagagca gattgtactg   4740

agagtgcacc atatgcggtg tgaaataccg cacagatgcg taaggagaaa ataccgcatc   4800

aggcgccatt cgccattcag gctgcgcaac tgttgggaag ggcgatcggt gcgggcctct   4860

tcgctattac gccagctggc gaaaggggga tgtgctgcaa ggcgattaag ttgggtaacg   4920

ccagggtttt cccagtcacg acgttgtaaa acgacggcca gtgaattcga gctcggtacc   4980

cggggatcct                                                          4990
```

<210> SEQ ID NO 98
<211> LENGTH: 3982
<212> TYPE: DNA
<213> ORGANISM: Artificial Sequence
<220> FEATURE:
<223> OTHER INFORMATION: Plasmid pKR163

<400> SEQUENCE: 98

```
gtacgaaacc aactgcgttt ggggctccag attaaacgac gccgtttcgt tcctttcgct     60

tcacggctta acgatgtcgt ttctgtctgt gcccaaaaaa taaaggcatt tgttatttgc    120

accagatatt tactaagtgc accctagttt gacaagtagg cgataattac aaatagatgc    180

ggtgcaaata ataaattttg aaggaaataa ttacaaaaga acagaactta tatttacttt    240

attttaaaaa actaaaatga aagaacaaaa aaagtaaaaa atacaaaaaa tgtgctttaa    300

ccactttcat tatttgttac agaaagtatg attctactca aattgatctg ttgtatctgg    360

tgctgccttg tcacactggc gatttcaatc ccctaaagat atggtgcaaa ctgcgaagtg    420

atcaatatct gctcggttaa tttagattaa ttaataatat tcaacgtgat gtaccaaaaa    480

aagacaattt tttgctccat tgacaaatta aacctcatca aggtaatttc caaacctata    540

agcaaaaaaa tttcacatta attggcccgc aatcctatta gtcttattat actagagtag    600

gaaaaaaaac aattacacaa cttgtcttat tattctctat gctaatgaat atttttccct    660

tttgttagaa atcagtgttt cctaatttat tgagtattaa ttccactcac cgcatatatt    720

taccgttgaa taagaaaatt ttacacataa ttctttttaa gataaataat ttttttatac    780

tagatcttat atgattacgt gaagccaagt gggttatact aatgatatat aatgtttgat    840

agtaatcagt ttataaacca aatgcatgga aatgttacgt ggaagcacgt aaattaacaa    900

gcattgaagc aaatgcagcc accgcaccaa aaccacccca cttcacttcc acgtaccata    960

ttccatgcaa ctacaacacc ctaaaacttc aataaatgcc cccaccttca cttcacttca   1020

cccatcaata gcaagcggcc gcgaagttaa aagcaatgtt gtcacttgtc gtactaacac   1080

atgatgtgat agtttatgct agctagctat aacataagct gtctctgagt gtgttgtata   1140

ttaataaaga tcatcactgg tgaatggtga tcgtgtacgt accctactta gtaggcaatg   1200

gaagcactta gagtgtgctt tgtgcatggc cttgcctctg ttttgagact tttgtaatgt   1260

tttcgagttt aaatctttgc ctttgcgtac gtcgagtcga cctgcaggca tgcaagcttg   1320

gcgtaatcat ggtcatagct gtttcctgtg tgaaattgtt atccgctcac aattccacac   1380

aacatacgag ccggaagcat aaagtgtaaa gcctggggtg cctaatgagt gagctaactc   1440

acattaattg cgttgcgctc actgcccgct ttccagtcgg gaaacctgtc gtgccagctg   1500
```

-continued cattaatgaa tcggccaacg cgcggggaga ggcggtttgc gtattgggcg ctcttccgct 1560
tcctcgctca ctgactcgct gcgctcggtc gttcggctgc ggcgagcggt atcagctcac 1620
tcaaaggcgg taatacggtt atccacagaa tcaggggata acgcaggaaa gaacatgtga 1680
gcaaaaggcc agcaaaaggc caggaaccgt aaaaaggccg cgttgctggc gtttttccat 1740
aggctccgcc cccctgacga gcatcacaaa aatcgacgct caagtcagag gtggcgaaac 1800
ccgacaggac tataaagata ccaggcgttt ccccctggaa gctccctcgt gcgctctcct 1860
gttccgaccc tgccgcttac cggatacctg tccgcctttc tcccttcggg aagcgtggcg 1920
ctttctcata gctcacgctg taggtatctc agttcggtgt aggtcgttcg ctccaagctg 1980
ggctgtgtgc acgaaccccc cgttcagccc gaccgctgcg ccttatccgg taactatcgt 2040
cttgagtcca acccggtaag acacgactta tcgccactgg cagcagccac tggtaacagg 2100
attagcagag cgaggtatgt aggcggtgct acagagttct tgaagtggtg gcctaactac 2160
ggctacacta gaaggacagt atttggtatc tgcgctctgc tgaagccagt taccttcgga 2220
aaaagagttg gtagctcttg atccggcaaa caaaccaccg ctggtagcgg tggttttttt 2280
gtttgcaagc agcagattac gcgcagaaaa aaaggatctc aagaagatcc tttgatcttt 2340
tctacggggt ctgacgctca gtggaacgaa aactcacgtt aagggatttt ggtcatgaga 2400
ttatcaaaaa ggatcttcac ctagatcctt ttaaattaaa aatgaagttt taaatcaatc 2460
taaagtatat atgagtaaac ttggtctgac agttaccaat gcttaatcag tgaggcacct 2520
atctcagcga tctgtctatt tcgttcatcc atagttgcct gactccccgt cgtgtagata 2580
actacgatac gggagggctt accatctggc cccagtgctg caatgatacc gcgagaccca 2640
cgctcaccgg ctccagattt atcagcaata aaccagccag ccggaagggc cgagcgcaga 2700
agtggtcctg caactttatc cgcctccatc cagtctatta attgttgccg ggaagctaga 2760
gtaagtagtt cgccagttaa tagtttgcgc aacgttgttg ccattgctac aggcatcgtg 2820
gtgtcacgct cgtcgtttgg tatggcttca ttcagctccg gttcccaacg atcaaggcga 2880
gttacatgat cccccatgtt gtgcaaaaaa gcggttagct ccttcggtcc tccgatcgtt 2940
gtcagaagta agttggccgc agtgttatca ctcatggtta tggcagcact gcataattct 3000
cttactgtca tgccatccgt aagatgcttt tctgtgactg gtgagtactc aaccaagtca 3060
ttctgagaat agtgtatgcg gcgaccgagt tgctcttgcc cggcgtcaat acgggataat 3120
accgcgccac atagcagaac tttaaaagtg ctcatcattg gaaaacgttc ttcggggcga 3180
aaactctcaa ggatcttacc gctgttgaga tccagttcga tgtaacccac tcgtgcaccc 3240
aactgatctt cagcatcttt tactttcacc agcgtttctg ggtgagcaaa aacaggaagg 3300
caaaatgccg caaaaaaggg aataagggcg acacggaaat gttgaatact catactcttc 3360
ctttttcaat attattgaag catttatcag ggttattgtc tcatgagcgg atacatattt 3420
gaatgtattt agaaaaataa acaaataggg gttccgcgca catttccccg aaaagtgcca 3480
cctgacgtct aagaaaccat tattatcatg acattaacct ataaaaatag gcgtatcacg 3540
aggccctttc gtctcgcgcg tttcggtgat gacggtgaaa acctctgaca catgcagctc 3600
ccggagacgg tcacagcttg tctgtaagcg gatgccggga gcagacaagc ccgtcagggc 3660
gcgtcagcgg gtgttggcgg gtgtcggggc tggcttaact atgcggcatc agagcagatt 3720
gtactgagag tgcaccatat gcggtgtgaa ataccgcaca gatgcgtaag gagaaaatac 3780
cgcatcaggc gccattcgcc attcaggctg cgcaactgtt gggaagggcg atcggtgcgg 3840
gcctcttcgc tattacgcca gctggcgaaa gggggatgtg ctgcaaggcg attaagttgg 3900

-continued

```
gtaacgccag ggttttccca gtcacgacgt tgtaaaacga cggccagtga attcgagctc   3960

ggtacccggg gatcctctag ac                                            3982


<210> SEQ ID NO 99
<211> LENGTH: 8878
<212> TYPE: DNA
<213> ORGANISM: Artificial Sequence
<220> FEATURE:
<223> OTHER INFORMATION: Plasmid pY34

<400> SEQUENCE: 99

ggccgcacag gccgcacaat ggcgactcga cagcgaactg ccaccactgt tgtggtcgag     60

gaccttccca aggtcactct tgaggccaag tctgaacctg tgttccccga tatcaagacc    120

atcaaggatg ccattcccgc gcactgcttc cagccctcgc tcgtcacctc attctactac    180

gtcttccgcg attttgccat ggtctctgcc ctcgtctggg ctgctctcac ctacatcccc    240

agcatccccg accagaccct ccgcgtcgca gcttggatgg tctacggctt cgtccagggt    300

ctgttctgca ccggtgtctg gattctcggc catgagtgcg gccacggtgc tttctctctc    360

cacggaaagg tcaacaatgt gaccggctgg ttcctccact cgttcctcct cgtcccctac    420

ttcagctgga agtactctca ccaccgccac caccgcttca ccggccacat ggatctcgac    480

atggctttcg tccccaagac tgagcccaag ccctccaagt cgctcatgat tgctggcatt    540

gacgtcgccg agcttgttga ggacaccccc gctgctcaga tggtcaagct catcttccac    600

cagcttttcg gatggcaggc gtacctcttc ttcaacgcta gctctggcaa gggcagcaag    660

cagtgggagc ccaagactgg cctctccaag tggttccgag tcagtcactt cgagcctacc    720

agcgctgtct tccgccccaa cgaggccatc ttcatcctca tctccgatat cggtcttgct    780

ctaatgggaa ctgctctgta ctttgcttcc aagcaagttg gtgtttcgac cattctcttc    840

ctctaccttg ttccctacct gtgggttcac cactggctcg ttgccattac ctacctccac    900

caccaccaca ccgagctccc tcactacacc gctgagggct ggacctacgt caagggagct    960

ctcgccactg tcgaccgtga gtttggcttc atcggaaagc acctcttcca cggtatcatt   1020

gagaagcacg ttgttcacca tctcttccct aagatcccct tctacaaggc tgacgaggcc   1080

accgaggcca tcaagcccgt cattggcgac cactactgcc acgacgaccg aagcttcctg   1140

ggccagctgt ggaccatctt cggcacgctc aagtacgtcg agcacgaccc tgcccgaccc   1200

ggtgccatgc gatggaacaa ggactaggct aggcggccgc caccgcggcc cgagattccg   1260

gcctcttcgg ccgccaagcg acccgggtgg acgtctagag gtacctagca attaacagat   1320

agtttgccgg tgataattct cttaacctcc cacactcctt tgacataacg atttatgtaa   1380

cgaaactgaa atttgaccag atattgtgtc cgcggtggag ctccagcttt tgttcccttt   1440

agtgagggtt aatttcgagc ttggcgtaat catggtcata gctgtttcct gtgtgaaatt   1500

gttatccgct cacaattcca cacaacgtac gagccggaag cataaagtgt aaagcctggg   1560

gtgcctaatg agtgagctaa ctcacattaa ttgcgttgcg ctcactgccc gctttccagt   1620

cgggaaacct gtcgtgccag ctgcattaat gaatcggcca acgcgcgggg agaggcggtt   1680

tgcgtattgg gcgctcttcc gcttcctcgc tcactgactc gctgcgctcg gtcgttcggc   1740

tgcggcgagc ggtatcagct cactcaaagg cggtaatacg gttatccaca gaatcagggg   1800

ataacgcagg aaagaacatg tgagcaaaag gccagcaaaa ggccaggaac cgtaaaaagg   1860

ccgcgttgct ggcgtttttc cataggctcc gcccccctga cgagcatcac aaaaatcgac   1920

gctcaagtca gaggtggcga aacccgacag gactataaag ataccaggcg tttccccctg   1980
```

-continued

```
gaagctccct cgtgcgctct cctgttccga ccctgccgct taccggatac ctgtccgcct   2040
ttctcccttc gggaagcgtg gcgctttctc atagctcacg ctgtaggtat ctcagttcgg   2100
tgtaggtcgt tcgctccaag ctgggctgtg tgcacgaacc ccccgttcag cccgaccgct   2160
gcgccttatc cggtaactat cgtcttgagt ccaacccggt aagacacgac ttatcgccac   2220
tggcagcagc cactggtaac aggattagca gagcgaggta tgtaggcggt gctacagagt   2280
tcttgaagtg gtggcctaac tacggctaca ctagaaggac agtatttggt atctgcgctc   2340
tgctgaagcc agttaccttc ggaaaaagag ttggtagctc ttgatccggc aaacaaacca   2400
ccgctggtag cggtggtttt tttgtttgca agcagcagat tacgcgcaga aaaaaaggat   2460
ctcaagaaga tcctttgatc ttttctacgg ggtctgacgc tcagtggaac gaaaactcac   2520
gttaagggat tttggtcatg agattatcaa aaaggatctt cacctagatc cttttaaatt   2580
aaaaatgaag ttttaaatca atctaaagta tatatgagta aacttggtct gacagttacc   2640
aatgcttaat cagtgaggca cctatctcag cgatctgtct atttcgttca tccatagttg   2700
cctgactccc cgtcgtgtag ataactacga tacgggaggg cttaccatct ggccccagtg   2760
ctgcaatgat accgcgagac ccacgctcac cggctccaga tttatcagca ataaaccagc   2820
cagccggaag ggccgagcgc agaagtggtc ctgcaacttt atccgcctcc atccagtcta   2880
ttaattgttg ccgggaagct agagtaagta gttcgccagt taatagtttg cgcaacgttg   2940
ttgccattgc tacaggcatc gtggtgtcac gctcgtcgtt tggtatggct tcattcagct   3000
ccggttccca acgatcaagg cgagttacat gatcccccat gttgtgcaaa aaagcggtta   3060
gctccttcgg tcctccgatc gttgtcagaa gtaagttggc cgcagtgtta tcactcatgg   3120
ttatggcagc actgcataat tctcttactg tcatgccatc cgtaagatgc ttttctgtga   3180
ctggtgagta ctcaaccaag tcattctgag aatagtgtat gcggcgaccg agttgctctt   3240
gcccggcgtc aatacgggat aataccgcgc cacatagcag aactttaaaa gtgctcatca   3300
ttggaaaacg ttcttcgggg cgaaaactct caaggatctt accgctgttg agatccagtt   3360
cgatgtaacc cactcgtgca cccaactgat cttcagcatc ttttactttc accagcgttt   3420
ctgggtgagc aaaaacagga aggcaaaatg ccgcaaaaaa gggaataagg gcgacacgga   3480
aatgttgaat actcatactc ttcctttttc aatattattg aagcatttat cagggttatt   3540
gtctcatgag cggatacata tttgaatgta tttagaaaaa taaacaaata ggggttccgc   3600
gcacatttcc ccgaaaagtg ccacctgacg cgccctgtag cggcgcatta agcgcggcgg   3660
gtgtggtggt tacgcgcagc gtgaccgcta cacttgccag cgccctagcg cccgctcctt   3720
tcgctttctt cccttccttt ctcgccacgt tcgccggctt tccccgtcaa gctctaaatc   3780
gggggctccc tttagggttc cgatttagtg ctttacggca cctcgacccc aaaaaacttg   3840
attagggtga tggttcacgt agtgggccat cgccctgata gacggttttt cgccctttga   3900
cgttggagtc cacgttcttt aatagtggac tcttgttcca aactggaaca acactcaacc   3960
ctatctcggt ctattctttt gatttataag ggattttgcc gatttcggcc tattggttaa   4020
aaaatgagct gatttaacaa aaatttaacg cgaattttaa caaaatatta acgcttacaa   4080
tttccattcg ccattcaggc tgcgcaactg ttgggaaggg cgatcggtgc gggcctcttc   4140
gctattacgc cagctggcga aagggggatg tgctgcaagg cgattaagtt gggtaacgcc   4200
agggttttcc cagtcacgac gttgtaaaac gacggccagt gaattgtaat acgactcact   4260
atagggcgaa ttgggtaccg ggcccccccct cgaggtcgat ggtgtcgata agcttgatat   4320
cgaattcatg tcacacaaac cgatcttcgc ctcaaggaaa cctaattcta catccgagag   4380
```

actgccgaga tccagtctac actgattaat tttcgggcca ataatttaaa aaaatcgtgt 4440
tatataatat tatatgtatt atatatatac atcatgatga tactgacagt catgtcccat 4500
tgctaaatag acagactcca tctgccgcct ccaactgatg ttctcaatat ttaaggggtc 4560
atctcgcatt gtttaataat aaacagactc catctaccgc ctccaaatga tgttctcaaa 4620
atatattgta tgaacttatt tttattactt agtattatta gacaacttac ttgctttatg 4680
aaaaacactt cctatttagg aaacaattta taatggcagt tcgttcattt aacaatttat 4740
gtagaataaa tgttataaat gcgtatggga aatcttaaat atggatagca taaatgatat 4800
ctgcattgcc taattcgaaa tcaacagcaa cgaaaaaaat cccttgtaca acataaatag 4860
tcatcgagaa atatcaacta tcaaagaaca gctattcaca cgttactatt gagattatta 4920
ttggacgaga atcacacact caactgtctt tctctcttct agaaatacag gtacaagtat 4980
gtactattct cattgttcat acttctagtc atttcatccc acatattcct tggatttctc 5040
tccaatgaat gacattctat cttgcaaatt caacaattat aataagatat accaaagtag 5100
cggtatagtg gcaatcaaaa agcttctctg gtgtgcttct cgtatttatt tttattctaa 5160
tgatccatta aaggtatata tttatttctt gttatataat ccttttgttt attacatggg 5220
ctggatacat aaaggtattt tgatttaatt ttttgcttaa attcaatccc ccctcgttca 5280
gtgtcaactg taatggtagg aaattaccat acttttgaag aagcaaaaaa aatgaaagaa 5340
aaaaaaaatc gtatttccag gttagacgtt ccgcagaatc tagaatgcgg tatgcggtac 5400
attgttcttc gaacgtaaaa gttgcgctcc ctgagatatt gtacattttt gcttttacaa 5460
gtacaagtac atcgtacaac tatgtactac tgttgatgca tccacaacag tttgttttgt 5520
tttttttgt ttttttttt tctaatgatt cattaccgct atgtatacct acttgtactt 5580
gtagtaagcc gggttattgg cgttcaatta atcatagact tatgaatctg cacggtgtgc 5640
gctgcgagtt acttttagct tatgcatgct acttgggtgt aatattggga tctgttcgga 5700
aatcaacgga tgctcaaccg atttcgacag taataatttg aatcgaatcg gagcctaaaa 5760
tgaacccgag tatatctcat aaaattctcg gtgagaggtc tgtgactgtc agtacaaggt 5820
gccttcatta tgccctcaac cttaccatac ctcactgaat gtagtgtacc tctaaaaatg 5880
aaatacagtg ccaaaagcca aggcactgag ctcgtctaac ggacttgata tacaaccaat 5940
taaaacaaat gaaaagaaat acagttcttt gtatcatttg taacaattac cctgtacaaa 6000
ctaaggtatt gaaatcccac aatattccca aagtccaccc ctttccaaat tgtcatgcct 6060
acaactcata taccaagcac taacctacca aacaccacta aaaccccaca aaatatatct 6120
taccgaatat acagtaacaa gctaccacca cactcgttgg gtgcagtcgc cagcttaaag 6180
atatctatcc acatcagcca caactccctt cctttaataa accgactaca cccttggcta 6240
ttgaggttat gagtgaatat actgtagaca agacactttc aagaagactg tttccaaaac 6300
gtaccactgt cctccactac aaacacaccc aatctgcttc ttctagtcaa ggttgctaca 6360
ccggtaaatt ataaatcatc atttcattag cagggcaggg cccttttat agagtcttat 6420
acactagcgg accctgccgg tagaccaacc cgcaggcgcg tcagtttgct ccttccatca 6480
atgcgtcgta gaaacgactt actccttctt gagcagctcc ttgaccttgt tggcaacaag 6540
tctccgacct cggaggtgga ggaagagcct ccgatatcgg cggtagtgat accagcctcg 6600
acggactcct tgacggcagc ctcaacagcg tcaccggcgg gcttcatgtt aagagagaac 6660
ttgagcatca tggcggcaga cagaatggtg gcaatggggt tgaccttctg cttgccgaga 6720
tcgggggcag atccgtgaca gggctcgtac agaccgaacg cctcgttggt gtcgggcaga 6780
gaagccagag aggcggaggg cagcagaccc agagaaccgg ggatgacgga ggcctcgtcg 6840
gagatgatat cgccaaacat gttggtggtg atgatgatac cattcatctt ggagggctgc 6900
ttgatgagga tcatggcggc cgagtcgatc agctggtggt tgagctcgag ctggggggaat 6960 tcgtccttga ggactcgagt gacagtcttt cgccaaagtc gagaggaggc cagcacgttg 7020
gccttgtcaa gagaccacac gggaagaggg gggttgtgct gaagggccag gaaggcggcc 7080
attcgggcaa ttcgctcaac ctcaggaacg gagtaggtct cggtgtcgga agcgacgcca 7140
gatccgtcat cctcctttcg ctctccaaag tagatacctc cgacgagctc tcggacaatg 7200
atgaagtcgg tgccctcaac gtttcggatg ggggagagat cggcgagctt gggcgacagc 7260
agctggcagg gtcgcaggtt ggcgtacagg ttcaggtcct ttcgcagctt gaggagaccc 7320
tgctcgggtc gcacgtcggt tcgtccgtcg ggagtggtcc atacggtgtt ggcagcgcct 7380
ccgacagcac cgagcataat agagtcagcc tttcggcaga tgtcgagagt agcgtcggtg 7440
atgggctcgc cctccttctc aatggcagct cctccaatga gtcggtcctc aaacacaaac 7500
tcggtgccgg aggcctcagc aacagacttg agcaccttga cggcctcggc aatcacctcg 7560
gggccacaga agtcgccgcc gagaagaaca atcttcttgg agtcagtctt ggtcttctta 7620
gtttcgggtt ccattgtgga tgtgtgtggt tgtatgtgtg atgtggtgtg tggagtgaaa 7680
atctgtggct ggcaaacgct cttgtatata tacgcacttt tgcccgtgct atgtggaaga 7740
ctaaacctcc gaagattgtg actcaggtag tgcggtatcg gctagggacc caaaccttgt 7800
cgatgccgat agcgctatcg aacgtacccc agccggccgg gagtatgtcg gaggggacat 7860
acgagatcgt caagggtttg tggccaactg gtatttaaat gatgtcgacg cagtaggatg 7920
tcctgcacgg gtctttttgt ggggtgtgga gaaaggggtg cttggagatg gaagccggta 7980
gaaccgggct gcttgtgctt ggagatggaa gccggtagaa ccgggctgct tggggggatt 8040
tggggccgct gggctccaaa gaggggtagg catttcgttg ggttacgta attgcggcat 8100 ttgggtcctg cgcgcatgtc ccattggtca gaattagtcc ggataggaga cttatcagcc 8160
aatcacagcg ccggatccac ctgtaggttg ggttgggtgg gagcacccct ccacagagta 8220
gagtcaaaca gcagcagcaa catgatagtt gggggtgtgc gtgttaaagg aaaaaaaaga 8280
agcttgggtt atattcccgc tctatttaga ggttgcggga tagacgccga cggagggcaa 8340
tggcgccatg gaaccttgcg gatatcgata cgccgcggcg gactgcgtcc gaaccagctc 8400
cagcagcgtt ttttccgggc cattgagccg actgcgaccc cgccaacgtg tcttggccca 8460
cgcactcatg tcatgttggt gttgggaggc cactttttaa gtagcacaag gcacctagct 8520
cgcagcaagg tgtccgaacc aaagaagcgg ctgcagtggt gcaaacgggg cggaaacggc 8580
gggaaaaagc cacgggggca cgaattgagg cacgccctcg aatttgagac gagtcacggc 8640
cccattcgcc cgcgcaatgg ctcgccaacg cccggtcttt tgcaccacat caggttaccc 8700
caagccaaac ctttgtgtta aaaagcttaa catattatac cgaacgtagg tttgggcggg 8760
cttgctccgt ctgtccaagg caacatttat ataagggtct gcatcgccgg ctcaattgaa 8820 tctttttct tcttctcttc tctatattca ttcttgaatt aaacacacat caatccgc 8878

<210> SEQ ID NO 100
<211> LENGTH: 5207
<212> TYPE: DNA
<213> ORGANISM: Artificial Sequence
<220> FEATURE:
<223> OTHER INFORMATION: Plasmid pKR863

<400> SEQUENCE: 100

-continued

```
ggccgcgaag ttaaaagcaa tgttgtcact tgtcgtacta acacatgatg tgatagttta     60
tgctagctag ctataacata agctgtctct gagtgtgttg tatattaata aagatcatca    120
ctggtgaatg gtgatcgtgt acgtacccta cttagtaggc aatggaagca cttagagtgt    180
gctttgtgca tggccttgcc tctgttttga gacttttgta atgttttcga gtttaaatct    240
ttgcctttgc gtacgtcgag tcgacctgca ggcatgcaag cttggcgtaa tcatggtcat    300
agctgtttcc tgtgtgaaat tgttatccgc tcacaattcc acacaacata cgagccggaa    360
gcataaagtg taaagcctgg ggtgcctaat gagtgagcta actcacatta attgcgttgc    420
gctcactgcc cgctttccag tcgggaaacc tgtcgtgcca gctgcattaa tgaatcggcc    480
aacgcgcggg gagaggcggt ttgcgtattg ggcgctcttc cgcttcctcg ctcactgact    540
cgctgcgctc ggtcgttcgg ctgcggcgag cggtatcagc tcactcaaag gcggtaatac    600
ggttatccac agaatcaggg gataacgcag gaaagaacat gtgagcaaaa ggccagcaaa    660
aggccaggaa ccgtaaaaag gccgcgttgc tggcgttttt ccataggctc cgcccccctg    720
acgagcatca caaaaatcga cgctcaagtc agaggtggcg aaacccgaca ggactataaa    780
gataccaggc gtttccccct ggaagctccc tcgtgcgctc tcctgttccg accctgccgc    840
ttaccggata cctgtccgcc tttctccctt cgggaagcgt ggcgctttct catagctcac    900
gctgtaggta tctcagttcg gtgtaggtcg ttcgctccaa gctgggctgt gtgcacgaac    960
cccccgttca gcccgaccgc tgcgccttat ccggtaacta tcgtcttgag tccaacccgg   1020
taagacacga cttatcgcca ctggcagcag ccactggtaa caggattagc agagcgaggt   1080
atgtaggcgg tgctacagag ttcttgaagt ggtggcctaa ctacggctac actagaagga   1140
cagtatttgg tatctgcgct ctgctgaagc cagttacctt cggaaaaaga gttggtagct   1200
cttgatccgg caaacaaacc accgctggta gcggtggttt ttttgtttgc aagcagcaga   1260
ttacgcgcag aaaaaaagga tctcaagaag atcctttgat cttttctacg gggtctgacg   1320
ctcagtggaa cgaaaactca cgttaaggga ttttggtcat gagattatca aaaaggatct   1380
tcacctagat ccttttaaat taaaaatgaa gttttaaatc aatctaaagt atatatgagt   1440
aaacttggtc tgacagttac caatgcttaa tcagtgaggc acctatctca gcgatctgtc   1500
tatttcgttc atccatagtt gcctgactcc ccgtcgtgta gataactacg atacgggagg   1560
gcttaccatc tggccccagt gctgcaatga taccgcgaga cccacgctca ccggctccag   1620
atttatcagc aataaaccag ccagccggaa gggccgagcg cagaagtggt cctgcaactt   1680
tatccgcctc catccagtct attaattgtt gccgggaagc tagagtaagt agttcgccag   1740
ttaatagttt gcgcaacgtt gttgccattg ctacaggcat cgtggtgtca cgctcgtcgt   1800
ttggtatggc ttcattcagc tccggttccc aacgatcaag gcgagttaca tgatccccca   1860
tgttgtgcaa aaaagcggtt agctccttcg gtcctccgat cgttgtcaga agtaagttgg   1920
ccgcagtgtt atcactcatg gttatggcag cactgcataa ttctcttact gtcatgccat   1980
ccgtaagatg cttttctgtg actggtgagt actcaaccaa gtcattctga gaatagtgta   2040
tgcggcgacc gagttgctct tgcccggcgt caatacggga taataccgcg ccacatagca   2100
gaactttaaa agtgctcatc attggaaaac gttcttcggg gcgaaaactc tcaaggatct   2160
taccgctgtt gagatccagt tcgatgtaac ccactcgtgc acccaactga tcttcagcat   2220
cttttacttt caccagcgtt tctgggtgag caaaaacagg aaggcaaaat gccgcaaaaa   2280
agggaataag ggcgacacgg aaatgttgaa tactcatact cttccttttt caatattatt   2340
gaagcattta tcagggttat tgtctcatga gcggatacat atttgaatgt atttagaaaa   2400
```

-continued

```
ataaacaaat aggggttccg cgcacatttc cccgaaaagt gccacctgac gtctaagaaa   2460
ccattattat catgacatta acctataaaa ataggcgtat cacgaggccc tttcgtctcg   2520
cgcgtttcgg tgatgacggt gaaaacctct gacacatgca gctcccggag acggtcacag   2580
cttgtctgta agcggatgcc gggagcagac aagcccgtca gggcgcgtca gcgggtgttg   2640
gcgggtgtcg gggctggctt aactatgcgg catcagagca gattgtactg agagtgcacc   2700
atatgcggtg tgaaataccg cacagatgcg taaggagaaa ataccgcatc aggcgccatt   2760
cgccattcag gctgcgcaac tgttgggaag ggcgatcggt gcgggcctct tcgctattac   2820
gccagctggc gaaaggggga tgtgctgcaa ggcgattaag ttgggtaacg ccagggtttt   2880
cccagtcacg acgttgtaaa acgacggcca gtgaattcga gctcggtacc cggggatcct   2940
ctagacgtac gaaaccaact gcgtttgggg ctccagatta aacgacgccg tttcgttcct   3000
ttcgcttcac ggcttaacga tgtcgtttct gtctgtgccc aaaaaataaa ggcatttgtt   3060
atttgcacca gatatttact aagtgcaccc tagtttgaca agtaggcgat aattacaaat   3120
agatgcggtg caaataataa attttgaagg aaataattac aaaagaacag aacttatatt   3180
tactttattt taaaaaacta aaatgaaaga acaaaaaaag taaaaaatac aaaaaatgtg   3240
ctttaaccac tttcattatt tgttacagaa agtatgattc tactcaaatt gatctgttgt   3300
atctggtgct gccttgtcac actggcgatt tcaatcccct aaagatatgg tgcaaactgc   3360
gaagtgatca atatctgctc ggttaattta gattaattaa taatattcaa cgtgatgtac   3420
caaaaaaaga caatttttg ctccattgac aaattaaacc tcatcaaggt aatttccaaa   3480
cctataagca aaaaaatttc acattaattg gcccgcaatc ctattagtct tattatacta   3540
gagtaggaaa aaaaacaatt acacaacttg tcttattatt ctctatgcta atgaatattt   3600
ttccctttg ttagaaatca gtgtttccta atttattgag tattaattcc actcaccgca   3660
tatatttacc gttgaataag aaaattttac acataattct ttttaagata aataattttt   3720
ttatactaga tcttatatga ttacgtgaag ccaagtgggt tatactaatg atatataatg   3780
tttgatagta atcagtttat aaaccaaatg catggaaatg ttacgtggaa gcacgtaaat   3840
taacaagcat tgaagcaaat gcagccaccg caccaaaacc accccacttc acttccacgt   3900
accatattcc atgcaactac aacaccctaa aacttcaata aatgccccca ccttcacttc   3960
acttcaccca tcaatagcaa gcggccgcac aatggcgact cgacagcgaa ctgccaccac   4020
tgttgtggtc gaggaccttc ccaaggtcac tcttgaggcc aagtctgaac ctgtgttccc   4080
cgatatcaag accatcaagg atgccattcc cgcgcactgc ttccagccct cgctcgtcac   4140
ctcattctac tacgtcttcc gcgattttgc catggtctct gccctcgtct gggctgctct   4200
cacctacatc cccagcatcc ccgaccagac cctccgcgtc gcagcttgga tggtctacgg   4260
cttcgtccag ggtctgttct gcaccggtgt ctggattctc ggccatgagt gcggccacgg   4320
tgctttctct ctccacggaa aggtcaacaa tgtgaccggc tggttcctcc actcgttcct   4380
cctcgtcccc tacttcagct ggaagtactc tcaccaccgc caccaccgct tcaccggcca   4440
catggatctc gacatggctt tcgtccccaa gactgagccc aagccctcca agtcgctcat   4500
gattgctggc attgacgtcg ccgagcttgt tgaggacacc cccgctgctc agatggtcaa   4560
gctcatcttc caccagcttt tcggatggca ggcgtacctc ttcttcaacg ctagctctgg   4620
caagggcagc aagcagtggg agcccaagac tggcctctcc aagtggttcc gagtcagtca   4680
cttcgagcct accagcgctg tcttccgccc caacgaggcc atcttcatcc tcatctccga   4740
tatcggtctt gctctaatgg gaactgctct gtactttgct tccaagcaag ttggtgtttc   4800
```

-continued gaccattctc ttcctctacc ttgttcccta cctgtgggtt caccactggc tcgttgccat 4860
tacctacctc caccaccacc acaccgagct ccctcactac accgctgagg gctggaccta 4920
cgtcaaggga gctctcgcca ctgtcgaccg tgagtttggc ttcatcggaa agcacctctt 4980
ccacggtatc attgagaagc acgttgttca ccatctcttc cctaagatcc ccttctacaa 5040
ggctgacgag gccaccgagg ccatcaagcc cgtcattggc gaccactact gccacgacga 5100
ccgaagcttc ctgggccagc tgtggaccat cttcggcacg ctcaagtacg tcgagcacga 5160
ccctgcccga cccggtgcca tgcgatggaa caaggactag gctaggc 5207

<210> SEQ ID NO 101
<211> LENGTH: 9035
<212> TYPE: DNA
<213> ORGANISM: Artificial Sequence
<220> FEATURE:
<223> OTHER INFORMATION: Plasmid pKR869

<400> SEQUENCE: 101
gtacgtctag aggatccgtc gacggcgcgc ccgatcatcc ggatatagtt cctcctttca 60
gcaaaaaacc cctcaagacc cgtttagagg ccccaagggg ttatgctagt tattgctcag 120
cggtggcagc agccaactca gcttcctttc gggctttgtt agcagccgga tcgatccaag 180
ctgtacctca ctattccttt gccctcggac gagtgctggg gcgtcggttt ccactatcgg 240
cgagtacttc tacacagcca tcggtccaga cggccgcgct tctgcgggcg atttgtgtac 300
gcccgacagt cccggctccg gatcggacga ttgcgtcgca tcgaccctgc gcccaagctg 360
catcatcgaa attgccgtca accaagctct gatagagttg gtcaagacca atgcggagca 420
tatacgcccg gagccgcggc gatcctgcaa gctccggatg cctccgctcg aagtagcgcg 480
tctgctgctc catacaagcc aaccacggcc tccagaagaa gatgttggcg acctcgtatt 540
gggaatcccc gaacatcgcc tcgctccagt caatgaccgc tgttatgcgg ccattgtccg 600
tcaggacatt gttggagccg aaatccgcgt gcacgaggtg ccggacttcg gggcagtcct 660
cggcccaaag catcagctca tcgagagcct gcgcgacgga cgcactgacg gtgtcgtcca 720
tcacagtttg ccagtgatac acatggggat cagcaatcgc gcatatgaaa tcacgccatg 780
tagtgtattg accgattcct tgcggtccga atgggccgaa cccgctcgtc tggctaagat 840
cggccgcagc gatcgcatcc atagcctccg cgaccggctg cagaacagcg ggcagttcgg 900
tttcaggcag gtcttgcaac gtgacaccct gtgcacggcg ggagatgcaa taggtcaggc 960
tctcgctgaa ttccccaatg tcaagcactt ccggaatcgg gagcgcggcc gatgcaaagt 1020
gccgataaac ataacgatct ttgtagaaac catcggcgca gctatttacc cgcaggacat 1080
atccacgccc tcctacatcg aagctgaaag cacgagattc ttcgccctcc gagagctgca 1140
tcaggtcgga gacgctgtcg aacttttcga tcagaaactt ctcgacagac gtcgcggtga 1200
gttcaggctt ttccatgggt atatctcctt cttaaagtta aacaaaatta tttctagagg 1260
gaaaccgttg tggtctccct atagtgagtc gtattaattt cgcgggatcg agatctgatc 1320
aacctgcatt aatgaatcgg ccaacgcgcg gggagaggcg gtttgcgtat tgggcgctct 1380
tccgcttcct cgctcactga ctcgctgcgc tcggtcgttc ggctgcggcg agcggtatca 1440
gctcactcaa aggcggtaat acggttatcc acagaatcag gggataacgc aggaaagaac 1500
atgtgagcaa aaggccagca aaaggccagg aaccgtaaaa aggccgcgtt gctggcgttt 1560
ttccataggc tccgcccccc tgacgagcat cacaaaaatc gacgctcaag tcagaggtgg 1620
cgaaacccga caggactata aagataccag gcgtttcccc ctggaagctc cctcgtgcgc 1680

-continued

```
tctcctgttc cgaccctgcc gcttaccgga tacctgtccg cctttctccc ttcgggaagc   1740
gtggcgcttt ctcaatgctc acgctgtagg tatctcagtt cggtgtaggt cgttcgctcc   1800
aagctgggct gtgtgcacga accccccgtt cagcccgacc gctgcgcctt atccggtaac   1860
tatcgtcttg agtccaaccc ggtaagacac gacttatcgc cactggcagc agccactggt   1920
aacaggatta gcagagcgag gtatgtaggc ggtgctacag agttcttgaa gtggtggcct   1980
aactacggct acactagaag gacagtattt ggtatctgcg ctctgctgaa gccagttacc   2040
ttcggaaaaa gagttggtag ctcttgatcc ggcaaacaaa ccaccgctgg tagcggtggt   2100
tttttgttt gcaagcagca gattacgcgc agaaaaaaag gatctcaaga agatcctttg   2160
atcttttcta cggggtctga cgctcagtgg aacgaaaact cacgttaagg gattttggtc   2220
atgacattaa cctataaaaa taggcgtatc acgaggccct ttcgtctcgc gcgtttcggt   2280
gatgacggtg aaaacctctg acacatgcag ctcccggaga cggtcacagc ttgtctgtaa   2340
gcggatgccg ggagcagaca agcccgtcag ggcgcgtcag cgggtgttgg cgggtgtcgg   2400
ggctggctta actatgcggc atcagagcag attgtactga gagtgcacca tatggacata   2460
ttgtcgttag aacgcggcta caattaatac ataaccttat gtatcataca catacgattt   2520
aggtgacact atagaacggc gcgccaagct gggtctagaa ctagaaacgt gatgccactt   2580
gttattgaag tcgattacag catctattct gttttactat ttataacttt gccatttctg   2640
acttttgaaa actatctctg gatttcggta tcgctttgtg aagatcgagc aaaagagacg   2700
ttttgtggac gcaatggtcc aaatccgttc tacatgaaca aattggtcac aatttccact   2760
aaaagtaaat aaatggcaag ttaaaaaagg aatatgcatt ttactgattg cctaggtgag   2820
ctccaagaga agttgaatct acacgtctac caaccgctaa aaaaagaaaa acattgatat   2880
gtaacctgat tccattagct tttgacttct tcaacagatt ctctacttag atttctaaca   2940
gaaatattat tactagcaca tcattttcag tctcactaca gcaaaaaatc caacggcaca   3000
atacagacaa caggagatat cagactacag agatagatag atgctactgc atgtagtaag   3060
ttaaataaaa ggaaaataaa atgtcttgct accaaaacta ctacagacta tgatgctcac   3120
cacaggccaa atcctgcaac taggacagca ttatcttata tatattgtac aaaacaagca   3180
tcaaggaaca tttggtctag gcaatcagta cctcgttcta ccatcaccct cagttatcac   3240
atccttgaag gatccattac tgggaatcat cggcaacaca tgctcctgat ggggcacaat   3300
gacatcaaga aggtaggggc caggggtgtc caacattctc tgaattgccg ctctaagctc   3360
ttccttcttc gtcactcgcg ctgccggtat cccacaagca tcagcaaact tgagcatgtt   3420
tgggaatatc tcgctctcgc tagacggatc tccaagatag gtgtgagctc tattggactt   3480
gtagaaccta tcctccaact gaaccaccat acccaaatgc tgattgttca acaacaatat   3540
cttaactggg agattctcca ctcttatagt ggccaactcc tgaacattca tgatgaaact   3600
accatcccca tcaatgtcaa ccacaacagc cccagggtta gcaacagcag caccaatagc   3660
cgcaggcaat ccaaaaccca tggctccaag accccctgag gtcaaccact gcctcggtct   3720
cttgtacttg taaaactgcg cagcccacat ttgatgctgc ccaaccccag tactaacaat   3780
agcatctcca ttagtcaact catcaagaac ctcgatagca tgctgcggag aaatcgcgtc   3840
ctggaatgtc ttgtaaccca atggaaactt gtgtttctgc acattaatct cttctctcca   3900
acctccaaga tcaaacttac cctccactcc tttctcctcc aaaatcatat taattccctt   3960
caaggccaac ttcaaatccg cgcaaaccga cacgtgcgcc tgcttgttct tcccaatctc   4020
ggcagaatca atatcaatgt gaacaatctt agccctacta gcaaaagcct caagcttccc   4080
```

-continued agtaacacgg tcatcaaacc ttaccccaaa ggcaagcaac aaatcactat tgtcaacagc 4140
atagttagca taaacagtac catgcatacc cagcatctga agggaatatt catcaccaat 4200
aggaaaagtt ccaagaccca ttaaagtgct agcaacggga ataccagtga gttcaacaaa 4260
gcgcctcaat tcagcactgg aattcaaact gccaccgccg acgtagagaa cgggcttttg 4320
ggcctccatg atgagtctga caatgtgttc caattgggcc tcggcggggg gcctgggcag 4380
cctggcgagg taaccgggga ggttaacggg ctcgtcccaa ttaggcacgg cgagttgctg 4440
ctgaacgtct ttgggaatgt cgatgaggac cggaccgggg cggccggagg tggcgacgaa 4500
gaaagcctcg gcgacgacgc gggggatgtc gtcgacgtcg aggatgaggt agttgtgctt 4560
cgtgatggat ctgctcacct ccacgatcgg ggtttcttgg aaggcgtcgg tgccgatcat 4620
ccggcgggcg acctggccgg tgatggcgac gactgggacg ctgtccatta aagcgtcggc 4680
gaggccgctc acgaggttgg tggcgccggg gccggaggtg gcaatgcaga cgccggggag 4740
gccggaggaa cgcgcgtagc cttcggcggc gaagacgccg ccctgctcgt ggcgcgggag 4800
cacgttgcgg atggcggcgg agcgcgtgag cgcctggtgg atctccatcg acgcaccgcc 4860
ggggtacgcg aacaccgtcg tcacgccctg cctctccagc gcctccacaa ggatgtccgc 4920
gcccttgcga ggttcgccgg aggcgaaccg tgacacgaag ggctccgtgg tcggcgcttc 4980
cttggtgaag ggcgccgccg tggggggttt ggagatggaa catttgattt tgagagcgtg 5040
gttgggtttg gtgagggttt gatgagagag agggagggtg gatctagtaa tgcgtttggg 5100
gaaggtgggg tgtgaagagg aagaagagaa tcgggtggtt ctggaagcgg tggccgccat 5160
tgtgttgtgt ggcatggtta tacttcaaaa actgcacaac aagcctagag ttagtaccta 5220
aacagtaaat ttacaacaga gagcaaagac acatgcaaaa atttcagcca taaaaaaagt 5280
tataatagaa tttaaagcaa aagtttcatt ttttaaacat atatacaaac aaactggatt 5340
tgaaggaagg gattaattcc cctgctcaaa gtttgaattc ctattgtgac ctatactcga 5400
ataaaattga agcctaagga atgtatgaga aacaagaaaa caaaacaaaa ctacagacaa 5460
acaagtacaa ttacaaaatt cgctaaaatt ctgtaatcac caaaccccat ctcagtcagc 5520
acaaggccca aggtttattt tgaaataaaa aaaaagtgat tttatttctc ataagctaaa 5580
agaaagaaag gcaattatga aatgatttcg actagatctg aaagtccaac gcgtattccg 5640
cagatattaa agaaagagta gagtttcaca tggatcctag atggacccag ttgaggaaaa 5700
agcaaggcaa agcaaaccag aagtgcaaga tccgaaattg aaccacggaa tctaggattt 5760
ggtagaggga gaagaaaagt accttgagag gtagaagaga agagaagagc agagagatat 5820
atgaacgagt gtgtcttggt ctcaactctg aagcgatacg agtttagagg ggagcattga 5880
gttccaattt atagggaaac cgggtggcag gggtgagtta atgacggaaa agcccctaag 5940
taacgagatt ggattgtggg ttagattcaa ccgtttgcat ccgcggctta gattggggaa 6000
gtcagagtga atctcaaccg ttgactgagt tgaaaattga atgtagcaac caattgagcc 6060
aaccccagcc tttgcccttt gattttgatt tgtttgttgc atactttta tttgtcttct 6120
ggttctgact ctctttctct cgtttcaatg ccaggttgcc tactcccaca ccactcacaa 6180
gaagattcta ctgttagtat taaatatttt ttaatgtatt aaatgatgaa tgcttttgta 6240
aacagaacaa gactatgtct aataagtgtc ttgcaacatt ttttaagaaa ttaaaaaaaa 6300
tatatttatt atcaaaatca aatgtatgaa aaatcatgaa taatataatt tttatacattt 6360
ttttaaaaaa tcttttaatt tcttaattaa tatcttaaaa ataatgatta atatttaacc 6420
caaaataatt agtatgattg gtaaggaaga tatccatgtt atgtttggat gtgagtttga 6480

-continued

```
tctagagcaa agcttactag agtcgacctg caggtcgact cgacgtacga aaccaactgc   6540
gtttggggct ccagattaaa cgacgccgtt tcgttccttt cgcttcacgg cttaacgatg   6600
tcgtttctgt ctgtgcccaa aaaataaagg catttgttat ttgcaccaga tatttactaa   6660
gtgcacccta gtttgacaag taggcgataa ttacaaatag atgcggtgca aataataaat   6720
tttgaaggaa ataattacaa aagaacagaa cttatattta ctttatttta aaaaactaaa   6780
atgaaagaac aaaaaaagta aaaaatacaa aaaatgtgct ttaaccactt tcattatttg   6840
ttacagaaag tatgattcta ctcaaattga tctgttgtat ctggtgctgc cttgtcacac   6900
tggcgatttc aatcccctaa agatatggtg caaactgcga agtgatcaat atctgctcgg   6960
ttaatttaga ttaattaata atattcaacg tgatgtacca aaaaaagaca attttttgct   7020
ccattgacaa attaaacctc atcaaggtaa tttccaaacc tataagcaaa aaaatttcac   7080
attaattggc ccgcaatcct attagtctta ttatactaga gtaggaaaaa aaacaattac   7140
acaacttgtc ttattattct ctatgctaat gaatattttt cccttttgtt agaaatcagt   7200
gtttcctaat ttattgagta ttaattccac tcaccgcata tatttaccgt tgaataagaa   7260
aattttacac ataattcttt ttaagataaa taattttttt atactagatc ttatatgatt   7320
acgtgaagcc aagtgggtta tactaatgat atataatgtt tgatagtaat cagtttataa   7380
accaaatgca tggaaatgtt acgtggaagc acgtaaatta acaagcattg aagcaaatgc   7440
agccaccgca ccaaaaccac cccacttcac ttccacgtac catattccat gcaactacaa   7500
caccctaaaa cttcaataaa tgcccccacc ttcacttcac ttcacccatc aatagcaagc   7560
ggccgcacaa tggcgactcg acagcgaact gccaccactg ttgtggtcga ggaccttccc   7620
aaggtcactc ttgaggccaa gtctgaacct gtgttccccg atatcaagac catcaaggat   7680
gccattcccg cgcactgctt ccagccctcg ctcgtcacct cattctacta cgtcttccgc   7740
gattttgcca tggtctctgc cctcgtctgg gctgctctca cctacatccc cagcatcccc   7800
gaccagaccc tccgcgtcgc agcttggatg gtctacggct tcgtccaggg tctgttctgc   7860
accggtgtct ggattctcgg ccatgagtgc ggccacggtg ctttctctct ccacggaaag   7920
gtcaacaatg tgaccggctg gttcctccac tcgttcctcc tcgtccccta cttcagctgg   7980
aagtactctc accaccgcca ccaccgcttc accggccaca tggatctcga catggctttc   8040
gtccccaaga ctgagcccaa gccctccaag tcgctcatga ttgctggcat tgacgtcgcc   8100
gagcttgttg aggacacccc cgctgctcag atggtcaagc tcatcttcca ccagcttttc   8160
ggatggcagg cgtacctctt cttcaacgct agctctggca agggcagcaa gcagtgggag   8220
cccaagactg gcctctccaa gtggttccga gtcagtcact tcgagcctac cagcgctgtc   8280
ttccgcccca acgaggccat cttcatcctc atctccgata tcggtcttgc tctaatggga   8340
actgctctgt actttgcttc caagcaagtt ggtgtttcga ccattctctt cctctacctt   8400
gttccctacc tgtgggttca ccactggctc gttgccatta cctacctcca ccaccaccac   8460
accgagctcc ctcactacac cgctgagggc tggacctacg tcaagggagc tctcgccact   8520
gtcgaccgtg agtttggctt catcggaaag cacctcttcc acggtatcat tgagaagcac   8580
gttgttcacc atctcttccc taagatcccc ttctacaagg ctgacgaggc caccgaggcc   8640
atcaagcccg tcattggcga ccactactgc cacgacgacc gaagcttcct gggccagctg   8700
tggaccatct tcggcacgct caagtacgtc gagcacgacc ctgcccgacc cggtgccatg   8760
cgatggaaca aggactaggc taggcggccg cgaagttaaa agcaatgttg tcacttgtcg   8820
tactaacaca tgatgtgata gtttatgcta gctagctata acataagctg tctctgagtg   8880
```

tgttgtatat taataaagat catcactggt gaatggtgat cgtgtacgta ccctacttag 8940
taggcaatgg aagcacttag agtgtgcttt gtgcatggcc ttgcctctgt tttgagactt 9000
ttgtaatgtt ttcgagttta aatctttgcc tttgc 9035

<210> SEQ ID NO 102
<211> LENGTH: 5108
<212> TYPE: DNA
<213> ORGANISM: Artificial Sequence
<220> FEATURE:
<223> OTHER INFORMATION: Plasmid pKR270

<400> SEQUENCE: 102
ggccgcattt cgcaccaaat caatgaaagt aataatgaaa agtctgaata agaatactta 60
ggcttagatg cctttgttac ttgtgtaaaa taacttgagt catgtacctt tggcggaaac 120
agaataaata aaaggtgaaa ttccaatgct ctatgtataa gttagtaata cttaatgtgt 180
tctacggttg tttcaatatc atcaaactct aattgaaact ttagaaccac aaatctcaat 240
cttttcttaa tgaaatgaaa aatcttaatt gtaccatgtt tatgttaaac accttacaat 300
tggttggaga ggaggaccaa ccgatgggac aacattggga gaaagagatt caatggagat 360
ttggatagga gaacaacatt ctttttcact tcaatacaag atgagtgcaa cactaaggat 420
atgtatgaga ctttcagaag ctacgacaac atagatgagt gaggtggtga ttcctagcaa 480
gaaagacatt agaggaagcc aaaatcgaac aaggaagaca tcaagggcaa gagacaggac 540
catccatctc aggaaaagga gctttgggat agtccgagaa gttgtacaag aaattttttg 600
gagggtgagt gatgcattgc tggtgacttt aactcaatca aaattgagaa agaaagaaaa 660
gggagggggc tcacatgtga atagaaggga aacgggagaa ttttacagtt ttgatctaat 720
gggcatccca gctagtggta acatattcac catgtttaac cttcacgtac gtctagagga 780
tccccgggta ccgagctcga attcactggc cgtcgtttta caacgtcgtg actgggaaaa 840
ccctggcgtt acccaactta atcgccttgc agcacatccc cctttcgcca gctggcgtaa 900
tagcgaagag gcccgcaccg atcgcccttc ccaacagttg cgcagcctga atggcgaatg 960
gcgcctgatg cggtattttc tccttacgca tctgtgcggt atttcacacc gcatatggtg 1020
cactctcagt acaatctgct ctgatgccgc atagttaagc cagccccgac acccgccaac 1080
acccgctgac gcgccctgac gggcttgtct gctcccggca tccgcttaca gacaagctgt 1140
gaccgtctcc gggagctgca tgtgtcagag gttttcaccg tcatcaccga aacgcgcgag 1200
acgaaagggc ctcgtgatac gcctattttt ataggttaat gtcatgataa taatggtttc 1260
ttagacgtca ggtggcactt ttcggggaaa tgtgcgcgga acccctattt gtttattttt 1320
ctaaatacat tcaaatatgt atccgctcat gagacaataa ccctgataaa tgcttcaata 1380
atattgaaaa aggaagagta tgagtattca acatttccgt gtcgccctta ttcccttttt 1440
tgcggcattt tgccttcctg tttttgctca cccagaaacg ctggtgaaag taaaagatgc 1500
tgaagatcag ttgggtgcac gagtgggtta catcgaactg gatctcaaca gcggtaagat 1560
ccttgagagt tttcgccccg aagaacgttt tccaatgatg agcactttta aagttctgct 1620
atgtggcgcg gtattatccc gtattgacgc cgggcaagag caactcggtc gccgcataca 1680
ctattctcag aatgacttgg ttgagtactc accagtcaca gaaaagcatc ttacggatgg 1740
catgacagta agagaattat gcagtgctgc cataaccatg agtgataaca ctgcggccaa 1800
cttacttctg acaacgatcg gaggaccgaa ggagctaacc gcttttttgc acaacatggg 1860
ggatcatgta actcgccttg atcgttggga accggagctg aatgaagcca taccaaacga 1920

-continued

```
cgagcgtgac accacgatgc ctgtagcaat ggcaacaacg ttgcgcaaac tattaactgg   1980
cgaactactt actctagctt cccggcaaca attaatagac tggatggagg cggataaagt   2040
tgcaggacca cttctgcgct cggcccttcc ggctggctgg tttattgctg ataaatctgg   2100
agccggtgag cgtgggtctc gcggtatcat tgcagcactg gggccagatg gtaagccctc   2160
ccgtatcgta gttatctaca cgacggggag tcaggcaact atggatgaac gaaatagaca   2220
gatcgctgag ataggtgcct cactgattaa gcattggtaa ctgtcagacc aagtttactc   2280
atatatactt tagattgatt taaaacttca tttttaattt aaaaggatct aggtgaagat   2340
cctttttgat aatctcatga ccaaaatccc ttaacgtgag ttttcgttcc actgagcgtc   2400
agaccccgta gaaaagatca aaggatcttc ttgagatcct ttttttctgc gcgtaatctg   2460
ctgcttgcaa acaaaaaaac caccgctacc agcggtggtt tgtttgccgg atcaagagct   2520
accaactctt tttccgaagg taactggctt cagcagagcg cagataccaa atactgtcct   2580
tctagtgtag ccgtagttag gccaccactt caagaactct gtagcaccgc ctacatacct   2640
cgctctgcta atcctgttac cagtggctgc tgccagtggc gataagtcgt gtcttaccgg   2700
gttggactca agacgatagt taccggataa ggcgcagcgg tcgggctgaa cggggggttc   2760
gtgcacacag cccagcttgg agcgaacgac ctacaccgaa ctgagatacc tacagcgtga   2820
gctatgagaa agcgccacgc ttcccgaagg gagaaaggcg gacaggtatc cggtaagcgg   2880
cagggtcgga acaggagagc gcacgaggga gcttccaggg ggaaacgcct ggtatcttta   2940
tagtcctgtc gggtttcgcc acctctgact tgagcgtcga tttttgtgat gctcgtcagg   3000
ggggcggagc ctatggaaaa acgccagcaa cgcggccttt ttacggttcc tggccttttg   3060
ctggcctttt gctcacatgt tctttcctgc gttatcccct gattctgtgg ataaccgtat   3120
taccgccttt gagtgagctg ataccgctcg ccgcagccga acgaccgagc gcagcgagtc   3180
agtgagcgag gaagcggaag agcgcccaat acgcaaaccg cctctccccg cgcgttggcc   3240
gattcattaa tgcagctggc acgacaggtt tcccgactgg aaagcgggca gtgagcgcaa   3300
cgcaattaat gtgagttagc tcactcatta ggcaccccag gctttacact ttatgcttcc   3360
ggctcgtatg ttgtgtggaa ttgtgagcgg ataacaattt cacacaggaa acagctatga   3420
ccatgattac gccaagcttg catgcctgca ggctagccta agtacgtact caaaatgcca   3480
acaaataaaa aaaaagttgc tttaataatg ccaaaacaaa ttaataaaac acttacaaca   3540
ccggattttt tttaattaaa atgtgccatt taggataaat agttaatatt tttaataatt   3600
atttaaaaag ccgtatctac taaaatgatt tttatttggt tgaaaatatt aatatgttta   3660
aatcaacaca atctatcaaa attaaactaa aaaaaaaata agtgtacgtg gttaacatta   3720
gtacagtaat ataagaggaa aatgagaaat taagaaattg aaagcgagtc taatttttaa   3780
attatgaacc tgcatatata aaaggaaaga aagaatccag gaagaaaaga aatgaaacca   3840
tgcatggtcc cctcgtcatc acgagtttct gccatttgca atagaaacac tgaaacacct   3900
ttctctttgt cacttaattg agatgccgaa gccacctcac accatgaact tcatgaggtg   3960
tagcacccaa ggcttccata gccatgcata ctgaagaatg tctcaagctc agcaccctac   4020
ttctgtgacg tgtccctcat tcaccttcct ctcttcccta taaataacca cgcctcaggt   4080
tctccgcttc acaactcaaa cattctctcc attggtcctt aaacactcat cagtcatcac   4140
cgcggccgca tggagtcgat tgcgccattc ctcccatcaa agatgccgca agatctgttt   4200
atggaccttg ccaccgctat cggtgtccgg gccgcgccct atgtcgatcc tctcgaggcc   4260
gcgctggtgg cccaggccga gaagtacatc cccacgattg tccatcacac gcgtgggttc   4320
```

-continued

```
ctggtcgcgg tggagtcgcc tttggcccgt gagctgccgt tgatgaaccc gttccacgtg    4380

ctgttgatcg tgctcgctta tttggtcacg gtctttgtgg gcatgcagat catgaagaac    4440

tttgagcggt tcgaggtcaa gacgttttcg ctcctgcaca acttttgtct ggtctcgatc    4500

agcgcctaca tgtgcggtgg gatcctgtac gaggcttatc aggccaacta tggactgttt    4560

gagaacgctg ctgatcatac cttcaagggt cttcctatgg ccaagatgat ctggctcttc    4620

tacttctcca agatcatgga gtttgtcgac accatgatca tggtcctcaa gaagaacaac    4680

cgccagatct ccttcttgca cgtttaccac cacagctcca tcttcaccat ctggtggttg    4740

gtcacctttg ttgcacccaa cggtgaagcc tacttctctg ctgcgttgaa ctcgttcatc    4800

catgtgatca tgtacggcta ctacttcttg tcggccttgg gcttcaagca ggtgtcgttc    4860

atcaagttct acatcacgcg ctcgcagatg acacagttct gcatgatgtc ggtccagtct    4920

tcctgggaca tgtacgccat gaaggtcctt ggccgccccg gatacccctt cttcatcacg    4980

gctctgcttt ggttctacat gtggaccatg ctcggtctct tctacaactt ttacagaaag    5040

aacgccaagt tggccaagca ggccaaggcc gacgctgcca aggagaaggc aaggaagttg    5100

cagtaagc                                                             5108
```

```
<210> SEQ ID NO 103
<211> LENGTH: 39
<212> TYPE: DNA
<213> ORGANISM: Artificial Sequence
<220> FEATURE:
<223> OTHER INFORMATION: Smart(TM) IV oligonucleotide

<400> SEQUENCE: 103

aagcagtggt atcaacgcag agtggccatt acggccggg                           39

<210> SEQ ID NO 104
<211> LENGTH: 59
<212> TYPE: DNA
<213> ORGANISM: Artificial Sequence
<220> FEATURE:
<223> OTHER INFORMATION: CDSIII/3'PCR primer
<220> FEATURE:
<221> NAME/KEY: misc_feature
<222> LOCATION: (28)..(57)
<223> OTHER INFORMATION: thymidine (dT); see BD Biosciences Clontech's
      SMART cDNA technology
<220> FEATURE:
<221> NAME/KEY: misc_feature
<222> LOCATION: (59)..(59)
<223> OTHER INFORMATION: n is a, c, g, or t

<400> SEQUENCE: 104

attctagagg ccgaggcggc cgacatgttt tttttttttt tttttttttt tttttttvn     59

<210> SEQ ID NO 105
<211> LENGTH: 23
<212> TYPE: DNA
<213> ORGANISM: Artificial Sequence
<220> FEATURE:
<223> OTHER INFORMATION: 5'-PCR primer

<400> SEQUENCE: 105

aagcagtggt atcaacgcag agt                                            23

<210> SEQ ID NO 106
<211> LENGTH: 20
<212> TYPE: DNA
<213> ORGANISM: Artificial Sequence
<220> FEATURE:
<223> OTHER INFORMATION: Primer EuEF3
```

<220> FEATURE:
<221> NAME/KEY: misc_feature
<222> LOCATION: (3)..(3)
<223> OTHER INFORMATION: n is a, c, g, or t

<400> SEQUENCE: 106
ytncarttyt tycaycaytt 20

<210> SEQ ID NO 107
<211> LENGTH: 7
<212> TYPE: PRT
<213> ORGANISM: Artificial Sequence
<220> FEATURE:
<223> OTHER INFORMATION: Primer EuEF3 (translation)

<400> SEQUENCE: 107

Leu Gln Phe Phe His His Leu
1 5

<210> SEQ ID NO 108
<211> LENGTH: 20
<212> TYPE: DNA
<213> ORGANISM: Artificial Sequence
<220> FEATURE:
<223> OTHER INFORMATION: Primer EuER3

<400> SEQUENCE: 108
ttraaytgda tdatytgcat 20

<210> SEQ ID NO 109
<211> LENGTH: 7
<212> TYPE: PRT
<213> ORGANISM: Artificial Sequence
<220> FEATURE:
<223> OTHER INFORMATION: Primer EuER3 (translation)

<400> SEQUENCE: 109

Met Gln Ile Ile Gln Phe Asn
1 5

<210> SEQ ID NO 110
<211> LENGTH: 22
<212> TYPE: DNA
<213> ORGANISM: Artificial Sequence
<220> FEATURE:
<223> OTHER INFORMATION: Primer 389Elo-5-1

<400> SEQUENCE: 110
gaatgaaccc attcaaaaac ac 22

<210> SEQ ID NO 111
<211> LENGTH: 22
<212> TYPE: DNA
<213> ORGANISM: Artificial Sequence
<220> FEATURE:
<223> OTHER INFORMATION: Primer 389Elo-5-2

<400> SEQUENCE: 111
gatccaaata gattccccag aa 22

<210> SEQ ID NO 112
<211> LENGTH: 22
<212> TYPE: DNA
<213> ORGANISM: Artificial Sequence
<220> FEATURE:
<223> OTHER INFORMATION: Primer DNR CDS 5'-2

<400> SEQUENCE: 112
caacgcagag tggccattac gg 22

<210> SEQ ID NO 113
<211> LENGTH: 21
<212> TYPE: DNA
<213> ORGANISM: Artificial Sequence
<220> FEATURE:
<223> OTHER INFORMATION: Primer 389Elo-5-4

<400> SEQUENCE: 113
gtaaacttca agatcacgaa g 21

<210> SEQ ID NO 114
<211> LENGTH: 22
<212> TYPE: DNA
<213> ORGANISM: Artificial Sequence
<220> FEATURE:
<223> OTHER INFORMATION: Primer 389Elo-3-1

<400> SEQUENCE: 114
gttcattcac tttgttatgt ac 22

<210> SEQ ID NO 115
<211> LENGTH: 22
<212> TYPE: DNA
<213> ORGANISM: Artificial Sequence
<220> FEATURE:
<223> OTHER INFORMATION: Primer 389Elo-3-2

<400> SEQUENCE: 115
ctggactcgg ctgatgaagt tc 22

<210> SEQ ID NO 116
<211> LENGTH: 29
<212> TYPE: DNA
<213> ORGANISM: Artificial Sequence
<220> FEATURE:
<223> OTHER INFORMATION: Primer 389ELO-F

<400> SEQUENCE: 116
aagatcccat ggctgcggtg atagaggtc 29

<210> SEQ ID NO 117
<211> LENGTH: 37
<212> TYPE: DNA
<213> ORGANISM: Artificial Sequence
<220> FEATURE:
<223> OTHER INFORMATION: Primer 389ELO-R1

<400> SEQUENCE: 117
aagatcgcgg ccgcctattg gaccttttta tctgcag 37

<210> SEQ ID NO 118
<211> LENGTH: 7222
<212> TYPE: DNA
<213> ORGANISM: Artificial Sequence
<220> FEATURE:
<223> OTHER INFORMATION: Plasmid pFBAIN-MOD1

<400> SEQUENCE: 118
catggatcca ggcctgttaa cggccattac ggcctgcagg atccgaaaaa acctcccaca 60
cctccccctg aacctgaaac ataaaatgaa tgcaattgtt gttgttaact tgtttattgc 120
agcttataat ggttacaaat aaagcaatag catcacaaat ttcacaaata aagcattttt 180
ttcactgcat tctagttgtg gtttgtccaa actcatcaat gtatcttatc atgtctgcgg 240

```
ccgcaagtgt ggatggggaa gtgagtgccc ggttctgtgt gcacaattgg caatccaaga    300
tggatggatt caacacaggg atatagcgag ctacgtggtg gtgcgaggat atagcaacgg    360
atatttatgt ttgacacttg agaatgtacg atacaagcac tgtccaagta caatactaaa    420
catactgtac atactcatac tcgtacccgg gcaacggttt cacttgagtg cagtggctag    480
tgctcttact cgtacagtgt gcaatactgc gtatcatagt ctttgatgta tatcgtattc    540
attcatgtta gttgcgtacg agccggaagc ataaagtgta aagcctgggg tgcctaatga    600
gtgagctaac tcacattaat tgcgttgcgc tcactgcccg ctttccagtc gggaaacctg    660
tcgtgccagc tgcattaatg aatcggccaa cgcgcgggga gaggcggttt gcgtattggg    720
cgctcttccg cttcctcgct cactgactcg ctgcgctcgg tcgttcggct gcggcgagcg    780
gtatcagctc actcaaaggc ggtaatacgg ttatccacag aatcagggga taacgcagga    840
aagaacatgt gagcaaaagg ccagcaaaag gccaggaacc gtaaaaaggc cgcgttgctg    900
gcgtttttcc ataggctccg cccccctgac gagcatcaca aaaatcgacg ctcaagtcag    960
aggtggcgaa acccgacagg actataaaga taccaggcgt ttccccctgg aagctccctc   1020
gtgcgctctc ctgttccgac cctgccgctt accggatacc tgtccgcctt tctcccttcg   1080
ggaagcgtgg cgctttctca tagctcacgc tgtaggtatc tcagttcggt gtaggtcgtt   1140
cgctccaagc tgggctgtgt gcacgaaccc cccgttcagc ccgaccgctg cgccttatcc   1200
ggtaactatc gtcttgagtc caacccggta agacacgact tatcgccact ggcagcagcc   1260
actggtaaca ggattagcag agcgaggtat gtaggcggtg ctacagagtt cttgaagtgg   1320
tggcctaact acggctacac tagaaggaca gtatttggta tctgcgctct gctgaagcca   1380
gttaccttcg gaaaaagagt tggtagctct tgatccggca aacaaaccac cgctggtagc   1440
ggtggttttt ttgtttgcaa gcagcagatt acgcgcagaa aaaaaggatc tcaagaagat   1500
cctttgatct tttctacggg gtctgacgct cagtggaacg aaaactcacg ttaagggatt   1560
ttggtcatga gattatcaaa aaggatcttc acctagatcc ttttaaatta aaaatgaagt   1620
tttaaatcaa tctaaagtat atatgagtaa acttggtctg acagttacca atgcttaatc   1680
agtgaggcac ctatctcagc gatctgtcta tttcgttcat ccatagttgc ctgactcccc   1740
gtcgtgtaga taactacgat acgggagggc ttaccatctg gccccagtgc tgcaatgata   1800
ccgcgagacc cacgctcacc ggctccagat ttatcagcaa taaaccagcc agccggaagg   1860
gccgagcgca gaagtggtcc tgcaacttta tccgcctcca tccagtctat taattgttgc   1920
cgggaagcta gagtaagtag ttcgccagtt aatagtttgc gcaacgttgt tgccattgct   1980
acaggcatcg tggtgtcacg ctcgtcgttt ggtatggctt cattcagctc cggttcccaa   2040
cgatcaaggc gagttacatg atcccccatg ttgtgcaaaa aagcggttag ctccttcggt   2100
cctccgatcg ttgtcagaag taagttggcc gcagtgttat cactcatggt tatggcagca   2160
ctgcataatt ctcttactgt catgccatcc gtaagatgct tttctgtgac tggtgagtac   2220
tcaaccaagt cattctgaga atagtgtatg cggcgaccga gttgctcttg cccggcgtca   2280
atacgggata ataccgcgcc acatagcaga actttaaaag tgctcatcat tggaaaacgt   2340
tcttcggggc gaaaactctc aaggatctta ccgctgttga gatccagttc gatgtaaccc   2400
actcgtgcac ccaactgatc ttcagcatct tttactttca ccagcgtttc tgggtgagca   2460
aaaacaggaa ggcaaaatgc cgcaaaaaag ggaataaggg cgacacggaa atgttgaata   2520
ctcatactct tcctttttca atattattga agcatttatc agggttattg tctcatgagc   2580
ggatacatat ttgaatgtat ttagaaaaat aaacaaatag gggttccgcg cacatttccc   2640
```

-continued

```
cgaaaagtgc cacctgacgc gccctgtagc ggcgcattaa gcgcggcggg tgtggtggtt   2700
acgcgcagcg tgaccgctac acttgccagc gccctagcgc ccgctccttt cgctttcttc   2760
ccttcctttc tcgccacgtt cgccggcttt ccccgtcaag ctctaaatcg ggggctccct   2820
ttagggttcc gatttagtgc tttacggcac ctcgacccca aaaaacttga ttagggtgat   2880
ggttcacgta gtgggccatc gccctgatag acggtttttc gccctttgac gttggagtcc   2940
acgttcttta atagtggact cttgttccaa actggaacaa cactcaaccc tatctcggtc   3000
tattcttttg atttataagg gattttgccg atttcggcct attggttaaa aaatgagctg   3060
atttaacaaa aatttaacgc gaattttaac aaaatattaa cgcttacaat ttccattcgc   3120
cattcaggct gcgcaactgt tgggaagggc gatcggtgcg ggcctcttcg ctattacgcc   3180
agctggcgaa agggggatgt gctgcaaggc gattaagttg ggtaacgcca gggttttccc   3240
agtcacgacg ttgtaaaacg acggccagtg aattgtaata cgactcacta tagggcgaat   3300
tgggtaccgg gccccccctc gaggtcgatg gtgtcgataa gcttgatatc gaattcatgt   3360
cacacaaacc gatcttcgcc tcaaggaaac ctaattctac atccgagaga ctgccgagat   3420
ccagtctaca ctgattaatt ttcgggccaa taatttaaaa aaatcgtgtt atataatatt   3480
atatgtatta tatatataca tcatgatgat actgacagtc atgtcccatt gctaaataga   3540
cagactccat ctgccgcctc caactgatgt tctcaatatt taaggggtca tctcgcattg   3600
tttaataata aacagactcc atctaccgcc tccaaatgat gttctcaaaa tatattgtat   3660
gaacttattt ttattactta gtattattag acaacttact tgctttatga aaaacacttc   3720
ctatttagga aacaatttat aatggcagtt cgttcattta acaatttatg tagaataaat   3780
gttataaatg cgtatgggaa atcttaaata tggatagcat aaatgatatc tgcattgcct   3840
aattcgaaat caacagcaac gaaaaaaatc ccttgtacaa cataaatagt catcgagaaa   3900
tatcaactat caaagaacag ctattcacac gttactattg agattattat tggacgagaa   3960
tcacacactc aactgtcttt ctctcttcta gaaatacagg tacaagtatg tactattctc   4020
attgttcata cttctagtca tttcatccca catattcctt ggatttctct ccaatgaatg   4080
acattctatc ttgcaaattc aacaattata ataagatata ccaaagtagc ggtatagtgg   4140
caatcaaaaa gcttctctgg tgtgcttctc gtatttattt ttattctaat gatccattaa   4200
aggtatatat ttatttcttg ttatataatc cttttgttta ttacatgggc tggatacata   4260
aaggtatttt gatttaattt tttgcttaaa ttcaatcccc cctcgttcag tgtcaactgt   4320
aatggtagga aattaccata cttttgaaga agcaaaaaaa atgaaagaaa aaaaaaatcg   4380
tatttccagg ttagacgttc cgcagaatct agaatgcggt atgcggtaca ttgttcttcg   4440
aacgtaaaag ttgcgctccc tgagatattg tacatttttg cttttacaag tacaagtaca   4500
tcgtacaact atgtactact gttgatgcat ccacaacagt ttgttttgtt ttttttgtt   4560
ttttttttt ctaatgattc attaccgcta tgtataccta cttgtacttg tagtaagccg   4620
ggttattggc gttcaattaa tcatagactt atgaatctgc acggtgtgcg ctgcgagtta   4680
cttttagctt atgcatgcta cttgggtgta atattgggat ctgttcggaa atcaacggat   4740
gctcaatcga tttcgacagt aattaattaa gtcatacaca agtcagcttt cttcgagcct   4800
catataagta taagtagttc aacgtattag cactgtaccc agcatctccg tatcgagaaa   4860
cacaacaaca tgccccattg gacagatcat gcggatacac aggttgtgca gtatcataca   4920
tactcgatca gacaggtcgt ctgaccatca tacaagctga acaagcgctc catacttgca   4980
cgctctctat atacacagtt aaattacata tccatagtct aacctctaac agttaatctt   5040
```

```
ctggtaagcc tcccagccag ccttctggta tcgcttggcc tcctcaatag gatctcggtt   5100
ctggccgtac agacctcggc cgacaattat gatatccgtt ccggtagaca tgacatcctc   5160
aacagttcgg tactgctgtc cgagagcgtc tcccttgtcg tcaagaccca ccccgggggt   5220
cagaataagc cagtcctcag agtcgccctt aggtcggttc tgggcaatga agccaaccac   5280
aaactcgggg tcggatcggg caagctcaat ggtctgcttg gagtactcgc cagtggccag   5340
agagcccttg caagacagct cggccagcat gagcagacct ctggccagct tctcgttggg   5400
agaggggact aggaactcct tgtactggga gttctcgtag tcagagacgt cctccttctt   5460
ctgttcagag acagtttcct cggcaccagc tcgcaggcca gcaatgattc cggttccggg   5520
tacaccgtgg gcgttggtga tatcggacca ctcggcgatt cggtgacacc ggtactggtg   5580
cttgacagtg ttgccaatat ctgcgaactt tctgtcctcg aacaggaaga aaccgtgctt   5640
aagagcaagt tccttgaggg ggagcacagt gccggcgtag gtgaagtcgt caatgatgtc   5700
gatatgggtt ttgatcatgc acacataagg tccgacctta tcggcaagct caatgagctc   5760
cttggtggtg gtaacatcca gagaagcaca caggttggtt ttcttggctg ccacgagctt   5820
gagcactcga gcggcaaagg cggacttgtg gacgttagct cgagcttcgt aggagggcat   5880
tttggtggtg aagaggagac tgaaataaat ttagtctgca gaacttttta tcggaacctt   5940
atctggggca gtgaagtata tgttatggta atagttacga gttagttgaa cttatagata   6000
gactggacta tacggctatc ggtccaaatt agaaagaacg tcaatggctc tctgggcgtc   6060
gcctttgccg acaaaaatgt gatcatgatg aaagccagca atgacgttgc agctgatatt   6120
gttgtcggcc aaccgcgccg aaaacgcagc tgtcagaccc acagcctcca acgaagaatg   6180
tatcgtcaaa gtgatccaag cacactcata gttggagtcg tactccaaag gcggcaatga   6240
cgagtcagac agatactcgt cgaaaacagt gtacgcagat ctactataga ggaacattta   6300
aattgccccg gagaagacgg ccaggccgcc tagatgacaa attcaacaac tcacagctga   6360
ctttctgcca ttgccactag gggggggcct ttttatatgg ccaagccaag ctctccacgt   6420
cggttgggct gcacccaaca ataaatgggt agggttgcac caacaaaggg atgggatggg   6480
gggtagaaga tacgaggata acggggctca atggcacaaa taagaacgaa tactgccatt   6540
aagactcgtg atccagcgac tgacaccatt gcatcatcta agggcctcaa aactacctcg   6600
gaactgctgc gctgatctgg acaccacaga ggttccgagc actttaggtt gcaccaaatg   6660
tcccaccagg tgcaggcaga aaacgctgga acagcgtgta cagtttgtct taacaaaaag   6720
tgagggcgct gaggtcgagc agggtggtgt gacttgttat agcctttaga gctgcgaaag   6780
cgcgtatgga tttggctcat caggccagat tgagggtctg tggacacatg tcatgttagt   6840
gtacttcaat cgcccccctgg atatagcccc gacaataggc cgtggcctca tttttttgcc   6900
ttccgcacat ttccattgct cggtacccac accttgcttc tcctgcactt gccaacctta   6960
atactggttt acattgacca acatcttaca agcggggggc ttgtctaggg tatatataaa   7020
cagtggctct cccaatcggt tgccagtctc ttttttcctt tctttcccca cagattcgaa   7080
atctaaacta cacatcacag aattccgagc cgtgagtatc cacgacaaga tcagtgtcga   7140
gacgacgcgt tttgtgtaat gacacaatcc gaaagtcgct agcaacacac actctctaca   7200
caaactaacc cagctctggt ac                                            7222
```

<210> SEQ ID NO 119
<211> LENGTH: 7779
<212> TYPE: DNA
<213> ORGANISM: Artificial Sequence
<220> FEATURE:
<223> OTHER INFORMATION: Plasmid pFBAIN-389Elo

<400> SEQUENCE: 119

```
ggccgcaagt gtggatgggg aagtgagtgc ccggttctgt gtgcacaatt ggcaatccaa     60
gatggatgga ttcaacacag ggatatagcg agctacgtgg tggtgcgagg atatagcaac    120
ggatatttat gtttgacact tgagaatgta cgatacaagc actgtccaag tacaatacta    180
aacatactgt acatactcat actcgtaccc gggcaacggt ttcacttgag tgcagtggct    240
agtgctctta ctcgtacagt gtgcaatact gcgtatcata gtctttgatg tatatcgtat    300
tcattcatgt tagttgcgta cgagccggaa gcataaagtg taaagcctgg ggtgcctaat    360
gagtgagcta actcacatta attgcgttgc gctcactgcc cgctttccag tcgggaaacc    420
tgtcgtgcca gctgcattaa tgaatcggcc aacgcgcggg gagaggcggt ttgcgtattg    480
ggcgctcttc cgcttcctcg ctcactgact cgctgcgctc ggtcgttcgg ctgcggcgag    540
cggtatcagc tcactcaaag gcggtaatac ggttatccac agaatcaggg gataacgcag    600
gaaagaacat gtgagcaaaa ggccagcaaa aggccaggaa ccgtaaaaag gccgcgttgc    660
tggcgttttt ccataggctc cgcccccctg acgagcatca caaaaatcga cgctcaagtc    720
agaggtggcg aaacccgaca ggactataaa gataccaggc gtttccccct ggaagctccc    780
tcgtgcgctc tcctgttccg accctgccgc ttaccggata cctgtccgcc tttctccctt    840
cgggaagcgt ggcgctttct catagctcac gctgtaggta tctcagttcg gtgtaggtcg    900
ttcgctccaa gctgggctgt gtgcacgaac cccccgttca gcccgaccgc tgcgccttat    960
ccggtaacta tcgtcttgag tccaacccgg taagacacga cttatcgcca ctggcagcag   1020
ccactggtaa caggattagc agagcgaggt atgtaggcgg tgctacagag ttcttgaagt   1080
ggtggcctaa ctacggctac actagaagga cagtatttgg tatctgcgct ctgctgaagc   1140
cagttacctt cggaaaaaga gttggtagct cttgatccgg caaacaaacc accgctggta   1200
gcggtggttt ttttgtttgc aagcagcaga ttacgcgcag aaaaaaagga tctcaagaag   1260
atcctttgat cttttctacg gggtctgacg ctcagtggaa cgaaaactca cgttaaggga   1320
ttttggtcat gagattatca aaaaggatct tcacctagat ccttttaaat taaaaatgaa   1380
gttttaaatc aatctaaagt atatatgagt aaacttggtc tgacagttac caatgcttaa   1440
tcagtgaggc acctatctca gcgatctgtc tatttcgttc atccatagtt gcctgactcc   1500
ccgtcgtgta gataactacg atacgggagg gcttaccatc tggccccagt gctgcaatga   1560
taccgcgaga cccacgctca ccggctccag atttatcagc aataaaccag ccagccggaa   1620
gggccgagcg cagaagtggt cctgcaactt tatccgcctc catccagtct attaattgtt   1680
gccgggaagc tagagtaagt agttcgccag ttaatagttt gcgcaacgtt gttgccattg   1740
ctacaggcat cgtggtgtca cgctcgtcgt ttggtatggc ttcattcagc tccggttccc   1800
aacgatcaag gcgagttaca tgatccccca tgttgtgcaa aaaagcggtt agctccttcg   1860
gtcctccgat cgttgtcaga agtaagttgg ccgcagtgtt atcactcatg gttatggcag   1920
cactgcataa ttctcttact gtcatgccat ccgtaagatg cttttctgtg actggtgagt   1980
actcaaccaa gtcattctga gaatagtgta tgcggcgacc gagttgctct tgcccggcgt   2040
caatacggga taataccgcg ccacatagca gaactttaaa agtgctcatc attggaaaac   2100
gttcttcggg gcgaaaactc tcaaggatct taccgctgtt gagatccagt tcgatgtaac   2160
ccactcgtgc acccaactga tcttcagcat cttttacttt caccagcgtt tctgggtgag   2220
caaaaacagg aaggcaaaat gccgcaaaaa agggaataag ggcgacacgg aaatgttgaa   2280
```

-continued

```
tactcatact cttccttttt caatattatt gaagcattta tcagggttat tgtctcatga   2340
gcggatacat atttgaatgt atttagaaaa ataaacaaat aggggttccg cgcacatttc   2400
cccgaaaagt gccacctgac gcgccctgta gcggcgcatt aagcgcggcg ggtgtggtgg   2460
ttacgcgcag cgtgaccgct acacttgcca gcgccctagc gcccgctcct ttcgctttct   2520
tcccttcctt tctcgccacg ttcgccggct ttccccgtca agctctaaat cgggggctcc   2580
ctttagggtt ccgatttagt gctttacggc acctcgaccc caaaaaactt gattagggtg   2640
atggttcacg tagtgggcca tcgccctgat agacggtttt tcgccctttg acgttggagt   2700
ccacgttctt taatagtgga ctcttgttcc aaactggaac aacactcaac cctatctcgg   2760
tctattcttt tgatttataa gggattttgc cgatttcggc ctattggtta aaaaatgagc   2820
tgatttaaca aaaatttaac gcgaatttta acaaaatatt aacgcttaca atttccattc   2880
gccattcagg ctgcgcaact gttgggaagg gcgatcggtg cgggcctctt cgctattacg   2940
ccagctggcg aaagggggat gtgctgcaag gcgattaagt tgggtaacgc cagggttttc   3000
ccagtcacga cgttgtaaaa cgacggccag tgaattgtaa tacgactcac tatagggcga   3060
attgggtacc gggccccccc tcgaggtcga tggtgtcgat aagcttgata tcgaattcat   3120
gtcacacaaa ccgatcttcg cctcaaggaa acctaattct acatccgaga gactgccgag   3180
atccagtcta cactgattaa ttttcgggcc aataatttaa aaaaatcgtg ttatataata   3240
ttatatgtat tatatatata catcatgatg atactgacag tcatgtccca ttgctaaata   3300
gacagactcc atctgccgcc tccaactgat gttctcaata tttaaggggt catctcgcat   3360
tgtttaataa taaacagact ccatctaccg cctccaaatg atgttctcaa aatatattgt   3420
atgaacttat ttttattact tagtattatt agacaactta cttgctttat gaaaaacact   3480
tcctatttag gaaacaattt ataatggcag ttcgttcatt taacaattta tgtagaataa   3540
atgttataaa tgcgtatggg aaatcttaaa tatggatagc ataaatgata tctgcattgc   3600
ctaattcgaa atcaacagca acgaaaaaaa tcccttgtac aacataaata gtcatcgaga   3660
aatatcaact atcaaagaac agctattcac acgttactat tgagattatt attggacgag   3720
aatcacacac tcaactgtct ttctctcttc tagaaataca ggtacaagta tgtactattc   3780
tcattgttca tacttctagt catttcatcc cacatattcc ttggatttct ctccaatgaa   3840
tgacattcta tcttgcaaat tcaacaatta taataagata taccaaagta gcggtatagt   3900
ggcaatcaaa aagcttctct ggtgtgcttc tcgtatttat ttttattcta atgatccatt   3960
aaaggtatat atttatttct tgttatataa tccttttgtt tattacatgg gctggataca   4020
taaaggtatt ttgatttaat tttttgctta aattcaatcc cccctcgttc agtgtcaact   4080
gtaatggtag gaaattacca tacttttgaa gaagcaaaaa aaatgaaaga aaaaaaaaat   4140
cgtatttcca ggttagacgt tccgcagaat ctagaatgcg gtatgcggta cattgttctt   4200
cgaacgtaaa agttgcgctc cctgagatat tgtacatttt tgcttttaca agtacaagta   4260
catcgtacaa ctatgtacta ctgttgatgc atccacaaca gtttgttttg tttttttttg   4320
tttttttttt ttctaatgat tcattaccgc tatgtatacc tacttgtact tgtagtaagc   4380
cgggttattg gcgttcaatt aatcatagac ttatgaatct gcacggtgtg cgctgcgagt   4440
tacttttagc ttatgcatgc tacttgggtg taatattggg atctgttcgg aaatcaacgg   4500
atgctcaatc gatttcgaca gtaattaatt aagtcataca caagtcagct ttcttcgagc   4560
ctcatataag tataagtagt tcaacgtatt agcactgtac ccagcatctc cgtatcgaga   4620
aacacaacaa catgccccat tggacagatc atgcggatac acaggttgtg cagtatcata   4680
```

catactcgat cagacaggtc gtctgaccat catacaagct gaacaagcgc tccatacttg 4740
cacgctctct atatacacag ttaaattaca tatccatagt ctaacctcta acagttaatc 4800
ttctggtaag cctcccagcc agccttctgg tatcgcttgg cctcctcaat aggatctcgg 4860
ttctggccgt acagacctcg gccgacaatt atgatatccg ttccggtaga catgacatcc 4920
tcaacagttc ggtactgctg tccgagagcg tctcccttgt cgtcaagacc caccccgggg 4980
gtcagaataa gccagtcctc agagtcgccc ttaggtcggt tctgggcaat gaagccaacc 5040
acaaactcgg ggtcggatcg ggcaagctca atggtctgct tggagtactc gccagtggcc 5100
agagagccct tgcaagacag ctcggccagc atgagcagac ctctggccag cttctcgttg 5160
ggagagggga ctaggaactc cttgtactgg gagttctcgt agtcagagac gtcctccttc 5220
ttctgttcag agacagtttc ctcggcacca gctcgcaggc cagcaatgat tccggttccg 5280
ggtacaccgt gggcgttggt gatatcggac cactcggcga ttcggtgaca ccggtactgg 5340
tgcttgacag tgttgccaat atctgcgaac tttctgtcct cgaacaggaa gaaaccgtgc 5400
ttaagagcaa gttccttgag ggggagcaca gtgccggcgt aggtgaagtc gtcaatgatg 5460
tcgatatggg ttttgatcat gcacacataa ggtccgacct tatcggcaag ctcaatgagc 5520
tccttggtgg tggtaacatc cagagaagca cacaggttgg ttttcttggc tgccacgagc 5580
ttgagcactc gagcggcaaa ggcggacttg tggacgttag ctcgagcttc gtaggagggc 5640
attttggtgg tgaagaggag actgaaataa atttagtctg cagaactttt tatcggaacc 5700
ttatctgggg cagtgaagta tatgttatgg taatagttac gagttagttg aacttataga 5760
tagactggac tatacggcta tcggtccaaa ttagaaagaa cgtcaatggc tctctgggcg 5820
tcgcctttgc cgacaaaaat gtgatcatga tgaaagccag caatgacgtt gcagctgata 5880
ttgttgtcgg ccaaccgcgc cgaaaacgca gctgtcagac ccacagcctc caacgaagaa 5940
tgtatcgtca aagtgatcca agcacactca tagttggagt cgtactccaa aggcggcaat 6000
gacgagtcag acagatactc gtcgaaaaca gtgtacgcag atctactata gaggaacatt 6060
taaattgccc cggagaagac ggccaggccg cctagatgac aaattcaaca actcacagct 6120
gactttctgc cattgccact aggggggggc ctttttatat ggccaagcca agctctccac 6180
gtcggttggg ctgcacccaa caataaatgg gtagggttgc accaacaaag ggatgggatg 6240
gggggtagaa gatacgagga taacggggct caatggcaca aataagaacg aatactgcca 6300
ttaagactcg tgatccagcg actgacacca ttgcatcatc taagggcctc aaaactacct 6360
cggaactgct gcgctgatct ggacaccaca gaggttccga gcactttagg ttgcaccaaa 6420
tgtcccacca ggtgcaggca gaaaacgctg gaacagcgtg tacagtttgt cttaacaaaa 6480
agtgagggcg ctgaggtcga gcagggtggt gtgacttgtt atagccttta gagctgcgaa 6540
agcgcgtatg gatttggctc atcaggccag attgagggtc tgtggacaca tgtcatgtta 6600
gtgtacttca atcgcccccct ggatatagcc ccgacaatag gccgtggcct catttttttg 6660
ccttccgcac atttccattg ctcggtaccc acaccttgct tctcctgcac ttgccaacct 6720
taatactggt ttacattgac caacatctta caagcggggg gcttgtctag ggtatatata 6780
aacagtggct ctcccaatcg gttgccagtc tctttttttcc tttctttccc cacagattcg 6840
aaatctaaac tacacatcac agaattccga gccgtgagta tccacgacaa gatcagtgtc 6900
gagacgacgc gttttgtgta atgacacaat ccgaaagtcg ctagcaacac acactctcta 6960
cacaaactaa cccagctctg gtaccatggc tgcggtgata gaggtcgcca acgagtttgt 7020
agccatcacg gcagaaacgc tccccaaagt tgactatcaa cgactatggc gagacattta 7080
cagttgtgag ctactgtatt tctccattgc cttcgtgatc ttgaagttta cgttgggcga 7140
gttgagcgac agcggaaaaa agattttgag agtgttgttc aagtggtaca atctcttcat 7200
gtccgtgttc tccttggtgt ctttcctttg catgggctat gccatttata ccgtgggcct 7260
atactctaac gaatgcgaca gggctttcga caactcgttg ttccgctttg caacaaaggt 7320
gttctactac agtaagtttt tggagtacat cgactctttt tatcttccgc tcatggccaa 7380
gccgctgtct ttcctgcaat tcttccatca cttgggagcc cccatggaca tgtggctctt 7440
tgtccaatat tctggggaat ctatttggat ctttgtgttt ttgaatgggt tcattcactt 7500
tgttatgtac gggtactact ggactcggct gatgaagttc aatttcccaa tgcccaagca 7560
gttgattacc gcgatgcaga tcacgcagtt caacgttggt ttctacctcg tgtggtggta 7620
caaagatatt ccctgctacc gaaaggatcc catgcgaatg ttggcctgga tcttcaatta 7680
ctggtatgtt gggactgtct tgctgctgtt cattaatttc ttcgtcaaat cctatgtgtt 7740
cccaaagccg aagactgcag ataaaaaggt ccaataggc 7779

<210> SEQ ID NO 120
<211> LENGTH: 3511
<212> TYPE: DNA
<213> ORGANISM: Artificial Sequence
<220> FEATURE:
<223> OTHER INFORMATION: Plasmid pE389S

<400> SEQUENCE: 120
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcaggcgcc 240
attcgccatt caggctgcgc aactgttggg aagggcgatc ggtgcgggcc tcttcgctat 300
tacgccagct ggcgaaaggg ggatgtgctg caaggcgatt aagttgggta acgccagggt 360
tttcccagtc acgacgttgt aaaacgacgg ccagtgaatt cgagctcggt acctcgcgaa 420
tgcatctaga tccatggctg ccgtcatcga ggtggccaac gagttcgtcg ctatcactgc 480
cgagaccctt cccaaggtgg actatcagcg actctggcga gacatctact cctgcgagct 540
cctgtacttc tccattgctt tcgtcatcct caagtttacc cttggcgagc tctcggattc 600
tggcaaaaag attctgcgag tgctgttcaa gtggtacaac ctcttcatgt ccgtcttttc 660
gctggtgtcc ttcctctgta tgggttacgc catctacacc gttggactgt actccaacga 720
atgcgacaga gctttcgaca acagcttgtt ccgatttgcc accaaggtct tctactattc 780
caagtttctg gagtacatcg actctttcta ccttcccctc atggccaagc ctctgtcctt 840
tctgcagttc tttcatcact tgggagctcc tatggacatg tggctcttcg tgcagtactc 900
tggcgaatcc atttggatct ttgtgttcct gaacggattc attcactttg tcatgtacgg 960
ctactattgg acacggctga tgaagttcaa ctttcccatg cccaagcagc tcattaccgc 1020
aatgcagatc acccagttca acgttggctt ctacctcgtg tggtggtaca aggacattcc 1080
ctgttaccga aaggatccca tgcgaatgct ggcctggatc ttcaactact ggtacgtcgg 1140
taccgttctt ctgctcttca tcaacttctt tgtcaagtcc tacgtgtttc ccaagcctaa 1200
gactgccgac aaaaaggtcc agtagcggcc gcatcggatc ccgggcccgt cgactgcaga 1260
ggcctgcatg caagcttggc gtaatcatgg tcatagctgt ttcctgtgtg aaattgttat 1320
ccgctcacaa ttccacacaa catacgagcc ggaagcataa agtgtaaagc ctggggtgcc 1380
taatgagtga gctaactcac attaattgcg ttgcgctcac tgcccgcttt ccagtcggga 1440
aacctgtcgt gccagctgca ttaatgaatc ggccaacgcg cggggagagg cggtttgcgt 1500
attgggcgct cttccgcttc ctcgctcact gactcgctgc gctcggtcgt tcggctgcgg 1560
cgagcggtat cagctcactc aaaggcggta atacggttat ccacagaatc aggggataac 1620
gcaggaaaga acatgtgagc aaaaggccag caaaaggcca ggaaccgtaa aaaggccgcg 1680
ttgctggcgt ttttccatag gctccgcccc cctgacgagc atcacaaaaa tcgacgctca 1740
agtcagaggt ggcgaaaccc gacaggacta taaagatacc aggcgtttcc ccctggaagc 1800
tccctcgtgc gctctcctgt tccgaccctg ccgcttaccg gatacctgtc cgcctttctc 1860
ccttcgggaa gcgtggcgct ttctcatagc tcacgctgta ggtatctcag ttcggtgtag 1920
gtcgttcgct ccaagctggg ctgtgtgcac gaaccccccg ttcagcccga ccgctgcgcc 1980
ttatccggta actatcgtct tgagtccaac ccggtaagac acgacttatc gccactggca 2040
gcagccactg gtaacaggat tagcagagcg aggtatgtag gcggtgctac agagttcttg 2100
aagtggtggc ctaactacgg ctacactaga agaacagtat ttggtatctg cgctctgctg 2160
aagccagtta ccttcggaaa aagagttggt agctcttgat ccggcaaaca aaccaccgct 2220
ggtagcggtg gtttttttgt ttgcaagcag cagattacgc gcagaaaaaa aggatctcaa 2280
gaagatcctt tgatcttttc tacggggtct gacgctcagt ggaacgaaaa ctcacgttaa 2340
gggattttgg tcatgagatt atcaaaaagg atcttcacct agatcctttt aaattaaaaa 2400
tgaagtttta aatcaatcta aagtatatat gagtaaactt ggtctgacag ttaccaatgc 2460
ttaatcagtg aggcacctat ctcagcgatc tgtctatttc gttcatccat agttgcctga 2520
ctccccgtcg tgtagataac tacgatacgg gagggcttac catctggccc cagtgctgca 2580
atgataccgc gagacccacg ctcaccggct ccagatttat cagcaataaa ccagccagcc 2640
ggaagggccg agcgcagaag tggtcctgca actttatccg cctccatcca gtctattaat 2700
tgttgccggg aagctagagt aagtagttcg ccagttaata gtttgcgcaa cgttgttgcc 2760
attgctacag gcatcgtggt gtcacgctcg tcgtttggta tggcttcatt cagctccggt 2820
tcccaacgat caaggcgagt tacatgatcc cccatgttgt gcaaaaaagc ggttagctcc 2880
ttcggtcctc cgatcgttgt cagaagtaag ttggccgcag tgttatcact catggttatg 2940
gcagcactgc ataattctct tactgtcatg ccatccgtaa gatgcttttc tgtgactggt 3000
gagtactcaa ccaagtcatt ctgagaatag tgtatgcggc gaccgagttg ctcttgcccg 3060
gcgtcaatac gggataatac cgcgccacat agcagaactt taaaagtgct catcattgga 3120
aaacgttctt cggggcgaaa actctcaagg atcttaccgc tgttgagatc cagttcgatg 3180
taacccactc gtgcacccaa ctgatcttca gcatctttta ctttcaccag cgtttctggg 3240
tgagcaaaaa caggaaggca aaatgccgca aaaaagggaa taagggcgac acggaaatgt 3300
tgaatactca tactcttcct ttttcaatat tattgaagca tttatcaggg ttattgtctc 3360
atgagcggat acatatttga atgtatttag aaaaataaac aaataggggt tccgcgcaca 3420
tttccccgaa aagtgccacc tgacgtctaa gaaaccatta ttatcatgac attaacctat 3480
aaaaataggc gtatcacgag gccctttcgt c 3511

<210> SEQ ID NO 121
<211> LENGTH: 8165
<212> TYPE: DNA
<213> ORGANISM: Artificial Sequence
<220> FEATURE:
<223> OTHER INFORMATION: Plasmid pZUF17

<400> SEQUENCE: 121
gtacgagccg gaagcataaa gtgtaaagcc tggggtgcct aatgagtgag ctaactcaca 60
ttaattgcgt tgcgctcact gcccgctttc cagtcgggaa acctgtcgtg ccagctgcat 120
taatgaatcg gccaacgcgc ggggagaggc ggtttgcgta ttgggcgctc ttccgcttcc 180
tcgctcactg actcgctgcg ctcggtcgtt cggctgcggc gagcggtatc agctcactca 240
aaggcggtaa tacggttatc cacagaatca ggggataacg caggaaagaa catgtgagca 300
aaaggccagc aaaaggccag gaaccgtaaa aaggccgcgt tgctggcgtt tttccatagg 360
ctccgccccc ctgacgagca tcacaaaaat cgacgctcaa gtcagaggtg gcgaaacccg 420
acaggactat aaagatacca ggcgtttccc cctggaagct ccctcgtgcg ctctcctgtt 480
ccgaccctgc cgcttaccgg atacctgtcc gcctttctcc cttcgggaag cgtggcgctt 540
tctcatagct cacgctgtag gtatctcagt tcggtgtagg tcgttcgctc caagctgggc 600
tgtgtgcacg aaccccccgt tcagcccgac cgctgcgcct tatccggtaa ctatcgtctt 660
gagtccaacc cggtaagaca cgacttatcg ccactggcag cagccactgg taacaggatt 720
agcagagcga ggtatgtagg cggtgctaca gagttcttga agtggtggcc taactacggc 780
tacactagaa ggacagtatt tggtatctgc gctctgctga agccagttac cttcggaaaa 840
agagttggta gctcttgatc cggcaaacaa accaccgctg gtagcggtgg tttttttgtt 900
tgcaagcagc agattacgcg cagaaaaaaa ggatctcaag aagatccttt gatcttttct 960
acggggtctg acgctcagtg gaacgaaaac tcacgttaag ggattttggt catgagatta 1020
tcaaaaagga tcttcaccta gatcctttta aattaaaaat gaagttttaa atcaatctaa 1080
agtatatatg agtaaacttg gtctgacagt taccaatgct taatcagtga ggcacctatc 1140
tcagcgatct gtctatttcg ttcatccata gttgcctgac tccccgtcgt gtagataact 1200
acgatacggg agggcttacc atctggcccc agtgctgcaa tgataccgcg agacccacgc 1260
tcaccggctc cagatttatc agcaataaac cagccagccg gaagggccga gcgcagaagt 1320
ggtcctgcaa ctttatccgc ctccatccag tctattaatt gttgccggga agctagagta 1380
agtagttcgc cagttaatag tttgcgcaac gttgttgcca ttgctacagg catcgtggtg 1440
tcacgctcgt cgtttggtat ggcttcattc agctccggtt cccaacgatc aaggcgagtt 1500
acatgatccc ccatgttgtg caaaaaagcg gttagctcct tcggtcctcc gatcgttgtc 1560
agaagtaagt tggccgcagt gttatcactc atggttatgg cagcactgca taattctctt 1620
actgtcatgc catccgtaag atgcttttct gtgactggtg agtactcaac caagtcattc 1680
tgagaatagt gtatgcggcg accgagttgc tcttgcccgg cgtcaatacg ggataatacc 1740
gcgccacata gcagaacttt aaaagtgctc atcattggaa aacgttcttc ggggcgaaaa 1800
ctctcaagga tcttaccgct gttgagatcc agttcgatgt aacccactcg tgcacccaac 1860
tgatcttcag catcttttac tttcaccagc gtttctgggt gagcaaaaac aggaaggcaa 1920
aatgccgcaa aaaagggaat aagggcgaca cggaaatgtt gaatactcat actcttcctt 1980
tttcaatatt attgaagcat ttatcagggt tattgtctca tgagcggata catatttgaa 2040
tgtatttaga aaaataaaca aataggggtt ccgcgcacat ttccccgaaa agtgccacct 2100
gacgcgccct gtagcggcgc attaagcgcg gcgggtgtgg tggttacgcg cagcgtgacc 2160
gctacacttg ccagcgccct agcgcccgct cctttcgctt tcttcccttc ctttctcgcc 2220
acgttcgccg gctttccccg tcaagctcta aatcgggggc tccctttagg gttccgattt 2280
agtgctttac ggcacctcga ccccaaaaaa cttgattagg gtgatggttc acgtagtggg 2340

-continued

```
ccatcgccct gatagacggt ttttcgccct ttgacgttgg agtccacgtt ctttaatagt   2400
ggactcttgt tccaaactgg aacaacactc aaccctatct cggtctattc ttttgattta   2460
taagggattt tgccgatttc ggcctattgg ttaaaaaatg agctgattta acaaaaattt   2520
aacgcgaatt ttaacaaaat attaacgctt acaatttcca ttcgccattc aggctgcgca   2580
actgttggga agggcgatcg gtgcgggcct cttcgctatt acgccagctg gcgaaagggg   2640
gatgtgctgc aaggcgatta agttgggtaa cgccagggtt ttcccagtca cgacgttgta   2700
aaacgacggc cagtgaattg taatacgact cactataggg cgaattgggt accgggcccc   2760
ccctcgaggt cgatggtgtc gataagcttg atatcgaatt catgtcacac aaaccgatct   2820
tcgcctcaag gaaacctaat tctacatccg agagactgcc gagatccagt ctacactgat   2880
taattttcgg gccaataatt taaaaaaatc gtgttatata atattatatg tattatatat   2940
atacatcatg atgatactga cagtcatgtc ccattgctaa atagacagac tccatctgcc   3000
gcctccaact gatgttctca atatttaagg ggtcatctcg cattgtttaa taataaacag   3060
actccatcta ccgcctccaa atgatgttct caaaatatat tgtatgaact tatttttatt   3120
acttagtatt attagacaac ttacttgctt tatgaaaaac acttcctatt taggaaacaa   3180
tttataatgg cagttcgttc atttaacaat ttatgtagaa taaatgttat aaatgcgtat   3240
gggaaatctt aaatatggat agcataaatg atatctgcat tgcctaattc gaaatcaaca   3300
gcaacgaaaa aaatcccttg tacaacataa atagtcatcg agaaatatca actatcaaag   3360
aacagctatt cacacgttac tattgagatt attattggac gagaatcaca cactcaactg   3420
tctttctctc ttctagaaat acaggtacaa gtatgtacta ttctcattgt tcatacttct   3480
agtcatttca tcccacatat tccttggatt tctctccaat gaatgacatt ctatcttgca   3540
aattcaacaa ttataataag atataccaaa gtagcggtat agtggcaatc aaaaagcttc   3600
tctggtgtgc ttctcgtatt tatttttatt ctaatgatcc attaaaggta tatatttatt   3660
tcttgttata taatcctttt gtttattaca tgggctggat acataaaggt attttgattt   3720
aattttttgc ttaaattcaa tccccccctcg ttcagtgtca actgtaatgg taggaaatta   3780
ccatactttt gaagaagcaa aaaaaatgaa agaaaaaaaa aatcgtattt ccaggttaga   3840
cgttccgcag aatctagaat gcggtatgcg gtacattgtt cttcgaacgt aaaagttgcg   3900
ctccctgaga tattgtacat ttttgctttt acaagtacaa gtacatcgta caactatgta   3960
ctactgttga tgcatccaca acagtttgtt ttgttttttt ttgttttttt tttttctaat   4020
gattcattac cgctatgtat acctacttgt acttgtagta agccgggtta ttggcgttca   4080
attaatcata gacttatgaa tctgcacggt gtgcgctgcg agttactttt agcttatgca   4140
tgctacttgg gtgtaatatt gggatctgtt cggaaatcaa cggatgctca atcgatttcg   4200
acagtaatta attaagtcat acacaagtca gctttcttcg agcctcatat aagtataagt   4260
agttcaacgt attagcactg tacccagcat ctccgtatcg agaaacacaa caacatgccc   4320
cattggacag atcatgcgga tacacaggtt gtgcagtatc atacatactc gatcagacag   4380
gtcgtctgac catcatacaa gctgaacaag cgctccatac ttgcacgctc tctatataca   4440
cagttaaatt acatatccat agtctaacct ctaacagtta atcttctggt aagcctccca   4500
gccagccttc tggtatcgct tggcctcctc aataggatct cggttctggc cgtacagacc   4560
tcggccgaca attatgatat ccgttccggt agacatgaca tcctcaacag ttcggtactg   4620
ctgtccgaga gcgtctccct tgtcgtcaag acccaccccg gggtcagaa taagccagtc   4680
ctcagagtcg cccttaggtc ggttctgggc aatgaagcca accacaaact cggggtcgga   4740
```

tcgggcaagc tcaatggtct gcttggagta ctcgccagtg gccagagagc ccttgcaaga 4800
cagctcggcc agcatgagca gacctctggc cagcttctcg ttgggagagg ggactaggaa 4860
ctccttgtac tgggagttct cgtagtcaga gacgtcctcc ttcttctgtt cagagacagt 4920
ttcctcggca ccagctcgca ggccagcaat gattccggtt ccgggtacac cgtgggcgtt 4980
ggtgatatcg gaccactcgg cgattcggtg acaccggtac tggtgcttga cagtgttgcc 5040
aatatctgcg aactttctgt cctcgaacag gaagaaaccg tgcttaagag caagttcctt 5100
gagggggagc acagtgccgg cgtaggtgaa gtcgtcaatg atgtcgatat gggttttgat 5160
catgcacaca taaggtccga ccttatcggc aagctcaatg agctccttgg tggtggtaac 5220
atccagagaa gcacacaggt tggttttctt ggctgccacg agcttgagca ctcgagcggc 5280
aaaggcggac ttgtggacgt tagctcgagc ttcgtaggag ggcattttgg tggtgaagag 5340
gagactgaaa taaatttagt ctgcagaact ttttatcgga accttatctg gggcagtgaa 5400
gtatatgtta tggtaatagt tacgagttag ttgaacttat agatagactg gactatacgg 5460
ctatcggtcc aaattagaaa gaacgtcaat ggctctctgg gcgtcgcctt tgccgacaaa 5520
aatgtgatca tgatgaaagc cagcaatgac gttgcagctg atattgttgt cggccaaccg 5580
cgccgaaaac gcagctgtca gacccacagc ctccaacgaa gaatgtatcg tcaaagtgat 5640
ccaagcacac tcatagttgg agtcgtactc caaaggcggc aatgacgagt cagacagata 5700
ctcgtcgact caggcgacga cggaattcct gcagcccatc tgcagaattc aggagagacc 5760
gggttggcgg cgtatttgtg tcccaaaaaa cagccccaat tgccccggag aagacggcca 5820
ggccgcctag atgacaaatt caacaactca cagctgactt tctgccattg ccactagggg 5880
ggggcctttt tatatggcca agccaagctc tccacgtcgg ttgggctgca cccaacaata 5940
aatgggtagg gttgcaccaa caaagggatg ggatgggggg tagaagatac gaggataacg 6000
gggctcaatg gcacaaataa gaacgaatac tgccattaag actcgtgatc cagcgactga 6060
caccattgca tcatctaagg gcctcaaaac tacctcggaa ctgctgcgct gatctggaca 6120
ccacagaggt tccgagcact ttaggttgca ccaaatgtcc caccaggtgc aggcagaaaa 6180
cgctggaaca gcgtgtacag tttgtcttaa caaaaagtga gggcgctgag gtcgagcagg 6240
gtggtgtgac ttgttatagc ctttagagct gcgaaagcgc gtatggattt ggctcatcag 6300
gccagattga gggtctgtgg acacatgtca tgttagtgta cttcaatcgc cccctggata 6360
tagccccgac aataggccgt ggcctcattt ttttgccttc cgcacatttc cattgctcgg 6420
tacccacacc ttgcttctcc tgcacttgcc aaccttaata ctggtttaca ttgaccaaca 6480
tcttacaagc ggggggcttg tctagggtat atataaacag tggctctccc aatcggttgc 6540
cagtctcttt tttcctttct ttccccacag attcgaaatc taaactacac atcacacaat 6600
gcctgttact gacgtcctta agcgaaagtc cggtgtcatc gtcggcgacg atgtccgagc 6660
cgtgagtatc cacgacaaga tcagtgtcga gacgacgcgt tttgtgtaat gacacaatcc 6720
gaaagtcgct agcaacacac actctctaca caaactaacc cagctctcca tggctgagga 6780
taagaccaag gtcgagttcc ctaccctgac tgagctgaag cactctatcc ctaacgcttg 6840
ctttgagtcc aacctcggac tctcgctcta ctacactgcc cgagcgatct tcaacgcatc 6900
tgcctctgct gctctgctct acgctgcccg atctactccc ttcattgccg ataacgttct 6960
gctccacgct ctggtttgcg ccacctacat ctacgtgcag ggtgtcatct tctggggttt 7020
ctttaccgtc ggtcacgact gtggtcactc tgccttctcc cgataccact ccgtcaactt 7080
catcattggc tgcatcatgc actctgccat tctgactccc ttcgagtcct ggcgagtgac 7140
ccaccgacac catcacaaga acactggcaa cattgataag gacgagatct tctaccctca 7200
tcggtccgtc aaggacctcc aggacgtgcg acaatgggtc tacaccctcg gaggtgcttg 7260
gtttgtctac ctgaaggtcg gatatgctcc tcgaaccatg tcccactttg acccctggga 7320
ccctctcctg cttcgacgag cctccgctgt catcgtgtcc ctcggagtct gggctgcctt 7380
cttcgctgcc tacgcctacc tcacatactc gctcggcttt gccgtcatgg gcctctacta 7440
ctatgctcct ctctttgtct ttgcttcgtt cctcgtcatt actaccttct tgcatcacaa 7500
cgacgaagct actccctggt acggtgactc ggagtggacc tacgtcaagg gcaacctgag 7560
ctccgtcgac cgatcgtacg gagctttcgt ggacaacctg tctcaccaca ttggcaccca 7620
ccaggtccat cacttgttcc ctatcattcc ccactacaag ctcaacgaag ccaccaagca 7680
ctttgctgcc gcttaccctc acctcgtgag acgtaacgac gagcccatca ttactgcctt 7740
cttcaagacc gctcacctct ttgtcaacta cggagctgtg cccgagactg ctcagatttt 7800
caccctcaaa gagtctgccg ctgcagccaa ggccaagagc gactaagcgg ccgcaagtgt 7860
ggatggggaa gtgagtgccc ggttctgtgt gcacaattgg caatccaaga tggatggatt 7920
caacacaggg atatagcgag ctacgtggtg gtgcgaggat atagcaacgg atatttatgt 7980
ttgacacttg agaatgtacg atacaagcac tgtccaagta caatactaaa catactgtac 8040
atactcatac tcgtacccgg gcaacggttt cacttgagtg cagtggctag tgctcttact 8100
cgtacagtgt gcaatactgc gtatcatagt ctttgatgta tatcgtattc attcatgtta 8160
gttgc 8165

<210> SEQ ID NO 122
<211> LENGTH: 7879
<212> TYPE: DNA
<213> ORGANISM: Artificial Sequence
<220> FEATURE:
<223> OTHER INFORMATION: Plasmid pZUFE389S

<400> SEQUENCE: 122
catggctgcc gtcatcgagg tggccaacga gttcgtcgct atcactgccg agacccttcc 60
caaggtggac tatcagcgac tctggcgaga catctactcc tgcgagctcc tgtacttctc 120
cattgctttc gtcatcctca agtttaccct tggcgagctc tcggattctg gcaaaaagat 180
tctgcgagtg ctgttcaagt ggtacaacct cttcatgtcc gtcttttcgc tggtgtcctt 240
cctctgtatg ggttacgcca tctacaccgt tggactgtac tccaacgaat gcgacagagc 300
tttcgacaac agcttgttcc gatttgccac caaggtcttc tactattcca agtttctgga 360
gtacatcgac tctttctacc ttcccctcat ggccaagcct ctgtcctttc tgcagttctt 420
tcatcacttg ggagctccta tggacatgtg gctcttcgtg cagtactctg gcgaatccat 480
ttggatcttt gtgttcctga acggattcat tcactttgtc atgtacggct actattggac 540
acggctgatg aagttcaact ttcccatgcc caagcagctc attaccgcaa tgcagatcac 600
ccagttcaac gttggcttct acctcgtgtg gtggtacaag gacattccct gttaccgaaa 660
ggatcccatg cgaatgctgg cctggatctt caactactgg tacgtcggta ccgttcttct 720
gctcttcatc aacttctttg tcaagtccta cgtgtttccc aagcctaaga ctgccgacaa 780
aaaggtccag tagcggccgc aagtgtggat ggggaagtga gtgcccggtt ctgtgtgcac 840
aattggcaat ccaagatgga tggattcaac acagggatat agcgagctac gtggtggtgc 900
gaggatatag caacggatat ttatgtttga cacttgagaa tgtacgatac aagcactgtc 960
caagtacaat actaaacata ctgtacatac tcatactcgt acccgggcaa cggtttcact 1020

```
tgagtgcagt ggctagtgct cttactcgta cagtgtgcaa tactgcgtat catagtcttt   1080
gatgtatatc gtattcattc atgttagttg cgtacgagcc ggaagcataa agtgtaaagc   1140
ctggggtgcc taatgagtga gctaactcac attaattgcg ttgcgctcac tgcccgcttt   1200
ccagtcggga aacctgtcgt gccagctgca ttaatgaatc ggccaacgcg cggggagagg   1260
cggtttgcgt attgggcgct cttccgcttc ctcgctcact gactcgctgc gctcggtcgt   1320
tcggctgcgg cgagcggtat cagctcactc aaaggcggta atacggttat ccacagaatc   1380
aggggataac gcaggaaaga acatgtgagc aaaaggccag caaaaggcca ggaaccgtaa   1440
aaaggccgcg ttgctggcgt ttttccatag gctccgcccc cctgacgagc atcacaaaaa   1500
tcgacgctca agtcagaggt ggcgaaaccc gacaggacta taaagatacc aggcgtttcc   1560
ccctggaagc tccctcgtgc gctctcctgt tccgaccctg ccgcttaccg gatacctgtc   1620
cgcctttctc ccttcgggaa gcgtggcgct ttctcatagc tcacgctgta ggtatctcag   1680
ttcggtgtag gtcgttcgct ccaagctggg ctgtgtgcac gaaccccccg ttcagcccga   1740
ccgctgcgcc ttatccggta actatcgtct tgagtccaac ccggtaagac acgacttatc   1800
gccactggca gcagccactg gtaacaggat tagcagagcg aggtatgtag gcggtgctac   1860
agagttcttg aagtggtggc ctaactacgg ctacactaga aggacagtat ttggtatctg   1920
cgctctgctg aagccagtta ccttcggaaa aagagttggt agctcttgat ccggcaaaca   1980
aaccaccgct ggtagcggtg gtttttttgt ttgcaagcag cagattacgc gcagaaaaaa   2040
aggatctcaa gaagatcctt tgatcttttc tacggggtct gacgctcagt ggaacgaaaa   2100
ctcacgttaa gggattttgg tcatgagatt atcaaaaagg atcttcacct agatcctttt   2160
aaattaaaaa tgaagtttta aatcaatcta aagtatatat gagtaaactt ggtctgacag   2220
ttaccaatgc ttaatcagtg aggcacctat ctcagcgatc tgtctatttc gttcatccat   2280
agttgcctga ctccccgtcg tgtagataac tacgatacgg gagggcttac catctggccc   2340
cagtgctgca atgataccgc gagacccacg ctcaccggct ccagatttat cagcaataaa   2400
ccagccagcc ggaagggccg agcgcagaag tggtcctgca actttatccg cctccatcca   2460
gtctattaat tgttgccggg aagctagagt aagtagttcg ccagttaata gtttgcgcaa   2520
cgttgttgcc attgctacag gcatcgtggt gtcacgctcg tcgtttggta tggcttcatt   2580
cagctccggt tcccaacgat caaggcgagt tacatgatcc cccatgttgt gcaaaaaagc   2640
ggttagctcc ttcggtcctc cgatcgttgt cagaagtaag ttggccgcag tgttatcact   2700
catggttatg gcagcactgc ataattctct tactgtcatg ccatccgtaa gatgcttttc   2760
tgtgactggt gagtactcaa ccaagtcatt ctgagaatag tgtatgcggc gaccgagttg   2820
ctcttgcccg gcgtcaatac gggataatac cgcgccacat agcagaactt taaaagtgct   2880
catcattgga aaacgttctt cggggcgaaa actctcaagg atcttaccgc tgttgagatc   2940
cagttcgatg taacccactc gtgcacccaa ctgatcttca gcatctttta ctttcaccag   3000
cgtttctggg tgagcaaaaa caggaaggca aaatgccgca aaaaagggaa taagggcgac   3060
acggaaatgt tgaatactca tactcttcct ttttcaatat tattgaagca tttatcaggg   3120
ttattgtctc atgagcggat acatatttga atgtatttag aaaaataaac aaataggggt   3180
tccgcgcaca tttccccgaa aagtgccacc tgacgcgccc tgtagcggcg cattaagcgc   3240
ggcgggtgtg gtggttacgc gcagcgtgac cgctacactt gccagcgccc tagcgcccgc   3300
tcctttcgct ttcttccctt cctttctcgc cacgttcgcc ggctttcccc gtcaagctct   3360
aaatcggggg ctccctttag ggttccgatt tagtgcttta cggcacctcg accccaaaaa   3420
```

```
acttgattag ggtgatggtt cacgtagtgg gccatcgccc tgatagacgg tttttcgccc   3480
tttgacgttg gagtccacgt tctttaatag tggactcttg ttccaaactg gaacaacact   3540
caaccctatc tcggtctatt cttttgattt ataagggatt ttgccgattt cggcctattg   3600
gttaaaaaat gagctgattt aacaaaaatt taacgcgaat tttaacaaaa tattaacgct   3660
tacaatttcc attcgccatt caggctgcgc aactgttggg aagggcgatc ggtgcgggcc   3720
tcttcgctat tacgccagct ggcgaaaggg ggatgtgctg caaggcgatt aagttgggta   3780
acgccagggt tttcccagtc acgacgttgt aaaacgacgg ccagtgaatt gtaatacgac   3840
tcactatagg gcgaattggg taccgggccc cccctcgagg tcgatggtgt cgataagctt   3900
gatatcgaat tcatgtcaca caaaccgatc ttcgcctcaa ggaaacctaa ttctacatcc   3960
gagagactgc cgagatccag tctacactga ttaattttcg ggccaataat ttaaaaaaat   4020
cgtgttatat aatattatat gtattatata tatacatcat gatgatactg acagtcatgt   4080
cccattgcta aatagacaga ctccatctgc cgcctccaac tgatgttctc aatatttaag   4140
gggtcatctc gcattgttta ataataaaca gactccatct accgcctcca aatgatgttc   4200
tcaaaatata ttgtatgaac ttatttttat tacttagtat tattagacaa cttacttgct   4260
ttatgaaaaa cacttcctat ttaggaaaca atttataatg gcagttcgtt catttaacaa   4320
tttatgtaga ataaatgtta taaatgcgta tgggaaatct taaatatgga tagcataaat   4380
gatatctgca ttgcctaatt cgaaatcaac agcaacgaaa aaaatccctt gtacaacata   4440
aatagtcatc gagaaatatc aactatcaaa gaacagctat tcacacgtta ctattgagat   4500
tattattgga cgagaatcac acactcaact gtctttctct cttctagaaa tacaggtaca   4560
agtatgtact attctcattg ttcatacttc tagtcatttc atcccacata ttccttggat   4620
ttctctccaa tgaatgacat tctatcttgc aaattcaaca attataataa gatataccaa   4680
agtagcggta tagtggcaat caaaaagctt ctctggtgtg cttctcgtat ttatttttat   4740
tctaatgatc cattaaaggt atatatttat ttcttgttat ataatccttt tgtttattac   4800
atgggctgga tacataaagg tattttgatt taatttttg cttaaattca atcccccctc   4860
gttcagtgtc aactgtaatg gtaggaaatt accatacttt tgaagaagca aaaaaaatga   4920
aagaaaaaaa aaatcgtatt tccaggttag acgttccgca gaatctagaa tgcggtatgc   4980
ggtacattgt tcttcgaacg taaaagttgc gctccctgag atattgtaca tttttgcttt   5040
tacaagtaca agtacatcgt acaactatgt actactgttg atgcatccac aacagtttgt   5100
tttgtttttt tttgtttttt tttttctaa tgattcatta ccgctatgta tacctacttg   5160
tacttgtagt aagccgggtt attggcgttc aattaatcat agacttatga atctgcacgg   5220
tgtgcgctgc gagttacttt tagcttatgc atgctacttg ggtgtaatat tgggatctgt   5280
tcggaaatca acggatgctc aatcgatttc gacagtaatt aattaagtca tacacaagtc   5340
agctttcttc gagcctcata taagtataag tagttcaacg tattagcact gtacccagca   5400
tctccgtatc gagaaacaca acaacatgcc ccattggaca gatcatgcgg atacacaggt   5460
tgtgcagtat catacatact cgatcagaca ggtcgtctga ccatcataca agctgaacaa   5520
gcgctccata cttgcacgct ctctatatac acagttaaat tacatatcca tagtctaacc   5580
tctaacagtt aatcttctgg taagcctccc agccagcctt ctggtatcgc ttggcctcct   5640
caataggatc tcggttctgg ccgtacagac ctcggccgac aattatgata tccgttccgg   5700
tagacatgac atcctcaaca gttcggtact gctgtccgag agcgtctccc ttgtcgtcaa   5760
gacccacccc gggggtcaga ataagccagt cctcagagtc gcccttaggt cggttctggg   5820
```

```
caatgaagcc aaccacaaac tcggggtcgg atcgggcaag ctcaatggtc tgcttggagt   5880

actcgccagt ggccagagag cccttgcaag acagctcggc cagcatgagc agacctctgg   5940

ccagcttctc gttgggagag gggactagga actccttgta ctgggagttc tcgtagtcag   6000

agacgtcctc cttcttctgt tcagagacag tttcctcggc accagctcgc aggccagcaa   6060

tgattccggt tccgggtaca ccgtgggcgt tggtgatatc ggaccactcg gcgattcggt   6120

gacaccggta ctggtgcttg acagtgttgc caatatctgc gaactttctg tcctcgaaca   6180

ggaagaaacc gtgcttaaga gcaagttcct tgagggggag cacagtgccg gcgtaggtga   6240

agtcgtcaat gatgtcgata tgggttttga tcatgcacac ataaggtccg accttatcgg   6300

caagctcaat gagctccttg gtggtggtaa catccagaga agcacacagg ttggttttct   6360

tggctgccac gagcttgagc actcgagcgg caaaggcgga cttgtggacg ttagctcgag   6420

cttcgtagga gggcattttg gtggtgaaga ggagactgaa ataaatttag tctgcagaac   6480

tttttatcgg aaccttatct ggggcagtga agtatatgtt atggtaatag ttacgagtta   6540

gttgaactta tagatagact ggactatacg gctatcggtc caaattagaa agaacgtcaa   6600

tggctctctg ggcgtcgcct ttgccgacaa aaatgtgatc atgatgaaag ccagcaatga   6660

cgttgcagct gatattgttg tcggccaacc gcgccgaaaa cgcagctgtc agacccacag   6720

cctccaacga agaatgtatc gtcaaagtga tccaagcaca ctcatagttg gagtcgtact   6780

ccaaaggcgg caatgacgag tcagacagat actcgtcgac tcaggcgacg acggaattcc   6840

tgcagcccat ctgcagaatt caggagagac cgggttggcg gcgtatttgt gtcccaaaaa   6900

acagccccaa ttgccccgga gaagacggcc aggccgccta gatgacaaat tcaacaactc   6960

acagctgact ttctgccatt gccactaggg gggggccttt ttatatggcc aagccaagct   7020

ctccacgtcg gttgggctgc acccaacaat aaatgggtag ggttgcacca acaaagggat   7080

gggatggggg gtagaagata cgaggataac ggggctcaat ggcacaaata agaacgaata   7140

ctgccattaa gactcgtgat ccagcgactg acaccattgc atcatctaag ggcctcaaaa   7200

ctacctcgga actgctgcgc tgatctggac accacagagg ttccgagcac tttaggttgc   7260

accaaatgtc ccaccaggtg caggcagaaa acgctggaac agcgtgtaca gtttgtctta   7320

acaaaaagtg agggcgctga ggtcgagcag ggtggtgtga cttgttatag cctttagagc   7380

tgcgaaagcg cgtatggatt tggctcatca ggccagattg agggtctgtg gacacatgtc   7440

atgttagtgt acttcaatcg ccccctggat atagccccga caataggccg tggcctcatt   7500

tttttgcctt ccgcacattt ccattgctcg gtacccacac cttgcttctc ctgcacttgc   7560

caaccttaat actggtttac attgaccaac atcttacaag cggggggctt gtctagggta   7620

tatataaaca gtggctctcc caatcggttg ccagtctctt ttttcctttc tttccccaca   7680

gattcgaaat ctaaactaca catcacacaa tgcctgttac tgacgtcctt aagcgaaagt   7740

ccggtgtcat cgtcggcgac gatgtccgag ccgtgagtat ccacgacaag atcagtgtcg   7800

agacgacgcg ttttgtgtaa tgacacaatc cgaaagtcgc tagcaacaca cactctctac   7860

acaaactaac ccagctctc                                                7879
```

<210> SEQ ID NO 123
<211> LENGTH: 13
<212> TYPE: PRT
<213> ORGANISM: Artificial Sequence
<220> FEATURE:
<223> OTHER INFORMATION: delta-9 elongase motif
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: X = L or F
<220> FEATURE:
<221> NAME/KEY: misc_feature
<222> LOCATION: (5)..(8)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid

<400> SEQUENCE: 123

```
Tyr Asn Xaa Xaa Xaa Xaa Xaa Xaa Ser Xaa Xaa Ser Phe
1               5                   10
```

<210> SEQ ID NO 124
<211> LENGTH: 15
<212> TYPE: PRT
<213> ORGANISM: Artificial Sequence
<220> FEATURE:
<223> OTHER INFORMATION: delta-9 elongase motif
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: X = E or D
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: MISC_FEATURE
<222> LOCATION: (12)..(12)
<223> OTHER INFORMATION: X = T or S
<220> FEATURE:
<221> NAME/KEY: misc_feature
<222> LOCATION: (13)..(14)
<223> OTHER INFORMATION: Xaa can be any naturally occurring amino acid

<400> SEQUENCE: 124

```
Phe Tyr Xaa Ser Lys Xaa Xaa Xaa Tyr Xaa Asp Xaa Xaa Xaa Leu
1               5                   10                  15
```

<210> SEQ ID NO 125
<211> LENGTH: 9
<212> TYPE: PRT
<213> ORGANISM: Artificial Sequence
<220> FEATURE:
<223> OTHER INFORMATION: delta-9 elongase motif
<220> FEATURE:
<221> NAME/KEY: MISC_FEATURE
<222> LOCATION: (2)..(2)
<223> OTHER INFORMATION: X = Q or H
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 125

```
Leu Xaa Xaa Phe His His Xaa Gly Ala
```

1 5

<210> SEQ ID NO 126
<211> LENGTH: 14
<212> TYPE: PRT
<213> ORGANISM: Artificial Sequence
<220> FEATURE:
<223> OTHER INFORMATION: delta-9 elongase motif
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(12)
<223> OTHER INFORMATION: Xaa can be any naturally occurring amino acid
<220> FEATURE:
<221> NAME/KEY: MISC_FEATURE
<222> LOCATION: (13)..(13)
<223> OTHER INFORMATION: X = K or R or N

<400> SEQUENCE: 126

Met Tyr Xaa Tyr Tyr Xaa Xaa Xaa Xaa Xaa Xaa Xaa Xaa Phe
1 5 10

<210> SEQ ID NO 127
<211> LENGTH: 8
<212> TYPE: PRT
<213> ORGANISM: Artificial Sequence
<220> FEATURE:
<223> OTHER INFORMATION: delta-9 elongase motif
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: X = I or L or M
<220> FEATURE:
<221> NAME/KEY: misc_feature
<222> LOCATION: (6)..(7)
<223> OTHER INFORMATION: Xaa can be any naturally occurring amino acid

<400> SEQUENCE: 127

Lys Xaa Leu Xaa Thr Xaa Xaa Gln
1 5

<210> SEQ ID NO 128
<211> LENGTH: 7
<212> TYPE: PRT
<213> ORGANISM: Artificial Sequence
<220> FEATURE:
<223> OTHER INFORMATION: delta-9 elongase motif
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 128

Trp Xaa Phe Asn Tyr Xaa Tyr
1 5

<210> SEQ ID NO 129
<211> LENGTH: 9
<212> TYPE: PRT
<213> ORGANISM: Artificial Sequence
<220> FEATURE:
<223> OTHER INFORMATION: delta-9 elongase motif -continued

```
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid

<400> SEQUENCE: 129

Tyr Xaa Gly Xaa Val Xaa Xaa Leu Phe
1               5
```